US012741019B2

(12) United States Patent
Carfi et al.

(10) Patent No.: US 12,741,019 B2
(45) Date of Patent: Sep. 22, 2026

(54) VARIANT STRAIN-BASED CORONAVIRUS VACCINES

(71) Applicant: ModernaTX, Inc., Cambridge, MA (US)

(72) Inventors: Andrea Carfi, Cambridge, MA (US); Guillaume Stewart-Jones, Cambridge, MA (US); Hamilton Bennett, Cambridge, MA (US); Kai Wu, Cambridge, MA (US); Darin Edwards, Cambridge, MA (US); Gwo-Yu Chuang, Cambridge, MA (US); David Reid, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

(21) Appl. No.: 19/455,921

(22) Filed: Jan. 22, 2026

(65) Prior Publication Data

US 2026/0137772 A1 May 21, 2026

Related U.S. Application Data

(60) Division of application No. 19/294,594, filed on Aug. 8, 2025, which is a continuation of application No. 18/272,496, filed as application No. PCT/US2022/012614 on Jan. 14, 2022.

(60) Provisional application No. 63/284,570, filed on Nov. 30, 2021, provisional application No. 63/283,905, filed on Nov. 29, 2021, provisional application No. 63/241,963, filed on Sep. 8, 2021, provisional application No. 63/222,925, filed on Jul. 16, 2021, provisional application No. 63/193,547, filed on May 26, 2021, provisional application No. 63/173,979, filed on Apr. 12, 2021, provisional application No. 63/161,433, filed on Mar. 15, 2021, provisional application No. 63/140,920, filed on Jan. 24, 2021, provisional application No. 63/138,228, filed on Jan. 15, 2021.

(51) Int. Cl.

| | |
|---|---|
| ***A61K 39/215*** | (2006.01) |
| ***A61P 31/14*** | (2006.01) |
| ***C07K 14/005*** | (2006.01) |
| *A61K 39/00* | (2006.01) |

(52) U.S. Cl.
CPC ............ *A61K 39/215* (2013.01); *A61P 31/14* (2018.01); *C07K 14/005* (2013.01); *A61K 2039/53* (2013.01); *A61K 2039/545* (2013.01); *A61K 2039/70* (2013.01); *C12N 2770/20034* (2013.01)

(58) Field of Classification Search
CPC .............. A61K 39/215; A61K 2039/53; C12N 2770/20034
See application file for complete search history.

(56) References Cited

U.S. PATENT DOCUMENTS

| | | | |
|---|---|---|---|
| 3,906,092 | A | 9/1975 | Hilleman et al. |
| 4,790,987 | A | 12/1988 | Compans et al. |
| 5,169,628 | A | 12/1992 | Wathen |
| 5,427,782 | A | 6/1995 | Compans et al. |
| 6,225,091 | B1 | 5/2001 | Klein et al. |
| 6,500,419 | B1 | 12/2002 | Hone et al. |
| 6,514,948 | B1 | 2/2003 | Raz et al. |
| 7,001,890 | B1 | 2/2006 | Wagner et al. |
| 7,208,161 | B1 | 4/2007 | Murphy et al. |
| 7,449,324 | B2 | 11/2008 | Fouchier et al. |
| 7,531,342 | B2 | 5/2009 | Fouchier et al. |
| 7,671,186 | B2 | 3/2010 | Klein et al. |
| 7,704,720 | B2 | 4/2010 | Tang et al. |
| 7,803,918 | B2 | 9/2010 | Hoek |
| 7,862,813 | B2 | 1/2011 | Bjork |
| 8,058,069 | B2 | 11/2011 | Yaworski et al. |
| 8,217,016 | B2 | 7/2012 | Hoerr et al. |
| 8,252,289 | B2 | 8/2012 | Eleouët et al. |
| 8,460,680 | B2 | 6/2013 | Chow et al. |
| 8,546,550 | B2 | 10/2013 | Lipford et al. |
| 8,691,966 | B2 | 4/2014 | Kariko et al. |
| 8,703,906 | B2 | 4/2014 | Baumhof et al. |
| 8,710,200 | B2 | 4/2014 | Schrum et al. |
| 8,722,341 | B2 | 5/2014 | Fouchier et al. |
| 8,734,853 | B2 | 5/2014 | Sood et al. |
| 8,754,062 | B2 | 6/2014 | de Fougerolles et al. |
| 8,822,663 | B2 | 9/2014 | Schrum et al. |
| 8,841,433 | B2 | 9/2014 | Fouchier et al. |
| 8,889,146 | B2 | 11/2014 | Blais et al. |
| 8,916,696 | B2 | 12/2014 | Rossi et al. |
| 8,927,206 | B2 | 1/2015 | De Jong et al. |
| 8,968,746 | B2 | 3/2015 | Baumhof et al. |

(Continued)

FOREIGN PATENT DOCUMENTS

| | | | |
|---|---|---|---|
| AU | 2015210364 | A1 | 3/2017 |
| CA | 2473135 | A1 | 6/2003 |

(Continued)

OTHER PUBLICATIONS

Lin, H.-X., et al., 2008, Identification of residues in the receptor-binding domain (RBD) of the spike protein of human coronavirus NL63 that are critical for the RBD-ACE2 receptor interaction, J. Gen. Virol. 89:1015-1024.*

(Continued)

*Primary Examiner* — Jeffrey S Parkin
(74) *Attorney, Agent, or Firm* — Fish & Richardson P.C.

(57) ABSTRACT

The disclosure provides coronavirus mRNA vaccines, including vaccines directed against spike proteins of one or more variant strains of SARS-CoV-2, as well as methods of using the vaccines.

14 Claims, 86 Drawing Sheets

Specification includes a Sequence Listing.

(56) References Cited

U.S. PATENT DOCUMENTS 8,980,864 B2 3/2015 Hoge et al.
8,999,380 B2 4/2015 Bancel et al.
9,192,651 B2 11/2015 Chakraborty et al.
9,192,661 B2 11/2015 Jain et al.
9,220,755 B2 12/2015 Bancel et al.
9,221,891 B2 12/2015 Bancel et al.
9,254,265 B2 2/2016 Geall et al.
9,271,996 B2 3/2016 de Fougerolles et al.
9,283,287 B2 3/2016 Bancel et al.
9,295,689 B2 3/2016 de Fougerolles et al.
9,303,079 B2 4/2016 Bancel et al.
9,376,726 B2 6/2016 Fouchier et al.
9,464,124 B2 10/2016 Bancel et al.
9,512,456 B2 12/2016 Wang et al.
9,533,047 B2 1/2017 de Fougerolles et al.
9,567,653 B2 2/2017 Fouchier et al.
9,572,874 B2 2/2017 Fotin-Mleczek et al.
9,572,896 B2 2/2017 Bancel et al.
9,597,380 B2 3/2017 Chakraborty et al.
9,623,095 B2 4/2017 Kallen et al.
9,669,089 B2 6/2017 Thess et al.
9,675,668 B2 6/2017 Bancel et al.
9,758,795 B2 9/2017 Cullis et al.
9,790,531 B2 10/2017 Wang et al.
9,803,199 B2 10/2017 Koizumi et al.
9,868,691 B2 1/2018 Benenato et al.
9,872,900 B2 1/2018 Ciaramella et al.
9,937,196 B2 4/2018 Jain et al.
10,017,543 B2 7/2018 Kwong et al.
10,022,425 B2 7/2018 Bancel et al.
10,022,435 B2 7/2018 Ciaramella et al.
10,023,626 B2 7/2018 Bolen et al.
10,064,934 B2 9/2018 Ciaramella et al.
10,064,935 B2 9/2018 Ciaramella et al.
10,093,702 B2 10/2018 Li et al.
10,111,967 B2 10/2018 Folin-Mleczek et al.
10,124,055 B2 11/2018 Ciaramella et al.
10,143,758 B2 12/2018 Guild et al.
10,188,748 B2 1/2019 Mulbe et al.
10,207,010 B2 2/2019 Besin et al.
10,232,055 B2 3/2019 Kariko et al.
10,238,731 B2 3/2019 Ciaramella et al.
10,258,698 B2 4/2019 Hoge et al.
10,272,150 B2 4/2019 Ciaramella et al.
10,273,269 B2 4/2019 Ciaramella
10,286,086 B2 5/2019 Roy et al.
10,307,475 B2 6/2019 Wong et al.
10,322,089 B2 6/2019 Lobovkina et al.
10,323,076 B2 6/2019 Ellsworth et al.
10,335,486 B2 7/2019 Frederick et al.
10,342,760 B2 7/2019 Ramsay et al.
10,385,088 B2 8/2019 Fraley et al.
10,406,112 B2 9/2019 Martini et al.
10,441,653 B2 10/2019 Hoerr et al.
10,449,244 B2 10/2019 Ciaramella et al.
10,465,190 B1 11/2019 Chen et al.
10,493,143 B2 12/2019 Ciaramella et al.
10,501,513 B2 12/2019 Bancel et al.
10,519,455 B2 12/2019 Martini et al.
10,526,629 B2 1/2020 Rabideau et al.
10,543,269 B2 1/2020 Ciaramella et al.
10,590,161 B2 3/2020 Issa et al.
10,646,549 B2 5/2020 Frederick et al.
10,653,712 B2 5/2020 Hoge
10,653,767 B2 5/2020 Ciaramella et al.
10,682,406 B2 6/2020 Thess et al.
10,695,419 B2 6/2020 Ciaramella et al.
10,702,599 B2 7/2020 Ciaramella et al.
10,702,600 B1 7/2020 Ciaramella et al.
10,730,924 B2 8/2020 Ticho et al.
10,821,175 B2 11/2020 Gindy et al.
10,849,920 B2 12/2020 Hoge et al.
10,857,105 B2 12/2020 Benenato et al.
10,881,730 B2 1/2021 Huang et al.
10,906,944 B2 2/2021 He et al.
10,912,826 B2 2/2021 Thess et al.
10,925,958 B2 2/2021 Ciaramella
10,933,127 B2 3/2021 Ciaramella et al.
10,960,070 B2 3/2021 Graham et al.
10,993,918 B2 5/2021 Martini et al.
11,001,861 B2 5/2021 Martini et al.
11,027,025 B2 6/2021 Hoge et al.
11,045,540 B2 6/2021 Ciaramella
11,066,355 B2 7/2021 Benenato et al.
11,078,247 B2 8/2021 Fotin-Mleczek et al.
11,103,578 B2 8/2021 Ciaramella et al.
11,141,476 B2 10/2021 Rauch
11,266,735 B2 3/2022 Kallen et al.
11,311,615 B2 4/2022 Haruta
11,351,242 B1 6/2022 Lori et al.
11,377,470 B2 7/2022 Issa et al.
11,384,352 B2 7/2022 Miracco
11,406,703 B2 8/2022 Kramarczyk et al.
11,464,848 B2 10/2022 Ciaramella et al.
11,485,960 B2 11/2022 Dousis et al.
11,497,807 B2 11/2022 Ciaramella et al.
11,524,066 B2 12/2022 Jasny et al.
11,541,112 B2 1/2023 Smith et al.
11,564,893 B2 1/2023 Smith
11,576,961 B2 2/2023 Ciaramella et al.
11,583,504 B2 2/2023 Brader
11,638,693 B2 5/2023 Geall
11,638,694 B2 5/2023 Geall
11,643,441 B1 5/2023 Ciaramella et al.
11,666,534 B2 6/2023 Geall
11,696,892 B2 7/2023 Hansson et al.
11,696,946 B2 7/2023 Ciaramella
11,737,979 B2 8/2023 Karmali et al.
11,744,801 B2 9/2023 Schariter et al.
11,752,206 B2 9/2023 Ciaramella et al.
11,766,401 B2 9/2023 Geall
11,786,467 B2 10/2023 Geall
11,786,607 B2 10/2023 Hoge et al.
11,801,227 B2 10/2023 Benenato et al.
11,845,777 B2 12/2023 He et al.
11,851,694 B1 12/2023 Mauger et al.
11,866,696 B2 1/2024 Issa et al.
11,872,278 B2 1/2024 Ciaramella et al.
11,905,525 B2 2/2024 Brito et al.
11,911,453 B2 2/2024 Ciaramella et al.
11,912,982 B2 2/2024 Issa et al.
11,918,644 B2 3/2024 Ciaramella
11,969,506 B2 4/2024 Patel et al.
12,070,495 B2 8/2024 Lusso et al.
12,090,235 B2 9/2024 Horhota et al.
12,123,030 B2 10/2024 Benenato et al.
12,128,113 B2 10/2024 Benenato et al.
12,150,980 B2 11/2024 Ciaramella et al.
12,151,029 B2 11/2024 Hennessy et al.
12,186,387 B2 1/2025 Muik et al.
12,201,680 B2 1/2025 Thess et al.
12,318,443 B2 6/2025 Ciaramella
12,329,811 B2 6/2025 Nachbagauer et al.
12,383,508 B2 8/2025 Almarsson et al.
12,403,335 B2 9/2025 Ciaramella et al.
12,403,336 B2 9/2025 Ciaramella et al.
12,453,766 B2 10/2025 Ciaramella et al.
12,460,259 B2 11/2025 Elich et al.
12,508,308 B2 12/2025 Jasny et al.
2003/0092653 A1 5/2003 Kisich et al.
2003/0232061 A1 12/2003 Fouchier et al.
2004/0005545 A1 1/2004 Fouchier et al.
2004/0096451 A1 5/2004 Young et al.
2005/0032730 A1 2/2005 Von Der Mulbe et al.
2005/0059624 A1 3/2005 Hoerr et al.
2005/0250723 A1 11/2005 Hoerr et al.
2006/0002958 A1 1/2006 Naylor et al.
2006/0024668 A1 2/2006 Hoek
2006/0172003 A1 8/2006 Meers et al.
2006/0228367 A1 10/2006 Ulbrandt et al.
2007/0280929 A1 12/2007 Hoerr et al.
2008/0025914 A1 1/2008 Bjork
2008/0025944 A1 1/2008 Hoerr et al.
2008/0171079 A1 7/2008 Hanan et al.

(56) References Cited

U.S. PATENT DOCUMENTS

2008/0171711 A1 7/2008 Hoerr et al.
2009/0123529 A1 5/2009 Xiaomao
2009/0162395 A1 6/2009 Crowe et al.
2010/0203076 A1 8/2010 Fotin-Mleczek et al.
2010/0239608 A1 9/2010 Mulbe et al.
2010/0272747 A1 10/2010 Chow et al.
2010/0291156 A1 11/2010 Barner et al.
2010/0305196 A1 12/2010 Probst et al.
2011/0135645 A1 6/2011 Williamson et al.
2011/0250225 A1 10/2011 Fotin-Mleczek et al.
2011/0269950 A1 11/2011 Mulbe et al.
2012/0009221 A1 1/2012 Hoerr et al.
2012/0045471 A1 2/2012 Haller et al.
2012/0101148 A1 4/2012 Aking et al.
2012/0177701 A1 7/2012 Ilyinskii et al.
2012/0213812 A1 8/2012 Lipford et al.
2012/0219573 A1 8/2012 Baumhof et al.
2012/0276209 A1 11/2012 Cullis et al.
2013/0007828 A1 1/2013 Kister et al.
2013/0022538 A1 1/2013 Rossi
2013/0078281 A1 3/2013 He et al.
2013/0102034 A1 4/2013 Schrum et al.
2013/0121988 A1 5/2013 Hoerr et al.
2013/0142818 A1 6/2013 Baumhof et al.
2013/0183355 A1 7/2013 Jain et al.
2013/0195867 A1 8/2013 Hoerr et al.
2013/0195967 A1 8/2013 Guild et al.
2013/0195969 A1 8/2013 Geall et al.
2013/0202684 A1 8/2013 Geall et al.
2013/0236974 A1 9/2013 De Fougerolles
2013/0243848 A1 9/2013 Lobovkina et al.
2013/0245103 A1 9/2013 de Fougerolles et al.
2013/0259923 A1 10/2013 Bancel et al.
2013/0266640 A1 10/2013 De Fougerolles et al.
2013/0295043 A1 11/2013 Kallen et al.
2013/0336998 A1 12/2013 Kallen et al.
2014/0024076 A1 1/2014 Tang et al.
2014/0037660 A1 2/2014 Folin-Mleczek et al.
2014/0105966 A1 4/2014 Bancel et al.
2014/0147432 A1 5/2014 Bancel et al.
2014/0148502 A1 5/2014 Bancel et al.
2014/0193482 A1 7/2014 Bancel et al.
2014/0206752 A1 7/2014 Afeyan et al.
2014/0255472 A1 9/2014 Geall et al.
2014/0271829 A1 9/2014 Lilja et al.
2014/0308304 A1 10/2014 Manoharan et al.
2014/0370497 A1 12/2014 Fouchier et al.
2014/0378538 A1 12/2014 Bancel
2015/0051268 A1 2/2015 Bancel et al.
2015/0056253 A1 2/2015 Bancel et al.
2015/0093413 A1 4/2015 Thess et al.
2015/0126589 A1 5/2015 Geiger et al.
2015/0141499 A1 5/2015 Bancel et al.
2015/0307542 A1 10/2015 Roy et al.
2015/0315541 A1 11/2015 Bancel et al.
2015/0335728 A1 11/2015 Wong et al.
2016/0022580 A1 1/2016 Ramsay et al.
2016/0024140 A1 1/2016 Issa et al.
2016/0024141 A1 1/2016 Issa et al.
2016/0032273 A1 2/2016 Shahrokh et al.
2016/0038612 A1 2/2016 Hoge et al.
2016/0039884 A1 2/2016 Li et al.
2016/0046675 A1 2/2016 Kwong et al.
2016/0151474 A1 6/2016 Kallen et al.
2016/0194368 A1 7/2016 Hoge et al.
2016/0194625 A1 7/2016 Hoge et al.
2016/0243221 A1 8/2016 Hoge et al.
2016/0271272 A1 9/2016 Bancel et al.
2016/0317647 A1 11/2016 Ciaramella et al.
2016/0331828 A1 11/2016 Ciaramella et al.
2016/0361411 A1 12/2016 Gindy et al.
2017/0002041 A1 1/2017 Hauser et al.
2017/0043037 A1 2/2017 Kariko et al.
2017/0065675 A1 3/2017 Bancel et al.
2017/0130255 A1 5/2017 Wang et al.
2017/0202979 A1 7/2017 Chakraborty et al.
2017/0204152 A1 7/2017 Nelson et al.
2017/0340724 A1 11/2017 Ciaramella et al.
2018/0000953 A1 1/2018 Almarsson et al.
2018/0002393 A1 1/2018 Bancel et al.
2018/0008694 A1 1/2018 Ciaramella et al.
2018/0028645 A1 2/2018 Ciaramella et al.
2018/0028664 A1 2/2018 Besin et al.
2018/0161422 A1 6/2018 Probst et al.
2018/0237849 A1 8/2018 Thompson
2018/0243225 A1 8/2018 Ciaramella
2018/0243230 A1 8/2018 Smith
2018/0256628 A1 9/2018 Hoge et al.
2018/0271795 A1 9/2018 Martini et al.
2018/0271970 A1 9/2018 Ciaramella et al.
2018/0273977 A1 9/2018 Mousavi et al.
2018/0274009 A1 9/2018 Marquardt et al.
2018/0280496 A1 10/2018 Ciaramella et al.
2018/0289792 A1 10/2018 Ciaramella et al.
2018/0303929 A1 10/2018 Ciaramella et al.
2018/0311336 A1 11/2018 Ciaramella et al.
2018/0311343 A1 11/2018 Huang et al.
2018/0318409 A1 11/2018 Valiante et al.
2018/0326039 A1 11/2018 Haruta
2018/0363019 A1 12/2018 Hoge
2018/0369374 A1 12/2018 Frederick et al.
2018/0371047 A1 12/2018 Ticho et al.
2019/0002890 A1 1/2019 Martini et al.
2019/0008938 A1 1/2019 Ciaramella et al.
2019/0008948 A1 1/2019 Ciaramella et al.
2019/0015501 A1 1/2019 Ciaramella et al.
2019/0085368 A1 3/2019 Bancel et al.
2019/0099481 A1 4/2019 Ciaramella et al.
2019/0125839 A1 5/2019 Frederick et al.
2019/0175517 A1 6/2019 Martini et al.
2019/0175727 A1 6/2019 Huang et al.
2019/0192646 A1 6/2019 Cohen et al.
2019/0192653 A1 6/2019 Hoge et al.
2019/0240317 A1 8/2019 Ciaramella et al.
2019/0241633 A1 8/2019 Fotin-Mleczek et al.
2019/0275170 A1 9/2019 Benenato et al.
2019/0298657 A1 10/2019 Martini et al.
2019/0298658 A1 10/2019 Benenato et al.
2019/0300906 A1 10/2019 Martini et al.
2019/0314292 A1 10/2019 Benenato et al.
2019/0314493 A1 10/2019 Ciaramella et al.
2019/0336452 A1 11/2019 Brader
2019/0336595 A1 11/2019 Ciaramella
2019/0351040 A1 11/2019 Valiante et al.
2019/0351047 A1 11/2019 Jasny et al.
2019/0351048 A1 11/2019 Rauch
2019/0382774 A1 12/2019 Hoge et al.
2019/0390181 A1 12/2019 Benenato et al.
2020/0030432 A1 1/2020 Ciaramella et al.
2020/0032274 A1 1/2020 Mauger et al.
2020/0038499 A1 2/2020 Narayanan et al.
2020/0054737 A1 2/2020 Ciaramella et al.
2020/0061185 A1 2/2020 Graham et al.
2020/0069599 A1 3/2020 Smith et al.
2020/0069793 A1 3/2020 Ciaramella
2020/0069794 A1 3/2020 Ciaramella et al.
2020/0071689 A1 3/2020 Miracco
2020/0085916 A1 3/2020 Martini et al.
2020/0109420 A1 4/2020 Brito et al.
2020/0129445 A1 4/2020 Patel et al.
2020/0129608 A1 4/2020 Ciaramella et al.
2020/0129615 A1 4/2020 Ciaramella et al.
2020/0163878 A1 5/2020 Baurnhof et al.
2020/0197510 A1 6/2020 Ciaramella et al.
2020/0239869 A1 7/2020 Issa et al.
2020/0254086 A1 8/2020 Hoge et al.
2020/0282046 A1 9/2020 Ciaramella et al.
2020/0282047 A1 9/2020 Ciaramella et al.
2020/0297634 A1 9/2020 Karmali et al.
2020/0306191 A1 10/2020 Schariter et al.
2020/0338004 A1 10/2020 Hansson et al.
2020/0368162 A1 11/2020 Martini
2020/0368343 A1 11/2020 Ciaramella et al.
2020/0399322 A1 12/2020 Baumhof et al.

(56) References Cited

U.S. PATENT DOCUMENTS

2020/0405844 A1 12/2020 Ciaramella et al.
2020/0407402 A1 12/2020 He et al.
2021/0023199 A1 1/2021 Kallen et al.
2021/0030866 A1 2/2021 Kallen et al.
2021/0046173 A1 2/2021 Ciaramella et al.
2021/0060175 A1 3/2021 Baumhof et al.
2021/0087135 A1 3/2021 Benenato et al.
2021/0128716 A1 5/2021 Probst et al.
2021/0139543 A1 5/2021 He et al.
2021/0145982 A1 5/2021 Hoge et al.
2021/0162037 A1 6/2021 Jasny et al.
2021/0163919 A1 6/2021 Issa et al.
2021/0187097 A1 6/2021 Ciaramella et al.
2021/0206818 A1 7/2021 Huang et al.
2021/0217484 A1 7/2021 Giessel et al.
2021/0220467 A1 7/2021 Ciaramella et al.
2021/0228707 A1 7/2021 Mektar et al.
2021/0228708 A1 7/2021 Smith et al.
2021/0268086 A1 9/2021 Zhong et al.
2021/0309976 A1 10/2021 Dousis et al.
2021/0378980 A1 12/2021 Horhota et al.
2022/0031631 A1 2/2022 Almarsson et al.
2022/0047518 A1 2/2022 Hennessy et al.
2022/0054653 A1 2/2022 Martini et al.
2022/0062175 A1 3/2022 Smith et al.
2022/0125899 A1 4/2022 Ashburn et al.
2022/0145381 A1 5/2022 Elich et al.
2022/0175906 A1 6/2022 Ciaramella et al.
2022/0193223 A1 6/2022 Ciaramella et al.
2022/0236253 A1 7/2022 Hopson
2022/0241399 A1 8/2022 Lusso et al.
2022/0257746 A1 8/2022 Ciaramella et al.
2022/0347292 A1 11/2022 Panther et al.
2022/0348900 A1 11/2022 Shamashkin et al.
2022/0349006 A1 11/2022 Amato et al.
2022/0378904 A1 12/2022 Panther et al.
2022/0401551 A1 12/2022 Kramarczyk et al.
2022/0409720 A1 12/2022 Ciaramella
2023/0000970 A1 1/2023 Nachbagauer et al.
2023/0020362 A1 1/2023 Ciaramella et al.
2023/0044692 A1 2/2023 Ciaramella et al.
2023/0114180 A1 4/2023 Ciaramella et al.
2023/0116376 A1 4/2023 Ciaramella
2023/0142529 A1 5/2023 White et al.
2023/0173060 A1 6/2023 Benmohamed
2023/0181481 A1 6/2023 White et al.
2023/0190761 A1 6/2023 Brader et al.
2023/0212645 A1 7/2023 Marquardt et al.
2023/0270836 A1 8/2023 Ciaramella et al.
2023/0287437 A1 9/2023 Smith et al.
2023/0303632 A1 9/2023 Ciaramella
2023/0310576 A1 10/2023 Ciaramella et al.
2023/0338506 A1 10/2023 Shaw et al.
2023/0338512 A1 10/2023 Muik et al.
2023/0346907 A1 11/2023 Ciaramella et al.
2023/0346914 A1 11/2023 Stewart-Jones et al.
2023/0355743 A1 11/2023 Stewart-Jones et al.
2023/0374079 A1 11/2023 Ciaramella
2023/0381301 A1 11/2023 Ciaramella et al.
2023/0390379 A1 12/2023 Ciaramella et al.
2024/0000917 A1 1/2024 Ciaramella
2024/0100145 A1 3/2024 Bollman et al.
2024/0100151 A1 3/2024 Carfi et al.
2024/0139309 A1 5/2024 Carfi et al.
2024/0156952 A1 5/2024 Ciaramella et al.
2024/0173400 A1 5/2024 Ciaramella et al.
2024/0181030 A1 6/2024 Himansu et al.
2024/0207392 A1 6/2024 Chandramouli et al.
2024/0209068 A1 6/2024 Deal et al.
2024/0216500 A1 7/2024 Nachbagauer et al.
2024/0226277 A1 7/2024 Nachbagauer et al.
2024/0229109 A1 7/2024 Rabideau et al.
2024/0285754 A1 8/2024 Stewart-Jones
2024/0293534 A1 9/2024 Stewart-Jones
2024/0299525 A1 9/2024 Ciaramella et al.
2024/0299531 A1 9/2024 Stewart-Jones et al.
2024/0335526 A1 10/2024 Ciaramella et al.
2024/0358819 A1 10/2024 Stewart-Jones
2024/0366745 A1 11/2024 Ciaramella et al.
2024/0382581 A1 11/2024 Stewart-Jones
2025/0041407 A1 2/2025 Ciaramella
2025/0121220 A1 4/2025 Ciaramella et al.
2025/0121221 A1 4/2025 Ciaramella et al.
2025/0367278 A1 12/2025 Carfi et al.

FOREIGN PATENT DOCUMENTS

CA 3194325 A1 5/2022
CN 110951756 A 4/2020
CN 110974950 A 4/2020
CN 110974954 A 4/2020
CN 111088283 A 5/2020
CN 111218458 A 6/2020
CN 111218459 A 6/2020
CN 111303254 A 6/2020
CN 111518175 A 8/2020
CN 111592602 A 8/2020
CN 111848753 A 10/2020
CN 111939250 A 11/2020
CN 111978377 A 11/2020
CN 112023035 A 12/2020
CN 112028976 A 12/2020
CN 112043825 A 12/2020
CN 112048005 A 12/2020
CN 112094327 A 12/2020
CN 112220920 A 1/2021
CN 112226445 A 1/2021
CN 112266411 A 1/2021
CN 112321688 A 2/2021
CN 112358533 A 2/2021
CN 112480217 A 3/2021
CN 112546211 A 3/2021
CN 112626089 A 4/2021
CN 112794884 A 5/2021
EP 1026253 A2 8/2000
EP 1083232 B1 2/2005
EP 1905844 A2 2/2008
EP 2548960 A1 1/2013
EP 3452101 A2 3/2019
EP 3608308 A1 2/2020
EP 3718565 B1 4/2022
EP 4008357 B1 12/2022
JP 2013-544504 A 12/2013
JP 2015-518472 A 7/2015
JP 2016-515815 A 6/2016
JP 2017-513956 A 6/2017
JP 2018-537521 A 12/2018
JP 2023-511633 A 3/2023
JP 2023-513544 A 3/2023
WO WO 1987/005326 A1 9/1987
WO WO 1990/011092 A2 10/1990
WO WO 1993/014778 A1 8/1993
WO WO 1995/024485 A2 9/1995
WO WO 1995/026204 A1 10/1995
WO WO 1995/033835 A1 12/1995
WO WO 1996/040945 A2 12/1996
WO WO 1998/058956 A1 12/1998
WO WO 1999/033982 A2 7/1999
WO WO 2003/072720 A2 9/2003
WO WO 2004/076645 A1 9/2004
WO WO 2005/009346 A2 2/2005
WO WO 2005/027963 A2 3/2005
WO WO 2005/118813 A2 12/2005
WO WO 2006/009011 A1 1/2006
WO WO 2006/056027 A1 6/2006
WO WO 2006/071903 A2 7/2006
WO WO 2006/095259 A2 9/2006
WO WO 2007/024708 A2 3/2007
WO WO 2007/038862 A1 4/2007
WO WO 2007/094854 A2 8/2007
WO WO 2007/095976 A2 8/2007
WO WO 2008/052770 A2 5/2008
WO WO 2009/030254 A1 3/2009
WO WO 2009/030481 A1 3/2009

(56) References Cited

FOREIGN PATENT DOCUMENTS

WO WO 2009/095226 A1 8/2009
WO WO 2009/127230 A1 10/2009
WO WO 2010/037408 A1 4/2010
WO WO 2010/037539 A1 4/2010
WO WO 2010/042877 A1 4/2010
WO WO 2010/054401 A1 5/2010
WO WO 2010/054406 A1 5/2010
WO WO 2010/088927 A1 8/2010
WO WO 2010/129709 A1 11/2010
WO WO 2010/144740 A1 12/2010
WO WO 2010/149743 A2 12/2010
WO WO 2011/005799 A2 1/2011
WO WO 2011/026641 A9 3/2011
WO WO 2011/068810 A1 6/2011
WO WO 2011/069529 A1 6/2011
WO WO 2011/069586 A1 6/2011
WO WO 2011/140627 A1 11/2011
WO WO 2011/144358 A1 11/2011
WO WO 2012/006369 A2 1/2012
WO WO 2012/006372 A1 1/2012
WO WO 2012/006377 A2 1/2012
WO WO 2012/006378 A1 1/2012
WO WO 2012/019630 A1 2/2012
WO WO 2012/019780 A1 2/2012
WO WO 2012/030901 A1 3/2012
WO WO 2012/031043 A1 3/2012
WO WO 2012/031046 A2 3/2012
WO WO 2012/045082 A2 4/2012
WO WO 2012/051211 A2 4/2012
WO WO 2012/068295 A1 5/2012
WO WO 2012/116714 A1 9/2012
WO WO 2012/116715 A1 9/2012
WO WO 2012/116810 A1 9/2012
WO WO 2012/116811 A1 9/2012
WO WO 2012/135805 A2 10/2012
WO WO 2013/006825 A1 1/2013
WO WO 2013/006834 A1 1/2013
WO WO 2012/045075 A1 4/2013
WO WO 2013/052523 A1 4/2013
WO WO 2013/055905 A1 4/2013
WO WO 2013/090186 A1 6/2013
WO WO 2013/090648 A1 6/2013
WO WO 2013/102203 A1 7/2013
WO WO 2013/120628 A1 8/2013
WO WO 2013/120629 A1 8/2013
WO WO 2013/151664 A1 10/2013
WO WO 2013/151736 A2 10/2013
WO WO 2013/185069 A1 12/2013
WO WO 2014/089239 A1 6/2014
WO WO 2014/089486 A1 6/2014
WO WO 2014/144196 A1 9/2014
WO WO 2014/144711 A1 9/2014
WO WO 2014/152027 A1 9/2014
WO WO 2014/152030 A1 9/2014
WO WO 2014/152200 A1 9/2014
WO WO 2014/152211 A1 9/2014
WO WO 2014/152774 A1 9/2014
WO WO 2014/152940 A1 9/2014
WO WO 2014/159813 A1 10/2014
WO WO 2014/160243 A1 10/2014
WO WO 2015/005253 A1 1/2015
WO WO 2015/024668 A2 2/2015
WO WO 2015/048744 A2 4/2015
WO WO 2015/081155 A1 6/2015
WO WO 2015/085318 A2 6/2015
WO WO 2015/095340 A1 6/2015
WO WO 2015/095346 A1 6/2015
WO WO 2015/101414 A2 7/2015
WO WO 2015/101415 A1 7/2015
WO WO 2015/130584 A2 9/2015
WO WO 2015/143335 A1 9/2015
WO WO 2015/164674 A1 10/2015
WO WO 2016/103238 A1 6/2016
WO WO 2016/123864 A1 8/2016
WO WO 2016/138160 A1 9/2016
WO WO 2016/164762 A1 10/2016
WO WO 2016/201377 A1 12/2016
WO WO 2017/011773 A2 1/2017
WO WO 2017/015457 A1 1/2017
WO WO 2017/015463 A2 1/2017
WO WO 2017/019935 A1 2/2017
WO WO 2017/020026 A1 2/2017
WO WO 2017/062513 A1 4/2017
WO WO 2017/066789 A1 4/2017
WO WO 2017/070601 A1 4/2017
WO WO 2017/070616 A2 4/2017
WO WO 2017/070618 A1 4/2017
WO WO 2017/070620 A2 4/2017
WO WO 2017/070622 A1 4/2017
WO WO 2017/070623 A1 4/2017
WO WO 2017/070626 A2 4/2017
WO WO 2017/075038 A1 5/2017
WO WO 2017/075531 A1 5/2017
WO WO 2017/081082 A2 5/2017
WO WO 2017/112865 A1 6/2017
WO WO 2017/127750 A1 7/2017
WO WO 2017/174564 A1 10/2017
WO WO 2017/191274 A2 11/2017
WO WO 2017/201333 A1 11/2017
WO WO 2017/201340 A2 11/2017
WO WO 2017/201342 A1 11/2017
WO WO 2017/201347 A1 11/2017
WO WO 2017/201349 A1 11/2017
WO WO 2018/006052 A1 1/2018
WO WO 2018/053209 A1 3/2018
WO WO 2018/075980 A1 4/2018
WO WO 2018/081459 A1 5/2018
WO WO 2018/081462 A1 5/2018
WO WO 2018/089851 A2 5/2018
WO WO 2018/107088 A2 6/2018
WO WO 2018/111967 A1 6/2018
WO WO 2018/115527 A2 6/2018
WO WO 2018/144082 A1 8/2018
WO WO 2018/144778 A1 8/2018
WO WO 2018/151816 A1 8/2018
WO WO 2018/157009 A1 8/2018
WO WO 2018/170245 A1 9/2018
WO WO 2018/170256 A1 9/2018
WO WO 2018/170260 A1 9/2018
WO WO 2018/170270 A1 9/2018
WO WO 2018/170347 A1 9/2018
WO WO 2018/175783 A1 9/2018
WO WO 2018/187590 A1 10/2018
WO WO 2018/200737 A1 11/2018
WO WO 2018/232355 A1 12/2018
WO WO 2018/232357 A1 12/2018
WO WO 2019/018765 A1 1/2019
WO WO 2019/036670 A2 2/2019
WO WO 2019/036682 A1 2/2019
WO WO 2019/036683 A1 2/2019
WO WO 2019/036685 A1 2/2019
WO WO 2019/055807 A1 3/2019
WO WO 2019/103993 A1 5/2019
WO WO 2019/148101 A1 8/2019
WO WO 2019/202035 A1 10/2019
WO WO 2020/006242 A1 1/2020
WO WO 2020/056370 A1 3/2020
WO WO 2020/061284 A1 3/2020
WO WO 2020/061295 A1 3/2020
WO WO 2020/061367 A1 3/2020
WO WO 2020/097291 A1 5/2020
WO WO 2020/172239 A1 8/2020
WO WO 2020/185811 A1 9/2020
WO WO 2020/190750 A1 9/2020
WO WO 2020/243561 A1 12/2020
WO WO 2021/030533 A1 2/2021
WO WO 2021/178971 A1 2/2021
WO WO 2021/050864 A1 3/2021
WO WO 2021/055811 A1 3/2021
WO WO 2021/138447 A1 7/2021
WO WO 2021/147025 A1 7/2021
WO WO 2021/154763 A1 8/2021
WO WO 2021/154812 A1 8/2021
WO WO 2021/155243 A1 8/2021

(56) References Cited

FOREIGN PATENT DOCUMENTS

| | | | |
|---|---|---|---|
| WO | WO 2021/155274 | A1 | 8/2021 |
| WO | WO 2021/155733 | A1 | 8/2021 |
| WO | WO 2021/156267 | A1 | 8/2021 |
| WO | WO 2021/159040 | A2 | 8/2021 |
| WO | WO 2021/159118 | A2 | 8/2021 |
| WO | WO 2021/159130 | A2 | 8/2021 |
| WO | WO 2021/160346 | A1 | 8/2021 |
| WO | WO 2021/163365 | A1 | 8/2021 |
| WO | WO 2021/198706 | A2 | 10/2021 |
| WO | WO 2021/204175 | A1 | 10/2021 |
| WO | WO 2021/211343 | A1 | 10/2021 |
| WO | WO 2021/213945 | A1 | 10/2021 |
| WO | WO 2021/159040 | A9 | 11/2021 |
| WO | WO 2021/222304 | A1 | 11/2021 |
| WO | WO 2021/226436 | A1 | 11/2021 |
| WO | WO 2021/231901 | A1 | 11/2021 |
| WO | WO 2021/231929 | A1 | 11/2021 |
| WO | WO 2021/231963 | A1 | 11/2021 |
| WO | WO 2021/237084 | A1 | 11/2021 |
| WO | WO 2021/239880 | A1 | 12/2021 |
| WO | WO 2021/247817 | A1 | 12/2021 |
| WO | WO 2021/262672 | A1 | 12/2021 |
| WO | WO 2022/009121 | A1 | 1/2022 |
| WO | WO 2022/032154 | A2 | 2/2022 |
| WO | WO 2022/043551 | A2 | 3/2022 |
| WO | WO 2022/067010 | A1 | 3/2022 |
| WO | WO 2022/076562 | A1 | 4/2022 |
| WO | WO 2022/099003 | A1 | 5/2022 |
| WO | WO 2022/101469 | A1 | 5/2022 |
| WO | WO 2022/104265 | A1 | 5/2022 |
| WO | WO 2022/137133 | A1 | 6/2022 |
| WO | WO 2022/150717 | A1 | 7/2022 |
| WO | WO 2022/155524 | A1 | 7/2022 |
| WO | WO 2022/155530 | A1 | 8/2022 |
| WO | WO 2022/187698 | A1 | 9/2022 |
| WO | WO 2022/197624 | A1 | 9/2022 |
| WO | WO 2022/204491 | A1 | 9/2022 |
| WO | WO 2022/212191 | A1 | 10/2022 |
| WO | WO 2022/212442 | A1 | 10/2022 |
| WO | WO 2022/212711 | A2 | 10/2022 |
| WO | WO 2022/221335 | A1 | 10/2022 |
| WO | WO 2022/221336 | A1 | 10/2022 |
| WO | WO 2022/221359 | A1 | 10/2022 |
| WO | WO 2022/221440 | A1 | 10/2022 |
| WO | WO 2022/226277 | A1 | 10/2022 |
| WO | WO 2022/226318 | A1 | 10/2022 |
| WO | WO 2022/232585 | A1 | 11/2022 |
| WO | WO 2022/233629 | A1 | 11/2022 |
| WO | WO 2022/241103 | A1 | 11/2022 |
| WO | WO 2022/245888 | A1 | 11/2022 |
| WO | WO 2022/266010 | A1 | 12/2022 |
| WO | WO 2022/266012 | A1 | 12/2022 |
| WO | WO 2022/266389 | A1 | 12/2022 |
| WO | WO 2023/283642 | A2 | 1/2023 |
| WO | WO 2023/283645 | A1 | 1/2023 |
| WO | WO 2023/283651 | A1 | 1/2023 |
| WO | WO 2023/014649 | A1 | 2/2023 |
| WO | WO 2023/018773 | A1 | 2/2023 |
| WO | WO 2023/018923 | A1 | 2/2023 |
| WO | WO 2023/019181 | A1 | 2/2023 |
| WO | WO 2023/056401 | A1 | 4/2023 |
| WO | WO 2023/069625 | A1 | 4/2023 |
| WO | WO 2023/069895 | A1 | 4/2023 |
| WO | WO 2023/069900 | A1 | 4/2023 |
| WO | WO 2023/076358 | A1 | 5/2023 |
| WO | WO 2023/076658 | A1 | 5/2023 |
| WO | WO 2023/081311 | A1 | 5/2023 |
| WO | WO 2023/092069 | A1 | 5/2023 |
| WO | WO 2023/094713 | A2 | 6/2023 |
| WO | WO 2023/107999 | A2 | 6/2023 |
| WO | WO 2023/114307 | A1 | 6/2023 |
| WO | WO 2023/132885 | A1 | 7/2023 |
| WO | WO 2023/135333 | A1 | 7/2023 |
| WO | WO 2023/137149 | A1 | 7/2023 |
| WO | WO 2023/147091 | A1 | 8/2023 |
| WO | WO 2023/150256 | A1 | 8/2023 |
| WO | WO 2023/154818 | A1 | 8/2023 |
| WO | WO 2023/196914 | A1 | 10/2023 |
| WO | WO 2023/201204 | A1 | 10/2023 |
| WO | WO 2023/201294 | A1 | 10/2023 |
| WO | WO 2023/201296 | A1 | 10/2023 |
| WO | WO 2023/212696 | A1 | 11/2023 |
| WO | WO 2023/225524 | A1 | 11/2023 |
| WO | WO 2023/250119 | A1 | 12/2023 |
| WO | WO 2024/010993 | A1 | 1/2024 |
| WO | WO 2024/015890 | A1 | 1/2024 |
| WO | WO 2024/026005 | A1 | 2/2024 |
| WO | WO 2024/030369 | A1 | 2/2024 |
| WO | WO 2024/050483 | A1 | 3/2024 |
| WO | WO 2024/097874 | A1 | 5/2024 |

OTHER PUBLICATIONS

Guo, Y., et al., 2009, Identification of a New Region of SARS-CoV S Protein Critical for Viral Entry, J. Mol. Biol. 394:600-605.*

Bader, W., et al., 2022, Quasispecies Analysis of SARS-CoV-2 of 15 Different Lineages during the First Year of the Pandemic Prompts Scratching under the Surface of Consensus Genome Sequences, Int. J. Mol. Sci. 23:15658, pp. 1-18.*

Colson, P., et al., Aug. 2023, From viral democratic genomes to viral wild bunch of quasispecies, J. Med. Virol. 9:e29209, pp. 1-15.*

U.S. Appl. No. 62/972,886, Wrapp et al., filed Feb. 11, 2020.

U.S. Appl. No. 63/032,502, Hsieh et al., filed May 29, 2020.

[No Author Listed] "Lineage list," Last accessed Oct. 17, 2023, at <https://cov-lineages.org/lineage_list.html>, 77 pages.

[No Author Listed], "2022 Breakthrough Prize in Life Sciences Awarded to Penn Medicine mRNA Pioneers Drew Weissman and Katalin Karikó," Press Release, Sep. 9, 2021, 3 pages.

[No Author Listed], "3rd International mRNA Health Conference Program," mRNA Conference, Berlin, Germany, Nov. 11, 2015, 28 pages.

[No Author Listed], "A Phase 3, Randomized, Stratified, Observer-Blind, Placebo-Controlled Study to Evaluate the Efficacy, Safety, and Immunogenicity of mRNA-1273 SARS-CoV-2 Vaccine in Adults Aged 18 Years and Older," ModernaTX, Inc. Protocol mRNA-1273-P301, Amendment 3, Aug. 20, 2020, 135 pages.

[No Author Listed], "An Audience with Moncef Slaoui," Nat Rev Drug Discov., Jul. 1, 2015, 14:452-453.

[No Author Listed], "Background document on the mRNA-1273 vaccine (Moderna) against COVID-19," World Health Organization, Feb. 3, 2021, Accessed from <https://www.who.int/publications/iiitem/background-document-on-the-rnrna-1273-vaccine-(moderna)-against-covid-19>, 41 pages.

[No Author Listed], "BioNTech Expands Clinical Oncology Portfolio with First Patient Dosed in Phase 2 Trial of mRNA-based Individualized Immunotherapy BNT122 in Colorectal Cancer Patients," Press Release, BioNTech, Oct. 1, 2021, 2 pages.

[No Author Listed], "BioNTech Fourth Quarter and Full-Year 2019 Results," BioNTech, Mar. 31, 2020, 15 pages.

[No Author Listed], "BioNTech SE Annual Report (Form 20-F) 179, F-12," United States Securities and Exchange Commission, Mar. 30, 2021, 739 pages.

[No Author Listed], "BioNTech SE Annual Report (Form 20-F) 81," United States Securities and Exchange Commission, Mar. 30, 2022, 700 pages.

[No Author Listed], "BioNTech Signs Collaboration Agreement with Pfizer to Develop mRNA-based Vaccines for Prevention of Influenza," Press Release, Aug. 16, 2018, 3 pages.

[No Author Listed], "BNT162 COVID-19 Vaccine Program Update," BioNTech, Apr. 23, 2020, 15 pages.

[No Author Listed], "Canada Exercises Increased Option for 20 Million Doses of mRNA Vaccine Against COVID-19 (mRNA-1273)," Moderna Press Release, Sep. 22, 2020, 2 pages.

[No Author Listed], "Center for Drug Evaluation and Research Approval Package for New Drug Application No. 50-718/S-50 for Doxil®," Approved Dec. 28, 2015, 97 pages.

(56) References Cited

OTHER PUBLICATIONS

[No Author Listed], "Classification of Omicron (B.1.1.529): SARS-Co V-2Variant of Concern," World Health Organization, Nov. 26, 2021, 3 pages.
[No Author Listed], "Clinical trial NCT04528719: A Dose Escalation Study to Evaluate Safety, Reactogenicity, and Immunogenicity of mRNA-1345 in Healthy Adults and in Children Who Are Respiratory Syncytial Virus Seropositive," (ModernaTX, Inc.), Aug. 27, 2020, retrieved on 15 Mar. 15, 2021, retrieved from URL <https://www.clinicaltrials.gov/ct2/show/NCT04528719?term=NCT04528719&draw=2&rank=1>, 9 pages.
[No Author Listed], "Comirnaty (mRNA-1273) EMA SmPC," Summary of Product Characteristics, Dec. 1, 2021, 276 pages.
[No Author Listed], "Comirnaty Dosing Schedule for People 12 Years of Age & Older (2023-2024 Formula)," Pfizer-BioNTech, Oct. 2023, 2 pages.
[No Author Listed], "Coronavirus (COVID-19) Update: FDA Authorizes Changes to Simplify Use of Bivalent mRNA COVID-19 Vaccines," FDA News Release, Apr. 18, 2023, 3 pages.
[No Author Listed], "Coronavirus (COVID-19) Update: FDA Issues Policies to Guide Medical Product Developers Addressing Virus Variants," FDA News Release, Feb. 22, 2021, 5 pages.
[No Author Listed], "Could COVID-19 vaccines be tweaked to cover new coronavirus variants?," Gavi, the Vaccine Alliance, Published Jan. 14, 2021, last accessed on Apr. 26, 2022, retrieved from URL <https://www.gavi.org/vaccineswork/could-covid-19-vaccines-be-tweaked-cover-new-coronavirus-variants>, 5 pages.
[No Author Listed], "COVID-19 Vaccine Development Program," Pfizer, Jul. 1, 2020, 18 pages.
[No Author Listed], "DARPA Awards Moderna Therapeutics a Grant for up to $25 Million to Develop Messenger RNA Therapeutics," News Release, Moderna, Oct. 2, 2013, 1 page.
[No Author Listed], "Delivery means to avoid degradation of RNA preparations: Lipid nanoparticles (LNPs) for RNA delivery," CosmoBio, Retrieved from the Internet: <https://www.cosmobio.co.jp/product/detail/lipid-nanoparticles-for-rna-delivery-ecl.asp?entry_id=43081>, Last Accessed: Oct. 23, 2023, 10 pages (Machine Translation).
[No Author Listed], "Dosing Schedule for Ages 12 Years of Age and Older with Pfizer-BioNTech COVID-19 Vaccine," Bivalent (Original and Omicron BA.4/BA.5), Apr. 2023, 7-9.
[No Author Listed], "European Commission Authorizes COVID 19 Vaccine Moderna in Europe," Jan. 6, 2021, Accessed from <https://www.drugs.com/clinical_trials/european-commission-authorizes-covid-19-vaccine-moderna-europe-19152.html>, 5 pages.
[No Author Listed], "Experimental COVID-19 Vaccine Protects Upper and Lower Airways in Nonhuman Primates," NIH News Release, Jul. 28, 2020, 4 pages.
[No Author Listed], "Experimental COVID-19 Vaccine Safe, Generates Immune Response," NIH News Release, Jul. 14, 2020, 4 pages.
[No Author Listed], "Fact Sheet for Healthcare Providers Administering Vaccine: Emergency Use Authorization of Pfizer-BioNTech COVID-19 Vaccine (2023-2024 Formula) for 6 Months through 11 Years of Age," Pfizer-BioNTech, Sep. 2023, 59 pages.
[No Author Listed], "Goldman Sachs Virtual 41st Annual Global Healthcare Conference," Pfizer Inc., Jun. 9, 2020, 13 pages.
[No Author Listed], "Heroes of Chemistry recognized for contributions to health, medicine and more," American Chemical Society, Jul. 20, 2022, 2 pages.
[No Author Listed], "History of Changes for Study: NCT04283461, Safety and Immunogenicity Study of2019-nCoV Vaccine (mRNA-1273) for Prophylaxis of SARS-CoV-2 Infection (COVID-19)," ClinicalTrials.gov, Version submitted Dec. 8, 2022, 8 pages.
[No Author Listed], "History of Changes for Study: NCT04283461, Safety and Immunogenicity Study of2019-nCoV Vaccine (mRNA-1273) for Prophylaxis of SARS-CoV-2 Infection (COVID-19)," Version submitted Mar. 11, 2021, 10 pages.
[No Author Listed], History of Changes for Study: NCT04405076, Dose-Confirmation Study to Evaluate the Safety, Reactogenicity, and Immunogenicity of mRNA-1273 COVID-19 Vaccine in Adults Aged 18 Years and Older, Version submitted Dec. 6, 2022, 6 pages.
[No Author Listed], "Increase in Manufacturing Capacity for COVID-19 Vaccines from Janssen, Moderna, and BioNTech/Pfizer," European Medicines Agency, Dec. 16, 2021, 4 pages.
[No Author Listed], "Katalin Kariko and Drew Weissman awarded Horwitz Prize for pioneering research on COVID-19 vaccines," Columbia University Irving Medical Center, Aug. 16, 2021, <https://www.cuimc.columbia.edu/news/horwitz-prize-2021> (last accessed Aug. 24, 2023), 12 pages.
[No Author Listed], "Katalin Karikó Laureate de la Grande Medaille 2021 de L'Academie des Sciences, Press Release," De L'Academie des Sciences, Sep. 28, 2021, 2 pages.
[No Author Listed], "Messenger RNA Pioneer Katalin Karikó Receives European Inventor Award 2022 for Lifetime Achievement," Press Release, European Patent Office, Jun. 21, 2022, 4 pages.
[No Author Listed], "Messenger RNA" definition, Collins Dictionary of Science, 2005, p. 514.
[No Author Listed], "Messenger RNA" definition, The Penguin Dictionary of Science, 2009, 3 pages.
[No Author Listed], "Messenger RNA" definition, Webster's New World Medical Dictionary, 3rd Ed., 2008, p. 271.
[No Author Listed], "Messenger RNA," Jun. 19, 2013, retrieved from URL <http://en.wikipedia.org/wiki/Messenger RNA>, 10 pages.
[No Author Listed], "Moderna Advances Late-Stage Development of its Vaccine (mRNA-1273) Against COVID-19," Moderna Press Release, Jun. 11, 2020, 3 pages.
[No Author Listed], "Moderna and Lonza Announce Worldwide Strategic Collaboration to Manufacture Moderna's Vaccine (mRNA-1273) Against Novel Coronavirus," Moderna Press Release, May 1, 2020, 3 pages.
[No Author Listed], "Moderna Announces Award from U.S. Government Agency BARDA for up to $483 Million to Accelerate Development of mRNA Vaccine (mRNA-1273) Against Novel Coronavirus," Moderna Press Release, Apr. 16, 2020, 3 pages.
[No Author Listed], "Moderna Announces Expansion of BARDA Agreement to Support Larger Phase 3 Program for Vaccine (mRNA-1273) Against COVID-19," Moderna Press Release, Jul. 26, 2020, 3 pages.
[No Author Listed], "Moderna Announces FDA Authorization of Moderna COVID 19 Vaccine in U.S.," Moderna Press Release, Dec. 19, 2020, 3 pages.
[No Author Listed], "Moderna Announces First Participant Dosed in NIH-led Phase 1 Study of mRNA Vaccine (mRNA-1273) Against Novel Coronavirus," Moderna Press Release, Mar. 16, 2020, 2 pages.
[No Author Listed], "Moderna Announces First Participant Dosed in Phase 2 Study of Omicron-Specific Booster Candidate and Publication of Data on Booster Durability Against Omicron Variant," News Release, Moderna, Jan. 26, 2022, 4 pages.
[No Author Listed], "Moderna Announces First Participant Dosed in Phase 2 Study of Omicron-Specific Booster Candidate," News Release, Mar. 10, 2022, 2 pages.
[No Author Listed], "Moderna Announces First Participants in Each Age Cohort Dosed in Phase 2 Study of mRNA Vaccine (mRNA-1273) Against Novel Coronavirus," Moderna Press Release, May 29, 2020, 2 pages.
[No Author Listed], "Moderna Announces Funding Award from CEPI to Accelerate Development of Messenger RNA (mRNA) Vaccine Against Novel Coronavirus," News Release, Moderna, Jan. 23, 2020, 2 pages.
[No Author Listed], "Moderna Announces IND Submitted to U.S. FDA for Phase 2 Study of mRNA Vaccine (mRNA-1273) Against Novel Coronavirus," Moderna Press Release, Apr. 27, 2020, 3 pages.
[No Author Listed], "Moderna Announces it has Shipped Variant-Specific Vaccine Candidate, mRNA-1273.351, to NIH for Clinical Study," Moderna Press Release, Feb. 24, 2021, 3 pages.
[No Author Listed], "Moderna Announces Phase 3 COVE Study of mRNA Vaccine Against COVID-19 (mRNA-1273) Begins," Moderna Press Release, Jul. 27, 2020, 3 pages.

(56) References Cited

OTHER PUBLICATIONS

[No Author Listed], "Moderna Announces Positive Interim Phase 1 Data for its mRNA Vaccine (mRNA-1273) Against Novel Coronavirus," Moderna Press Release, May 18, 2020, 3 pages.
[No Author Listed], "Moderna Announces Progress Across Broad Portfolio and all Three Clinical Stage Therapeutic Areas at 2020 R&D Day," Moderna Press Release, Sep. 17, 2020, 4 pages.
[No Author Listed], "Moderna Announces Publication in The New England Journal of Medicine of Interim Results From Older Adult Age Cohorts in Phase 1 Study of its mRNA Vaccine Against COVID-19 (mRNA-1273)," Moderna Press Release, Sep. 29, 2020, 7 pages.
[No Author Listed], "Moderna Announces Publication in The New England Journal of Medicine of Interim Results From Phase 1 Study of Its mRNA Vaccine Against COVID-19 (mRNA-1273)," Moderna Press Release, Jul. 14, 2020, 5 pages.
[No Author Listed], "Moderna Announces Publication in The New England Journal of Medicine of Non-Human Primate Preclinical Viral Challenge Study of its mRNA Vaccine Against COVID-19 (mRNA-1273)," Moderna Press Release, Jul. 28, 2020, 3 pages.
[No Author Listed], "Moderna Announces Strategy to Address Omicron (B.1.1.529) SARS-CoV-2 Variant," Press Release, Moderna, Nov. 26, 2021, 2 pages.
[No Author Listed], "Moderna Announces Supply Agreement with U.S. Government for Initial 100 Million Doses of mRNA Vaccine Against COVID-19 (mRNA-1273)," Moderna Press Release, Aug. 11, 2020, 3 pages.
[No Author Listed], "Moderna Completes Enrollment of Phase 2 Study of its mRNA Vaccine Against COVID-19 (mRNA-1273)," Moderna Press Release, Jul. 8, 2020, 2 pages.
[No Author Listed], "Moderna Confirms Advanced Discussions with European Commission to Supply Europe with 80 Million Doses of mRNA Vaccine Against COVID-19 (mRNA-1273)," Moderna Press Release, Aug. 24, 2020, 3 pages.
[No Author Listed], "Moderna Confirms Discussions with the Ministry of Health, Labour and Welfare to Supply Japan with 40 Million Doses of mRNA Vaccine Against COVID-19 (mRNA-1273)," Moderna Press Release, Aug. 28, 2020, 2 pages.
[No Author Listed], "Moderna has no plans to share its COVID-19 vaccine recipe," Associated Press, Oct. 11, 2021, 2 pages.
[No Author Listed], "Moderna Inc to Discuss Updates on Respiratory Syncytial Virus (RSV) Vaccine Program Call," Edited Transcript. Refinitiv., Oct. 8, 2020, 14 pages.
[No Author Listed], "Moderna Provides Business Update and Announces Three New Development Programs in Infectious Disease Vaccines," Press Release, Jan. 11, 2021, 5 pages.
[No Author Listed], "Moderna Receives FDA Authorization for Emergency Use of Omicron-Targeting Bivalent COVID-19 Booster Vaccine for Adults 18 Years and Older," News Release, Moderna, Aug. 31, 2022, 5 pages.
[No Author Listed], "Moderna Receives FDA Fast Track Designation for mRNA Vaccine (mRNA-1273) Against Novel Coronavirus," Moderna Press Release, May 12, 2020, 2 pages.
[No Author Listed], "Moderna Reports Fourth Quarter and Fiscal Year 2020 Financial Results and Provides Business Updates," Press Release, Feb. 25, 2021, 9 pages.
[No Author Listed], "Moderna Ships mRNA Vaccine Against Novel Coronavirus (mRNA-1273) for Phase 1 Study," Moderna Press Release, Feb. 24, 2020, 2 pages.
[No Author Listed], "Moderna's COVID-19 Vaccine Candidate Meets its Primary Efficacy Endpoint in the First Interim Analysis of the Phase 3 COVE Study," Moderna Press Release, Nov. 16, 2020, 3 pages.
[No Author Listed], "Moderna's Update Patent Pledge," Press Release, Moderna, Mar. 7, 2022, 2 pages.
[No Author Listed], "Modified mRNA Vaccines, 2021 Lasker-DeBakey Clinical Medical Research Award," 2021, retrieved on Nov. 14, 2022, retrieved from URL <https://laskerfoundation.org/winners/modified-mrna-vaccines/>, 17 pages.
[No Author Listed], "NIH Clinical Trial of Investigational Vaccine for COVID-19 begins," NIH News Release, Mar. 16, 2020, 3 pages.
[No Author Listed], "NIH-Moderna Investigational COVID-19 Vaccine Shows Promise in Mouse Studies," NIH News Release, Aug. 5, 2020, 4 pages.
[No Author Listed], "Penn mRNA Scientists Drew Weissman and Katalin Karikó Receive 2021 Lasker Award, America's Top Biomedical Research Prize," Penn News Release, Sep. 24, 2021, 6 pages.
[No Author Listed], "Pfizer and BioNTech Announce Early Positive Data from an Ongoing Phase 1/2 Study of mRNA-based Vaccine Candidate against SARS-CoV-2," Press Release, Jul. 1, 2020, 8 pages.
[No Author Listed], "Pfizer and BioNTech Announce Early Positive Update from German Phase 1/2 Study of COVID-19 Vaccine Study, Including First T Cell Response Data," Press Release, Jul. 20, 2020, 6 pages.
[No Author Listed], "Pfizer and BioNTech Announce Phase 3 Trial Data Showing High Efficacy of a Booster Dose of Their COVID-19 Vaccine," Press Release, Pfizer, Oct. 21, 2021, 10 pages.
[No Author Listed], "Pfizer and BioNTech Choose Lead mRNA Vaccine Candidate Against COVID-19 and Commence Pivotal Phase 2/3 Global Study," Press Release, Jul. 27, 2020, 7 pages.
[No Author Listed], "Pfizer and BioNTech Granted FDA Emergency Use Authorization of Omicron BA.4/BA.5-Adapted Bivalent COVID-19 Vaccine Booster for Ages 12 Years and Older," Pfizer, Aug. 31, 2022, 12 pages.
[No Author Listed], "Pfizer and BioNTech Receive Expanded U.S. Emergency Use Authorization for an Additional COVID-19 Vaccine Booster in Individuals Aged 50 Years and Older," Press Release, Pfizer, Mar. 29, 2022, 12 pages.
[No Author Listed], "Pfizer and BioNTech Submit Applications to U.S. FDA for Omicron XBB.1.5-Adapted Monovalent COVID-19 Vaccine," Pfizer, Jun. 23, 2023, 8 pages.
[No Author Listed], "Pfizer and BioNTech Submit Supplemental Biologics License Application for U.S. FDA Approval of Omicron BA.4/BA.5-Adapted Bivalent COVID-19 Vaccine for Ages 12 Years and Older as Primary Series or Booster," Pfizer, Feb. 24, 2023, 12 pages.
[No Author Listed], "Pfizer Inc to discuss data from an ongoing phase 1/2 study of mRNA-based vaccine candidate against SARS_CoV-2 Call," Edited Transcript, Thomson Reuters, Jul. 1, 2020, 15 pages.
[No Author Listed], "Pfizer reports fourth-quarter and full-year 2021 results," Pfizer, Feb. 8, 2022, 41 pages.
[No Author Listed], "Phase 3 Clinical Trial of Investigational Vaccine for COVID-19 Begins," NIH News Release, Jul. 27, 2020, 3 pages.
[No Author Listed], "Pioneering Scientists Awarded the Albany Prize, America's Most Distinguished Prize in Medicine, for Research Leading to Covid-19 Vaccines," The Albany Prize, Aug. 26, 2021, 4 pages.
[No Author Listed], "RBC capital Markets Global Healthcare Conference," Pfizer Inc., May 19, 2020, 9 pages.
[No Author Listed], "Reflection paper on the regulatory requirements for vaccines intended to provide protection against variant strain(s) of SARS-CoV-2," European Medicines Agency, EMA/117973/2021, Feb. 23, 2021, 7 pages.
[No Author Listed], "Remarks by President Trump and Members of the Coronavirus Task Force in Meeting with Pharmaceutical Companies," The White House, Mar. 2, 2022, 31 pages.
[No Author Listed], "SARS-CoV-2 Variant Classifications and Definitions," CDC, <https://www.cdc.gov/coronavirus/2019-ncov/variants/variant-classifications.html>, Updated Sep. 1, 2023, 5 pages.
[No Author Listed], "SARS-CoV-2 variants of concern as of May 4, 2023," European Centre for Disease Prevention and Control, Last accessed May 16, 2023 at <https://www.ecdc.europa.eu/en/covid-19/variants-concern>, 7 pages.
[No Author Listed], "Spikevax (mRNA-1273) EMA SmPC (summary of product characteristics)," Jan. 20, 2021, 137 pages.
[No Author Listed], "Statement by Moderna on Intellectual Property Matters during the COVID-19 Pandemic," Press Release, Moderna, Oct. 8, 2020, 1 page.

(56) References Cited

OTHER PUBLICATIONS

[No Author Listed], "Statement from NIH and BARDA on the FDA Emergency Use Authorization of the Moderna COVID-19 Vaccines," COVID.gov, Dec. 18, 2020, 3 pages.
[No Author Listed], "Two Pioneering RNA Scientists Win the 2021 Dr. Paul Janssen Award for Biomedical Research," Press Release, Johnson & Johnson, Sep. 28, 2021, 2 pages.
[No Author Listed], "U.S. FDA Grants Emergency Use Authorization for Novavax COVID-19 Vaccine, Adjuvanted for Individuals Aged 18 and Over," Press Release, Novavax, Jul. 13, 2022, 5 pages.
[No Author Listed], "Vaccine information fact sheet for recipients and caregivers about Comirnaty (COVID-19 Vaccine, mRNA) and the Pfizer-BioNTech COVID-19 vaccine to prevent coronavirus disease 2019 (COVID-19) for use in individuals 12 years of age and older," Pfizer-BioNTech, Jul. 8, 2022, 9 pages.
[No Author Listed], List of past and pending litigations, Prepared Oct. 24, 2023, 1 page.
[No Author Listed], Moderna Patents, retrieved on Jul. 1, 2024, retrieved from URL <https://www.modernatx.com/en-US/patents>, 1 page.
[No Author Listed], Pfizer-BioNTech COVID-19 Vaccine Information Sheet, Sep. 11, 2023, 3 pages.
[No Author Listed], Q2 2020 Earnings Call, BioNTech SE, Aug. 11, 2020, 26 pages.
[No Author Listed], Who Drug Information, 2021, 35(2), 341 pages.
[No Author Listed], Who Drug Information, 2021, 35(2):578-579.
Abbasi, "COVID-19 and mRNA Vaccines-First Large Test for a New Approach," JAMA. Sep. 22, 2020, 324(12):1125-1127.
Adney et al., "Efficacy of an Adjuvanted Middle East Respiratory Syndrome Coronavirus Spike Protein Vaccine in Dromedary Camels and Alpacas," Viruses., Mar. 2, 2019, 11(3):E212.
Agnihothram, "Summary Basis for Regulatory Action—STN 125752/0," Review Committee Chair, Jan. 30, 2022, 30 pages.
Agrawal et al., "Immunization with inactivated Middle East Respiratory Syndrome coronavirus vaccine leads to lung immunopathology on challenge with live virus," Hum Vaccin Immunother., Sep. 2016, 12(9):2351-2356.
Ahmad et al., "New multivalent cationic lipids reveal bell curve for transfection efficiency versus membrane charge density: lipid-DNA complexes for gene delivery," J Gene Med., Jun. 2005, 7(6):739-748.
Ahmed et al., "Biochemistry, Lipids," Statpearls Publishing, May 1, 2023, retrieved from URL <https://www.ncbi.nlm.nih.gov/books/NBK525952>, 5 pages.
Akinc et al., "A combinatorial library of lipid-like materials for delivery of RNAi therapeutics," Nat Biotechnol., May 2008, 26(5):561-569.
Akinc et al., "Targeted Delivery of RNAi Therapeutics With Endogenous and Exogenous Ligand-Based Mechanisms," Molecular Therapy, 2010, 18(7):1357-1364.
Al Kahlout et al., "Comparative Serological Study for the Prevalence of Anti-MERS Coronavirus Antibodies in High- and Low-Risk Groups in Qatar," J Immunol Res., Feb. 18, 2019, 2019(1):1386740.
Alberer et al., "Safety and immunogenicity of a mRNA rabies vaccine in healthy adults: an open-label, non-randomised, prospective, first-in-human phase 1 clinical trial," The Lancet, Jul. 25, 2017, 390(10101):1511-1520.
Aliprantis et al., "A phase 1, randomized, placebo-controlled study to evaluate the safety and immunogenicity of an mRNA-based RSV prefusion F protein vaccine in healthy younger and older adults," Hum Vaccin Immunother., May 4, 2021, 17(5):1248-1261.
Allen et al., "Liposomal drug delivery systems: From concept to clinical applications," Adv. Drug Deliv. Rev., 2013, 65:36-48.
*Alnylam Pharmaceuticals, Inc.*, Plaintiff, v. *Moderna, Inc. et al.*, Defendants, (D. Del. 22-cv-335-CFC) D.I. 1—Complaint for Patent Infringement, Mar. 17, 2022, 14 pages.
*Alnylam Pharmaceuticals, Inc.*, Plaintiff, v. *Moderna, Inc. et al.*, Defendants, (D. Del. 22-cv-335-CFC) D.I. 128—Final Judgement, Aug. 30, 2023, 2 pages.
*Alnylam Pharmaceuticals, Inc.*, Plaintiff, v. *Moderna, Inc. et al.*, Defendants, (D. Del. 22-cv-335-CFC) D.I. 130—Notice of Appeal to the U.S. Court of Appeals for the Federal Circuit, Aug. 31, 2023, 3 pages.
*Alnylam Pharmaceuticals, Inc.*, Plaintiff, v. *Moderna, Inc. et al.*, Defendants, (D. Del. 22-cv-335-CFC) D.I. 87—Answer to the Complaint, May 10, 2023, 44 pages.
*Alnylam Pharmaceuticals, Inc.*, Plaintiff, v. *Moderna, Inc. et al.*, Defendants, (D. Del. 23-cv-580-CFC) D.I. 1—Complaint for Patent Infringement, May 26, 2023, 28 pages.
*Alnylam Pharmaceuticals, Inc.*, Plaintiff, v. *Moderna, Inc. et al.*, Defendants, (D. Del. 23-cv-580-CFC) D.I. 12—Answer to the Complaint, Jul. 17, 2023, 37 pages.
*Alnylam Pharmaceuticals, Inc.*, Plaintiff, v. *Moderna, Inc.*, Defendant, (Fed. Circ. 2023-2357) D.I. 8—Docketing Statement, Sep. 21, 2023, 2 pages.
Altieri et al., "The influence of 4-thiouridine labeling on pre-mRNA splicing outcomes," PLoS One., Dec. 13, 2021, 16(12):e0257503, 13 pages.
Anderson et al., "Safety and Immunogenicity of SARS-CoV-2 mRNA-1273 Vaccine in Older Adults," New England Journal of Medicin, Sep. 29, 2020, 383(25):2427-38.
Andries et al., "$N^1$-methylpseudouridine-incorporated mRNA outperforms pseudouridine-incorporated mRNA by providing enhanced protein expression and reduced immunogenicity in mammalian cell lines and mice," Journal of Controlled Release, Nov. 10, 2015, 217:337-44.
*Arbutus BioPharma Corp. et al.*, Plaintiffs, v. *Moderna, Inc. et al.*, Defendants, (D. Del. 22-cv-252-MSG) D.I. 1—Complaint for Patent Infringement, Feb. 28, 2022, 51 pages.
*Arbutus BioPharma Corp. et al.*, Plaintiffs, v. *Moderna, Inc. et al.*, Defendants, (D. Del. 22-cv-252-MSG) D.I. 31—District Court Memorandum, Nov. 2, 2022, 16 pages.
*Arbutus BioPharma Corp. et al.*, Plaintiffs, v. *Moderna, Inc. et al.*, Defendants, (D. Del. 22-cv-252-MSG) D.I. 35—Answer to the Complaint, Nov. 30, 2022, 83 pages.
*Arbutus BioPharma Corp. et al.*, Plaintiffs, v. *Moderna, Inc. et al.*, Defendants, (D. Del. 22-cv-252-MSG) D.I. 64—District Court Memorandum, Mar. 10, 2023, 4 pages.
Archer, "Induction of a T-cell specific antigen on bone marrow lymphocytes with thymus RNA," Immunology, Jan. 1978, 34(1):123-9.
Arthur, "Pfizer predicts $54bn in 2022 revenue from Comirnaty and Paxlovid," BioPharmaReporter, Feb. 8, 2022, retrieved from Internet Archive: Wayback Machine URL <https://web.archive.org/web/20220208163637/https://www.biopharma-reporter.com/Article/2022/02/08/Pfizer-predicts-54bn-in-2022-sales-from-Comirnaty-and-Paxlovid>, 3 pages.
Ashley et al., "Bone Marrow-generated Dendritic Cells Pulsed with Tumor Extracts or Tumor RNA Induce Antitumor Immunity against Central Nervous System Tumors," J Exp Med., Oct. 6, 1997, 186(7):1177-82.
Atkins et al., "The molecular pathogenesis of Semliki Forest virus: a model virus made useful?," Journal of General Virology, Sep. 1999, 80(9):2287-2297.
Atsmon et al., "Safety and Immunogenicity of Multimeric-001—a Novel Universal Influenza Vaccine," J Clin Immunol., Jun. 2012, 32(3):595-603.
Austin et al., "Split-Dose Administration Enhances Immune Responses Elicited by a mRNA/Lipid Nanoparticle Vaccine Expressing Respiratory Syncytial Virus F Protein," Mol Pharm., Jan. 2, 2023, 20(1):279-289.
Baden et al., "Efficacy and Safety of the mRNA-1273 SARS-CoV-2 Vaccine," New England Journal of Medicine, Feb. 4, 2021, 384(5):403-16.
Bahl et al., "Preclinical and Clinical Demonstration of Immunogenicity by mRNA Vaccines against H10N8 and H7N9 Influenza Viruses," Molecular Therapy, Jun. 7, 2017, 25(6):1316-27.
Bancel, "Our Global Commitment to Vaccine Access," Moderna, Oct. 8, 2021, 1 page.
Bangham et al., "Diffusion of univalent ions across the lamellae of swollen phospholipids," J Mol Biol., Aug. 1965, 13(1):238-52.

(56) References Cited

OTHER PUBLICATIONS

Barbier et al., "The clinical progress of mRNA vaccines and immunotherapies," Nature Biotechnology, Jun. 2022, 40(6):840-54.
Bear, "Gene expression and regulation," Lewin's Cells, 2011, Chapter 4:105-68.
Bennett et al., "Cholesterol Enhances Cationic Liposome Mediated DNA Transfection of Human Respiratory Epithelial Cells" Biosci Rep., Feb. 1995, 15(1):47-53.
Bermudez, "We decided not to enforce our patent during the pandemic," Noubar Afeyan, co-founder of Moderna, BBC News World, May 6, 2021, 11 pages.
Bettinger et al., "Peptide-mediated RNA delivery: a novel approach for enhanced transfection of primary and post-mitotic cells," Nucleic Acids Res., Sep. 15, 2001, 29(18):3882-91.
Bharali et al., "Nanoparticles and cancer therapy: a concise review with emphasis on dendrimers," Int J Nanomedicine., 2009, 4:1-7.
Bhavana et al., "COVID-19: Pathophysiology, treatment options, nanotechnology approaches, and research agenda to combating the SARS-CoV2 pandemic," Life Sciences, Nov. 15, 2020, 261:118336.
Bisht et al., "Severe acute respiratory syndrome coronavirus spike protein expressed by attenuated vaccinia virus protectively immunizes mice," PNAS, Apr. 27, 2004, 101(17):6641-6646.
Bogers et al., "Potent immune responses in rhesus macaques induced by nonviral delivery of a self-amplifying RNA vaccine expressing HIV type 1 envelope with a cationic nanoemulsion," J Infect Dis., Mar. 15, 2015, 211(6):947-955.
Bok et al., "Accelerated COVID-19 vaccine development: milestones, lessons, and prospects," Immunity, Aug. 10, 2021, 54(8):1636-1651.
Bonehill et al., "Single-step antigen loading and activation of dendritic cells by mRNA electroporation for the purpose of therapeutic vaccination in melanoma patients," Clin Cancer Res., May 2009, 15(10):3366-3375.
Bose et al., "Role of nucleolin in human parainfluenza virus type 3 infection of human lung epithelial cells," J Viral., Aug. 2004, 78(15):8146-8158.
Bourla, "An Open Letter from Pfizer Chairman and CEO to Colleagues," Pfizer, May 7, 2021, 3 pages.
Brito et al., "A Cationic Nanoemulsion for the Delivery of Next-generation RNA Vaccines," The American Society of Gene & Cell Therapy, Dec. 2014, 22(12):2118-2129.
Bruxvoort et al., "Real-world effectiveness of the mRNA-1273 vaccine against COVID-19: Interim results from a prospective observational cohort study," Lancet Reg Health Am., Feb. 2022, 6:100134.
Buchholz et al., "Contributions of the structural proteins of severe acute respiratory syndrome coronavirus to protective immunity," PNAS, Jun. 29, 2004, 101(26):9804-9809.
Buschmann et al., "Chitosans for Delivery of Nucleic Acids," Advanced Drug Delivery Reviews, Aug. 2013, 65(9):1234-1270.
Buschmann et al., "Nanomaterial Delivery Systems for mRNA Vaccines," Vaccines (Basel), Jan. 19, 2021, 9(1):65, 30 pages.
Byoung-Shik et al., "Intranasal immunization with plasmid DNA encoding spike protein of SARS-coronavirus/polyethylenimine nanoparticles elicits antigen-specific humoral and cellular immune responses," BMC Immunol., Dec. 31, 2010, 11:65, 9 pages.
Callaway, "Omicron likely to weaken COVID vaccine protection," Nature, Dec. 2021, 600(7889):367-368.
Carvalho et al., "The first 12 months of COVID-19: a timeline of immunological insights," Nat Rev Immunol., Apr. 2021, 21(4):245-256.
Cassimeris et al., "Lewin's Cells, Second Edition" 2011, Jones and Bartlett Publishers, 109 Pages.
Cele et al., "SARS-CoV-2 Omicron has extensive but incomplete escape of Pfizer BNT162b2 elicited neutralization and requires ACE2 for infection," medRxiv, 2021, 15 pages.
Cerutti et al., "Potent SARS-CoV-2 neutralizing antibodies directed against spike N-terminal domain target a single supersite," Cell Host Microbe, May 12, 2021, 29(5):819-833.
Chalkias et al., "Safety, immunogenicity and antibody persistence of a bivalent Beta-containing booster vaccine against COVID-19: a phase 2/3 trial," Nature Medicine, Oct. 6, 2022, 28:2388-2397.
Chan et al., "Genomic characterization of the 2019 novel human-pathogenic coronavirus isolated from a patient with atypical pneumonia after visiting Wuhan," Emerg Microbes Infect., Jan. 28, 2020, 9(1):221-236.
Chang et al., "Recent Insights into the Developments of Therapeutics Against Coronavirus Disease by Targeting N Protein," Drug Discovery Today, Apr. 2016, 21(4):562-572.
Chaudhary et al., "mRNA vaccines for infectious diseases: principles, delivery and clinical translation," Nature Reviews Drug Discovery, November 20201, 20(11):817-838.
Chen et al., "A novel neutralizing monoclonal antibody targeting the N-terminal domain of the MERS-CoV spike protein," Emerg Microbes Infect. May 24, 2017, 6(5):e37; Erratum in: Emerg Microbes Infect., Jun. 28, 2017, 6(6):e60.
Chen et al., "Emerging coronaviruses: Genome structure, replication, and pathogenesis," J Med Viral., Apr. 2020, 92(4):418-423; Erratum in: J Med Viral., Oct. 2020, 92(10):2249.
Chen et al., "Vaccine design of hemagglutinin glycoprotein against influenza," Trends Biotechnol., Sep. 2011, 29(9):426-434.
Cheng et al., "Selective ORgan Targeting (SORT) nanoparticles for tissue specific mRNA delivery and CRISPR/Cas gene editing," Nat Nanotechnol., Apr. 2020, 15(4):313-320.
Cherry et al., "SARS: The First Pandemic of the 21st Century," Pediatric Research, 2004, 56(1):1-5.
Chi et al., "A neutralizing human antibody binds to the N-terminal domain of the Spike protein of SARS-Co V-2," Science, Aug. 7, 2020, 369(6504):650-655.
Choi et al., "2'-O-methylation in mRNA disrupts tRNA decoding during translation elongation," Nat Struct Mol Biol., Mar. 2018, 25(3):208-216.
Choi et al., "Safety and immunogenicity of SARS-Co V-2 variant mRNA vaccine boosters in healthy adults: an interim analysis," Nat Med., Nov. 2021, 27(11):2025-2031.
Choi et al., "Serum Neutralizing Activity of mRNA-1273 against SARS-Co V-2 Variants," Journal of Virology, Nov. 9, 2021, 95(23):e0131321.
Chu et al., "Immune Memory Response After a Booster Injection of mRNA-1273 for Severe Acute Respiratory Syndrome Coronavirus-2 (SARS-Co V-2)," MedRxiv, Oct. 2021, 52 pages.
Clancy et al., "Translation: DNA to mRNA to Protein," Nature Education, 2008, 1(1):101, 7 pages.
Cobb et al., "Who discovered messenger RNA?," Curr Biol., Jun. 29, 2015, 25(13):R526-32.
Coelho et al., "Safety and Efficacy of RNAi Therapy for Transthyretin Amyloidosis," New Engl J Med., Aug. 29, 2013, 369(9):819-829.
Cohen, "New crop of mRNA vaccines aim for accessibility," Science, Apr. 7, 2022, 376(6589):120-121.
Cohen, "Scientists are moving at record speed to create new coronavirus vaccines—but they may come too late," Science Insider, Jan. 27, 2020, 7 pages.
Cohen, "Scientists question Moderna invention claim in COVID-19 vaccine dispute," Science Insider, Aug. 29, 2022, 3 pages.
Comirnaty, "Highlights of Prescribing Information," FDA Label, Jul. 2022, 27 pages.
Comirnaty, "Highlights of Prescribing Information," FDA Label, Oct. 2023, 36 pages.
Comirnaty, "Highlights of Prescribing Information," FDA Label, Oct. 2024, 37 pages.
Conry et al., "Characterization of a messenger RNA polynucleotide vaccine vector," Cancer Res., Apr. 1995, 55(7):1397-1400.
Cooper et al., "Chapters 1, 7, and 8," in The Cell: A Molecular Approach, 5th Ed., 2009, 163 pages.
Corbett et al., "Evaluation of the mRNA-1273 Vaccine against SARS-CoV-2 in Nonhuman Primates," N Engl J Med., Oct. 15, 2020; 383(16):1544-55.
Corbett et al., "SARS-CoV-2 mRNA vaccine design enabled by prototype pathogen preparedness," Nature, Oct. 2020, 586(7830):567-571.
Cox et al., "FluBlok, a recombinant hemagglutinin influenza vaccine," Influenza Other Respir Viruses., Nov. 2008, 2(6):211-219.

(56) References Cited

OTHER PUBLICATIONS

Cross, "Without these lipid shells, there would be no mRNA vaccines for COVID-19," Chem Eng News., Mar. 6, 2021, 99(8), 8 pages.
Cullis et al., "Lipid Nanoparticle Systems for Enabling Gene Therapies," Molecular Therapy, Jul. 5, 2017, 25(7):1467-1475.
Curriculum Vitae of Daniel O. Griffin, M.D., Ph.D., Aug. 23, 2023, 22 pages.
Curriculum Vitae of Deborah Fuller (Deposition Exhibit), filed in IPR2023-01359 on Aug. 30, 2024, 2 pages.
Curriculum Vitae of James J. Moon, Ph.D., filed in IPR2023-01359 on Aug. 28, 2023, 28 pages.
Dahlman et al., "In vivo endothelial siRNA delivery using polymeric nanoparticles with low molecular weight," Nature Nanotechnology, May 11, 2014, 9(8):648-655.
Dai et al., "Viral targets for vaccines against COVID-19," Nature Reviews Immunology, Feb. 2021, 21(2):73-82.
De Groot et al., "Part II—The Positive Sense Single Stranded RNA Viruses—Family Coronaviridae," Virus Taxonomy: Ninth Report of the International Committee on Taxonomy of Viruses, 2012, pp. 806-828.
Declaration of Amy K. Wigmore in IPR2023-01358 dated Apr. 16, 2024, 5 pages.
Declaration of Amy K. Wigmore in IPR2023-01359 dated Apr. 16, 2024, 5 pages.
Declaration of Andrew J. Danford in IPR2023-01358 dated Jul. 1, 2024, 5 pages.
Declaration of Daniel O. Griffin, M.D., Ph.D. in IPR2023-01358 dated Aug. 27, 2023, 99 pages.
Declaration of Daniel O. Griffin, M.D., Ph.D. in IPR2023-01359 dated Aug. 27, 2023, 119 pages.
Declaration of Deborah H. Fuller, Ph.D., in IPR2023-01358 dated May 30, 2024 (public redacted version of Ex. 2199), 517 pages.
Declaration of Deborah H. Fuller, Ph.D., in IPR2023-01359 dated May 30, 2024. (public redacted version of Ex. 2199), 523 pages.
Declaration of Douglas L. Sawyer in IPR2023-01358 dated Jul. 17, 2024, 3 pages.
Declaration of Douglas L. Sawyer in IPR2023-01359 dated Jul. 17, 2024, 3 pages.
Declaration of Gabrielle Landes in IPR2023-01358 dated Apr. 25, 2024, 3 pages.
Declaration of Gabrielle Landes in IPR2023-01359 dated Apr. 25, 2024, 3 pages.
Declaration of James E. Malackowski in IPR2023-01358 dated May 29, 2024, 84 pages.
Declaration of James E. Malackowski in IPR2023-01359 dated May 29, 2024, 84 pages.
Declaration of James J. Moon, Ph.D. in IPR2023-01358 dated Apr. 25, 2023, 64 pages.
Declaration of James J. Moon, Ph.D. in IPR2023-01359 dated Apr. 25, 2023, 57 pages.
Declaration of Joshua L. Stern in IPR2023-01358 dated Apr. 17, 2024, 4 pages.
Declaration of Kathryn S. Kayali in IPR2023-01358 dated Apr. 16, 2024, 5 pages.
Declaration of Kathryn S. Kayali in IPR2023-01359 dated Apr. 26, 2024, 5 pages.
Declaration of Kevin S. Prussia in IPR2023-01358 dated Apr. 17, 2024, 4 pages.
Declaration of Kevin S. Prussia in IPR2023-01359 dated Apr. 17, 2024, 4 pages.
Declaration of L. Ross Pierce in IPR2023-01358 dated Aug. 30, 2024 (Redacted public version), 54 pages.
Declaration of L. Ross Pierce in IPR2023-01359 dated Aug. 30, 2024 (Redacted public version), 54 pages.
Declaration of M. Ryan Meuth in IPR2023-01358 dated Apr. 25, 2024, 3 pages.
Declaration of M. Ryan Meuth in IPR2023-01359 dated Apr. 25, 2024, 3 pages.
Declaration of Philp Krause, M.D., in IPR2023-01358 dated May 28, 2024 (public redacted version of Ex. 2200), 330 pages.
Declaration of Philp Krause, M.D., in IPR2023-01359 dated May 28, 2024 (public redacted version of Ex. 2200), 330 pages.
Declaration of Thomas H. L. Selby in IPR2023-01359 dated Apr. 26, 2024, 5 pages.
Declaration of W. Christopher Bakewell in IPR2023-01358 dated Aug. 30, 2024, 110 pages.
Declaration of W. Christopher Bakewell in IPR2023-01359 dated Aug. 30, 2024, 110 pages.
Declaration of Warren C.W. Chan, Ph.D. in IPR2023-01358 dated May 29, 2024, 136 pages.
Declaration of Warren C.W. Chan, Ph.D. in IPR2023-01359 dated May 29, 2024, 136 pages.
Deering et al., "Nucleic acid vaccines: prospects for non-viral delivery of mRNA vaccines," Expert Opin Drug Deliv., Jun. 2014 Jun. 11(6):885-99.
Defendants' Supplemental Patent-Related Disclosures, Exhibit C—Invalidity Contentions of U.S. Pat. No. 10,702,600, dated Jun. 27, 2023 (Excerpts), 100 pages.
Defendants' Patent-Related Disclosures, Exhibit C—Invalidity Contentions of U.S. Pat. No. 10,702,600, dated Mar. 31, 2023 (Excerpts), 5 pages.
Defendants' Patent-Related Disclosures, Exhibit D—Invalidity Contentions of U.S. Pat. No. No. 10,933,127, dated Mar. 31, 2023 (Excerpts), 5 pages.
Defendants' Supplemental Patent-Related Disclosures, Exhibit D—Invalidity Contentions of U.S. Pat. No. 10,933,127, Jun. 27, 2023 (Excerpts), 110 pages.
DeFrancesco, "The 'anti-hype' vaccine," Nat Biotechnol., Mar. 2017, 35(3):193-197.
Dejnirattisai et al., "Reduced neutralisation of SARS-CoV-2 omicron B.1.1.529 variant by post-immunisation serum," Lancet, Jan. 15, 2022, 399(10321):234-236.
Del Pozo-Rodríguez et al., "Lipid Nanoparticles as Vehicles for Macromolecules: Nucleic Acids and Peptides," Recent Pat Drug Deliv Formul., Sep. 2011, 5(3):214-226.
Deming et al, "Vaccine Efficacy in Senescent Mice Challenged with Recombinant SARS-CoV Bearing Epidemic and Zoonotic Spike Variants," PLoS Medicine, Dec. 2006, 3(12):e525, 17 pages.
Deposition of Daniel O. Griffin, M.D., Ph.D. in *BioNTech SE and Pfizer Inc.* v. *Moderna TX, Inc.*, in IPR2023-01358 and IPR2023-01359, May 22, 2024, 317 pages.
Deposition of Daniel O. Griffin, M.D., Ph.D. in *BioNTech SE and Pfizer Inc.* v. *Moderna TX, Inc.*, in IPR2023-01358 and IPR2023-01359, Sep. 20, 2024, 77 pages.
Deposition of Deborah Fuller, Ph.D. in *BioNTech SE and Pfizer Inc.* v. *Moderna TX, Inc.*, in IPR2023-01358 and IPR2023-01359, Aug. 2, 2024, 130 pages.
Deposition of James E. Malackowski in *BioNTech SE and Pfizer Inc.* v. *Moderna TX, Inc.*, in IPR2023-01358 and IPR2023-01359, Jul. 22, 2024, and Errata Sheet dated Aug. 27, 2024, 65 pages.
Deposition of James J. Moon, Ph.D. in *BioNTech SE and Pfizer Inc.* v. *Moderna TX, Inc.*, in IPR2023-01358 and IPR2023-01359, May 10, 2024, 190 pages.
Deposition of James J. Moon, Ph.D. in *BioNTech SE and Pfizer Inc.* v. *Moderna TX, Inc.*, in IPR2023-01358 and IPR2023-01359, Sep. 13, 2024, 51 pages.
Deposition of L. Ross Pierce, M.D., in *BioNTech SE and Pfizer Inc.* v. *Moderna TX, Inc.*, in IPR2023-01358 and IPR2023-01359, Oct. 4, 2024 (redacted version of Ex. 2256), 56 pages.
Deposition of Philip Krause, M.D. in *BioNTech SE and Pfizer Inc.* v. *Moderna TX, Inc.*, in IPR2023-01358 and IPR2023-01359, Aug. 14, 2024 (redacted), 158 pages.
Deposition of W. Christopher Bakewell in *BioNTech SE and Pfizer Inc.* v. *Moderna TX, Inc.*, in IPR2023-01358 and IPR2023-01359, Oct. 3, 2024, 64 pages.
Deposition of Warren C.W. Chan Ph.D. in *BioNTech SE and Pfizer Inc.* v. *Moderna TX, Inc.*, in IPR2023-01358 and IPR2023-01359, Jul. 30, 2024, 375 pages.
Diken et al., "Current Developments in Actively Personalized Cancer Vaccination with a Focus on RNA as the Drug Format," Prog Tumor Res., Sep. 4, 2015, 42:44-54.

(56) References Cited

OTHER PUBLICATIONS

Dimitriadis et al., "Translation of rabbit globin mRNA introduced by liposomes into mouse lymphocytes," Nature, Aug. 31, 1978, 274(5674):923-924.
Division of Microbiology and Infectious Diseases (DMID) Protocol No. 20-0003—mRMA-1273, Version 1.0 (Excerpts—Exhibit No. 2150 in IPR2023-01359), dated Feb. 14, 2020, 14 pages.
Division of Microbiology and Infectious Diseases (DMID) Protocol No. 20-0003—mRMA-1273, Version 3.0 (Excerpts—Exhibit No. 2149 in IPR2023-01358), dated Mar. 30, 2020, 13 pages.
Division of Microbiology and Infectious Diseases (DMID) Protocol No. 20-0003—mRMA-1273, Version 4.0 (Excerpts—Exhibit No. 2151 in IPR2023-01359), dated May 20, 2020, 16 pages.
Division of Microbiology and Infectious Diseases (DMID) Protocol, "Phase I, Open-Label, Dose-Ranging Study of the Safety and Immunogenicity of 2019-nCoV Vaccine (mRNA-1273) in Healthy Adults (Excerpts—Exhibit No. 2053 in IPR2023-01359)," dated Mar. 30, 2020, 8 pages.
Division of Microbiology and Infectious Diseases (DMID) Protocol, "Phase I, Open-Label, Dose-Ranging Study of the Safety and Immunogenicity of 2019-nCoV Vaccine (mRNA-1273) in Healthy Adults (Excerpts—Exhibit No. 2054 in IPR2023-01359)," dated Feb. 14, 2020, 10 pages.
Division of Microbiology and Infectious Diseases (DMID) Protocol, "Phase I, Open-Label, Dose-Ranging Study of the Safety and Immunogenicity of 2019-nCoV Vaccine (mRNA-1273) in Healthy Adults (Excerpts—Exhibit No. 2055 in IPR2023-01359)," dated May 20, 2020, 12 pages.
Dolgin, "Business: The billion-dollar biotech," Nature, Jun. 4, 2015, 522(7554):26-28.
Dormitzer, "Synthetic Vaccinology at Novartis," Presentation at The National Academy of Sciences Forum on Synthetic Biology, The Keck Center, Washington, D.C., Oct. 21, 2013, 12 pages.
Drummond et al., "The Evolutionary Consequences of Erroneous Protein Synthesis," Nature Reviews Genetics, Oct. 2009, 10(10:715-724.
Du et al., "Recombinant adeno-associated virus expressing the receptor-binding domain of severe acute respiratory syndrome coronavirus S protein elicits neutralizing antibodies: Implication for developing SARS vaccines," Virology, Sep. 15, 2006, 353(1):6-16.
Du et al., "The spike protein of SARS-CoV—a target for vaccine and therapeutic development," Nat Rev Microbial., Mar. 2009, 7(3):226-36.
Dufourc, "Sterols and membrane dynamics," J Chem Biol., Nov. 2008, 1(1-4):63-77.
El Sahly et al., "Efficacy of the mRNA-1273 SARS-CoV-2 Vaccine at Completion of Blinded Phase," New England Journal of Medicine, Nov. 4, 2021, 385(19):1774-1785.
Ellebedy et al., "Influenza Vaccines," Vaccine, Nov. 5, 2009, 27(Suppl 4):D65-D68.
Engler et al., "Half- vs Full-Dose Trivalent Inactivated Influenza Vaccine (2004-2005)—Age, Dose, and Sex Effects on Immune Responses," Arch Intern Med., Dec. 8, 2008, 168(22):2405-2414.
Erasmus et al., "A Nanostructured Lipid Carrier for Delivery of a Replicating Viral RNA Provides Single, Low-Dose Protection against Zika," Mol Ther., Oct. 3, 2018, 26(10):2507-2522.
Erasmus et al., "An Alphavirus-derived replicon RNA vaccine induces SARS-CoV-2 neutralizing antibody and T cell responses in mice and nonhuman primates," Science Translational Medicine, Aug. 5, 2020, 12(555):eabc9396, 11 pages.
Ernsting et al., "Factors Controlling the Pharmacokinetics, Biodistribution and Intratumoral Penetration of Nanoparticles," J. Control Release., Dec. 28, 2013, 172(3):782-794.
Escriou et al., "Protection from SARS coronavirus conferred by live measles vaccine expressing the spike glycoprotein," Virology, Mar. 2014, 452-453:32-41.
European Medicines Agency, "Assessment Report for COVID-19 Vaccine Moderna," dated Mar. 11, 2021, 169 pages.
European Medicines Agency, "Assessment Report for Spikevax," dated Sep. 14, 2023, 48 pages.
European Medicines Agency, "Nuvaxovid," retrieved on Jul. 11, 2024, retrieved from URL <https://www.ema.europa.eu/en/medicines/human/EPAR/nuvaxovid>, 12 pages.
Fauquet, "Taxonomy, Classification and Nomenclature of Viruses," Encyclopedia of Virology, Third Ed., 2008, pp. 9-23.
FDA, "E6(R2) Good Clinical Practice: Integrated Addendum to ICH E6(R1—Guidance for Industry," U.S. Department of Health and Human Services, Mar. 2018, 68 pages.
FDA, "Guidance for Industry E6 Good Clinical Practice: Consolidated Guidance," U.S. Department of Health and Human Services, Apr. 1996, 63 pages.
Felgner et al., "Lipofection: A highly efficient, lipid-mediated DNA-transfection procedure," PNAS, Nov. 1987, 84(21):7413-7417.
Final Written Decision in *BioNTech SE and Pfizer Inc.* v. *Moderna TX, Inc.*, IPR2023-01358, dated Mar. 5, 2025, 124 pages.
Final Written Decision in *BioNTech SE and Pfizer Inc.* v. *Moderna TX, Inc.*, IPR2023-01358, dated Mar. 5, 2025, 133 pages.
Fleeton et al., "Self-replicative RNA vaccines elicit protection against influenza A virus, respiratory syncytial virus, and a tickborne encephalitis virus," J Infect Dis., May 2001, 183(9):1395-1398.
Fujimori, "How this Once Little-Known Molecule is Disrupting Medicine," Pfizer, Jun. 2022, 7 pages.
Fuller, "How mRNA and DNA vaccines could soon treat cancers, HIV, autoimmune disorders and genetic diseases," The Conversation, Jan. 24, 2022, 5 pages.
Furuichi et al., "Viral and cellular mRNA capping: past and prospects," Adv Virus Res., 2000,55:135-84.
Furuichi, "Caps on Eukaryotic mRNAs," eLS, John Wiley & Sons, Jul. 2014, pp. 1-12.
Gallie, "The cap and poly (A) tail function synergistically to regulate mRNA translational efficiency," Genes Dev., Nov. 1991, 5(11):2108-16.
Gandhi et al., "Immunization of HIV-1-Infected Persons with Autologous Dendritic Cells Transfected with mRNA Encoding HIV-1 Gag and Nef: Results of a Randomized, Placebo-Controlled Clinical Trial," JAIDS Journal of Acquired Immune Deficiency Syndromes, Mar. 2016, 71(3):246-253.
Gao et al., "Nonviral Gene Delivery: What We Know and What Is Next," The AAPS Journal, Mar. 2007, 9(1):E92-E104.
Garde et al., "The story of mRNA: How a once-dismissed idea became a leading technology in the Covid vaccine race," STAT News, Nov. 10, 2020, 23 pages.
Geall et al., "Nonviral delivery of self-amplifying RNA vaccines," PNAS, Sep. 4, 2012, 109(36):14604-14609.
Geall et al., "RNA: the new revolution in nucleic acid vaccines," Seminars in immunology, Apr. 2013, 25(2):152-9.
Geall et al., "Using self-amplifying mRNA vaccines to facilitate a rapid response to pandemic influenza," Eur Pharm Rev., Jul. 3, 2014, 5 pages.
GenBank Accession No. 045512, "Severe acute respiratory syndrome coronavirus 2 isolate Wuhan-Hu-1, complete genome," Jul. 18, 2020, 15 pages.
GenBank Accession No. AGN52936.1, "spike glycoprotein [Middle East respiratory syndrome coronavirus]," Jun. 10, 2013, 3 pages.
GenBank Accession No. AHX22069, "fusion glycoprotein F0 [Human respirovirus 3]," May 14, 2014, 2 pages.
Genbank Accession No. MN908947.3, "Severe acute respiratory syndrome coronavirus 2 isolate Wuhan-Hu-1, complete genome," Jan. 13, 2020, 15 pages.
Geneseq Accession No. BCI53556, First entry: Jan. 14, 2016, 2 pages.
Geneseq Accession No. BGP67180, First entry: Sep. 19, 2019, 2 pages.
Gilboa et al., "Cancer immunotherapy with mRNA-transfected dendritic cells," Immunol Rev., Jun. 2004, 199:251-263.
Gilleron et al., "Image-Based Analysis of Lipid Nanoparticle-Mediated siRNA Delivery, Intracellular Trafficking and Endosomal Escape," Nature Biotech., Jul. 2013, 31(7):638-646.
Ginn et al., "Gene Therapy Clinical Trials Worldwide to 2017: An Update," The Journal of Gene Medicine, May 2018, 20(5):e3015, 16 pages.

(56) References Cited

OTHER PUBLICATIONS

GISAID Accession ID: EPI ISL_6640919, "hCoV-19/Botswana/R40B58_BHP_3321001245/2021," Submission Date: Nov. 23, 2021, 15 pages.
Glenn et al., "Safety and immunogenicity of a Sf9 insect cell-derived respiratory syncytial virus fusion protein nanoparticle vaccine," Vaccine, Jan. 7, 2013, 31(3):524-532.
Gorbalenya et al, "The species Severe acute respiratory syndrome related coronavirus: classifying 2019-nCoV and naming it SARS-CoV-2," Nature Microbiology, Mar. 2020, 5(4):536-544.
Graham et al., "Novel Vaccine Technologies: Essential Components of an Adequate Response to Emerging Viral Diseases," JAMA, Apr. 10, 2018, 319(14):1431-1432.
Greer et al., "Long-term protection in hamsters against human parainfluenza virus type 3 following mucosal or combinations of mucosal and systemic immunizations with chimeric alphavirus-based replicon particles," Scand J Immunol., Dec. 2007, 66(6):645-653.
Griffin et al., "A small CD11b+ human B1 cell subpopulation stimulates T cells and is expanded in lupus," Journal of Experimental Medicine, Dec. 19, 2011, 208(13):2591-2598.
Griffin et al., "Co-infection with Hepatitis C Virus Increases Mortality in HIV-1 Infected Patients Through Increased Liver-Related Deaths Rather Than By Increasing Malignancy Related Deaths," J. Aids and Clin. Res., 2016, 7(4): 3 pages.
Griffin et al., "Cytokine storm of a different flavour: the different cytokine signature of SARS-CoV-2 the cause of COVID-19 from the original SARS outbreak," Journal of Global Antimicrobial Resistance, Mar. 2021, 24:90-92.
Griffin et al., "Human B1 cells in umbilical cord and adult peripheral blood express the novel phenotype CD20+ CD27+ CD43+ CD70−," Journal of Experimental Medicine., Jan. 2011, 208(1):67-80.
Guevara et al., "Advances in Lipid Nanoparticles for mRNA-Based Cancer Immunotherapy," Front Chem., Oct. 23, 2020, 8:589959, 17 pages.
Guo et al., "An Engineered Receptor-Binding Domain Improves the Immunogenicity of Multivalent SARS-CoV-2 Vaccines," mBio, May-Jun. 2021, 12(3):e00930-21.
Guo et al., "Identification of a New Region of SARS-CoV S Protein Critical for Viral Entry," J. Mol. Biol., Dec. 11, 2009, 394(4):600-605.
Guo et al., "Nanoparticles escaping RES and endosome: Challenges for siRNA delivery for cancer therapy," J Nanomat., Jan. 2011, 742895:1-12.
Hartmann et al., "Part I RNA Synthesis and Detection," Handbook of RNA Biochemistry, Second Edition, 2014, pp. 1-27.
Hashiba et al., "The use of design of experiments with multiple responses to determine optimal formulations for in vivo hepatic mRNA delivery," J Control Release., Nov. 10, 2020, 327:467-476.
Hattinger et al., "Prophylactic mRNA Vaccination against Allergy Confers Long- Term Memory Responses and Persistent Protection in Mice," Journal of Immunology Research, 2015, 2015(1):797421, 12 pages.
Hatziantoniou et al., "Anaphylactic reactions to mRNA COVID-19 vaccines: A call for further study," Vaccine, May 6, 2021, 39(19):2605-2607.
He et al., "Receptor-binding domain of SARS-Co V spike protein induces highly potent neutralizing antibodies: implication for developing subunit vaccine," Biochem Biophys Res Commun., Nov. 12, 2004, 324(2):773-81.
He et al., "Single-component, self-assembling, protein nanoparticles presenting the receptor binding domain and stabilized spike as SARS-CoV-2 vaccine candidates," Sci Adv., Mar. 19, 2021, 7(12):eabf1591, 17 pages.
Hecker et al., "Non-Viral DNA and mRNA Gene Delivery to the CNS Pre-Operatively for Neuroprotection and Following Neurotrauma—681," Molecular Therapy, May 2004, 9(S1):S258.
Heinz et al., "Distinguishing features of current COVID-19 vaccines: knowns and unknowns of antigen presentation and modes of action," NPJ Vaccines, Aug. 16, 2021, 6(1):104.
Heiser et al., "Induction of Polyclonal Prostate Cancer-Specific CTL Using Dendritic Cells Transfected with Amplified Tumor RNA1," J Immunol., Mar. 2001, 166(5):2953-2960.
Hekele et al., "Rapidly produced SAM? vaccine against H7N9 influenza is immunogenic in mice," Emerging Microbes & Infections, Jan. 2013, 2:1-7.
Hemmer et al., "Minimal peptide length requirements for CD4+ T cell clones—implications for molecular mimicry and T cell survival," Int Immunol., Mar. 2000, 12(3):375-383.
Heyes et al., "Cationic lipid saturation influences intracellular delivery of encapsulated nucleic acids," Journal of Controlled Release, Oct. 2005, 107(2):276-287.
Hoernes et al., "Nucleotide modifications within bacterial messenger RNAs regulate their translation and are able to rewire the genetic code," Nucleic Acids Res., Jan. 29, 2016, 44(2):852-862.
Hoerr et al., "In vivo application of RNA leads to induction of specific cytotoxic T lymphocytes and antibodies," European Journal of Immunology, Jan. 2000, 30:1-7.
Hoerr et al., "Stabilized Messenger RNA (RNActiveTM) as a Tool for Innovative Gene Delivery—Abstract No. OP 57," Tissue Engineering, Apr. 2007, 13(4): 865-925.
Hoerr, "More than a messenger: A new class of drugs-mRNA-based therapeutics," Genetic Engineering & Biotechnology News, Jun. 18, 2013, retrieved on Mar. 25, 2016, retrieved from URL <http://www.genengnews.com/gen-articles/more-than-a-messenger-a-new-class-of-drugs-mrna-based-therapeutics/4916/>, 3 pages.
Holtkamp et al., "Modification of antigen-encoding RNA increases stability, translational efficacy, and T-cell stimulatory capacity of dendritic cells," Gene Therapy, Dec. 2006, 108(13):4009-4017.
Hope et al., "Reduction of Liposome Size and Preparation of Unilamellar Vesicles by Extrusion Techniques," Liposome Technology, 1993, Chapter 8, pp. 123-139.
Horr, "RNA vaccine for the induction of specific cytotoxic T lymphocytes (CTL) and antibodies," Dissertation for the degree of Doctor of Natural Sciences, Eberhard Karls University of Tübingen, 1999, 138 pages (English translation).
Hou et al., "Lipid nanoparticles for mRNA delivery," Nature Reviews Materials, Dec. 2012, 6(12):1078-1094.
Houser et al., "Influenza Vaccines: Challenges and Solutions," Cell Host Microbe., Mar. 11, 2015, 17(3):295-300.
Hsieh et al., "Structure-based design of prefusion-stabilized SARS-Co V-2 spikes," Science, Sep. 18, 2020, 369(6510):1501-1505.
Hu et al., "Cytosolic delivery mediated via electrostatic surface binding of protein, virus, or siRNA cargos to pH-responsive core-shell gel particles," Biomacromolecules, Apr. 2009, 10(4):756-765.
Huang et al., "Asymmetric 1-alkyl-2-acyl phosphatidylcholine: a helper lipid for enhanced non-viral gene delivery," Int J Pharm., May 2012, 427(1):64-70.
Huang et al., "Clinical features of patients infected with 2019 novel coronavirus in Wuhan, China," Lancet., Jan. 24, 2020, 395(10223):497-506.
Huang et al., "Construction and biological characterisation of recombinant porcine circovirus type 2 expressing the V5 epitope tag," Virus Res., Nov. 2011, 161(2):115-123.
Huang, "In Vivo Delivery of RNAi with Lipid-Based Nanoparticles," Ann. Rev. Biomed. Eng., 2011, 13:507-530.
Human Metapneumovirus (HM PV) Clinical Features, CDC Website, Sep. 5, 2019, retrieved from URL <https://www.cdc.gov/surveillance/nrevss/hmpv/clinical.html>, 5 pages.
Institution Decision in IPR2023-01358, dated Mar. 19, 2024, 97 pages.
Institution Decision in IPR2023-01359, dated Mar. 19, 2024, 96 pages.
International Preliminary Report on Patentability in International Application No. PCT/US2022/012607, mailed on Jul. 27, 2023, 12 pages.
International Preliminary Report on Patentability in International Application No. PCT/US2022/012614, mailed on Jul. 27, 2023, 12 pages.

(56) References Cited

OTHER PUBLICATIONS

International Search Report and Written Opinion in International Application No. PCT/US2016/058327, mailed on Jun. 29, 2017, 25 pages.
International Search Report and Written Opinion in International Application No. PCT/US2022/012607, mailed on May 18, 2022, 19 pages.
International Search Report and Written Opinion in International Application No. PCT/US2022/012614, mailed on Jul. 1, 2022, 19 pages.
Jackson et al., "An mRNA Vaccine against SARS-CoV-2—Preliminary Report," New England Journal of Medicine, Jul. 14, 2020, 383(20):1920-31.
Jaimes et al., "Phylogenetic Analysis and Structural Modeling of SARS-CoV-2 Spike Protein Reveals an Evolutionary Distinct and Proteolytically Sensitive Activation Loop," J Mol Biol., May 2020, 432(10):3309-3325.
Japanese Package Insert for Spikevax Intramuscular Injection (Monovalent: Omicron XBB.1.5), Oct. 2023, 17 pages (with English translation).
Jary et al., "Evolution of viral quasispecies during SARS-CoV-2 infection," Clin. Microbiol. Infect., Nov. 2020, 26(11):1560.e1-1560.e4, available online Jul. 24, 2020.
Jaume et al., "Anti-Severe Acute Respiratory Syndrome Coronavirus Spike Antibodies Trigger Infection of Human Immune Cells via a pH- and Cysteine Protease-Independent FcγR Pathway," Journal of Virology, Oct. 2011, 85(20):10582-10597.
Jayaraman et al., "Maximizing the potency of siRNA lipid nanoparticles for hepatic gene silencing in vivo," Angew Chem Int Ed Engl., Aug. 20, 2012,51(34):8529-8533.
Jeffs et al., "A Scalable, Extrusion-Free Method for Efficient Liposomal Encapsulation of Plasmid DNA," Pharmaceutical research., Mar. 2005, 22(2):362-372.
Jiaming et al., "The recombinant N-terminal domain of spike proteins is a potential vaccine against Middle East respiratory syndrome coronavirus (MERS-CoV) infection," Vaccine, Jan. 3, 2017, 35(1):10-18.
Jiang et al., "The Variation of SARS-CoV-2 and Advanced Research on Current Vaccines," Frontiers in Medicine, Jan. 18, 2022, 8:806641.
Jirikowski et al., "Reversal of diabetes insipidus in Brattleboro Rats: Intrahypothalamic injection of vasopressin mRNA," Science, Feb. 21, 1992, 255(5047):996-998.
Johanning et al., "A Sindbis virus mRNA polynucleotide vector achieves prolonged and high level heterologous gene expression in vivo," Nucleic Acids Res., May 11, 1995, 23(9):1495-1501.
Johansson et al., "Intradermal Electroporation of Naked Replicon RNA Elicits Strong Immune Responses," PLoS ONE, Jan. 2012, 1: Article e29732, 7 pages.
Jorquera et al., "Nanoparticle Vaccines Encompassing the Respiratory Syncytial Virus (RSV) G Protein CX3C Chemokine Motif Induce Robust Immunity Protecting from Challenge and Disease," PLoS One, Sep. 10, 2013;8(9):e74905, 13 pages.
Kallen et al., "A development that may evolve into a revolution in medicine: mRNA as the basis for novel, nucleotide-based vaccines and drugs," Ther Adv Vaccines., Jan. 2014, 2(1):10-31.
Kallen et al., "A novel, disruptive vaccination technology: self-adjuvanted RNActive(®) vaccines," Hum Vaccin Immunother., Oct. 2013, 9(10):2263-2276.
Kalra et al., "Virosomes: As a Drug Delivery Carrier," American Journal of Advanced Drug Delivery, 2013, 1:29-35.
Kam et al., "Antibodies against trimeric S glycoprotein protect hamsters against SARS-CoV challenge despite their capacity to mediate FcγRII-dependent entry into B cells in vitro," Vaccine, Jan. 8, 2007, 25(4):729-740.
Kanapathipillai et al., "Nanoparticle targeting of anti-cancer drugs that alter intracellular signaling or influence the tumor microenvironment," Adv. Drug Deliv. Rev., Dec. 15, 2014, 79-80, pp. 107-118.
Kanasty et al., "Delivery materials for siRNA therapeutics," Nat Mater., Nov. 2013, 12(11):967-977.
Kansteiner, "It's the end of the line for J&J's COVID shot in the US, CDC says," Fiercepharma, May 16, 2023, 2 pages.
Karikó et al., "Generating the optimal mRNA for therapy: HPLC purification eliminates immune activation and improves translation of nucleoside-modified, protein-encoding mRNA," Nucleic Acids Res., Nov. 2011, 39(21):e142, 10 pages.
Kariko et al., "Incorporation of pseudouridine into mRNA yields superior nonimmunogenic vector with increased translational capacity and biological stability," Mol Ther., Nov. 2008, 16(11):1833-40.
Karikó et al., "Increased erythropoiesis in mice injected with submicrogram quantities of pseudouridine-containing mRNA encoding erythropoietin," Molecular Therapy, 20(5):948-953.
Karikó et al., "Modified Uridines Are the Key to a Successful Message," Nature Reviews Immunology, Oct. 2021, 21(10):619.
Karikó et al., "Naturally occurring nucleoside modifications suppress the immunostimulatory activity of RNA: Implication for therapeutic RNA development," Current Opinion in Drug Discovery and Development, Sep. 2007, 10(5):523-532.
Karikó et al., "Suppression of RNA recognition by Toll-like receptors: The impact of nucleoside modification and the evolutionary origin of RNA," Immunity, Aug. 2005, 23:165-175.
Kauffman et al., "Materials for non-viral intracellular delivery of messenger RNA therapeutics," J Control Release., Oct. 28, 2016, 240:227-234.
Kauffman et al., "Optimization of Lipid Nanoparticle Formulations for mRNA Delivery in Vivo with Fractional Factorial and Definitive Screening Designs," Nano Lett., Nov. 11, 2015, 15(11):7300-7306.
Keegan, "The Lasker Awards: A History of "America's Nobels"," Cell Mentor, Sep. 11, 2018, 7 pages.
Keshwara et al., "Rabies-based vaccine induces potent immune responses against Nipah virus," NPJ Vaccines, Apr. 15, 2019, 4:15; Erratum in: NPJ Vaccines, May 13, 2019, 4:18, 10 pages.
Khoury et al., "Neutralizing antibody levels are highly predictive of immune protection from symptomatic SARS-CoV-2 infection," Nat Med., Jul. 2021, 27(7):1205-1211.
Kim et al., "Generation and Characterization of DNA Vaccines Targeting the Nucleocapsid Protein of Severe Acute Respiratory Syndrome Coronavirus," Virology, May 2004, 78(9):4638-4645.
King et al., "Virus Taxonomy: Classification and Nomenclature of Viruses. Ninth Report of the International Committee on Taxonomy of Viruses," Int Union of Microbiol Soc., 2012, 50 pages.
Kirchdoerfer et al., "Stabilized coronavirus spikes are resistant to conformational changes induced by receptor recognition or proteolysis," Sci Rep., Oct. 24, 2018, 8(1):15701.
Kisich et al., "Antimycobacterial agent based on mRNA encoding human beta-defensin 2 enables primary macrophages to restrict growth of *Mycobacterium tuberculosis*," Infect Immun., Apr. 2001, 69(4):2692-9.
Kolata, "Kati Karikó Helped Shield the World from the Coronavirus," New York Times, Apr. 8, 2021, Updated Sep. 24, 2021, 5 pages.
Koyama et al., "Analysis on GENIE reveals novel recurrent variants that affect molecular diagnosis of sizable number of cancer patients," BMC Cancer, Feb. 2019, 19(1):114.
Koyama et al., "Emergence of Drift Variants That May Affect COVID-19 Vaccine Development and Antibody Treatment," Pathogens, Apr. 26, 2020, 9(5):324.
Kozielski et al., "Bioreducible cationic polymer-based nanoparticles for efficient and environmentally triggered cytoplasmic siRNA delivery to primary human brain cancer cells," ACS Nano, Apr. 22, 2014, 8(4):3232-41.
Krammer et al., "Chimeric hemagglutinin influenza virus vaccine constructs elicit broadly protective stalk-specific antibodies," J Virol., Jun. 2013, ;87(12):6542-50.
Kramps et al., "Messenger RNA-based vaccines: progress, challenges, applications," Wiley Interdiscip Rev RNA., Nov.-Dec. 2013, 4(6):737-49.
Kranz et al., "Systemic RNA Delivery to Dendritic Cells Exploits Antiviral Defense for Cancer Immunotherapy," Nature, 2016, 534:396-411.
Kreiter et al., "Intranodal Vaccination with Naked Antigen-Encoding RNA Elicits Potent Prophylactic and Therapeutic Antitumoral Immunity," Cancer Research, Nov. 2010, 70:9031-9040.

(56) References Cited

OTHER PUBLICATIONS

Kreiter et al., “Tumor vaccination using messenger RNA: prospects of a future therapy,” Curr Opinion in Immun., Jun. 2011, 23(3):399-406.
Kresge, “The messenger RNA pioneers everyone ignored,” Bloomberg, Nov. 23, 2021, last accessed Aug. 24, 2023, retrieved from URL <https://www.bloomberg.com/news/newsletters/2021-11-23/themessenger-rna-pioneers-everyone-ignored>, 4 pages.
Kuhn et al., “mRNA as a versatile tool for exogenous protein expression,” Current Gene Therapy, Oct. 2012, 12(5):347-361.
Kumari et al., “A critical overview of current progress for COVID-19: development of vaccines, antiviral drugs, and therapeutic antibodies,” J. Biomed Sci., Sep. 2022, 29:68, 36 pages.
Kurimoto et al., “PEG-OligoRNA Hybridization of mRNA for Developing Sterically Stable Lipid Nanoparticles toward In Vivo Administration,” Molecules, Apr. 3, 2019, 24(7):1303.
Kutzler et al., “DNA Vaccines: Ready for Prime Time?,” Nature Reviews Genetics, 2008, 9:776-788.
Langer, “New methods of drug delivery,” Science, Sep. 28, 1990, 249:1527-1533.
Leal et al., “Phase I clinical trial of an intranodally administered mRNA-based therapeutic vaccine against HIV-1 infection,” AIDS, 2018, 32(17):2533-2545.
Leitner et al., “DNA and RNA-based vaccines: principles, progress and prospects,” Vaccine, Dec. 10, 1999, 18(9-10):765-77.
Leung et al., “Lipid nanoparticles for short interfering RNA delivery,” Adv Genet., Jan. 2014, 88:71-110.
Leuschner et al., “Therapeutic siRNA silencing in inflammatory monocytes in mice,” Nat Biotechnol., Oct. 9, 2011, 29(11):1005-10.
Li et al., “Application of ultra-high performance liquid chromatography for chemical characterization of liposome-based therapeutic small-interfering RNA,” American Pharmaceutical Review, Sep.-Oct. 2010, 13(6), 13 pages.
Li et al., “Cell Attachment Domains of the Porcine Epidemic Diarrhea Virus Spike Protein Are Key Targets of Neutralizing Antibodies,” J Virol., May 26, 2017, 91(12):e00273-17, 16 pages.
Li et al., “Effects of local structural transformation of lipid-like compounds on delivery of messenger RNA,” Sci Rep., Feb. 26, 2016, 6:22137, 8 pages.
Li et al., “Lipid-based nanoparticles for nucleic acid delivery,” Pharm Res., Mar. 2007, 24(3):438-49.
Li et al., “Overcoming obstacles to develop effective and safe siRNA therapeutics,” Expert Opin Biol Ther., May 2009, 9(5):609-19.
Li, “Receptor recognition mechanisms of coronaviruses: a decade of structural studies,” J Virol., Feb. 2015, 89(4):1954-64.
Li, “Structure, Function, and Evolution of Coronavirus Spike Proteins,” Annu Rev Viral., Sep. 29, 2016, 3(1):237-261.
Liang et al., “Efficient Targeting and Activation of Antigen-Presenting Cells In Vivo after Modified mRNA Vaccine Administration in Rhesus Macaques,” Molecular Therapy, Dec. 2017, 25(12):2635-2647.
Liang et al., “Enhanced Neutralizing Antibody Response Induced by Respiratory Syncytial Virus Prefusion F Protein Expressed by a Vaccine Candidate,” J Virol., Sep. 2015, 89(18):9499-510.
Lin et al., “Glycan Masking of Epitopes in the NTD and RBD of the Spike Protein Elicits Broadly Neutralizing Antibodies Against SARS-CoV-2 Variants,” Front Immunol., Dec. 2, 2021, 12:795741.
Lin et al., “Identification of residues in the receptor-binding domain (RBD) of the spike protein of human coronavirus NL63 that are critical for the RBD-ACE2 receptor interaction,” J. Gen. Virol., Apr. 2008, 89(4):1015-1024.
Lin et al., “Progress and challenges of mRNA vaccines,” Interdisc Med., Dec. 22, 2022, 1(1):e20220008, 5 pages.
Lin et al., “Three-dimensional imaging of lipid gene-carriers: membrane charge density controls universal transfection behavior in lamellar cationic liposome-DNA complexes,” Biophys J., May 2003, 84(5):3307-16.
Liu et al., “Chimeric severe acute respiratory syndrome coronavirus (SARS-CoV) S glycoprotein and influenza matrix 1 efficiently form virus-like particles (VLPs) that protect mice against challenge with SARS-CoV,” Vaccine, Sep. 2, 2011, 29(38):6606-13.
Liu et al., “Influence of polyethylene glycol density and surface lipid on pharmacokinetics and biodistribution of lipid-calcium-phosphate nanoparticles,” Biomaterials, Mar. 2014, 35(9):3027-34.
Liu et al., “Potent neutralizing antibodies against multiple epitopes on SARS-CoV-2 spike,” Nature, Aug. 20, 2020, 584(7821):450-456.
Liu et al., “The Membrane Protein of Severe Acute Respiratory Syndrome Coronavirus Acts as a Dominant Immunogen Revealed by a Clustering Region of Novel Functionally and Structurally Defined Cytotoxic T-Lymphocyte Epitopes,” The Journal of infectious diseases, Oct. 15, 2010, 202(8):1171-80.
Liu, “AstraZeneca withdraws US COVID vaccine application, shifts focus to antibody treatments,” Fierce Pharma, Nov. 10, 2022, 2 pages.
Loftus, “Moderna Signals It May Enforce Covid-19 Vaccine Patents in Wealthy Nations,” Wall Street Journal, Mar. 7, 2022, last accessed Jul. 1, 2024, retrieved from URL <https://www.wsj.com/articles/moderna-signals-it-may-enforce-covid-19-vaccine-patents-in-wealthy-nations-11646699609>, 4 pages.
Lorenzi et al., “Intranasal vaccination with messenger RNA as a new approach in gene therapy: Use against tuberculosis,” BMC Biotechnol., Oct. 2010, 10(77):1-11.
Lovelace Jr., et al., “Dr. Anthony Fauci says chance of coronavirus vaccine being highly effective is ‘not great’,” CNBC.com, Aug. 7, 2020, retrieved on Sep. 16, 2025, retrieved from URL <https://www.cnbc.com/2020/08/07/coronavirus-vaccine-dr-fauci-says-chances-of-it-being-highly-effective-is-not-great.html>, 4 pages.
Lu et al., “Bat-to-human: spike features determining ‘host jump’ of coronaviruses SARS-CoV, MERS-CoV, and beyond,” Trends Microbiol., Aug. 2015, 23(8):468-78.
Lu et al., “Genomic characterisation and epidemiology of 2019 novel coronavirus: implications for virus origins and receptor binding,” Lancet., Feb. 22, 2020, 395(10224):565-574.
Lu et al., “Immunogenicity of DNA Vaccines Expressing Human Immunodeficiency Virus Type 1 Envelope Glycoprotein With and Without Deletions in the V1/2 and V3 Regions,” AIDS Research & Human Retroviruses, Jan. 1998, 14(2):151-155.
Lutz et al., “Unmodified mRNA in LNPs constitutes a competitive technology for prophylactic vaccines,” NPJ Vaccines, Oct. 19, 2017, 2:29, 9 pages.
Ma et al., “Intranasal vaccination with recombinant receptor-binding domain of MERS-CoV spike protein induces much stronger local mucosal immune responses than subcutaneous immunization: Implication for designing novel mucosal MERS vaccines,” Vaccine, Apr. 11, 2014, 32(18):2100-8.
Maclachlan, “Lipid Nanoparticle-mediated delivery of messenger RNA. Presentation,” 1st International mRNA Health Conference, Tubingen, Germany, Oct. 24, 2013, Last accessed Dec. 22, 2016, URL <http://files.shareholder.com/downloads/ABEA-50QJTB/2628241206x0x699789/47543d12- db34-4e6e-88a9-f3ae5d97b1d2/MacLachlan_mRNA_Conf_2013.pdf>, 32 pages.
Magini et al., “Self-Amplifying mRNA Vaccines Expressing Multiple Conserved Influenza Antigens Confer Protection against Homologous and Heterosubtypic Viral Challenge,” PLoS One, Aug. 15, 2016, 11(8):e0161193, 25 pages.
Mandal et al., “Reprogramming human fibroblasts to pluripotency using modified mRNA,” Nat Protoc., Mar. 2013, 8(3):568-82.
Marshall et al., “Ch. 79: Regulation and Testing of Vaccines,” Plotkin's Vaccines, 7th edition, 2018, pp. 1547-1565.
Martin et al., “A SARS DNA Vaccine Induces Neutralizing Antibody and Cellular Immune Responses in Healthy Adults in a Phase I Clinical Trial,” Vaccine, Nov. 25, 26(50):6338-43.
Martinez-Flores et al., “SARS-CoV-2 Vaccines Based on the Spike Glycoprotein and Implications of New Viral Variants,” Front Immunol., Jul. 12, 2021, 12:701501.
Martinon et al., “Induction of virus-specific cytotoxic T lymphocytes in vivo by liposome-entrapped mRNA,” EurJ Immunol., Jul. 1993, 23(7):1719-22.
Mas et al., “Engineering, Structure and Immunogenicity of the Human Metapneumovirus F Protein in the Postfusion Conformation,” PLoS Pathog., Sep. 9, 2016, 12(9):e1005859, 21 pages.

(56) References Cited

OTHER PUBLICATIONS

McCallum et al., "N-terminal domain antigenic mapping reveals a site of vulnerability for SARS-CoV-2," Cell, Apr. 29, 2021, 184(9):2332-2347.
McDonnell et al. "Molecular Medicine: DNA vaccines," N Engl J Med., Jan. 4, 1996, 334(1):42-5.
McKay et al., "Self-amplifying RNA SARS-CoV-2 lipid nanoparticle vaccine candidate induces high neutralizing antibody titers in mice," Nat Commun., Jul. 9, 2020, 11(1):3523.
McLellan et al., "Structure and function of respiratory syncytial virus surface glycoproteins," Curr Top Microbiol Immunol., Dec. 21, 2013;372:83-104.
McLellan et al., "Structure of respiratory syncytial virus fusion glycoprotein in the postfusion conformation reveals preservation of neutralizing epitopes," J Virol., Aug. 2011, 85(15):7788-96.
McLellan et al., "Structure-based design of a fusion glycoprotein vaccine for respiratory syncytial virus," Science, Nov. 2013, 342(6158):592-8.
Mendonca et al., "Design of lipid-based nanoparticles for delivery of therapeutic nucleic acids," Drug Discov Today., Mar. 2023, 28(3):103505, 17 pages.
Miao et al., "Delivery of mRNA vaccines with heterocyclic lipids increases anti-tumor efficacy by STING-mediated immune cell activation," Nat Biotechnol., Oct. 2019, 37(10):1174-1185.
Midoux et al., "Lipid-based mRNA vaccine delivery systems," Expert Rev Vaccines, Feb. 2015, 14(2):221-34.
Mitchell et al., "RNA transfected dendritic cells as cancer vaccines," Curr Opin Mal Ther., Apr. 2000, 2(2):176-81.
Mitchell et al., "RNA-transfected dendritic cells in cancer immunotherapy," J Clin Invest., Nov. 2000, 106 (9):1065-9.
Mockey et al., "mRNA-based cancer vaccine: prevention of B16 melanoma progression and metastasis by systemic injection of MART1 mRNA histidylated lipopolyplexes," Cancer Gene Therapy, Jun. 2007, 14:802-814.
Moderna Form 10-K for the fiscal year ended Dec. 31, 2018, 308 pages.
Moderna Form 10-K for the fiscal year ended Dec. 31, 2022, 182 pages.
Moderna Form 10-Q for the quarterly period ended Jun. 30, 2024, 44 pages.
Moderna Form 8-K, Mar. 16, 2020, 11 pages.
Moderna, Inc. Form 10-K, 2020, 330 pages.
Moderna, Inc. Form 10-K, 2023, 219 pages.
Moderna, Inc., Patents, retrieved on Oct. 31, 2023, retrieved from URL <https://www.modernatx.com/patents>, 3 pages.
Moderna, Science & Technology Day, dated May 17, 2022, 136 pages.
Moderna, Vaccines and Related Biological Products Advisory Committee Presentation: Moderna COVID-19 Variant Vaccines; MOD_000767652-MOD_000767686, dated Jun. 15, 2023, 35 pages.
*ModernaTX, Inc. et al.* v. *Pfizer Inc. et al.* (D. Mass. 22-11378-RGS) D.I. 1—Complaint for Patent Infringement, Aug. 26, 2022, 39 pages.
*ModernaTX, Inc. et al.* v. *Pfizer Inc. et al.* (D. Mass. 22-11378-RGS) D.I. 105—District Court Memorandum and Order on Claim Construction, Aug. 1, 2023, 15 pages.
*ModernaTX, Inc. et al.* v. *Pfizer Inc. et al.* (D. Mass. 22-11378-RGS) D.I. 45—Answer to the Complaint, Dec. 5, 2022, 81 pages.
Modjarrad, "MERS-CoV vaccine candidates in development: The current landscape," Vaccine, Jun. 3, 2016, 34(26):2982-2987.
Moffat et al., "Functions of the C-Terminal Domain of Varicella-Zoster Virus Glycoprotein E in Viral Replication In Vitro and Skin and T-Cell Tropism In Vivo," Journal of Virology, Nov. 2004, 78(22):12406-12415.
Mok et al., "An Alphavirus Replicon-Based Human Metapneumovirus Vaccine Is Immunogenic and Protective in Mice and Cotton Rats," J Virol., Nov. 2008, 82(22):11410-11418.
Mullard, "COVID-19 vaccine success enables a bolder vision for mRNA cancer vaccines, says BioNTech CEO," Nat Rev Drug Discov., Jul. 2021, 20(7):500-501.
Muller et al., "Transfection of dendritic cells with RNA induces CD4- and COB-mediated T cell immunity against breast carcinomas and reveals the immunodominance of presented T cell epitopes," J Immunol., Jun. 15, 2003, 170(12):5892-6.
Mulligan et al., "Phase 1/11 study ofCOVID-19 RNA vaccine BNT162bl in adults," Nature, Oct. 2020, 586(7830):589-593.
Murphy, Excerpts from "Janeway's Immunobiology," 8th Ed., 2012, 250 pages.
Muthumani et al., "A synthetic consensus anti-spike protein DNA vaccine induces protective immunity against Middle East respiratory syndrome coronavirus in nonhuman primates," Sci Transl Med., Aug. 19, 2015, 7(301):301ra132, 29 pages.
Nakayama et al., "Comparison of Current Regulatory Status for Gene-Based Vaccines in the U.S., Europe and Japan," Vaccines, Mar. 2015, 3(1):186-202.
Nance et al., "Modifications in an Emergency: The Role of Nl-Methylpseudouridine in COVID-19 Vaccines," ACS Cent Sci., May 26, 2021, 7(5):748-756.
Narayanan et al., "Interplay between viruses and host mRNA degradation," Biochim Biophys Acta., Jun.-Jul. 2013, 1829(6-7):732-741.
National Human Genome Research Institute, "Central Dogma," 2023, NIH, URL: <https://www.genome.gov/geneticsglossary/Central-Dogma>, 4 pages.
National Human Genome Research Institute, "Double Helix," 2023, NIH, URL <https://www.genome.gov/geneticsglossary/Double-Helix>, 2 pages.
Non-Final Office Action in U.S. Appl. No. 18/762,384, dated Apr. 21, 2025, 9 pages.
Non-Final Office Action in U.S. Appl. No. 18/762,384, dated Sep. 11, 2024, 17 pages.
Notice of Allowance in U.S. Appl. No. 18/762,384, dated Feb. 5, 2025, 7 pages.
Notice of Allowance in U.S. Appl. No. 18/762,384, dated Oct. 17, 2024, 7 pages.
Onpattro, "Highlights of Prescribing Information," FDA Prescribing Label, Aug. 2018, 14 pages.
Oostvogels et al., "Phase 1 Assessment of the Safety and Immunogenicity of an mRNA-Lipid Nanoparticle Vaccine Candidate Against SARS-CoV-2 in Human Volunteers," medRxiv, Nov. 9, 2020, 38 pages.
Openshaw et al., "Immune Responses and Disease Enhancement During Respiratory Syncytial Virus Infection," Clinical Microbiology Reviews, Jul. 2005, 18(13):541-555.
Opposition against European Patent No. 3324979 B1, filed by BioNTech SE (Opponent) against ModernaTX, Inc. (Patentee) on Jul. 10, 2023, 86 pages.
Ostro et al., "Evidence for translation of rabbit globin mRNA after liposome-mediated insertion into a human cell line," Nature, Aug. 31, 1978, 274(5674):921-3.
Pallesen et al., "Immunogenicity and structures of a rationally designed prefusion MERS-CoV spike antigen," Proc Natl Acad Sci USA, Aug. 29, 2017, 114(35):E7348-E7357.
Paoletti, "Applications of Pox Virus Vectors to Vaccination: An Update," PNAS, Oct. 1996, 93(21):11349-11353.
Paramasivam et al., "Endosomal Escape of Delivered mRNA from Endosomal Recycling Tubules Visualized at the Nanoscale," Journal of Cell Biology, Dec. 9, 2021, 221(2):e202110137, 20 pages.
Pardi et al., "mRNA vaccines—a new era in vaccinology," Nat Rev Drug Discov., Apr. 2018, 17(4):261-279.
Pardi et al., "Nucleoside-modified mRNA vaccines induce potent T follicular helper and germinal center B cell responses," J Exp Med., Jun. 4, 2018, 215(6):1571-1588.
Pardi et al., "Zika virus protection by a single low-dose nucleoside-modified mRNA vaccination," Nature, Mar. 9, 2017, 543(7644):248-251.
Park et al., "Non-Viral COVID-19 Vaccine Delivery Systems," Advanced Drug Delivery Reviews, Feb. 2021, 169:137-151.
Park et al., "The Miracle Workers. Heroes of the Year.," TIME Magazine, Dec. 27, 2021, 17 pages.
Pascolo, "Messenger RNA-based vaccines," Expert Opin Biol Ther., Aug. 2004, 4(8):1285-94.

(56) References Cited

OTHER PUBLICATIONS

Pascolo, "Vaccination with messenger RNA (mRNA)," Handb Exp Pharmacol., 2008, 183:221-235.
Patel et al., "Naturally-occurring cholesterol analogues in lipid nanoparticles induce polymorphic shape and enhance intracellular delivery of mRNA," Nat Commun., Feb. 20, 2020, 11(1):983, 13 pages.
Patent Owner's Preliminary Response in IPR2023-01358 dated Dec. 8, 2023, 82 pages.
Patent Owner's Preliminary Response in IPR2023-01359 dated Dec. 7, 2023, 83 pages.
Patent Owner's Preliminary Statement Regarding Alleged Inconsistent Positions in IPR2023-01359 dated Jan. 16, 2024, 14 pages.
Patent Owner's Preliminary Statement Regarding Petitioner's Inconsistent Positions in IPR2023-01358 dated Jan. 16, 2024, 14 pages.
Patent Owner's Response in IPR2023-01358 dated May 31, 2024, 103 pages.
Patent Owner's Response in IPR2023-01359 dated May 31, 2024, 103 pages.
Patent Owner's Sur-Reply in IPR2023-01358 dated Oct. 16, 2024, 63 pages.
Patent Owner's Sur-Reply in IPR2023-01359 dated Oct. 16, 2024, 63 pages.
Patent Owner's Sur-Reply in Support of Preliminary Response in IPR2023-01358 dated Jan. 25, 2024, 13 pages.
Patent Owner's Sur-Reply in Support of Preliminary Response in IPR2023-01359 dated Jan. 25, 2024, 13 pages.
Patent Sublicense Agreement Between Cellscript, LLC and ModernaTx, Inc., dated Jun. 26, 2017, 36 pages.
Pathak et al., "Intra-host variability in global SARS-Co V-2 genomes as signatures of RNA editing: implications in viral and host response outcomes," bioRxiv, Dec. 9, 2020, 32 pages.
Peabody et al., "Termination-reinitiation occurs in the translation of mammalian cell mRNAs," Mol Cell Biol., Jul. 1986, 6(7):2695-703.
Peek et al., "Nanotechnology in vaccine delivery," Adv Drug Deliv Rev., May 22, 2008, 60(8):915-28.
Pegu et al., "Durability of mRNA-1273 vaccine-induced antibodies against SARS-Co V-2 variants," Science, Sep. 17, 2021, 373(6561):1372-1377.
Petition For Inter Partes Review of U.S. Pat. No. 10,702,600; *BioNTech SE and Pfizer Inc*. (Petitioners) v. *ModernaTX, Inc*. (Patent Owner), Filed Aug. 28, 2023, 87 pages.
Petition For Inter Partes Review of U.S. Pat. No. 10,933,127; *BioNTech SE and Pfizer Inc*. (Petitioners) v. *ModernaTX, Inc*. (Patent Owner), Filed Aug. 28, 2023, 89 pages.
Petition For Inter Partes Review of U.S. Pat. No. 8,058,069; (IPR2019-00554). *Moderna Therapeutics, Inc*. (Petitioner) v. *Arbutus Biopharma Corporation* (Patent Owner), Filed Nov. 15, 2011, 81 pages.
Petitioner's Preliminary Statement Regarding Patent Owner's Inconsistent Positions in IPR-2023-01358 dated Jan. 23, 2024, 8 pages.
Petitioner's Reply to Patent Owner's Preliminary Response in IPR2023-01358 dated Jan. 12, 2024, 15 pages.
Petitioner's Reply to Patent Owner's Preliminary Response in IPR2024-01359 dated Jan. 12, 2024, 15 pages.
Petitioner's Reply to Patent Owner's Response in IPR2023-01358 dated Aug. 30, 2024, 68 pages.
Petitioner's Reply to Patent Owner's Response in IPR2023-01359 dated Aug. 30, 2024, 69 pages.
Petsch et al., "Protective efficacy of in vitro synthesized, specific mRNA vaccines against influenza A virus infection," Nat Biotechnol., Dec. 2012, 30(12):1210-1216.
Phua et al., "Messenger RNA (mRNA) nanoparticle tumour vaccination," Nanoscale., Jul. 21, 2014, 6(14):7715-29.
Plotkin, "Vaccines: Past, Present and Future," Nature Medicine, Historical Perspective, Apr. 2005, 11(Suppl. 4):S5-S11.
Probst et al., "Characterization of the ribonuclease activity on the skin surface," Genet Vaccines Ther., May 29, 2006, 4:4, 9 pages.
*Promosome, LLC*, Plaintiff, v. *Moderna, Inc*., Defendant, Case No. S.D. Cal. 23-cv-1047-JES-DDL) D.I. 1—Complaint for Patent Infringement, Jun. 6, 2023, 51 pages.
*Promosome, LLC*, Plaintiff, v. *Moderna, Inc*., Defendant, Case No. S.D. Cal. 3:23-cv-1047-JES-DDL) D.I. 30—Notice of Dismissal, Sep. 19, 2023, 4 pages.
Pulford et al., "Liposome-siRNA-peptide complexes cross the blood-brain barrier and significantly decrease PrPC on neuronal cells and PrPRES in infected cell cultures," PLoS ONE, Jun. 2010, 5(6):e11085, 13 pages.
Pulliam et al., "Increased risk of SARS-CoV-2 reinfection associated with emergence of the Omicron variant in South Africa," medRxiv, Dec. 2021, 42 pages.
Rabinovich et al., "Synthetic messenger RNA as a tool for gene therapy," Hum. Gene Ther., Oct. 2006, 17:1027-1035.
Raj et al., "Dipeptidyl peptidase 4 is a functional receptor for the emerging human coronavirus-EMC," Nature, Mar. 14, 2013, 495(7440):251-4.
Ramamoorth et al., "Nonviral vectors in gene therapy—an overview," J Clin Diagn Res., Jan. 2015, 9(1):GE01-GE06.
Regalado, "Don't panic about the latest coronavirus mutations say drug companies," MIT Technology Review, Dec. 23, 2020, 5 pages.
Regalado, "Moderna believes it could update its coronavirus vaccine without a big new trial," MIT Technology Review, Jan. 13, 2021, 4 pages.
Regla-Nava et al., "Severe Acute Respiratory Syndrome Coronaviruses with Mutations in the E Protein Are Attenuated and Promising Vaccine Candidates," Journal of Virology, Apr. 2015, 89(7):3870-3887.
Reichmuth et al., "mRNA Vaccine Delivery Using Lipid Nanoparticles," Ther Deliv., May 2016, 7(5):319-34.
Ren et al., "Recent vaccine development for human metapneumovirus," J Gen Virol., Jul. 2015, 96(Pt 7):1515-20.
Reply Declaration of Daniel Griffin in IPR2023-01358 dated Aug. 30, 2024, 280 pages (Redacted public version).
Reply Declaration of Daniel Griffin in IPR2023-01359 dated Aug. 30, 2024, 281 pages (Redacted public version).
Reply Declaration of James Moon in IPR2023-01358 dated Aug. 30, 2024, 70 pages (Redacted public version).
Reply Declaration of James Moon in IPR2023-01359 dated Aug. 30, 2024, 70 pages (Redacted public version).
Rittig et al., "Intradermal vaccinations with RNA coding for TAA generate CD8+ and CD4+ immune responses and induce clinical benefit in vaccinated patients," Mol Ther., May 2011, 19(5):990-9.
Robbins et al., "Moderna Backs down in its Vaccine Patent Fight with the NIH," New York Times, Dec. 17, 2021, 1 page.
Rodriguez-Gascon et al., "Development of nucleic acid vaccines: use of self-amplifying RNA in lipid nanoparticles," Int J Nanomedicine., Apr. 10, 2014, 9:1833-1843.
Rossi et al., "IRES-based Venezuelan equine encephalitis vaccine candidate elicits protective immunity in mice," Virology, Mar. 15, 2013, 437(2):81-8.
Sahdev et al., "Biomaterials for Nanoparticle Vaccine Delivery Systems," Pharmaceutical Research, Oct. 2014, 31(10):2563-2582.
Sahin et al., "mRNA-based therapeutics—developing a new class of drugs," Nat Rev Drug Discov., Oct. 2014, 13(10):759-80.
Sahin et al., "Personalized RNA mutanome vaccines mobilize poly-specific therapeutic immunity against cancer," Nature, Jul. 13, 2017, 547(7662):222-226.
Salomon et al., "A liposomal RNA vaccine inducing neoantigen-specific CD4+ T cells augments the antitumor activity of local radiotherapy in mice," Oncoimmunology, Jun. 22, 2020, 9(1):1771925, 13 pages.
Santoro et al., "An efficient system for the evolution of aminoacyl-tRNA synthetase specificity," Nat Biotechnol., Oct. 2002, 20(10):1044-8.
Sarkar et al., "S glycoprotein diversity of the Omicron variant," medRxiv, Dec. 2021, 30 pages.
Schlake et al., "Developing mRNA-vaccine technologies," RNA Biol., Nov. 2012, 9(11):1319-30.
Schmitt et al., "In vitro induction of a bladder cancer-specific T-cell response by mRNA-transfected dendritic cells," J Cancer Res Clin Oncol., Feb. 2001, 127(3):203-6.

(56) References Cited

OTHER PUBLICATIONS

Schoenmaker et al., "mRNA-lipid nanoparticle COVID-19 vaccines: Structure and stability," Int J Pharm., May 15, 2021, 601:120586.
Schott et al., "Viral and non-viral approaches for transient delivery of mRNA and proteins," Current Gene Ther., Oct. 2011, 11 (5):382-398.
Schumann et al., "Multiple links between 5-methylcytosine content of mRNA and translation," BMC Biol., Apr. 15, 2020, 18(40):1-23.
Schuurhuis et al., "Ins and outs of dendritic cells," Int Arch Allergy Immunol., Mar. 2006, 140(1):53-72.
Segura et al., "Monitoring gene therapy by external imaging of mRNA: Pilot study on murine erythropoietin," Ther Drug Monit., Oct. 2007, 29(5):612-8.
Semple et al., "Efficient encapsulation of antisense oligonucleotides in lipid vesicles using ionizable aminolipids: Formation of novel small multilamellar vesicle structures," Biochimica et Biophysica ACTA, Feb. 2001, 1510(1-2):152-166.
Semple et al., "Rational design of cationic lipids for siRNA delivery," Nature Biotechnology, Feb. 2010, 28(2):172-178.
Shaw et al., "The Path to an RSV Vaccine," Current Opinion in Virology, Jun. 2013, 3(3):332-342.
Shidhadye et al., "Solid lipid nanoparticles and nanostructured lipid carriers—innovative generations of solid lipid carriers," Curr Drug Deliv., Oct. 2008, 5(4):324-31.
Shim et al., "Intranasal immunization with plasmid DNA encoding spike protein of SARS-coronavirus/polyethylenimine nanoparticles elicits antigen-specific humoral and cellular immune responses," BMC Immunol., Dec. 31, 2010, 11:65, 9 pages.
Shin et al., "Recent Advances in RNA Therapeutics and RNA Delivery Systems Based on Nanoparticles," Adv. Therap., Nov. 2018, 1(7):1800065.
Skidmore et al., "Emergence of a SARS-CoV-2 E484K variant of interest in Arizona," medRxiv, Mar. 28, 2021, 13 pages.
Skidmore et al., "Genomic Sequencing of SARS-CoV-2 E484K Variant B.1.243.1, Arizona, USA," Emerg Infect Dis., Oct. 2021, 27(10):2718-2720.
Slimko et al., "Codon optimization of Caenorhabditis elegans GluCl ion channel genes for mammalian cells dramatically improves expression levels," Journal of Neuroscience Methods, Mar. 30, 2003, 124(1):75-81.
Smits et al., "RNA-based gene transfer for adult stem cells and T cells," Leukemia, Nov. 2004, 18(11):1898-1902.
Sohn et al., "In-vivo particle mediated delivery of mRNA to mammalian tissues: ballistic and biological effects," Wound Rep and Regen., Jul.-Aug. 2001, 9(4):287-296.
Song et al., "Middle East Respiratory Syndrome Coronavirus Spike Protein Delivered by Modified Vaccinia Virus Ankara Efficiently Induces Virus-Neutralizing Antibodies," Journal of Virology, Nov. 2013, 87(21):11950-4.
Spikevax (COVID-19 Vaccine, mRNA), "Highlights of Prescribing Information," FDA Label, Apr. 2024, 45 pages.
Spikevax (COVID-19 Vaccine, mRNA), "Highlights of Prescribing Information," FDA Label, Jan. 2025, 43 pages.
Spikevax (COVID-19 Vaccine, mRNA), "Highlights of Prescribing Information," FDA Label, Sep. 2023, 45 pages.
Stanton et al., "Messenger RNA as a Novel Therapeutic Approach," Topics in Medicinal Chemistry RNA Therapeutics, Mar. 2017, 2 pages (Excerpts).
Steitz et al., "Effective Induction of Anti-Melanoma Immunity Following Genetic Vaccination with Synthetic mRNA Coding for the Fusion Protein EGFP.TRP2," Cancer Immunology, Mar. 2006, 55(3):246-253.
Stenler et al., "Safety and efficacy of DNA vaccines: Plasmids vs. minicircles," Human Vaccines & Immunotherapeutics, May 2014, 10(5):1306-8.
Stephenson et al., "Cross-reactivity to highly pathogenic avian influenza H5N1 viruses after vaccination with nonadjuvanted and MF59-adjuvanted influenza A/Duck/Singapore/97 (H5N3) vaccine: a potential priming strategy," J Infect Dis., Apr. 15, 2005, 191(8):1210-5.
Strong et al., "Incorporation of beta-globin untranslated regions into a Sindbis virus vector for augmentation of heterologous mRNA expression," Gene Ther., Jun. 1997, 4(6):624-7.
Sullenger et al., "Emerging clinical applications of RNA," Nature, Jul. 11, 2002, 418(6894):252-8.
Szebeni et al., "Activation of complement by therapeutic liposomes and other lipid excipient-based therapeutic products: prediction and prevention," Adv Drug Deliv Rev., Sep. 16, 2011, 63(12):1020-30.
Szebeni et al., "Complement activation as a bioequivalence issue relevant to the development of generic liposomes and other nanoparticulate drugs," Biochem Biophys Res Commun., Dec. 18, 2015, 468(3):490-7.
Szebeni, "Complement activation-related pseudoallergy: a stress reaction in blood triggered by nanomedicines and biologicals," Mol Immunol., Oct. 2014, 61(2):163-73.
Tam et al., "Advances in Lipid Nanoparticles for siRNA Delivery," Pharmaceutics, Sep. 18, 2013, 5(3):498-507.
Tavernier et al., "mRNA as gene therapeutic: How to control protein expression, J. of Controlled Release," Mar. 2011, 150(3):238-247.
Tegally et al., "Emergence and rapid spread of a new severe acute respiratory syndrome-related coronavirus 2 (SARS-Co V-2) lineage with multiple spike mutations in South Africa," medRxiv, Dec. 22, 2020, 19 pages.
Tenchov et al., "Lipid Nanoparticles—From Liposomes to mRNA Vaccine Delivery, a Landscape of Research Diversity and Advancement," ACS Nano., Jun. 28, 2021, 15(11):16982-17015.
Terada et al., "Characterization of Lipid Nanoparticles Containing Ionizable Cationic Lipids Using Design-of-Experiments Approach," Langmuir., Jan. 26, 2021, 37(3):1120-1128.
Teufel et al., "Human peripheral blood mononuclear cells transfected with messenger RNA stimulate antigen-specific cytotoxic T-lymphocytes in vitro," Cell Mol Life Sci., Aug. 2005, 62(15):1755-62.
Tews et al., "Chapter 2: Self-Replicating RNA," RNA Vaccines: Methods and Protocols, 2017, 1499:15-35.
Thery et al., "The cell biology of antigen presentation in dendritic cells," Curr Opin Immunol., Feb. 2001, 13(1):45-51.
Thess et al., "Sequence-engineered mRNA Without Chemical Nucleoside Modifications Enables an Effective Protein Therapy in Large Animals," Mol Ther., Sep. 2015, 23(9):1456-64.
To et al., "An overview of rational design of mRNA-based therapeutics and vaccines," Expert Opin Drug Discov., Nov. 2021, 16(11):1307-1317.
Ulmer et al., "RNA-based vaccines," Vaccine, Jun. 22, 2012, 30(30):4414-8.
UniProt KB Accession No. A0A059T4A1, "Influenza A virus A/Jiangxi/IPB13/2013(H10N8) hemagglutinin protein," Sep. 3, 2014, 5 pages.
UniProt KB Accession No. P59594, "SPIKE_CVHSA," Oct. 14, 2015, 9 pages.
Updated Curriculum Vitae of Daniel O. Griffin, Ph.D., dated Aug. 23, 2024, 24 pages.
Van Boheemen et al., "Genomic characterization of a newly discovered coronavirus associated with acute respiratory distress syndrome in humans," mBio., Nov. 20, 2012, 3(6):e00473-12, 9 pages.
Vardi et al., "Moderna's Mysterious Medicines," Forbes, Dec. 14, 2016, 5 pages.
Vardi, "Moderna's Mysterious Coronavirus Vaccine Delivery System," Forbes, Jul. 29, 2020, 9 pages.
Vennema et al., "Early death after feline Infectious Peritonitis Virus Challenge due to Recombinant Vaccinia Virus Immunization," Journal of Virology, Mar. 1990, 64(3):1407-1409.
Vergati et al., "Strategies for Cancer Vaccine Development," Journal of Biomedicine and Biotechnology, 2010, 2010:596432, 13 pages.
Verma et al., "Double-headed nucleosides: Synthesis and applications," Beilstein J Org Chem., Jun. 8, 2021, 17:1392-1439.
Vogel et al., "BNT162b vaccines protect rhesus macaques from SARS-CoV-2," Nature, Apr. 2021, 592(7853):283-289.
Von Niessen et al., "Improving mRNA-Based Therapeutic Gene Delivery by Expression-Augmenting 3' UTRs Identified by Cellular Library Screening," Mol Ther., Apr. 10, 2019, 27(4):824-836.
Walls et al., "Crucial steps in the structure determination of a coronavirus spike glycoprotein using cryo-electron microscopy," Protein Sci., Jan. 2017, 26(1):113-121.

(56) References Cited

OTHER PUBLICATIONS

Walls et al., "Tectonic conformational changes of a coronavirus spike glycoprotein promote membrane fusion," Proc Natl Acad Sci U S A., Oct. 17, 2017, 114(42):11157-11162.
Walsh et al., "Safety and Immunogenicity of Two RNA-Based Covid-19 Vaccine Candidates," N Engl J Med., Dec. 17, 2020, 383(25):2439-50.
Walter et al., "Evaluation of the BNT162b2 COVID-19 Vaccine in Children 5 to 11 Years of Age," New England J. Med., Jan. 6, 2022, 386:35-46.
Wan et al., "Comparison of Immunogenicity Between Codon Optimized HIV-1 Thailand Subtype B gp140 and gp145 Vaccines," Vaccine, Jun. 21, 2007, 25(26):4949-4959.
Wang et al., "An Evidence Based Perspective on mRNA-SARS-CoV-2 Vaccine Development," Med Sci Monit., May 5, 2020, 26:e924700.
Wang et al., "Antibody Resistance of SARS-CoV-2 Variants B.1.351 and B.1.1.7," bioRxiv [Preprint], Feb. 12, 2021; Update in: Nature, May 2021, 593(7857):130-135.
Wang et al., "Delivery of oligonucleotides with lipid nanoparticles," Adv Drug Deliv Rev., Jun. 29, 2015, 87:68-80.
Wang et al., "Evaluation of candidate vaccine approaches for MERS-CoV," Nature Communications, Jul. 2015, 6(1):7712, 11 pages.
Wang et al., "Increased Resistance of SARS-CoV-2 Variants B.1.351 and B.1.1.7 to Antibody Neutralization," bioRxiv, Jan. 26, 2021, 23 pages.
Wang et al., "Lipid Nanoparticles for the Delivery of Nucleic Acids," Nanoparticulate Drug Delivery Systems: Strategies, Technologies, and Applications, 2013, Chapter 3: 29 pages.
Wang et al., "mRNA vaccine-elicited antibodies to SARS-CoV-2 and circulating variants," Nature, Apr. 2021, 592(7855):616-622.
Wang et al., "Structural Definition of a Neutralization-sensitive Epitope on the MERS-CoV Sl-NTD," Cell Rep., Sep. 24, 2019, 28(13):3395-3405.
Wang et al., "Systemic delivery of modified mRNA encoding herpes simplex virus 1 thymidine kinase for targeted cancer gene therapy," Mol Ther., Feb. 2013, 21(2):358-367.
Weide et al., "Direct Injection of Protamine-protected mRNA: Results of a Phase 1/2 Vaccination Trial in Metastatic Melanoma Patients," Immunotherapy, Jun. 2009, 32(5):498-507.
Weide et al., "Results of the First Phase I/II Clinical Vaccination Trial with Direct Injection of mRNA," J. Immunotherapy, Feb. 2008, 31(2):180-188.
Weissman, "mRNA transcript therapy," Expert Rev Vaccines., Feb. 2015, 14(2):265-81.
Wen et al., "New Approaches for Immunization and Therapy against Human Metapneumovirus," Clin Vaccine Immunol., Aug. 2015, 22(8):858-866.
Whitehead et al., "Knocking down barriers: advances in siRNA delivery," Nat Rev Drug Discov., Feb. 2009, 8(2):129-138.
Whitt, "Generation of VSV pseudotypes using recombinant ΔG-VSV for studies on virus entry, identification of entry inhibitors, and immune responses to vaccines," J Virol Methods., Nov. 2010, 169(2):365-374.
Wilhelm et al., "Reduced Neutralization of SARS-Co V-2 Omicron Variant by Vaccine Sera and Monoclonal Antibodies," medRxiv, Dec. 2021, 9 pages.
Williams et al., "Human metapneumovirus isolate TN/92-4 fusion protein gene, complete cds," GenBank Accession No. EF051124.1, Nov. 29, 2007, 2 pages.
Withoff et al., "Replication-defective Recombinant Semliki Forest Virus Encoding GM-CSF as a Vector System for Rapid and Facile Generation of Autologous Human Tumor Cell Vaccines," Gene Therapy, 2001, (8):1515-1523.
Wolff et al., "Direct Gene Transfer into Mouse Muscle in Vivo," Science, Mar. 1990, 247(4949):1465-1468.
Wong et al., "An mRNA vaccine for influenza," Nat Biotechnol., Dec. 2012, 30(12):1202-1204.
Wrapp et al., "Cryo-EM structure of the 2019-nCoV spike in the prefusion conformation," Science, Feb. 19, 2020, 367(6483):1260-3.
Wu et al., "A new coronavirus associated with human respiratory disease in China," Nature, Mar. 12, 2020, 579(7798):265-269.
Wu et al., "mRNA-1273 vaccine induces neutralizing antibodies against spike mutants from global SARS-CoV-2 variants," bioRxiv, Jan. 25, 2021, 20 pages.
Wu et al., "Serum Neutralizing Activity Elicited by mRNA-1273 Vaccine," N Engl J Med., Apr. 15, 2021, 384(15):1468-1470.
Wu et al., "Variant SARS-CoV-2 mRNA vaccines confer broad neutralization as primary or booster series in mice," bioRxiv [Preprint], Oct. 7, 2021; Update in: Vaccine, Dec. 17, 2021, 39(51):7394-7400.
Xia, "Detailed Dissection and Critical Evaluation of the Pfizer/BioNTech and Moderna mRNA Vaccines," Vaccines (Basel), Jul. 3, 2021, 9(7):734, 19 pages.
Yamamoto et al., "Current prospects for mRNA gene delivery," European Journal of Pharmaceutics and Biopharmaceutics, Mar. 2009, 71(3):484-489.
Yang et al., "A DNA vaccine induces SARS coronavirus neutralization and protective immunity in mice," Nature, Apr. 2004, 428(6982):561-564.
Yang et al., "Evasion of Antibody Neutralization in Emerging Severe Acute Respiratory Syndrome Coronaviruses," PNAS, Jan. 18, 2005, 102(3):797-801.
Yang et al., "The structure and functions of coronavirus genomic 3' and 5' ends," Virus Res., Aug. 3, 2015, 206:120-133.
Ye et al., "Rational development of a combined mRNA vaccine against COVID-19 and influenza," NPJ Vaccines, Jul. 26, 2022, 7(1):84.
Yin et al., "Immunogenicity and protective efficacy of recombinant fusion proteins containing spike protein of infectious bronchitis virus and hemagglutinin of H3N2 influenza virus in chickens," Virus Res., Sep. 2, 2016, 223:206-212.
Yin et al., "Non-viral vectors for gene-based therapy," Nat Rev Genet., Aug. 2014, 15(8):541-555.
Yoo et al., "Synthesis and Processing of the Haemagglutinin-Esterase Glycoprotein of Bovine Coronavirus Encoded in the E3 Region of Adenovirus," J. Gen. Virology, 1992, 73:2591-2600.
Youn et al., "Modified mRNA as an alternative to plasmid DNA (pDNA) for transcript replacement and vaccination therapy," Expert Opin Biol Ther., Sep. 2015, 15(9):1337-1348.
Yuan et al., "Cryo-EM structures of MERS-CoV and SARS-Co V spike glycoproteins reveal the dynamic receptor binding domains," Nat Commun., Apr. 10, 2017, 8(1):15092.
Zangi et al., "Modified mRNA directs the fate of heart progenitor cells and induces vascular regeneration after myocardial infarction," Nat Biotechnol., Oct. 2013, 31(10):898-907.
Zeng et al., "Formulation and Delivery Technologies for mRNA Vaccines," Curr Top Microbial Immunol., Jun. 2, 2020, 440:71-110.
Zhang et al., "A Thermostable mRNA Vaccine against COVID-19," Cell, Sep. 3, 2020, 182(5):1271-1283.
Zhang et al., "Delivery of mRNA vaccine with a lipid-like material potentiates antitumor efficacy through Toll-like receptor 4 signaling," Proc Natl Acad Sci U S A, Feb. 9, 2021, 118(6):e2005191118, 12 pages.
Zhang et al., "Prefusion spike protein stabilization through computational mutagenesis," Proteins, Apr. 2021, 89(4):399-408.
Zhao et al., "Key Aspects of Coronavirus Avian Infectious Bronchitis Virus," Pathogens, May 11, 2023, 12(5):698, 14 pages.
Zhao et al., "Lipid Nanoparticles for Gene Delivery," Advances in Genetics, Elsevier, 2014, Chapter 2: 24 pages.
Zhao et al., "Nanoparticle vaccines," Vaccine, Jan. 9, 2014, 32(3):327-37.
Zhou et al., "Current RNA-Based Therapeutics in Clinical Trials," Current Gene Therapy, 2019, 19:172-196.
Zhou et al., "Evidence of escape of SARS-Co V-2 variant B.1.351 from natural and vaccine-induced sera," Cell, Apr. 29, 2021, 184(9):2348-2361.
Zhou et al., "RNA Melanoma Vaccine: Induction of Antitumor Immunity by Human Glycoprotein 100 mRNA Immunization," Hum Gene Ther., Nov. 1999, 10(16):2719-2724.

(56) References Cited

OTHER PUBLICATIONS

Zhukovsky et al., "Heterogeneity of Early Intermediates in Cell-Liposome Fusion Mediated by Influenza Hemagglutinin," Biophys J., Nov. 2006, 91(9):3349-3358.
Ziganshina et al., "Antibody-Dependent Enhancement with a Focus on SARS-CoV-2 and Anti-Glycan Antibodies," Viruses, Jul. 20, 2023, 15(7):1584, 20 pages.
Zumla et al., "Middle East respiratory syndrome," Lancet, Sep. 5, 2015, 386(9997):995-1007.
U.S. Appl. No. 18/272,512, filed Jul. 14, 2023, Carfi.
U.S. Appl. No. 18/272,496, filed Jul. 14, 2023, Carfi.
U.S. Appl. No. 19/294,594, filed Aug. 8, 2025, Carfi.

* cited by examiner

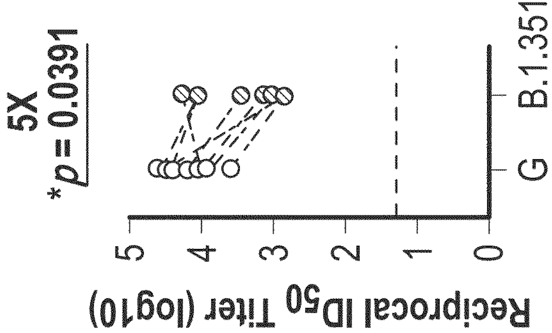
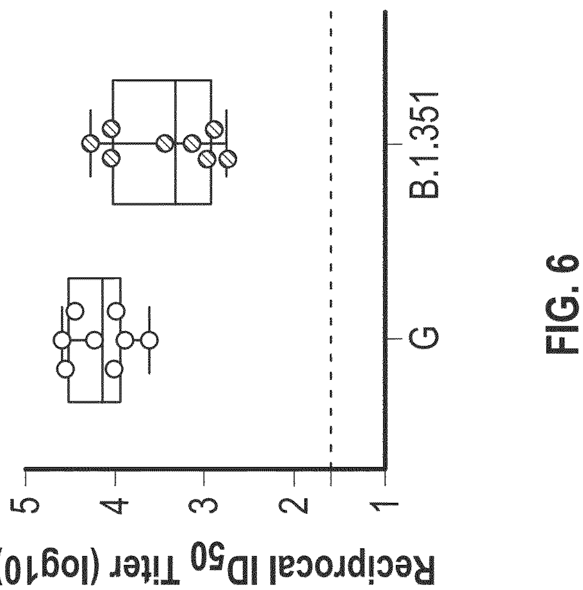
FIG. 6
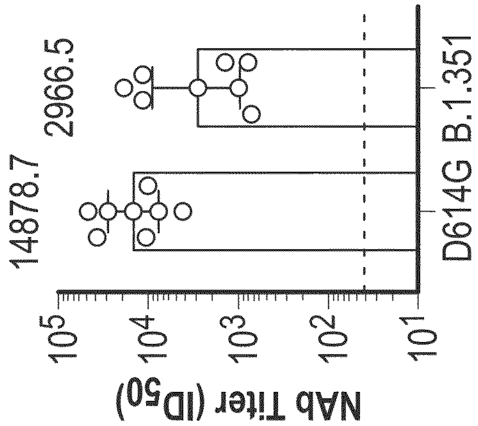

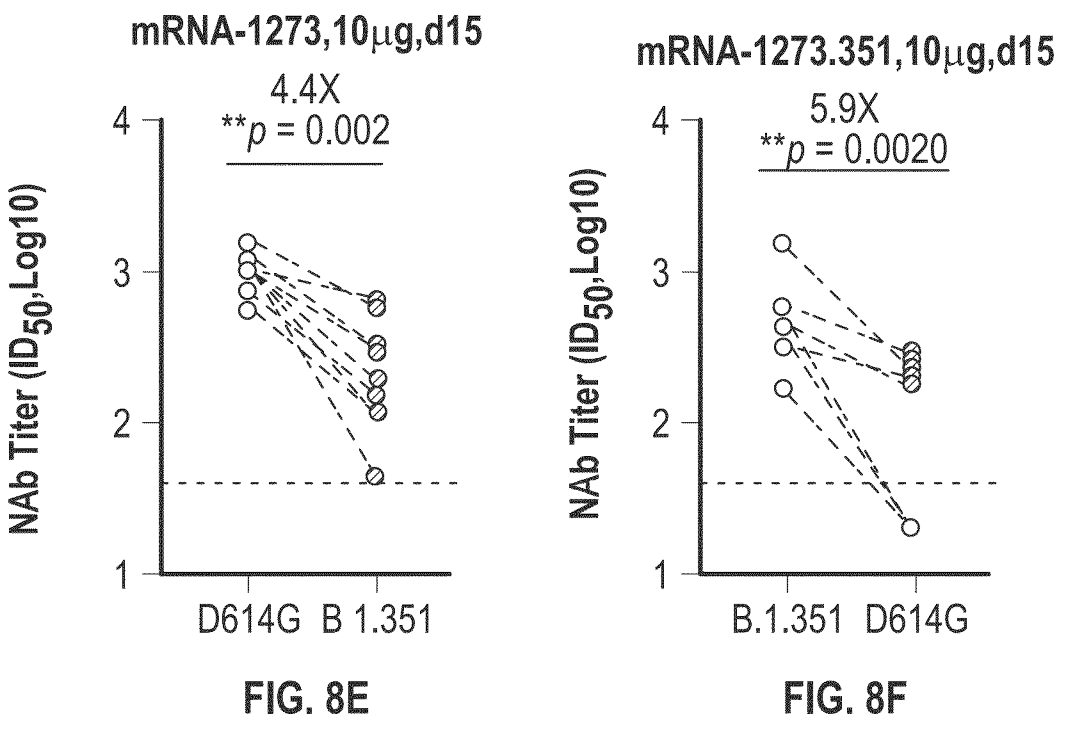
FIG. 8E
FIG. 8F
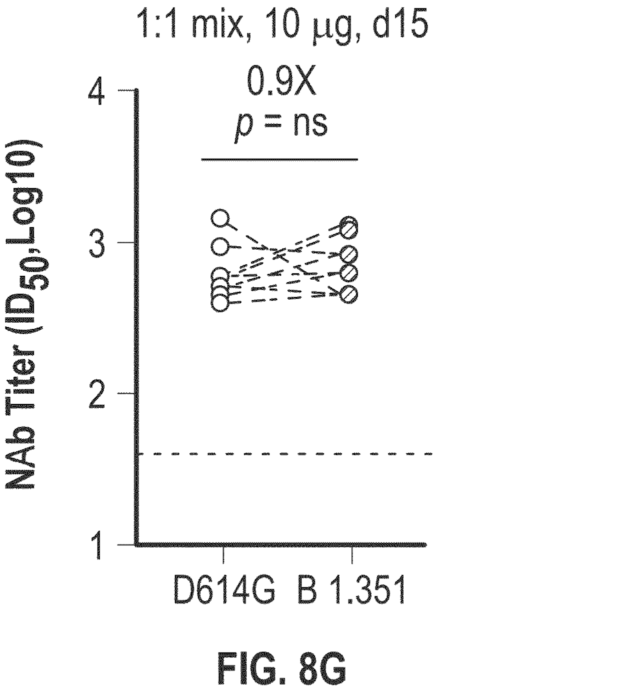
FIG. 8G

□ Two Doses of mRNA-1273,100 µg 1 week post 2nd dose
○ 3rd Dose of mRNA-1273, 50 µg 2 weeks post 3rd dose
◇ 3rd Dose of mRNA-1273.351, 50 µg 2 weeks post 3rd dose Reduction on B.1.351

Relative Titer Change

Virus: D614G

Virus: B.1.351

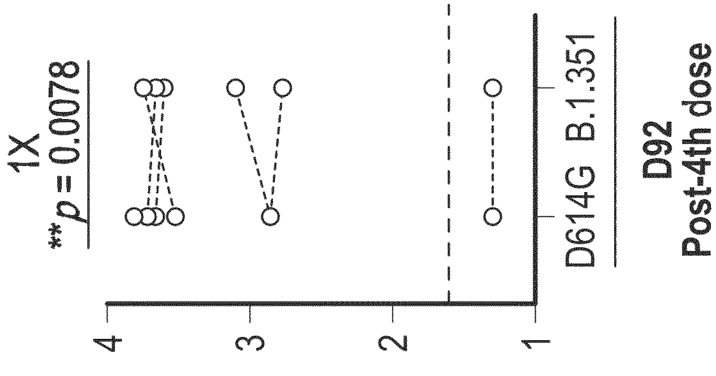
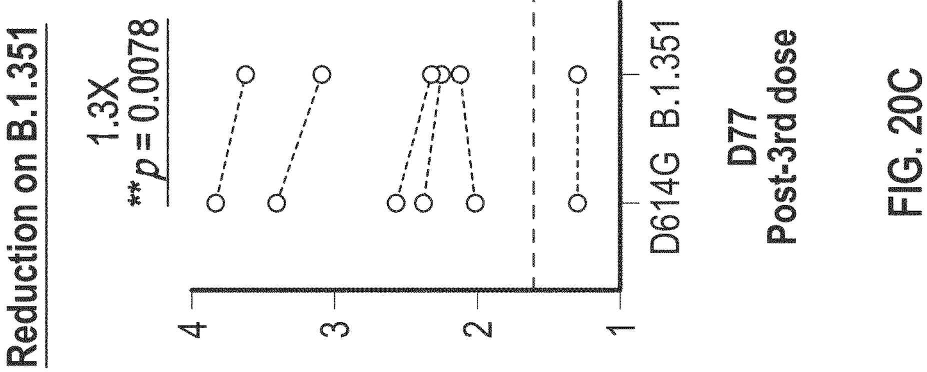
FIG. 20C
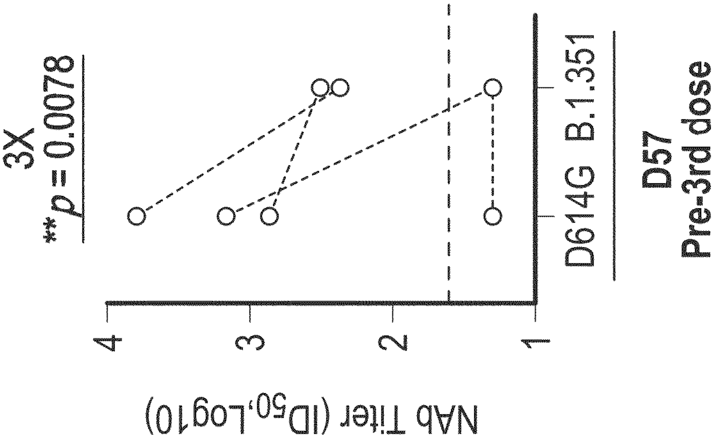

Part B, D15
mRNA-1273, 50ug
4.0X
5.1X
10.2X
2.5X
2.0X
4.1X
6.6X
5025
758
1234
2570
2034
493
978
1268
NAb Titer (ID50, Log10)
5
4
3
2
1
D614G
B.1.351
P.1
Cal.20C
B.1.526
A.VOI.V2
B.1.617.1
B.1.617.2

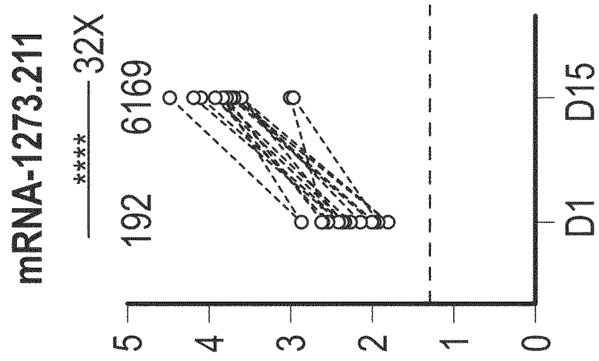
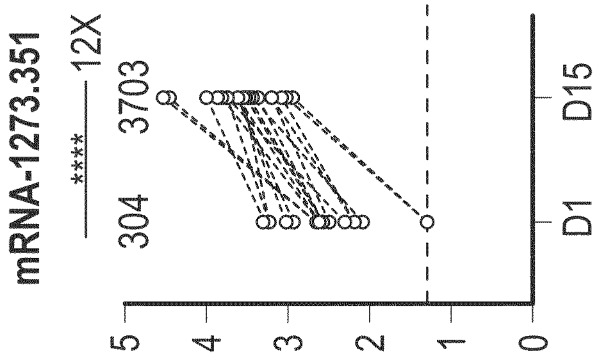
FIG. 34
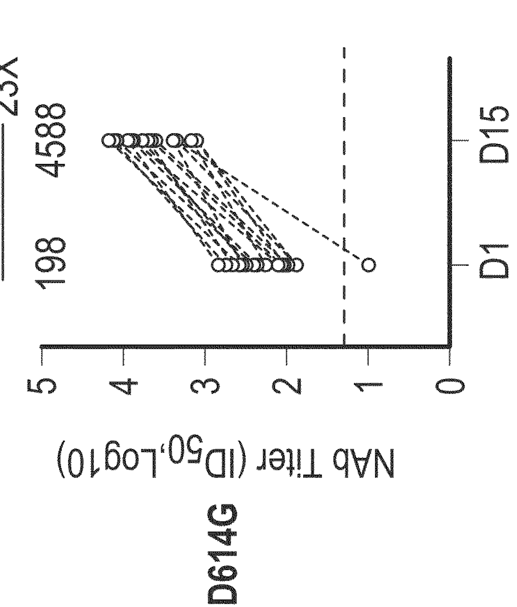

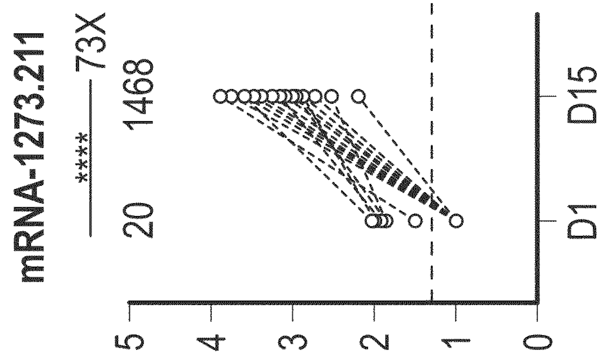
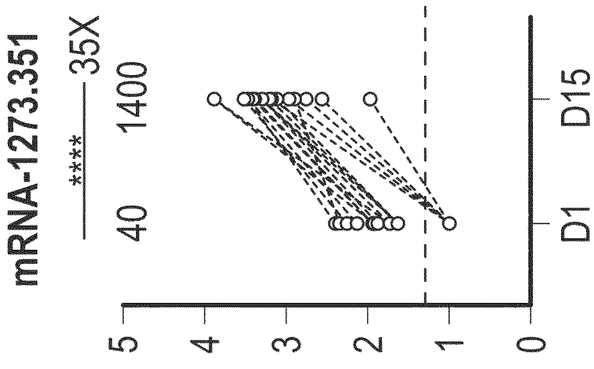
FIG. 34
(Continued)
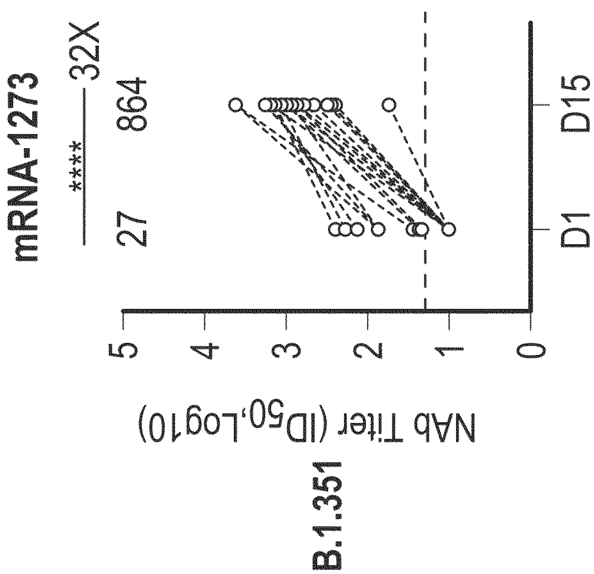

VARIANT STRAIN-BASED CORONAVIRUS VACCINES

RELATED APPLICATIONS

This application is a divisional of U.S. patent application Ser. No. 19/294,594, filed Aug. 8, 2025, which is a continuation of U.S. patent application Ser. No. 18/272,496, filed Jul. 14, 2023, which is a 35 U.S.C. § 371 of International Application No. PCT/US2022/012614, filed Jan. 14, 2022, which claims priority under 35 U.S.C. § 119(e) to U.S. Provisional Patent Application No. 63/138,228, filed Jan. 15, 2021, U.S. Provisional Patent Application No. 63/140,920, filed Jan. 24, 2021, U.S. Provisional Patent Application No. 63/161,433, filed Mar. 15, 2021, U.S. Provisional Patent Application No. 63/173,979, filed Apr. 12, 2021, U.S. Provisional Patent Application No. 63/193,547, filed May 26, 2021, U.S. Provisional Patent Application No. 63/222,925, filed Jul. 16, 2021, U.S. Provisional Patent Application No. 63/241,963, filed Sep. 8, 2021, U.S. Provisional Patent Application No. 63/283,905, filed Nov. 29, 2021, and U.S. Provisional Patent Application No. 63/284,570, filed Nov. 30, 2021, each of which are hereby incorporated by reference in their entireties.

SEQUENCE LISTING

This application contains a Sequence Listing that has been submitted electronically as an XML file named 45817-0208003_SL_ST26.xml. The XML file, created on Jan. 20, 2026, is 173,789 bytes in size. The material in the XML file is hereby incorporated by reference in its entirety.

BACKGROUND

Human coronaviruses are highly contagious enveloped, positive sense single-stranded RNA viruses of the Coronaviridae family. Two sub-families of Coronaviridae are known to cause human disease. The most important being the β-coronaviruses (betacoronaviruses). The β-coronaviruses are common etiological agents of mild to moderate upper respiratory tract infections. Outbreaks of novel coronavirus infections such as the infections caused by a coronavirus initially identified from the Chinese city of Wuhan in December 2019; however, have been associated with a high mortality rate death toll. This recently identified coronavirus, referred to as Severe Acute Respiratory Syndrome Coronavirus 2 (SARS-CoV-2) (formerly referred to as a "2019 novel coronavirus," or a "2019-nCoV") has rapidly infected hundreds of thousands of people. The pandemic disease that the SARS-CoV-2 virus causes has been named by World Health Organization (WHO) as COVID-19 (Coronavirus Disease 2019). The first genome sequence of a SARS-CoV-2 isolate (Wuhan-Hu-1; USA-WA1/2020 isolate) was released by investigators from the Chinese CDC in Beijing on Jan. 10, 2020 at Virological, a UK-based discussion forum for analysis and interpretation of virus molecular evolution and epidemiology. The sequence was then deposited in GenBank on Jan. 12, 2020, having Genbank Accession number MN908947.1. Subsequently, a number of SARS-CoV-2 strain variants have been identified, some of which are more infectious than the SARS-CoV-2 isolate.

As of the time of worldwide emergency use authorization of the authorized SARS-CoV-2 nucleic acid-based vaccines, there is not yet a strategy for combatting the recently-discovered and later-emerging SARS-CoV-2 variants of concern (VOC). The continuing health problems and mortality associated with coronavirus infections, particularly the SARS-CoV-2 pandemic, are of tremendous concern internationally. The public health crisis caused by SARS-CoV-2 and its variants reinforces the importance of rapidly developing effective and safe vaccine candidates against these viruses.

The emergence of SARS-CoV-2 variants with substitutions in the receptor binding domain (RBD) and N-terminal domain (NTD) of the viral S protein has raised concerns among scientists and health officials. The entry of coronavirus into host cells is mediated by interaction between the RBD of the viral S protein and host angiotensin-converting enzyme 2 (ACE2). Vaccine development has focused on inducing antibody responses against this region of SARS-CoV-2 S protein. More recently, a neutralization "supersite" has also been identified in the NTD. A significant decrease in vaccine efficacy has been correlated with amino acid substitutions in the RBD (eg, K417N, E484K, and N501Y) and NTD (eg, L18F, D80A, D215G, and Δ242-244) of the S protein. Some of the most recently circulating isolates containing these substitutions from the United Kingdom (B.1.1.7, Alpha), Republic of South Africa (B.1.351, Beta), Brazil (P.1 lineage, Gamma), New York (B.1.526, Iota), and California (B.1.427/B.1.429 or CAL.20C lineage, Epsilon), have shown a reduction in neutralization from convalescent serum in pseudovirus neutralization (PsVN) assays and resistance to certain monoclonal antibodies. In particular, mutations in the NTD subdomain, and specifically the neutralization supersite, are most extensive in the B.1.351 lineage virus. See McCallum, M. et al. N-terminal domain antigenic mapping reveals a site of vulnerability for SARS-CoV-2. *Cell*, doi:10.1016/j.cell.2021.03.028 (2021).

Using 2 orthogonal vesicular stomatitis virus (VSV) and lentivirus PsVN assays expressing S variants of 20E (EU1), 20A.EU2, D614G-N439K, mink cluster 5, B.1.1.7, P.1, B.1.427/B.1.429, B.1.1.7+E484K, and B.1.351, the assessment of the neutralizing capacity of sera from Phase 1 participants and non-human primates (NHPs) that received 2 doses of mRNA-1273 was reported. See Wu, K. et al. Serum Neutralizing Activity Elicited by mRNA-1273 Vaccine. *N Engl J Med*, doi:10.1056/NEJMc2102179 (2021). Subsequent studies demonstrated reduced neutralization titers against the full B.1.351 variant following mRNA-1273 vaccination, although levels are still significant and expected to be protective. Despite this prediction of continued efficacy of mRNA-1273 against this key variant of concern, the duration of vaccine mediated protection is still unknown.

There remains a need for development and evaluation of further COVID-19 vaccines against SARS-CoV-2 variants encoding the prefusion stabilized S protein of SARS-CoV-2 that incorporates key mutations present in variants, including L18F, D80A, D215G, L242-244del, R246I, K417N, E484K, N501Y, D614G, A701V, A67V, Δ69-70, T951, G142D/A143-145, Δ211/L212I, ins214EPE, G339D, S371L, S373P, S375F, N440K, G446S, S477N, T478K, E484A, Q493K, G496S, Q498R, Y505H, T547K, H655Y, N679K, P681H, N764K, D796Y, N856K, Q954H, N969K, L981F, and any combination thereof. Additional vaccines are necessary to expand the breadth of coverage to multiple circulating variants as well as the ancestral wild-type virus that is still circulating globally.

SUMMARY

A SARS-CoV-2 vaccine, mRNA-1273 (developed by Moderna Therapeutics), has been shown to elicit high viral neutralizing titers in Phase 1 trial human participants (Jackson et al, 2020; Anderson et al, 2020) and is highly efficacious in prevention of symptomatic COVID-19 disease and severe disease (Baden et al., 2020). However, the recent emergence of SARS-CoV-2 variants in the United Kingdom (B.1.1.7 lineage; alpha) and in South Africa (B.1.351 lineage; beta) have raised concerns due to their increased rates of transmission as well as their potential to circumvent immunity elicited by natural infection or vaccination (Volz et al., 2021; Tegally et al., 2020; Wibmer et al., 2021; Wang et al., 2021; Collier et al., 2021).

First detected in September 2020 in South England, the SARS-CoV-2 B.1.1.7 variant (alpha variant) has spread at a rapid rate and is associated with increased transmission and higher viral burden (Rambaut et al., 2020). This variant has seventeen mutations in the viral genome. Among them, eight mutations are located in the spike (S) protein, including 69-70 del, Y144 del, N501Y, A570D, P681H, T716I, S982A and D1118H. Two key features of this variant, the 69-70 deletion and the N501Y mutation in S protein, have generated concern among scientists and policy makers in the UK based on increased transmission and potentially increased mortality, resulting in further shutdowns. The 69-70 deletion is associated with reduced sensitivity to neutralization by SARS-CoV-2 human convalescent serum samples (Kemp et al, 2021). N501 is one of the six key amino acids interacting with ACE-2 receptor (Starr et al. 2020), and the tyrosine substitution has been shown to have increased binding affinity to the ACE-2 receptor (Chan et al., 2020).

The B.1.351 variant (beta variant) emerged in South Africa over the past few months, and, similar to the B.1.1.7 variant, increased rates of transmission and higher viral burden after infection have been reported (Tegally et al., 2020). The mutations located in the S protein are more extensive than the B.1.1.7 variant with changes of L18F, D80A, D215G, L242-244del, R246I, K417N, E484K, N501Y, D614G, and A701V, with three of these mutations located in the RBD (K417N, E484K, N501Y). B.1.351 shares key mutations in the RBD with a reported variant in Brazil (Tegally et al., 2020; Naveca et al., 2021). As the RBD is the predominant target for neutralizing antibodies, these mutations could impact the effectiveness of monoclonal antibodies already approved and in advanced development as well as of polyclonal antibody elicited by infection or vaccination in neutralizing the virus (Greaney et al., 2021, Wibmer et al, 2021).

Recent data have suggested that the key mutation present in the B.1.351 variant, E484K, confers resistance to SARS-CoV-2 neutralizing antibodies, potentially limiting the therapeutic effectiveness of monoclonal antibody therapies (Wang et al., 2021; Greaney et al., 2020; Weisblum et al., 2020; Liu et al., 2020; Wibmer et al., 2021). Moreover, the E484K mutation was shown to reduce neutralization against a panel of convalescent sera (Weisblum et al., 2020; Liu et al., 2020; Wibmer et al., 2021). In terms of vaccination, it is clear that mRNA-1273 induces significantly higher neutralizing titers than convalescent sera against the USA-WA1/2020 isolate (Jackson et al, 2020). A recent study using a recombinant VSV PsVN assay showed that sera of mRNA-1273 vaccinated participants had reduced neutralizing titers against E484K or K417N/E484K/N50Y combination (Wang et al, 2021), however there has been no assessment of sera from mRNA-1273 clinical trial participants against the full constellation of S mutations found in the B.1.1.7 or B.1.351 variants.

Neutralization of sera from mRNA-1273 vaccinated Phase 1 clinical trial participants against recombinant VSV-based SARS-CoV-2 PsVN assay with S protein from the original USA-WA1/2020 isolate, D614G variant, the B.1.1.7 and B.1.351 variants, and variants that have previously emerged (20E, 20A.EU2, D614G-N439K, and mink cluster 5 variant) was examined (data discussed in the Examples). The effect of both single mutations and combinations of mutations present in the RBD region of the S protein was assessed. In addition, orthogonal assessments in VSV and pseudotyped lentiviral neutralization assays were performed on sera from NHPs that received the mRNA-1273 vaccine at two different dose levels, as this has been a useful preclinical model for vaccine induced immunogenicity and protection. Using both of these assays provided confirmatory data on pseudovirus neutralization. Overall, this comprehensive pseudovirus neutralization analysis in humans and non-human primates that received mRNA-1273 provides a critical demonstration necessary to elucidate how vaccines may be impacted by SARS-CoV-2 variants.

The invention pertains, inter alia, to vaccines comprising a nucleic acid encoding a SARS-CoV-2 antigen, which varies by at least one amino acid mutation from the SARS-CoV-2 2P spike antigen (encoded by mRNA-1273). Such a vaccine, optionally referred to herein as a variant vaccine, can be administered to seropositive or seronegative subjects. For example, a subject may be naïve and not have antibodies that react with SARS-CoV-2 or may have preexisting antibodies to SARS-CoV-2 because they have previously had an infection with SARS-CoV-2 or may have previously been administered a dose of a vaccine (e.g., an mRNA vaccine) that induces antibodies against SARS-CoV-2. A variant vaccine may be the only vaccine comprising a nucleic acid encoding a SARS-CoV-2 antigen that a subject receives. Alternatively, a variant vaccine may be administered in combination with other vaccines comprising a nucleic acid encoding a SARS-CoV-2 antigen, as a prime and/or boost dose.

Thus, the disclosure, in some aspects provides a method comprising administering to a subject a vaccine comprising a nucleic acid encoding a SARS-CoV-2 spike antigen, optionally a 2P stabilized spike antigen of a second circulating SARS-CoV-2 virus, wherein the subject has previously been administered a first vaccine comprising a nucleic acid encoding a first SARS-CoV-2 2P stabilized spike antigen of a first circulating SARS-CoV-2 virus, and wherein each of the first and second 2P stabilized spike antigens are administered in an effective amount to induce an immune response specific for the first antigen and the second antigen, wherein the second circulating SARS-CoV-2 virus has a spike protein having an amino acid sequence with at least one amino acid mutation with respect to a spike protein amino acid sequence of the first circulating SARS-CoV-2 virus, and wherein the mutation is an amino acid substitution, deletion or insertion.

In some aspects, the disclosure provides a method comprising administering to a subject a first vaccine comprising a nucleic acid encoding a first SARS-CoV-2 2P stabilized spike antigen and administering to the subject a second vaccine comprising a nucleic acid encoding a second SARS-CoV-2 2P spike antigen, optionally a 2P stabilized spike antigen, wherein each of the nucleic acids encoding the first and second stabilized spike antigens are administered in an effective amount to induce an immune response specific for the respective encoded antigens, wherein the second encoded SARS-CoV-2 spike antigen has an amino acid sequence with at least one amino acid mutation with respect to the first encoded spike protein amino acid sequence, and wherein the mutation is an amino acid substitution, deletion, or insertion.

In another aspect, the disclosure provides a method comprising administering to a subject a first vaccine comprising a nucleic acid encoding a first SARS-CoV-2 2P stabilized spike antigen and administering to the subject a second vaccine comprising a nucleic acid encoding a second SARS-CoV-2 2P spike antigen, optionally a 2P stabilized spike antigen, wherein each of the nucleic acids encoding the first and second stabilized spike antigens are administered in an effective amount to induce an immune response specific for the respective encoded antigens, wherein the second encoded SARS-CoV-2 spike antigen has an amino acid sequence with at least one amino acid mutation with respect to the first encoded spike protein amino acid sequence, wherein the mutation is an amino acid substitution, deletion, or insertion, and wherein the first encoded SARS-CoV-2 spike antigen is of a first circulating SARS-CoV-2 virus and wherein the second encoded SARS-CoV-2 spike antigen is of a second circulating SARS-CoV-2 virus.

In some aspects, the disclosure provides a method comprising administering to a subject a first vaccine comprising a nucleic acid encoding a first SARS-CoV-2 2P stabilized spike antigen and administering to the subject a second vaccine comprising a nucleic acid encoding a second SARS-CoV-2 2P spike antigen, optionally a 2P stabilized spike antigen, wherein each of the nucleic acids encoding the first and second stabilized spike antigens are administered in an effective amount to induce an immune response specific for the respective encoded antigens, wherein the second encoded SARS-CoV-2 spike antigen has an amino acid sequence with at least one amino acid mutation with respect to the first encoded spike protein amino acid sequence, wherein the mutation is an amino acid substitution, deletion, or insertion, and wherein the first encoded SARS-CoV-2 spike antigen is representative of a first circulating SARS-CoV-2 virus and wherein the second encoded SARS-CoV-2 spike antigen is representative of a second circulating SARS-CoV-2 virus.

In some aspects, the disclosure provides a method comprising administering to a subject a first vaccine comprising a nucleic acid encoding a first SARS-CoV-2 2P stabilized spike antigen and administering to the subject a second vaccine comprising a nucleic acid encoding a second SARS-CoV-2 2P spike antigen, optionally a 2P stabilized spike antigen, wherein each of the nucleic acids encoding the first and second stabilized spike antigens are administered in an effective amount to induce an immune response specific for the respective encoded antigens, wherein the second encoded SARS-CoV-2 spike antigen has an amino acid sequence with at least one amino acid mutation with respect to the first encoded spike protein amino acid sequence, wherein the mutation is an amino acid substitution, deletion, or insertion, and wherein the first encoded SARS-CoV-2 spike antigen is representative of a plurality of first circulating SARS-CoV-2 viruses and/or wherein the second encoded SARS-CoV-2 spike antigen is representative of a second plurality of circulating SARS-CoV-2 viruses.

In some embodiments, the second circulating SARS-CoV-2 virus is an immunodominant emerging strain detected during a period when the first circulating SARS-CoV-2 virus is present in a subject population. In some embodiments, the second circulating SARS-CoV-2 virus and the first circulating SARS-CoV-2 virus are detectable in a subject population within at least one year. In some embodiments, the second circulating SARS-CoV-2 virus and the first circulating SARS-CoV-2 virus are detectable in a subject population during a same season. In some embodiments, the second circulating SARS-CoV-2 virus and the first circulating SARS-CoV-2 virus are detectable in a subject population during a same pandemic or endemic.

In some embodiments, the first nucleic acid encoding the SARS-CoV-2 2P stabilized spike antigen is a first nucleic acid encoding the first SARS-CoV-2 2P stabilized spike antigen.

In some embodiments, the first nucleic acid is a DNA or RNA. In some embodiments, the RNA is a messenger RNA (mRNA). In some embodiments, the nucleic acid encoding a second SARS-CoV-2 2P stabilized spike antigen of a second circulating SARS-CoV-2 virus is s second nucleic acid and is a messenger RNA (mRNA).

In some embodiments, the vaccine comprises the nucleic acid encoding the first SARS-CoV-2 spike antigen in combination with one or more additional spike protein-encoding nucleic acids. In some embodiments, the vaccine comprises the nucleic acid encoding the first SARS-CoV-2 spike antigen in combination with one or more additional nucleic acids encoding one or more SARS-CoV-2 antigens that are not spike protein-encoding nucleic acids.

In some embodiments, the immune response is a neutralizing antibody response against SARS-CoV-2. In some embodiments, the immune response is a T cell response against SARS-CoV-2.

In some embodiments, the first encoded antigen is administered to the subject as a first vaccine comprised of one or more prime or priming immunization and the second encoded antigen is administered to the subject as a boost.

In some embodiments, the second encoded antigen is administered to the subject as first vaccine comprised of one or more prime or priming immunizations and the first encoded antigen is administered to the subject as a boost.

In some embodiments, the first and second encoded antigens are administered to the subject together as a boost.

In some embodiments, the first encoded antigen is administered to the subject as a prime or priming immunization and as a boost to complete a vaccination.

In some embodiments, the first encoded antigen is administered to the subject as a prime or priming immunization and as a boost in an initial vaccination and the second encoded antigen is administered to the subject as a boost more than 3 months after the initial vaccination. In some embodiments, the first encoded antigen is administered to the subject as a prime or priming immunization and as a boost in an initial vaccination and the second encoded antigen is administered to the subject as a boost more than 6 months after the initial vaccination. In some embodiments, the boost is a seasonal boost or a pandemic shift boost. In some embodiments, the boost dose is 50 μg.

In some embodiments, the first antigen is a mRNA encoding the first SARS-CoV-2 spike antigen and wherein the spike antigen has an amino acid sequence of SEQ ID NO: 20. In some embodiments, the second antigen is a mRNA encoding the second SARS-CoV-2 spike antigen, wherein the spike antigen has an amino acid sequence with at least one amino acid mutation with respect to a protein of SEQ ID NO: 20, and wherein the mutation is an amino acid substitution, deletion or insertion.

In some aspects, the disclosure provides a composition comprising: a first messenger ribonucleic acid (mRNA) encoding a first SARS-CoV-2 spike antigen of a first circulating SARS-CoV-2 virus wherein the first SARS-CoV-2 spike antigen has an amino acid sequence of SEQ ID NO: 20 or an amino acid sequence with at least one amino acid mutation with respect to a protein of SEQ ID NO: 20 and a second mRNA encoding a second SARS-CoV-2 spike antigen of a second circulating SARS-CoV-2 virus, wherein the second SARS-CoV-2 spike antigen has an amino acid sequence with at least one amino acid mutation with respect to a protein of SEQ ID NO: 20, wherein the wherein the mutation is an amino acid substitution, deletion or insertion, and wherein the first SARS-CoV-2 spike antigen and the second SARS-CoV-2 spike antigen are different from one another.

In some embodiments, the composition further comprises a third messenger ribonucleic acid (mRNA) encoding a third SARS-CoV-2 spike antigen of a third SARS-CoV-2 virus, wherein the third SARS-CoV-2 spike antigen has an amino acid sequence with at least one amino acid mutation with respect to a protein of SEQ ID NO: 20, and wherein the mutation is an amino acid substitution, deletion or insertion.

In some embodiments, the composition further comprises a fourth messenger ribonucleic acid (mRNA) encoding a fourth SARS-CoV-2 spike antigen of a fourth SARS-CoV-2 virus, wherein the fourth SARS-CoV-2 spike antigen has an amino acid sequence with at least one amino acid mutation with respect to a protein of SEQ ID NO: 20, and wherein the mutation is an amino acid substitution, deletion or insertion.

In some embodiments, the composition further comprises a fifth messenger ribonucleic acid (mRNA) encoding a fifth SARS-CoV-2 spike antigen of a fifth SARS-CoV-2 virus, wherein the fifth SARS-CoV-2 spike antigen has an amino acid sequence with at least one amino acid mutation with respect to a protein of SEQ ID NO: 20, and wherein the mutation is an amino acid substitution, deletion or insertion.

In some embodiments, the composition further comprises a sixth messenger ribonucleic acid (mRNA) encoding a sixth SARS-CoV-2 spike antigen of a sixth SARS-CoV-2 virus, wherein the sixth SARS-CoV-2 spike antigen has an amino acid sequence with at least one amino acid mutation with respect to a protein of SEQ ID NO: 20, and wherein the mutation is an amino acid substitution, deletion or insertion.

In some embodiments, the first and second virus strains, and optionally the third, fourth, fifth and sixth virus strains are spreading in the population for at least a portion of 1 year.

The disclosure, in some aspects, provides a messenger ribonucleic acid (mRNA) encoding a SARS-CoV-2 2P stabilized spike protein, wherein the 2P stabilized spike protein has an amino acid sequence with at least one amino acid mutation with respect to a protein of SEQ ID NO: 20, wherein the mutation is an amino acid substitution, deletion or insertion, and wherein the 2P stabilized spike protein is a 2P stabilized version of a spike protein from a second circulating SARS-CoV-2 virus strain, and wherein a first circulating SARS-CoV-2 virus strain comprises a spike protein of SEQ ID NO: 36.

In some aspects of the disclosure, an mRNA encoding a protein having at least 90% or 95% sequence identity to a protein of any one of SEQ ID NOs: 5, 8, 11, 14, 17, 30, 33, 36, 39, and 42 is provided.

In some aspects of the disclosure, an mRNA having at least 90% or 95% sequence identity to an RNA of any one of SEQ ID NOs: 1, 6, 9, 12, 15, 28, 31, 34, 37, 40, 43, and 45 is provided.

In some aspects of the disclosure, an mRNA having at least 98% sequence identity to an RNA of any one of SEQ ID NOs: 1, 6, 9, 12, 15, 28, 31, 34, 37, 40, 43, and 45 is provided.

In some aspects of the disclosure, an mRNA comprising any one of SEQ ID NOs: 1, 6, 9, 12, 15, 28, 31, 34, 37, 40, 43, and 45 is provided.

In some embodiments, the mRNA comprises a chemical modification. In some embodiments, the mRNA is fully modified. In some embodiments, the chemical modification is 1-methylpseudouridine.

In some embodiments, the mRNAs are in a lipid nanoparticle and wherein the lipid nanoparticle comprises an ionizable amino lipid, a sterol, a neutral lipid, and a polyethylene glycol (PEG)-modified lipid. In some embodiments, the lipid nanoparticle comprises 40-55 mol % ionizable amino lipid, 30-45 mol % sterol, 5-15 mol % neutral lipid, and 1-5 mol % PEG-modified lipid. In some embodiments, the lipid nanoparticle comprises 40-50 mol % ionizable amino lipid, 35-45 mol % sterol, 10-15 mol % neutral lipid, and 2-4 mol % PEG-modified lipid. In some embodiments, the lipid nanoparticle comprises 45 mol %, 46 mol %, 47 mol %, 48 mol %, 49 mol %, or 50 mol % ionizable amino lipid.

In some embodiments, the ionizable amino lipid has the structure of Compound 1:

(Compound 1)

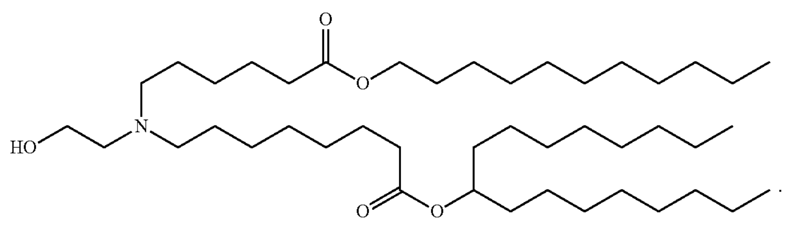

In some embodiments, the sterol is cholesterol or a derivative thereof. In some embodiments, the neutral lipid is 1,2 distearoyl-sn-glycero-3-phosphocholine (DSPC). In some embodiments, the PEG-modified lipid is 1,2 dimyristoyl-sn-glycerol, methoxypolyethyleneglycol (PEG2000 DMG).

The disclosure, in some aspects, provides a composition comprising: a first messenger ribonucleic acid (mRNA) encoding a first SARS-CoV-2 spike antigen of a first circulating SARS-CoV-2 virus wherein the first SARS-CoV-2 spike antigen has an amino acid sequence of SEQ ID NO: 20 and a second mRNA encoding a second SARS-CoV-2 spike antigen of a second circulating SARS-CoV-2 virus, wherein the second SARS-CoV-2 spike antigen has an amino acid sequence with at least one amino acid mutation with respect to a protein of SEQ ID NO: 20, wherein the mutation is an amino acid substitution, deletion or insertion, and wherein the first SARS-CoV-2 spike antigen and the second SARS-CoV-2 spike antigen are different from one another.

In some embodiments, the wherein the first SARS-CoV-2 spike antigen has an amino acid sequence with at least one amino acid mutation with respect to a protein of SEQ ID NO: 20, wherein the mutation is an amino acid substitution, deletion, or insertion.

The disclosure, in some aspects, provides a method comprising administering to a subject a vaccine comprising a first nucleic acid encoding a SARS-CoV-2 2P stabilized spike antigen, wherein the spike antigen has an amino acid sequence with at least one amino acid mutation with respect to a protein of SEQ ID NO: 20, and wherein the mutation is an amino acid substitution, deletion or insertion, wherein the subject is seropositive for a SARS-CoV-2 antigen of SEQ ID NO. 21 or 20.

Another aspect of the disclosure provides a method comprising administering to a subject a vaccine comprising a first nucleic acid encoding a SARS-CoV-2 2P stabilized spike antigen, wherein the spike antigen has an amino acid sequence with at least one amino acid mutation with respect to a protein of SEQ ID NO: 20, and wherein the mutation is an amino acid substitution, deletion or insertion, wherein the subject is seronegative for a SARS-CoV-2 antigen of SEQ ID NO. 21 or 20.

In some embodiments, the subject is administered a second dose of the vaccine between 2 weeks and 1 year after the first dose of vaccine is administered. In some embodiments, the subject is administered a second vaccine between 2 weeks and 1 year after the vaccine is administered, wherein the second vaccine comprises a second nucleic acid encoding a SARS-CoV-2 2P stabilized spike antigen of SEQ ID NO: 20. In some embodiments, the second vaccine comprises a mixture of the first and second nucleic acids, wherein the first nucleic acid and the second nucleic acid are present in the second vaccine at a ratio of 1:1.

In some embodiments, 50 μg of the vaccine comprising a nucleic acid encoding a SARS-CoV-2 spike antigen, optionally, a 2P stabilized spike antigen of a third circulating SARS-CoV-2 virus is administered to the subject. In some embodiments, the subject is administered an effective dose of the vaccine. In some embodiments, effective dose is 20 μg-50 μg. In some embodiments, the effective dose is 20 μg. In some embodiments, the effective dose is 25 μg. In some embodiments, the effective dose is 30 μg. In some embodiments, the effective dose is 40 g. In some embodiments, the effective dose is 50 μg.

In some embodiments, the vaccine comprises a nucleic acid encoding a SARS-CoV-2 spike antigen having at least 95% sequence identity to SEQ ID NO: 11. In some embodiments, the vaccine comprises a nucleic acid having at least 95% sequence identity to SEQ ID NO: 9. In some embodiments, the vaccine comprises a nucleic acid comprising SEQ ID NO: 9.

In some embodiments, the vaccine comprises a nucleic acid encoding a SARS-CoV-2 spike antigen having at least 95% sequence identity to SEQ ID NO: 30. In some embodiments, the vaccine comprises a nucleic acid having at least 95% sequence identity to SEQ ID NO: 28. In some embodiments, the vaccine comprises a nucleic acid comprising SEQ ID NO: 28.

In some embodiments, the vaccine comprises a nucleic acid encoding a SARS-CoV-2 spike antigen having at least 95% sequence identity to SEQ ID NO: 26. In some embodiments, the vaccine comprises a nucleic acid having at least 95% sequence identity to SEQ ID NO: 24. In some embodiments, the vaccine comprises a nucleic acid comprising SEQ ID NO: 24.

In some embodiments, the first vaccine or the second vaccine comprises: (a) a nucleic acid encoding a SARS-CoV-2 spike antigen comprising two proline substitutions; and (b) a nucleic acid encoding a SARS-CoV-2 spike antigen comprising SEQ ID NO: 11. In some embodiments, the first vaccine or the second vaccine comprises: (a) a nucleic acid encoding a SARS-CoV-2 spike antigen comprising two proline substitutions; and (b) a nucleic acid encoding a SARS-CoV-2 spike antigen comprising SEQ ID NO: 26. In some embodiments, the first vaccine or the second vaccine comprises: (a) a nucleic acid encoding a SARS-CoV-2 spike antigen comprising two proline substitutions; and (b) a nucleic acid encoding a SARS-CoV-2 spike antigen comprising SEQ ID NO: 30.

In some embodiments, the ratio of (a) to (b) is 1:1, 1:2, 1:3, 1:4, 2:1, 3:1, or 4:1.

In some embodiments, the second vaccine comprises: (a) the nucleic acid encoding a first SARS-CoV-2 2P spike antigen of a first circulating SARS-CoV-2 virus; and (b) the nucleic acid encoding a second SARS-CoV-2 2P spike antigen of a second circulating SARS-CoV-2 virus. In some embodiments, the ratio of (a) to (b) is 1:1, 1:2, 1:3, 1:4, 2:1, 3:1, or 4:1.

The disclosure, in some aspects provides a composition comprising 50 μg-250 μg of a first messenger ribonucleic acid (mRNA) comprising a first open reading frame (ORF) that encodes a first SARS-CoV-2 prefusion stabilized spike (S) protein and a second mRNA comprising a second ORF that encodes a second SARS-CoV-2 prefusion stabilized spike (S) protein; and a lipid nanoparticle comprising a mixture of lipids that comprises an ionizable amino lipid, a non-cationic lipid, a sterol, and a PEG-modified lipid.

In some embodiments, the composition comprises 50 μg of mRNA in total. In some embodiments, the ratio of the first mRNA to the second mRNA is 1:1.

In some embodiments, the mRNA comprises a chemical modification. In some embodiments, the mRNA is fully modified. In some embodiments, the chemical modification is 1-methylpseudouridine.

In some embodiments, the mRNA further comprises a 5' cap analog, optionally a 7mG(5')ppp(5')NlmpNp cap. In some embodiments, the mRNA further comprises a poly(A) tail, optionally having a length of 50 to 150 nucleotides (e.g., 100 nucleotides).

In some embodiments, the lipid nanoparticle comprises 40-55 mol % ionizable amino lipid, 30-45 mol % sterol, 5-15 mol % neutral lipid, and 1-5 mol % PEG-modified lipid. In some embodiments, the lipid nanoparticle comprises 40-50 mol % ionizable amino lipid, 35-45 mol % sterol, 10-15 mol % neutral lipid, and 2-4 mol % PEG-modified lipid. In some embodiments, the lipid nanoparticle comprises 45 mol %, 46 mol %, 47 mol %, 48 mol %, 49 mol %, or 50 mol % ionizable amino lipid. In some embodiments, the ionizable amino lipid has the structure of Compound 1:

(Compound 1)

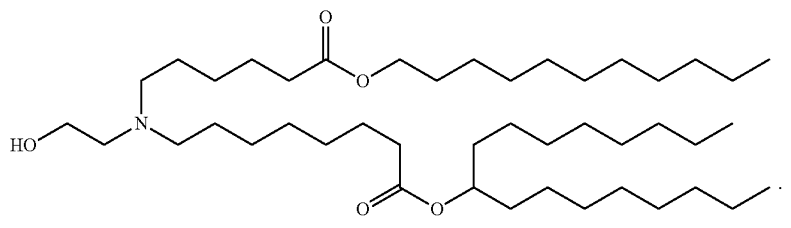

In some embodiments, the sterol is cholesterol or a derivative thereof. In some embodiments, the neutral lipid is 1,2 distearoyl-sn-glycero-3-phosphocholine (DSPC). In some embodiments, the PEG-modified lipid is 1,2 dimyristoyl-sn-glycerol, methoxypolyethyleneglycol (PEG2000 DMG).

In some embodiments, the composition further comprises Tris buffer, sucrose, and sodium acetate, or any combination thereof. In some embodiments, the composition further comprises 30-40 mM Tris buffer, 80-95 mg/mL sucrose, and 5-15 mM sodium acetate. In some embodiments, the composition has a pH value of 6-8, optionally 7.5.

In some embodiments, the disclosure provides a method comprising administering to a human subject, the composition described herein.

In some embodiments, the composition is administered intramuscularly, optionally into a deltoid region of the human subject.

In some embodiments, the human subject has previously been administered a SARS-CoV-2 vaccine. In some embodiments, the SARS-CoV-2 vaccine comprises an mRNA vaccine. In some embodiments, the mRNA vaccine comprises an mRNA comprising an ORF encoding a SARS-CoV-2 prefusion stabilized S protein. In some embodiments, the SARS-CoV-2 prefusion stabilized S protein comprises the first SARS-CoV-2 prefusion stabilized S protein. In some embodiments, the human subject has previously been administered at least one dose of the SARS-CoV-2 vaccine. In some embodiments, the human subject has previously been administered two doses of the SARS-CoV-2 vaccine.

In some embodiments, the method comprises administering the composition to the human subject at least six months after the most recent administration of the SARS-CoV-2 vaccine.

In some embodiments, the composition induces neutralizing antibody titers in the human subject. In some embodiments, the percentage of subjects with seroconversion after a single dose at Day 29 is at least 80%, at least 90%, at least 95% or 100%. In some embodiments, the percentage of subjects with seroconversion after a single dose at Day 29 is 100%.

A further aspect of the disclosure provides a method comprising administering to a subject a booster vaccine comprising a nucleic acid encoding a first SARS-CoV-2 antigen from a first SARS-CoV-2 virus, wherein the subject has previously been administered at least one prime dose of a first vaccine comprising a first nucleic acid encoding the SARS-CoV-2 antigen of the first the SARS-CoV-2 virus, wherein the booster vaccine is administered in an effective amount to induce a neutralizing immune response against a second SARS-CoV-2 virus, wherein the second SARS-CoV-2 virus comprises a second SARS-CoV-2 antigen, wherein the second SARS-CoV-2 antigen has an amino acid sequence with at least one amino acid mutation with respect to a corresponding protein antigen of the first SARS-CoV-2 virus, wherein the booster vaccine is administered in a dosage of 25-100 μg at least 6 months after a first dose of the first vaccine, and wherein the first antigen is a full length stabilized spike protein having a 2P mutation.

In some embodiments, the booster vaccine is administered in a dosage of 50 μg.

In some embodiments, the booster vaccine is administered at least about 6 months after a second dose of the first vaccine. In some embodiments, the booster vaccine is administered 6-12 months after a second dose of the first vaccine. In some embodiments, the booster vaccine is administered at least about 8 months after a second dose of the first vaccine.

In some embodiments, the boost dose is a seasonal boost or a pandemic shift boost to provide a neutralizing immune response against a plurality of variants of concern.

In some embodiments, the first vaccine or the second vaccine comprises: a nucleic acid encoding a SARS-CoV-2 spike antigen comprising two proline substitutions; and a nucleic acid encoding a SARS-CoV-2 spike antigen comprising SEQ ID NO: 33.

In some embodiments, the first vaccine or the second vaccine comprises: a nucleic acid encoding a SARS-CoV-2 spike antigen comprising two proline substitutions; and a nucleic acid encoding a SARS-CoV-2 spike antigen comprising SEQ ID NO: 36.

In some embodiments, the first vaccine or the second vaccine comprises: a nucleic acid encoding a SARS-CoV-2 spike antigen comprising two proline substitutions; and a nucleic acid encoding a SARS-CoV-2 spike antigen comprising SEQ ID NO: 39.

In some embodiments, the first vaccine or the second vaccine comprises: a nucleic acid encoding a SARS-CoV-2 spike antigen comprising two proline substitutions; and a nucleic acid encoding a SARS-CoV-2 spike antigen comprising SEQ ID NO: 42. In some embodiments, the vaccine comprises a nucleic acid having at least 95% sequence identity to SEQ ID NO: 40. In some embodiments, the vaccine comprises a nucleic acid comprising SEQ ID NO: 40. In some embodiments, the vaccine comprises a nucleic acid having at least 95% sequence identity to SEQ ID NO: 43. In some embodiments, the vaccine comprises a nucleic acid comprising SEQ ID NO: 43. In some embodiments, the vaccine comprises a nucleic acid having at least 95% sequence identity to SEQ ID NO: 45. In some embodiments, the vaccine comprises a nucleic acid comprising SEQ ID NO: 45.

BRIEF DESCRIPTION OF THE DRAWINGS

FIG. 1A shows the data from sera collected four weeks post-boost from Rhesus macaques (NHPs) immunized with 30 μg mRNA encoding Spike protein with two proline substitutions on a prime-boost schedule. FIG. 1B shows the data from sera collected one week post-boost from Phase 1 trial participants immunized with 100 μg mRNA encoding Spike protein with two proline substitutions on a prime-boost schedule. Neutralization was measured by a recombinant VSV-based SARS-CoV-2 pseudovirus neutralization assay incorporating full-length Spike protein of the USA-WA1/2020 isolate (D614) or the indicated Spike variants (from left to right: D614G, A222V-D614G, S477N-D614G, N439K-D614G, mink cluster 5 variant). The horizontal dotted lines indicate the lower limit of quantification (LLOQ). D=D614 of USA-WA1/2020 isolate, G=D614G variant.

FIGS. 3A-3B show the data from the 100 μg mRNA encoding Spike protein with two proline substitutions dose and FIG. 3C shows the data from the 30 μg mRNA encoding Spike protein with two proline substitutions dose. Individual animal numbers from the study are indicated above each graph. G=D614G.

FIG. 6 shows neutralization titers of murine serum samples. Serum was from mice administering 1 μg of mRNA encoding a Spike protein with two proline substitutions. G=D614 variant.

FIGS. 8A-8G show neutralization titers of murine serum samples. Sera were obtained from mice 15 days after administration of PBS (negative control) or 10 μg of mRNA encoding SARS-CoV-2 Spike proteins. FIG. 8A shows neutralization titers of sera obtained from mice administered 10 μg of mRNA-1273 encoding a Spike protein with two proline substitutions. FIG. 8B shows neutralization titers of sera obtained from mice administered 10 μg of mRNA-1273.351 encoding a Spike protein of the SARS-CoV-2 B.1.351 (RSA) variant. FIG. 8C shows neutralization titers of sera obtained from mice administered a 1:1 mixture of mRNA-1273 and mRNA-1273.351 (5 μg of each mRNA, 10 μg total mRNA). FIG. 8D shows neutralization titers of sera obtained from mice administered PBS. FIG. 8E shows a comparison of neutralization titers towards B.1.351 variant Spike protein and D614G variant Spike protein, using sera obtained from mice administered 10 μg mRNA-1273. FIG. 8F shows a comparison of neutralization titers towards B.1.351 variant Spike protein and D614G variant Spike protein, using sera obtained from mice administered 10 μg mRNA-1273.351. FIG. 8G shows a comparison of neutralization titers towards B.1.351 variant Spike protein and D614G variant Spike protein, using sera obtained from mice administered a 1:1 mixture of mRNA-1273 and mRNA-1273.351 (5 μg of each mRNA, 10 μg total mRNA).

FIG. 10A shows binding towards SARS-CoV-2 Spike protein with two proline substitutions. FIG. 10B shows binding towards SARS-CoV-2 B.1.351 (RSA) variant Spike protein with two proline substitutions. FIG. 10C shows binding towards SARS-CoV-2 N protein. FIG. 10D shows binding towards the receptor-binding domain (RBD) of SARS-CoV-2 B.1.351 (RSA) variant Spike protein. Sera were obtained from mice administered PBS, 1 μg, or 10 μg mRNA encoding SARS-CoV-2 Spike protein with two proline substitutions (mRNA-1273), SARS-CoV-2 B.1.351 Spike protein (RSA-full), SARS-CoV-2 Spike protein with two proline substitutions and a D614G mutation (WH202020_NatSP_2P_001_D614G), or a 1:1 mixture of mRNA-1273 and mRNA-1273.351 (0.5 μg or 5 μg of each mRNA, 1 μg or 10 μg total mRNA).

FIG. 13A shows neutralizing assay titers of sera obtained prior to administration of the booster dose, based on neutralization of VSV pseudoviruses expressing a Spike protein with a D614G mutation relative to wild-type sequence (left bar), a Spike protein having the mutations associated with the B.1.351 variant (middle bar), and a Spike protein having the mutations associated with the P.1 variant. FIG. 13B shows neutralizing assay titers of sera obtained 14 days after administration of the booster dose towards the same pseudoviruses expressing the same Spike proteins tested in FIG. 13A. In FIGS. 13A-13B, the geometric mean neutralizing antibody titer, shown above the bar, is denoted by the top of the bar and the 95% confidence intervals are shown by the error bars. FIGS. 13C-13E show the change in neutralizing antibody titers from day 1 (prior to administration of the booster dose) to day 15 (14 days after administration of the booster dose), towards VSV pseudoviruses expressing a D614G Spike protein (FIG. 13C), B.1.351 Spike protein (FIG. 13D), and P.1 Spike protein (FIG. 13E). The fold increases for day 15/day 1 are shown above the bars. ****=p<0.0001 by the Wilcoxon matched-pairs signed rank test. For all plots, the titers for individual participants are shown by the circles. The horizontal dotted lines indicate the lower limit of quantification (LLOQ).

FIG. 14A shows neutralizing assay titers of sera obtained prior to administration of the booster dose, based on neutralization of VSV pseudoviruses expressing a Spike protein with a D614G mutation relative to wild-type sequence (left bar), a Spike protein having the mutations associated with the B.1.351 variant (middle bar), and a Spike protein having the mutations associated with the P.1 variant. FIG. 14B shows neutralizing assay titers of sera obtained 14 days after administration of the booster dose, towards the same pseudoviruses expressing the same Spike proteins tested in FIG. 14A. In FIGS. 14A-14B, the geometric mean neutralizing antibody titer, shown above the bar, is denoted by the top of the bar and the 95% confidence intervals are shown by the error bars. FIGS. 14C-14E show the change in neutralizing antibody titers from day 1 (prior to administration of the booster dose) to day 15 (14 days after administration of the booster dose), towards VSV pseudoviruses expressing a D614G Spike protein (FIG. 14C), B.1.351 Spike protein (FIG. 14D), and P.1 Spike protein (FIG. 14E). The fold increases for day 15/day 1 are shown above the bars. ****=$p<0.0001$ by the Wilcoxon matched-pairs signed rank test. For all plots, the titers for individual participants are shown by the circles. The horizontal dotted lines indicate the lower limit of quantification (LLOQ).

FIGS. 15A-15B show the reduction in neutralizing antibody titers towards B.1.351 Spike protein relative to a D614G Spike protein in sera obtained prior to administration of a booster dose containing 50 μg mRNA-1273 (FIG. 15A), or on day 15, 14 days after booster dose administration (FIG. 15B). FIGS. 15C-15D show the reduction in neutralizing antibody titers towards B.1.351 Spike protein relative to a D614G Spike protein in sera obtained prior administration of a booster dose containing 50 μg mRNA-1273.351 (FIG. 15C), or on day 15, 14 days after booster dose administration (FIG. 15D). FIG. 15E shows neutralizing antibody titers towards pseudoviruses expressing a D614G Spike protein prior to administration of a booster dose (left of dashed line, squares), and neutralizing antibody titers towards a panel of pseudoviruses expressing a D614G, B.1.351, or P.1 Spike protein, 14 days after administration of 50 μg mRNA-1273 (circles) or 50 μg mRNA-1273.351 (diamonds). The horizontal dotted lines indicate the lower limit of quantification (LLOQ). For bar plots, geometric mean neutralizing antibody titer, shown above the bar, is denoted by the top of the box and the 95% confidence intervals are shown by the error bars.

FIG. 16A shows neutralization titers of sera towards pseudoviruses expressing a D614G, B.1.617.1-v1, B.1.617.1-v2, or A.VOI-V2 Spike protein. FIG. 16B shows the relative reduction in neutralization towards B.1.617.1-v1, B.1.617.1-v2, or A.VOI-V2 Spike proteins, relative to D614G Spike protein. FIG. 16C shows neutralization titers towards B.1.617.1-v1 Spike protein, of sera obtained from human subjects that were administered two doses of 100 μg mRNA-1273 (left bar), followed by a booster dose of 50 μg mRNA-1273 ($2^{nd}$ bar), 50 μg mRNA-1273.351 ($3^{rd}$ bar), or 50 μg mRNA-1273.211 ($4^{th}$ bar). Horizontal bars represent the increase in neutralization titers towards B.1.617.1-v1 after administration of a booster dose, relative to sera from subjects administered-only two doses of 100 μg mRNA-1273. The horizontal dotted lines indicate the lower limit of quantification (LLOQ).

FIG. 17A shows the neutralizing antibody titer at each time point, based on neutralization of pseudoviruses comprising a SARS-CoV-2 Spike protein with a D614G mutation (left bars) or the mutations associated with the South Africa B.1.351 variant. FIG. 17B shows, for each Spike protein tested in FIG. 17A, the kinetics of neutralization titers from day 212 through day 248. FIG. 17C shows, at each time point, the relative change in neutralization titers towards a B.1.35.1-Spike-protein compared to a Spike protein comprising only a D614G mutation. FIG. 17D shows reference neutralization titers of sera from day 36, two weeks after a second dose, towards D614G Spike protein. The horizontal dotted lines indicate the lower limit of quantification (LLOQ). For bar plots, geometric mean neutralizing antibody titer, shown above the bar, is denoted by the top of the box and the 95% confidence intervals are shown by the error bars.

FIG. 18A shows the neutralizing antibody titer at each time point, based on neutralization of pseudoviruses comprising a SARS-CoV-2 Spike protein with a D614G mutation (left bars) or the mutations associated with the South Africa B.1.351 variant. FIG. 18B shows, for each Spike protein tested in FIG. 18A, the kinetics of neutralization titers from day 212 through day 248. FIG. 18C shows, at each time point, the relative change in neutralization titers towards a B.1.351 Spike protein compared to a Spike protein comprising only a D614G mutation. FIG. 18D shows reference neutralization titers of sera from day 36, two weeks after a second dose, towards D614G Spike protein. The horizontal dotted lines indicate the lower limit of quantification (LLOQ). For bar plots, geometric mean neutralizing antibody titer, shown above the bar, is denoted by the top of the box and the 95% confidence intervals are shown by the error bars.

FIG. 19A shows the neutralizing antibody titer at each time point, based on neutralization of pseudoviruses comprising a SARS-CoV-2 Spike protein with a D614G mutation (left bars) or the mutations associated with the South Africa B.1.351 variant. FIG. 19B shows, for each Spike protein tested in FIG. 19A, the kinetics of neutralization titers from day 57 through day 92. FIG. 19C shows, at each time point, the relative change in neutralization titers towards a B.1.351 Spike protein compared to a Spike protein comprising only a D614G mutation. The horizontal dotted lines indicate the lower limit of quantification (LLOQ). For bar plots, geometric mean neutralizing antibody titer, shown above the bar, is denoted by the top of the box and the 95% confidence intervals are shown by the error bars.

FIGS. 20A-20C show neutralization titers of murine serum samples. Sera was obtained from mice that were administered 0.1 μg of mRNA-1273 on day 1 (prime dose) and again on day 22 (booster dose). Mice were administered 0.1 μg of mRNA-1273.351, encoding a Spike protein with the mutations associated with the B.1.351 SARS-CoV-2 variant, on day 58 (3rd dose), and day 78 (4th dose). Samples were taken at day 57 (before administration of the 3rd dose), day 77 (before administration of the 4th dose), and day 92 (14 days after administration of the 4th dose). FIG. 20A shows the neutralizing antibody titer at each time point, based on neutralization of pseudoviruses comprising a SARS-CoV-2 Spike protein with a D614G mutation (left bars) or the mutations associated with the South Africa B.1.351 variant. FIG. 20B shows, for each Spike protein tested in FIG. 20A, the kinetics of neutralization titers from day 57 through day 92. FIG. 20C shows, at each time point, the relative change in neutralization titers towards a B.1.351 Spike protein compared to a Spike protein comprising only a D614G mutation. The horizontal dotted lines indicate the lower limit of quantification (LLOQ). For bar plots, geometric mean neutralizing antibody titer, shown above the bar, is denoted by the top of the box and the 95% confidence intervals are shown by the error bars.

FIG. 21A shows total IgG specific to wild-type 2P-stabilized SARS-CoV-2 Spike protein, as measured by ELISA. FIG. 21B shows neutralization titers of day 36 serum samples from mice administered two doses of 1 μg mRNA-1273, towards pseudoviruses containing one of a panel of Spike proteins, including 1) a Spike protein with a D614G mutation, 2) a Spike protein with the mutations associated with the B.1.351 variant, 3) a Spike protein with the mutations associated with the P.1 variant, 4) a Spike protein with the mutations associated with the B.1.1.7 variant, and 5) a Spike protein with the mutations associated with the B.1.1.7 variant as well as an E484K mutation. FIG. 21C shows the relative reduction in neutralization titers for sera against each of the viruses tested in FIG. 21B, relative to the baseline of neutralization titers towards D614G Spike protein. FIG. 21D shows neutralization titers of day 36 serum samples from mice administered two doses of 1 μg mRNA-1273.351, towards pseudoviruses containing one of a panel of Spike proteins, including 1) a Spike protein with a D614G mutation, 2) a Spike protein with the mutations associated with the B.1.351 variant. 3) a Spike protein with the mutations associated with the P.1 variant, and 4) a Spike protein with the mutations associated with the B.1.1.7 variant as well as an E484K mutation. FIG. 21E shows the relative reduction in neutralization titers for sera against each of the viruses tested in FIG. 21D, relative to the baseline of neutralization titers towards D614G Spike protein. FIG. 21F shows neutralization titers of day 36 serum samples from mice administered two doses of 1 μg mRNA-1273.117, towards pseudoviruses containing one of a panel of Spike proteins, including 1) a Spike protein with a D614G mutation, 2) a Spike protein with the mutations associated with the B.1.351 variant, 3) a Spike protein with the mutations associated with the P.1 variant, 4) a Spike protein with the mutations associated with the B.1.1.7 variant, and 5) a Spike protein with the mutations associated with the B.1.1.7 variant as well as an E484K mutation. FIG. 21G shows the relative reduction in neutralization titers for sera against each of the viruses tested in FIG. 21F, relative to the baseline of neutralization titers towards D614G Spike protein. FIG. 21H shows reference neutralizing antibody titers of mice administered two doses of either mRNA-1273, mRNA-1273.351, or mRNA-1273.211 (1:1 mixture of 0.50 μg each mRNA-1273 and mRNA-1273.351) on days 1 and 22, with sera collected on day 36. Sera from each group of mice were tested against pseudoviruses containing one of a panel of Spike proteins, including 1) a Spike protein with a D614G mutation, 2) a Spike protein with the mutations associated with the B.1.351 variant, 3) a Spike protein with the mutations associated with the CAL.20C variant, 4) a Spike protein with the mutations associated with the P.1 variant. The horizontal dotted lines indicate the lower limit of quantification (LLOQ). For bar plots, geometric mean neutralizing antibody titer, shown above the bar, is denoted by the top of the box and the 95% confidence intervals are shown by the error bars.

FIG. 23A shows neutralization titers of human Phase 1 participant sera against D614G, B.1.617.1-v1, B.1.617.1-v2, and B.1.617.2. FIG. 23B shows the relative reduction in neutralization titers for sera against each of the viruses tested in FIG. 23A.

FIG. 24B shows the fold-reduction in neutralization titer against different variants relative to the neutralization titer of the D614G spike protein.

FIG. 26A) and from nasal swabs (FIG. 26B).

FIG. 27A) and from nasal swabs (FIG. 27B).

FIG. 28A shows a reduction in neutralization titers between the two viruses using live virus neutralization and FIG. 28B shows a reduction in neutralization titers between eh two viruses using pseudovirus neutralization.

FIG. 29A) and from nasal swabs (FIG. 29B) at two time points.

FIG. 30A) and from nasal swabs (FIG. 30B) at three different time points.

FIG. 38A shows the neutralization of D614G, B.1.617.1, and B.1.617.2 from sera collected from 11 Part B individuals immediately prior to the booster. Sera collected after the primary series or 2-weeks after the boost with mRNA-1273 (FIG. 38B), mRNA-1273.351 (FIG. 38C), or mRNA-1273.211 (FIG. 38D) were analyzed in PsVN assays. The GMT titers against the wild-type virus or variants measured in booster trial participants 2 weeks after the booster were evaluated versus peak titers measured against the wild-type virus after the primary series vaccination, and the fold change for each virus are shown. GMTs for each variant virus are listed above each graph. The D57 GMT titers is indicated by the grey line. Results from individual participants are represented as dots on each figure. N=20 for D614G, B.1.351, and P.1 assays. N=11 for B.1.427/B.1.429, B.1.526, A.VOI.V2, B.1.617.1, and B.1.617.2, with shaded dots indicating these participants.

FIG. 39A shows GMT neutralization titers against the wild-type virus (D614G) or variants (B.1.351, P.1, B.1.427/B.1.429, B.1.526, A.VOI.2, B.1.617.1, B.1.617.2). The GMT of 1 of the wild-type D614G virus COVE study benchmark measured at D57 in the pivotal P301 mRNA-1273 efficacy trial (n=59) is indicated by the black dotted line. FIG. 39B shows GMT ratio versus the Phase 3 GMT titer comparator, measured at D57 in the pivotal P301 mRNA-1273 efficacy trial. The GMT titers against the wild-type or variant viruses measured in booster trial participants 2 weeks after the booster were evaluated versus peak titers measured against the wild-type D614G virus after the primary series vaccination. The GMT of 1 is indicated by the dotted line. N=20 for D614G, B.1.351, and P.1. N=11 for B.1.427/B.1.429, B.1.526, A.VOI.V2, B.1.617.1, and B.1.617.2.

DETAILED DESCRIPTION

Figure 1A:
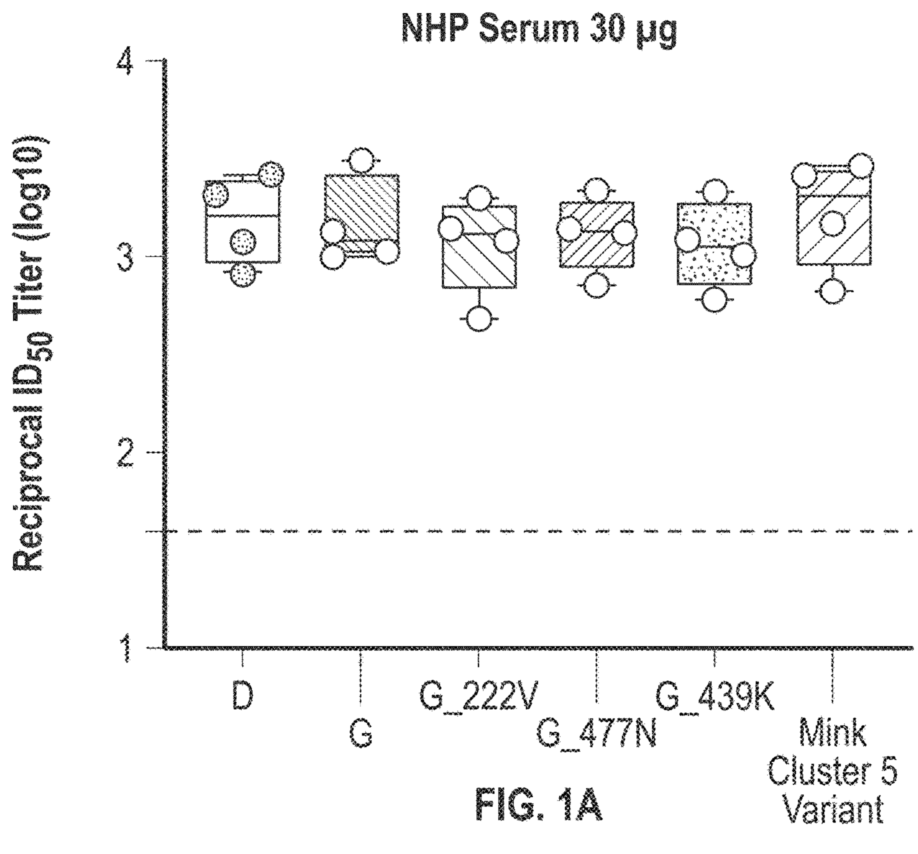
FIGS. 1A-1B show neutralization of SARS-CoV-2 pseudoviruses by serum from immunized non-human primates (NHP) or Phase 1 participants.

Severe acute respiratory syndrome coronavirus 2 (SARS-CoV-2) is a newly emerging respiratory virus with high morbidity and mortality. SARS-CoV-2 has rapidly spread around the world compared with SARS-CoV, which appeared in 2002, and Middle East respiratory syndrome coronavirus (MERS-CoV), which emerged in 2012. The World Health Organization (WHO) reports that, as of March 2021, the current outbreak of COVID-19 has had over 120 million confirmed cases worldwide with more than 2.65 million deaths. New cases of COVID-19 infection are on the rise and are still increasing rapidly. It is thus crucial that a variety of safe and effective vaccines and drugs be developed to prevent and treat COVID-19 and reduce the serious impact that COVID-19 is having across the world. Vaccines and drugs made using a variety of modalities, and vaccines having improved safety and efficacy, are imperative. There remains a need to accelerate the advanced design and development of vaccines and therapeutic drugs against coronavirus disease and in particular coronavirus 2019 (COVID-19).

On Jan. 7, 2020, severe acute respiratory syndrome coronavirus 2 (SARS-CoV-2) was identified as the etiological agent of a novel pneumonia that emerged in December 2019, in Wuhan City, Hubei province in China (Lu H. et al. (2020) *J Med Virol*. April; 92(4):401-402.). Soon after, the virus caused an outbreak in China and has spread to the world. According to the analysis of genomic structure of SARS-CoV-2, it belongs to β-coronaviruses (CoVs) (Chan et al. 2020 *Emerg Microbes Infect.*; 9(1):221-236).

Subsequently, a number of SARS-CoV-2 variant strains have emerged and have predominated in particular initial geographic areas. However, some variants that quickly predominate in one geographic area can spread rapidly around the globe. These variants are known as variants of concern (VOC). Two main variants have been found since the fall of 2020, including one in the United Kingdom (20B/501Y.V1, VOC 202012/01, or B.1.1.7 lineage, or alpha variant) and one in South Africa (20C/501Y.V2 or B.1.351 lineage, or beta variant). The two variants emerged separately from one another, but appear to have improved transmissibility relative to the USA-WA1/2020 isolate. Further, there are concerns that these variants as well as other circulating strains and any future variants may further mutate to avoid neutralization by existing vaccines and therapeutic modalities such as antibodies. In this way, the SARS-CoV-2 variants, and any other emerging mutant SARS-CoV-2 strains, are an international health concern.

The threat of emerging mutant strains of viruses presents a significant challenge to vaccine development. The compositions disclosed herein provide a significant advance in combatting the emerging viral strains that pose a global health concern. Disclosed herein are vaccines and vaccine protocols with broad viral neutralization capabilities that reduce the threat of infection from more than one strain of virus, through single or multiple administrations of the same or different combinations of antigens from different strains. For instance, the vaccination strategies disclosed herein, in some embodiments, comprise "primary series" of vaccinations and subsequent boost(s) of SARS-CoV-2 2P stabilized spike protein antigen. The primary series (also referred to herein as initial, original or first vaccine, vaccination) involves the administration of one or more vaccines (e.g. two vaccine administrations) of the SARS-CoV-2 2P stabilized spike protein antigen from the originally identified strain of SARS-CoV-2. The primary series of vaccine may be an mRNA vaccine encoding an antigen having an amino acid sequence of SEQ ID NO: 20. A subsequent booster or booster series of vaccines is then administered, for instance, shortly after the original vaccine or at a significantly later time in the vaccination protocol (e.g., after neutralizing Ab titers have dropped or after approval of a new strain vaccine.

In aspects disclosed herein, emerging SARS-CoV-2 variant strains are used to design mRNA "boost" as a supplement to prior administered SARS-CoV-2 vaccines and includes traditional boosts, seasonal boosts and pandemic shift boosts. A boost, as used herein refers to any subsequent dose. A traditional boost is a second dose of an antigen administered to a subject following a period of time, such as 21-28 days or even 2 weeks to 6 months. The traditional boost involves the administration of the same antigen representing the same virus strain to the subject in order to generate a robust immune response against that viral strain and optionally other variant strains.

During a pandemic or endemic, emerging viral strains may develop which are not effectively susceptible to neutralization with a vaccine designed against the original strain. In particular, SARS-CoV-2 emerging viral strains appear to arise through radial evolution; that is, with a variety of different mutations, as compared to linear evolution, in which mutations accumulate upon one another as the virus evolves. In such instances, a pandemic shift boost may be used to provide immune protection against emerging viral strains. A pandemic shift boost is a subsequent vaccine which is administered to a subject following a complete course of a first vaccine. The complete course of the first vaccine may comprise one or more administrations of the first vaccine. The pandemic shift boost is comprised of a vaccine that includes an antigen which is derived from a variant viral strain that has emerged during a pandemic or endemic of the viral infection. The pandemic shift boost may be administered at any time following the administration of the first vaccine. The first vaccine may be a vaccine against the originally detected strain of the virus, a combination of the original strain of the virus and variant strain(s) of the virus, or variant strains of the virus, as long as the pandemic shift boost comprises a vaccine against a different variant strain of the virus from the first vaccine.

Additionally variant viral strains of SARS-CoV-2 may emerge at times outside of a pandemic or endemic. These strains may emerge, for instance, seasonally. Such variant strains may be used to design seasonal SARS-CoV2 vaccines which as delivered as a seasonal boost. A seasonal boost is a subsequent vaccine which is administered to a subject following a complete course of a first vaccine which happens outside of a pandemic or endemic, as variant strains arise. Viral surveillance methods are used in the design of traditional vaccines. However, due to the slow development time of traditional vaccines, the antigen design decisions are often made so far in advance that the vaccine does not match the viral strains circulating when the vaccines are administered. During the development period the viruses may mutate, or other strains may become more prevalent, such that the traditional vaccines become less effective. The traditional vaccines cannot adapt because they are already in production, and it would take additional time to design and manufacture a new vaccine. In contrast, the mRNA vaccines described herein are able to overcome these challenges. They can be produced in a matter of weeks, so that they can be designed against the coronaviruses circulating closer to the inoculation date. For instance, a seasonal or annual coronavirus vaccination program can be developed that rapidly develops a coronavirus vaccine in response to viral strains circulating at the time of vaccination. That is, it is thought that prediction of the viruses closer to a coronavirus season or other outbreak will be more accurate than predictions from several months before the season or the outbreak begins, and therefore the mRNA vaccines described herein will also be more effective because they are designed to target circulating viruses closer to the coronavirus season or scheduled inoculations. Thus, in exemplary aspects, the vaccines of the disclosure may be designed to combat seasonal coronavirus strains, and as such are vaccines for use in an upcoming or forthcoming Northern hemisphere season or Southern hemisphere season. Based on an understanding of circulating coronaviruses at a given point in time, the vaccines are designed to combat such viruses as they are predicted to be those that will be circulating or prevalent in the upcoming or forthcoming virus season. The mRNA vaccines can be designed in a matter of days and a recent vaccine developed by applicant preceded from design to manufactured vaccine in just over 5 weeks. Data can be captured and analyzed as to what viruses are circulating and with what prevalence, much closer to the start of an inoculation program such as seasonal vaccination.

A key protein on the surface of coronavirus, including the SARS-CoV-2 and mutant strains described herein, is the Spike (S) protein. A stabilized version of the spike protein having a two proline mutation relative to wild type SARS-CoV-2 has been developed and has an amino acid sequence of SEQ ID NO: 20. The 2P stabilized spike antigen is a full length spike protein including the 2Ps. The vaccination protocols described herein comprise various vaccines of full length 2P stabilized spike protein from the original SARS-CoV-2 strain and/or emerging variant SARS-CoV-2 strains, wherein each antigen includes the 2P mutation.

A variety of mRNA constructs have been designed and are disclosed herein. When formulated in appropriate delivery vehicles mRNA encoding a 2P stabilized version of the spike antigen of emerging variant strains are capable of inducing a strong immune response against SARS-CoV-2, thus producing effective and potent mRNA vaccines/boosters to provide the diversity essential to eradicating the original virus as well as subsequent strains. Intramuscular administration of the mRNA encoding various Spike protein antigens in an LNP, in particular, Spike protein subunit and domain antigens, results in delivery of the mRNA to immune tissues and cells of the immune system where it is rapidly translated into proteins antigens. Other immune cells, for example, B cells and T cells, are then able to recognize and mount an immune response against the encoded protein and ultimately create a long-lasting protective response against the coronavirus. Low immunogenicity, a drawback in protein vaccine development due to poor presentation to the immune system or incorrect folding of the antigens, is avoided through the use of the highly effective mRNA vaccines encoding spike protein, subunits and domains thereof disclosed herein.

Due to the constant evolving nature of viruses, scientists continuously monitor the sequences and strains of viruses circulating in humans. These various circulating strains may be used as boosts or individual vaccines as disclosed herein, or additionally to design multivalent mRNA vaccines. Viral surveillance can be used to provide annual or seasonal (or other scheduled) information to select the precise virus strains to be used as the basis of mRNA vaccines. Once circulating strains are identified, the composition of a vaccine that targets two or three (or more) most representative virus types in circulation can be developed based on those strains. This exercise of adding antigens from new strains to the vaccine can be repeated on an annual basis or other time frame as required to maintain viral immunity in the population. As used herein, "population" or "subject population" refers to the global population, a regional population, or a national population. For example, a regional population may refer to a geographically distinct population (e.g., hemisphere, continent) or a region of a country, as some new strains may be more prevalent in certain regions of the world, continents, or countries. In some embodiments, the subject population is a national population (e.g., the population of the United States). The mRNA vaccines described herein, in some embodiments, encode multiple antigens from multiple circulating strains in a single lipid nanoparticle (LNP). The mRNA vaccines comprise, in some embodiments, a combination of at least two antigens, each derived from a unique strain of coronavirus.

Thus, the present disclosure provides compositions (e.g., mRNA vaccines) that elicit potent neutralizing antibodies against coronavirus antigens in subjects. Such a composition can be administered to seropositive or seronegative subjects. A seropositive subject may be naïve and not have antibodies that react with SARS-CoV-2. A seronegative subject may have preexisting antibodies to SARS-CoV-2 because they have previously had an infection with SARS-CoV-2 or may have previously been administered a dose of a vaccine (e.g., an mRNA vaccine) that induces antibodies against SARS-CoV-2. In some embodiments, a composition includes mRNA encoding at least one (e.g., one, two, or more) coronavirus antigens, such as SARS-CoV-2 antigens from different SARS-CoV-2 mutant strains (also referred to herein as variants). In some embodiments, the mRNA vaccine comprises multiple mRNAs encoding SARS-CoV-2 antigens from different variants in a single lipid nanoparticle. In some embodiments, the mRNA vaccine comprises an mRNA encoding a SARS-CoV-2 antigen comprising one or more mutations from at least two different SARS-CoV-2 variants (e.g., encoding a combination of the mutations and/or deletions found in the B.1.1.7 and 5021.V2 variants).

At least four groups of SARS-CoV-2 mutants are currently of concern due to increasing prevalence, higher hACE2 binding affinity, or reported escape from mAb and convalescent sera. One exemplary circulating strain (UK) of coronavirus is N501Y-UK, or B.1.1.7 (alpha variant), which has the following mutations: ΔH69-ΔV70-ΔY144-N501Y-A570D-P681H-T716I-S982A-D1118H. This strain has been observed to spread quickly through a region. N501Y causes increased binding affinity to hACE2, making viral uptake more likely. ΔH69-ΔV70 has been shown to have reduced sensitivity to convalescent sera and P681H locates immediately adjacent to furin cleavage site.

Another strain (South Africa), N501Y-SA (B.1.351) (beta variant) with a K417N-E484K-N501Y mutation has also shown fast regional spread and higher viral load in patients. E484K has been shown to have reduced sensitivity to convalescent sera. Both N501Y and E484K are located in the receptor binding domain (RBD) and these mutations increase RBD binding affinity to hACE2.

An additional strain, identified in Japan from four people traveling from Brazil, P.1 (B1.1.248; 20I/501Y.V1) (gamma variant) has emerged. This variant contains 12 mutations in its spike protein, including N501U and E484K. It is thought that the further mutations that may affect its ability to be recognized by antibodies and it is thought to be more transmissible than the wild-type virus (USA-WA1/2020 isolate).

An additional subclade of B.1.1.248 has emerged in Amazonas state, Brazil to cause concern over re-infection of people previously infected. The two subclades of B.1.1.28 are designated P.2 (alias of B.1.1.28.2) and P.1 (alias of B.1.1.28.1). To be clear, the variant of concern (VOC) is the subclade designated P.1 (alias of B.1.1.28.1) that has caused a noted re-infection of a woman previously infected and who previously had recovered. The reinfection may be the result of limited or transitory immunity induced in the initial infection or it may reflect a superior ability of the new strain to evade previous immune responses. This new strain contains 12 spike protein mutations including 3 in the RBD (K417T, E484K, N501Y) and one new N-glycosylation site at T20N. The S protein mutations include the following 12 mutations: L18F, T20N, P26S, D138Y, R190S, K417T, E484K, N501Y, D614G, H655Y, T1027I, V1176F (see Naveca et al., SARS-CoV-2 reinfection by the new Variant of Concern (VOC) P.1 in Amazonas, Brazil, 2021). The reinfection caused similar moderate symptoms as the initial infection, but recorded a higher viral load in nasopharyngal and pharyngeal samples. The reinfection may be the result of the E484K mutation in the spike protein and its ability to facilitate evasion of SARS-CoV-2 neutralizing antibodies.

The B.1.429 (also called CAL.20C or 542R.V1) strain (epsilon variant) was found at Cedars-Sinai Medical Center in Los Angeles. The variant contains five mutations: I4205V (ORF1a), D1183Y (ORF1b), and S13I, W152C, and L452R (spike protein) (Zhang et al., medRxiv preprint, Jan. 20, 2021). The L452R mutation is located within the RBD and has been found to be resistant to certain monoclonal antibodies against the spike protein.

In Germany, a new variant has been detected in 35 out of 73 new patients in Garmisch-Partenkirchen. The variant is currently being sequenced, although at least one point mutation has been detected in the spike protein.

In India, two related variants, both belonging to the B.1.617.1 subclade, have emerged. The genome of one B.1.617.1 variant, referred to as v1, or B.1.617.1 v1 (kappa variant), encodes a Spike protein having the following 8 substitutions: T951, G142D, E154K, L452R, E484Q, D614G, P681R, and Q1071H. The genome of the other B.1.617.1 variant, referred to as v2, or B.1.617.1 v2, encodes a Spike protein with the following 8 substitutions: G142D, E154K, L452R, E484Q, D614G, P681R, Q1071H, and H1101D.

Also in India, another variant, belonging to the B.1.617.2 subclade, has emerged. The genome of the B.1.617.2 (Delta) variant encodes a Spike protein having the following ten substitutions: T19R, G142D, E156G, F157, R158, L452R, T478K, D614G, P681R, D950N, in addition to two deletions: F157del and R158del.

In Angola, a new variant, referred to as A.VOI.V2, with multiple Spike protein mutations has been detected through genomic surveillance. The genome of the A.VOI.V2 variant encodes a Spike protein having the following 15 mutations, including 10 substitutions and 5 amino acid deletions: D80Y, ΔY144, ΔI210, D215G, ΔR246, ΔS247, ΔY248, L249M, W258L, R346K, T478R, E484K, H655Y, P681H, and Q957H.

A variant of interest (VOI), lambda (C.37) has been investigated. The variant was first documented in Peru and is most frequently found in South America. It has relatively high risk scores, due mainly to its high number of deletions in the N-terminal domain (NTD) and it is possible that its RSYLTPGD246-253N mutation may increase its ability to evade neutralizing antibodies.

Another variant of interest (VOI), mu (B.1621) has been reported and first documented in Colombia. The variant comprises an insertion, 146N, and several amino acid substitutions in the Spike protein (Y144T, Y145S, R346K, E484K, N501Y and P681H).

Two additional related variants, B.1.243 and B.1.243.1 have been found primarily in North America (Arizona). The B.1.243.1 variant has the E484K mutation, in addition to a further Spike protein mutation (V213G), which may render it more resistant to neutralizing antibodies.

A variant of concern, Omicron (B.1.11529), having multiple Spike protein mutations was detected initially in Botswana. The mutations observed in the variant include those found in the Delta variant that are believed to increase transmissibility and mutations, and those seen in the Beta and Delta variants that are believed to promote immune escape. In particular, the genome of the Omicron variant encodes a Spike protein having the following mutations: A67V, Δ69-70, T951, G142D/A143-145, Δ211/L212I, ins214EPE, G339D, S371L, S373P, S375F, K417N, N440K, G446S, S477N, T478K, E484A, Q493K, G496S, Q498R, N501Y, Y505H, T547K, D614G, H655Y, N679K, P681H, N764K, D796Y, N856K, Q954H, N969K, and L981F.

These exemplary strains and other newly emerging strains are candidates for the methods and formulations disclosed herein. mRNA encoding antigens from these and other coronavirus strains have been designed for mRNA vaccines.

In some embodiments, the mRNA vaccines described herein may be administered as a prime or priming immunization (e.g., the first administration of a coronavirus vaccine to a subject). In some embodiments, the mRNA vaccines described herein may be administered as a booster, that is, a dose administered after the prime or priming immunization, as described herein. In some embodiments, the booster and the prime or priming immunization comprise the same mRNA or mRNAs. In other embodiments, the booster and the prime or priming immunization comprise different mRNA or mRNAs. In other embodiments multiple mRNA vaccines encoding different antigens (each directed at a strain or multiple strains) may be administered together or in tandem to provide a wide spectrum neutralization platform against multiple coronavirus strains. Combinations of mRNAs have been demonstrated to be particularly effective in vivo and, quite surprisingly, even producing robust immune responses against variant strains that are not part of the vaccine. For instance, it was shown that when a multivalent mRNA-vaccine was administered as a booster it elicited robust and comparable neutralizing titers against both variant strains of the viruses not included in the prime or boost.

The genome of SARS-CoV-2 is a single-stranded positive-sense RNA (+ssRNA) with the size of 29.8-30 kb encoding about 9860 amino acids (Chan et al. 2000, supra; Kim et al. 2020 *Cell*, May 14; 181(4):914-921.e10.). SARS-CoV-2 is a polycistronic mRNA with 5'-cap and 3'-poly-A tail. The SARS-CoV-2 genome is organized into specific genes encoding structural proteins and nonstructural proteins (Nsps). The order of the structural proteins in the genome is 5'-replicase (open reading frame (ORF)1/ab)-structural proteins [Spike (S)-Envelope (E)-Membrane (M)-Nucleocapsid (N)]-3'. The genome of coronaviruses includes a variable number of open reading frames that encode accessory proteins, nonstructural proteins, and structural proteins (Song et al. 2019 *Viruses;* 11 (1):p. 59). Most of the antigenic peptides are located in the structural proteins (Cui et al. 2019 *Nat. Rev. Microbiol.;* 17(3):181-192). Spike surface glycoprotein (S), a small envelope protein (E), matrix protein (M), and nucleocapsid protein (N) are four main structural proteins. Since S-protein contributes to cell tropism and virus entry and also it is capable to induce neutralizing antibodies (NAb) and protective immunity, it can be considered one of the most important targets in coronavirus vaccine development among all other structural proteins. Moreover, amino acid sequence analysis has shown that S-protein contains conserved regions among the coronaviruses, which may be the basis for universal vaccine development The compositions of the invention, e.g., vaccine compositions, feature nucleic acids, in particular, mRNAs, designed to encode an antigen of interest, e.g., an antigen derived from a betacoronavirus structural protein, in particular, antigens derived from SARS-CoV-2 Spike protein. The compositions of the invention, e.g., vaccine compositions, do not comprise antigens per se, but rather comprise nucleic acids, in particular, mRNA(s) that encode antigens or antigenic sequences once delivered to a cell, tissue or subject. Delivery of nucleic acids, in particular mRNA(s) is achieved by formulating said nucleic acids in appropriate carriers or delivery vehicles (e.g., lipid nanoparticles) such that upon administration to cells, tissues or subjects, nucleic acid is taken up by cells which, in turn, express protein(s) encoded by the nucleic acids, e.g., mRNAs.

Antigens, as used herein, are proteins capable of inducing an immune response (e.g., causing an immune system to produce antibodies against the antigens). The vaccines of the present disclosure provide a unique advantage over traditional protein-based vaccination approaches in which protein antigens are purified or produced in vitro, e.g., recombinant protein production technologies. The vaccines of the present disclosure feature mRNA encoding the desired antigens, which when introduced into the body, i.e., administered to a mammalian subject (for example a human) in vivo, cause the cells of the body to express the desired antigens. In order to facilitate delivery of the mRNAs of the present disclosure to the cells of the body, the mRNAs are encapsulated in lipid nanoparticles (LNPs). Upon delivery and uptake by cells of the body, the mRNAs are translated in the cytosol and protein antigens are generated by the host cell machinery. The protein antigens are presented and elicit an adaptive humoral and cellular immune response. Neutralizing antibodies are directed against the expressed protein antigens and hence the protein antigens are considered relevant target antigens for vaccine development. Herein, use of the term "antigen" encompasses immunogenic proteins and immunogenic fragments (an immunogenic fragment that induces (or is capable of inducing) an immune response to a (at least one) SARS-CoV-2 variant), unless otherwise stated. It should be understood that the term "protein" encompasses peptides and the term "antigen" encompasses antigenic fragments. Other molecules may be antigenic such as bacterial polysaccharides or combinations of protein and polysaccharide structures, but for the viral vaccines included herein, viral proteins, fragments of viral proteins and designed and or mutated proteins derived from SARS-CoV-2 are the antigens provided herein.

Many proteins have a quaternary or three-dimensional structure, which consists of more than one polypeptide or several polypeptide chains that associate into an oligomeric molecule. As used herein the term "subunit" refers to a single protein molecule, for example, a polypeptide or polypeptide chain resulting from processing of a nascent protein molecule, which subunit assembles (or "coassembles") with other protein molecules (e.g., subunits or chains) to form a protein complex. Proteins can have a relatively small number of subunits and therefore be described as "oligomeric" or can consist of a large number of subunits and therefore be described as "multimeric". The subunits of an oligomeric or multimeric protein may be identical, homologous or totally dissimilar and dedicated to disparate tasks.

Proteins or protein subunits can further comprise domains. As used herein, the term "domain" refers to a distinct functional and/or structural unit within a protein. Typically, a "domain" is responsible for a particular function or interaction, contributing to the overall role of a protein. Domains can exist in a variety of biological contexts. Similar domains (i.e., domains sharing structural, functional and/or sequence homology) can exist within a single protein or can exist within distinct proteins having similar or different functions. A protein domain is often a conserved part of a given protein tertiary structure or sequence that can function and exist independently of the rest of the protein or subunit thereof.

In structural and molecular biology, identical, homologous or similar subunits or domains can help to classify newly identified or novel proteins, as was done immediately upon publication of the SARS-CoV-2 viral genomic sequence.

As used herein, the term antigen is distinct from the term "epitope" which is a substructure of an antigen, e.g., a polypeptide, such as 7-10 amino acids, or carbohydrate structure, which may be recognized by an antigen binding site but is insufficient to induce an immune response. The art describes protein antigens that are delivered to subjects or immune cells in isolated form, e.g., isolated protein, polypeptide or peptide antigens, however, the design, testing, validation, and production of protein antigens can be costly and time-consuming, especially when producing proteins at large scale. By contrast, mRNA technology is amenable to rapid design and testing of mRNA constructs encoding a variety of antigens. Moreover, rapid production of mRNA coupled with formulation in appropriate delivery vehicles (e.g., lipid nanoparticles), can proceed quickly and can rapidly produce mRNA vaccines at large scale. Potential benefit also arises from the fact that antigens encoded by the mRNAs of the invention are expressed by the cells of the subject, e.g., are expressed by the human body, and thus the subject, e.g., the human body, serves as the "factory" to produce the antigens which, in turn, elicits the desired immune response.

The compositions, as provided herein, may include an RNA or multiple RNAs encoding two or more antigens of the same or different viral strains. Also provided herein are combination vaccines that include RNA encoding one or more coronavirus antigens and one or more antigen(s) of a different organism. Thus, the vaccines of the present disclosure may be combination vaccines that target one or more antigens of the same strain/species, or one or more antigens of different strains/species, e.g., antigens which induce immunity to organisms which are found in the same geographic areas where the risk of coronavirus infection is high or organisms to which an individual is likely to be exposed to when exposed to a coronavirus (e.g., COVID-19).

In some embodiments, the second or subsequent circulating SARS-CoV-2 virus is an immunodominant antigen from an emerging strain. An immunodominant antigen of an emerging strain is assessed with respect to the strain from which the antigen is derived, relative to a different strain of the virus, such as the original strain or other variant thereof. An immunodominant antigen of the emerging strain induces a stronger immune response against the emerging strain than against the different strain. In some embodiments, an immunodominant antigen of the emerging strain is more infective than a different strain of the virus, such as the original strain or other variant thereof.

Encoded Coronavirus Spike (S) Protein Antigens

The envelope spike (S) proteins of known betacoronaviruses determine the virus host tropism and entry into host cells. Coronavirus spike (S) protein is a choice antigen for the vaccine design as it can induce neutralizing antibodies and protective immunity. S protein is critical for SARS-CoV-2 infection. The organization of the S protein is similar among betacoronaviruses, such as SARS-CoV-2, SARS-CoV, MERS-CoV, HKU1-CoV, MHV-CoV and NL63-CoV.

As used herein, the term "Spike protein" refers to a glycoprotein that that forms homotrimers protruding from the envelope (viral surface) of viruses including betacoronaviruses. Trimerized Spike protein facilitates entry of the virion into a host cell by binding to a receptor on the surface of a host cell followed by fusion of the viral and host cell membranes. The S protein is a highly glycosylated and large type I transmembrane fusion protein that is made up of 1,160 to 1,400 amino acids, depending upon the type of virus. Betacoronavirus Spike proteins comprise between about 1100 to 1500 amino acids.

SARS-CoV-2 spike (S) protein is a choice antigen for the vaccine design as it can induce neutralizing antibodies and protective immunity. mRNAs of the invention are designed to produce SARS-CoV-2 Spike proteins (i.e., encode Spike proteins such that Spike protein is expressed when the mRNA is delivered to a cell or tissue, for example a cell or tissue in a subject), as well as antigenic variants thereof. The skilled artisan will understand that, while an essentially full length or complete Spike protein may be necessary for a virus, e.g., a betacoronavirus, to perform its intended function of facilitating virus entry into a host cell, a certain amount of variation in Spike protein structure and/or sequence is tolerated when seeking primarily to elicit an immune response against Spike protein. For example, minor truncation, e.g., of one to a few, possibly up to 5 or up to 10 amino acids from the N- or C-terminus of the encoded Spike protein, e.g., encoded Spike protein antigen, may be tolerated without changing the antigenic properties of the protein. Likewise, variation (e.g., conservative substitution) of one to a few, possibly up to 5 or up to 10 amino acids (or more) of the encoded Spike protein, e.g., encoded Spike protein antigen, may be tolerated without changing the antigenic properties of the protein. In some embodiments, the Spike protein is a stabilized Spike protein, for example, the Spike protein is stabilized by two proline substitutions (a 2P mutation).

In some embodiments, the Spike protein is from a different virus strain. A strain is a genetic variant of a microorganism (e.g., a virus). New viral strains can be created due to mutation or swapping of genetic components when two or more viruses infect the same cell in nature, for example, by antigenic drift or antigenic shift.

Antigenic drift is a kind of genetic variation in viruses, arising by the accumulation of mutations in the virus genes that code for virus-surface proteins that host antibodies recognize. This results in a new strain of virus particles that is not effectively inhibited by the antibodies that prevented infection by previous strains. This makes it easier for the changed virus to spread throughout a partially immune population.

Antigenic shift is the process by which two or more different strains of a virus, or strains of two or more different viruses, combine to form a new subtype having a mixture of the surface antigens of the two or more original strains. The term is often applied specifically to influenza, as that is the best-known example, but the process is also known to occur with other viruses. Antigenic shift is a specific case of reassortment or viral shift that confers a phenotypic change. Antigenic shift is contrasted with antigenic drift, which is the natural mutation over time of known strains of a virus which may lead to a loss of immunity, or in vaccine mismatch. Antigenic shift is often associated with a major reorganization of viral surface antigens, resulting in a reassortment change the virus's phenotype drastically.

A virus strain as used herein is a genetic variant or of a virus that is characterized by a differing isoform of one or more surface proteins of the virus. In the case of SARS-CoV-2, for example, a different amino acid sequence in the SARS-CoV-2 spike protein where the immune response in an individual to the new strain is less effective than to the strain used to immunize or first infect the individual. A new virus strain may arise from natural mutation or a combination of natural mutation and immune selection due to an ongoing immune response in an immunized or previously infected individual. A new virus strain can differ by one, two, three or more amino acid mutations in regions of the spike protein responsible for a viral function such as receptor binding or viral fusion with a target cell. A spike protein from a new strain may differ from the parental strain by as much as 90%, 91%, 92%, 93%, 94%, 95%, 96%, 97%, 98%, or 99% identity at the amino acid level.

A natural virus strain is a variant of a given virus that is recognizable because it possesses some "unique phenotypic characteristics" that remain stable (e.g., stable and heritable biological, serological, and/or molecular characters) under natural conditions. Such "unique phenotypic characteristics" are biological properties different from the compared reference virus, such as unique antigenic properties, host range (e.g., infecting a different kind of host), symptoms of disease caused by the strain, different type of disease caused by the strain (e.g., transmitted by different means), etc. A "unique phenotypic characteristic" can be detected clinically (e.g., clinical manifestations detected in a host infected with the strain) or within a comparative animal experiment in which a researcher skilled in the art of virology can distinguish between the reference control virus-infected animal and the animal infected with the alleged new strain, without knowing which animal received which virus and without having any information about the differences between the two viruses. Importantly, a virus variant with a simple difference in genome sequence is not a separate strain if there is no recognizable distinct viral phenotype. The extent of genomic sequence variation is irrelevant for the classification of a variant as a strain since a distinct phenotype sometimes arises from few mutations.

As an example, in some embodiments, the mRNA encodes an antigen from at least one virus strain variant or comprises mutations from at least one virus strain that is not wild-type SARS-CoV-2. In some embodiments, the vaccine comprises mRNA encoding a Spike protein associated with the B.1.1.7 lineage (UK) variant (20B/501Y.V1 VOC 202012/01). The B.1.1.7 lineage variant has a mutation in the receptor binding domain (RBD) of the Spike protein at position 501, where amino acid asparagine (N) has been replaced with tyrosine (Y); an N501Y mutation. Further, the variant has a 69/70 deletion, which occurs spontaneously numerous times, leading to conformation changes in the Spike protein, a P681H mutation near the S1/S2 furin cleavage site, and a ORF8 stop codon (Q27 stop) caused by a mutation in ORF8. The 501.V2 (South Africa, SA) variant comprises multiple mutations in the Spike protein, including N501Y, and E484K, but does not have a deletion at 69/70. The E484K mutation is considered to be an "escape" mutation relative to at least one form of monoclonal antibody against SARS-CoV-2, such that it may change the antigenicity of the virus. Other mutations that have been discovered include the D614G mutation, which is thought to increase the transmission rate of the virus, and the N543Y mutation (emerged from mink farms in the Netherlands and Denmark). In some embodiments, the Spike protein comprises mutations from more than one variant (e.g., a combination of mutations found in the B.1.1.7 and 502Y.V2 variants). Table 2, below, presents examples of Spike protein mutations in SARS-CoV-2 variants.

TABLE 2

Spike mutations in SARS-CoV-2 variants

| Variant Name | Amino Acid Changes in Spike |
| --- | --- |
| 20A.EU1 | A222V-D614G |
| 20A.EU2 | S477N-D614G |
| N439K-D614G | N439K-D614G |
| Mink Cluster 5 Variant | ΔH69ΔV70-Y453F-D614G-I692V-M1229I |
| B.1.1.7 (a.k.a., 20I/501Y.V1, VOC 202012/01) | ΔH69ΔV70-ΔY144-N501Y-A570D-D614G-P681H-T716I-S982A-D1118H |
| B.1.1.7-E484K | ΔH69ΔV70-ΔY144-E484K-N501Y-A570D-D614G-P681H-T716I-S982A-D1118H |
| B.1.351 (a.k.a., 20H/501Y.V2) | L18F-D80A-D215G-ΔL242ΔA243ΔL244-R246I-K417N-E484K-N501Y-D614G-A701V |
| P.1 | L18F-T20N-P26S-D138Y-R190S-K417T-E484K-N501Y-D614G-H655Y-T1027I |
| B.1.429 (a.k.a., CAL.20C) | S13I, W152C, L452R, D614G |
| B.1.617.1 v1 (a.k.a., India Variant v1) | T95I-G142D-E154K-L452R-E484Q-D614G-P681R-Q1071H |
| B.1.617.1 v2 (a.k.a., India Variant v2) | G142D-E154K-L452R-E484Q-D614G-P681R-Q1071H-H1101D |
| B.1.617.2 (Delta variant; Indian) | T19R-G142D-E156G-F157del-R158del-L452R-T478K-D614G-P681R-D950N |
| A.VOI.V2 (a.k.a. Angola Variant) | D80Y-ΔY144-ΔI210-D215G-ΔR246-ΔS247-ΔY248-L249M-W258L-R346K-T478R-E484K-H655Y-P681H-Q957H |
| B.1.1.529 (Omicron variant; Botswana) | A67V, Δ69-70, T95I, G142D/Δ143-145, Δ211/L212I, ins214EPE, G339D, S371L, S373P, S375F, K417N, N440K, G446S, S477N, T478K, E484A, Q493K, G496S, Q498R, N501Y, Y505H, T547K, D614G, H655Y, N679K, P681H, N764K, D796Y, N856K, Q954H, N969K, L981F |

In exemplary embodiments, a Spike protein, e.g., an encoded Spike protein antigen, has the amino acid sequence set forth in any one of SEQ ID NOs: 5, 8, 11, 14, 17, 23, 26, 30, 33, 36, 39, and 42. In other embodiments, a Spike protein, e.g., an encoded Spike protein antigen, has no greater than 100, no greater than 90, no greater than 80, no greater than 70, no greater than 60, no greater than 50, no greater than 40, no greater than 30, no greater than 20, no greater than 10, or no greater than 5 amino acid substitutions and/or deletions as compared to (when aligned with) a Spike protein having the amino acid sequence as set forth in any one of SEQ ID NOs: 5, 8, 11, 14, 17, 23, 26, 30, 33, 36, 39, and 42. Where minor variations are made in encoded Spike protein sequences, the variant preferably has the same activity as the reference Spike protein sequence and/or has the same immune specificity as the reference Spike protein, as determined for example, in immunoassays (e.g., enzyme-linked immunosorbent assays (ELISA assays).

S proteins of coronaviruses can be divided into two important functional subunits, of which include the N-terminal S1 subunit, which forms of the globular head of the S protein, and the C-terminal S2 region that forms the stalk of the protein and is directly embedded into the viral envelope. Upon interaction with a potential host cell, the S1 subunit will recognize and bind to receptors on the host cell, specifically angiotensin-converting enzyme 2 (ACE2) receptors, whereas the S2 subunit, which is the most conserved component of the S protein, will be responsible for fusing the envelope of the virus with the host cell membrane. (See e.g., Shang et al., PLoS Pathog. 2020 March; 16(3): e1008392.). Each monomer of trimeric S protein trimer contains the two subunits, S1 and S2, mediating attachment and membrane fusion, respectively. As part of the infection process in vivo, the two subunits are separated from each other by an enzymatic cleavage process. S protein is first cleaved by furin-mediated cleavage at the S1/S2 site in infected cells. In vivo, a subsequent serine protease-mediated cleavage event occurs at the S2' site within S1. In SARS-CoV2, the S1/S2 cleavage site is at amino acids 676-TQTNSPRRAR/SVA-688 (SEQ ID NO: 47). The S2' cleavage site is at amino acids 811-KPSKR/SFI-818 (SEQ ID NO: 48).

As used herein, for example in the context of designing SARS-CoV-2 S protein antigens encoded by the nucleic acids, e.g., mRNAs, of the invention, the term "S1 subunit" (e.g., S1 subunit antigen) refers to the N-terminal subunit of the Spike protein beginning at the S protein N-terminus and ending at the S1/S2 cleavage site whereas the term "S2 subunit" (e.g., S2 subunit antigen) refers to the C-terminal subunit of the Spike protein beginning at the S1/S2 cleavage site and ending at the C-terminus of the Spike protein. As described supra, the skilled artisan will understand that, while an essentially full length or complete Spike protein S1 or S2 subunit may be necessary for receptor binding or membrane fusion, respectively, a certain amount of variation in S1 or S2 structure and/or sequence is tolerated when seeking primarily to elicit an immune response against Spike protein subunits. For example, minor truncation, e.g., of one to a few, possibly up to 4, 5, 6, 7, 8, 9 or 10 amino acids from the N- or C-terminus of the encoded subunit, e.g., encoded S1 or S2 protein antigens, may be tolerated without changing the antigenic properties of the protein. Likewise, variation (e.g., conservative substitution) of one to a few, possibly up to 4, 5, 6, 7, 8, 9 or 10 amino acids (or more) of the encoded Spike protein subunits, e.g., encoded S1 or S2 protein antigen, may be tolerated without changing the antigenic properties of the protein(s). In exemplary embodiments, a Spike protein, e.g., an encoded Spike protein antigen, has the amino acid sequence set forth in any one of SEQ ID NOs: 5, 8, 11, 14, 17, 20, 23, 26, 29, 30, 32, 33, 36, 39, and 42.

In some embodiments, the mRNA vaccine encodes an antigen having at least one of the following mutations relative to the USA-WA1/2020 isolate: E484K, D614G, K417N, N501Y, L18F, D80A, D215G, R246I, A701V, A570D, P861H, T716I, S982A, D1118H. In some embodiments, the mRNA vaccine encodes an antigen having at least one of the following mutations relative to the SARS-CoV-2 S protein of SEQ ID NO: 20 (2P mutation version of WT): E484K, D614G, K417N, N501Y, L18F, D80A, D215G, R246I, A701V, A570D, P861H, T716I, S982A, D1118H. In some embodiments, the mRNA encodes an antigen having 2, 3, 4, 5, 6, 7, 8, 9, 10, 11, 12, 13, or all 14 of the mutations listed. In some embodiments, the mRNA encodes an antigen that has one or more deletions relative to the SARS-CoV-2 S protein of SEQ ID NO: 20. Exemplary deletions include, but are not limited to, positions, 69, 70, 144, and 242-244. In some embodiments, the mRNA encodes an antigen having 1, 2, 3, 4, 5, or 6 deletions. In some embodiments, the mRNA encoding an antigen has 1, 2, 3, 4, 5, or 6 deletions, and 1, 2, 3, 4, 5, 6, 7, 8, 9, 10, 11, 12, 13, or 14 mutations or any combination thereof.

In some embodiments, the mRNA vaccine comprises 1, 2, 3, 4, 5, or 6 mRNAs encoding different antigens, wherein each antigen comprises at least one mutation and/or at least one deletion. In some embodiments, the mRNA vaccine further comprises an mRNA encoding a wild-type SARS-CoV-2 S protein antigen or the antigenic fragment thereof. The mRNA vaccine, in some embodiments, is in a lipid nanoparticle (that is, the lipid nanoparticle comprises 1, 2, 3, 4, 5, or 6 mRNAs encoding different antigens).

In some aspects, compositions of the disclosure comprise at least: a first mRNA encoding a first SARS-CoV-2 spike antigen of a first SARS-CoV-2 virus wherein the first SARS-CoV-2 spike antigen has an amino acid sequence of SEQ ID NO: 20 or an amino acid sequence with at least one amino acid mutation, deletion, or both amino acid mutation and deletion with respect to a protein of SEQ ID NO: 20 and a second mRNA encoding a second SARS-CoV-2 spike antigen of a second SARS-CoV-2 virus wherein the second SARS-CoV-2 spike antigen has an amino acid sequence with at least one amino acid mutation, deletion, or both amino acid mutation and deletion with respect to a protein of SEQ ID NO: 20. In some embodiments, the first SARS-CoV-2 virus is a first circulating SARS-CoV-2 virus. In some embodiments, the second SARS-CoV-2 virus is a second circulating SARS-CoV-2 virus. In some embodiments, the first and second mRNAs are present in the composition in a 1:1, 1:2, 1:3, or 1:4 ratio. In another embodiment, the first and second mRNAs are present in the composition in a 2:1, 3:1 or 4:1 ratio. In some embodiments, the first and second mRNA are present in the composition in a 1:1 ratio. In one embodiment, the first mRNA encodes SEQ ID NO: 20 (2P mutation version of WT) and the second mRNA encodes SEQ ID NO: 11 (mRNA-1273.351; WH2020_NatSP_2P_L18F_D80A_D215G_L242_244del_R246I_K417N_E484K_N501Y_D614G_A701V). In one embodiment, the first mRNA encodes SEQ ID NO: 20 (2P mutation version of WT) and the second mRNA encodes SEQ ID NO: 26 (S2P_IN_B.1.617.2; now known as the Delta variant and comprising the following mutations: T19R, G142D, E156G, F157del, R158del, L452R, T478K, D614G, P681R, and D950N). In one embodiment, the first mRNA encodes SEQ ID NO: 20 (2P mutation version of WT) and the second mRNA encodes SEQ ID NO: 30 (S2P_IN_B.1.617.2; comprising the following mutations: T19R, T951, G142D, E156G, F157del, R158del, L452R, T478K, D614G, P681R, D950N). "Circulating viruses", as used herein, refers to viruses that have been in circulation for 1 month, 2 months, 3 months, 4 months, 5 months, 6 months, 7 months, 8 months, 9 months, 10 months, 11 months, a portion of a year, 1 year, 1.5 years, 2 years, 3 years, or longer.

In some embodiments, the composition further comprises a third mRNA encoding a third SARS-CoV-2 spike antigen of a third SARS-CoV-2 virus, wherein the third SARS-CoV-2 spike antigen has an amino acid sequence with at least one amino acid mutation with respect to a protein sequence of SEQ ID NO: 20.

In some embodiments, the composition further comprises a fourth mRNA encoding a fourth SARS-CoV-2 spike antigen of a fourth SARS-CoV-2 virus, wherein the fourth SARS-CoV-2 spike antigen has an amino acid sequence with at least one amino acid mutation with respect to a protein of SEQ ID NO: 20.

In some embodiments, the composition further comprises a fifth mRNA encoding a fifth SARS-CoV-2 spike antigen of a fifth SARS-CoV-2 virus, wherein the fifth SARS-CoV-2 spike antigen has an amino acid sequence with at least one amino acid mutation with respect to a protein of SEQ ID NO: 20.

In some embodiments, the composition further comprises a sixth mRNA encoding a sixth SARS-CoV-2 spike antigen of a sixth SARS-CoV-2 virus, wherein the sixth SARS-CoV-2 spike antigen has an amino acid sequence with at least one amino acid mutation with respect to a protein of SEQ ID NO: 20.

In some embodiments, the first and second antigens are antigens of the spike protein. In some embodiments, the third, fourth, fifth, and/or sixth antigens are antigens of the spike protein.

In some embodiments, the mRNAs are present in the composition in an equal amount (e.g., a 1:1 weight/weight ratio or a 1:1 molar ratio), for example, a ratio of 1:1 (:1:1:1:1) of mRNA encoding distinct coronavirus antigens. As used herein, a "weight/weight ratio" or wt/wt ratio or wt:wt ratio refers to the ratio between the weights (masses) of the different components. A "molar ratio" refers to the ratio between different components (e.g., the number of mRNA encoding each antigen). In some embodiments, the ratio is 1:1, 1:2, 1:3, 1:4, 2:1, 3:1, or 4:1. In each embodiment or aspect of the invention, it is understood that the featured vaccines include the mRNAs encapsulated within LNPs. While it is possible to encapsulate each unique mRNA in its own LNP, the mRNA vaccine technology enjoys the significant technological advantage of being able to encapsulate several mRNAs in a single LNP product. In other embodiments the vaccines are separate vaccines that are not co-formulated, but may be admixed separately before administration or simply administered separately.

Exemplary sequences of the coronavirus antigens and the RNA encoding the coronavirus antigens of the compositions of the present disclosure (e.g., SARS-CoV-2 variant antigens) are provided in Table 1. In some embodiments, the mRNA vaccines comprise a sequence that has at least 90%, 91%, 92%, 93%, 94%, 95%, 96%, 97%, 98%, or 99% identity to a sequence selected from SEQ ID NOs: 1, 6, 9, 12, 15, 21, 24, 28, 31, 34, 37, 40, 43, and 45. In some embodiments, the mRNA vaccines encode a polypeptide that is 90%, 91%, 92%, 93%, 94%, 95%, 96%, 97%, 98%, 99% or identical to a sequence selected from SEQ ID NOs: 5, 8, 11, 14, 17, 23, 26, 30, 33, 36, 39, and 42.

Nucleic Acids

The compositions of the present disclosure comprise a (at least one) messenger RNA (mRNA) having an open reading frame (ORF) encoding a coronavirus antigen. In some embodiments, the mRNA further comprises a 5' UTR, 3' UTR, a poly(A) tail and/or a 5' cap analog.

It should also be understood that the coronavirus vaccine of the present disclosure may include any 5' untranslated region (UTR) and/or any 3' UTR. Exemplary UTR sequences include SEQ ID NOs: 2, 4, 50, and 51; however, other UTR sequences may be used or exchanged for any of the UTR sequences described herein. In some embodiments, a 5' UTR of the present disclosure comprises a sequence selected from SEQ ID NO: 50 (GGGAAAUA AGAGAGAAAAGAAGAGUAAGAAGAAAUAUAAG AGCCACC) and SEQ ID NO: 2 (GG-GAAAUAAGAGAGAAAAGAAGAGUAAGAAGAAA UAUAAGACCCCGGCGCCGC CACC). In some embodiments, a 3' UTR of the present disclosure comprises a sequence selected from SEQ ID NO: 51 (UGAUAAUAGGCUGGAGCCUCGGUGGCCAUGCUU CUUGCCCCUUGGGCCUCCCCCCAGCCCCUC-CUCCCCUUCCUGCACCCGUACCCCCG UGGUC-UUUGAAUAAAGUCUGAGUGGGCGGC) and SEQ ID NO: 4 (UGAUAA UAGGCUGGAGCCUCGGUGGCC-UAGCUUCUUGCCCCUUGGGCCUCCCCCCAGCCCC UCCUCCCCUUCCUGCACCCGUACCCCCGUGGUC-UUUGAAUAAAGUCUGAGUGGGC GGC). UTRs may also be omitted from the RNA polynucleotides provided herein.

Nucleic acids comprise a polymer of nucleotides (nucleotide monomers). Thus, nucleic acids are also referred to as polynucleotides. Nucleic acids may be or may include, for example, deoxyribonucleic acids (DNAs), ribonucleic acids (RNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) and/or chimeras and/or combinations thereof.

Messenger RNA (mRNA) is any RNA that encodes a (at least one) protein (a naturally-occurring, non-naturally-occurring, or modified polymer of amino acids) and can be translated to produce the encoded protein in vitro, in vivo, in situ, or ex vivo. The skilled artisan will appreciate that, except where otherwise noted, nucleic acid sequences set forth in the instant application may recite "T"s in a representative DNA sequence but where the sequence represents mRNA, the "T"s would be substituted for "U"s. Thus, any of the DNAs disclosed and identified by a particular sequence identification number herein also disclose the corresponding mRNA sequence complementary to the DNA, where each "T" of the DNA sequence is substituted with "U."

An open reading frame (ORF) is a continuous stretch of DNA or RNA beginning with a start codon (e.g., methionine (ATG or AUG)) and ending with a stop codon (e.g., TAA, TAG or TGA, or UAA, UAG or UGA). An ORF typically encodes a protein. It will be understood that the sequences disclosed herein may further comprise additional elements, e.g., 5' and 3' UTRs, but that those elements, unlike the ORF, need not necessarily be present in an RNA polynucleotide of the present disclosure.

Variants

In some embodiments, the compositions of the present disclosure include RNA that encodes a SARS-CoV-2 antigen variant. Antigen variants or other polypeptide variants refers to molecules that differ in their amino acid sequence from a wild-type, native, or reference sequence. The antigen/polypeptide variants may possess substitutions, deletions, and/or insertions at certain positions within the amino acid sequence, as compared to a native or reference sequence. Examples of SARS-CoV-2 antigen variants are provided in Table 1. Ordinarily, variants possess at least 50% identity to a wild-type, native or reference sequence. In some embodiments, variants share at least 90% identity with a wild-type, native, or reference sequence. In some embodiments, the nucleic acid vaccines described herein encode SARS-CoV-2 variants comprising 1, 2, 3, 4, or more mutations relative to a reference sequence. In some embodiments, the nucleic acid vaccines described herein encode SARS-CoV-2 variants comprising less than 20, 18, 15, 12, or 10 mutations relative to a reference sequence. In some embodiments, the nucleic acid vaccines described herein encode SARS-CoV-2 variants having 1-50 1-40, 1-30, 1-25, 1-20, 1-15, 1-10, 5-50, 5-40, 5-30, 5-25, 5-20, 5-15, 5-10, 10-50, 10-40, 10-30, 10-25, 10-20, 10-15, 20-50, 20-40, 20-30, 20-25, 25-50, 25-40, 25-30, 30-50, 30-40, 40-50 mutations (e.g., substitutions). As used herein, "mutation" refers to an amino acid substitution, insertion, or deletion. A reference sequence refers to a naturally-occurring strain, for example, a naturally-occurring circulating strain of SARS-CoV-2.

Variant antigens/polypeptides encoded by nucleic acids of the disclosure may contain amino acid changes that confer any of a number of desirable properties, e.g., that enhance their immunogenicity, enhance their expression, and/or improve their stability or PK/PD properties in a subject. Variant antigens/polypeptides can be made using routine mutagenesis techniques and assayed as appropriate to determine whether they possess the desired property. Assays to determine expression levels and immunogenicity are well known in the art and exemplary such assays are set forth in the Examples section. Similarly, PK/PD properties of a protein variant can be measured using art recognized techniques, e.g., by determining expression of antigens in a vaccinated subject over time and/or by looking at the durability of the induced immune response. The stability of protein(s) encoded by a variant nucleic acid may be measured by assaying thermal stability or stability upon urea denaturation or may be measured using in silico prediction. Methods for such experiments and in silico determinations are known in the art.

In some embodiments, a composition comprises an RNA or an RNA ORF that comprises a nucleotide sequence of any one of the sequences provided herein, or comprises a nucleotide sequence at least 90%, at least 95%, at least 96%, at least 97%, at least 98%, or at least 99% identical to a nucleotide sequence of any one of the sequences provided herein.

The term "identity" refers to a relationship between the sequences of two or more polypeptides (e.g. antigens) or polynucleotides (nucleic acids), as determined by comparing the sequences. Identity also refers to the degree of sequence relatedness between or among sequences as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related antigens or nucleic acids can be readily calculated by known methods. "Percent (%) identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide (e.g., antigen) have at least 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al (1997), "Gapped BLAST and PSI-BLAST: a new generation of protein database search programs", Nucleic Acids Res. 25:3389-3402). Another popular local alignment technique is based on the Smith-Waterman algorithm (Smith, T. F. & Waterman, M. S. (1981) "Identification of common molecular subsequences." J. Mol. Biol. 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." J. Mol. Biol. 48:443-453). More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm.

As such, polynucleotides encoding peptides or polypeptides containing substitutions, insertions and/or additions, deletions and covalent modifications with respect to reference sequences, in particular the polypeptide (e.g., antigen) sequences disclosed herein, are included within the scope of this disclosure. For example, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble or linked to a solid support. In some embodiments, sequences for (or encoding) signal sequences, termination sequences, transmembrane domains, linkers, multimerization domains (such as, e.g., foldon regions) and the like may be substituted with alternative sequences that achieve the same or a similar function. In some embodiments, cavities in the core of proteins can be filled to improve stability, e.g., by introducing larger amino acids. In other embodiments, buried hydrogen bond networks may be replaced with hydrophobic resides to improve stability. In yet other embodiments, glycosylation sites may be removed and replaced with appropriate residues. Such sequences are readily identifiable to one of skill in the art. It should also be understood that some of the sequences provided herein contain sequence tags or terminal peptide sequences (e.g., at the N-terminal or C-terminal ends) that may be deleted, for example, prior to use in the preparation of an mRNA vaccine.

As recognized by those skilled in the art, protein fragments, functional protein domains, and homologous proteins are also considered to be within the scope of coronavirus antigens of interest. For example, provided herein is any protein fragment (meaning a polypeptide sequence at least one amino acid residue shorter than a reference antigen sequence but otherwise identical) of a reference protein, provided that the fragment is immunogenic and confers a protective immune response to the coronavirus. In addition to variants that are identical to the reference protein but are truncated, in some embodiments, an antigen includes 2, 3, 4, 5, 6, 7, 8, 9, 10, or more mutations, as shown in any of the sequences provided or referenced herein. Antigens/antigenic polypeptides can range in length from about 4, 6, or 8 amino acids to full length proteins.

Stabilizing Elements

Naturally-occurring eukaryotic mRNA molecules can contain stabilizing elements, including, but not limited to untranslated regions (UTR) at their 5'-end (5' UTR) and/or at their 3'-end (3' UTR), in addition to other structural features, such as a 5'-cap structure or a 3'-poly(A) tail. Both the 5' UTR and the 3' UTR are typically transcribed from the genomic DNA and are elements of the premature mRNA. Characteristic structural features of mature mRNA, such as the 5'-cap and the 3'-poly(A) tail are usually added to the transcribed (premature) mRNA during mRNA processing.

In some embodiments, a composition includes an RNA polynucleotide having an open reading frame encoding at least one antigenic polypeptide having at least one modification, at least one 5' terminal cap, and is formulated within a lipid nanoparticle. 5'-capping of polynucleotides may be completed concomitantly during the in vitro-transcription reaction using the following chemical RNA cap analogs to generate the 5'-guanosine cap structure according to manufacturer protocols: 3'-O-Me-m7G(5')ppp(5') G [the ARCA cap]; G(5')ppp(5')A; G(5')ppp(5')G; m7G(5')ppp(5')A; m7G (5')ppp(5')G (New England BioLabs, Ipswich, MA). 5'-capping of modified RNA may be completed post-transcriptionally using a Vaccinia Virus Capping Enzyme to generate the "Cap 0" structure: m7G(5')ppp(5')G (New England BioLabs, Ipswich, MA). Cap 1 structure may be generated using both Vaccinia Virus Capping Enzyme and a 2'-0 methyl-transferase to generate: m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase. Enzymes may be derived from a recombinant source.

The 3'-poly(A) tail is typically a stretch of adenine nucleotides added to the 3'-end of the transcribed mRNA. It can, in some instances, comprise up to about 400 adenine nucleotides. In some embodiments, the length of the 3'-poly (A) tail may be an essential element with respect to the stability of the individual mRNA.

In some embodiments, a composition includes a stabilizing element. Stabilizing elements may include for instance a histone stem-loop. A stem-loop binding protein (SLBP), a 32 kDa protein has been identified. It is associated with the histone stem-loop at the 3'-end of the histone messages in both the nucleus and the cytoplasm. Its expression level is regulated by the cell cycle; it peaks during the S-phase, when histone mRNA levels are also elevated. The protein has been shown to be essential for efficient 3'-end processing of histone pre-mRNA by the U7 snRNP. SLBP continues to be associated with the stem-loop after processing, and then stimulates the translation of mature histone mRNAs into histone proteins in the cytoplasm. The RNA binding domain of SLBP is conserved through metazoa and protozoa; its binding to the histone stem-loop depends on the structure of the loop. The minimum binding site includes at least three nucleotides 5' and two nucleotides 3' relative to the stem-loop.

In some embodiments, an mRNA includes a coding region, at least one histone stem-loop, and optionally, a poly(A) sequence or polyadenylation signal. The poly(A) sequence or polyadenylation signal generally should enhance the expression level of the encoded protein. The encoded protein, in some embodiments, is not a histone protein, a reporter protein (e.g. Luciferase, GFP, EGFP, β-Galactosidase, EGFP), or a marker or selection protein (e.g. alpha-Globin, Galactokinase and Xanthine:guanine phosphoribosyl transferase (GPT)).

In some embodiments, an mRNA includes the combination of a poly(A) sequence or polyadenylation signal and at least one histone stem-loop, even though both represent alternative mechanisms in nature, acts synergistically to increase the protein expression beyond the level observed with either of the individual elements. The synergistic effect of the combination of poly(A) and at least one histone stem-loop does not depend on the order of the elements or the length of the poly(A) sequence.

In some embodiments, an mRNA does not include a histone downstream element (HDE). "Histone downstream element" (HDE) includes a purine-rich polynucleotide stretch of approximately 15 to 20 nucleotides 3' of naturally occurring stem-loops, representing the binding site for the U7 snRNA, which is involved in processing of histone pre-mRNA into mature histone mRNA. In some embodiments, the nucleic acid does not include an intron.

An mRNA may or may not contain an enhancer and/or promoter sequence, which may be modified or unmodified or which may be activated or inactivated. In some embodiments, the histone stem-loop is generally derived from histone genes and includes an intramolecular base pairing of two neighbored partially or entirely reverse complementary sequences separated by a spacer, consisting of a short sequence, which forms the loop of the structure. The unpaired loop region is typically unable to base pair with either of the stem loop elements. It occurs more often in RNA, as is a key component of many RNA secondary structures but may be present in single-stranded DNA as well. Stability of the stem-loop structure generally depends on the length, number of mismatches or bulges, and base composition of the paired region. In some embodiments, wobble base pairing (non-Watson-Crick base pairing) may result. In some embodiments, the at least one histone stem-loop sequence comprises a length of 15 to 45 nucleotides.

In some embodiments, an mRNA has one or more AU-rich sequences removed. These sequences, sometimes referred to as AURES are destabilizing sequences found in the 3'UTR. The AURES may be removed from the RNA vaccines. Alternatively, the AURES may remain in the RNA vaccine.

Signal Peptides

In some embodiments, a composition comprises an mRNA having an ORF that encodes a signal peptide fused to the coronavirus antigen. Signal peptides, comprising the N-terminal 15-60 amino acids of proteins, are typically needed for the translocation across the membrane on the secretory pathway and, thus, universally control the entry of most proteins both in eukaryotes and prokaryotes to the secretory pathway. In eukaryotes, the signal peptide of a nascent precursor protein (pre-protein) directs the ribosome to the rough endoplasmic reticulum (ER) membrane and initiates the transport of the growing peptide chain across it for processing. ER processing produces mature proteins, wherein the signal peptide is cleaved from precursor proteins, typically by an ER-resident signal peptidase of the host cell, or they remain uncleaved and function as a membrane anchor. A signal peptide may also facilitate the targeting of the protein to the cell membrane.

A signal peptide may have a length of 15-60 amino acids. For example, a signal peptide may have a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. In some embodiments, a signal peptide has a length of 20-60, 25-60, 30-60, 35-60, 40-60, 45-60, 50-60, 55-60, 15-55, 20-55, 25-55, 30-55, 35-55, 40-55, 45-55, 50-55, 15-50, 20-50, 25-50, 30-50, 35-50, 40-50, 45-50, 15-45, 20-45, 25-45, 30-45, 35-45, 40-45, 15-40, 20-40, 25-40, 30-40, 35-40, 15-35, 20-35, 25-35, 30-35, 15-30, 20-30, 25-30, 15-25, 20-25, or 15-20 amino acids.

Signal peptides from heterologous genes (which regulate expression of genes other than coronavirus antigens in nature) are known in the art and can be tested for desired properties and then incorporated into a nucleic acid of the disclosure.

Scaffold Moieties

The mRNA vaccines as provided herein, in some embodiments, encode fusion proteins that comprise coronavirus antigens linked to one another or scaffold moieties. In some embodiments, such scaffold moieties impart desired properties to an antigen encoded by a nucleic acid of the disclosure. For example, scaffold proteins may improve the immunogenicity of an antigen, e.g., by altering the structure of the antigen, altering the uptake and processing of the antigen, and/or causing the antigen to bind to a binding partner.

In some embodiments, the scaffold moiety is protein that can self-assemble into protein nanoparticles that are highly symmetric, stable, and structurally organized, with diameters of 10-150 nm, a highly suitable size range for optimal interactions with various cells of the immune system. In some embodiments, viral proteins or virus-like particles can be used to form stable nanoparticle structures. Examples of such viral proteins are known in the art. For example, in some embodiments, the scaffold moiety is a hepatitis B surface antigen (HBsAg). HBsAg forms spherical particles with an average diameter of ~22 nm and which lacked nucleic acid and hence are non-infectious (Lopez-Sagaseta, J. et al. Computational and Structural Biotechnology Journal 14 (2016) 58-68). In some embodiments, the scaffold moiety is a hepatitis B core antigen (HBcAg) self-assembles into particles of 24-31 nm diameter, which resembled the viral cores obtained from HBV-infected human liver. HBcAg produced in self-assembles into two classes of differently sized nanoparticles of 300 Å and 360 Å diameter, corresponding to 180 or 240 protomers. In some embodiments, the coronavirus antigen is fused to HBsAG or HBcAG to facilitate self-assembly of nanoparticles displaying the coronavirus antigen.

In some embodiments, bacterial protein platforms may be used. Non-limiting examples of these self-assembling proteins include ferritin, lumazine and encapsulin.

Ferritin is a protein whose main function is intracellular iron storage. Ferritin is made of 24 subunits, each composed of a four-alpha-helix bundle, that self-assemble in a quaternary structure with octahedral symmetry (Cho K. J. et al. *J Mol Biol.* 2009; 390:83-98). Several high-resolution structures of ferritin have been determined, confirming that *Helicobacter pylori* ferritin is made of 24 identical protomers, whereas in animals, there are ferritin light and heavy chains that can assemble alone or combine with different ratios into particles of 24 subunits (Granier T. et al. *J Biol Inorg Chem.* 2003; 8:105-111; Lawson D. M. et al. *Nature.* 1991; 349:541-544). Ferritin self-assembles into nanoparticles with robust thermal and chemical stability. Thus, the ferritin nanoparticle is well-suited to carry and expose antigens.

Lumazine synthase (LS) is also well-suited as a nanoparticle platform for antigen display. LS, which is responsible for the penultimate catalytic step in the biosynthesis of riboflavin, is an enzyme present in a broad variety of organisms, including archaea, bacteria, fungi, plants, and eubacteria (Weber S. E. Flavins and Flavoproteins. Methods and Protocols, Series: Methods in Molecular Biology. 2014). The LS monomer is 150 amino acids long and consists of beta-sheets along with tandem alpha-helices flanking its sides. A number of different quaternary structures have been reported for LS, illustrating its morphological versatility: from homopentamers up to symmetrical assemblies of 12 pentamers forming capsids of 150 Å diameter. Even LS cages of more than 100 subunits have been described (Zhang X. et al. J Mol Biol. 2006; 362:753-770).

Encapsulin, a novel protein cage nanoparticle isolated from thermophile *Thermotoga maritima*, may also be used as a platform to present antigens on the surface of self-assembling nanoparticles. Encapsulin is assembled from 60 copies of identical 31 kDa monomers having a thin and icosahedral T=1 symmetric cage structure with interior and exterior diameters of 20 and 24 nm, respectively (Sutter M. et al. Nat Struct Mol Biol. 2008, 15: 939-947). Although the exact function of encapsulin in *T. maritima* is not clearly understood yet, its crystal structure has been recently solved and its function was postulated as a cellular compartment that encapsulates proteins such as DyP (Dye decolorizing peroxidase) and Flp (Ferritin like protein), which are involved in oxidative stress responses (Rahmanpour R. et al. FEBS J. 2013, 280: 2097-2104).

In some embodiments, an RNA of the present disclosure encodes a coronavirus antigen fused to a foldon domain. The foldon domain may be, for example, obtained from bacteriophage T4 fibritin (see, e.g., Tao Y, et al. *Structure.* 1997 Jun. 15; 5(6):789-98).

Linkers and Cleavable Peptides

In some embodiments, the mRNAs of the disclosure encode more than one polypeptide, referred to herein as fusion proteins. In some embodiments, the mRNA further encodes a linker located between at least one or each domain of the fusion protein. The linker can be, for example, a cleavable linker or protease-sensitive linker. In some embodiments, the linker is selected from the group consisting of F2A linker, P2A linker, T2A linker, E2A linker, and combinations thereof. This family of self-cleaving peptide linkers, referred to as 2A peptides, has been described in the art (see for example, Kim, J. H. et al. (2011) *PLoS ONE* 6:e18556). In some embodiments, the linker is an F2A linker. In some embodiments, the linker is a GGGS (SEQ ID NO: 49) linker. In some embodiments, the fusion protein contains three domains with intervening linkers, having the structure: domain-linker-domain-linker-domain.

Cleavable linkers known in the art may be used in connection with the disclosure. Exemplary such linkers include: F2A linkers, T2A linkers, P2A linkers, E2A linkers (See, e.g., WO2017127750). The skilled artisan will appreciate that other art-recognized linkers may be suitable for use in the constructs of the disclosure (e.g., encoded by the nucleic acids of the disclosure). The skilled artisan will likewise appreciate that other polycistronic constructs (mRNA encoding more than one antigen/polypeptide separately within the same molecule) may be suitable for use as provided herein.

Sequence Optimization

In some embodiments, an ORF encoding an antigen of the disclosure is codon optimized. Codon optimization methods are known in the art. For example, an ORF of any one or more of the sequences provided herein may be codon optimized. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g., glycosylation sites); add, remove or shuffle protein domains; insert or delete restriction sites; modify ribosome binding sites and mRNA degradation sites; adjust translational rates to allow the various domains of the protein to fold properly; or reduce or eliminate problem secondary structures within the polynucleotide. Codon optimization tools, algorithms and services are known in the art—non-limiting examples include services from GeneArt (Life Technologies), DNA2.0 (Menlo Park CA) and/or proprietary methods. In some embodiments, the open reading frame (ORF) sequence is optimized using optimization algorithms.

In some embodiments, a codon optimized sequence shares less than 95% sequence identity to a naturally-occurring or wild-type sequence ORF (e.g., a naturally-occurring or wild-type mRNA sequence encoding a coronavirus antigen). In some embodiments, a codon optimized sequence shares less than 90% sequence identity to a naturally-occurring or wild-type sequence (e.g., a naturally-occurring or wild-type mRNA sequence encoding a coronavirus antigen). In some embodiments, a codon optimized sequence shares less than 85% sequence identity to a naturally-occurring or wild-type sequence (e.g., a naturally-occurring or wild-type mRNA sequence encoding a coronavirus antigen). In some embodiments, a codon optimized sequence shares less than 80% sequence identity to a naturally-occurring or wild-type sequence (e.g., a naturally-occurring or wild-type mRNA sequence encoding a coronavirus antigen). In some embodiments, a codon optimized sequence shares less than 75% sequence identity to a naturally-occurring or wild-type sequence (e.g., a naturally-occurring or wild-type mRNA sequence encoding a coronavirus antigen).

In some embodiments, a codon optimized sequence shares between 65% and 85% (e.g., between about 67% and about 85% or between about 67% and about 80%) sequence identity to a naturally-occurring or wild-type sequence (e.g., a naturally-occurring or wild-type mRNA sequence encoding a coronavirus antigen). In some embodiments, a codon optimized sequence shares between 65% and 75% or about 80% sequence identity to a naturally-occurring or wild-type sequence (e.g., a naturally-occurring or wild-type mRNA sequence encoding a coronavirus antigen).

In some embodiments, a codon-optimized sequence encodes an antigen that is as immunogenic as, or more immunogenic than (e.g., at least 10%, at least 20%, at least 30%, at least 40%, at least 50%, at least 100%, or at least 200% more), than a coronavirus antigen encoded by a non-codon-optimized sequence.

When transfected into mammalian host cells, the modified mRNAs have a stability of between 12-18 hours, or greater than 18 hours, e.g., 24, 36, 48, 60, 72, or greater than 72 hours and are capable of being expressed by the mammalian host cells.

In some embodiments, a codon optimized RNA may be one in which the levels of G/C are enhanced. The G/C-content of nucleic acid molecules (e.g., mRNA) may influence the stability of the RNA. RNA having an increased amount of guanine (G) and/or cytosine (C) residues may be functionally more stable than RNA containing a large amount of adenine (A) and thymine (T) or uracil (U) nucleotides. As an example, WO02/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

Chemically Unmodified Nucleotides

In some embodiments, an mRNA is not chemically modified and comprises the standard ribonucleotides consisting of adenosine, guanosine, cytosine and uridine. In some embodiments, nucleotides and nucleosides of the present disclosure comprise standard nucleoside residues such as those present in transcribed RNA (e.g. A, G, C, or U). In some embodiments, nucleotides and nucleosides of the present disclosure comprise standard deoxyribonucleosides such as those present in DNA (e.g. dA, dG, dC, or dT).

Chemical Modifications

The compositions of the present disclosure comprise, in some embodiments, an RNA having an open reading frame encoding a coronavirus antigen, wherein the nucleic acid comprises nucleotides and/or nucleosides that can be standard (unmodified) or modified as is known in the art. In some embodiments, nucleotides and nucleosides of the present disclosure comprise modified nucleotides or nucleosides. Such modified nucleotides and nucleosides can be naturally-occurring modified nucleotides and nucleosides or non-naturally occurring modified nucleotides and nucleosides. Such modifications can include those at the sugar, backbone, or nucleobase portion of the nucleotide and/or nucleoside as are recognized in the art.

In some embodiments, a naturally-occurring modified nucleotide or nucleotide of the disclosure is one as is generally known or recognized in the art. Non-limiting examples of such naturally occurring modified nucleotides and nucleotides can be found, inter alia, in the widely recognized MODOMICS database.

In some embodiments, a non-naturally occurring modified nucleotide or nucleoside of the disclosure is one as is generally known or recognized in the art. Non-limiting examples of such non-naturally occurring modified nucleotides and nucleosides can be found, inter alia, in published US application Nos. PCT/US2012/058519; PCT/US2013/075177; PCT/US2014/058897; PCT/US2014/058891; PCT/US2014/070413; PCT/US2015/36773; PCT/US2015/36759; PCT/US2015/36771; or PCT/IB2017/051367 all of which are incorporated by reference herein.

Hence, nucleic acids of the disclosure (e.g., DNA nucleic acids and RNA nucleic acids, such as mRNA nucleic acids) can comprise standard nucleotides and nucleosides, naturally-occurring nucleotides and nucleosides, non-naturally-occurring nucleotides and nucleosides, or any combination thereof.

Nucleic acids of the disclosure (e.g., DNA nucleic acids and RNA nucleic acids, such as mRNA nucleic acids), in some embodiments, comprise various (more than one) different types of standard and/or modified nucleotides and nucleosides. In some embodiments, a particular region of a nucleic acid contains one, two or more (optionally different) types of standard and/or modified nucleotides and nucleosides.

In some embodiments, a modified RNA nucleic acid (e.g., a modified mRNA nucleic acid), introduced to a cell or organism, exhibits reduced degradation in the cell or organism, respectively, relative to an unmodified nucleic acid comprising standard nucleotides and nucleosides.

In some embodiments, a modified RNA nucleic acid (e.g., a modified mRNA nucleic acid), introduced into a cell or organism, may exhibit reduced immunogenicity in the cell or organism, respectively (e.g., a reduced innate response) relative to an unmodified nucleic acid comprising standard nucleotides and nucleosides.

Nucleic acids (e.g., RNA nucleic acids, such as mRNA nucleic acids), in some embodiments, comprise non-natural modified nucleotides that are introduced during synthesis or post-synthesis of the nucleic acids to achieve desired functions or properties. The modifications may be present on internucleotide linkages, purine or pyrimidine bases, or sugars. The modification may be introduced with chemical synthesis or with a polymerase enzyme at the terminal of a chain or anywhere else in the chain. Any of the regions of a nucleic acid may be chemically modified.

The present disclosure provides for modified nucleosides and nucleotides of a nucleic acid (e.g., RNA nucleic acids, such as mRNA nucleic acids). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside, including a phosphate group. Modified nucleotides may by synthesized by any useful method, such as, for example, chemically, enzymatically, or recombinantly, to include one or more modified or non-natural nucleosides. Nucleic acids can comprise a region or regions of linked nucleosides. Such regions may have variable backbone linkages. The linkages can be standard phosphodiester linkages, in which case the nucleic acids would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures, such as, for example, in those nucleic acids having at least one chemical modification. One example of such non-standard base pairing is the base pairing between the modified nucleotide inosine and adenine, cytosine or uracil. Any combination of base/sugar or linker may be incorporated into nucleic acids of the present disclosure.

In some embodiments, modified nucleobases in nucleic acids (e.g., RNA nucleic acids, such as mRNA nucleic acids) comprise 1-methyl-pseudouridine (m1ψ), 1-ethyl-pseudouridine (e1ψ), 5-methoxy-uridine (mo5U), 5-methyl-cytidine (m5C), and/or pseudouridine (ψ). In some embodiments, modified nucleobases in nucleic acids (e.g., RNA nucleic acids, such as mRNA nucleic acids) comprise 5-methoxymethyl uridine, 5-methylthio uridine, 1-methoxymethyl pseudouridine, 5-methyl cytidine, and/or 5-methoxy cytidine. In some embodiments, the polyribonucleotide includes a combination of at least two (e.g., 2, 3, 4 or more) of any of the aforementioned modified nucleobases, including but not limited to chemical modifications.

In some embodiments, a mRNA of the disclosure comprises 1-methyl-pseudouridine (m1ψ) substitutions at one or more or all uridine positions of the nucleic acid.

In some embodiments, a mRNA of the disclosure comprises 1-methyl-pseudouridine (m1ψ) substitutions at one or more or all uridine positions of the nucleic acid and 5-methyl cytidine substitutions at one or more or all cytidine positions of the nucleic acid.

In some embodiments, a mRNA of the disclosure comprises pseudouridine (ψ) substitutions at one or more or all uridine positions of the nucleic acid.

In some embodiments, a mRNA of the disclosure comprises pseudouridine (ψ) substitutions at one or more or all uridine positions of the nucleic acid and 5-methyl cytidine substitutions at one or more or all cytidine positions of the nucleic acid.

In some embodiments, a mRNA of the disclosure comprises uridine at one or more or all uridine positions of the nucleic acid.

In some embodiments, mRNAs are uniformly modified (e.g., fully modified, modified throughout the entire sequence) for a particular modification. For example, a nucleic acid can be uniformly modified with 1-methyl-pseudouridine, meaning that all uridine residues in the mRNA sequence are replaced with 1-methyl-pseudouridine. Similarly, a nucleic acid can be uniformly modified for any type of nucleoside residue present in the sequence by replacement with a modified residue such as those set forth above.

The nucleic acids of the present disclosure may be partially or fully modified along the entire length of the molecule. For example, one or more or all or a given type of nucleotide (e.g., purine or pyrimidine, or any one or more or all of A, G, U, C) may be uniformly modified in a nucleic acid of the disclosure, or in a predetermined sequence region thereof (e.g., in the mRNA including or excluding the poly(A) tail). In some embodiments, all nucleotides X in a nucleic acid of the present disclosure (or in a sequence region thereof) are modified nucleotides, wherein X may be any one of nucleotides A, G, U, C, or any one of the combinations A+G, A+U, A+C, G+U, G+C, U+C, A+G+U, A+G+C, G+U+C or A+G+C.

The nucleic acid may contain from about 1% to about 100% modified nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The mRNAs may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the nucleic acids may contain a modified pyrimidine such as a modified uracil or cytosine. In some embodiments, at least 5%, at least 10%, at least 25%, at least 50%, at least 80%, at least 90% or 100% of the uracil in the nucleic acid is replaced with a modified uracil (e.g., a 5-substituted uracil). The modified uracil can be replaced by a compound having a single unique structure or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the nucleic acid is replaced with a modified cytosine (e.g., a 5-substituted cytosine). The modified cytosine can be replaced by a compound having a single unique structure or can be replaced by a plurality of compounds having different structures (e.g., 2, 3, 4 or more unique structures).

Untranslated Regions (UTRs)

The mRNAs of the present disclosure may comprise one or more regions or parts which act or function as an untranslated region. Where mRNAs are designed to encode at least one antigen of interest, the nucleic may comprise one or more of these untranslated regions (UTRs). Wild-type untranslated regions of a nucleic acid are transcribed but not translated. In mRNA, the 5' UTR starts at the transcription start site and continues to the start codon but does not include the start codon; whereas, the 3' UTR starts immediately following the stop codon and continues until the transcriptional termination signal. There is growing body of evidence about the regulatory roles played by the UTRs in terms of stability of the nucleic acid molecule and translation. The regulatory features of a UTR can be incorporated into the polynucleotides of the present disclosure to, among other things, enhance the stability of the molecule. The specific features can also be incorporated to ensure controlled down-regulation of the transcript in case they are misdirected to undesired organs sites. A variety of 5'UTR and 3'UTR sequences are known and available in the art.

A 5' UTR is region of an mRNA that is directly upstream (5') from the start codon (the first codon of an mRNA transcript translated by a ribosome). A 5' UTR does not encode a protein (is non-coding). Natural 5'UTRs have features that play roles in translation initiation. They harbor signatures like Kozak sequences which are commonly known to be involved in the process by which the ribosome initiates translation of many genes. Kozak sequences have the consensus CCR(A/G)CCAUGG (SEQ ID NO: 52), where R is a purine (adenine or guanine) three bases upstream of the start codon (AUG), which is followed by another 'G'.5'UTR also have been known to form secondary structures which are involved in elongation factor binding.

In some embodiments of the disclosure, a 5' UTR is a heterologous UTR, i.e., is a UTR found in nature associated with a different ORF. In another embodiment, a 5' UTR is a synthetic UTR, i.e., does not occur in nature. Synthetic UTRs include UTRs that have been mutated to improve their properties, e.g., which increase gene expression as well as those which are completely synthetic. Exemplary 5' UTRs include *Xenopus* or human derived a-globin or b-globin (U.S. Pat. Nos. 8,278,063; 9,012,219), human cytochrome b-245 a polypeptide, and hydroxysteroid (17b) dehydrogenase, and Tobacco etch virus (U.S. Pat. Nos. 8,278,063, 9,012,219). CMV immediate-early 1 (IE1) gene (US20140206753, WO2013/185069), the sequence GGGAUCCUACC (SEQ ID NO: 24) (WO2014144196) may also be used. In another embodiment, 5' UTR of a TOP gene is a 5' UTR of a TOP gene lacking the 5' TOP motif (the oligopyrimidine tract) (e.g., WO/2015101414, WO2015101415, WO/2015/062738, WO2015024667, WO2015024667; 5' UTR element derived from ribosomal protein Large 32 (L32) gene (WO/2015101414, WO2015101415, WO/2015/062738), 5' UTR element derived from the 5'UTR of an hydroxysteroid (17-β) dehydrogenase 4 gene (HSD17B4) (WO2015024667), or a 5' UTR element derived from the 5' UTR of ATP5A1 (WO2015024667) can be used. In some embodiments, an internal ribosome entry site (IRES) is used instead of a 5' UTR.

In some embodiments, a 5' UTR of the present disclosure comprises a sequence selected from SEQ ID NO: 2 and SEQ ID NO: 21.

A 3' UTR is region of an mRNA that is directly downstream (3') from the stop codon (the codon of an mRNA transcript that signals a termination of translation). A 3' UTR does not encode a protein (is non-coding). Natural or wild type 3' UTRs are known to have stretches of adenosines and uridines embedded in them. These AU rich signatures are particularly prevalent in genes with high rates of turnover. Based on their sequence features and functional properties, the AU rich elements (AREs) can be separated into three classes (Chen et al, 1995): Class I AREs contain several dispersed copies of an AUUUA motif within U-rich regions. C-Myc and MyoD contain class I AREs. Class II AREs possess two or more overlapping UUAUUUA(U/A)(U/A) nonamers. Molecules containing this type of AREs include GM-CSF and TNF-a. Class III ARES are less well defined. These U rich regions do not contain an AUUUA motif. c-Jun and Myogenin are two well-studied examples of this class. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of nucleic acids (e.g., RNA) of the disclosure. When engineering specific nucleic acids, one or more copies of an ARE can be introduced to make nucleic acids of the disclosure less stable and thereby curtail translation and decrease production of the resultant protein. Likewise, AREs can be identified and removed or mutated to increase the intracellular stability and thus increase translation and production of the resultant protein. Transfection experiments can be conducted in relevant cell lines, using nucleic acids of the disclosure and protein production can be assayed at various time points post-transfection. For example, cells can be transfected with different ARE-engineering molecules and by using an ELISA kit to the relevant protein and assaying protein produced at 6 hour, 12 hour, 24 hour, 48 hour, and 7 days post-transfection.

Those of ordinary skill in the art will understand that 5'UTRs that are heterologous or synthetic may be used with any desired 3' UTR sequence. For example, a heterologous 5'UTR may be used with a synthetic 3'UTR with a heterologous 3'UTR.

Non-UTR sequences may also be used as regions or subregions within a nucleic acid. For example, introns or portions of introns sequences may be incorporated into regions of nucleic acid of the disclosure. Incorporation of intronic sequences may increase protein production as well as nucleic acid levels.

Combinations of features may be included in flanking regions and may be contained within other features. For example, the ORF may be flanked by a 5' UTR which may contain a strong Kozak translational initiation signal and/or a 3' UTR which may include an oligo(dT) sequence for templated addition of a poly-A tail. 5' UTR may comprise a first polynucleotide fragment and a second polynucleotide fragment from the same and/or different genes such as the 5' UTRs described in US Patent Application Publication No. 20100293625 and PCT/US2014/069155, herein incorporated by reference in its entirety.

It should be understood that any UTR from any gene may be incorporated into the regions of a nucleic acid. Furthermore, multiple wild-type UTRs of any known gene may be utilized. It is also within the scope of the present disclosure to provide artificial UTRs which are not variants of wild type regions. These UTRs or portions thereof may be placed in the same orientation as in the transcript from which they were selected or may be altered in orientation or location. Hence a 5' or 3' UTR may be inverted, shortened, lengthened, made with one or more other 5' UTRs or 3' UTRs. As used herein, the term "altered" as it relates to a UTR sequence, means that the UTR has been changed in some way in relation to a reference sequence. For example, a 3' UTR or 5' UTR may be altered relative to a wild-type or native UTR by the change in orientation or location as taught above or may be altered by the inclusion of additional nucleotides, deletion of nucleotides, swapping or transposition of nucleotides. Any of these changes producing an "altered" UTR (whether 3' or 5') comprise a variant UTR.

In some embodiments, a double, triple or quadruple UTR such as a 5' UTR or 3' UTR may be used. As used herein, a "double" UTR is one in which two copies of the same UTR are encoded either in series or substantially in series. For example, a double beta-globin 3' UTR may be used as described in US Patent publication 20100129877, the contents of which are incorporated herein by reference in its entirety.

It is also within the scope of the present disclosure to have patterned UTRs. As used herein "patterned UTRs" are those UTRs which reflect a repeating or alternating pattern, such as ABABAB or AABBAABBAABB or ABCABCABC or variants thereof repeated once, twice, or more than 3 times. In these patterns, each letter, A, B, or C represent a different UTR at the nucleotide level.

In some embodiments, flanking regions are selected from a family of transcripts whose proteins share a common function, structure, feature or property. For example, polypeptides of interest may belong to a family of proteins which are expressed in a particular cell, tissue or at some time during development. The UTRs from any of these genes may be swapped for any other UTR of the same or different family of proteins to create a new polynucleotide. As used herein, a "family of proteins" is used in the broadest sense to refer to a group of two or more polypeptides of interest which share at least one function, structure, feature, localization, origin, or expression pattern.

The untranslated region may also include translation enhancer elements (TEE). As a non-limiting example, the TEE may include those described in US Application No. 20090226470, herein incorporated by reference in its entirety, and those known in the art.

Non-Coding Sequences

Aspects of the disclosure relate to multivalent RNA compositions which comprise mRNAs, e.g., 2-15 mRNA polynucleotides each comprising a distinct open reading frame (ORF) encoding a coronavirus virus antigenic polypeptide, wherein each mRNA polynucleotide comprises one or more non-coding sequences in an untranslated region (UTR) having unique identifier sequences (non-coding sequences). In some embodiments the non-coding sequence is a unique non-coding sequence. In some embodiments, each mRNA in a multivalent vaccine composition comprises its own unique non-coding sequence. As used herein, "non-coding sequence" refers to a sequence of a biological molecule (e.g., nucleic acid, protein, etc.) that when combined with the sequence another biological molecule serves to identify the other biological molecule. Typically, a non-coding sequence is a heterologous sequence that is incorporated within or appended to a sequence of a target biological molecule and utilized as a reference in order to identify a target molecule of interest. In some embodiments, a non-coding sequence is a sequence of a nucleic acid (e.g., a heterologous or synthetic nucleic acid) that is incorporated within or appended to a target nucleic acid and utilized as a reference in order to identify the target nucleic acid. In some embodiments, a non-coding sequence is of the formula (N)n. In some embodiments, n is an integer in the range of 5 to 20, 5 to 10, 10 to 20, 7 to 20, or 7 to 30. In some embodiments, n is 2, 3, 4, 5, 6, 7, 8, 9, 10, 11, 12, 13, 14, 15, 16, 17, 18, 19, 20, 21, 22, 23, 24, 25, 26, 27, 28, 29, 30 or more. In some embodiments, each N is a nucleotide that is independently selected from A, G, T, U, and C, or analogues thereof. Thus, some embodiments comprise nucleic acids (e.g., mRNAs) that (i) have a target sequence of interest (e.g., a coding sequence (e.g., that encodes an antigen protein or antigenic polypeptide)); and (ii) comprises a unique non-coding sequence.

In some embodiments, one or more in vitro transcribed mRNAs comprise one or more non-coding sequences in an untranslated region (UTR), such as a 5' UTR or 3' UTR. Inclusion of a non-coding sequence in the UTR of an mRNA prevents non-coding sequence from being translated into a peptide. In some embodiments, a non-coding sequence is positioned in a 3' UTR of an mRNA. In some embodiments, the non-coding sequence is positioned upstream of the polyA tail of the mRNA. In some embodiments, the non-coding sequence is positioned downstream of (e.g., after) the polyA tail of the mRNA. In some embodiments, the non-coding sequence is positioned between the last codon of the ORF of the mRNA and the first "A" of the polyA tail of the mRNA. In some embodiments, a polynucleotide non-coding sequence positioned in a UTR comprises between 1 and 10 nucleotides (e.g., 1, 2, 3, 4, 5, 6, 7, 8, 9, or 10 nucleotides). In some embodiments, UTR comprising a polynucleotide non-coding sequence further comprises one or more (e.g., 1, 2, 3, or more) RNAse cleavage sites, such as RNase H cleavage sites. In some embodiments, each different RNA of a multivalent RNA composition comprises a different (e.g., unique) non-coding sequence. In some embodiments, RNAs of a multivalent RNA composition are detected and/or purified according to the polynucleotide non-coding sequences of the RNAs. In some embodiments, the mRNA non-coding sequences are used to identify the presence of mRNA or determine a relative ratio of different mRNAs in a sample (e.g., a reaction product or a drug product). In some embodiments, the mRNA non-coding sequences are detected using one or more of deep sequencing, PCR, and Sanger sequencing. Exemplary non-coding sequences include: AACGUGAU; AAACAUCG; ATGCCUAA; AGUGGUCA; ACCACUGU; ACAUUGGC; CAGAUCUG; CAUCAAGU; CGCUGAUC; ACAAGCUA; CUGUAGCC; AGUACAAG; AACAACCA; AACCGAGA; AACGCUUA; AAGACGGA; AAGGUACA; ACACAGAA; ACAGCAGA; ACCUCCAA; ACGCUCGA; ACGUAUCA; ACUAUGCA; AGAGUCAA; AGAUCGCA; AGCAGGAA; AGUCACUA; AUCCUGUA; AUUGAGGA; CAACCACA; GACUAGUA; CAAUGGAA; CACUUCGA; CAGCGUUA; CAUAC- CAA; CCAGUUCA; CCGAAGUA; ACAGUG; CGAUGU; UUAGGC; AUCACG; and UGACCA.

In some embodiments the multivalent RNA composition is produced by a method comprising:

(a) combining a linearized first DNA molecule encoding the first mRNA polynucleotide, a linearized second DNA molecule encoding the second mRNA polynucleotide, and, optionally, a linearized third, fourth, fifth, sixth, seventh, eighth, ninth or tenth DNA molecule encoding the third, fourth, fifth, sixth, seventh, eighth, ninth or tenth mRNA polynucleotide into a single reaction vessel, wherein the first DNA molecule, the second DNA molecule, and the third, fourth, fifth, sixth, seventh, eighth, ninth or tenth DNA molecule are obtained from different sources; and (b) simultaneously in vitro transcribing the linearized first DNA molecule, the linearized second DNA molecule and the optional linearized third, fourth, fifth, sixth, seventh, eighth, ninth or tenth DNA molecule to obtain a multivalent RNA composition. The different sources may be bacterial cell cultures which may not be co-cultured. In some embodiments the amounts of the first, second and third, fourth, fifth, sixth, seventh, eighth, ninth or tenth DNA molecules present in the reaction mixture prior to the start of the IVT have been normalized.

In Vitro Transcription of RNA cDNA encoding the polynucleotides described herein may be transcribed using an in vitro transcription (IVT) system. In vitro transcription of RNA is known in the art and is described in International Publication WO 2014/152027, which is incorporated by reference herein in its entirety. In some embodiments, the RNA of the present disclosure is prepared in accordance with any one or more of the methods described in WO 2018/053209 and WO 2019/036682, each of which is incorporated by reference herein.

In some embodiments, the RNA transcript is generated using a non-amplified, linearized DNA template in an in vitro transcription reaction to generate the RNA transcript. In some embodiments, the template DNA is isolated DNA. In some embodiments, the template DNA is cDNA. In some embodiments, the cDNA is formed by reverse transcription of an RNA polynucleotide, for example, but not limited to coronavirus mRNA. In some embodiments, cells, e.g., bacterial cells, e.g., *E. coli*, e.g., DH-1 cells are transfected with the plasmid DNA template. In some embodiments, the transfected cells are cultured to replicate the plasmid DNA which is then isolated and purified. In some embodiments, the DNA template includes a RNA polymerase promoter, e.g., a T7 promoter located 5' to and operably linked to the gene of interest.

In some embodiments, an in vitro transcription template encodes a 5' untranslated (UTR) region, contains an open reading frame, and encodes a 3' UTR and a poly(A) tail. The particular nucleic acid sequence composition and length of an in vitro transcription template will depend on the mRNA encoded by the template.

A "5' untranslated region" (UTR) refers to a region of an mRNA that is directly upstream (i.e., 5') from the start codon (i.e., the first codon of an mRNA transcript translated by a ribosome) that does not encode a polypeptide. When RNA transcripts are being generated, the 5' UTR may comprise a promoter sequence. Such promoter sequences are known in the art. It should be understood that such promoter sequences will not be present in a vaccine of the disclosure.

A "3' untranslated region" (UTR) refers to a region of an mRNA that is directly downstream (i.e., 3') from the stop codon (i.e., the codon of an mRNA transcript that signals a termination of translation) that does not encode a polypeptide.

An "open reading frame" is a continuous stretch of DNA beginning with a start codon (e.g., methionine (ATG)), and ending with a stop codon (e.g., TAA, TAG or TGA) and encodes a polypeptide.

A "poly(A) tail" is a region of mRNA that is downstream, e.g., directly downstream (i.e., 3'), from the 3' UTR that contains multiple, consecutive adenosine monophosphates. A poly(A) tail may contain 10 to 300 adenosine monophosphates. For example, a poly(A) tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a poly(A) tail contains 50 to 250 adenosine monophosphates. In a relevant biological setting (e.g., in cells, in vivo) the poly(A) tail functions to protect mRNA from enzymatic degradation, e.g., in the cytoplasm, and aids in transcription termination, and/or export of the mRNA from the nucleus and translation.

In some embodiments, a nucleic acid includes 200 to 3,000 nucleotides. For example, a nucleic acid may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides).

An in vitro transcription system typically comprises a transcription buffer, nucleotide triphosphates (NTPs), an RNase inhibitor and a polymerase.

The NTPs may be manufactured in house, may be selected from a supplier, or may be synthesized as described herein. The NTPs may be selected from, but are not limited to, those described herein including natural and unnatural (modified) NTPs.

Any number of RNA polymerases or variants may be used in the method of the present disclosure. The polymerase may be selected from, but is not limited to, a phage RNA polymerase, e.g., a T7 RNA polymerase, a T3 RNA polymerase, a SP6 RNA polymerase, and/or mutant polymerases such as, but not limited to, polymerases able to incorporate modified nucleic acids and/or modified nucleotides, including chemically modified nucleic acids and/or nucleotides. Some embodiments exclude the use of DNase.

In some embodiments, the RNA transcript is capped via enzymatic capping. In some embodiments, the RNA comprises 5' terminal cap, for example, 7mG(5')ppp(5')NlmpNp.

Chemical Synthesis

Solid-phase chemical synthesis. Nucleic acids the present disclosure may be manufactured in whole or in part using solid phase techniques. Solid-phase chemical synthesis of nucleic acids is an automated method wherein molecules are immobilized on a solid support and synthesized step by step in a reactant solution. Solid-phase synthesis is useful in site-specific introduction of chemical modifications in the nucleic acid sequences.

Liquid Phase Chemical Synthesis. The synthesis of nucleic acids of the present disclosure by the sequential addition of monomer building blocks may be carried out in a liquid phase.

Combination of Synthetic Methods. The synthetic methods discussed above each has its own advantages and limitations. Attempts have been conducted to combine these methods to overcome the limitations. Such combinations of methods are within the scope of the present disclosure. The use of solid-phase or liquid-phase chemical synthesis in combination with enzymatic ligation provides an efficient way to generate long chain nucleic acids that cannot be obtained by chemical synthesis alone.

Ligation of Nucleic Acid Regions or Subregions

Assembling nucleic acids by a ligase may also be used. DNA or RNA ligases promote intermolecular ligation of the 5' and 3' ends of polynucleotide chains through the formation of a phosphodiester bond. Nucleic acids such as chimeric polynucleotides and/or circular nucleic acids may be prepared by ligation of one or more regions or subregions. DNA fragments can be joined by a ligase catalyzed reaction to create recombinant DNA with different functions. Two oligodeoxynucleotides, one with a 5' phosphoryl group and another with a free 3' hydroxyl group, serve as substrates for a DNA ligase.

Purification

Purification of the nucleic acids described herein may include, but is not limited to, nucleic acid clean-up, quality assurance and quality control. Clean-up may be performed by methods known in the arts such as, but not limited to, AGENCOURT® beads (Beckman Coulter Genomics, Danvers, MA), poly-T beads, LNA™ oligo-T capture probes (EXIQON® Inc, Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC). The term "purified" when used in relation to a nucleic acid such as a "purified nucleic acid" refers to one that is separated from at least one contaminant. A "contaminant" is any substance that makes another unfit, impure or inferior. Thus, a purified nucleic acid (e.g., DNA and RNA) is present in a form or setting different from that in which it is found in nature, or a form or setting different from that which existed prior to subjecting it to a treatment or purification method.

A quality assurance and/or quality control check may be conducted using methods such as, but not limited to, gel electrophoresis, UV absorbance, or analytical HPLC.

In some embodiments, the nucleic acids may be sequenced by methods including, but not limited to reverse-transcriptase-PCR.

Quantification

In some embodiments, the nucleic acids of the present disclosure may be quantified in exosomes or when derived from one or more bodily fluid. Bodily fluids include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes may be retrieved from an organ selected from the group consisting of lung, heart, pancreas, stomach, intestine, bladder, kidney, ovary, testis, skin, colon, breast, prostate, brain, esophagus, liver, and placenta.

Assays may be performed using construct specific probes, cytometry, qRT-PCR, real-time PCR, PCR, flow cytometry, electrophoresis, mass spectrometry, or combinations thereof while the exosomes may be isolated using immunohistochemical methods such as enzyme linked immunosorbent assay (ELISA) methods. Exosomes may also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of nucleic acids remaining or delivered. This is possible because the nucleic acids of the present disclosure, in some embodiments, differ from the endogenous forms due to the structural or chemical modifications.

In some embodiments, the nucleic acid may be quantified using methods such as, but not limited to, ultraviolet visible spectroscopy (UV/Vis). A non-limiting example of a UV/Vis spectrometer is a NANODROP® spectrometer (ThermoFisher, Waltham, MA). The quantified nucleic acid may be analyzed in order to determine if the nucleic acid may be of proper size, check that no degradation of the nucleic acid has occurred. Degradation of the nucleic acid may be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

Lipid Nanoparticles (LNPs)

In some embodiments, the mRNA of the disclosure is formulated in a lipid nanoparticle (LNP). It is to be understood that "a lipid nanoparticle," as used herein refers to a single LNP or a population of LNPs. Lipid nanoparticles typically comprise ionizable amino (cationic) lipid, non-cationic lipid, sterol and PEG lipid components along with the nucleic acid cargo of interest. The lipid nanoparticles of the disclosure can be generated using components, compositions, and methods as are generally known in the art, see for example PCT/US2016/052352; PCT/US2016/068300; PCT/US2017/037551; PCT/US2015/027400; PCT/US2016/047406; PCT/US2016000129; PCT/US2016/014280; PCT/US2016/014280; PCT/US2017/038426; PCT/US2014/027077; PCT/US2014/055394; PCT/US2016/52117; PCT/US2012/069610; PCT/US2017/027492; PCT/US2016/059575 and PCT/US2016/069491 all of which are incorporated by reference herein in their entirety.

Vaccines of the present disclosure are typically formulated in lipid nanoparticle. In some embodiments, the lipid nanoparticle comprises at least one ionizable amino lipid, at least one non-cationic lipid, at least one sterol, and/or at least one polyethylene glycol (PEG)-modified lipid.

In some embodiments, the lipid nanoparticle comprises 20-60 mol % ionizable amino lipid. In some embodiments, the lipid nanoparticle comprises 20-55 mol % ionizable amino lipid. For example, the lipid nanoparticle may comprise 20-50 mol %, 20-40 mol %, 20-30 mol %, 30-60 mol %, 30-50 mol %, 30-40 mol %, 40-60 mol %, 40-50 mol %, or 50-60 mol % ionizable amino lipid. In some embodiments, the lipid nanoparticle comprises 20 mol %, 30 mol %, 40 mol %, 50 mol %, or 60 mol % ionizable amino lipid. In some embodiments, the lipid nanoparticle comprises 40 mol %, 41 mol %, 42 mol %, 43 mol %, 44 mol % 45 mol %, 46 mol %, 47 mol %, 48 mol %, 49 mol %, 50 mol %, or 60 mol % ionizable amino lipid.

In some embodiments, the lipid nanoparticle comprises 5-25 mol % non-cationic lipid. For example, the lipid nanoparticle may comprise 5-20 mol %, 5-15 mol %, 5-10 mol %, 10-25 mol %, 10-20 mol %, 10-25 mol %, 15-25 mol %, 15-20 mol %, or 20-25 mol % non-cationic lipid. In some embodiments, the lipid nanoparticle comprises 5 mol %, 10 mol %, 15 mol %, 20 mol %, or 25 mol % non-cationic lipid.

In some embodiments, the lipid nanoparticle comprises 25-55 mol % sterol. For example, the lipid nanoparticle may comprise 25-50 mol %, 25-45 mol %, 25-40 mol %, 25-35 mol %, 25-30 mol %, 30-55 mol %, 30-50 mol %, 30-45 mol %, 30-40 mol %, 30-35 mol %, 35-55 mol %, 35-50 mol %, 35-45 mol %, 35-40 mol %, 40-55 mol %, 40-50 mol %, 40-45 mol %, 45-55 mol %, 45-50 mol %, or 50-55 mol % sterol. In some embodiments, the lipid nanoparticle comprises 25 mol %, 30 mol %, 35 mol %, 40 mol %, 45 mol %, 50 mol %, or 55 mol % sterol.

In some embodiments, the lipid nanoparticle comprises 0.5-15 mol % PEG-modified lipid. For example, the lipid nanoparticle may comprise 0.5-10 mol %, 0.5-5 mol %, 1-15 mol %, 1-10 mol %, 1-5 mol %, 2-15 mol %, 2-10 mol %, 2-5 mol %, 5-15 mol %, 5-10 mol %, or 10-15 mol %. In some embodiments, the lipid nanoparticle comprises 0.5 mol %, 1 mol %, 2 mol %, 3 mol %, 4 mol %, 5 mol %, 6 mol %, 7 mol %, 8 mol %, 9 mol %, 10 mol %, 11 mol %, 12 mol %, 13 mol %, 14 mol %, or 15 mol % PEG-modified lipid.

In some embodiments, the lipid nanoparticle comprises 20-60 mol % ionizable amino lipid, 5-25 mol % non-cationic lipid, 25-55 mol % sterol, and 0.5-15 mol % PEG-modified lipid. In some embodiments, the lipid nanoparticle comprises 40-50 mol % ionizable amino lipid, 5-15 mol % neutral lipid, 20-40 mol % cholesterol, and 0.5-3 mol % PEG-modified lipid. In some embodiments, the lipid nanoparticle comprises 45-50 mol % ionizable amino lipid, 9-13 mol % neutral lipid, 35-45 mol % cholesterol, and 2-3 mol % PEG-modified lipid. In some embodiments, the lipid nanoparticle comprises 48 mol % ionizable amino lipid, 11 mol % neutral lipid, 68.5 mol % cholesterol, and 2.5 mol % PEG-modified lipid.

In some embodiments, an ionizable amino lipid of the disclosure comprises a compound of Formula (I):

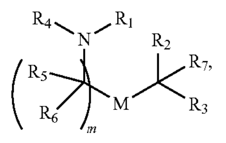

(I)

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a carbocycle, heterocycle, —OR, —O$(CH_2)_n$N$(R)_2$, —C(O)OR, —OC(O)R, —$CX_3$, —$CX_2$H, —$CXH_2$, —CN, —N$(R)_2$, —C(O)N$(R)_2$, —N(R)C(O)R, —N(R)S$(O)_2$R, —N(R)C(O)N$(R)_2$, —N(R)C(S)N$(R)_2$, —N(R)$R_8$, —O$(CH_2)_n$OR, —N(R)C(=N$R_9$)N$(R)_2$, —N(R)C(=CH$R_9$)N$(R)_2$, —OC(O)N$(R)_2$, —N(R)C(O)OR, —N(OR)C(O)R, —N(OR)S$(O)_2$R, —N(OR)C(O)OR, —N(OR)C(O)N$(R)_2$, —N(OR)C(S)N$(R)_2$, —N(OR)C(=N$R_9$)N$(R)_2$, —N(OR)C(=CH$R_9$)N$(R)_2$, —C(=N$R_9$)N$(R)_2$, —C(=N$R_9$)R, —C(O)N(R)OR, and —C(R)N$(R)_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S$(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S$(O)_2$R, —S$(O)_2$N$(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is —$(CH_2)_n$Q, —$(CH_2)_n$CHQR, —CHQR, or —CQ$(R)_2$, then (i) Q is not —N$(R)_2$ when n is 1, 2, 3, 4 or 5, or (ii) Q is not 5, 6, or 7-membered heterocycloalkyl when n is 1 or 2.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O$(CH_2)_n$N$(R)_2$, —C(O)OR, —OC(O)R, —$CX_3$, —$CX_2$H, —$CXH_2$, —CN, —C(O)N$(R)_2$, —N(R)C(O)R, —N(R)S$(O)_2$R, —N(R)C(O)N$(R)_2$, —N(R)C(S)N$(R)_2$, —CRN$(R)_2$C(O)OR, —N(R)$R_8$, —O$(CH_2)_n$OR, —N(R)C(=N$R_9$)N$(R)_2$, —N(R)C(=CH$R_9$)N$(R)_2$, —OC(O)N$(R)_2$, —N(R)C(O)OR, —N(OR)C(O)R, —N(OR)S$(O)_2$R, —N(OR)C(O)OR, —N(OR)C(O)N$(R)_2$, —N(OR)C(S)N$(R)_2$, —N(OR)C(=N$R_9$)N$(R)_2$, —N(QR)C(=CH$R_9$)N$(R)_2$, —C(=N$R_9$)N$(R)_2$, —C(=N$R_9$)R, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino; and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—CRN(R)_2C(O)OR$, $—N(R)R_8$, $—O(CH_2)_nOR$, $—N(R)C(=NR_9)N(R)_2$, $—N(R)C(=CHR_9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C(=NR_9)N(R)_2$, $—N(OR)C(=CHR_9)N(R)_2$, $—C(=NR_9)R$, —C(O)N(R)OR and $—C(=NR_9)N(R)_2$, and each n is independently selected from 1, 2, 3, 4, and 5; and when Q is a 5- to 14-membered heterocycle and (i) $R_4$ is $—(CH_2)_nQ$ in which n is 1 or 2, or (ii) $R_4$ is $—(CH_2)_nCHQR$ in which n is 1, or (iii) $R_4$ is —CHQR, and $—CQ(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—CRN(R)_2C(O)OR$, $—N(R)R_8$, $—O(CH_2)_nOR$, $—N(R)C(=NR_9)N(R)_2$, $—N(R)C(=CHR_9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C(=NR_9)N(R)_2$, $—N(OR)C(=CHR_9)N(R)_2$, $—C(=NR_9)R$, —C(O)N(R)OR, and $—C(=NR_9)N(R)_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently-selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_n$Q or —$(CH_2)_n$CHQR, where Q is —$N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_n$Q, —$(CH_2)_n$CHQR, —CHQR, and —$CQ(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{18}$ alkyl, $C_{2-18}$ alkenyl, —R*YR", —YR', and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA):

(IA)

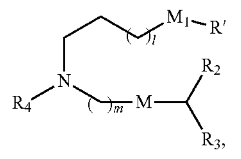

or a salt or isomer thereof, wherein 1 is selected from 1, 2, 3, 4, and 5; m is selected from 5, 6, 7, 8, and 9; $M_1$ is a bond or M'; $R_4$ is unsubstituted $C_{1-3}$ alkyl, or —$(CH_2)_n$Q, in which Q is OH, —NHC(S)$N(R)_2$, —NHC(O)$N(R)_2$, —N(R)C(O)R, —N(R)$S(O)_2$R, —N(R)$R_8$, —NHC(═$NR_9$)$N(R)_2$, —NHC(═$CHR_9$)$N(R)_2$, —OC(O)$N(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (II):

(II)

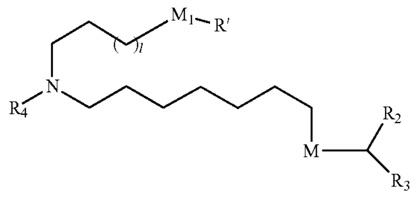

(II) or a salt or isomer thereof, wherein 1 is selected from 1, 2, 3, 4, and 5; $M_1$ is a bond or M'; $R_4$ is unsubstituted $C_{1-3}$ alkyl, or —$(CH_2)_n$Q, in which n is 2, 3, or 4, and Q is OH, —NHC(S)$N(R)_2$, —NHC(O)$N(R)_2$, —N(R)C(O)R, —N(R)$S(O)_2$R, —N(R)$R_8$, —NHC(═$NR_9$)$N(R)_2$, —NHC(═$CHR_9$)$N(R)_2$, —OC(O)$N(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (IIa), (IIb), (IIc), or (IIe):

(IIa)

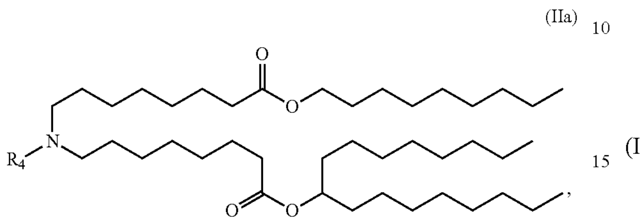

(IIb)

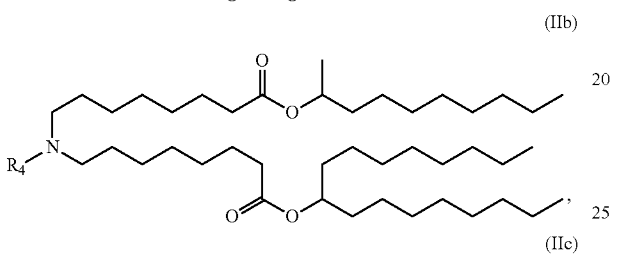

(IIc)

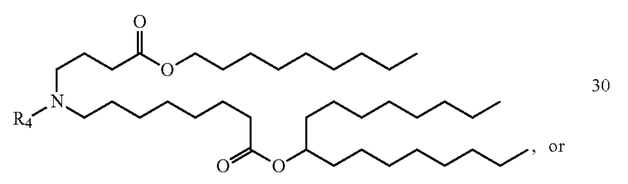

or

-continued (IIe)

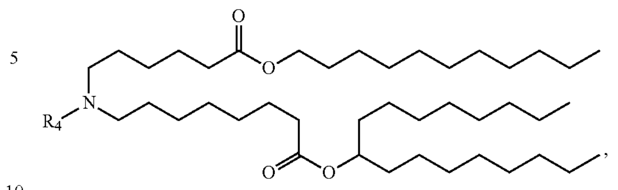

or a salt or isomer thereof, wherein $R_4$ is as described herein.

In some embodiments, a subset of compounds of Formula (I) includes those of Formula (IId):

(IId)

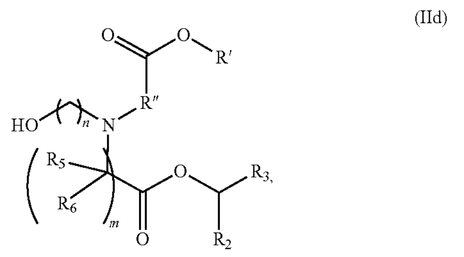

or a salt or isomer thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, an ionizable amino lipid of the disclosure comprises a compound having structure:

(Compound I)

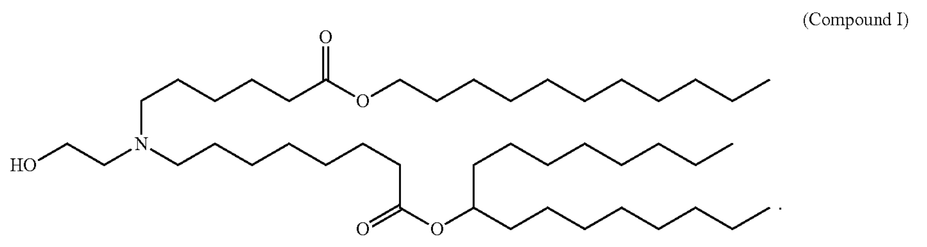 [SMILES: CCCCCCCCCCCOC(=O)CCCCCN(CCO)CCCCCCCC(=O)OC(CCCCCCCC)CCCCCCCC]

In some embodiments, an ionizable amino lipid of the disclosure comprises a compound having structure:

(Compound II)

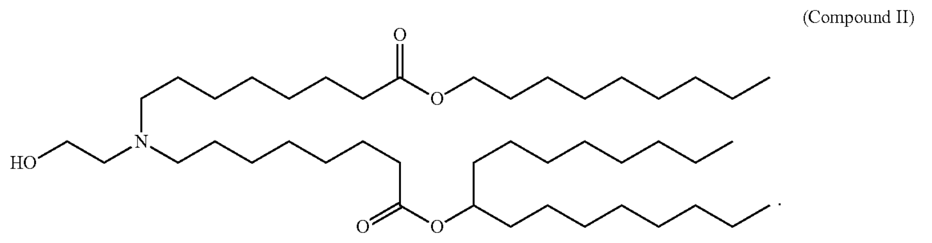 [SMILES: CCCCCCCCCOC(=O)CCCCCCCN(CCO)CCCCCCCC(=O)OC(CCCCCCCC)CCCCCCCC]

In some embodiments, a non-cationic lipid of the disclosure comprises 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-gly cero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

In some embodiments, a PEG modified lipid of the disclosure comprises a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In some embodiments, the PEG-modified lipid is DMG-PEG, PEG-c-DOMG (also referred to as PEG-DOMG), PEG-DSG and/or PEG-DPG.

In some embodiments, a sterol of the disclosure comprises cholesterol, fecosterol, sitosterol, ergosterol, campesterol, stigmasterol, brassicasterol, tomatidine, ursolic acid, alpha-tocopherol, and mixtures thereof.

In some embodiments, a LNP of the disclosure comprises an ionizable amino lipid of Compound 1, wherein the non-cationic lipid is DSPC, the structural lipid that is cholesterol, and the PEG lipid is DMG-PEG (e.g., PEG2000-DMG).

In some embodiments, the lipid nanoparticle comprises 45-55 mole percent (mol %) ionizable amino lipid (e.g., Compound 1). For example, lipid nanoparticle may comprise 45-47, 45-48, 45-49, 45-50, 45-52, 46-48, 46-49, 46-50, 46-52, 46-55, 47-48, 47-49, 47-50, 47-52, 47-55, 48-50, 48-52, 48-55, 49-50, 49-52, 49-55, or 50-55 mol % ionizable amino lipid (e.g., Compound 1). For example, lipid nanoparticle may comprise 45, 46, 47, 48, 49, 50, 51, 52, 53, 54, or 55 mol % ionizable amino lipid.

In some embodiments, the lipid nanoparticle comprises 5-15 mol % non-cationic (neutral) lipid (e.g., DSPC). For example, the lipid nanoparticle may comprise 5-6, 5-7, 5-8, 5-9, 5-10, 5-11, 5-12, 5-13, 5-14, 5-15, 6-7, 6-8, 6-9, 6-10, 6-11, 6-12, 6-13, 6-14, 6-15, 7-8, 7-9, 7-10, 7-11, 7-12, 7-13, 7-14, 7-15, 8-9, 8-10, 8-11, 8-12, 8-13, 8-14, 8-15, 9-10, 9-11, 9-12, 9-13, 9-14, 9-15, 10-11, 10-12, 10-13, 10-14, 10-15, 11-12, 11-13, 11-14, 11-15, 12-13, 12-14, 13-14, 13-15, or 14-15 mol % non-cationic (neutral) lipid (e.g., DSPC). For example, the lipid nanoparticle may comprise 5, 6, 7, 8, 9, 10, 11, 12, 13, 14, or 15 mol % DSPC.

In some embodiments, the lipid nanoparticle comprises 35-40 mol % sterol (e.g., cholesterol). For example, the lipid nanoparticle may comprise 35-36, 35-37, 35-38, 35-39, 35-40, 36-37, 36-38, 36-39, 36-40, 37-38, 37-39, 37-40, 38-39, 38-40, or 39-40 mol % cholesterol. For example, the lipid nanoparticle may comprise 35, 35.5, 36, 36.5, 37, 37.5, 38, 38.5, 39, 39.5, or 40 mol % cholesterol.

In some embodiments, the lipid nanoparticle comprises 1-3 mol % DMG-PEG. For example, the lipid nanoparticle may comprise 1-1.5, 1-2, 1-2.5, 1-3, 1.5-2, 1.5-2.5, 1.5-3, 2-2.5, 2-3, or 2.5-3. mol % DMG-PEG. For example, the lipid nanoparticle may comprise 1, 1.5, 2, 2.5, or 3 mol % DMG-PEG.

In some embodiments, the lipid nanoparticle comprises 50 mol % ionizable amino lipid, 10 mol % DSPC, 38.5 mol % cholesterol, and 1.5 mol % DMG-PEG. In some embodiments, the lipid nanoparticle comprises 48 mol % ionizable amino lipid, 11 mol % DSPC, 38.5 mol % cholesterol, and 2.5 mol % PEG2000-DMG.

In some embodiments, an LNP of the disclosure comprises an N:P ratio of from about 2:1 to about 30:1.

In some embodiments, an LNP of the disclosure comprises an N:P ratio of about 6:1.

In some embodiments, an LNP of the disclosure comprises an N:P ratio of about 3:1.

In some embodiments, an LNP of the disclosure comprises a wt/wt ratio of the ionizable amino lipid component to the RNA of from about 10:1 to about 100:1.

In some embodiments, an LNP of the disclosure comprises a wt/wt ratio of the ionizable amino lipid component to the RNA of about 20:1.

In some embodiments, an LNP of the disclosure comprises a wt/wt ratio of the ionizable amino lipid component to the RNA of about 10:1.

In some embodiments, an LNP of the disclosure has a mean diameter from about 50 nm to about 150 nm.

In some embodiments, an LNP of the disclosure has a mean diameter from about 70 nm to about 120 nm.

Multivalent Vaccines

The compositions, as provided herein, may include RNA or multiple RNAs encoding two or more antigens of the same or different species. In some embodiments, composition includes an RNA or multiple RNAs encoding two or more coronavirus antigens. In some embodiments, the RNA may encode 1, 2, 3, 4, 5, 6, 7, 8, 9, or 10, or more coronavirus antigens.

In some embodiments, two or more different mRNA encoding antigens may be formulated in the same lipid nanoparticle. In other embodiments, two or more different RNA encoding antigens may be formulated in separate lipid nanoparticles (each RNA formulated in a single lipid nanoparticle). The lipid nanoparticles may then be combined and administered as a single vaccine composition (e.g., comprising multiple RNA encoding multiple antigens) or may be administered separately. In some embodiments, when the composition comprises two different RNA encoding antigens, the ratio of RNA encoding antigens is 1:1, 1:2, 1:4, 4:1, or 2:1.

Initial or First Vaccine

In some embodiments the first or initial vaccine is an mRNA vaccine encoding a 2P stabilized spike protein. For instance, the initial or first vaccine may be an mRNA encoding a spike antigen having an amino acid sequence of SEQ ID NO: 20. In other embodiments the first vaccine may be any vaccine modality comprising a 2P stabilized spike protein. As a non-limiting example, the first vaccine composition may be a recombinant vaccine. As used herein, "recombinant vaccine" refers to a vaccine made by genetic engineering, the process and method of manipulating the genetic material of an organism. In most cases, a recombinant vaccine encompasses one or more nucleic acids encoding protein antigens that have either been produced and purified in a heterologous expression system (e.g., bacteria or yeast) or purified from large amounts of the pathogenic organism. Following administration, a vaccinated person produces antibodies to the one or more protein antigens, thus protecting him/her from disease. In some embodiments, the recombinant vaccine is a vectored vaccine. Viral vectored vaccines comprise a polynucleotide sequence not of viral origin (i.e., a polynucleotide heterologous to the virus), that encodes a peptide, polypeptide, or protein capable of eliciting an immune response in a host contacted with the vector. Expression of the polynucleotide results in the generation of a neutralizing antibody response and/or a cell mediated response, e.g., a cytotoxic T cell response. Examples of viral vectored vaccines include, but are not limited to, those developed by Oxford/AstraZeneca (COVID-19 Vaccine AstraZeneca), CanSino Biological Inc./Beijing Institute of Biotechnology, Gamaleya Research Institute, Zydus Cadila, Institut Pasteur/Themis/University of Pittsburgh Center for Vaccine Research, University of Hong Kong, and Altimmune (NasoVAX). In some embodiments, the recombinant vaccine is a nucleic acid-based (e.g., DNA, mRNA) coronavirus vaccine. Exemplary DNA vaccines include-those being developed by Inovio Pharmaceuticals (INO-4800), Genexine Consortium (GX-19), OncoSec and the Cancer Institute (CORVax12 and TAVO™), Karolinska Institute/Cobra Biologics, Osaka University/Anges/Takara Bio, and Takis/Applied DNA Sciences/Evvivax. Exemplary mRNA vaccines include those being developed by BioNTech/Pfizer, Imperial College London, Curevac, and Walvax Biotech/People's Liberation Army (PLA) Academy of Military Science.

Pharmaceutical Formulations

Provided herein are compositions (e.g., pharmaceutical compositions), methods, kits and reagents for prevention or treatment of coronavirus in humans and other mammals, for example. The compositions provided herein can be used as therapeutic or prophylactic agents. They may be used in medicine to prevent and/or treat a coronavirus infection.

In some embodiments, the SARS-CoV-2 vaccine containing RNA as described herein can be administered to a subject (e.g., a mammalian subject, such as a human subject), and the RNA polynucleotides are translated in vivo to produce an antigenic polypeptide-(antigen).

An "effective amount" of a composition (e.g., comprising RNA) is based, at least in part, on the target tissue, target cell type, means of administration, physical characteristics of the RNA (e.g., length, nucleotide composition, and/or extent of modified nucleosides), other components of the vaccine; and other determinants, such as age, body weight, height, sex and general health of the subject. Typically, an effective amount of a composition provides an induced or boosted immune response as a function of antigen production in the cells of the subject. In some embodiments, an effective amount of the composition containing RNA polynucleotides having at least one chemical modifications are more efficient than a composition containing a corresponding unmodified polynucleotide encoding the same antigen or a peptide antigen. Increased antigen production may be demonstrated by increased cell transfection (the percentage of cells transfected with the RNA vaccine), increased protein translation and/or expression from the polynucleotide, decreased nucleic acid degradation (as demonstrated, for example, by increased duration of protein translation from a modified polynucleotide), or altered antigen specific immune response of the host cell.

The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences.

In some embodiments, the compositions (comprising polynucleotides and their encoded polypeptides) in accordance with the present disclosure may be used for treatment or prevention of a coronavirus infection. A composition may be administered prophylactically or therapeutically as part of an active immunization scheme to healthy individuals or early in infection during the incubation phase or during active infection after onset of symptoms. In some embodiments, the amount of RNA provided to a cell, a tissue or a subject may be an amount effective for immune prophylaxis.

A composition may be administered with other prophylactic or therapeutic compounds. As a non-limiting example, a prophylactic or therapeutic compound may be an adjuvant or a booster. As used herein, when referring to a prophylactic composition, such as a vaccine, the term "booster" refers to an extra administration of the vaccine composition and may include a traditional boost, seasonal boost or a pandemic shift boost. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, or 6 months, 7 months, 8 months, 9 months, 10 months, 11 months, one year, or more. In some embodiments, the time of administration between the initial administration of the prophylactic composition and the booster is at least 6 months. In exemplary embodiments, the time of administration between the initial administration of the prophylactic composition and the booster may be, but is not limited to, 1 week, 2 weeks, 3 weeks, 1 month, 2 months, 3 months, or 6 months. As is described herein, the booster may comprise the same or different mRNAs as compared to the earlier administration of the prophylactic composition. In some embodiments, the booster may comprise a combination of the same mRNA from the earlier administration of the prophylactic composition and at least one different mRNA. In some embodiments, the ratio of the mRNA from the earlier administration of the prophylactic composition and the at least one different mRNA is 1:1, 1:2, 1:4, 4:1, or 2:1. In one embodiment, the ratio is 1:1. In some embodiments, the booster may comprise different mRNAs as compared to the earlier administration of the prophylactic compositions. In some embodiments, such a booster may comprise 1, 2, 3, 4 or more mRNAs that were not present in the prophylactic composition. In some embodiments, the ratio of two mRNA polynucleotides (none of which were in the prophylactic composition) in the booster is 1:1, 1:2, 1:4, 4:1, or 2:1. In one embodiment, the ratio is 1:1. A boost or booster dose may be administered more than once, for example 2, 3, 4, 5, 6 or more times after the initial prophylactic (prime) dose. In some embodiments, a subsequent boost is administered within weeks, e.g., within 3-4 weeks of the first (or previous) boost. In some embodiments, a second boost is administered 1, 2, 3, 4, 5, 6, 7, 8, 9, 10, 11, 12, or more weeks after the first (or previous) boost. The booster, in some embodiments is monovalent (e.g., the mRNA encodes a single antigen). In some embodiments, the booster is multivalent (e.g., the mRNA encodes more than one antigen).

In some embodiments, the booster dose is 5 μg-30 μg, 5 μg-25 μg, 5 μg-20 μg, 5 μg 15 μg, 5 μg-10 μg, 10 μg-30 μg, 10 μg-25 μg, 10 μg-20 μg, 10 μg-15 μg, 15 μg-30 μg, 15 μg-25 μg, 15 μg-20 μg, 20 μg-30 μg, 25 μg-30 μg, or 25 μg-300 μg. In some embodiments, the booster dose is 10 μg-60 μg, 10 μg-55 μg, 10 μg-50 μg, 10 μg-45 μg, 10 μg-40 μg, 10 μg-35 μg, 10 μg-30 μg, 10 μg-25 μg, 10 μg-20 μg, 15 μg-60 μg, 15 μg-55 μg, 15 μg-50 μg, 15 μg-45 μg, 15 μg-40 μg, 15 μg-35 μg, 15 μg-30 μg, 15 μg-25 μg, 15 μg-20 μg, 20 μg-60 μg, 20 μg-55 μg, 20 μg-50 μg, 20 μg-45 μg, 20 μg-40 μg, 20 μg-35 μg, 20 μg-30 μg, 20 μg-25 μg, 25 μg-60 μg, 25 μg-55 μg, 25 μg-50 μg, 25 μg-45 μg, 25 μg-40 μg, 25 μg-35 μg, 25 μg-30 μg, 30 μg-60 μg, 30 μg-55 μg, 30 μg-50 μg, 30 μg-45 μg, 30 μg-40 μg, 30 μg-35 μg, 35 μg-60 μg, 35 μg-55 μg, 35 μg-50 μg, 35 μg-45 μg, 35 μg-40 μg, 40 μg-60 μg, 40 μg-55 μg, 40 μg-50 μg, 40 μg-45 μg, 45 μg-60 μg, 45 μg-55 μg, 45 μg-50 μg, 50 μg-60 μg, 50 μg-55 μg, or 55 μg-60 μg. In some embodiments, the booster dose is at least 10 μg and less than 25 μg of the composition. In some embodiments, the booster dose is at least 5 μg and less than 25 μg of the composition. For example, the booster dose is 5 μg, 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 110 μg, 120 μg, 130 μg, 140 μg, 150 μg, 160 μg, 170 μg, 180 μg, 190 μg, 200 μg, 250 μg, or 300 μg. In some embodiments, the booster dose is 50 μg.

In some embodiments, a composition may be administered intramuscularly, intranasally or intradermally, similarly to the administration of inactivated vaccines known in the art.

A composition may be utilized in various settings depending on the prevalence of the infection or the degree or level of unmet medical need. As a non-limiting example, the RNA vaccines may be utilized to treat and/or prevent a variety of infectious disease. RNA vaccines have superior properties in that they produce much larger antibody titers, better neutralizing immunity, produce more durable immune responses, and/or produce responses earlier than commercially available vaccines.

Provided herein are pharmaceutical compositions including RNA and/or complexes optionally in combination with one or more pharmaceutically acceptable excipients.

The RNA may be formulated or administered alone or in conjunction with one or more other components. For example, an immunizing composition may comprise other components including, but not limited to, adjuvants.

In some embodiments, an immunizing composition does not include an adjuvant (it is adjuvant free).

An RNA may be formulated or administered in combination with one or more pharmaceutically-acceptable excipients. In some embodiments, vaccine compositions comprise at least one additional active substances, such as, for example, a therapeutically-active substance, a prophylactically-active substance, or a combination of both. Vaccine compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety).

In some embodiments, an immunizing composition is administered to humans, human patients or subjects. For the purposes of the present disclosure, the phrase "active ingredient" generally refers to the RNA vaccines or the polynucleotides contained therein, for example, RNA polynucleotides (e.g., mRNA polynucleotides) encoding antigens.

Formulations of the vaccine compositions described herein may be prepared by any method known or hereafter developed in the art of pharmacology. In general, such preparatory methods include the step of bringing the active ingredient (e.g., mRNA polynucleotide) into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

In some embodiments, an RNA is formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected with the RNA (e.g., for transplantation into a subject), hyaluronidase, nanoparticle mimics and combinations thereof.

Dosing/Administration

Provided herein are immunizing compositions (e.g., RNA vaccines), methods, kits and reagents for prevention and/or treatment of coronavirus infection in humans and other mammals. Immunizing compositions can be used as therapeutic or prophylactic agents. In some embodiments, immunizing compositions are used to provide prophylactic protection from coronavirus infection. In some embodiments, immunizing compositions are used to treat a coronavirus infection. In some embodiments, embodiments, immunizing compositions are used in the priming of immune effector cells, for example, to activate peripheral blood mononuclear cells (PBMCs) ex vivo, which are then infused (re-infused) into a subject.

A subject may be any mammal, including non-human primate and human subjects. Typically, a subject is a human subject.

In some embodiments, an immunizing composition (e.g., RNA vaccine) is administered to a subject (e.g., a mammalian subject, such as a human subject) in an effective amount to induce an antigen-specific immune response. The RNA encoding the coronavirus spike protein antigen is expressed and translated in vivo to produce the antigen, which then stimulates an immune response in the subject.

Prophylactic protection from a coronavirus can be achieved following administration of an immunizing composition (e.g., an RNA vaccine) of the present disclosure. Immunizing compositions can be administered once, twice, three times, four times or more but it is likely sufficient to administer the vaccine once (optionally followed by a single booster). It is possible, although less desirable, to administer an immunizing composition to an infected individual to achieve a therapeutic response. Dosing may need to be adjusted accordingly.

A method of eliciting an immune response in a subject against a coronavirus antigen (or multiple antigens) is provided in aspects of the present disclosure. In some embodiments, a method involves administering to the subject an immunizing composition comprising a mRNA having an open reading frame encoding a coronavirus antigen, thereby inducing in the subject an immune response specific to the coronavirus antigen, wherein anti-antigen antibody titer in the subject is increased following vaccination relative to anti-antigen antibody titer in a subject vaccinated with a prophylactically effective dose of a traditional vaccine against the antigen. An "anti-antigen antibody" is a serum antibody the binds specifically to the antigen.

A prophylactically effective dose is an effective dose that prevents infection with the virus at a clinically acceptable level. In some embodiments, the effective dose is a dose listed in a package insert for the vaccine. A traditional vaccine, as used herein, refers to a vaccine other than the mRNA vaccines of the present disclosure. For instance, a traditional vaccine includes, but is not limited, to live microorganism vaccines, killed microorganism vaccines, subunit vaccines, protein antigen vaccines, DNA vaccines, virus like particle (VLP) vaccines, etc. In exemplary embodiments, a traditional vaccine is a vaccine that has achieved regulatory approval and/or is registered by a national drug regulatory body, for example the Food and Drug Administration (FDA) in the United States or the European Medicines Agency (EMA).

In some embodiments, the anti-antigen antibody titer in the subject is increased 1 log to 10 log following vaccination relative to anti-antigen antibody titer in a subject vaccinated with a prophylactically effective dose of a traditional vaccine against the coronavirus or an unvaccinated subject. In some embodiments, the anti-antigen antibody titer in the subject is increased 1 log, 2 log, 3 log, 4 log, 5 log, or 10 log following vaccination relative to anti-antigen antibody titer in a subject vaccinated with a prophylactically effective dose of a traditional vaccine against the coronavirus or an unvaccinated subject.

A method of eliciting an immune response in a subject against a coronavirus is provided in other aspects of the disclosure. The method involves administering to the subject a composition comprising an mRNA comprising an open reading frame encoding a coronavirus antigen, thereby inducing in the subject an immune response specific to the coronavirus, wherein the immune response in the subject is equivalent to an immune response in a subject vaccinated with a traditional-vaccine against the coronavirus at 2 times to 100 times the dosage level relative to the composition.

In some embodiments, the immune response in the subject is equivalent to an immune response in a subject vaccinated with a traditional vaccine at twice the dosage level relative to a composition of the present disclosure. In some embodiments, the immune response in the subject is equivalent to an immune response in a subject vaccinated with a traditional vaccine at three times the dosage level relative to a composition of the present disclosure. In some embodiments, the immune response in the subject is equivalent to an immune response in a subject vaccinated with a traditional vaccine at 4 times, 5 times, 10 times, 50 times, or 100 times the dosage level relative to a composition of the present disclosure. In some embodiments, the immune response in the subject is equivalent to an immune response in a subject vaccinated with a traditional vaccine at 10 times to 1000 times the dosage level relative to a composition of the present disclosure. In some embodiments, the immune response in the subject is equivalent to an immune response in a subject vaccinated with a traditional vaccine at 100 times to 1000 times the dosage level relative to a composition of the present disclosure.

In other embodiments, the immune response is assessed by determining [protein] antibody titer in the subject. In other embodiments, the ability of serum or antibody from an immunized subject is tested for its ability to neutralize viral uptake or reduce coronavirus transformation of human B lymphocytes. In other embodiments, the ability to promote a robust T cell response(s) is measured using art recognized techniques.

Other aspects the disclosure provide methods of eliciting an immune response in a subject against a coronavirus by administering to the subject composition comprising an mRNA having an open reading frame encoding a coronavirus antigen, thereby inducing in the subject an immune response specific to the coronavirus antigen, wherein the immune response in the subject is induced 2 days to 10 weeks earlier relative to an immune response induced in a subject vaccinated with a prophylactically effective dose of a traditional vaccine against the coronavirus. In some embodiments, the immune response in the subject is induced in a subject vaccinated with a prophylactically effective dose of a traditional vaccine at 2 times to 100 times the dosage level relative to a composition of the present disclosure.

In some embodiments, the immune response in the subject is induced 2 days, 3 days, 1 week, 2 weeks, 3 weeks, 5 weeks, or 10 weeks earlier relative to an immune response induced in a subject vaccinated with a prophylactically effective dose of a traditional vaccine.

Also provided herein are methods of eliciting an immune response in a subject against a coronavirus by administering to the subject an mRNA having an open reading frame encoding a first antigen, wherein the RNA does not include a stabilization element, and wherein an adjuvant is not co-formulated or co-administered with the vaccine.

A composition may be administered by any route that results in a therapeutically effective outcome. These include, but are not limited, to intradermal, intramuscular, intranasal, and/or subcutaneous administration. The present disclosure provides methods comprising administering RNA vaccines to a subject in need thereof. The exact amount required will vary from subject to subject, depending on the species, age, and general condition of the subject, the severity of the disease, the particular composition, its mode of administration, its mode of activity, and the like. The RNA is typically formulated in dosage unit form for ease of administration and uniformity of dosage. It will be understood, however, that the total daily usage of the RNA may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The effective amount (e.g., effective dose) of the RNA, as provided herein, may be as low as 20 μg, administered for example as a single dose or as two 10 μg doses. In some embodiments, the effective amount (e.g., effective dose) is a total dose of 20 μg-300 μg 5 μg-30 μg, 5 μg-25 μg, 5 μg-20 μg, 5 μg-15 μg, 5 μg-10 μg, 10 μg-30 μg, 10 μg-25 μg, 10 μg-20 μg, 10 μg-15 μg, 15 μg-30 μg, 15 μg-25 μg, 15 μg-20 μg, 20 μg-30 μg, 25 μg-30 μg, or 25 μg-300 μg. In some embodiments, the effective dose (e.g., effective amount) is at least 10 μg and less than 25 μg of the composition. In some embodiments, the effective dose (e.g., effective amount) is at least 5 μg and less than 25 μg of the composition. For example, the effective amount may be a total dose of 5 μg, 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 110 μg, 120 μg, 130 μg, 140 μg, 150 μg, 160 μg, 170 μg, 180 μg, 190 μg, 200 μg, 250 μg, or 300 μg. In some embodiments, the effective amount (e.g., effective dose) is a total dose of 10 μg. In some embodiments, the effective amount is a total dose of 20 μg (e.g., two 10 μg doses). In some embodiments, the effective amount is a total dose of 25 μg. In some embodiments, the effective amount is a total dose of 30 μg. In some embodiments, the effective amount is a total dose of 50 μg. In some embodiments, the effective amount is a total dose of 60 μg (e.g., two 30 μg doses). In some embodiments, the effective amount is a total dose of 75 μg. In some embodiments, the effective amount is a total dose of 100 μg. In some embodiments, the effective amount is a total dose of 150 μg. In some embodiments, the effective amount is a total dose of 200 μg. In some embodiments, the effective amount is a total dose of 250 μg. In some embodiments, the effective amount is a total dose of 300 μg. Any of the doses provided above may be an effective amount for a booster dose; for example, in some embodiments, the booster dose is a total dose of 50 μg. In some embodiments, the composition comprises two or more mRNA polynucleotides and effective amount is a total dose of 20 μg (e.g., 10 μg of a first mRNA and 10 μg of a second mRNA). In some embodiments, the composition comprises two or more mRNA polynucleotides and effective amount is a total dose of 50 μg (e.g., 25 μg of a first mRNA and 25 μg of a second mRNA). In some embodiments, the composition comprises two or more mRNA polynucleotides and effective amount is a total dose of 100 μg (e.g., 50 μg of a first mRNA and 50 μg of a second mRNA).

The RNA described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

Vaccine Efficacy

Some aspects of the present disclosure provide formulations of the compositions (e.g., RNA vaccines), wherein the RNA is formulated in an effective amount to produce an antigen specific immune response in a subject (e.g., production of antibodies specific to a coronavirus antigen). "An effective amount" is a dose of the RNA effective to produce an antigen-specific immune response. Also provided herein are methods of inducing an antigen-specific immune response in a subject.

As used herein, an immune response to a vaccine or LNP of the present disclosure is the development in a subject of a humoral and/or a cellular immune response to a (one or more) coronavirus protein(s) present in the vaccine. For purposes of the present disclosure, a "humoral" immune response refers to an immune response mediated by antibody molecules, including, e.g., secretory (IgA) or IgG molecules, while a "cellular" immune response is one mediated by T-lymphocytes (e.g., CD4+ helper and/or CD8+ T cells (e.g., CTLs) and/or other white blood cells. One important aspect of cellular immunity involves an antigen-specific response by cytolytic T-cells (CTLs). CTLs have specificity for peptide antigens that are presented in association with proteins encoded by the major histocompatibility complex (MHC) and expressed on the surfaces of cells. CTLs help induce and promote the destruction of intracellular microbes or the lysis of cells infected with such microbes. Another aspect of cellular immunity involves and antigen-specific response by helper T-cells. Helper T-cells act to help stimulate the function and focus the activity nonspecific effector cells against cells displaying peptide antigens in association with MHC molecules on their surface. A cellular immune response also leads to the production of cytokines, chemokines, and other such molecules produced by activated T-cells and/or other white blood cells including those derived from CD4+ and CD8+ T-cells.

In some embodiments, the antigen-specific immune response is characterized by measuring an anti-coronavirus antigen antibody titer produced in a subject administered a composition as provided herein. An antibody titer is a measurement of the amount of antibodies within a subject, for example, antibodies that are specific to a particular antigen or epitope of an antigen. Antibody titer is typically expressed as the inverse of the greatest dilution that provides a positive result. Enzyme-linked immunosorbent assay (ELISA) is a common assay for determining antibody titers, for example.

A variety of serological tests can be used to measure antibody against encoded antigen of interest, for example, SAR-CoV-2 virus or SAR-CoV-2 viral antigen, e.g., SAR-CoV-2 spike or S protein, of domain thereof. These tests include the hemagglutination-inhibition test, complement fixation test, fluorescent antibody test, enzyme-linked immunosorbent assay (ELISA), and plaque reduction neutralization test (PRNT). Each of these tests measures different antibody activities. In exemplary embodiments, A plaque reduction neutralization test, or PRNT (e.g., PRNT50 or PRNT90) is used as a serological correlate of protection. PRNT measures the biological parameter of in vitro virus neutralization and is the most serologically virus-specific test among certain classes of viruses, correlating well to serum levels of protection from virus infection.

The basic design of the PRNT allows for virus-antibody interaction to occur in a test tube or microtiter plate, and then measuring antibody effects on viral infectivity by plating the mixture on virus-susceptible cells, preferably cells of mammalian origin. The cells are overlaid with a semi-solid media that restricts spread of progeny virus. Each virus that initiates a productive infection produces a localized area of infection (a plaque), that can be detected in a variety of ways. Plaques are counted and compared back to the starting concentration of virus to determine the percent reduction in total virus infectivity. In PRNT, the serum sample being tested is usually subjected to serial dilutions prior to mixing with a standardized amount of virus. The concentration of virus is held constant such that, when added to susceptible cells and overlaid with semi-solid media, individual plaques can be discerned and counted. In this way, PRNT end-point titers can be calculated for each serum sample at any selected percent reduction of virus activity.

In functional assays intended to assess vaccinal immunogenicity, the serum sample dilution series for antibody titration should ideally start below the “seroprotective” threshold titer. Regarding SARS-CoV-2 neutralizing antibodies, the “seroprotective” threshold titer remains unknown; but a seropositivity threshold of 1:10 can be considered a seroprotection threshold in certain embodiments.

In some embodiments a neutralizing immune response is an immune response that produces a level of antibodies that meet or exceed a seroprotection threshold.

PRNT end-point titers are expressed as the reciprocal of the last serum dilution showing the desired-percent reduction in plaque counts. The PRNT titer can be calculated based on a 50% or greater reduction in plaque counts (PRNT50). A PRNT50 titer is preferred over titers using higher cut-offs (e.g., PRNT90) for vaccine sera, providing more accurate results from the linear portion of the titration curve.

There are several ways to calculate PRNT titers. The simplest and most widely used way to calculate titers is to count plaques and report the titer as the reciprocal of the last serum dilution to show >50% reduction of the input plaque count as based on the back-titration of input plaques. Use of curve fitting methods from several serum dilutions may permit calculation of a more precise result. There are a variety of computer analysis programs available for this (e.g., SPSS or GraphPad Prism).

In some embodiments, an antibody titer is used to assess whether a subject has had an infection or to determine whether immunizations are required. In some embodiments, an antibody titer is used to determine the strength of an autoimmune response, to determine whether a booster immunization is needed, to determine whether a previous vaccine was effective, and to identify any recent or prior infections. In accordance with the present disclosure, an antibody titer may be used to determine the strength of an immune response induced in a subject by a composition (e.g., RNA vaccine).

In some embodiments, an anti-coronavirus antigen antibody titer produced in a subject is increased by at least 1 log relative to a control. For example, anti-coronavirus antigen antibody titer produced in a subject may be increased by at least 1.5, at least 2, at least 2.5, or at least 3 log relative to a control. In some embodiments, the anti-coronavirus antigen antibody titer produced in the subject is increased by 1, 1.5, 2, 2.5 or 3 log relative to a control. In some embodiments, the anti-coronavirus antigen antibody titer produced in the subject is increased by 1-3 log relative to a control. For example, the anti-coronavirus antigen antibody titer produced in a subject may be increased by 1-1.5, 1-2, 1-2.5, 1-3, 1.5-2, 1.5-2.5, 1.5-3, 2-2.5, 2-3, or 2.5-3 log relative to a control.

In some embodiments, the anti-coronavirus antigen antibody titer produced in a subject is increased at least 2 times relative to a control. For example, the anti-coronavirus antigen n antibody titer produced in a subject may be increased at least 3 times, at least 4 times, at least 5 times, at least 6 times, at least 7 times, at least 8 times, at least 9 times, or at least 10 times relative to a control. In some embodiments, the anti-coronavirus antigen antibody titer produced in the subject is increased 2, 3, 4, 5, 6, 7, 8, 9, or 10 times relative to a control. In some embodiments, the anti-coronavirus antigen antibody titer produced in a subject is increased 2-10 times relative to a control. For example, the anti-coronavirus antigen antibody titer produced in a subject may be increased 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5; 5-10, 5-9, 5-8, 5-7, 5-6, 6-10, 6-9, 6-8, 6-7, 7-10, 7-9, 7-8, 8-10, 8-9, or 9-10 times relative to a control.

In some embodiments, an antigen-specific immune response is measured as a ratio of geometric mean titer (GMT), referred to as a geometric mean ratio (GMR), of serum neutralizing antibody titers to coronavirus. A geometric mean titer (GMT) is the average antibody titer for a group of subjects calculated by multiplying all values and taking the nth root of the number, where n is the number of subjects with available data.

A control, in some embodiments, is an anti-coronavirus antigen antibody titer produced in a subject who has not been administered a composition (e.g., RNA vaccine). In some embodiments, a control is an anti-coronavirus antigen antibody titer produced in a subject administered a recombinant or purified protein vaccine. Recombinant protein vaccines typically include protein antigens that either have been produced in a heterologous expression system (e.g., bacteria or yeast) or purified from large amounts of the pathogenic organism.

In some embodiments, the ability of a composition (e.g., RNA vaccine) to be effective is measured in a murine model. For example, a composition may be administered to a murine model and the murine model assayed for induction of neutralizing antibody titers. Viral challenge studies may also be used to assess the efficacy of a vaccine of the present disclosure. For example, a composition may be administered to a murine model, the murine model challenged with virus, and the murine model assayed for survival and/or immune response (e.g., neutralizing antibody response, T cell response (e.g., cytokine response)).

In some embodiments, an effective amount of a composition (e.g., RNA vaccine) is a dose that is reduced compared to the standard of care dose of a recombinant protein vaccine. A “standard of care,” as provided herein, refers to a medical or psychological treatment guideline and can be general or specific. “Standard of care” specifies appropriate treatment based on scientific evidence and collaboration between medical professionals involved in the treatment of a given condition. It is the diagnostic and treatment process that a physician/clinician should follow for a certain type of patient, illness or clinical circumstance. A “standard of care dose,” as provided herein, refers to the dose of a recombinant or purified protein vaccine, or a live attenuated or inactivated vaccine, or a VLP vaccine, that a physician/clinician or other medical professional would administer to a subject to treat or prevent coronavirus infection or a related condition, while following the standard of care guideline for treating or preventing coronavirus infection or a related condition.

In some embodiments, the anti-coronavirus antigen antibody titer produced in a subject administered an effective amount of an composition is equivalent to an anti-coronavirus antigen antibody titer produced in a control subject administered a standard of care dose of a recombinant or purified protein vaccine, or a live attenuated or inactivated vaccine, or a VLP vaccine.

Vaccine efficacy may be assessed using standard analyses (see, e.g., Weinberg et al., J Infect Dis. 2010 Jun. 1; 201(11):1607-10). For example, vaccine efficacy may be measured by double-blind, randomized, clinical controlled trials. Vaccine efficacy may be expressed as a proportionate reduction in disease attack rate (AR) between the unvaccinated (ARU) and vaccinated (ARV) study cohorts and can be calculated from the relative risk (RR) of disease among the vaccinated group with use of the following formulas:

$$\text{Efficacy} = (ARU - ARV)/ARU \times 100; \text{ and}$$

$$\text{Efficacy} = (1 - RR) \times 100.$$

Likewise, vaccine effectiveness may be assessed using standard analyses (see, e.g., Weinberg et al., J Infect Dis. 2010 Jun. 1; 201(11):1607-10). Vaccine effectiveness is an assessment of how a vaccine (which may have already proven to have high vaccine efficacy) reduces disease in a population. This measure can assess the net balance of benefits and adverse effects of a vaccination program, not just the vaccine itself, under natural field conditions rather than in a controlled clinical trial. Vaccine effectiveness is proportional to vaccine efficacy (potency) but is also affected by how well target groups in the population are immunized, as well as by other non-vaccine-related factors that influence the 'real-world' outcomes of hospitalizations, ambulatory visits, or costs. For example, a retrospective case control analysis may be used, in which the rates of vaccination among a set of infected cases and appropriate controls are compared. Vaccine effectiveness may be expressed as a rate difference, with use of the odds ratio (OR) for developing infection despite vaccination:

$$\text{Effectiveness} = (1 - OR) \times 100.$$

In some embodiments, efficacy of the composition (e.g., RNA vaccine) is at least 60% relative to unvaccinated control subjects. For example, efficacy of the composition may be at least 65%, at least 70%, at least 75%, at least 80%, at least 85%, at least 95%, at least 98%, or 100% relative to unvaccinated control subjects.

Sterilizing Immunity. Sterilizing immunity refers to a unique immune status that prevents effective pathogen infection into the host. In some embodiments, the effective amount of a composition of the present disclosure is sufficient to provide sterilizing immunity in the subject for at least 1 year. For example, the effective amount of a composition of the present disclosure is sufficient to provide sterilizing immunity in the subject for at least 2 years, at least 3 years, at least 4 years, or at least 5 years. In some embodiments, the effective amount of a composition of the present disclosure is sufficient to provide sterilizing immunity in the subject at an at least 5-fold lower dose relative to control. For example, the effective amount may be sufficient to provide sterilizing immunity in the subject at an at least 10-fold lower, 15-fold, or 20-fold lower dose relative to a control.

Detectable Antigen. In some embodiments, the effective amount of a composition of the present disclosure is sufficient to produce detectable levels of coronavirus antigen as measured in serum of the subject at 1-72 hours post administration.

Titer. An antibody titer is a measurement of the number of antibodies within a subject, for example, antibodies that are specific to a particular antigen (e.g., an anti-coronavirus antigen). Antibody titer is typically expressed as the inverse of the greatest dilution that provides a positive result. Enzyme-linked immunosorbent assay (ELISA) is a common assay for determining antibody titers, for example.

A neutralizing immune response is an immune response that is a neutralizing antibody response and/or an effective neutralizing T cell response. In some embodiments a neutralizing antibody response produces a level of antibodies that meet or exceed a seroprotection threshold.

An effective T cell response is a response which produces a baseline level of viral activated or viral specific T cells including CD8+ and CD4+T helper type 1 cells. CD8+ cytotoxic T lymphocytes typically clear the intracellular virus compartment and CD4+ T cells exert various functions in the body such as helping B and other T cells, promoting memory generation and indirect or direct cytotoxic activity. In some embodiments the effective T cells comprises a high proportion of CD8+ T cells and/or CD4+ T cells, relative to a baseline level (in a naïve subject). In some embodiments these T cells are differentiated towards an early-differentiated memory phenotype with co-expression of CD27 and CD28.

In some embodiments, the effective amount of a composition of the present disclosure is sufficient to produce a 1,000-10,000 neutralizing antibody titer produced by neutralizing antibody against the coronavirus antigen as measured in serum of the subject at 1-72 hours post administration. In some embodiments, the effective amount is sufficient to produce a 1,000-5,000 neutralizing antibody titer produced by neutralizing antibody against the coronavirus antigen as measured in serum of the subject at 1-72 hours post administration. In some embodiments, the effective amount is sufficient to produce a 5,000-10,000 neutralizing antibody titer produced by neutralizing antibody against the coronavirus antigen as measured in serum of the subject at 1-72 hours post administration.

In some embodiments, the neutralizing antibody titer is at least 100 $NT_{50}$. For example, the neutralizing antibody titer may be at least 200, 300, 400, 500, 600, 700, 800, 900 or 1000 $NT_{50}$. In some embodiments, the neutralizing antibody titer is at least 10,000 $NT_{50}$. In some embodiments, the neutralizing antibody titer is at least 100 neutralizing units per milliliter. (NU/mL). For example, the neutralizing antibody titer may be at least 200, 300, 400, 500, 600, 700, 800, 900 or 1000 NU/mL. In some embodiments, the neutralizing antibody titer is at least 10,000 NU/mL.

In some embodiments, an anti-coronavirus antigen antibody titer produced in the subject is increased by at least 1 log relative to a control. For example, an anti-coronavirus antigen antibody titer produced in the subject may be increased by at least 2, 3, 4, 5, 6, 7, 8, 9 or 10 log relative to a control.

In some embodiments, an anti-coronavirus antigen antibody titer produced in the subject is increased at least 2 times relative to a control. For example, an anti-coronavirus antigen antibody titer produced in the subject is increased by at least 3, 4, 5, 6, 7, 8, 9 or 10 times relative to a control.

In some embodiments, a geometric mean, which is the nth root of the product of n numbers, is generally used to describe proportional growth. Geometric mean, in some embodiments, is used to characterize antibody titer produced in a subject.

A control may be, for example, an unvaccinated subject, or a subject administered a live attenuated viral vaccine, an inactivated viral vaccine, or a protein subunit vaccine.

ADDITIONAL EMBODIMENTS

1. A method comprising administering to a subject a vaccine comprising a nucleic acid encoding a SARS-CoV-2 spike antigen, optionally a 2P stabilized spike antigen of a second circulating SARS-CoV-2 virus, wherein the subject has previously been administered a first vaccine comprising a nucleic acid encoding a first SARS-CoV-2 2P stabilized spike antigen of a first circulating SARS-CoV-2 virus, and wherein each of the first and second 2P stabilized spike antigens are administered in an effective amount to induce an immune response specific for the first antigen and the second antigen, wherein the second circulating SARS-CoV-2 virus has a spike protein having an amino acid sequence with at least one amino acid mutation with respect to a spike protein amino acid sequence of the first circulating SARS-CoV-2 virus, and wherein the mutation is an amino acid substitution, deletion or insertion.

2. A method comprising administering to a subject a first vaccine comprising a nucleic acid encoding a first SARS-CoV-2 2P stabilized spike antigen and administering to the subject a second vaccine comprising a nucleic acid encoding a second SARS-CoV-2 spike antigen, optionally a 2P stabilized spike antigen, wherein each of the nucleic acids encoding the first and second stabilized spike antigens are administered in an effective amount to induce an immune response specific for the respective encoded antigens, wherein the second encoded SARS-CoV-2 spike antigen has an amino acid sequence with at least one amino acid mutation with respect to the first encoded spike protein amino acid sequence, and wherein the mutation is an amino acid substitution, deletion, or insertion.

3. A method comprising administering to a subject a first vaccine comprising a nucleic acid encoding a first SARS-CoV-2 2P stabilized spike antigen and administering to the subject a second vaccine comprising a nucleic acid encoding a second SARS-CoV-2 spike antigen, optionally a 2P stabilized spike antigen, wherein each of the nucleic acids encoding the first and second stabilized spike antigens are administered in an effective amount to induce an immune response specific for the respective encoded antigens, wherein the second encoded SARS-CoV-2 spike antigen has an amino acid sequence with at least one amino acid mutation with respect to the first encoded spike protein amino acid sequence, wherein the mutation is an amino acid substitution, deletion, or insertion, and wherein the first encoded SARS-CoV-2 spike antigen is of a first circulating SARS-CoV-2 virus and wherein the second encoded SARS-CoV-2 spike antigen is of a second circulating SARS-CoV-2 virus.

4. A method comprising administering to a subject a first vaccine comprising a nucleic acid encoding a first SARS-CoV-2 2P stabilized spike antigen and administering to the subject a second vaccine comprising a nucleic acid encoding a second SARS-CoV-2 spike antigen, optionally a 2P stabilized spike antigen, wherein each of the nucleic acids encoding the first and second stabilized spike antigens are administered in an effective amount to induce an immune response specific for the respective encoded antigens, wherein the second encoded SARS-CoV-2 spike antigen has an amino acid sequence with at least one amino acid mutation with respect to the first encoded spike protein amino acid sequence, wherein the mutation is an amino acid substitution, deletion, or insertion, and wherein the first encoded SARS-CoV-2 spike antigen is representative of a first circulating SARS-CoV-2 virus and wherein the second encoded SARS-CoV-2 spike antigen is representative of a second circulating SARS-CoV-2 virus.

5. A method comprising administering to a subject a first vaccine comprising a nucleic acid encoding a first SARS-CoV-2 2P stabilized spike antigen and administering to the subject a second vaccine comprising a nucleic acid encoding a second SARS-CoV-2 spike antigen, optionally a 2P stabilized spike antigen, wherein each of the nucleic acids encoding the first and second stabilized spike antigens are administered in an effective amount to induce an immune response specific for the respective encoded antigens, wherein the second encoded SARS-CoV-2 spike antigen has an amino acid sequence with at least one amino acid mutation with respect to the first encoded spike protein amino acid sequence, wherein the mutation is an amino acid substitution, deletion, or insertion, and wherein the first encoded SARS-CoV-2 spike antigen is representative of a plurality of first circulating SARS-CoV-2 viruses and/or wherein the second encoded SARS-CoV-2 spike antigen is representative of a second plurality of circulating SARS-CoV-2 viruses.

6. The method of any one of paragraphs 1-5, wherein the first antigen is a mRNA encoding the first SARS-CoV-2 spike antigen and wherein the spike antigen has an amino acid sequence of SEQ ID NO: 20.

7. The method of any one of paragraphs 1-6, wherein the second antigen is a mRNA encoding the second SARS-CoV-2 spike antigen, wherein the spike antigen has an amino acid sequence with at least one amino acid mutation with respect to a protein of SEQ ID NO: 20, and wherein the mutation is an amino acid substitution, deletion or insertion.

8. A composition comprising: a first messenger ribonucleic acid (mRNA) encoding a first SARS-CoV-2 spike antigen of a first circulating SARS-CoV-2 virus wherein the first SARS-CoV-2 spike antigen has an amino acid sequence of SEQ ID NO: 20 or an amino acid sequence with at least one amino acid mutation with respect to a protein of SEQ ID NO: 20 and a second mRNA encoding a second SARS-CoV-2 spike antigen of a second circulating SARS-CoV-2 virus, wherein the second SARS-CoV-2 spike antigen has an amino acid sequence with at least one amino acid mutation with respect to a protein of SEQ ID NO: 20, wherein the wherein the mutation is an amino acid substitution, deletion or insertion, and wherein the first SARS-CoV-2 spike antigen and the second SARS-CoV-2 spike antigen are different from one another.

9. The composition of paragraph 8, wherein the composition further comprises a third messenger ribonucleic acid (mRNA) encoding a third SARS-CoV-2 spike antigen of a third SARS-CoV-2 virus, wherein the third SARS-CoV-2 spike antigen has an amino acid sequence with at least one amino acid mutation with respect to a protein of SEQ ID NO: 20, and wherein the mutation is an amino acid substitution, deletion or insertion.

10. The composition of paragraph 9, wherein the composition further comprises a fourth messenger ribonucleic acid (mRNA) encoding a fourth SARS-CoV-2 spike antigen of a fourth SARS-CoV-2 virus, wherein the fourth SARS-CoV-2 spike antigen has an amino acid sequence with at least one amino acid mutation with respect to a protein of SEQ ID NO: 20, and wherein the mutation is an amino acid substitution, deletion or insertion.

11. The composition of paragraph 10, wherein the composition further comprises a fifth messenger ribonucleic acid (mRNA) encoding a fifth SARS-CoV-2 spike antigen of a fifth SARS-CoV-2 virus, wherein the fifth SARS-CoV-2 spike antigen has an amino acid sequence with at least one amino acid mutation with respect to a protein of SEQ ID NO: 20, and wherein the mutation is an amino acid substitution, deletion or insertion.

12. The composition of paragraph 11, wherein the composition further comprises a sixth messenger ribonucleic acid (mRNA) encoding a sixth SARS-CoV-2 spike antigen of a sixth SARS-CoV-2 virus, wherein the sixth SARS-CoV-2 spike antigen has an amino acid sequence with at least one amino acid mutation with respect to a protein of SEQ ID NO: 20, and wherein the mutation is an amino acid substitution, deletion or insertion.

nanoparticle comprises an ionizable amino lipid, a sterol, a neutral lipid, and a polyethylene glycol (PEG)-modified lipid.

23. The mRNA of paragraph 22, wherein the lipid nanoparticle comprises 40-55 mol % ionizable amino lipid, 30-45 mol % sterol, 5-15 mol % neutral lipid, and 1-5 mol % PEG-modified lipid.

24. The mRNA of any one of paragraphs 22-23, wherein the lipid nanoparticle comprises 40-50 mol % ionizable amino lipid, 35-45 mol % sterol, 10-15 mol % neutral lipid, and 2-4 mol % PEG-modified lipid.

25. The mRNA of any one of paragraphs 22-24, wherein the lipid nanoparticle comprises 45 mol %, 46 mol %, 47 mol %, 48 mol %, 49 mol %, or 50 mol % ionizable amino lipid.

26. The mRNA of any one of paragraphs 22-25, wherein the ionizable amino lipid has the structure of Compound 1:

(Compound 1)

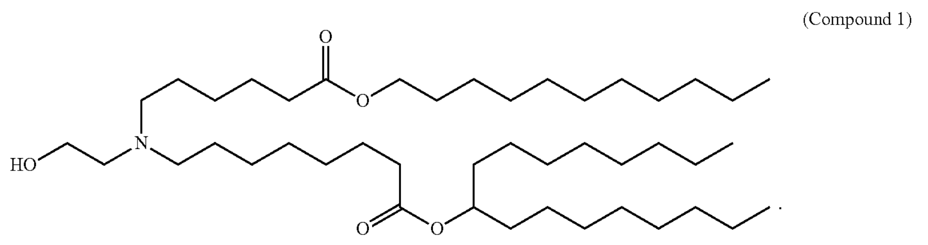 [SMILES: CCCCCCCCCCCOC(=O)CCCCCN(CCO)CCCCCCCC(=O)OC(CCCCCCCC)CCCCCCCC]

13. The composition of any one of paragraphs 8-12, wherein the first and second virus strains, and optionally the third, fourth, fifth and sixth virus strains are spreading in the population for at least a portion of 1 year.

14. A messenger ribonucleic acid (mRNA) encoding a SARS-CoV-2 2P stabilized spike protein, wherein the 2P stabilized spike protein has an amino acid sequence with at least one amino acid mutation with respect to a protein of SEQ ID NO: 20, wherein the mutation is an amino acid substitution, deletion or insertion, and wherein the 2P stabilized spike protein is a 2P stabilized version of a spike protein from a second circulating SARS-CoV-2 virus strain, and wherein a first circulating SARS-CoV-2 virus strain comprises a spike protein of SEQ ID NO: 11.

15. An mRNA, wherein the mRNA encodes a protein having at least 95% sequence identity to a protein of any one of SEQ ID NOs: 5, 8, 11, 14, 17, 23, 36, 30, 33, 36, 39, and 42.

16. An mRNA, wherein the mRNA has at least 95% sequence identity to an RNA of any one of SEQ ID NOs: 1, 6, 9, 12, 15, 21, 24, 28, 31, 34, 37, 40, 43, and 45.

17. An mRNA, wherein the mRNA has at least 98% sequence identity to an RNA of any one of SEQ ID NOs: 1, 6, 9, 12, 15, 21, 24, 28, 31, 34, 37, 40, 43, and 45.

18. An mRNA, wherein the mRNA comprises an RNA of any one of SEQ ID NOs: 1, 6, 9, 12, 15, 21, 24, 28, 31, 34, 37, 40, 43, and 45.

19. The mRNA of any one of paragraphs 14-18, wherein the mRNA comprises a chemical modification.

20. The mRNA of paragraph 19, wherein the mRNA is fully modified.

21. The mRNA of paragraph 19 or 20, wherein the chemical modification is 1-methylpseudouridine.

22. The mRNA of any one of paragraphs 14-21, wherein the mRNAs are in a lipid nanoparticle and wherein the lipid 27. The mRNA of any one of any one of paragraphs 22-26, wherein the sterol is cholesterol or a derivative thereof.

28. The mRNA of any one of paragraphs 22-27, wherein the neutral lipid is 1,2 distearoyl-sn-glycero-3-phosphocholine (DSPC).

29. The mRNA of any one of paragraphs 22-28, wherein the PEG-modified lipid is 1,2 dimyristoyl-sn-glycerol, methoxypolyethyleneglycol (PEG2000 DMG).

30. A method comprising administering to a subject a vaccine comprising a first nucleic acid encoding a SARS-CoV-2 2P stabilized spike antigen, wherein the spike antigen has an amino acid sequence with at least one amino acid mutation with respect to a protein of SEQ ID NO: 20, and wherein the mutation is an amino acid substitution, deletion or insertion, wherein the subject is seropositive for a SARS-CoV-2 antigen of SEQ ID NO. 21 or 20.

31. A method comprising administering to a subject a vaccine comprising a first nucleic acid encoding a SARS-CoV-2 2P stabilized spike antigen, wherein the spike antigen has an amino acid sequence with at least one amino acid mutation with respect to a protein of SEQ ID NO: 20, and wherein the mutation is an amino acid substitution, deletion or insertion, wherein the subject is seronegative for a SARS-CoV-2 antigen of SEQ ID NO. 21 or 20.

32. The method of paragraph 30 or 31, wherein the subject is administered a second dose of the vaccine between 2 weeks and 1 year after the first dose of vaccine is administered.

33. The method of paragraph 31 or 32, wherein the subject is administered a second vaccine between 2 weeks and 1 year after the vaccine is administered, wherein the second vaccine comprises a second nucleic acid encoding a SARS-CoV-2 2P stabilized spike antigen of SEQ ID NO: 20.

34. The method of paragraph 33, wherein the second vaccine comprises a mixture of the first and second nucleic acids, wherein the first nucleic acid and the second nucleic acid are present in the second vaccine at a ratio of 1:1.

35. The method of any one of paragraphs 30-34, where 50 μg of the vaccine comprising a nucleic acid encoding a SARS-CoV-2 spike antigen, optionally, a 2P stabilized spike antigen of a third circulating SARS-CoV-2 virus is administered to the subject.

36. The method of any one of paragraphs 30-35, wherein the vaccine comprises a nucleic acid encoding a SARS-CoV-2 spike antigen having at least 95% sequence identity to SEQ ID NO: 11.

37. The method of any one of paragraphs 30-36, wherein the vaccine comprises a nucleic acid having at least 95% sequence identity to SEQ ID NO: 9.

38. The method of paragraph 37, wherein the vaccine comprises a nucleic acid comprising SEQ ID NO: 9.

39. The method of any-one of paragraphs 1-7 and 30-38, wherein the first vaccine or the second vaccine comprises: (a) a nucleic acid encoding a SARS-CoV-2 spike antigen comprising two proline substitutions; and (b) a nucleic acid encoding a SARS-CoV-2 spike antigen comprising SEQ ID NO: 11.

40. The method of any one of paragraphs 1-7 and 30-38, wherein the first vaccine or the second vaccine comprises: (a) a nucleic acid encoding a SARS-CoV-2 spike antigen comprising two proline substitutions; and (b) a nucleic acid encoding a SARS-CoV-2 spike antigen comprising SEQ ID NO: 26.

41. The method of any one of paragraphs 1-7 and 30-38, wherein the first vaccine or the second vaccine comprises: (a) a nucleic acid encoding a SARS-CoV-2 spike antigen comprising two proline substitutions; and (b) a nucleic acid encoding a SARS-CoV-2 spike antigen comprising SEQ ID NO: 30.

42. The method of any one of paragraphs 39-41, wherein the ratio of (a) to (b) is 1:1, 1:2, 1:3, 1:4, 2:1, 3:1, or 4:1.

43. The method of any one of paragraphs 1-7 and 30-38, wherein the second vaccine comprises: (a) the nucleic acid encoding a first SARS-CoV-2 2P spike antigen of a first circulating SARS-CoV-2 virus; and (b) the nucleic acid encoding a second SARS-CoV-2 2P spike antigen of a second circulating SARS-CoV-2 virus.

44. The method of paragraph 43, wherein the ratio of (a) to (b) is 1:1, 1:2, 1:3, 1:4, 2:1, 3:1, or 4:1.

45. A method comprising: administering to a subject a booster vaccine comprising a nucleic acid encoding a first SARS-CoV-2 antigen from a first SARS-CoV-2 virus, wherein the subject has previously been administered at least one prime dose of a first vaccine comprising a first nucleic acid encoding the SARS-CoV-2 antigen of the first the SARS-CoV-2 virus, wherein the booster vaccine is administered in an effective amount to induce a neutralizing immune response against a second SARS-CoV-2 virus, wherein the second SARS-CoV-2 virus comprises a second SARS-CoV-2 antigen, wherein the second SARS-CoV-2 antigen has an amino acid sequence with at least one amino acid mutation with respect to a corresponding protein antigen of the first SARS-CoV-2 virus, wherein the booster vaccine is administered in a dosage of 25-100 μg at least 6 months after a first dose of the first vaccine, and wherein the first antigen is a full length stabilized spike protein having a 2P mutation.

46. The method of paragraph 45, wherein the booster vaccine is administered in a dosage of 50 μg.

47. The method of paragraph 45 or 46, wherein the booster vaccine is administered at least about 6 months after a second dose of the first vaccine.

48. The method of paragraph 45 or 46, wherein the booster vaccine is administered 6-12 months after a second dose of the first vaccine.

49. The method of paragraph 45 or 46, wherein the booster vaccine is administered at least about 8 months after a second dose of the first vaccine.

50. The method of any one of paragraphs 45-49, wherein the boost dose is a seasonal boost or a pandemic shift boost to provide a neutralizing immune response against a plurality of variants of concern.

51. The method of any one of paragraphs 1-7 and 30-38, wherein the first vaccine or the second vaccine comprises: (a) a nucleic acid encoding a SARS-CoV-2 spike antigen comprising two proline substitutions; and (b) a nucleic acid encoding a SARS-CoV-2 spike antigen comprising SEQ ID NO: 33.

52. The method of any one of paragraphs 1-7 and 30-38, wherein the first vaccine or the second vaccine comprises: (a) a nucleic acid encoding a SARS-CoV-2 spike antigen comprising two proline substitutions; and (b) a nucleic acid encoding a SARS-CoV-2 spike antigen comprising SEQ ID NO: 36.

53. The method of any one of paragraphs 1-7 and 30-38, wherein the first vaccine or the second vaccine comprises: (a) a nucleic acid encoding a SARS-CoV-2 spike antigen comprising two proline substitutions; and (b) a nucleic acid encoding a SARS-CoV-2 spike antigen comprising SEQ ID NO: 39.

54. The method of any one of paragraphs 1-7 and 30-38, wherein the first vaccine or the second vaccine comprises: (a) a nucleic acid encoding a SARS-CoV-2 spike antigen comprising two proline substitutions; and (b) a nucleic acid encoding a SARS-CoV-2 spike antigen comprising SEQ ID NO: 42.

55. The method of any one of paragraphs 1-7 and 30-54 and the composition of any one of paragraphs 8-29, wherein at least one mRNA further comprises one or more non-coding sequences in an untranslated region (UTR), optionally a 5' UTR or 3' UTR.

56. The method or composition of paragraph 55, wherein all of the mRNAs further comprise one or more non-coding sequences in an UTR, optionally a 5' UTR or 3' UTR.

57. The method or composition of paragraph 56, wherein the non-coding sequence is positioned in a 3' UTR of an mRNA, upstream of the polyA tail of the mRNA.

58. The method or composition of paragraph 56, wherein the non-coding sequence is positioned in a 3' UTR of an mRNA, downstream of the polyA tail of the mRNA.

59. The method or composition of paragraph 56, wherein the non-coding sequence is positioned in a 3' UTR of an mRNA between the last codon of the ORF of the mRNA and the first "A" of the polyA tail of the mRNA.

60. The method or composition of paragraph 56, wherein the non-coding sequence comprises between 1 and 10 nucleotides.

61. The method or composition of anyone of paragraphs 55-60, wherein the non-coding sequence comprises one or more RNAse cleavage sites.

62. The method or composition of paragraph 61, wherein the RNAse cleavage site comprises an RNase H cleavage site.

EXAMPLES

Example 1. MRNA Vaccine Induces Human Neutralizing Antibodies Against Spike Mutants from Global SARS-CoV-2 Variants Severe acute respiratory syndrome coronavirus-2 (SARS-CoV-2) is the causative infection of a global pandemic that has led to more than 2 million deaths worldwide. The Moderna mRNA-1273 vaccine has demonstrated ~94% efficacy in a Phase 3 study and has been approved under Emergency Use Authorization. The emergence of SARS-CoV-2 variants with mutations in the spike protein, most recently circulating isolates containing these substitutions from the United Kingdom (B.1.1.7), Republic of South Africa (B.1.351), Brazil (P.1 lineage), New York (B.1.526), and California (B.1.427/B.1.429 or CAL.20C lineage), has led to lower neutralization from convalescent serum by pseudovirus neutralization (PsVN) assays and resistance to certain monoclonal antibodies. Here, using two orthogonal VSV and lentivirus PsVN assays expressing spike variants of 20E.(EU1), 20A.EU2, D614G-N439, mink cluster 5, B.1.1.7 (UK) and B.1.351 (RSA) variants, the neutralizing capacity of sera from human subjects or non-human primates that received mRNA-1273 were assessed. No significant impact on neutralization against the B.1.1.7 variant was detected in either case; however, reduced neutralization was measured against the mutations present in B.1.351. Geometric mean titer (GMT) of human sera from clinical trial participants in VSV PsVN assay using D614G spike was 1/1852. VSV pseudoviruses with spike containing K417N-E484K-N501Y-D614G and full B.1.351 mutations resulted in 2.7 and 6.4-fold reduction, respectively, when compared to the D614G VSV pseudovirus. Importantly, the VSV PsVN GMT of these human sera to the full B.1.351 spike variant was still 1/290, with all sera evaluated able to fully neutralize. Similarly, sera from NHPs immunized with 3.0 or 100 μg of mRNA-1273 had VSV PsVN GMTs of ~1/323 or 1/404, respectively, against the full B.1.351 spike variant with a ~5 to 10-fold reduction compared to D614G. Testing vaccine immune sera against a variety of pseudoviruses, the B.1.351 variant showed the greatest decrease in PsVN activity when compared to neutralizing activity against the D614G pseudovirus. Nevertheless, the GMT of VSV PsVN titers in human vaccine sera against the B.1.351 variant remained at ~1/300. The studies are described in more detail below.

In this study, neutralization of sera from Phase 1 clinical trial participants vaccinated with mRNA encoding Spike protein with two proline substitutions ("mRNA vaccine") against recombinant vesicular stomatitis virus (VSV)-based SARS-CoV-2 in a pseudovirus neutralization (PsVN) assay was assessed with Spike protein from the USA-WA1/2020 isolate, later arising variants including the D614G variant, the B.1.1.7 and B.1.1.351 variants, and variants that previously emerged (20E.EU1, 20A.EU2, D614G-N439K, and mink cluster 5 variant). The effect of both single mutations and combinations of mutations present in the receptor binding domain (RBD) region of the S protein were examined. Orthogonal assessments in VSV and pseudotyped lentiviral neutralization assays were also performed on sera from non-human primates (NHPs) that received the mRNA encoding Spike protein with two proline substitutions vaccine at two different doses.

To assess the ability of the mRNA vaccine to elicit potently neutralizing antibodies against this broad spectrum of SARS-CoV-2 variants, the sera of from mRNA-immunized NHPs that received 30 μg administered twice and participants in the Phase 1 clinical study immunized with the mRNA vaccine at the approved dose of 100 μg given twice were analyzed. Neutralization activity of immune sera was measured with SARS-CoV-2 full-length Spike pseudotyped recombinant VSV-ΔG-firefly luciferase virus, and in PsVN assays against homotypic SARS-CoV-2 D614, which contains the Spike protein of the USA-WA1/2020 isolate (D614), the D614G version, or Spike protein from 20A.EU1, 20A.EU2 and mink cluster 5 variants (Table 2).

TABLE 2

Spike mutations in SARS-CoV-2 variants

| Variant Name | Amino Acid Changes in Spike |
| --- | --- |
| 20A.EU1 | A222V-D614G |
| 20A.EU2 | S477N-D614G |
| N439K-D614G | N439K-D614G |
| Mink Cluster 5 Variant | ΔH69ΔV70-Y453F-D614G-I692V-M1229I |
| B.1.1.7 (a.k.a., 20I/501Y.V1, VOC 202012/01) | ΔH69ΔV70-ΔY144-N501Y-A570D-D614G-P681H-T716I-S982A-D1118H |
| B.1.351 (a.k.a., 20H/501Y.V2) | L18F-D80A-D215G-ΔL242ΔA243ΔL244-R246I-K417N-E484K-N501Y-D614G-A701V |

Figure 1B:
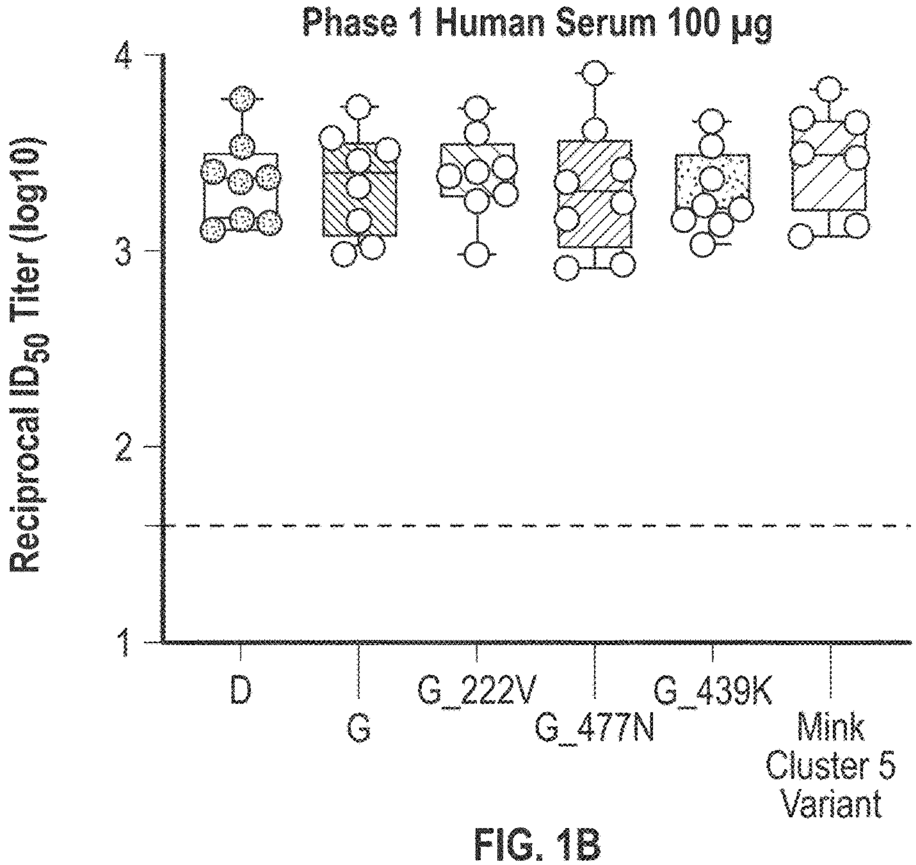

Results demonstrated that the antibody response elicited by the mRNA-1273 vaccine provides similar levels of neutralization against these SARS-CoV-2 Spike variants that emerged prior to the B.1.1.7 and B.1.351 lineages as against the USA-WA1/2020 (D614) strain. This observation includes the G614 variant that has been shown have higher neutralization titers in lentiviral pseudovirus neutralization assays (FIGS. 1A-1B). One of these Spike variants is from mink cluster 5 variant of Denmark, which contains 69-70 del in addition to other mutations (Y453F-I692V-M1229I).

Sera from NHPs vaccinated on day 1 and 29 with 30 or 100 μg mRNA vaccines were analyzed next. Neutralizing antibody responses were measured using orthogonal assessments with both the lentiviral and the VSV-based PsVN assays. Pseudoviruses in both assays incorporated the full-length Spike protein, conferring the USA-WA1/2020 (D614), G614, isolated, partial, or complete set of mutations that are present in the B.1.1.7 and B.1.351 lineages (Table 3).

TABLE 3

| Spike variants evaluated the PsVN assay assessment of mRNA vaccinated NHP sera | | | |
|---|---|---|---|
| Pseudovirus | Strain | Partial or full Spike mutants | Mutations |
| VSV | All | | D614G |
| | B.1.1.7 | Full | ΔH69ΔV70-ΔY144-N501Y-A570D-D614G-P681H-T716I-S982A-D1118H |
| | B.1.351 | Partial | K417N-E484K-N501Y-D614G |
| | B.1.351 | Full | L18F-D80A-D215G-ΔL242ΔA243ΔL244-R246I-K417N-E484K-N501Y-D614G-A701V |

Figure 2A:
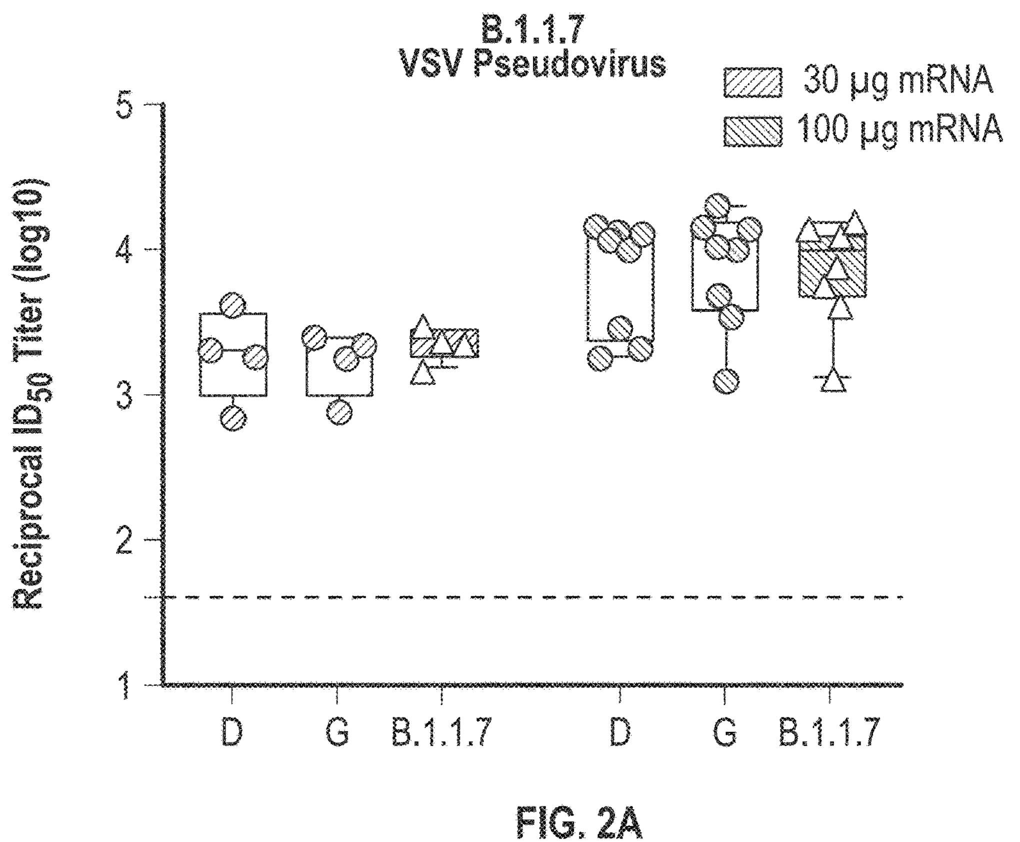
FIGS. 2A-2B show neutralizing antibodies in NHPs against the original (D614), D614G, and Spike variants. Rhesus macaques (NHPs) were immunized with 100 or 30 μg mRNA encoding Spike protein with two proline substitutions on a prime-boost schedule, and sera were collected 4 weeks post the boost. Neutralization was measured by a recombinant VSV-based pseudovirus neutralization assay (FIGS. 2A-2B). The assays incorporated full-length Spike protein of the original D614 (D), D614G (G), or the indicated Spike variants present in the B.1.1.7 variant (FIG. 2A) or B.1.351 variant (FIG. 2B). The horizontal dotted lines indicate the lower limit of quantification (LLOQ). D=D614 of USA-WA1/2020 isolate, G=D614G variant.

The mutations present in the B.1.1.7 variant, either the complete set of Spike mutations or specific mutations (Table 3) had minimal effect on neutralization in both the VSV and lentiviral neutralization assays. In the VSV assay, no difference was observed between the D614 and the G614 viruses, and there was potent neutralization measured against both (FIG. 2A). Moreover, no decrease in neutralization titers was measured from the B.1.1.7 mutations.

Figure 2B:
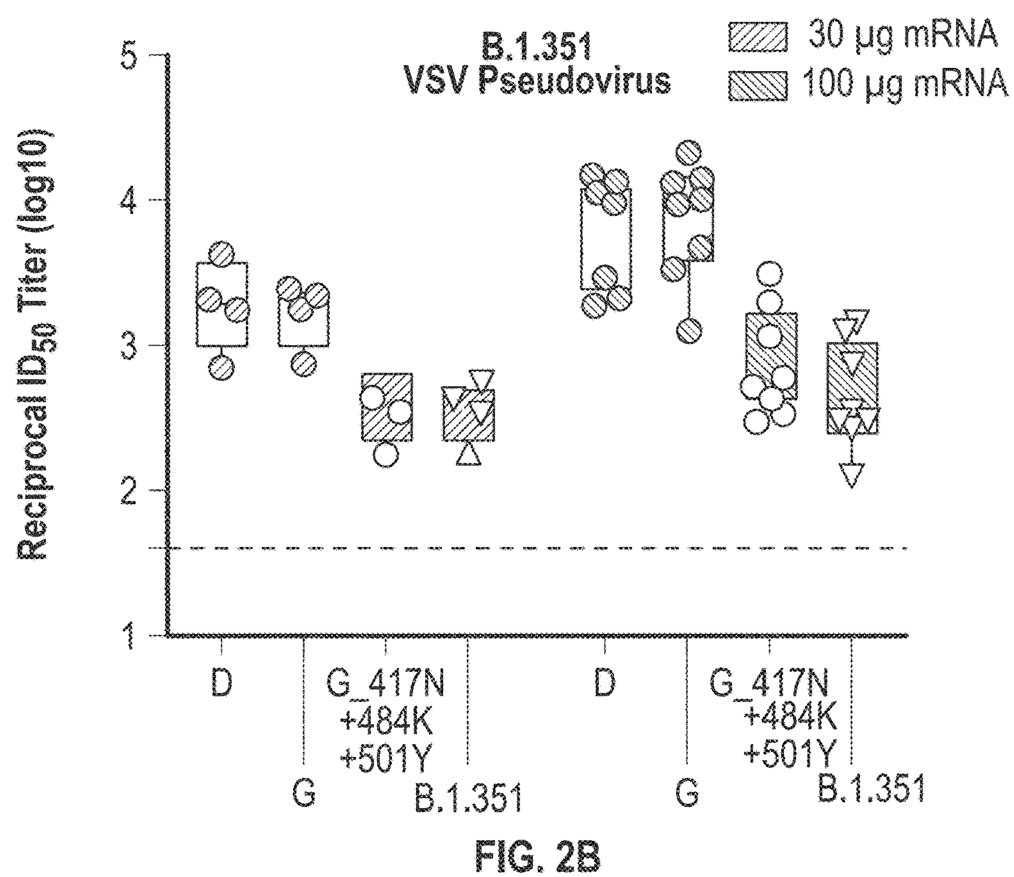
Figure 3A:
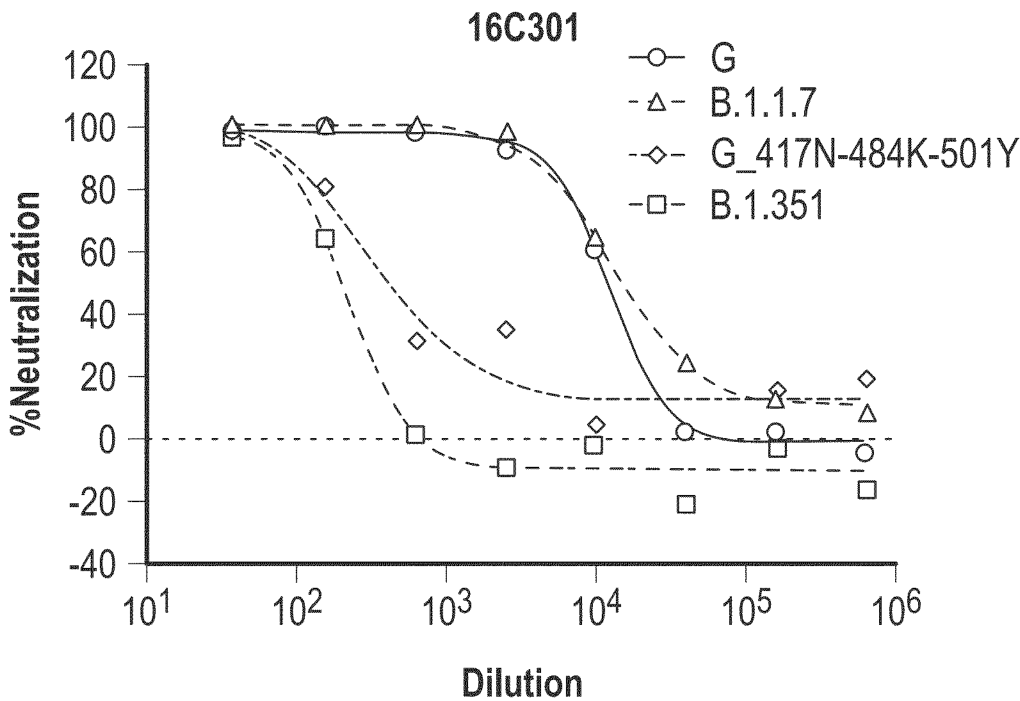
FIGS. 3A-3C show neutralization curves of NHP samples in the VSV-based pseudovirus neutralization assay.
Figure 3A:
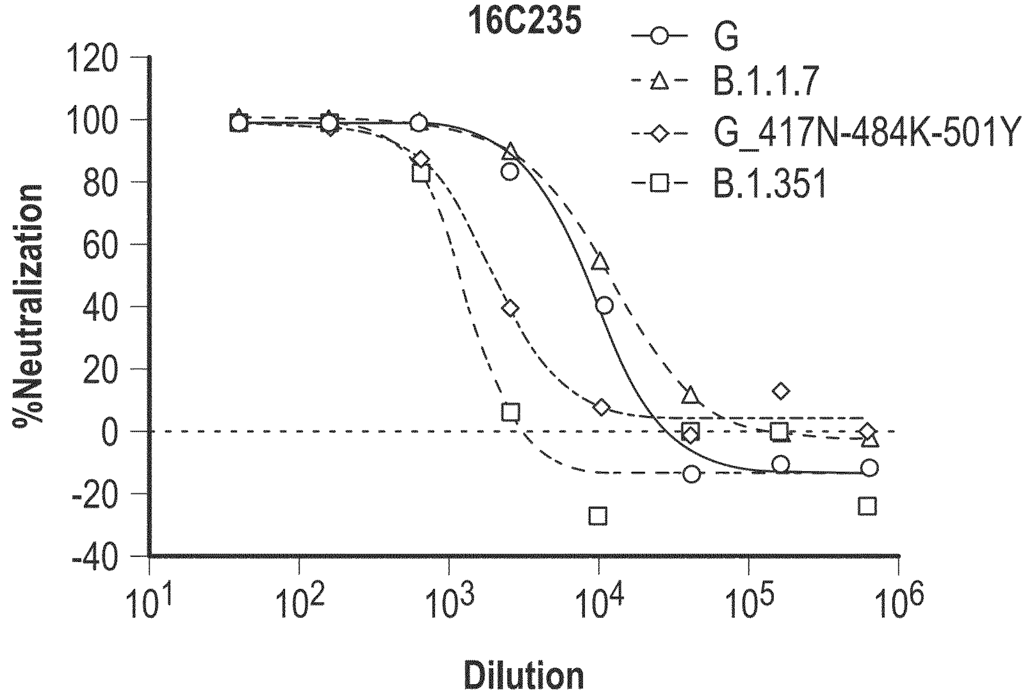
Figure 3A:
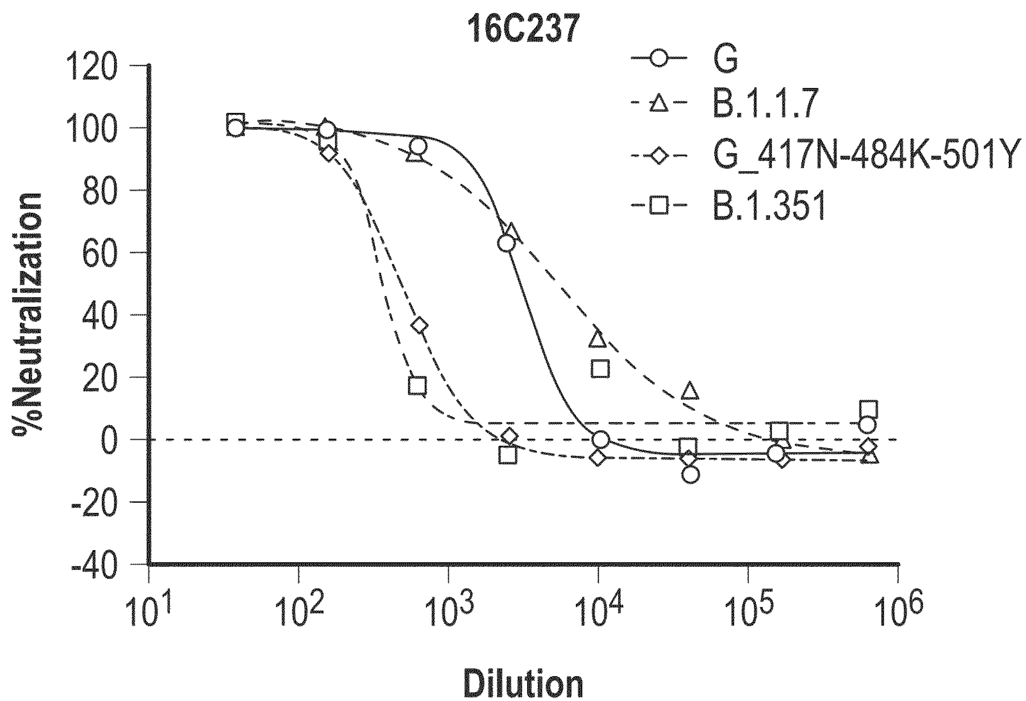
Figure 3A:
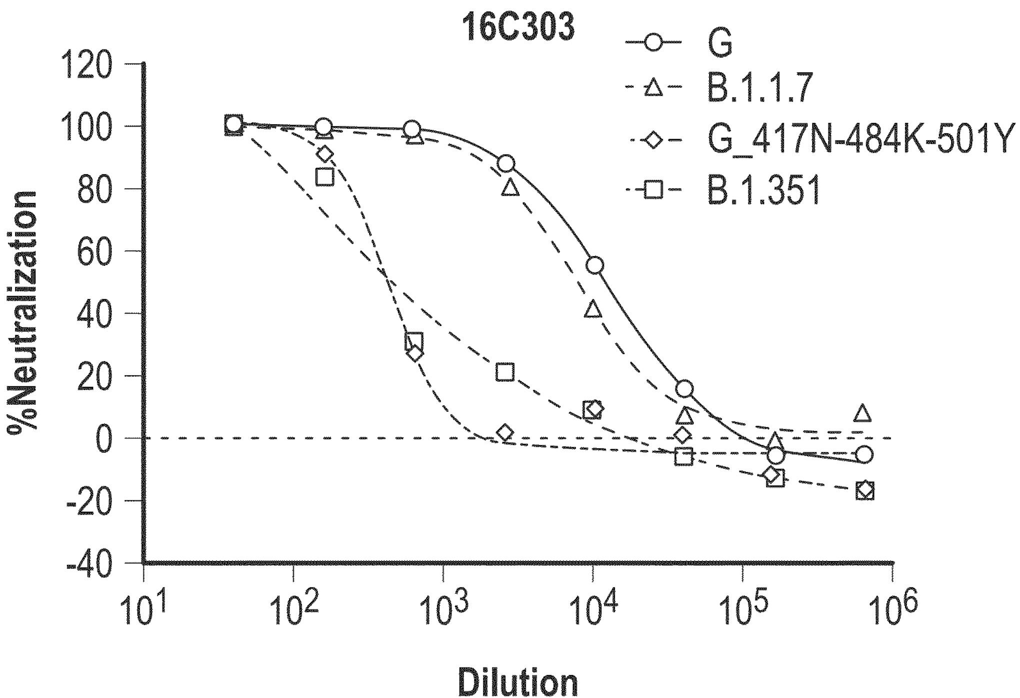
Figure 3B:
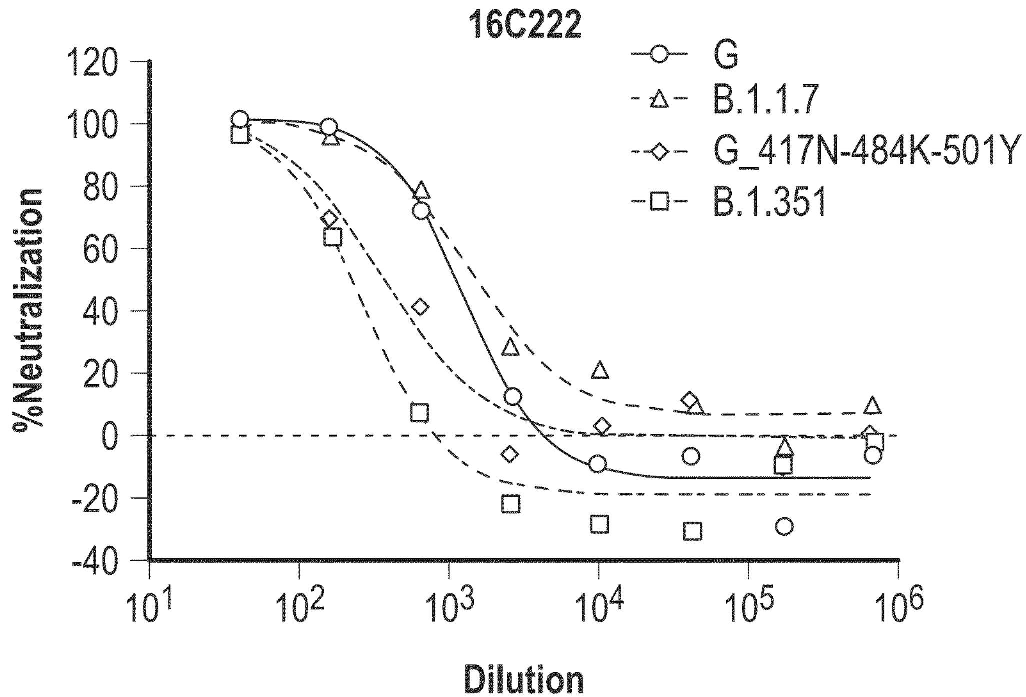
Figure 3B:
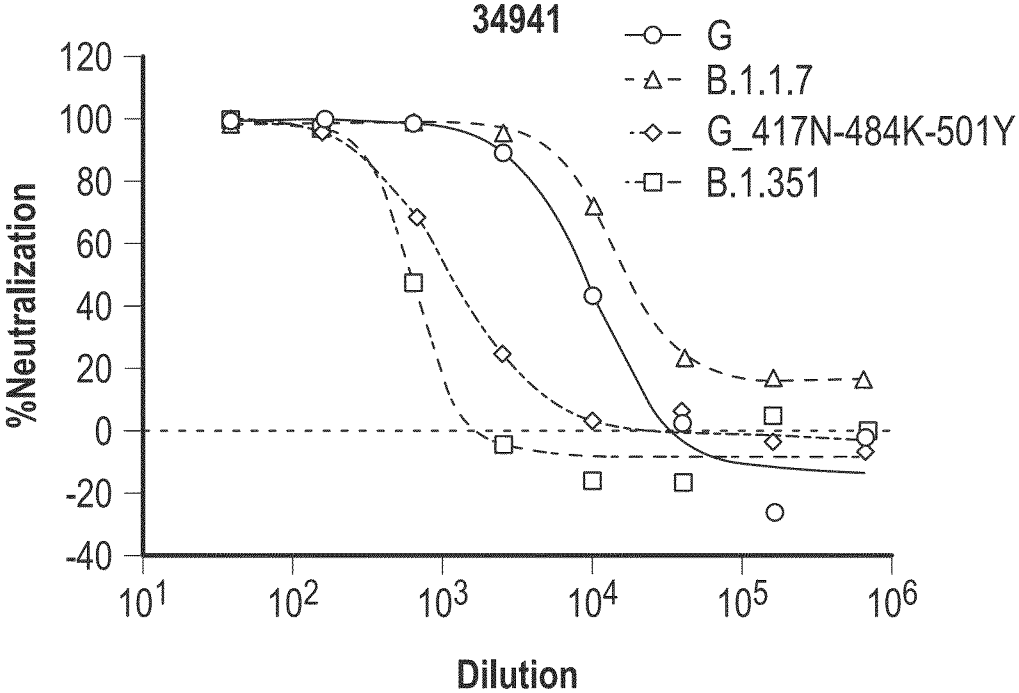
Figure 3B:
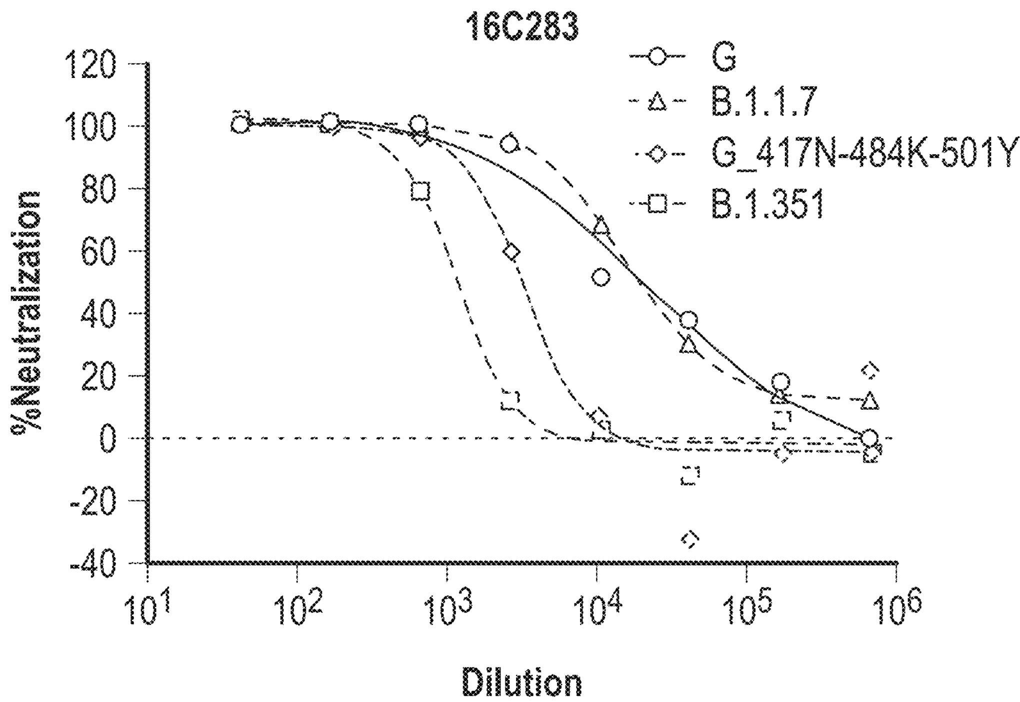
Figure 3B:
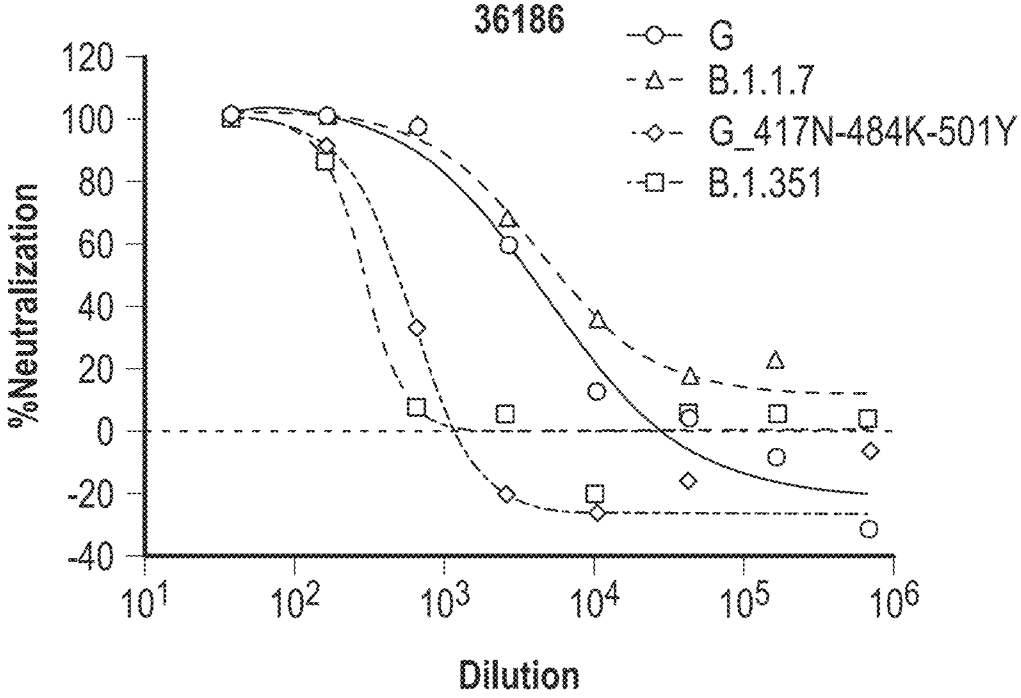
Figure 3C:
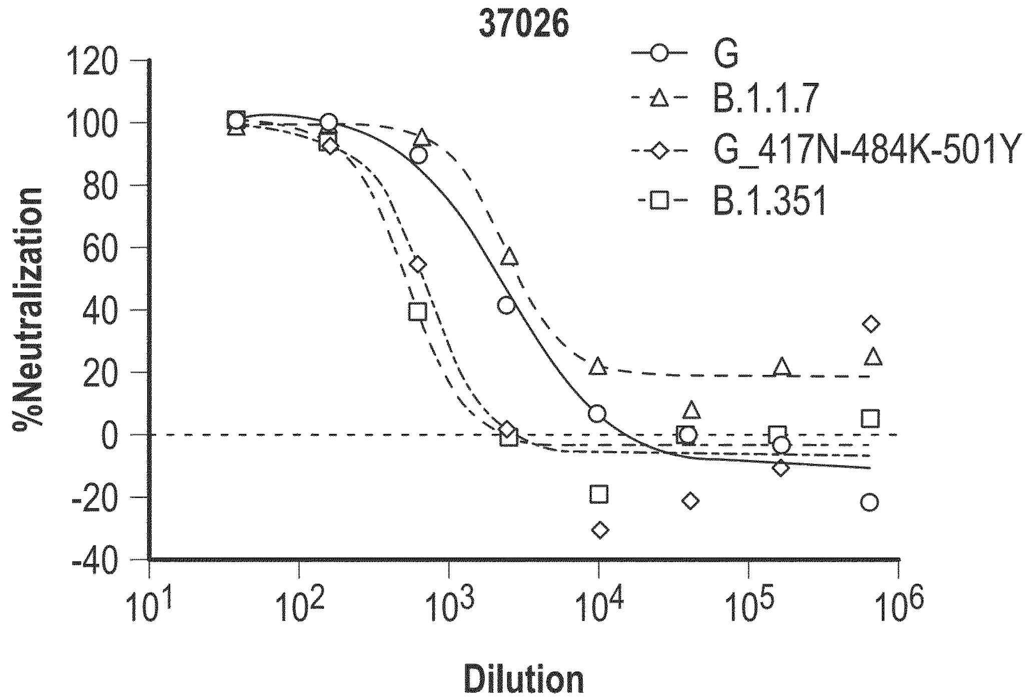
Figure 3C:
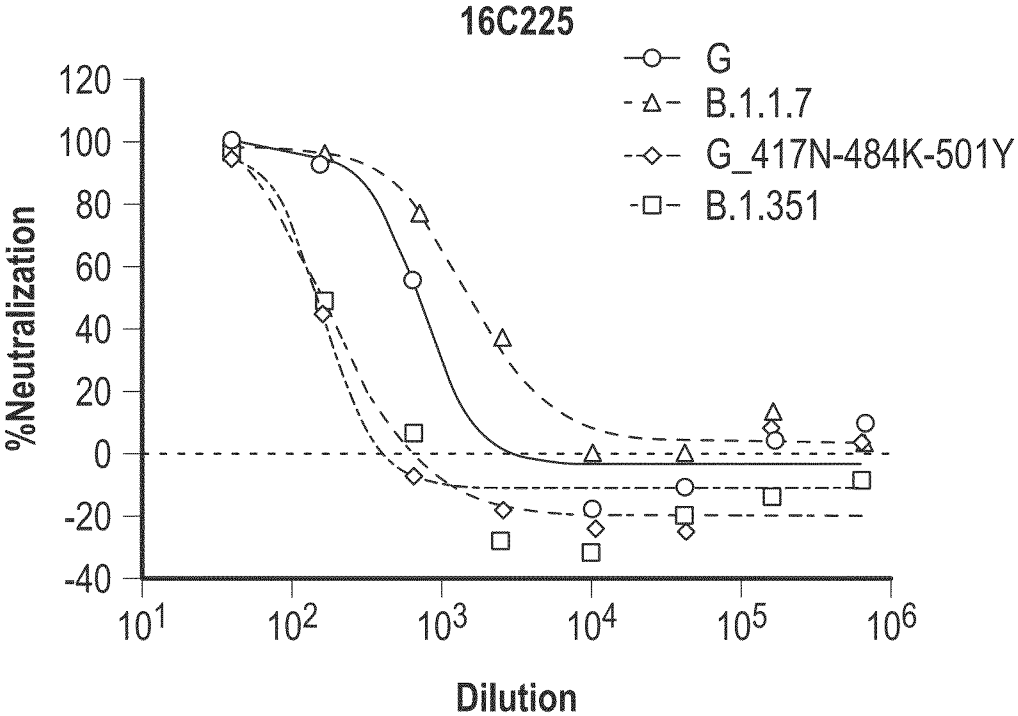
Figure 3C:
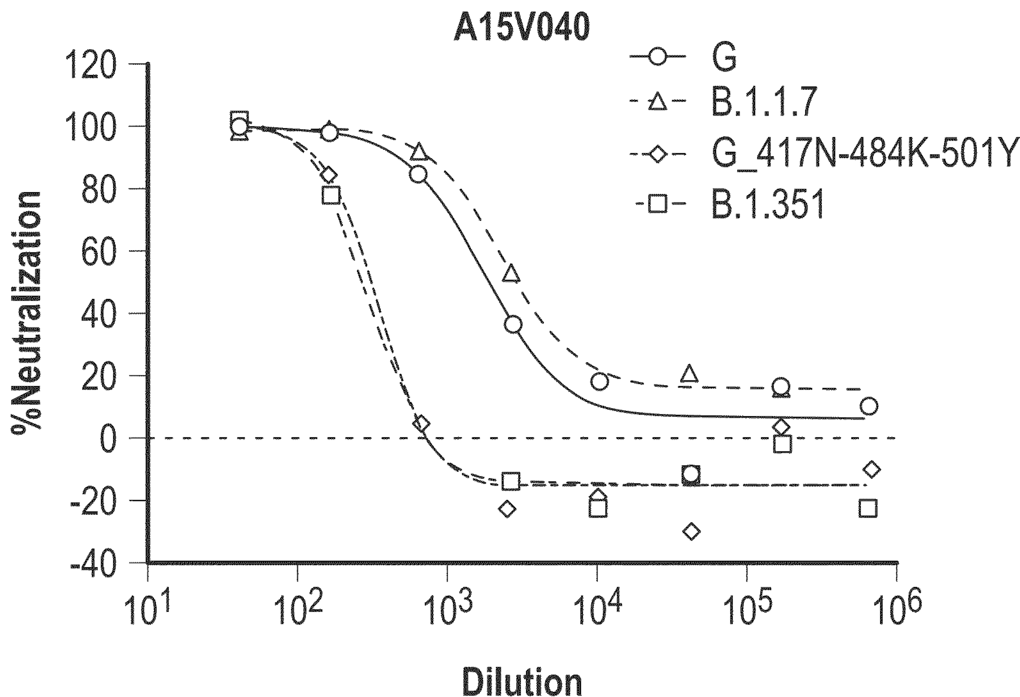
Figure 3C:
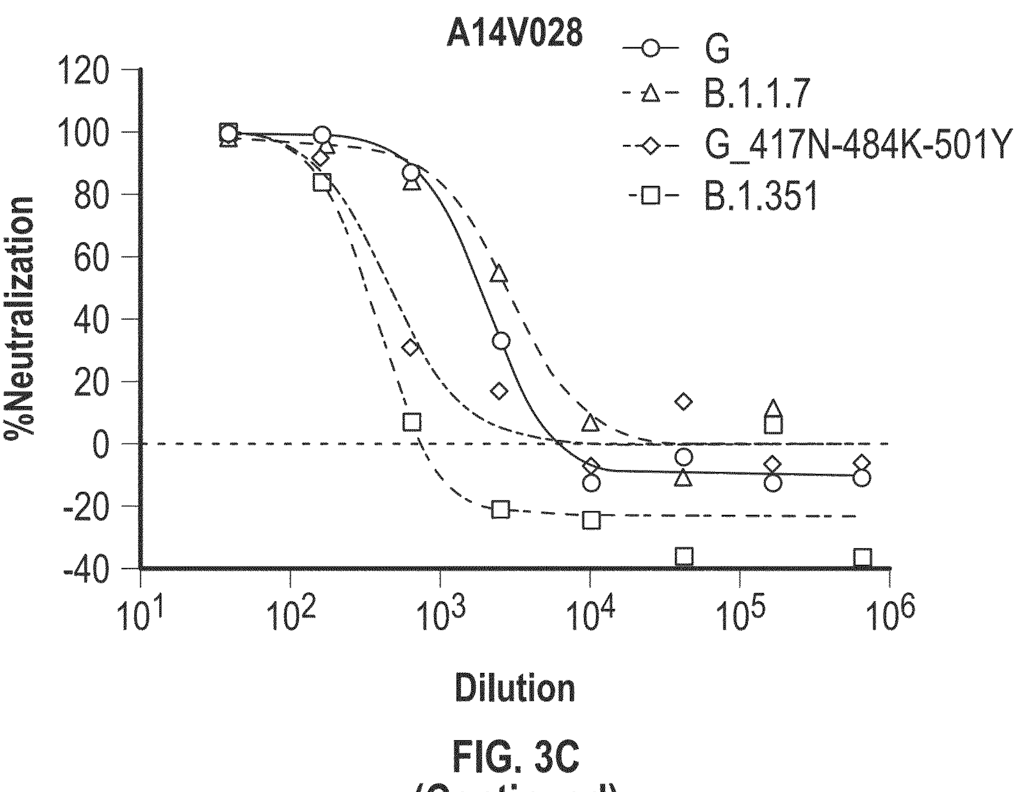

A significant drop in neutralization titers was measured against both the full panel of Spike mutations and specific mutations in the B.1.351 variant, listed in Table 3. In the VSV assay, a 4.3- and 4.8-fold drop in neutralization titers from sera collected from 30 μg dosed animals and a 9.6 and >10-fold drop in neutralization titers from sera from 100 μg dosed animals were measured against the partial or full panel of mutations, respectively (FIG. 2B). Neutralization titers remained high, at or above the level elicited by vaccination of NHPs with a 10 μg dose of mRNA vaccines that were protected from high-dose viral challenge with the WA strain (Corbett et al, 2020, Evaluation of the mRNA-1273 Vaccine against SARS-CoV-2 in Nonhuman Primates. N Engl J Med 383, 1544-1555). All samples were still able to fully neutralize the virus although at lower dilutions as shown by the neutralization curves from the assay (FIG. 3A-3C).

Figure 4A:
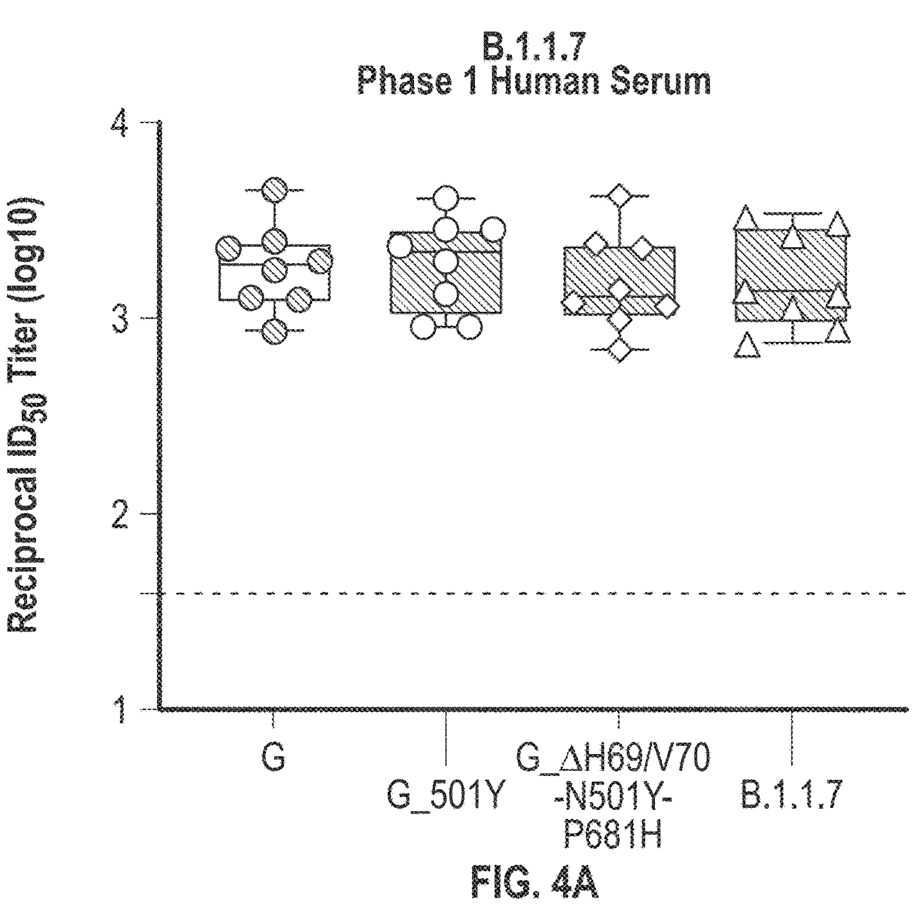
FIGS. 4A-4D show the results of neutralization assays against B.1.1.7 and B.1.351 from human sera collected from humans after administration of mRNA encoding Spike protein with two proline substitutions. The Phase 1 trial participant sera from administration of mRNA encoding Spike protein with two proline substitutions were collected seven days after the boosting, on day 36. Neutralization was measured by a recombinant VSV-based pseudovirus neutralization assay that incorporated D614G (G) or the indicated Spike mutations present in the B.1.1.7 variant (FIGS. 4A, 4C) or B.1.351 variant (FIGS. 4B, 4D). Results from individual participant sera are represented as dots on each figure, with lines connecting the D614G and variant neutralization titers (FIGS. 4C, 4D). The horizontal dotted lines indicate the lower limit of quantification (LLOQ). D=D614 USA-WA1/2020 isolate, G=D614G variant.
Figure 4B:
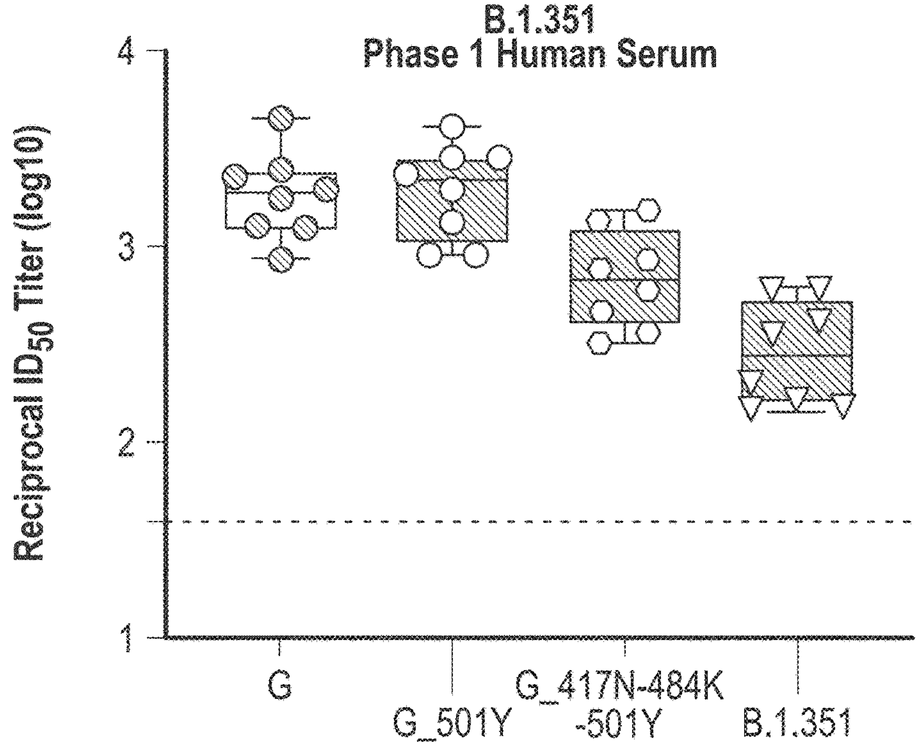
Figure 4C:
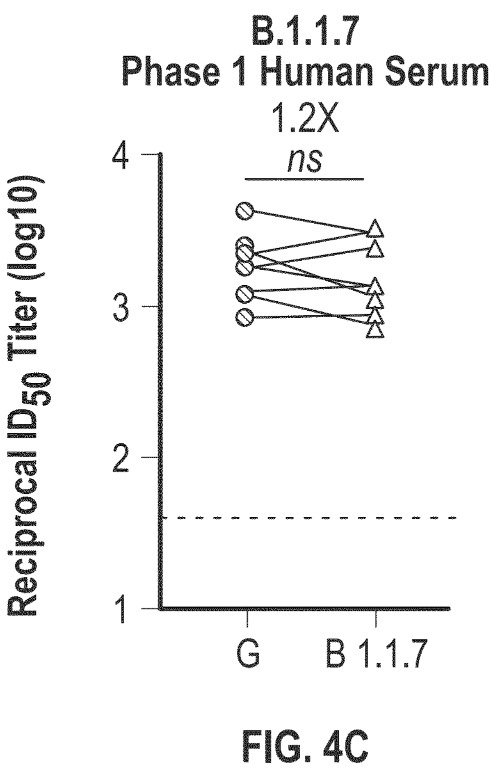
Figure 4D:
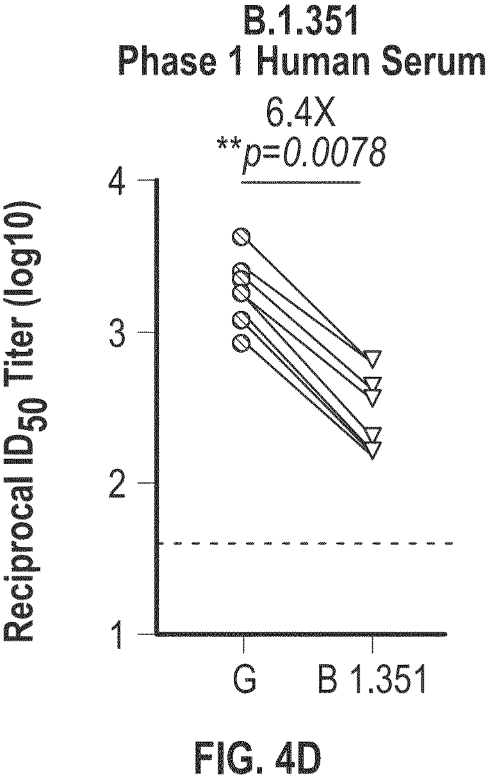

Next, mRNA Phase 1 human sera's neutralization against B.1.1.7 and B.1.351 was examined. The mutations present in the B.1.1.7 variant, either the full panel of Spike mutations or specific mutations (Table 3) had minimal effect on neutralization of human mRNA vaccine phase 1 participant sera (FIG. 4A). In the VSV assay, no significant decrease in neutralization titers were measured from the B.1.1.7 mutations, either partial set of mutations (D614G_N501Y, D614G_ΔH69ΔV70_N501Y_P681H) or the full B.1.1.7 variant (FIG. 4C).

Figure 5A:
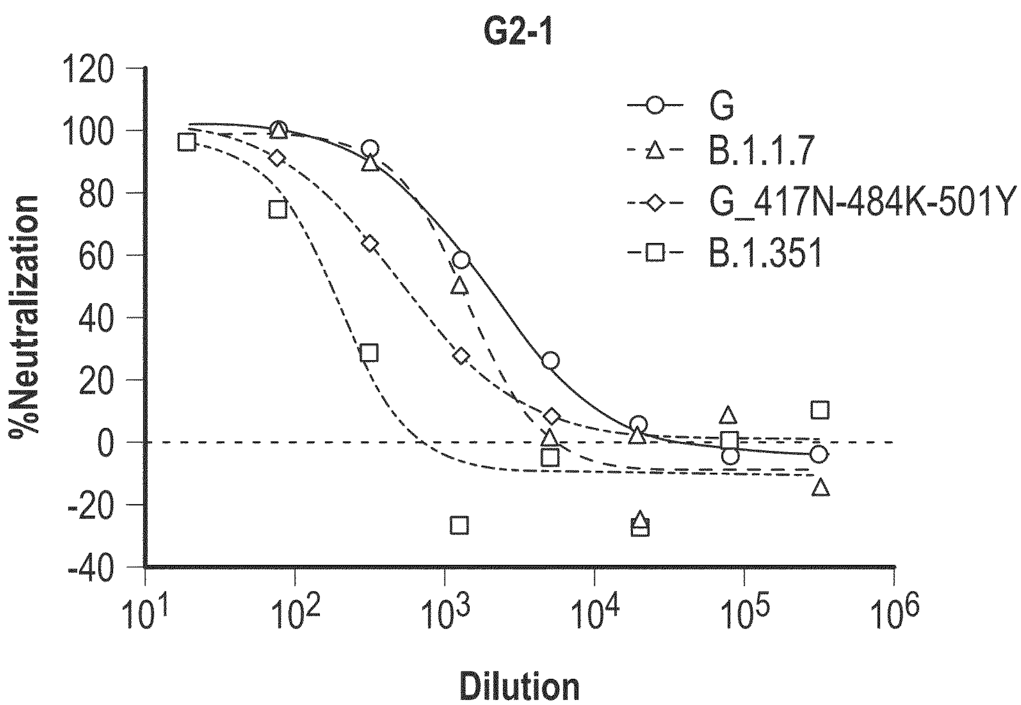
FIGS. 5A-5B show neutralization curves of human serum samples in the VSV-based pseudovirus neutralization assay. Serum from each clinical trial participant is represented as a separate graph. G=D614G variant.
Figure 5A:
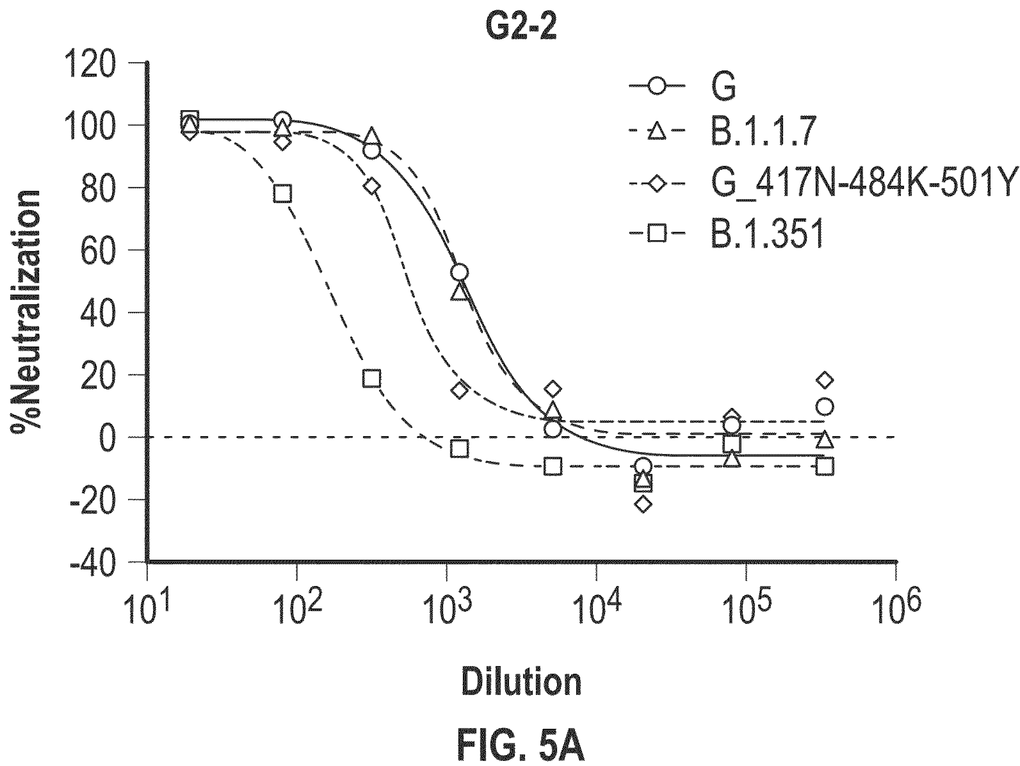
Figure 5A:
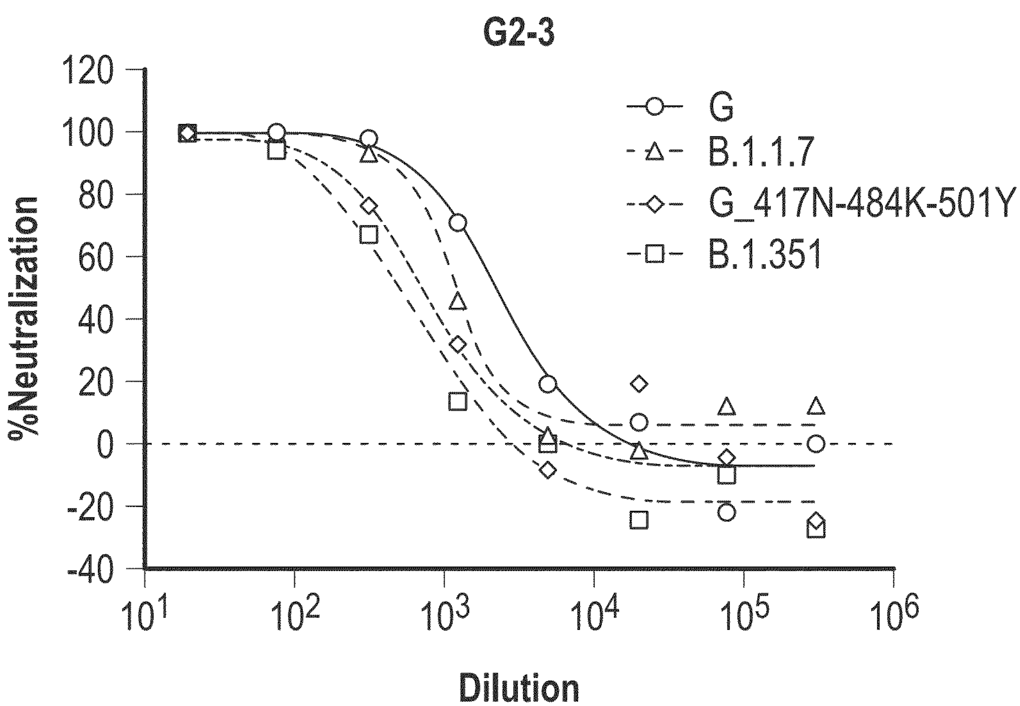
Figure 5A:
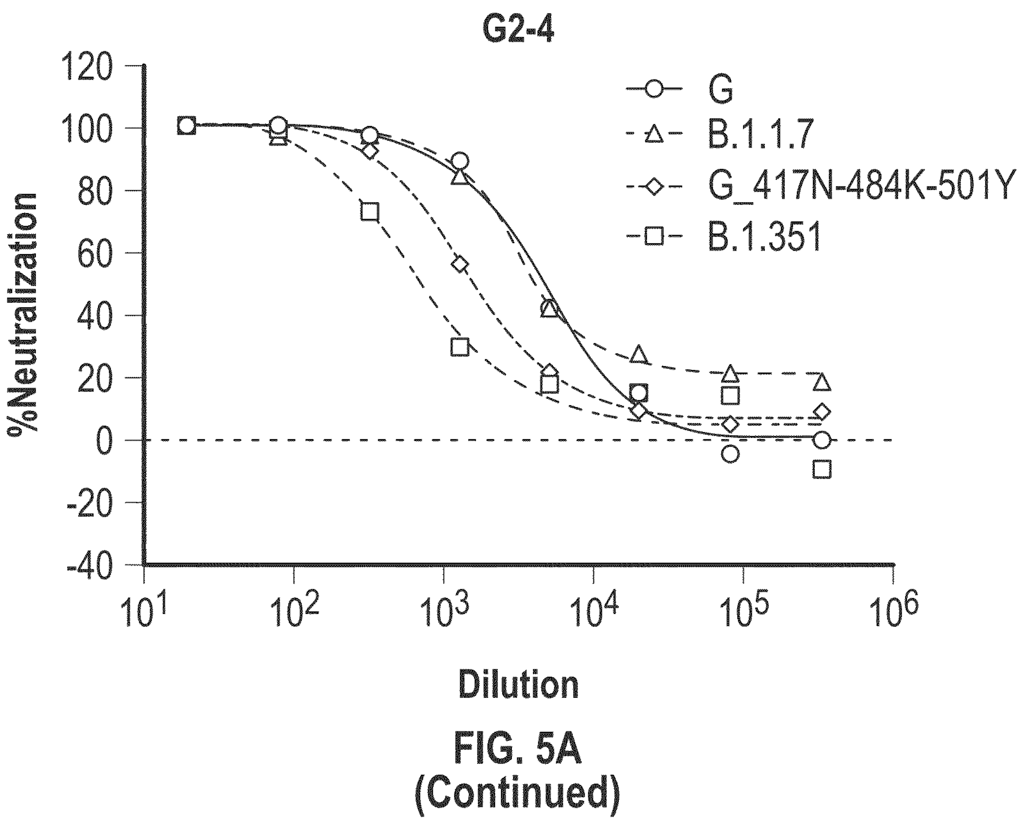
Figure 5B:
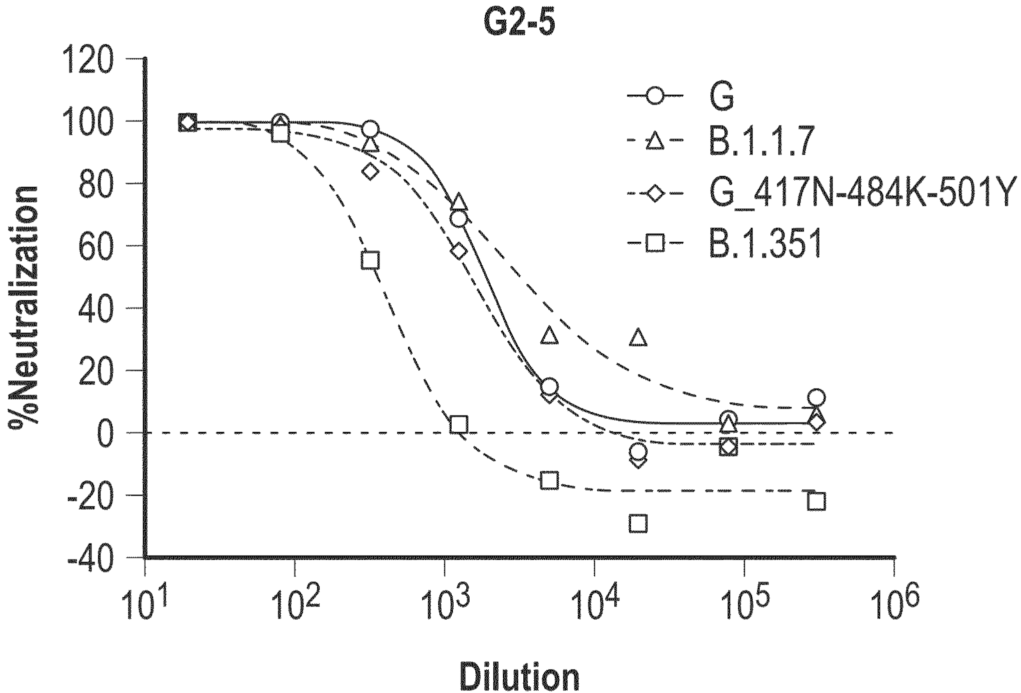
Figure 5B:
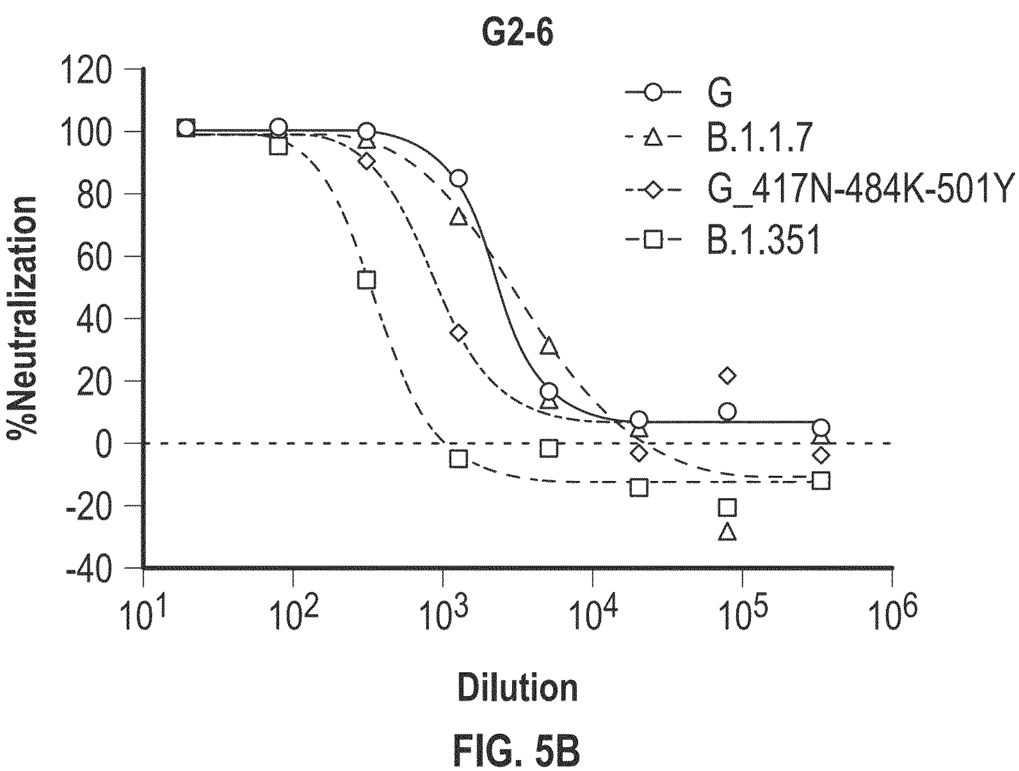
Figure 5B:
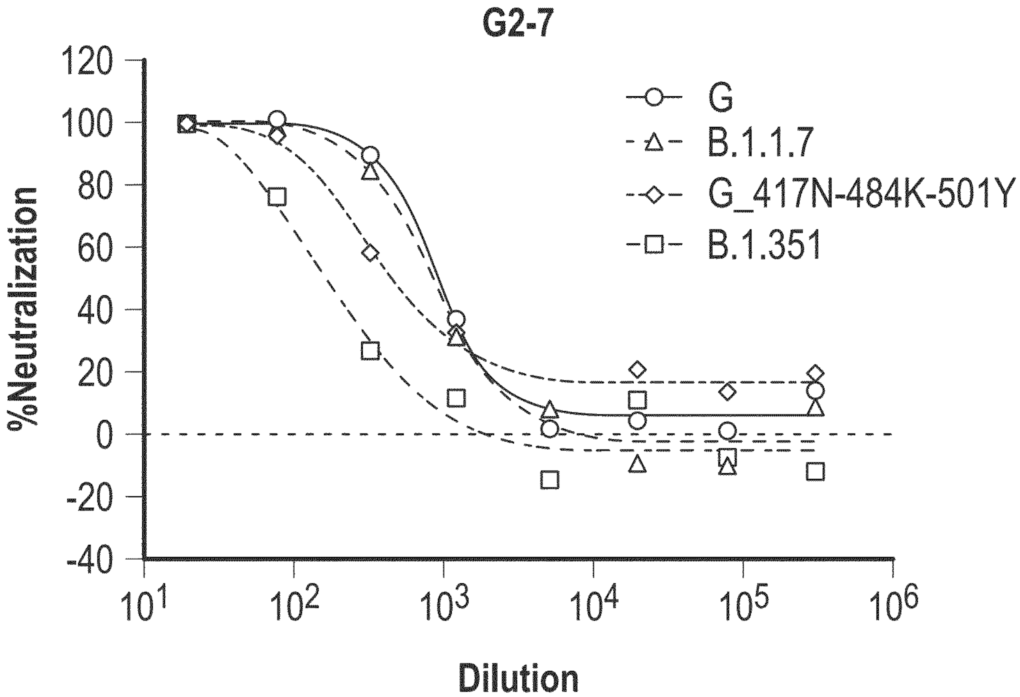
Figure 5B:
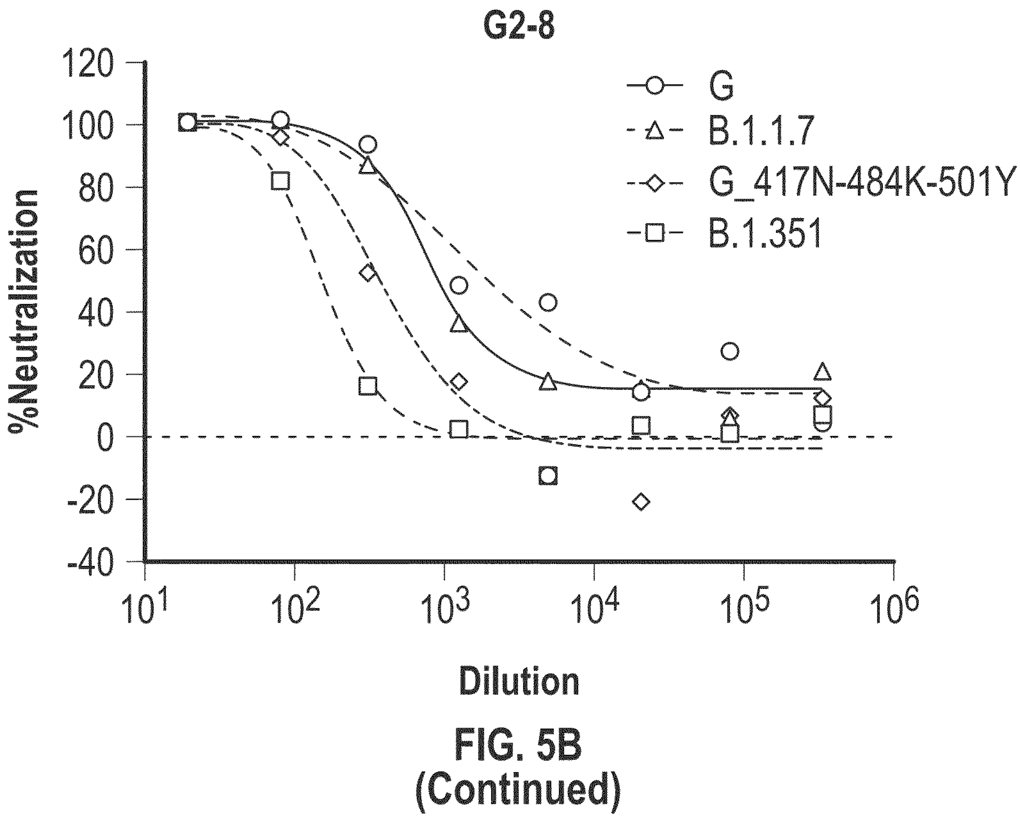

In contrast, a significant drop in neutralization titers were measured against both the full panel of Spike mutations and specific mutations in the B.1.351 variant, listed in Table 3. In the VSV assay, using Phase 1 one week post-boost clinical trial samples, a 2.7- and 6.4-fold reduction in neutralization titers against the partial or full panel of mutations, respectively, was detected (FIG. 4B). Despite diminished neutralizing responses against the B.1.351 variant, neutralization titers were still generally high, and all sera samples completely neutralized the VSV pseudovirus, albeit at lower dilutions as depicted by the neutralization assay curves (FIGS. 5A-5B). Individual animal numbers from the study are indicated above each group.

Discussion

In this study, the neutralization capacity of sera from eight Phase 1 clinical trial participants (aged 18-55 years) who received two 100 μg doses of the mRNA vaccine, and NHPs immunized with two doses of 30 μg or 100 μg of the mRNA vaccine were assessed. Neutralization was measured against the original D614 Spike, the dominant D614G Spike variant, mutations in 20A.EU1, 20A.EU2, mink cluster 5 variant, N439K-D614G, and either the full panel or key mutations found in the B.1.1.7 and B.1.351 variants strains. The 30 μg dose in NHPs was selected, as it elicits similar neutralizing titers against both D614 and D614G VSV pseudoviruses to those of humans receiving two 100-μg doses of the mRNA vaccine. Assessing the 30-μg dose in NHPs may help elucidate any dose-dependent effects on neutralizing responses toward the new Spike variants.

Both single and combined mutations of interest found in the B.1.1.7 or B.1.351 variants were evaluated in vitro, utilizing a VSV-pseudovirus reporter system. In analyses of both human and NHP sera, the neutralizing responses against the original D614 and the D614G Spike variant were first determined to provide a baseline for comparison with the newer, more elusive variants. Consistent with prior analyses, all eight samples from Phase 1 participants demonstrated robust neutralizing responses against both D614 and D614G SARS-CoV-2 Spikes. Additionally, mRNA-immunized NHPs showed neutralizing antibody titers in line with established efficacy reports (Corbett et al. SARS-CoV-2 mRNA vaccine design enabled by prototype pathogen preparedness. Nature (2020), 586, 567-571).

No significant impact on neutralization was observed from either the full set of mutations found in the B.1.1.7 variant or the N501Y and the 69-70 deletion. Although these mutations have been reported to lessen neutralization from convalescent sera and to increase infectivity, sera from the Phase 1 participants and NHPs immunized with mRNA-1273 were able to neutralize the B.1.1.7 variant to the same level as the D614G virus.

Consistent with other recent reports (Wang et al. (2021) mRNA vaccine-elicited antibodies to SARS-CoV-2 and circulating variants. BioRxiv 2021.01.15.426911), assessing neutralization of some of the mutations found in B.1.351, there was a 2.7-fold reduction in neutralization after incorporation of the 3 mutations found in the RBD (K417N-E484K-N501Y) and a 6.4-fold reduction in neutralization when the full panel of mutations was included. The VSV-based pseudovirus neutralization titer against the full panel of mutations remained at 1/300 and all samples were able to fully neutralize the mutant viruses. The data in NHP showed a >10 or 4.8-fold reduction from 100 and 30 μg dose groups, respectively, compared to D614G; however, the VSV-based PsVN titer against the full panel of mutations at both doses was ~1/300. All samples from the clinical trial subjects and NHP fully neutralized the variant viruses at lower dilutions of sera, demonstrating that, despite the reduction in neutralization titers, the polyclonal sera were still able to fully neutralize the virus. A true $ID_{50}$ shift was observed, meaning all sera showed a reduction in ID50 titers but none showed lack of neutralization.

The data from this sample set shows that, in humans and NHP, there is no reduction in PsVN assay pseudovirus neutralization titers against the B.1.1.7 variant and a ~5-fold reduction against the B.1.351 variant. Nevertheless, the pseudovirus neutralization titer against the B.1.351 in both humans and NHP is still ~1/300. Prior studies have shown that pseudovirus neutralization titers against D614G correlate with viral neutralization titers. The VSV pseudovirus neutralization titers in humans after two doses of mRNA-1273 was 1/1852 in the VSV PsVN assay, and protection was ~95%.

Protection was also observed even after a single immunization with much lower neutralization titers, suggesting that the current mRNA vaccine regimen is inducing immune responses likely to be well above a protective threshold. This is also supported by NHP data in which vaccination of NHPs with only 10 μg mRNA protects animals from SARS-CoV-2 challenge (Corbett, NEJM 2020b), although immune response and neutralization titers are well below what is measured after administration of 30 or 100 ug of mRNA-1273 as shown herein.

It seems likely that neutralization titers against the E484K and B.1.351 by sera from NHP vaccinated twice with 30 μg of the mRNA vaccine or from human Phase 1 trial participants vaccinated with 100 μg mRNA vaccine would be sufficient to mediate protection against viral challenge with these variants. Together, these data indicate that, despite the decreased neutralization potency against the B.1.351 variant, vaccination with the mRNA vaccine is likely to protect from the B.1.351 variant. It is important to prepare for the emergence of any variants that may be able to escape from these antibody neutralization responses induced by the current vaccines and to be ready to induce broader neutralization capability to suppress further emerging variants.

Methods

Animal Studies. Rhesus macaques (NHPs) were immunized with 10 or 30 μg mRNA encoding Spike protein with two proline substitutions ("mRNA vaccine") on a prime-boost schedule, and sera was collected 4 weeks after the boosting dose (day 56).

Clinical Trial. Humans were immunized with 100 μg mRNA encoding Spike protein with two proline substitutions ("mRNA vaccine") on a prime-boost schedule and sera was collected 1 week post the boost (day 36). Study protocols and results are reported in Jackson, et al. (2020). See An mRNA Vaccine against SARS-CoV-2—Preliminary Report. N Engl J Med 2020; 383:1920-1931.

Recombinant VSV-based Pseudovirus Neutralization. Codon-optimized full-length spike protein of the USA-WA1/2020 isolate (D614), D614G, or the indicated spike variants listed in Tables 2 and 3 were cloned into pCAGGS vector. To make SARS-CoV-2 full-length spike pseudotyped recombinant VSV-ΔG-firefly luciferase virus, BHK-21/WI-2 cells (Kerafast, EH1011) were transfected with the spike expression plasmid and subsequently infected with VSVΔG-firefly-luciferase as previously described (Whitt, 2010, Journal of Virological Methods 169, 365-374). For the neutralization assay, serially diluted serum samples were mixed with pseudovirus and incubated at 37° C. for 45 minutes. The virus-serum mix was subsequently used to infect A549-hACE2-TMPRSS2 cells for 18 hours at 37° C. before adding ONE-Glo reagent (Promega E6120) for measurement of luciferase signal (relative luminescence unit; RLU). The percentage of neutralization was calculated based on RLU of the virus only control, and subsequently analyzed using four-parameter logistic curve (Prism 8).

Example 2: Coronavirus Strain Challenge

The instant study is designed to test the efficacy in hamsters, mice and/or rabbits of candidate coronavirus vaccines comprising an mRNA as disclosed herein encoding a coronavirus antigen (e.g., the spike (S) protein, the S1 subunit (S1) of the spike protein; or the S2 subunit (S2) of the spike protein, a domain etc), such as a SARS-CoV-2 antigen, against a lethal challenge with a coronavirus. Animals are challenged with a lethal dose (10×LD90; ~100 plaque-forming units; PFU) of coronavirus.

The animals used are ~6-8 week old animals in groups of ~10. Animals are vaccinated on weeks 0 and 3 via an IM, ID or IV route of administration. Candidate vaccines are chemically modified or unmodified. Animal serum is tested for microneutralization. Animals are then challenged with ~1 LD90 of coronavirus on week ~6-8 via an IN, IM, ID or IV route of administration. Endpoint is day ~13-15 post infection, death or euthanasia. Animals displaying severe illness as determined by >30% weight loss, extreme lethargy or paralysis are euthanized. Body temperature and weight are assessed and recorded daily.

Example 3—In Vivo Expression of SARS-CoV-2 mRNA Vaccine Constructs

BALB/c mice, 6-8 weeks of age, are administered either 2 μg or 10 μg of a COVID-19 construct or Tris buffer (as a control) intramuscularly in each hind leg. The constructs comprise any of the mRNA encoding antigens disclosed herein in cationic (amino) lipid nanoparticles, 10.7 mM sodium acetate, 8.7% sucrose, 20 mM Tris (pH 7.5). One day later, spleens and lymph nodes are collected to detect protein expression using flow cytometry.

Example 4—SARS-CoV-2 mRNA Protects Humanized Mice from Lethal Challenge

Humanized DPP4 $288/330^{+/+}$ mice are immunized at weeks 0 and 3 weeks with 0.01, 0.1, or 1 μg of SARS-CoV-2 mRNA encoding antigens. Mock-immunized mice are immunized with PBS. Four weeks post-boost, mice are challenged with a lethal dose of mouse-adapted SARS-CoV. Following challenge, mice are monitored for weight loss and signs of viral infection. At days 3 and 5 post-challenge, lungs from 5 mice/group are harvested for analysis of viral titers and hemorrhage.

Example 5—SARS-CoV-2 mRNA Strain Variant Immunogenicity

BALB/c mice, 6-8 weeks of age, were administered either 1 μg or 10 μg of mRNA encoding a SARS-CoV-2 antigen or PBS (as a control) intramuscularly in one hind leg (formulated as a 50 μL dose) on day 1 and day 22. Seventeen groups were tested (n=10 mice/group): PBS, and then both dosage levels of mRNA encoding Spike protein with two proline substitutions (SEQ ID NO: 18), WH2020_NatSP 2P_E484K_D614G (SEQ ID NO: 1), WH2020_NatSP_2P_K417N.E484K_N501Y_D614G (SEQ ID NO: 6), WH2020 NatSP_2P_L18F_D80A_D215G_L242_244del_R246I_K417N_E484K_N501Y_D614G_A701V (SEQ ID NO: 9), WH2020_NatSP_2P_H69del_V70del Y144del_N501Y_A570D_D614G_P681H_T716I_S982A_D1118h (SEQ ID NO: 12), a 1:1 mix of SEQ ID NO: 1 and SEQ ID NO: 6 (5 μg+5 μg, or 0.5 μg+0.5 μg), a 1:1 mix of SEQ ID NO: 1 and SEQ ID NO: 9 (5 μg+5 μg, or 0.5 μg+0.5 μg), and the D614G variant. In each vaccine, the mRNA was formulated in lipid nanoparticles (LNPs) including 0.5-15% PEG-modified lipid; 5-25% non-cationic lipid, 25-55% sterol, and 20-60% ionizable amino lipid. The PEG-modified lipid was 1,2 dimyristoyl-sn-glycerol, methoxypolyethyleneglycol (PEG2000 DMG), the non-cationic lipid was 1,2 distearoyl-sn-glycero-3-phosphocholine (DSPC), the sterol was cholesterol, and the ionizable amino lipid had the structure of Compound 1, for example. An overview of this dosing schedule is provided in Table 4.

8F). Furthermore, a 1:1 mix of both mRNA-1273 and mRNA-1273.351 (5 μg of each mRNA) elicited similar neutralization titers against both Spike proteins, with no significant difference (FIGS. 8C, 8G).

Figure 9:
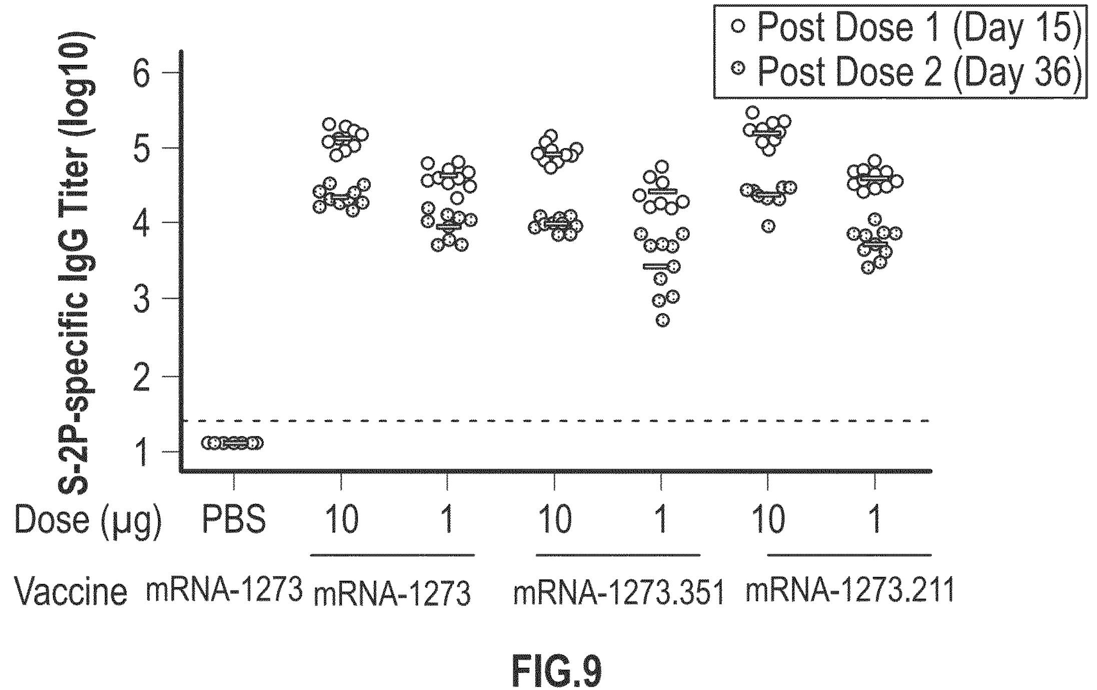
FIG. 9 shows titers of IgG specific to a SARS-CoV-2 Spike protein with two proline substitutions. Sera were obtained from mice administered PBS, 1 μg, or 10 μg mRNA encoding SARS-CoV-2 Spike protein with two proline substitutions (mRNA-1273), SARS-CoV-2 B.1.351 Spike protein (Mrna-1273.351), or a 1:1 mixture of mRNA-1273 and mRNA-1273.351 (0.5 μg or 5 μg of each mRNA, 1 μg or 10 μg total mRNA).
Figures 10A, 10B:
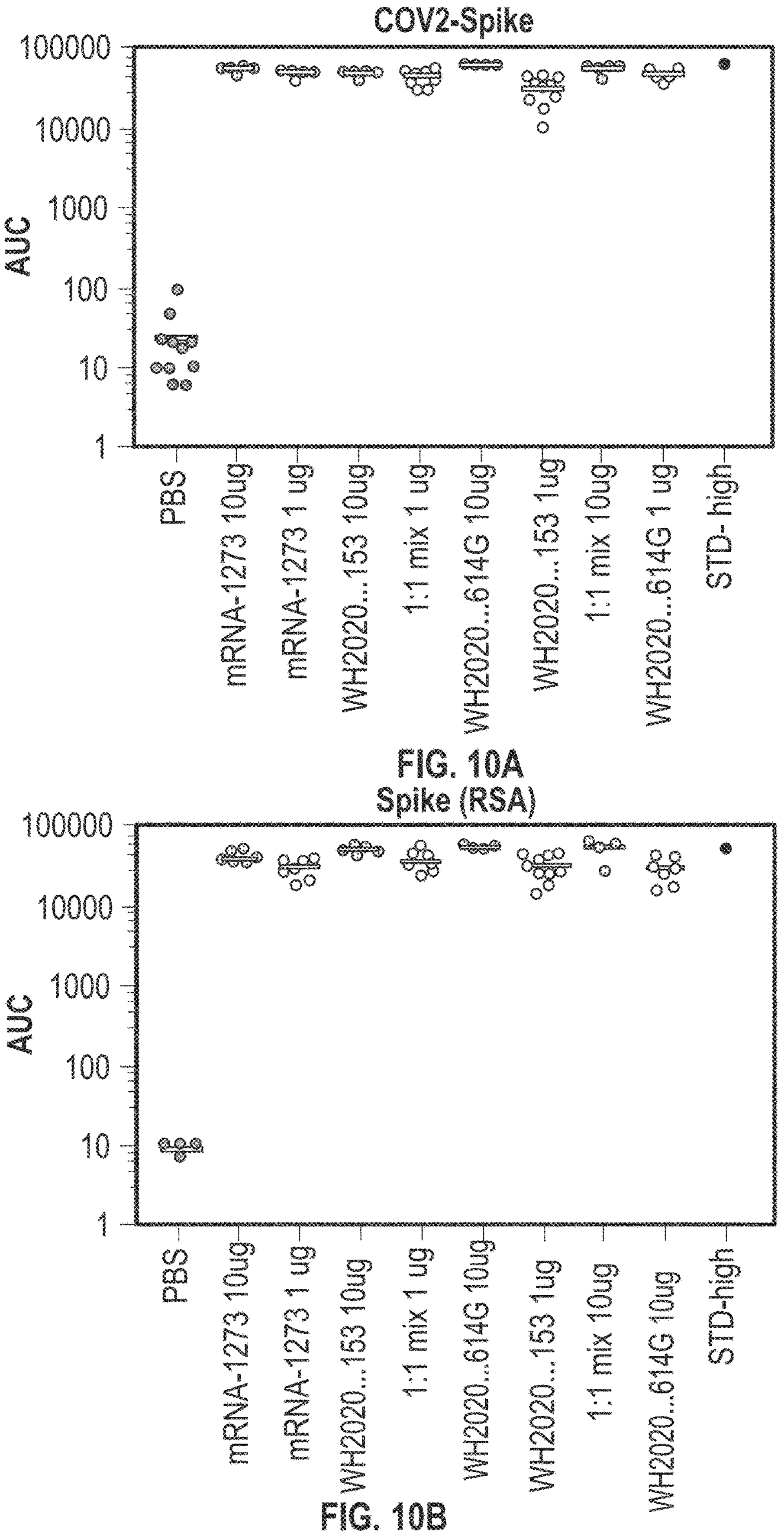
FIGS. 10A-10D show the ability of sera elicited by mice immunized with mRNA encoding SARS-CoV-2 Spike proteins to bind SARS-CoV-2 antigens.
Figures 10C, 10D:
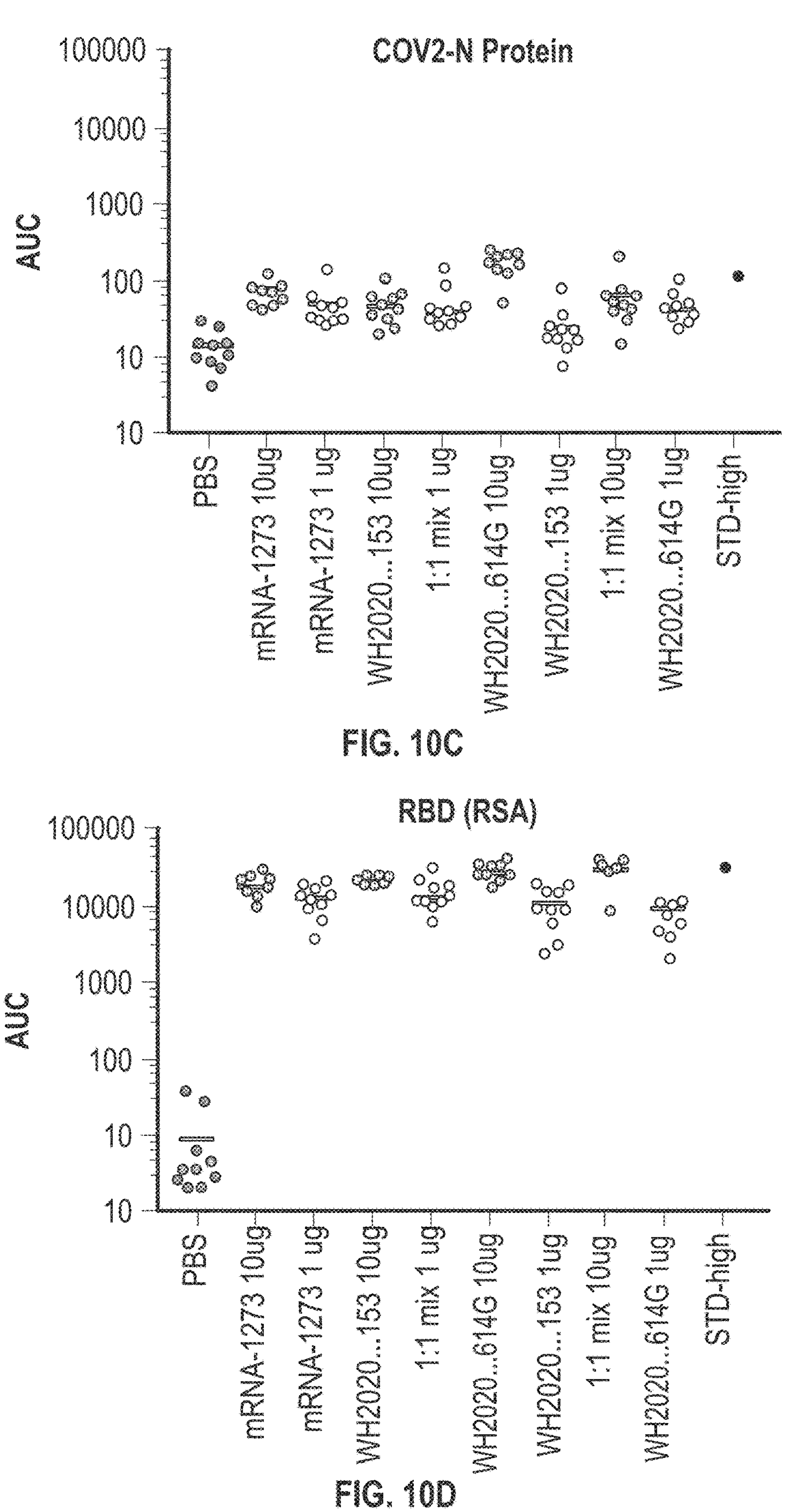

Sera of mice immunized with the compositions listed in Table 4 were collected at day 15 post-administration of a first dose, and day 36 post-administration of a second dose, and evaluated by ELISA to quantify titers of IgG specific to 2P-stabilized SARS-CoV-2 Spike protein (FIG. 9). Relative to mRNA-1273, mRNA-1273.351 elicited lower IgG titers specific to WA.1 S-2P protein, but a 1:1 mixture of mRNA-1273 and mRNA-1273.351 elicited similar titers to an equivalent dose, in terms of total RNA, of mRNA-1273 at the 15 day measurement (FIG. 9). Increased S-2P binding titers were measured after the second dose (day 36). These results demonstrated that both mRNA-1273.351 and mRNA-1273.211 were active and immunogenic. Slightly lower antibody levels were seen for mRNA-1273.351 versus mRNA-1273, potentially due to the coating S-2P protein used in the ELISA being homologous to mRNA-1273.

TABLE 4

Administration schedule of SARS-CoV-2 mRNA variants.

| | N= | TA | Dose Mass (μg/animal) | Dose Regime | Read-out |
|---|---|---|---|---|---|
| 1 | 10 | PBS | | Two | ELISA |
| 2 | 10 | mRNA encoding Spike protein with | 10 | doses, | (S-2P) & |
| 3 | 10 | two proline substitutions | 1 | prime on | Neutralization |
| 8 | 10 | WH2020_NatSP_2P_L18F_D80A_D215G_L242_244del_ | 10 | Day 1 and | |
| 9 | 10 | R246I_K417N_E484K_N501Y_D614G_A701V (mRNA-1273.351) | 1 | boost on Day 22 | |
| 14 | 10 | 1:1 mix of mRNA-1273 & | 10 (5 + 5) | | |
| 15 | 10 | WH2020_NatSP_2P_L18F_D80A_D215G_L242_244del_ R246I_K417N_E484K_N501Y_D614G_A701V (mRNA-1273.351) | 1 (0.5 + 0.5) | | |
| 16 | 10 | WH2020_NatSP_2P_001_D614G | 10 | | |
| 17 | 10 | | 1 | | |

Blood samples were taken from the mice on day 15 and day 36 and analyzed by ELISA and neutralization assays as described herein. Briefly, codon-optimized full-length spike protein of the original SARS-CoV-2 isolate and the D614G mutation (Wild-type or D614G), or the Spike protein variants listed herein (e.g., B.1.351, P.1, CAL.20C) were cloned into pCAGGS vectors. To make SARS-CoV-2 full-length spike pseudotyped recombinant VSV-ΔG-firefly luciferase virus, BHK-21/WI-2 cells (Kerafast, EH1011) were transfected with the spike expression plasmid and subsequently infected with VSVΔG-firefly-luciferase as previously described (Whitt, 2010). For the neutralization assays, serially diluted serum samples were mixed with pseudovirus and incubated at 37C for 45 minutes. The virus-serum mix was subsequently used to infect A549-hACE2-TMPRSS2 cells for 18 hours at 37C before adding ONE-Glo reagent (Promega E6120) for measurement of luciferase signal (relative luminescence unit; RLU). The percentage of neutralization was calculated based on RLU of the virus only control, and subsequently analyzed using four-parameter logistic curve (Prism 8). The results of these immunogenicity investigations are shown FIGS. 8A-10D.

Figure 8A:
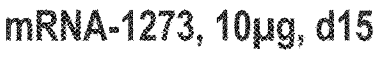
Figure 8A:
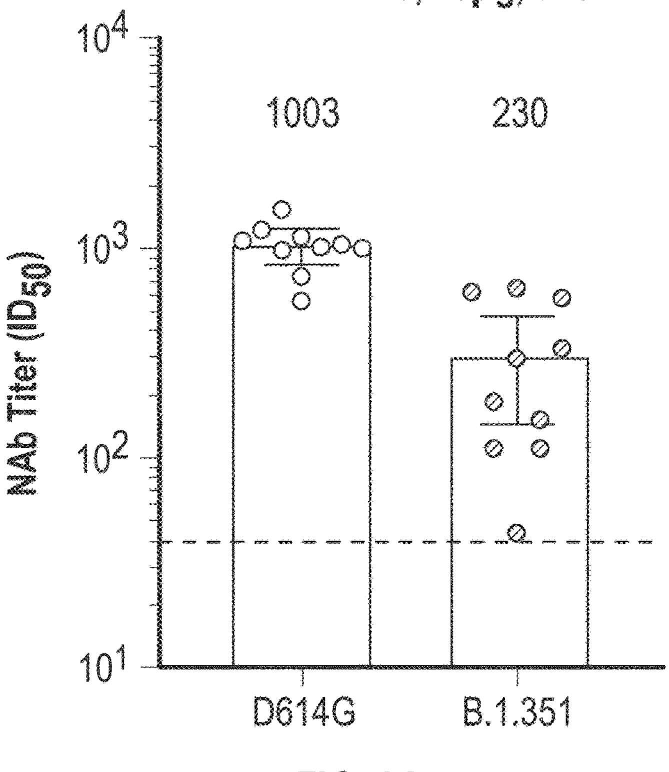
Figure 8B:
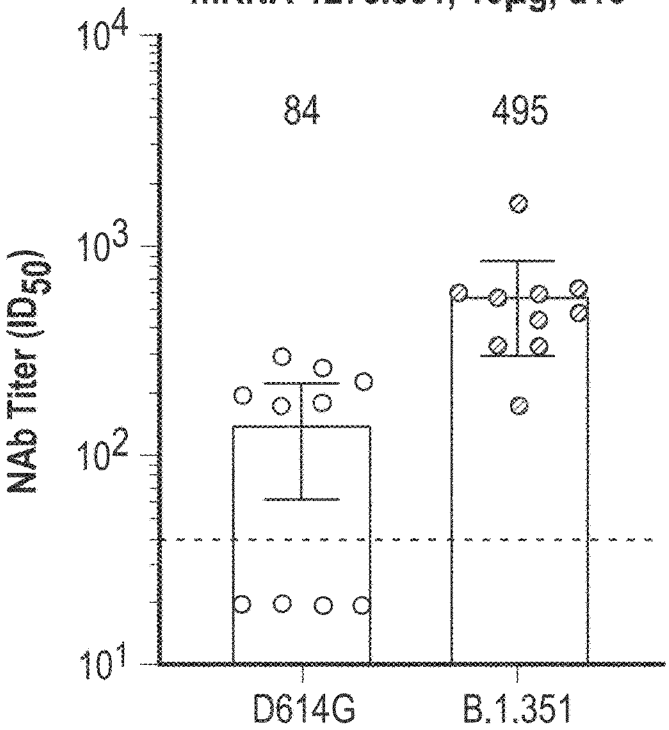
Figure 8C:
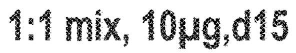
Figure 8C:
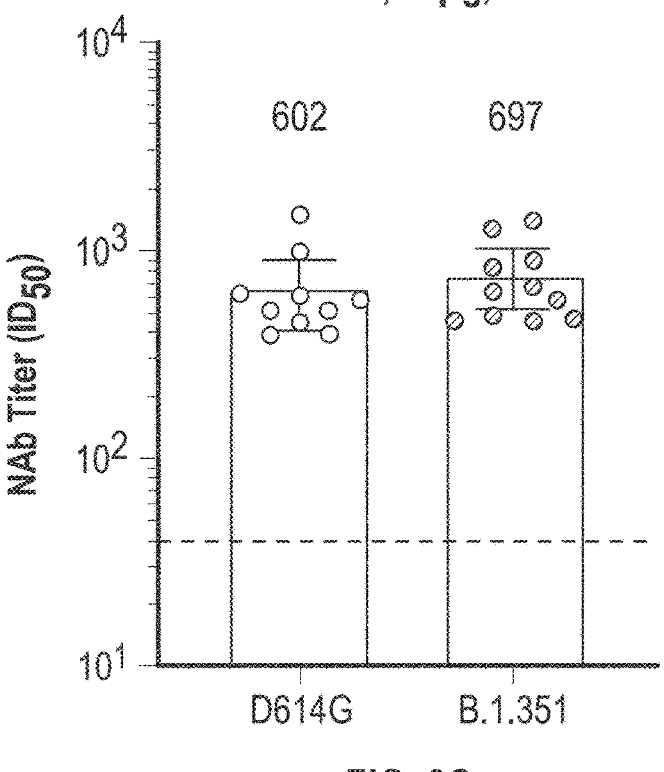
Figure 8D:
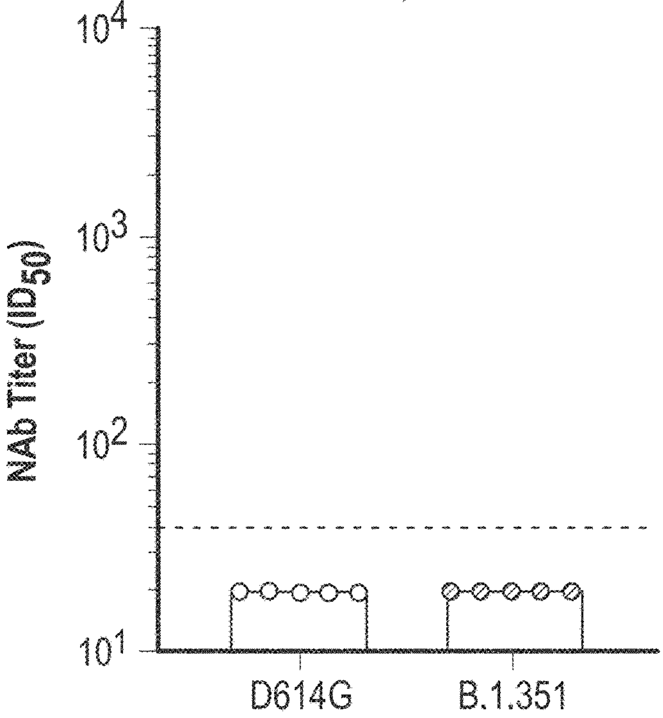

Sera of mice immunized with the compositions listed in Table 4 were collected at day 15 post-administration of a first dose, and evaluated in a pseudovirus neutralization assay, as described above. mRNA-1273, encoding wild-type SARS-CoV-2 Spike protein stabilized with 2P substitutions, elicited 4.4× higher neutralization titers against the VSV PSV with the D614G Spike protein than the B.1.351 Spike protein (FIGS. 8A, 8E). Conversely, mRNA-1273.351, encoding SARS-CoV-2 Spike protein with 2P stabilizing substitutions and the variants listed in Table 4, elicited 5.9× higher neutralization titers against the B.1.351 Spike protein than against the D614G variant Spike protein (FIGS. 8B, 8F).

Sera of mice immunized with the 1 μg compositions listed in Table 4 were collected at day 36 post-administration of a second dose, and evaluated neutralizing antibody titers against the D614G variant Spike protein and against the B.1.351 Spike protein variant. The data is shown in Table 5 below, where mRNA-1273 is mRNA encoding Spike protein with two proline substitutions, mRNA-1273.351 is WH2020 NatSP_2P_L18F_D80A_D215G_L242_244del_R246I_K 417N_E484K_N501Y_D614G_A701V and mRNA-1273.211 is a 1:1 ratio of mRNA-1273:mRNA-1273.351.

TABLE 5

Neutralization Titers (1 μg Dose)

| Virus | Vaccine | NAb Titer ($ID_{50}$) |
|---|---|---|
| D614G | mRNA-1273 | 16749 |
| D614G | mRNA-1273.351 | 2733 |
| D614G | mRNA-1273.211 | 14832 |
| B.1.351 | mRNA-1273 | 7788 |
| B.1.351 | mRNA-1273.351 | 10948 |
| B.1.351 | mRNA-1273.211 | 19031 |

The data demonstrate that mRNA-1273.211 elicits a robust and comparable neutralizing titer against the D614G and B.1.351 Spike protein variants (1.3× change from D614G to B.1.351). Its response closely matched that of mRNA-1273 against the D614G variant. Similarly, mRNA- 1273.351 elicited a robust neutralizing titer against the B.1.351 Spike protein variant; however, its neutralizing antibody titer was 1.6-fold lower than that of mRNA-1273.211. The neutralizing activity of mRNA-1273.351 against D614G was found to be approximately 4-fold lower than that against B.1.351 Spike protein variant. mRNA-1273 was found to have a 2.1-fold lower neutralizing activity against the B.1.351 Spike protein variant as compared to the D614G Spike protein variant.

The experiment was also performed with a 10 μg dose. The results from the study are shown in Table 6 below.

TABLE 6

| Neutralization Titers (10 μg Dose) | | |
|---|---|---|
| Virus | Vaccine | NAb Titer ($ID_{50}$) |
| D614G | mRNA-1273 | 358533 |
| D614G | mRNA-1273.351 | 111722 |
| D614G | mRNA-1273.211 | 220529 |
| B.1.351 | mRNA-1273 | 150199 |
| B.1.351 | mRNA-1273.351 | 216332 |
| B.1.351 | mRNA-1273.211 | 245387 |

The data largely follows the trend from the 1 μg dose group. The titer of the mRNA-1273.211 against the D614G spike protein variant is about 2-fold lower than that of mRNA-1273. The gap of mRNA-1273 between the two variants is also approximately 2-fold at both dose levels. Notably, the gap of mRNA-1273.351 neutralizing antibody titer levels against the two variants at the 10 μg dose becomes smaller (2-fold) than at the 1 μg dose (approximately 4-fold).

The sera of mice immunized with 1 μg compositions listed in Table 4 were collected at day 36 post-administration of a second dose, and evaluated with respect to neutralizing antibody titers against the D614G variant Spike protein, the CAL.20C Spike protein variant, and the P.1 Spike protein variant. The data is shown in Table 7 below.

TABLE 7

| Neutralization Titers (1 μg Dose) | | |
|---|---|---|
| Virus | Vaccine | NAb Titer ($ID_{50}$) |
| D614G | mRNA-1273 | 16410 |
| D614G | mRNA-1273.351 | 2460 |
| D614G | mRNA-1273.211 | 12902 |
| CAL.20C | mRNA-1273 | 6847 |
| CAL.20C | mRNA-1273.351 | 1821 |
| CAL.20C | mRNA-1273.211 | 4089 |
| P.1 | mRNA-1273 | 8293 |
| P.1 | mRNA-1273.351 | 3230 |
| P.1 | mRNA-1273.211 | 10620 |

The data demonstrate that mRNA-1273.211 elicits a similar neutralization titer against D614G and the P.1 Spike protein variant. mRNA-1273.351 immunized mice were found to have a 4- to 6-fold drop of neutralizing antibody titer against the P.1, D614G, and CAL.20C Spike protein variants when compared to the neutralization titer to the B.1.351 Spike protein variant. Without wishing to be bound by theory, it is thought that the extensive N-terminal domain mutations in the B.1.351 Spike protein may drift its immunogenicity away from the D614G and P.1 variants. Both mRNA-1273 and mRNA-1273.211 has similar 3-fold drops in neutralization titer against CAL.20C (the relative titer change between the D614G variant and the CAL.20C variant was 2.4× for mRNA-1273 ($p=0.0078$), 1.4× for mRNA-1273.351, and 3.2× for mRNA-1273.211 ($p=0.0078$)). The relative titer change between the D614G variant and the P.1 variant was 2.0× for mRNA-1273, 0.8× for mRNA-1273.351, and 1.2× for mRNA-1273.211.

Additional spike variant antigen designs were similarly tested, including WH2020_NatSP_2P_E484K_D614G (SEQ ID NO: 1), WH2020 NatSP_2P_K417N_E484K_N501Y_D614G (SEQ ID NO: 6), WH2020_NatSP_2P_L18F_D80A_D215G_L242_244del_R246I_K417N_E484K_N501Y_D614G_A701V (SEQ ID NO: 10), WH2020 NatSP 2P_H69del V70del Y144del N501Y_A570D_D614G_P681H_T716I_S982A_D1118h (SEQ ID NO: 12), and a 1:1 mix of SEQ ID NO: 10 and SEQ ID NO: 6 (0.5 μg+0.5 μg). The sera of mice immunized with 1 μg of the mRNA vaccines described above were collected at day 36 post-administration of a second dose, and evaluated with respect to neutralizing antibody titers against the D614G variant Spike protein and the B.1.351 Spike protein variant. The data is shown in Table 8 below.

TABLE 8

| Neutralization Titers (1 μg Dose) | | |
|---|---|---|
| Virus | Vaccine | NAb Titer ($ID_{50}$) |
| D614G | WH2020_NatSP_2P_E484K_D614G (SEQ ID NO: 1) | 9691 |
| D614G | WH2020_NatSP_2P_H69del_V70del_Y144del_N501Y_A570D_D614G_P681H_T716I_S982A_D1118h (SEQ ID NO: 12) | 6230 |
| D614G | WH2020_NatSP_2P_K417N_E484K_N501Y_D614G (SEQ ID NO: 6) | 16823 |
| D614G | 1:1 mix of SEQ ID NO: 10 and 6<br>WH2020_NatSP_2P_L18F_D80A_D215G_L242_244del_R246I_K417N_E484K_N501Y_D614G_A701V (SEQ ID NO: 10)<br>WH2020_NatSP_2P_K417N_E484K_N501Y_D614G (SEQ ID NO: 6) | 23390 |
| B.1.351 | WH2020_NatSP_2P_E484K_D614G (SEQ ID NO: 1) | 7397 |
| B.1.351 | WH2020_NatSP_2P_H69del_V70del_Y144del_N501Y_A570D_D614G_P681H_T716I_S982A_D1118h (SEQ ID NO: 12) | 2357 |
| B.1.351 | WH2020_NatSP_2P_K417N_E484K_N501Y_D614G (SEQ ID NO: 6) | 8566 |
| B.1.351 | 1:1 mix of SEQ ID NO: 10 and 6<br>WH2020_NatSP_2P_L18F_D80A_D215G_L242_244del_R246I_K417N_E484K_N501Y_D614G_A701V (SEQ ID NO: 10)<br>WH2020_NatSP_2P_K417N_E484K_N501Y_D614G (SEQ ID NO: 6) | 16091 |

It was found that the S2P-E484K-D614G and S2P-K417N-E484K-N501Y-D614G vaccines neutralized the D614G variant virus well, and each had a modest drop (1.5- to 2-fold) against the B.1.351 virus. Similar to the results observed with mRNA-1273.211 (1:1 mix of mRNA-1273 and mRNA-1273.351), the 1:1 mixture of mRNA-1273 and S2P-K417N_E484K_N501Y_D614G had consistently high neutralizing titers. In contrast to the mRNA-1273.211 vaccine; however, the 1:1 mixture of mRNA-1273 and S2P-K417N_E484K_N501Y_D614G had a less robust response to the B.1.351 Spike protein variant.

The study was repeated with the S2P-D614G (SEQ ID NO: 18) mRNA vaccine (1 μg doses). On day 36 (after two doses), sera were assayed to determine neutralizing antibody titers against different virus variants, as shown in Table 9.

TABLE 9

| Neutralization Titers (1 μg Dose) | | |
|---|---|---|
| Virus | Vaccine | NAb Titer ($ID_{50}$) |
| D614G | S2P-D614G | 23097 |
| B.1.351 | S2P-D614G | 13917 |
| CAL.20C | S2P-D614G | 19692 |
| P.1 | S2P-D614G | 21387 |
| B.1.1.7 + E484K | S2P-D614G | 15596 |

The data demonstrates that vaccine S2P-D614G elicited higher neutralizing antibody titers against the variants compared to other mRNA vaccines tested. Moreover, it showed a more consistent antibody titer than the other mRNA vaccines tested. For example, the neutralizing antibody titer measured against the D614G variant was 1.7-fold greater than against the B.1.351 variant. The neutralizing titer against the D614G variant was 1.2 fold higher than against the CAL.20C variant; against the D614G variant and against the P.1 variant was 1.1-fold greater. Finally, the neutralizing titer against the D614G variant was 1.5 fold higher than against the B.1.1.7+E484K variant.

Example 6—SARS-CoV-2 mRNA B.1.351 Variant Immunogenicity (10 Mutations Vs. 8 Mutations)

BALB/c mice, 6-8 weeks of age, are administered using either 0.1 μg, 1 μg, or 10 μg of mRNA encoding a SARS-CoV-2 Spike protein antigen or PBS (as a control) intramuscularly in one hind leg (formulated as a 50 μL dose) on day 1 and day 22. The mRNAs tested encode mRNA encoding Spike protein with two proline substitutions, WH2020_NatSP_2P, (SEQ ID NO: 18), WH2020_NatSP_2P_L18F_D80A_D215G_L242_244 del_R246I_K417N_E484K_N501Y_D614G_A701V (SEQ ID NO: 9); or WH2020_NatSP_2P_H69del_V70del_Y144del_N50 1Y_A570D_D614G_P681H_T716I_S982 A_D1118h (SEQ ID NO: 12). In each vaccine, the mRNA is formulated in lipid nanoparticles (LNPs) including 0.5-15% PEG-modified lipid, 5-25% non-cationic lipid, 25-55% sterol, and 20-60% ionizable amino lipid. The PEG-modified lipid is 1,2 dimyristoyl-sn-glycerol, methoxypolyethyleneglycol (PEG2000 DMG), the non-cationic lipid is 1,2 distearoyl-sn-glycero-3-phosphocholine (DSPC), the sterol is cholesterol, and the ionizable amino lipid has the structure of Compound 1, for example.

Blood samples are taken from the mice on day 21 and day 36 and the serum analyzed by ELISA and neutralization assays as described herein. Lungs and spleen are removed and further analyzed.

Example 7—SARS-CoV-2 mRNA B.1.351 Variant Third Dose Immunogenicity

BALB/c mice, 6-8 weeks of age, were administered either 0.1 μg or 1 μg of mRNA encoding a SARS-CoV-2 antigen or PBS (as a control) intramuscularly in one hind leg (formulated as a 50 μL dose) on day 1 and day 22. The mice were then administered a third dose at week 8 (day 57). In each vaccine, the mRNA was formulated in lipid nanoparticles (LNPs) including 0.5-15% PEG-modified lipid, 5-25% non-cationic lipid, 25-55% sterol, and 20-60% ionizable amino lipid. The PEG-modified lipid was 1,2 dimyristoyl-sn-glycerol, methoxypolyethyleneglycol (PEG2000 DMG), the non-cationic lipid was 1,2 distearoyl-sn-glycero-3-phosphocholine (DSPC), the sterol was cholesterol, and the ionizable amino lipid had the structure of Compound 1, for example. The administration schedule is provided in Table 10 below (note: mRNA-351 encodes wild-type SARS-CoV-2 with the following mutations: L18F-D80A-D215G-L242-244del-R246I-K417N-E484K-N501Y-D614G-A701V).

TABLE 10

| Administration Schedule | | | | | |
|---|---|---|---|---|---|
| GR | N= | TA | Dose Mass (ug/animal) | Prime/ boost | $3^{rd}$ dose |
| 1 | 5 | PBS | — | PBS | PBS |
| 2 | 8 | mRNA encoding the wild-type | 1 | Prime on day 1 | mRNA encoding the wild-type |
| 3 | 8 | Spike protein with two proline substitutions | 0.1 | and boost on day 22 with 1273 (1; 0.13 g) | Spike protein with two proline substitutions (1 ug) $3^{rd}$ dose on wk 8 |
| 4 | 8 | mRNA encoding the wild-type | 1 | | mRNA-351 (1 ug) $3^{rd}$ dose |
| 5 | 8 | Spike protein with two proline substitutions | 0.1 | | on wk 8 |
| 6 | 8 | mRNA encoding the wild-type | 1 | | 1:1 mix of mRNA encoding the wild-type Spike protein |
| 7 | 8 | Spike protein with two proline substitutions | 0.1 | | with two proline substitutions + mRNA-351 (1 ug) $3^{rd}$ dose on wk 8 |
| 8 | 8 | mRNA encoding the wild-type | 1 | | 1:2 mix of mRNA encoding |
| 9 | 8 | Spike protein with two proline substitutions | 0.1 | | the wild-type Spike protein with two proline substitutions + |

TABLE 10-continued

| Administration Schedule | | | | | |
|---|---|---|---|---|---|
| GR | N= | TA | Dose Mass (ug/animal) | Prime/ boost | $3^{rd}$ dose |
| | | | | | mRNA-351 (1 ug) $3^{rd}$ dose on wk 8 |
| 10 | 8 | mRNA encoding the wild-type | 1 | | 1:3 mix of mRNA encoding |
| 11 | 8 | Spike protein with two proline substitutions | 0.1 | | the wild-type Spike protein with two proline substitutions + mRNA-351 (1 ug) $3^{rd}$ dose on wk 8 |
| 12 | 8 | mRNA-351 | 1 | | mRNA-351(1 ug ) $3^{rd}$ dose |
| 13 | 8 | | 0.1 | | on wk 8 |
| 14 | 8 | 1:1 mix of mRNA encoding the | 1 | | 1:1 mix of mRNA encoding |
| 15 | 8 | wild-type Spike protein with two proline substitutions & mRNA-351 | 0.1 | | the wild-type Spike protein with two proline substitutions + mRNA-351 (1 ug) $3^{rd}$ dose on wk 8 |
| 16 | 8 | 1:2 mix of mRNA encoding the | 1 | | 1:2 mix of mRNA encoding |
| 17 | 8 | wild-type Spike protein with two proline substitutions & mRNA-351 | 0.1 | | the wild-type Spike protein with two proline substitutions + mRNA-351 (1 ug) $3^{rd}$ dose on wk 8 |
| 18 | 8 | 1:3 mix of mRNA encoding the | 1 | | 1:3 mix of mRNA encoding |
| 17 | 8 | wild-type Spike protein with two proline substitutions & mRNA-351 | 0.1 | | the wild-type Spike protein with two proline substitutions + mRNA-351 (1 ug) $3^{rd}$ dose on wk 8 |

Figure 41:
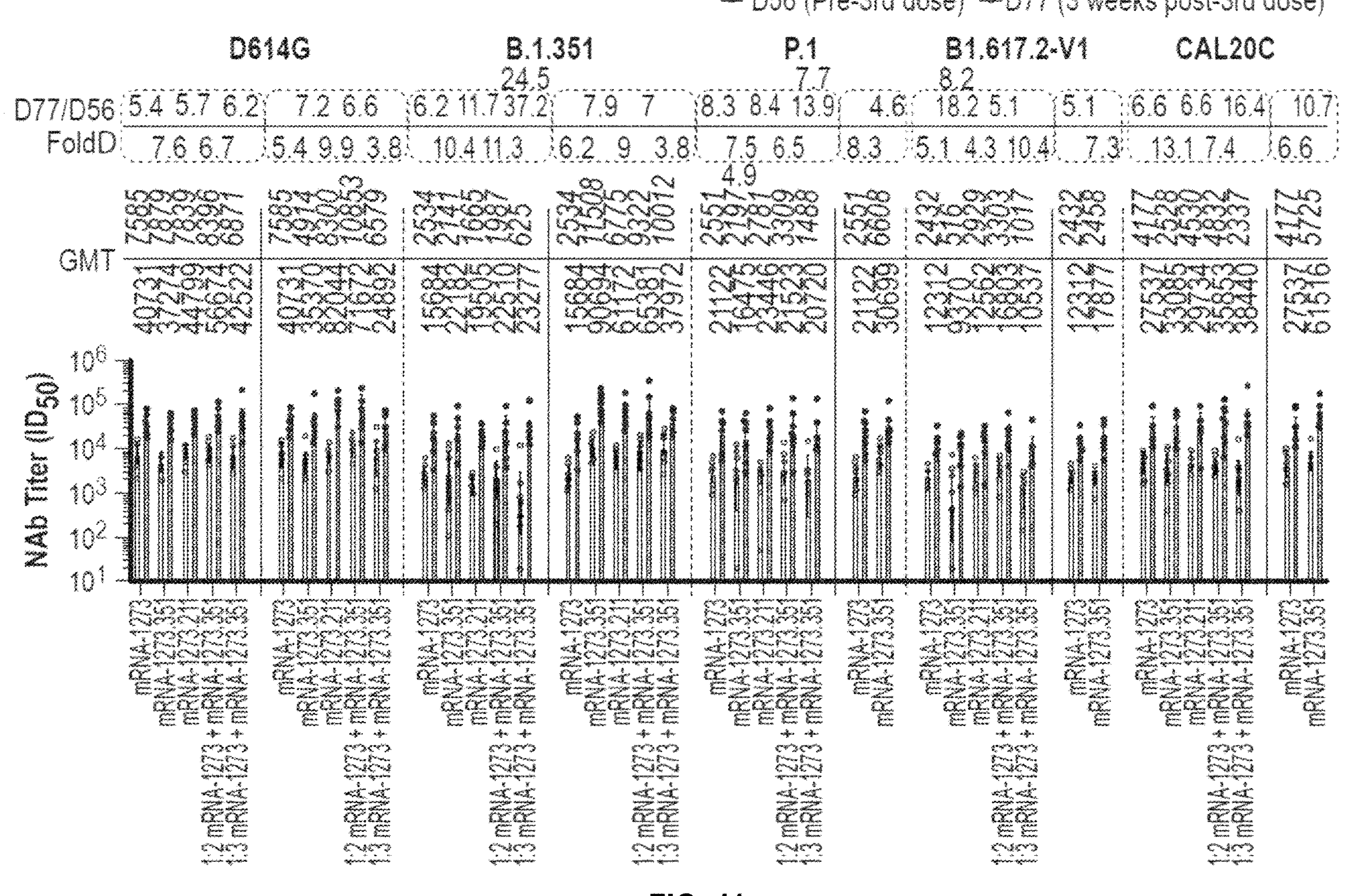
FIG. 41 is a graph showing neutralizing antibodies elicited by different vaccine formulations in mice before and after administration of a booster (third) vaccine formulation.

Blood samples were taken on days 21, 36, 56, and 77 and analyzed by ELISA and neutralization assays as described herein. The neutralizing titers are shown in FIG. 41, and demonstrate fold-increases between day 56 and day 77 of 4.6 to 37.2.

Figure 42A:
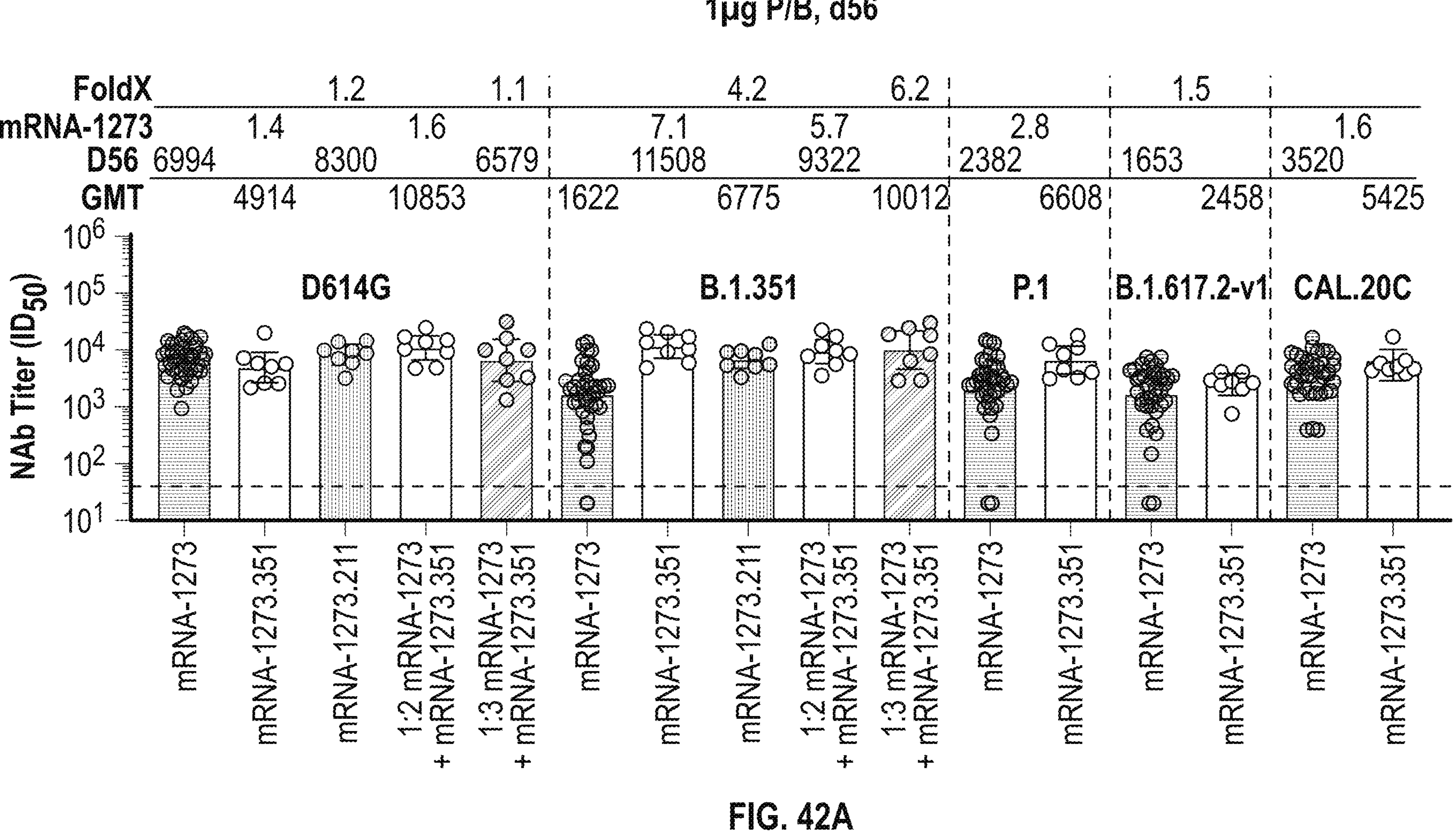
FIGS. 42A-42B are graphs showing neutralizing antibodies elicited by different vaccine formulations in mice after administration of two doses of vaccine on day 56 (before administration of a booster dose).
Figure 42B:
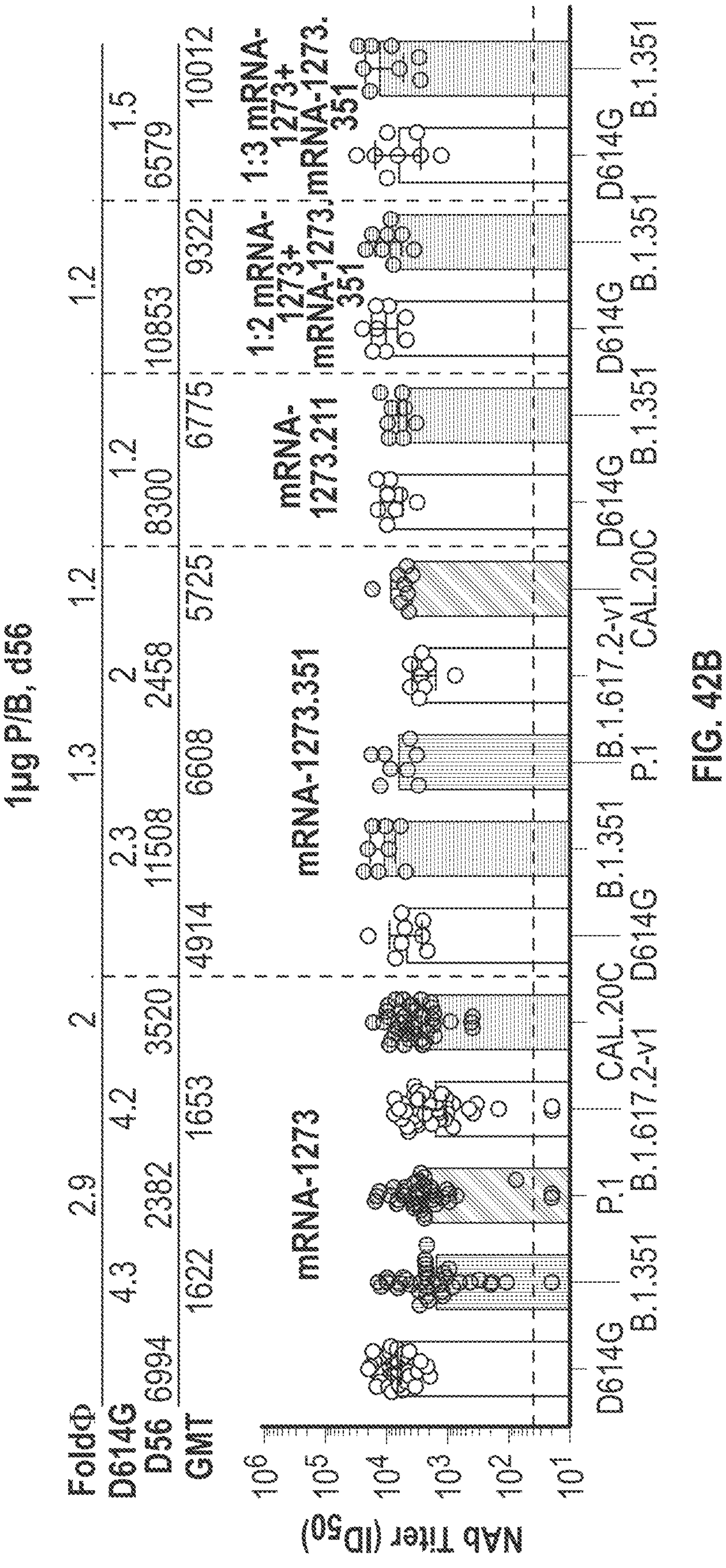

Overall, two doses of mRNA-1273 (n=40) consistently displayed a decrease in neutralizing antibody titer against B.1.351, P.1, B.1.617-2-v1, CAL.20C (FIGS. 42A-42B). In contrast, mRNA-1273.351 (n=8) had a 1.5-3-fold increase on neutralizing antibody titer against. P.1, B.1.617.2-v1, CAL.20C (FIGS. 42A-42B). The different ratios tested, 1:2 and 1:3 mRNA-1273+mRNA-1273.351 (n=8), were found to perform equally well as mRNA-1273.351 against B.1.351; however, the 1:2 mRNA-1273+mRNA-1273.351 vaccine (n=8) was found to have the highest neutralizing antibody titer against D614G (FIGS. 42A-42B).

Figure 43A:
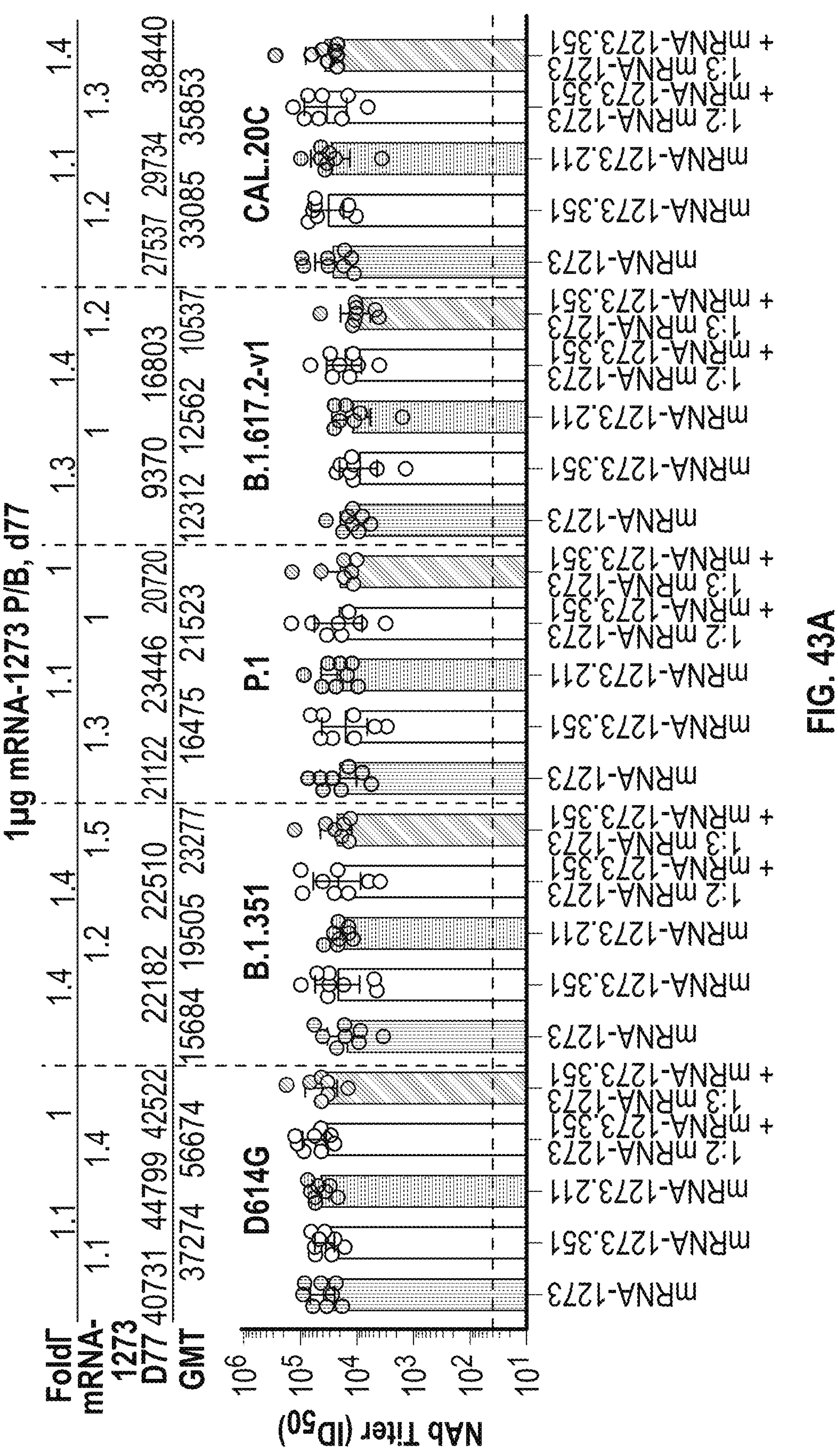
FIGS. 43A-43B are graphs showing neutralizing antibodies elicited by different vaccine formulations in mice on day 77, following administration of two doses of vaccine and administration of a booster dose.
Figure 43B:
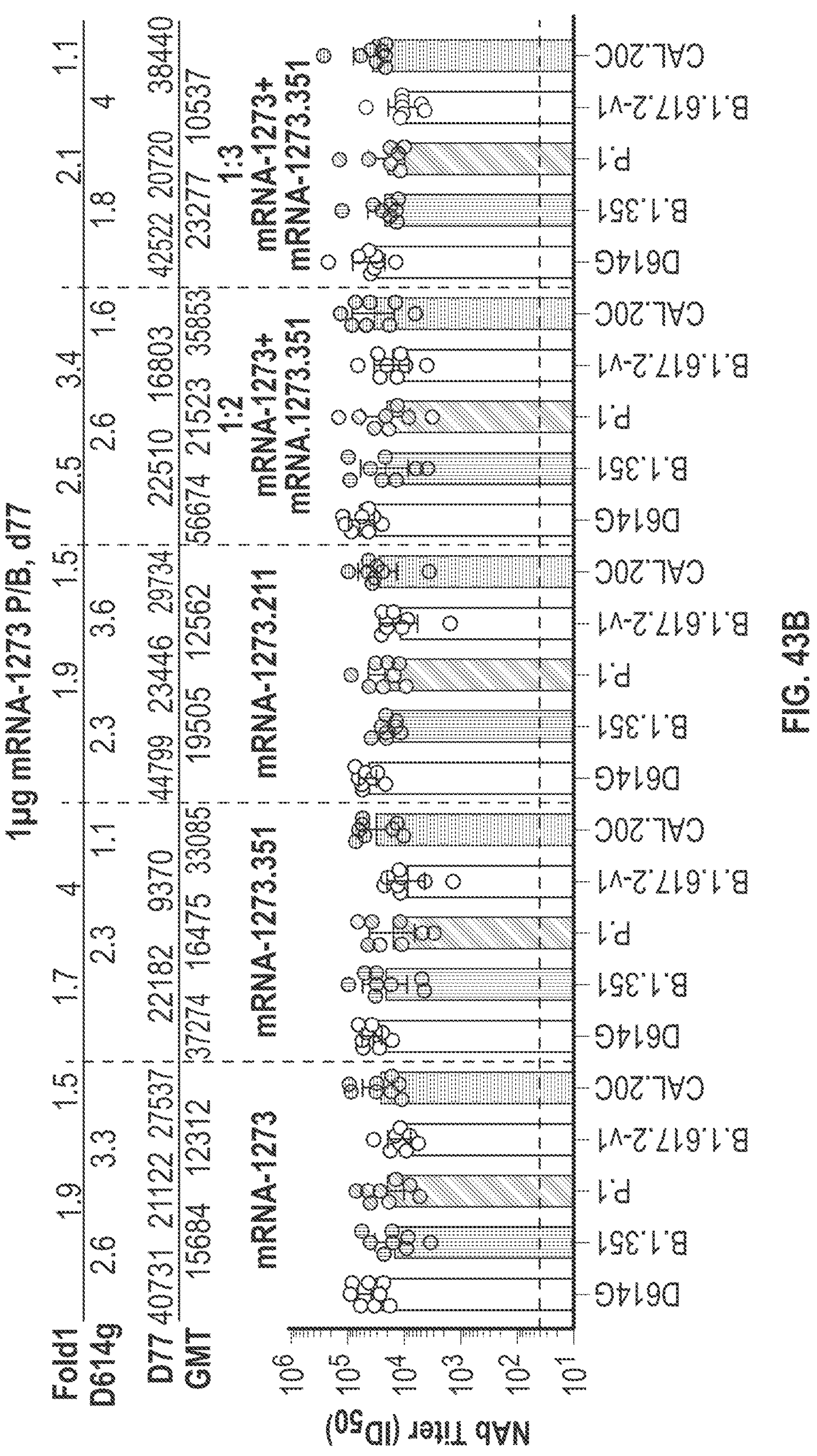
Figure 44A:
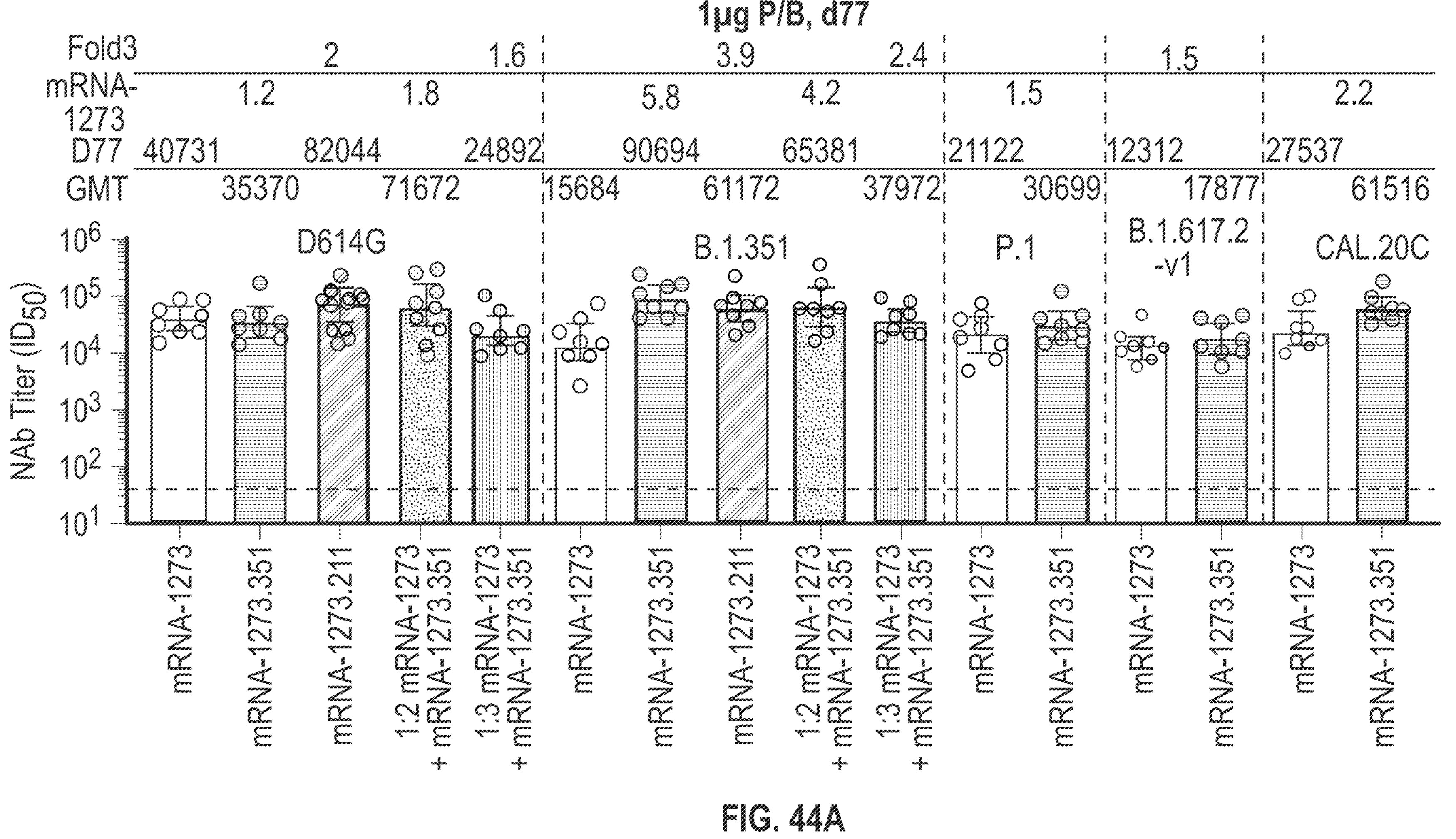
FIGS. 44A-44B are graphs showing neutralizing antibodies elicited by different vaccine formulations in mice on day 77, following administration of two doses of vaccine and administration of a booster dose. In each group, the three doses administered were the same vaccine formulation (dosage and mRNA encoding the antigen).
Figure 44B:
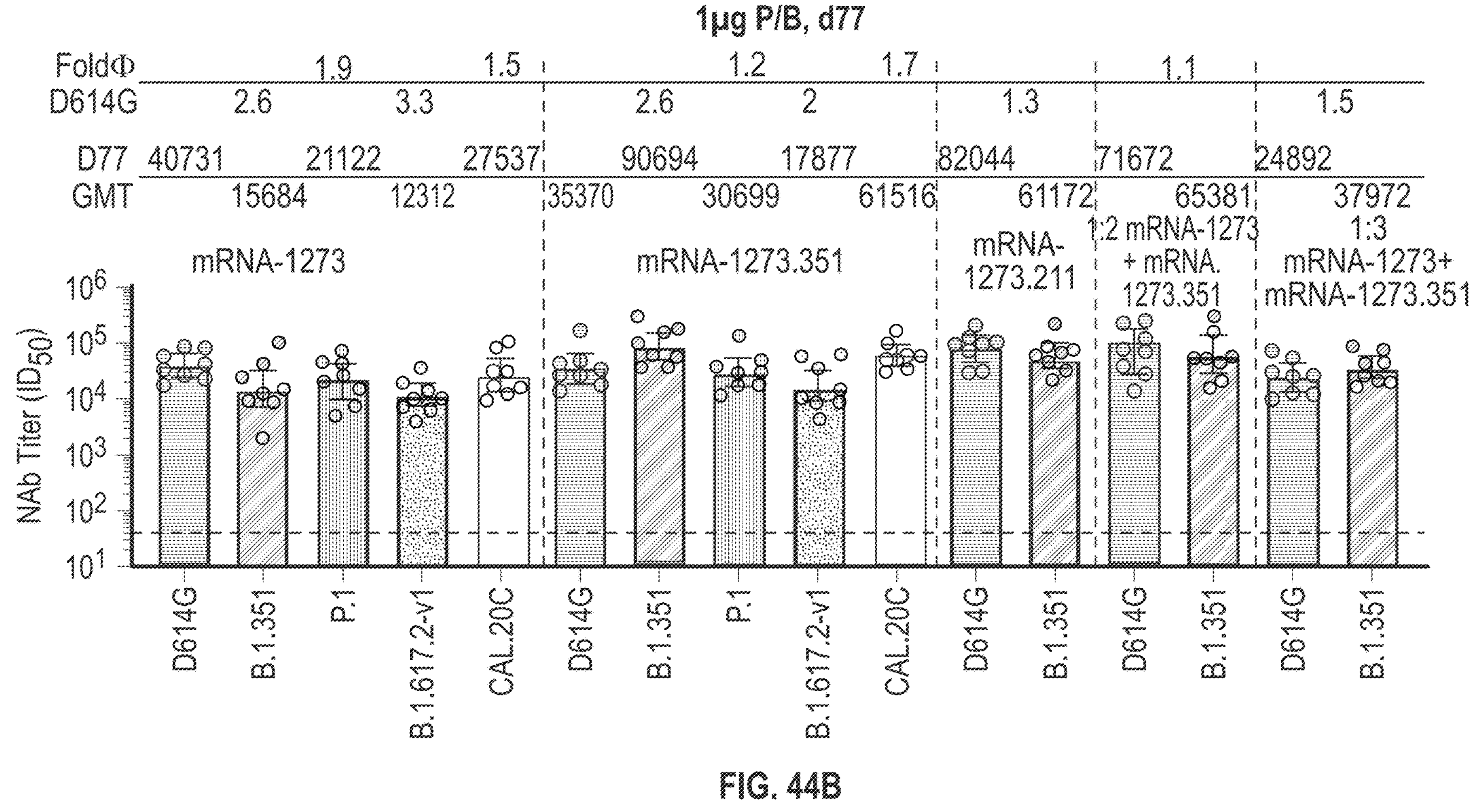

Three weeks after the third dose (booster), all vaccine formulations were found to have a reduction in neutralizing antibody titer compared to D614G, while all vaccine formulations seemed to behave equally well as mRNA-1273 across the full panel of viruses (FIGS. 43A-43B). In particular, mRNA-1273 was found to have a 1.5-3-fold reduction in neutralizing antibody titer against the full panel of viruses. In addition, mRNA-1273.211 and 1:2 mRNA-1273+mRNA-1273.351 performed equally well against D614G and B.1.351 but 1:3 mRNA-1273+mRNA-1273.351 seems to have a slightly lower neutralizing antibody titer (FIGS. 44A-44B). Ultimately, mRNA-1273.351 yielded the highest neutralizing antibody titer against B.1.351.

In summary, as a third dose (booster), all vaccine formulations appeared to perform equally well, although slightly better than the 1:3 mRNA-1273+mRNA-1273.351 formulation.

Example 8—Immunogenicity of SARS-CoV-2 mRNA ($3^{rd}$ and $4^{th}$ Doses)

BALB/c mice were immunized at days 1 and 22 with 1 μg of SEQ ID NO: 18 (WH2020_NatSP_2P) (n=8/group). The mice were subsequently administered a first booster dose (dose 3; 1 μg) on day 58 and a second booster dose (dose 4; 1 μg) on day 78 or a first booster dose (dose 3; 0.1 μg or 1 μg) on day 213 and a second booster dose (dose 4; 0.1 μg or 1 g) on day 234. The first and second booster doses comprised mRNA encoding wild-type SARS-CoV-2 with the following mutations: L18F-D80A-D215G-L242-244del-R246I-K417N-E484K-N501Y-D614G-A701V. In each vaccine, the mRNA was formulated in lipid nanoparticles (LNPs) including 0.5-15% PEG-modified lipid, 5-25% non-cationic lipid, 25-55% sterol, and 20-60% ionizable amino lipid. The PEG-modified lipid was 1,2 dimyristoyl-sn-glycerol, methoxypolyethyleneglycol (PEG2000 DMG), the non-cationic lipid was 1,2 distearoyl-sn-glycero-3-phosphocholine (DSPC), the sterol was cholesterol, and the ionizable amino lipid had the structure of Compound 1, for example.

Blood was collected one day before the first booster dose, one day before the second booster dose, and two weeks following the second booster dose, and analyzed by ELISA and neutralization assays as described herein. Briefly, pseudoviruses with Spike mutation D614G (comparator variant) and B.1.351 (L18F, D80A, D215G, Δ242-244, R246I, K417N, E484K, N501Y, A701V) were constructed. Neutralization assays were performed using a validated lentivirus-based Spike-pseudotyped virus assay in 293T cells stably transduced to overexpress ACE2 described in Shen et al. (SARS-CoV-2 variant B.1.1.7 is susceptible to neutralizing antibodies elicited by ancestral Spike vaccines. Cell Host & Microbe, in press 2021).

With respect to the groups that received booster doses on Day 213 and Day 234, the neutralizing antibody titer was found to drop about 2-fold over the six-month period. That is, on day 36, the neutralizing titer was 9940 and on day 212 (the day before the first booster dose), the neutralizing antibody titer was 6729.

Neutralizing antibody titers against the D614G variant and the B.1.351 variant were measured on day 212 (before the third dose, 1 μg) and day 233 (after the third dose). The data is shown in Table 11 below.

TABLE 11

| Neutralization Titers (1 μg Dose) | | |
|---|---|---|
| Virus | Day | NAb Titer ($ID_{50}$) |
| D614G | 212 | 6729 |
| D614G | 233 | 30386 |
| B.1.351 | 212 | 1015 |
| B.1.351 | 233 | 15524 |

As shown in Table 11, the neutralizing antibody titer was increased from day 212 to day 233 against the D614 variant Spike protein and more dramatically against the B.1.351 variant Spike protein. The relative titer change between day 212 and day 233 against the D614G variant was 4.5× and the relative titer change between day 212 and day 233 against the B.1.351 variant was 15×. The neutralizing antibody titer was 6.6× greater against the D614G variant than against the B.1.351 variant at day 212 (before administration of the booster); however, after the booster dose (day 233), the neutralization titers elicited against the D614G variant Spike protein were 2× those elicited by the B.1.351 variant Spike protein.

Similar trends were seen with the 0.1 μg dose. Neutralizing antibody titers against the D614G variant and the B.1.351 variant were measured on day 212 (before the third dose, 0.1 μg) and day 233 (after the third dose). The data is shown in Table 12 below.

TABLE 12

| Neutralization Titers (0.1 μg Dose) | | |
|---|---|---|
| Virus | Day | NAb Titer ($ID_{50}$) |
| D614G | 212 | 548 |
| D614G | 233 | 1985 |
| B.1.351 | 212 | 66 |
| B.1.351 | 233 | 274 |

As shown in Table 12, the neutralizing antibody titer was increased from day 212 to day 233 against the D614 variant Spike protein and the B.1.351 variant Spike protein. The relative titer change between day 212 and day 233 against the D614G variant was 3.6× and the relative titer change between day 212 and day 233 against the B.1.351 variant was 4.2×. The neutralizing antibody titer was 8.3× greater against the D614G variant than against the B.1.351 variant at day 212 (before administration of the booster); however, after the booster dose (day 233), the neutralization titers elicited against the D614G variant Spike protein were 7.2× those elicited by the B.1.351 variant Spike protein.

Figure 11:
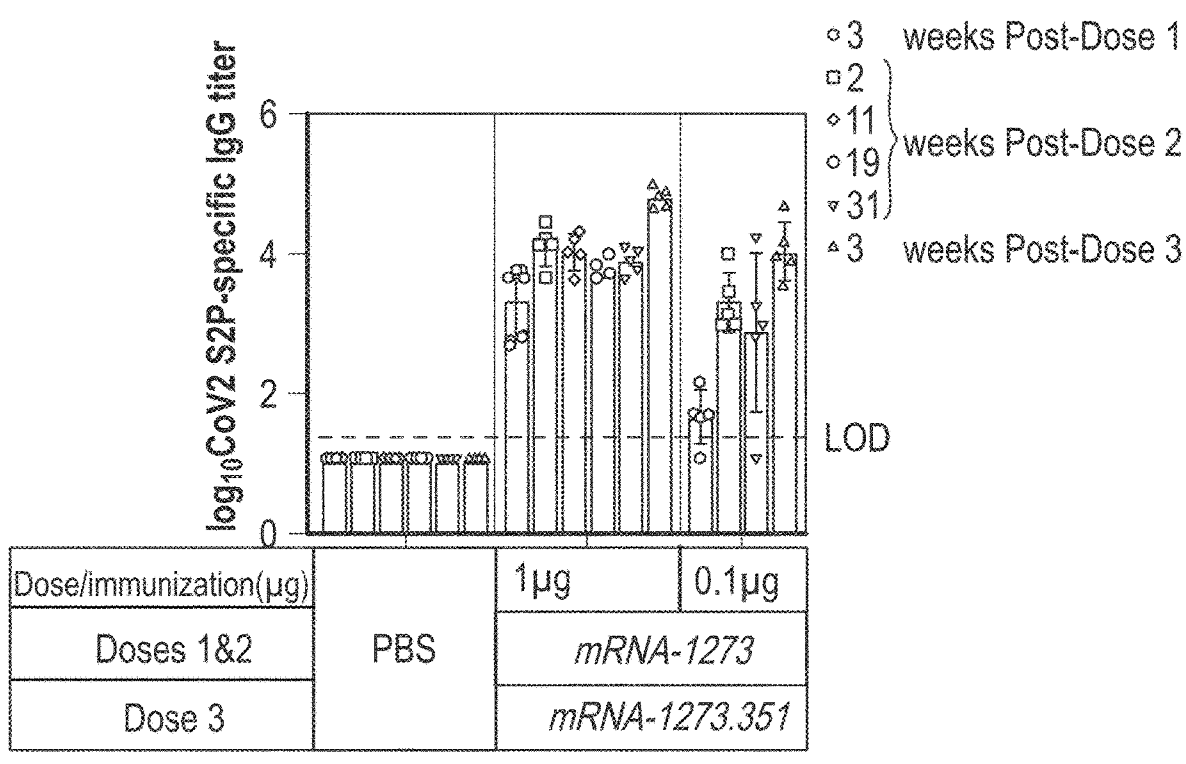
FIG. 11 shows neutralizing antibody titers in mice following 1, 2, or 3 doses of vaccine. Balb/c mice were immunized with 1 or 0.1 μg mRNA-1273 and were boosted with 1 or 0.1 μg mRNA-1273.351 on study day 213. Results from individual mouse sera is represented as dots on each figure, and the line is the mean of each group. The horizontal dotted line indicates the limit of detection (LOD).
Figure 12:
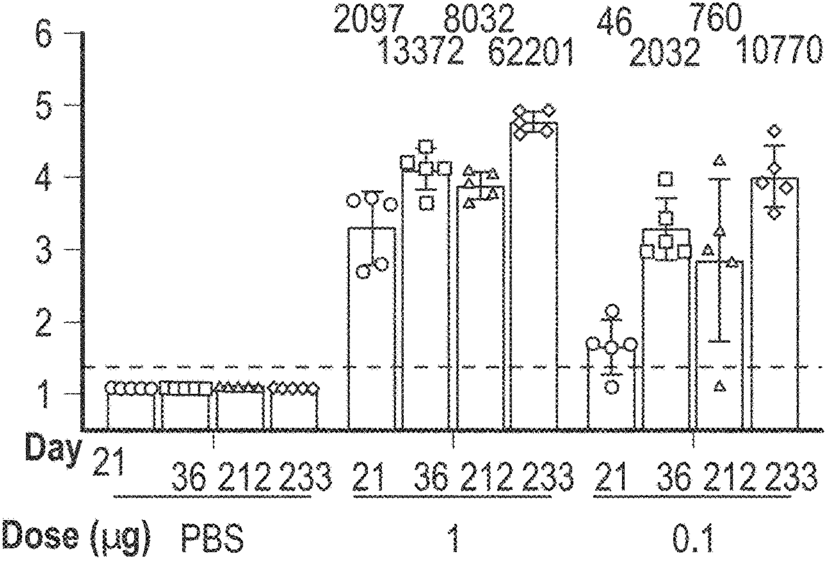
FIG. 12 shows neutralizing antibody titers in mice following 1, 2, or 3 doses of vaccine. BALB/c mice were immunized with 1 or 0.1 μg mRNA-1273 (dose 1 on day 1 and dose 2 on day 22) and were boosted with 1 or 0.1 μg mRNA-1273.351 on day 213. Results from individual mouse sera (n=5 per group) are represented as dots on each figure, and the line is the mean of each group. The horizontal dotted line indicates the LLOD for log 10 IgG titer at 1.602.

A summary of the study is presented in FIGS. 11-12.

These same trends were also observed in the groups that received booster doses on Day 58 and 78. BALB/c mice were immunized at days 1 and 22 with 1 μg of SEQ ID NO: 18 (WH2020 NatSP_2P) (n=8/group). The mice were subsequently administered a first booster dose (dose 3; 1 μg) on day 58. The first booster dose comprised mRNA encoding wild-type SARS-CoV-2 with the following mutations: L18F-D80A-D215G-L242-244del-R246I-K417N-E484K-N501Y-D614G-A701V. Serum samples collected on days 57 (before administration of the first booster dose) and on day 77 (after administration of the 1 μg booster dose). The data is shown in Table 13 below.

TABLE 13

| Neutralization Titers (1 μg Dose) | | |
|---|---|---|
| Virus | Day | NAb Titer ($ID_{50}$) |
| D614G | 57 | 4955 |
| D614G | 77 | 24508 |
| B.1.351 | 57 | 1015 |
| B.1.351 | 77 | 16967 |

As shown in Table 13, the neutralizing antibody titer was increased from day 57 to day 77 against the D614G variant Spike protein and the B.1.351 variant Spike protein. The relative titer change between day 57 and day 77 against the D614G variant was 4.9× (p=0.0156) and the relative titer change between day 57 and day 77 against the B.1.351 variant was 17× (p=0.0156). The neutralizing antibody titer was 4.9× greater (p=0.0156) against the D614G variant than against the B.1.351 variant at day 57 (before administration of the booster); however, after the booster dose (day 77), the neutralization titers elicited against the D614G variant Spike protein were 1.8× those elicited by the B.1.351 variant Spike protein.

Similar trends were seen with the 0.1 μg dose. Neutralizing antibody titers against the D614G variant and the B.1.351 variant were measured on day 57 (before the third dose, 0.1 μg) and day 77 (after the third dose). The data is shown in Table 14 below.

TABLE 14

| Neutralization Titers (0.1 μg Dose) | | |
|---|---|---|
| Virus | Day | NAb Titer ($ID_{50}$) |
| D614G | 57 | 72 |
| D614G | 77 | 376 |
| B.1.351 | 57 | 42 |
| B.1.351 | 77 | 290 |

As shown in Table 14, the neutralizing antibody titer was increased from day 57 to day 77 against the D614 variant Spike protein and the B.1.351 variant Spike protein. The relative titer change between day 57 and day 77 against the D614G variant was 5.2× (p=0.0313) and the relative titer change between day 57 and day 77 against the B.1.351 variant was 6.9× (p=0.0313). The neutralizing antibody titer was 1.7× greater against the D614G variant than against the B.1.351 variant at day 57 (before administration of the booster); however, after the booster dose (day 77), the neutralization titers elicited against the D614G variant Spike protein were 1.3× those elicited by the B.1.351 variant Spike protein.

Discussion

In this Example, mRNA-1273.351 and mRNA-1273.211 were evaluated in mice as a booster in animals previously vaccinated with mRNA-1273. As a primary vaccination series, both vaccines were potently immunogenic after dose 1, with both S-2P binding and neutralizing antibody titers significantly increasing after the second dose. mRNA-1273.351 elicited robust neutralizing titers against B.1.351. However, neutralizing activity of mRNA-1273.351 against D614G virus was 4-fold lower than that against the B.1.351 virus, and 6.3-fold lower against D614G compared to mRNA-1273. In contrast, the multivalent mRNA-1273.211 vaccine elicited robust and comparable neutralizing titers against both the D614G and B.1.351 viruses. In addition, vaccination with mRNA-1273.211 elicited neutralizing titers against the B.1.351 variant closely matching those observed against the D614G virus after mRNA-1273 vaccination.

A boosting regimen, mRNA-1273.351 was evaluated in animals vaccinated with mRNA-1273 approximately 7 months previously. Despite concerns about the ability to further boost immunity driven by a primary series of mRNA-1273, the third dose of mRNA-1273.351 dramatically boosted both S-2P binding antibody titers and D614G and B.1.351 PSV neutralization titers. Neutralizing titers against B.1.351 PSV was increased to a level that is well above the peak neutralizing titer against D614G after the second dose of mRNA-1273, the latter of which is fully protective for the mouse-adapted USA-WA1/2020 isolate in mice. In addition, the boost also increased neutralizing titers against D614G, although the fold-increase was less than that against B.1.351, as expected. Overall, the boost with mRNA-1273.351 dramatically increased both D614G and B.1.351 neutralization titers, with titers much higher than the previous day 36 peak and with a decreased fold of reduction against B.1.351 relative to D614G virus, when compared to pre-3rd dose.

Example 9: Protection and Durability of Coronavirus Vaccines in Non-Human Primates Non-human primates (NHPs) were used to examine the durability and protection of different combinations of vaccines. In one study, NHPs were vaccinated with mRNA encoding Spike protein with two proline substitutions ("mRNA vaccine") twice. At week 0, each NHP (n=8/group) was immunized with 100 μg or 30 μg of the mRNA vaccine. At week 4 or 5, the animals who were previously administered 100 μg of the mRNA vaccine are administered another 100 μg dose of the mRNA vaccine. Of the group that received a 30 μg dose of the vaccine, the animals are either administered another 30 μg dose or are not given a second dose. There is was a naïve control group that did not receive any mRNA vaccines. On week 12, the animals were challenged with $5\times10^5$ PFU of virus (either D614G or B.1.351). Following challenge, blood samples were drawn on days 2, 4, 7, and 14; nasal washes were performed on days 2, 4, 7, and 14; nasal swabs were taken on days 2, 4, and 7; bronchoalveolar lavage (BAL) was sampled on days 2, 4, 7, and 14, and lung pathology was performed on days 8 and 14 (n=4/group/day).

Figures 25A, 25B:
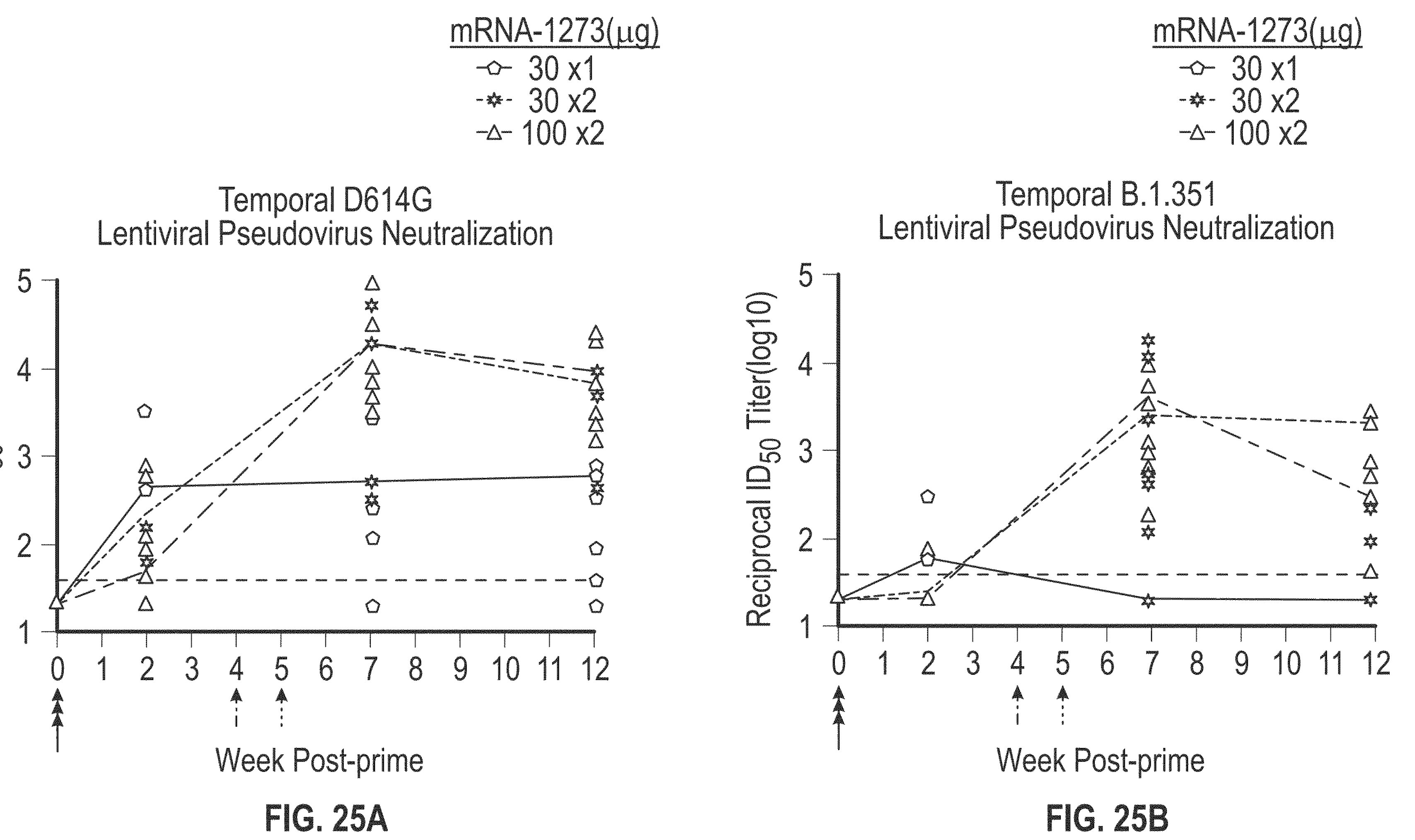
FIGS. 25A-25E show D614 and B.1.351 neutralization data in non-human primates (NHPs) using a lentiviral pseudovirus neutralization assay. Temporal studies for D614G (FIG. 25A) and B.1.351 (FIG. 25B) are shown. In addition, the reduction in neutralizing antibodies was analyzed for each group using lentiviral pseudovirus neutralization (FIG. 25C), VSV pseudovirus neutralization (FIG. 25D), and live virus neutralization (FIG. 25E).
Figures 25C, 25D:
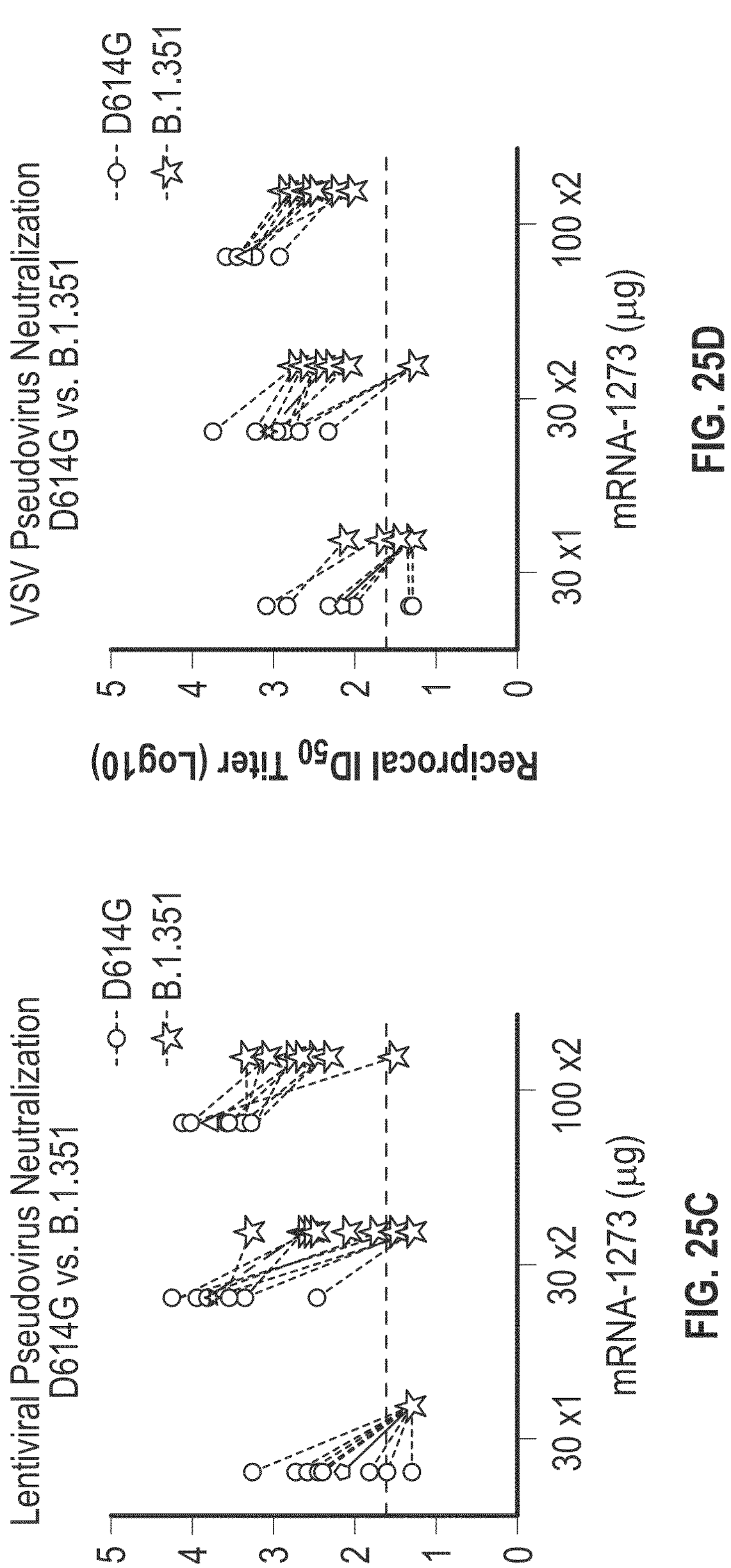
Figure 25E:
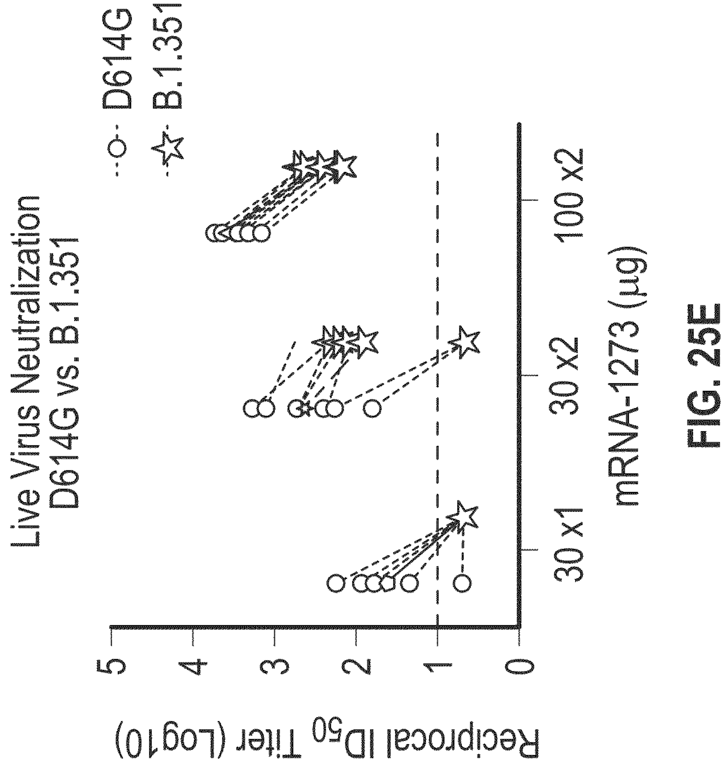
Figure 26A:
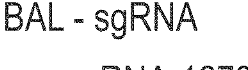
FIGS. 26A-26B show the results from 2020 NHP challenge studies following two doses of mRNA-1273 and challenge with USA-WA1/20. The graphs show the number of genome copies of the virus in lung samples (bronchoalveolar lavage, BAL, fluid.
Figure 26A:
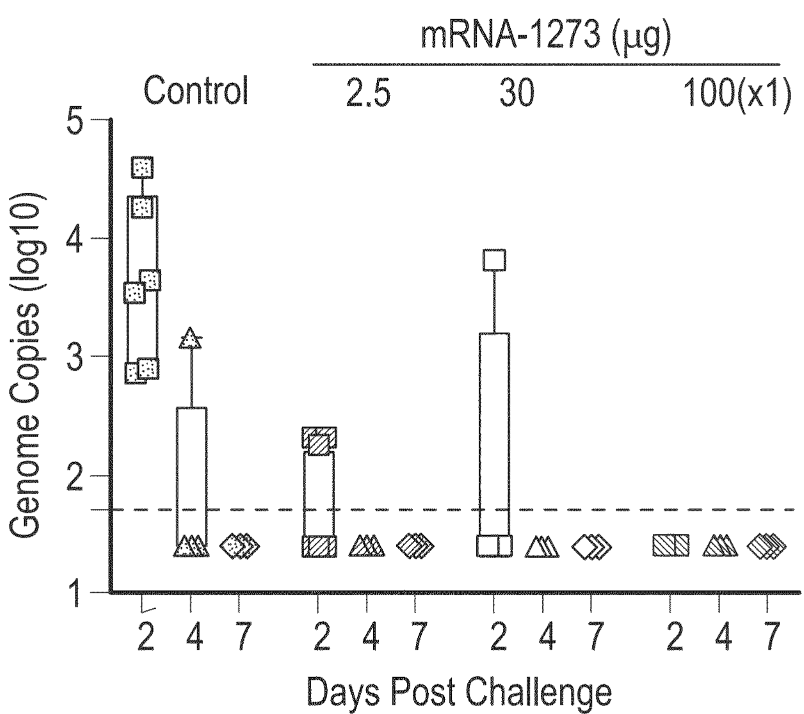
Figure 26B:
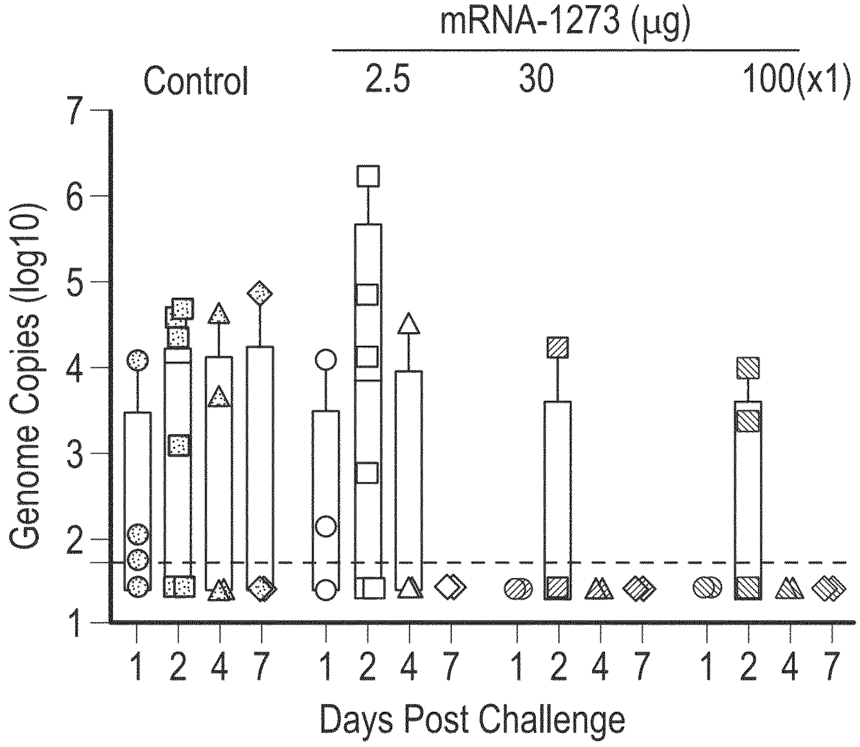
Figure 27A:
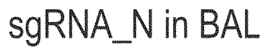
FIGS. 27A-27B show the results from 2021 NHP challenge studies following two doses of mRNA-1273 and challenge with USA-WA1/20. The graphs show the number of RNA genome copies of the virus in lung samples (bronchoalveolar lavage, BAL, fluid.
Figure 27A:
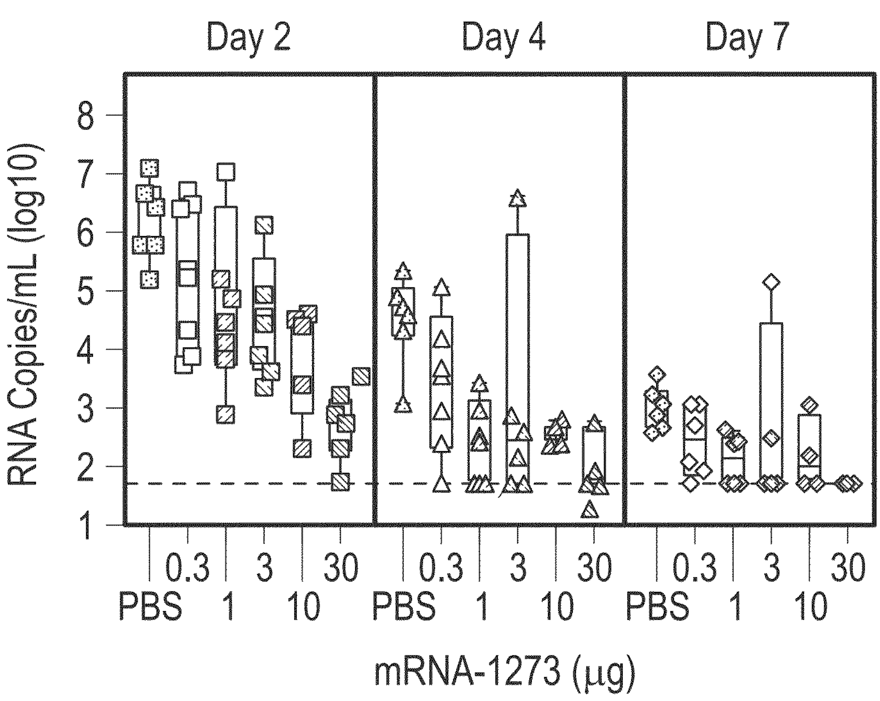
Figure 27B:
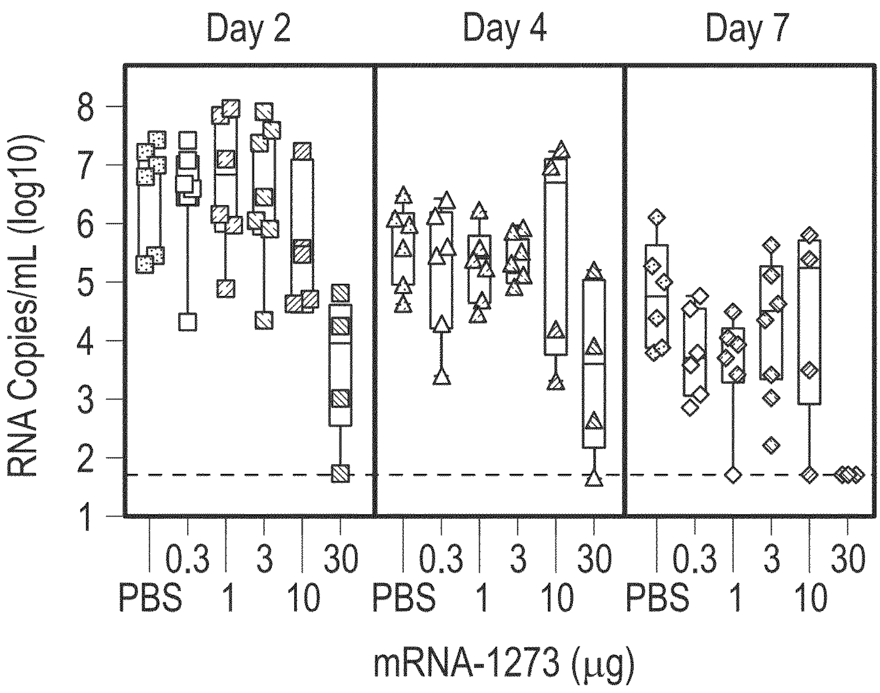
Figure 28A:
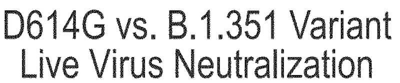
FIGS. 28A-28B show the results from 2021 NHP challenge studies following two doses of mRNA-1273 and challenge with D614G or B.1.351.
Figure 28A:
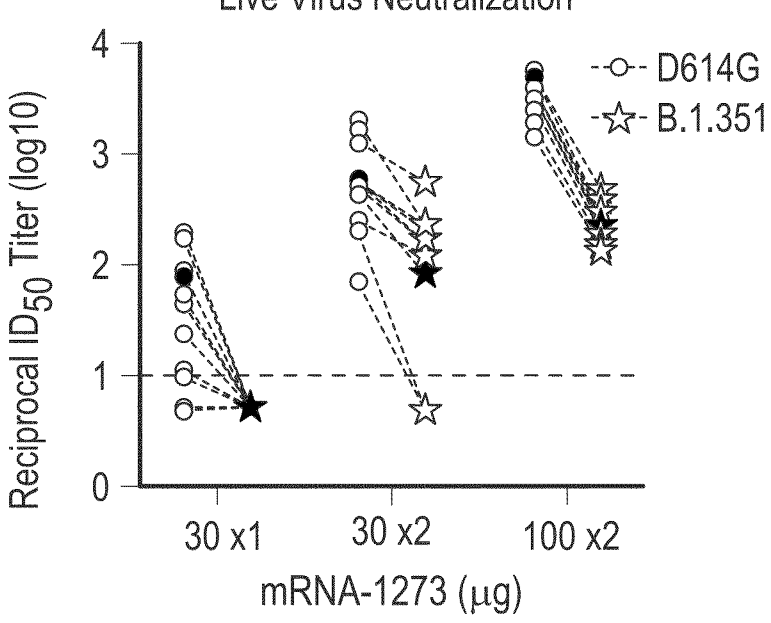
Figure 28B:
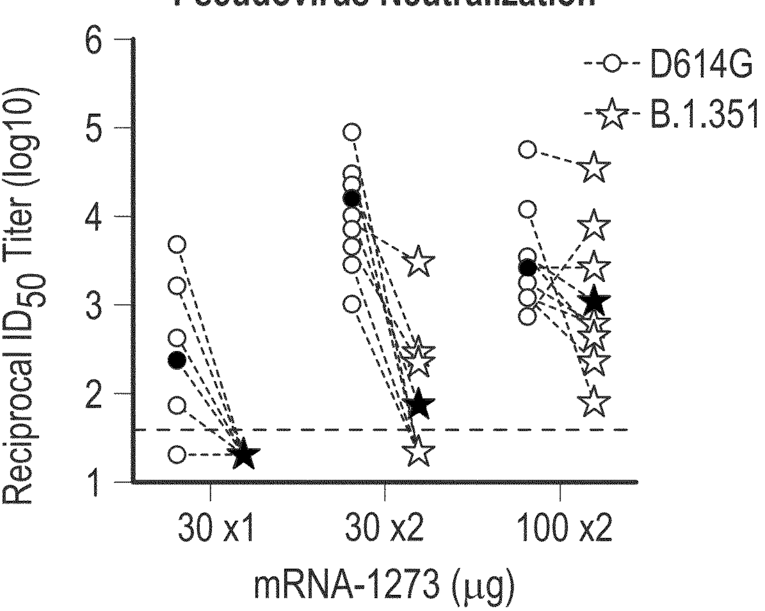
Figure 29A:
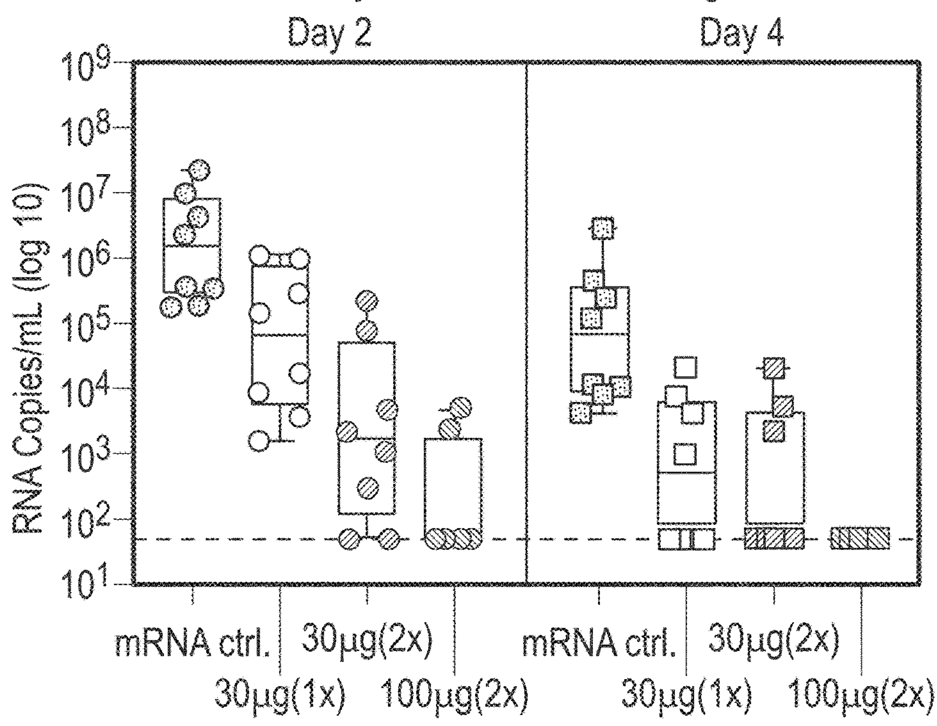
FIGS. 29A-29B show the results from 2021 NHP challenge studies following two doses of mRNA-1273 and challenge with D614G or B.1.351. The graphs show the number of RNA genome copies of the virus in lung samples (bronchoalveolar lavage, BAL, fluid.
Figure 29B:
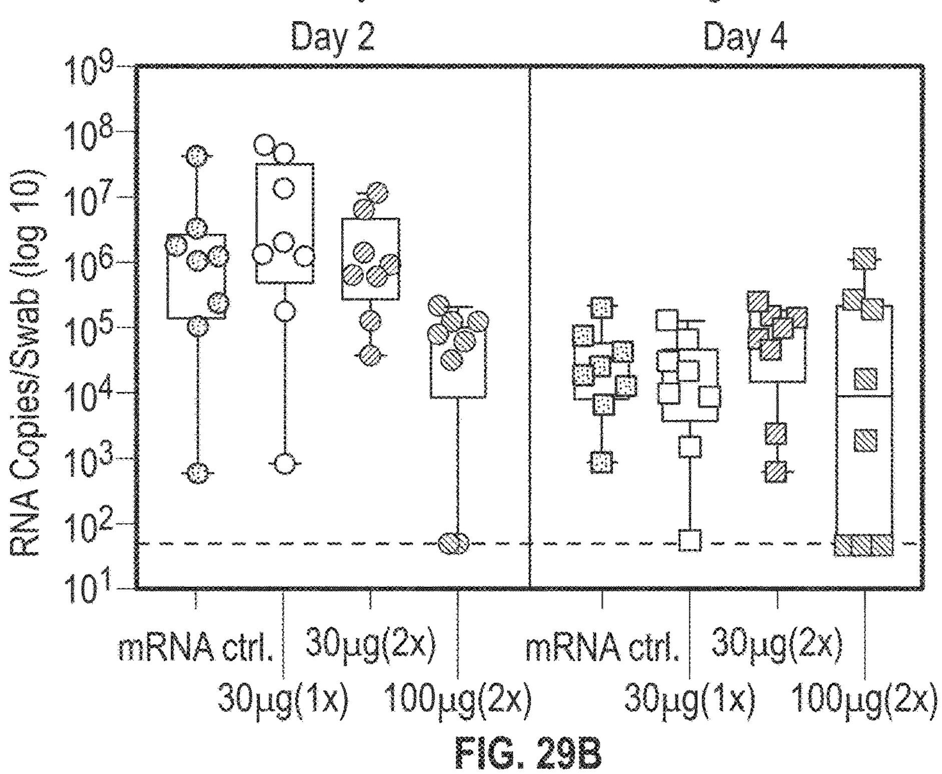
Figure 30A:
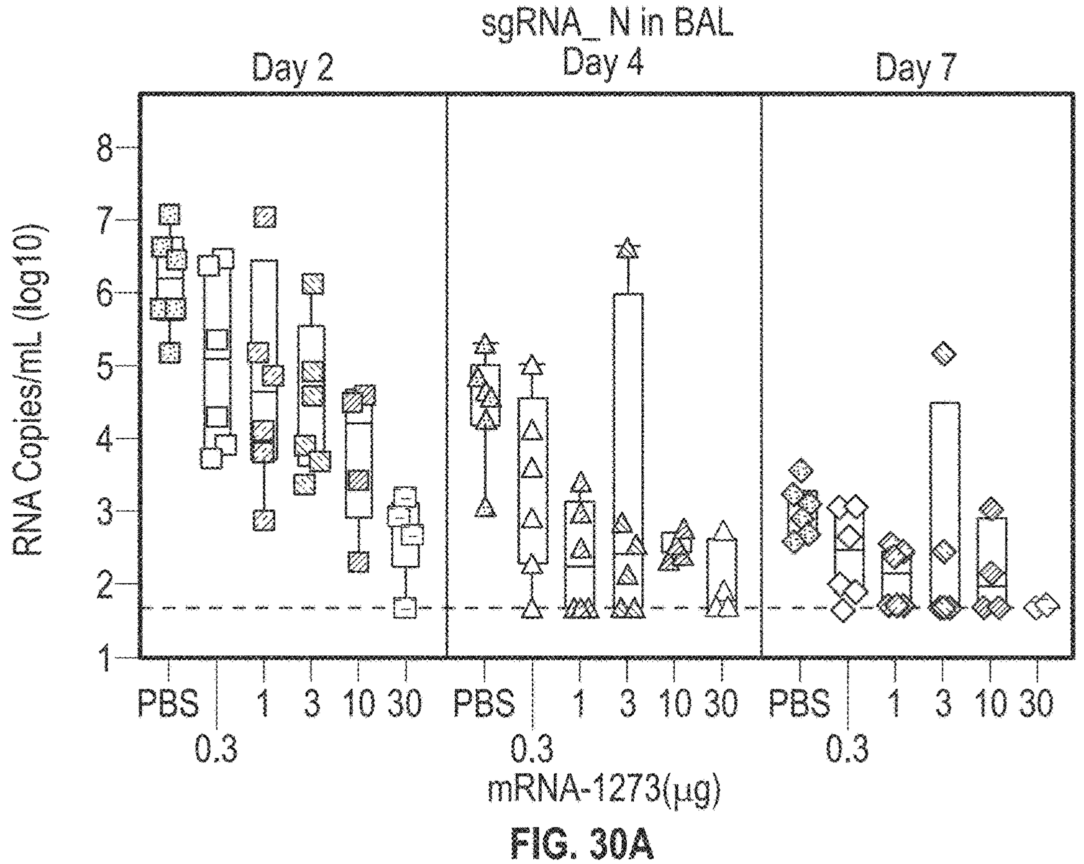
FIGS. 30A-30B show the results from 2021 NHP challenge studies following two doses of mRNA-1273 and challenge with USA-WA1/20. The graphs show the number of RNA genome copies of the virus in lung samples (bronchoalveolar lavage, BAL, fluid.
Figure 30B:
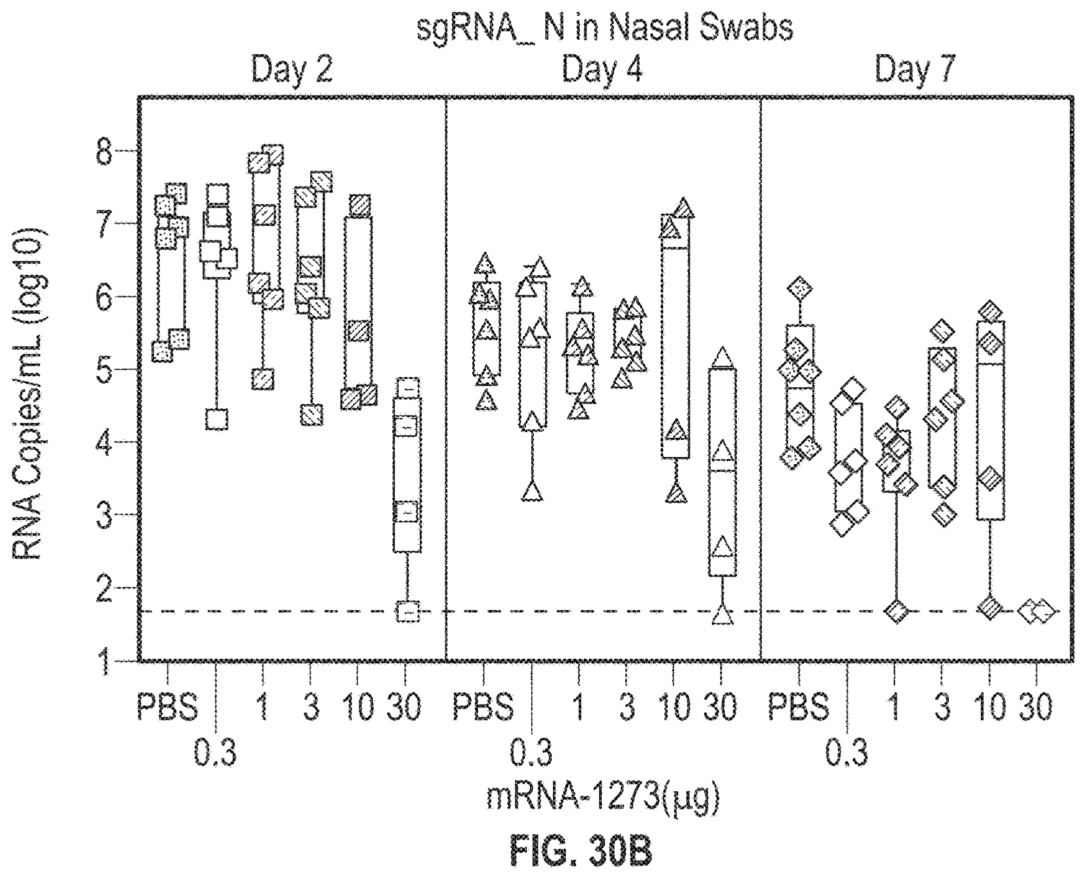

Neutralization titers were examined over time, as shown in FIGS. 25A and 25B and demonstrate a consistent titer that wanes slightly with time. Neutralizing antibody titers against B.1.351 were lower than those generated against D614G (FIGS. 25C-25E). As shown in FIGS. 26A-26B, the NHPs demonstrated full protection in nose and lungs following the 30 μg dose. In a later study, the 30 μg dose was found to be protective in the lower airway (BAL; FIG. 27A), but viral copies were detected in the nasal swab samples (FIG. 27B). Despite the robust challenge, the infection in the upper airway was rapidly controlled and the animals were considered to be protected, with the potential for transmission over a short time period. There was a reduction in neutralizing antibody titers against B.1.351 in animals vaccinated with mRNA-1273 (FIGS. 28A-28B) and viral replication was detected in the upper airway (FIG. 29B). The lower airway was protected (FIG. 29A). Moreover, protection was found against WA.1 and RSA (FIGS. 30A-30B), although viral replication in the upper airway suggests the potential for transmission.

In another study, animals are vaccinated with the mRNA vaccine twice (30 μg per dose) and then are administered a vaccine comprising mRNA encoding wild-type SARS-CoV-2 with the following mutations: L18F-D80A-D215G-L242-244del-R246I-K417N-E484K-N501Y-D614G-A701V (the B.1.351 Spike protein) or a combination of the mRNA vaccine and mRNA encoding the B.1.351 Spike protein. The animals are then challenged with the RSA isolate and examined to determine if the administration protocol boosts immunity and confer protection against the B.1.351 (RSA) isolate.

In a further study, animals are administered 10 μg, 30 μg, or 100 μg of an mRNA vaccine comprising mRNA encoding the B.1.351 Spike protein and then challenged with the RSA isolate to determine whether the vaccine mediates protection against RSA challenge and whether the dose of the vaccine influences the immunity and protection.

Example 10: Protection and Durability of Coronavirus Vaccines in Hamster Models

Hamsters (Golden Syrian Hamsters) are used to examine the durability and protection of different combinations of vaccines. In one study, hamsters are vaccinated with mRNA encoding Spike protein with two proline substitutions ("mRNA vaccine") twice or with mRNA encoding wild-type SARS-CoV-2 with the following mutations: L18F-D80A-D215G-L242-244del-R246I-K417N-E484K-N501Y-D614G-A701V (the B.1.351 Spike protein) twice. Each animal receives two doses of 25 μg, 5 μg, or 1 μg. The hamsters are then challenged with the RSA isolate to determine whether the titers generated are protective against the isolate.

In another study, hamsters are vaccinated with mRNA encoding the B.1.351 Spike protein twice. Each animal receives two doses of 25 μg, 5 μg, or 1 μg. The hamsters are then challenged with the RSA isolate or the WA1 isolate to determine whether the vaccine is protective against both isolates.

In a further study, animals are administered 25 μg, 5 μg, or 1 μg of an mRNA vaccine comprising mRNA encoding Spike protein with two proline substitutions in combination with mRNA encoding the B.1.351 Spike protein and then challenged with the WA1 isolate to determine whether the vaccine mediates protection against the challenge and whether the dose of the vaccine influences the immunity and protection.

In another study, animals are administered two doses of an mRNA vaccine comprising mRNA encoding Spike protein with two proline substitutions. The animals are then administered a 25 μg booster dose of the vaccine or 5 μg of a vaccine comprising mRNA encoding the B.1.351 Spike protein or a 1 μg of a vaccine comprising both an mRNA vaccine comprising mRNA encoding Spike protein with two proline substitutions (0.5 μg) and an mRNA encoding the B.1.351 Spike protein (0.5 μg).

Example 12: In Vitro Neutralization Screening

Figure 7:
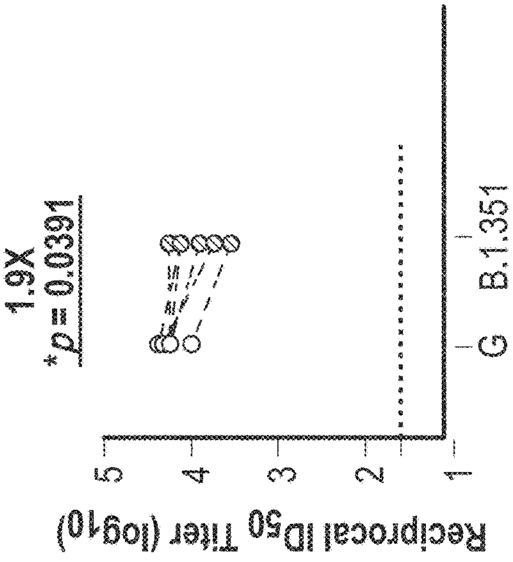
FIG. 7 shows neutralization titers of murine serum samples. Serum was from mice administered 1 μg of mRNA encoding a Spike protein having the D614G mutation. G=D614 variant.
Figure 7:
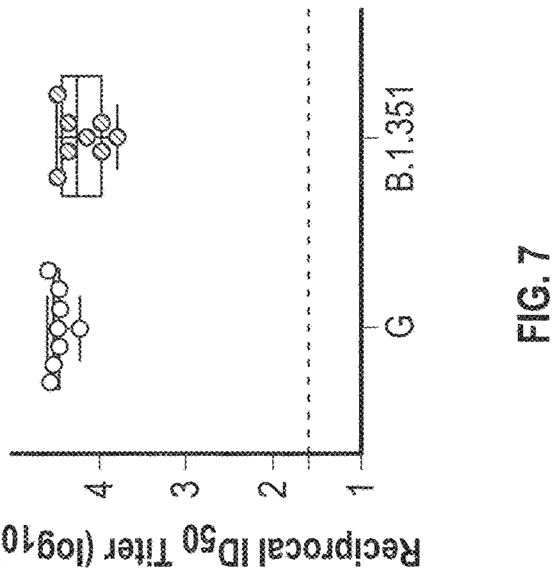
Figure 7:
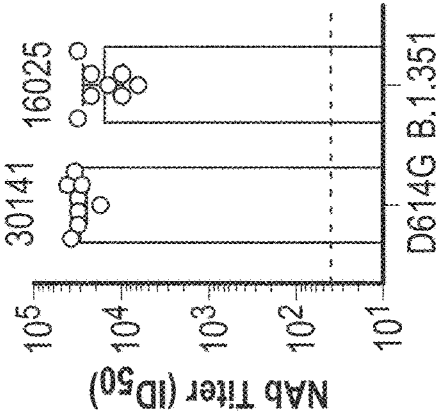

Codon-optimized full-length spike protein of the D614G variant or the spike protein of the B.1.351 variant were cloned into a pCAGGS vector. For the neutralization assay, serially diluted serum samples were mixed with pseudovirus and incubated at 37° C. for 45 minutes. The serum samples were from mice that had been administered 1 μg of mRNA encoding a Spike protein with two proline substitutions or mRNA encoding the D614G antigen. The virus-serum mix was subsequently used to infect A549-hACE2-TMPRSS2 cells for 18 hours at 37° C. before measuring neutralizing antibody titers. The results are shown in FIGS. 6 and 7 and demonstrate that the mRNA encoding a Spike protein with two proline substitutions had a 5-fold decrease in neutralization titer against the B.1.351 variant compared to the titer resulting from the D614G pseudovirus, while the mRNA encoding the D614G antigen resulted in a 1.9-fold decrease in neutralization titer between the D614 variant and the B.1.351 variant.

Example 13: Immunization of Human Subjects with a Wild-Type or Strain-Matched Booster Doses Human clinical trial participants were immunized by administration of two doses with 100 μg mRNA-1273 as described in Example 1. About 6 months after receiving the second dose of mRNA-1273, participants were administered a 3rd dose (booster dose) of either 50 μg mRNA-1273 (FIGS. 13A-13E), 50 μg mRNA-1273.351 (FIGS. 14A-14E), which encoded a 2P-stabilized SARS-CoV-2 Spike protein comprising the mutations associated with the B.1.351 SARS-CoV-2 variant. Sera were collected from participants immediately prior to administration of the booster dose (D1 or Day 1 in FIGS. 13A-15E), and again two weeks after administration of the booster dose (D15 or Day 15 in FIGS. 13A-15E). Sera from each time point were evaluated using a pseudovirus neutralization assay as described in Examples 1 and 12 to quantify neutralizing antibody titers towards pseudoviruses expressing one of 1) a D614G Spike protein, 2) a Spike protein with the mutations associated with the B.1.351 variant (B.1.351 Spike protein), or 3) a Spike protein with the mutations associated with the P.1 variant (P.1 Spike protein). The results of these neutralization assays, and the effects of each booster dose, are shown in FIGS. 13A-15E.

Figure 13B:
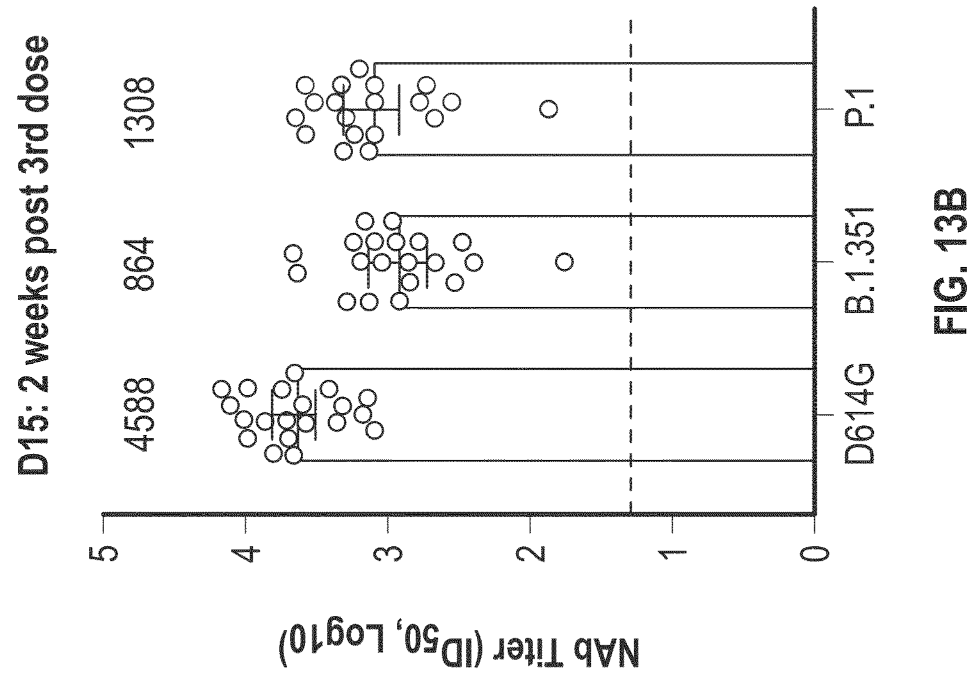
FIGS. 13A-13E show neutralizing antibody titers in humans following 2 doses of 100 μg mRNA-1273 (dose 1 on day 1 and dose 2 on day 22), and a $3^{rd}$ dose (booster dose) with 50 μg of mRNA-1273 6.2 to 6.7 months after day 1.
Figure 13A:
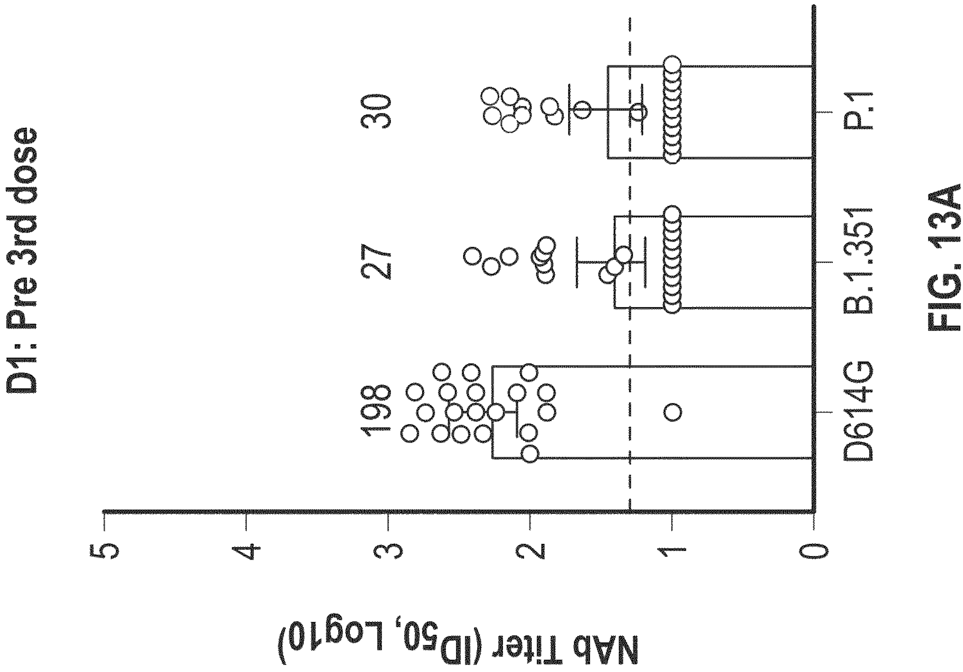
Figure 13E:
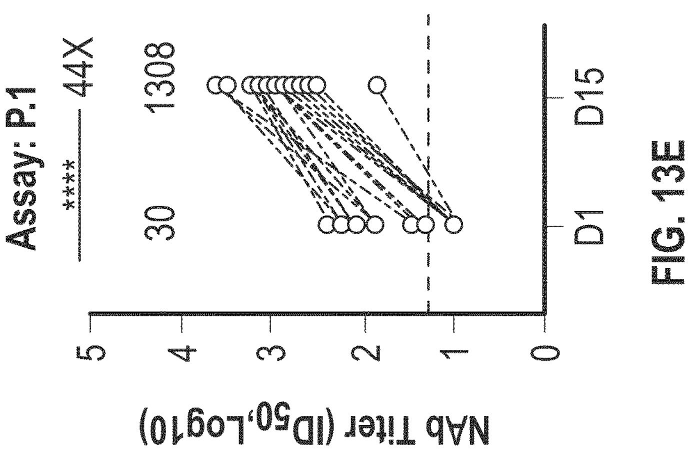
Figure 13D:
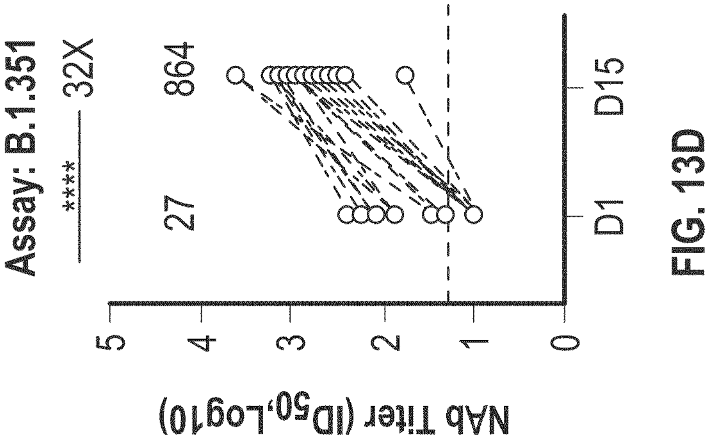
Figure 13C:
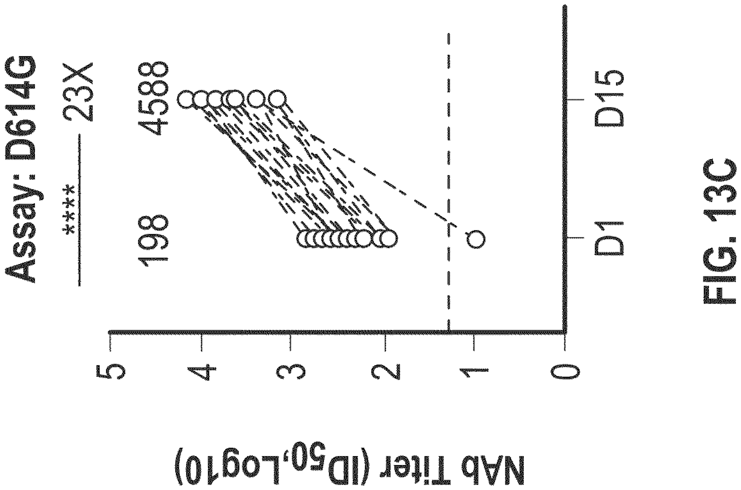
Figure 14B:
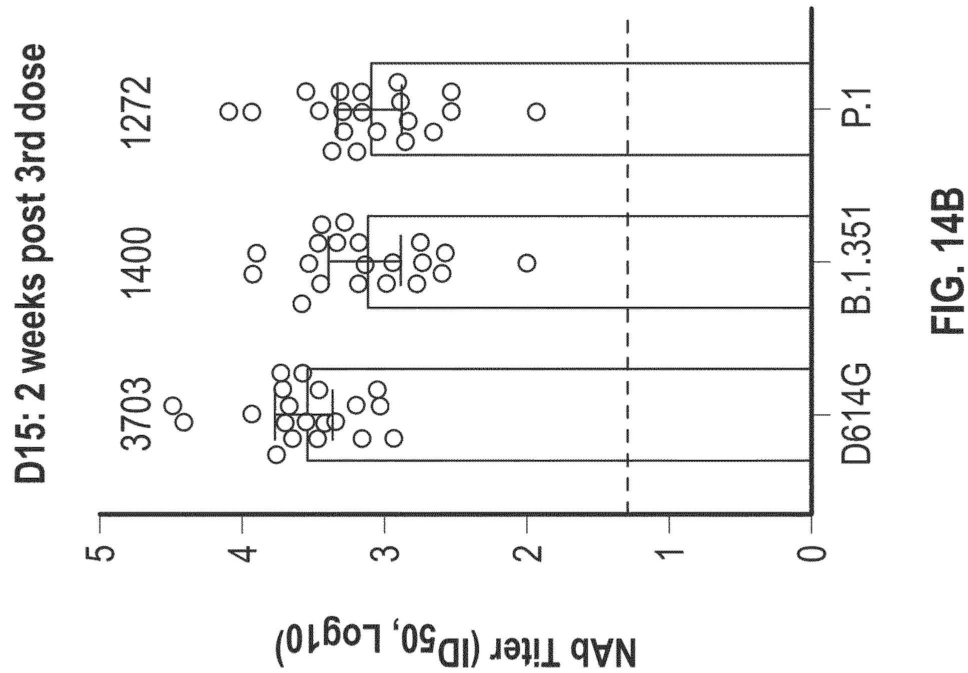
FIGS. 14A-14E show neutralizing antibody titers in humans following 2 doses of 100 μg mRNA-1273 (dose 1 on day 1 and dose 2 on day 22), and a $3^{rd}$ dose (booster dose) with 50 μg of mRNA-1273.351 6.2 to 6.7 months after day 1.
Figure 14A:
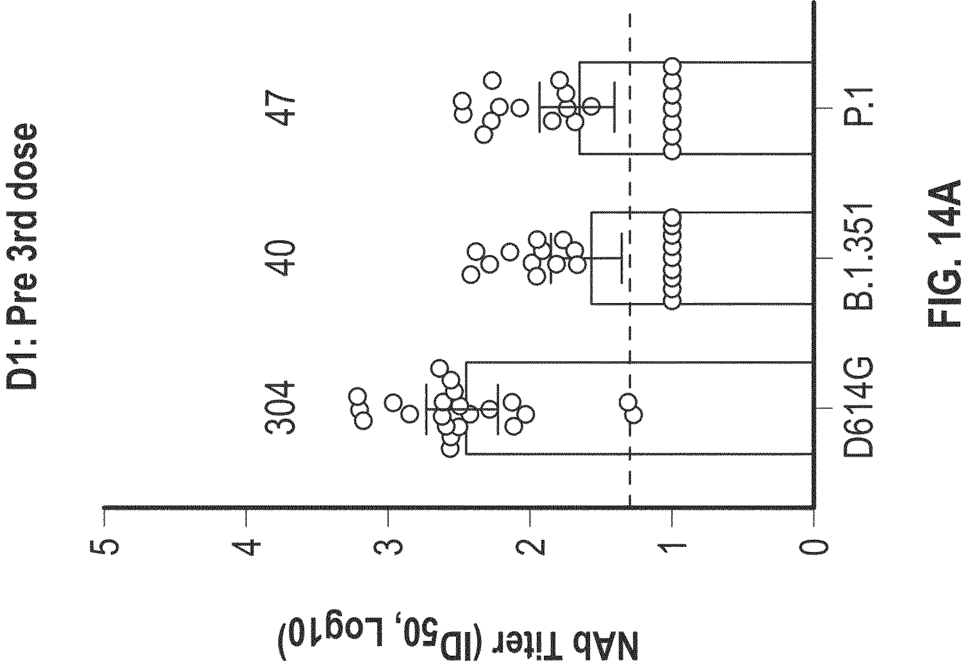
Figure 14E:
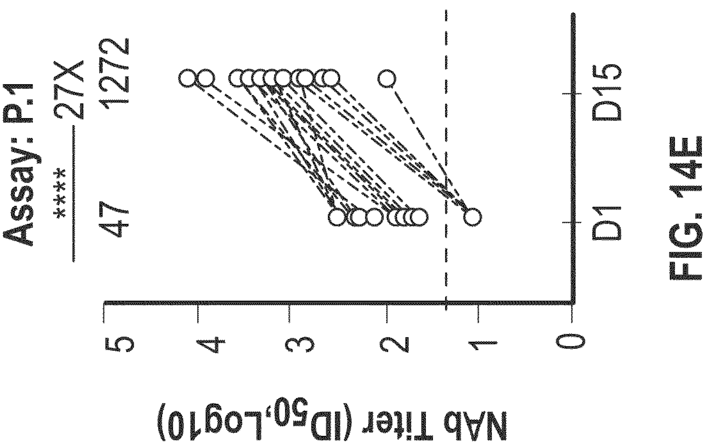
Figure 14D:
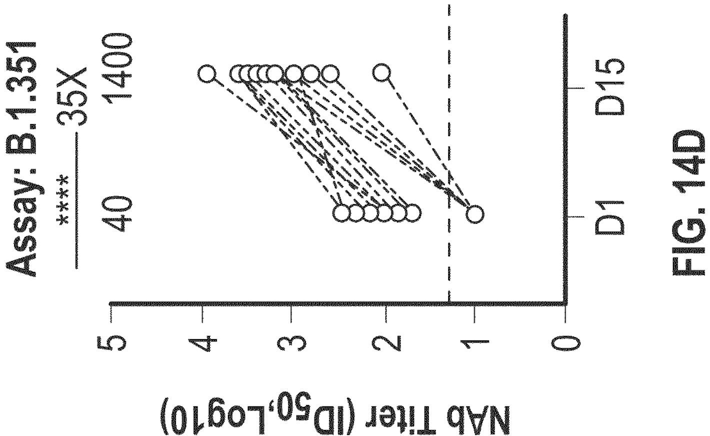
Figure 14C:
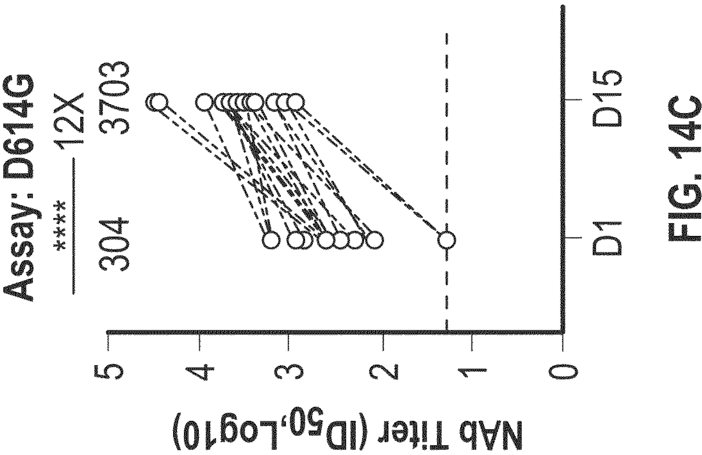
Figure 15A:
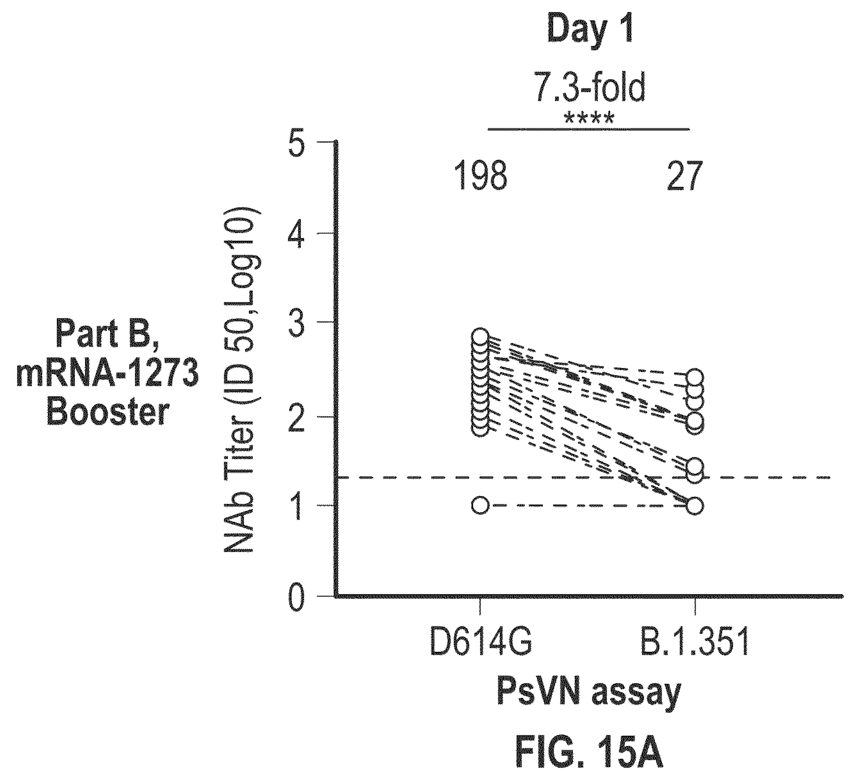
FIGS. 15A-15E show neutralizing antibody titers towards D614G and B.1.351 SARS-CoV-2 pseudoviruses, of sera from human participants administered two doses of mRNA-1273 and boosted with a $3^{rd}$ dose of either mRNA-1273, or mRNA-1273.351 encoding a Spike protein with the mutations associated with the B.1.351 variant.
Figure 15B:
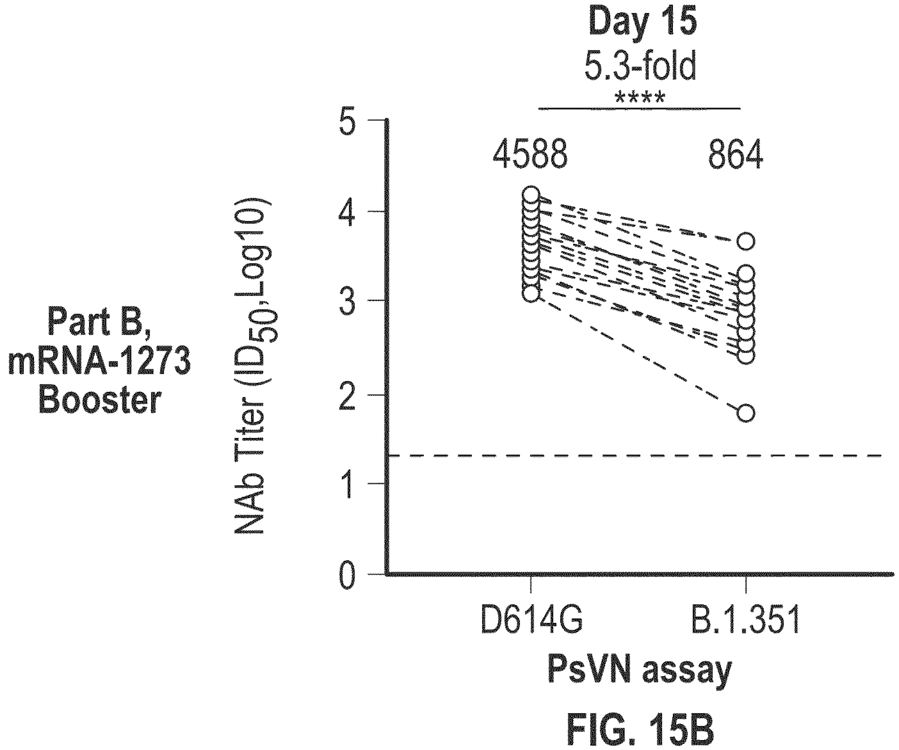
Figure 15C:
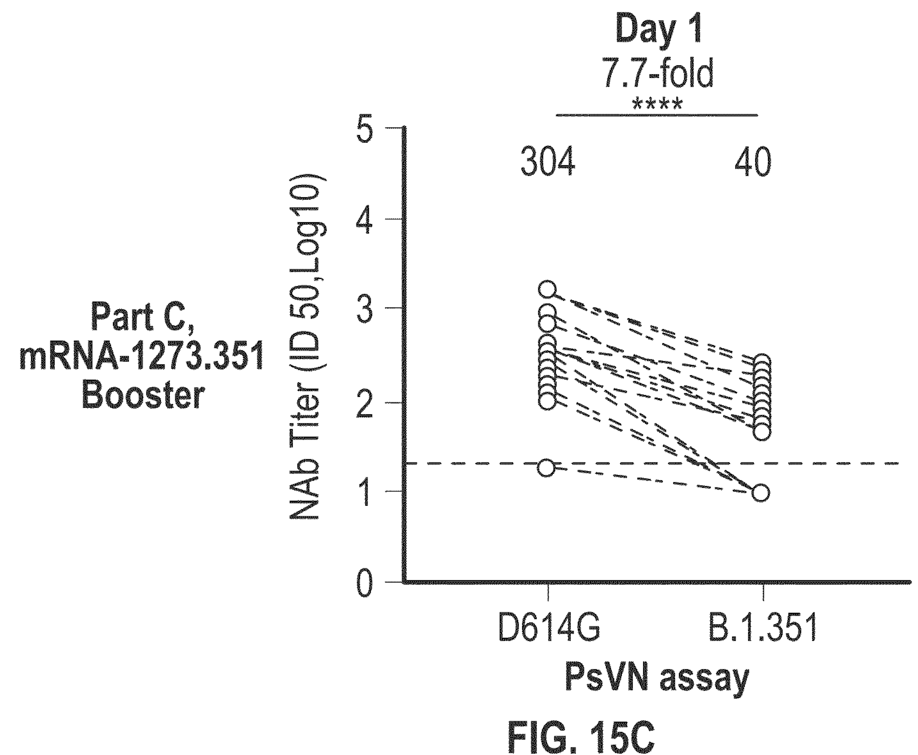
Figure 15D:
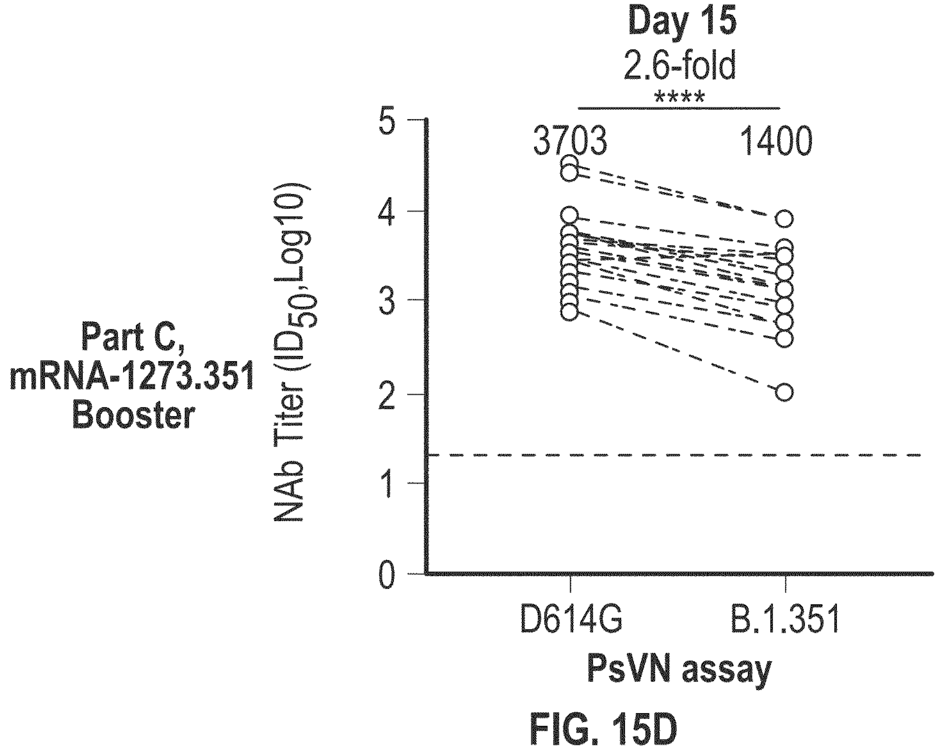
Figure 15E:
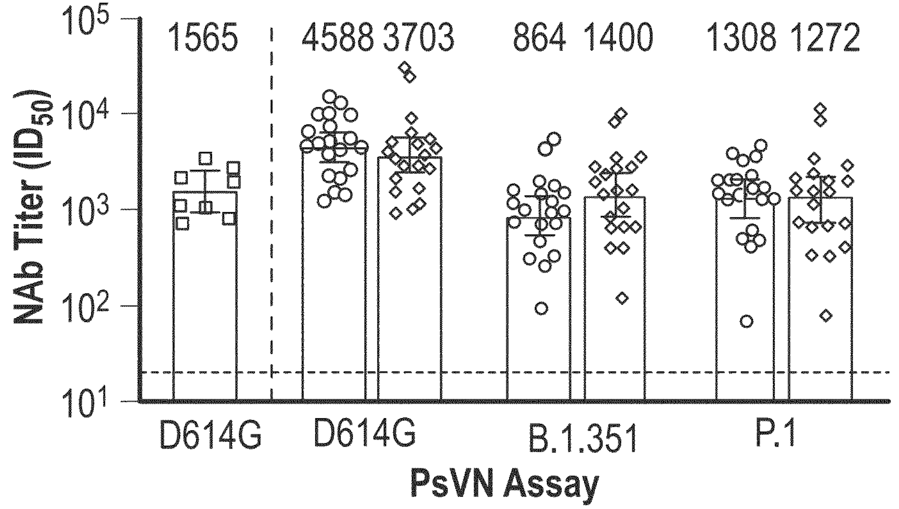

Six months after the second dose of mRNA-1273, and prior to the administration of booster doses, all groups still demonstrated neutralizing antibodies towards D614G Spike protein, but had minimal ability to neutralize B.1.351 or P.1 Spike proteins (FIGS. 13A, 14A). Administration of either the mRNA-1273 or mRNA-1273.351 booster dose (e.g., third total dose) markedly increased neutralizing antibody titers towards D614G, B.1.351, and P.1 Spike proteins, up to 44-fold compared to titers prior to booster dose administration (FIGS. 13C-13E, 14C-14E). Neutralizing antibody titers towards B.1.351 Spike protein were approximately 1.5 times greater in subjects administered the strain-matched mRNA-1273.351 booster dose (i.e., third total dose) instead of mRNA-1273, suggesting that strain-matched mRNA vaccines are effective at generating a robust antibody response towards the encoded protein (FIG. 13B, 14B). While mRNA-1273 elicited neutralizing antibodies towards D614G, B.1.351, and P.1 Spike proteins, neutralizing antibody titers towards B.1.351 Spike protein were uniformly lower than titers towards the D614G Spike protein (7.3-fold on day 1, 5.3-fold on day 15) (FIGS. 15A-15B). By contrast, administration of mRNA-1273.351 ameliorated this reduction in B.1.351-neutralizing titers relative to D614G-neutralizing titers, improving the difference from a 7.7-fold decrease prior to booster (third dose) administration, to a reduction of only 2.6-fold after mRNA-1273.351 booster (third dose) administration (FIGS. 15C-15D). Administration of either booster dose (third dose) elicited neutralizing antibodies towards B.1.351 and P.1 Spike proteins at titers that were comparable to those observed towards D614G Spike protein at 1 week after the second dose of mRNA-1273, suggesting mRNA-1273.351 is capable of eliciting a robust response to B.1.351 and other Spike proteins including the D614G strain (FIG. 15E). Surprisingly, both boosters increased neutralizing titers towards D614G Spike protein to titers that were 2- to 3-fold greater than those observed towards the same protein 1 week after the second dose of mRNA-1273, suggesting booster doses are useful for maintaining and even increasing neutralizing antibody responses to antigens encoded by previously administered mRNA vaccines.

Further reductions in the differences between the two assays may be found in samples collected from these participants at later timepoints, as the kinetics of the neutralizing antibody responses to the new epitopes in S-2P.351 protein encoded by mRNA-1273.351 may be different from the epitopes shared between the two immunogens. Strong homologous responses, both in terms of absolute titer and fold rise, assessed by the same strain in the assay used in the vaccine, were seen regardless of vaccine strain. Response to the wild-type virus was highest with boost of mRNA-1273 and response to B.1.351 was highest with mRNA-1273.351. In addition, heterologous responses, against variants when prototype vaccine was used to boost or against prototype after the mRNA-1273.351 booster were also seen. This supports the development of a variant vaccine as a booster dose to prevent infection caused by variant strains.

Figure 16A:
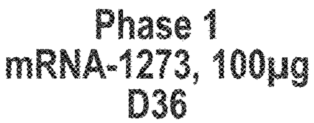
FIGS. 16A-16C show neutralizing antibody titers towards pseudoviruses expressing variant SARS-CoV-2 Spike proteins, of sera obtained from human participants administered two doses of 100 μg mRNA-1273 (FIGS. 16A-16B), and optionally administered a booster dose of 50 μg mRNA-1273, 50 μg mRNA-1273.351 encoding a B.1.351 variant Spike protein, or 50 μg of mRNA-1273.211 (1:1 mixture of mRNA-1273 and mRNA-1273.351) (FIG. 16C).
Figure 16A:
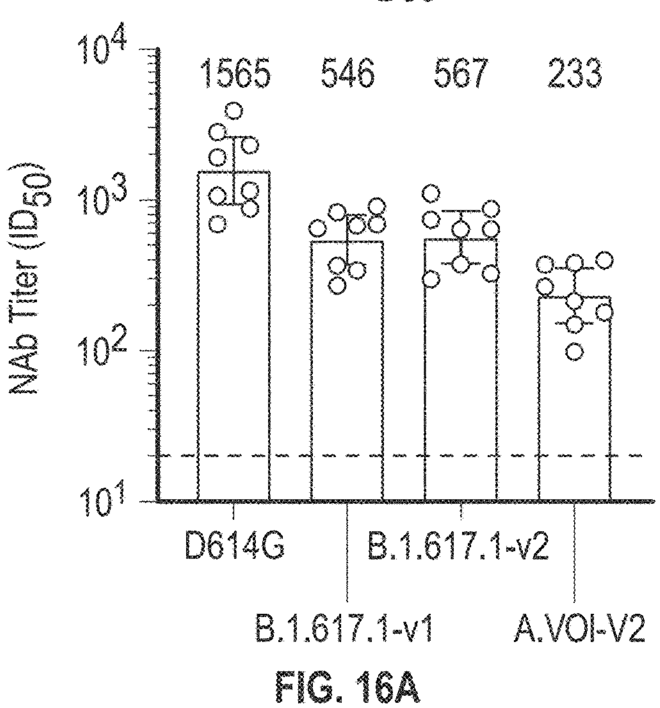
Figure 16B:
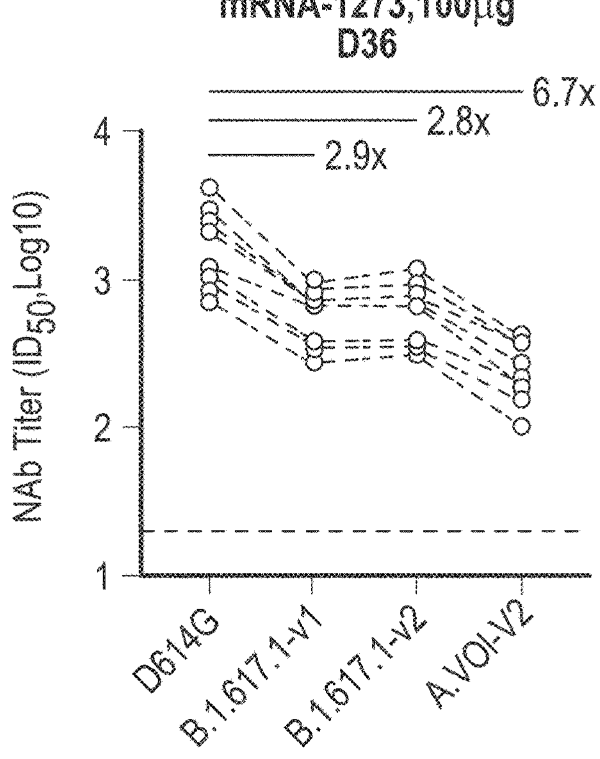
Figure 16C:
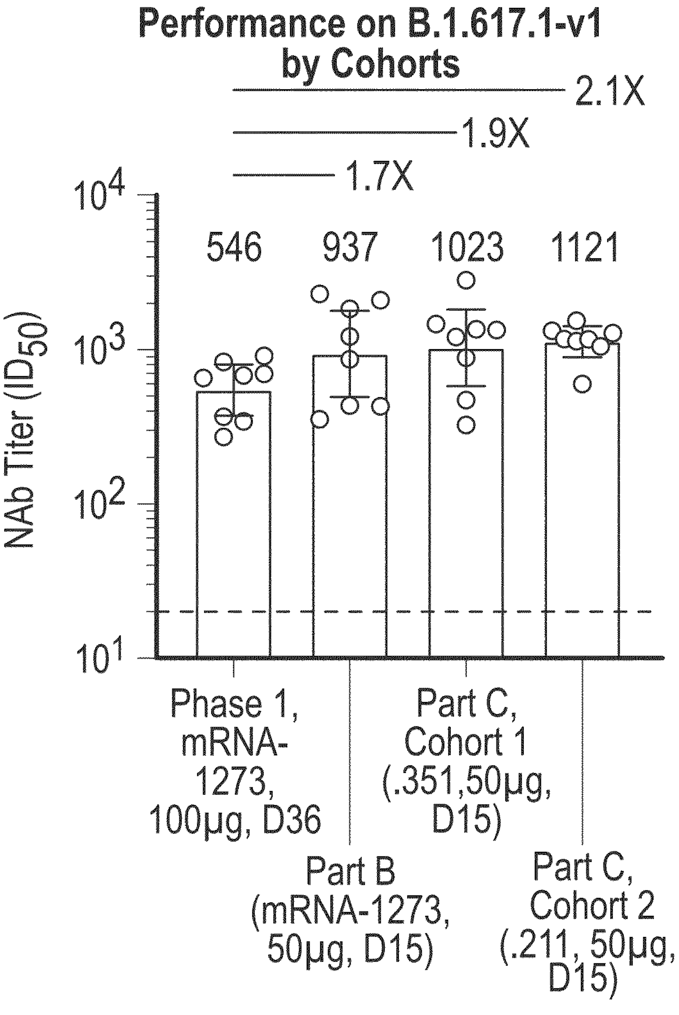

Example 14: Neutralization of Variant Spike Proteins by Antibodies Elicited after Two Doses of mRNA Encoding 2P-Stabilized Spike Protein Human subjects were immunized with two doses of 100 μg mRNA-1273, as described in Example 13. Sera collected at day 36, two weeks after the $2^{nd}$ dose with mRNA-1273, and evaluated for neutralizing antibody titers towards variant Spike proteins of the B.1.617.1-v1, B.1.617.1-v2, and A.VOI-V2 in a pseudovirus neutralization assay. The results of these neutralization assays are shown in FIGS. 16A-16C. Neutralizing antibody titers towards either B.1.617 variant Spike protein were about 3-fold lower than titers towards the reference D614G Spike protein, and 6.7-fold lower towards the A.VOI-V2 Spike protein than to D614G (FIGS. 16A-16B).

The booster doses described in Example 13; of 50 μg of either mRNA-1273, mRNA-1273.351, or mRNA-1273.211 (1:1 mixture of mRNA-1273 and mRNA-1273.351, 25 μg each) were administered and sera were collected 15 days later and tested for neutralizing antibody titers towards the B.1.617-v1 Spike protein. Relative to day 36 sera from subjects immunized with two doses of 100 μg mRNA-1273, these 50 μg booster doses improved neutralizing antibody titers towards the B.1.617-v1 Spike protein by 1.7- to 2.1-fold (FIG. 16C). Booster doses containing mRNA-1273.351, either alone or in combination, resulted in greater increases than mRNA-1273 alone. These results indicate that while neutralizing antibody titers may be lower towards variant Spike proteins than the Spike protein encoded by an initial administered mRNA, booster doses are capable of eliciting antibodies towards variant Spike proteins to provide some protection against heterologous SARS-CoV-2 infections.

Example 15: Immunization with $3^{rd}$ and $4^{th}$ Booster Doses of mRNAs Encoding Variant Spike Proteins at 6 Months BALB/c mice, 6-8 weeks of age, were administered either 1 μg (FIGS. 17A-17D) or 0.1 μg (FIGS. 18A-18D) of mRNA-1273, or PBS (as a control) intramuscularly in one hind leg (formulated as a 50 μL dose) on day 1 (1st dose, prime) and day 22 (2nd dose, booster). At days 213 (3rd dose) and 234 (4th dose), mice were administered either 1 μg (FIGS. 17A-17D) or 0.1 μg (FIGS. 18A-18D) of mRNA-1273.351, which contained the mutations associated with the B.1.351 variant. In each vaccine, the mRNA was formulated in lipid nanoparticles (LNPs) including 0.5-15% PEG-modified lipid, 5-25% non-cationic lipid, 25-55% sterol, and 20-60% ionizable amino lipid. The PEG-modified lipid was 1,2 dimyristoyl-sn-glycerol, methoxypolyethyleneglycol (PEG2000 DMG), was non-cationic lipid is 1,2 distearoyl-sn-glycero-3-phosphocholine (DSPC), the sterol was cholesterol, and the ionizable amino lipid had the structure of Compound 1, for example. Sera were collected from mice on days 212 (prior to 3rd dose), 233 (21 days after 3rd dose, prior to 4th dose), and 248 (14 days after 4th dose), and analyzed for neutralization titers against VSV-based pseudoviruses expressing a SARS-CoV-2 Spike protein comprising either 1) a D614G mutation relative to the sequence of the WH2020 full-length Spike protein, or 2) mutations associated with the B.1.351 variant.

Figure 17A:
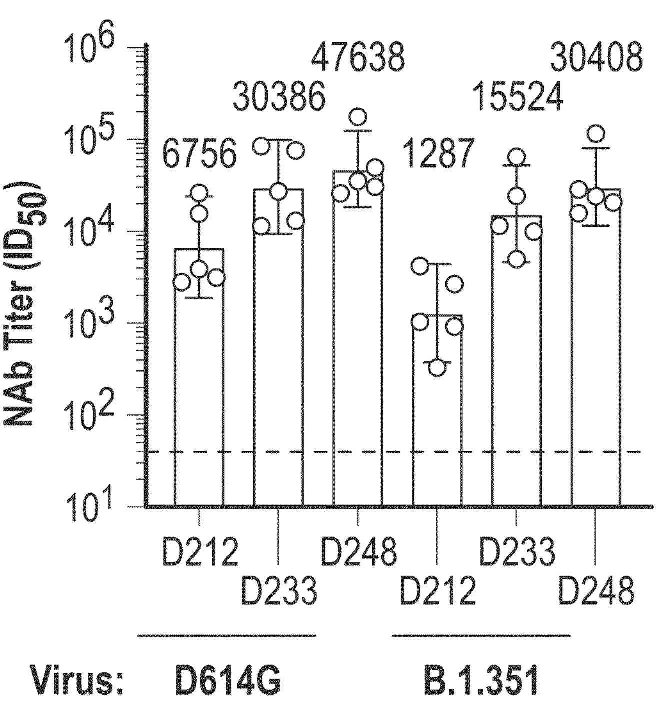
FIGS. 17A-17D show neutralization titers of murine serum samples. Sera was obtained from mice that were administered 1 μg of mRNA-1273 on day 1 (prime dose) and again on day 22 (booster dose). Mice were administered 1 μg of mRNA-1273.351, encoding a Spike protein with the mutations associated with the B.1.351 SARS-CoV-2 variant, on day 213 (3rd dose), and day 234 (4th dose). Samples were taken at day 212 (before administration of the 3rd dose), day 233 (before administration of the 4th dose), and day 248 (14 days after administration of the 4th dose).
Figure 17B:
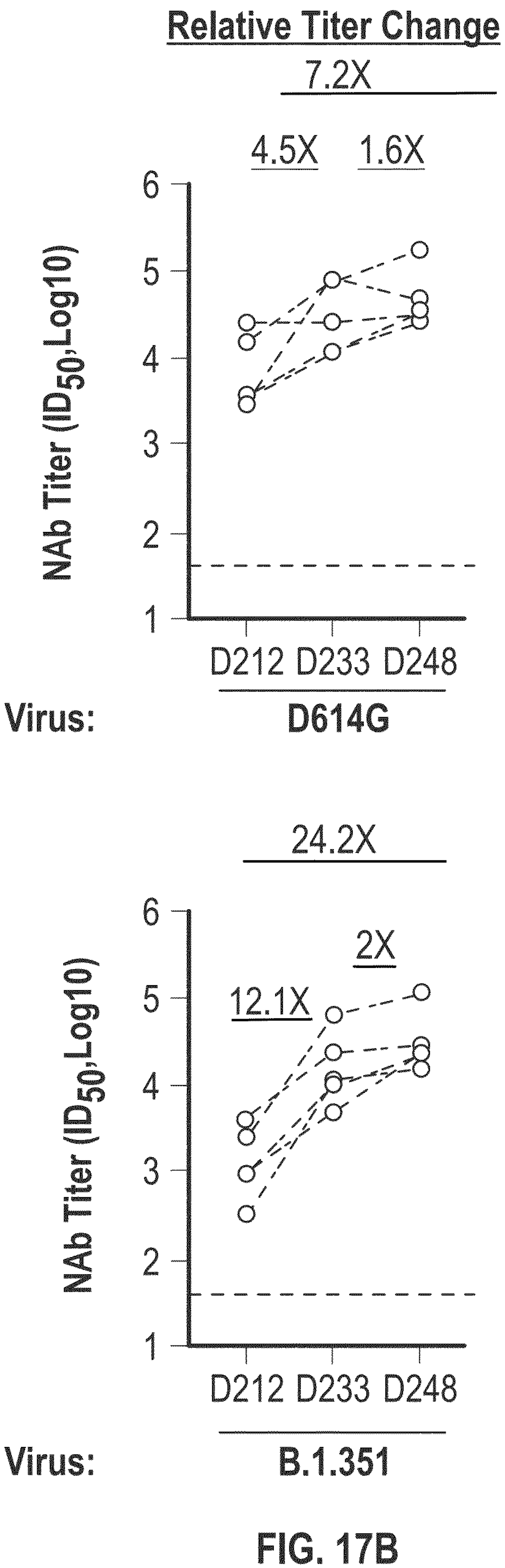
Figure 17C:
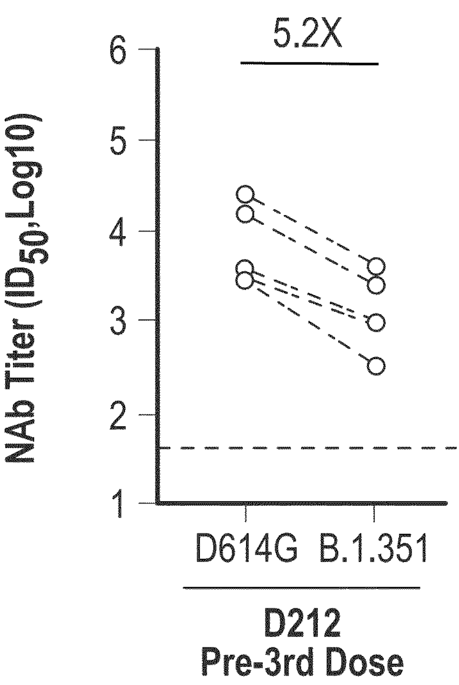
Figure 17C:
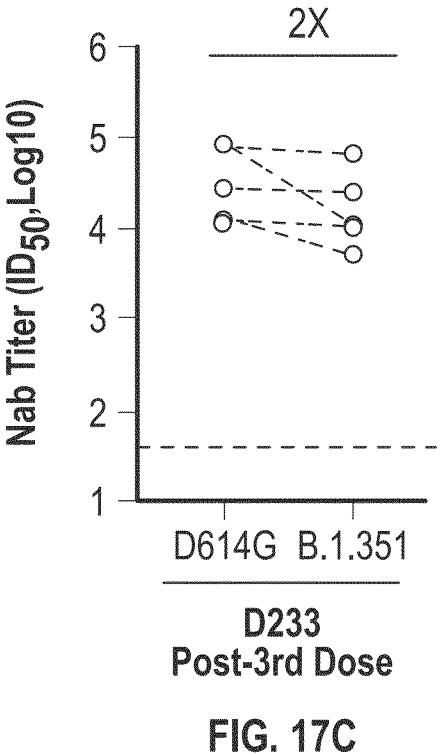
Figure 17C:
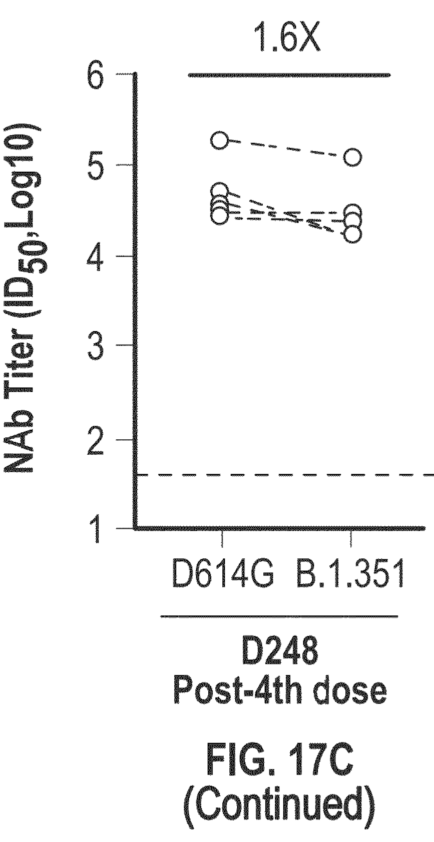
Figure 17D:
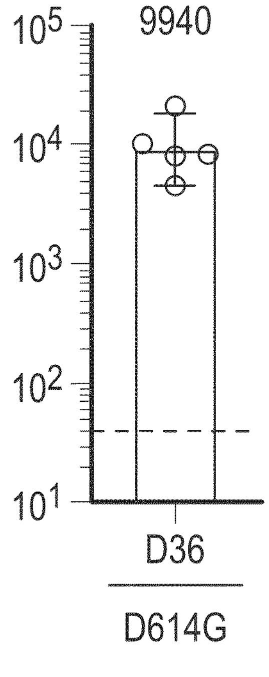

For mice administered 1 μg doses of mRNA in each vaccine, the results of these neutralization assays are shown in FIGS. 17A-17D. Each of the 3rd and 4th doses increased mean neutralization titers of sera against the D614G and B.1.351 Spike proteins (FIG. 17A). Neutralization titers towards each Spike protein increased over time, with this increase being more pronounced in neutralization titers towards the B.1.351 Spike protein (FIG. 17B). Prior to the 3rd dose, sera were approximately 5.2 times as effective at neutralizing the D614G Spike protein than the B.1.351 Spike protein (FIG. 17C). However, after each of the 3rd and 4th-doses, the reduction was less pronounced, with sera neutralizing the D614G Spike protein only 2-fold as well as the B.1.351 Spike protein after the $3^{rd}$ dose, and 1.6-fold as well after the 4th dose (FIG. 17C). Additionally, neutralization titers towards either Spike protein after the 4th dose were over 3-fold greater than reference neutralization titers towards the D614G Spike protein at day 36, 14 days after the 2nd dose (FIGS. 17A, 17D). These results indicate that the administration of mRNAs encoding variant Spike proteins effectively elicited neutralizing antibodies towards the variant Spike protein, and boost the antibody response to Spike proteins encoded by previously administered mRNAs.

Figure 18A:
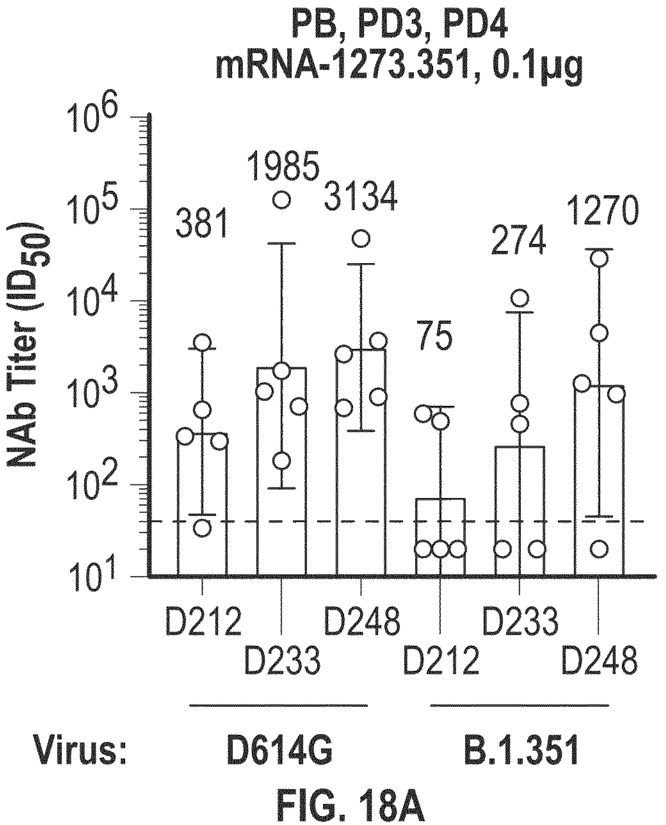
FIGS. 18A-18D show neutralization titers of murine serum samples. Sera was obtained from mice that were administered 0.1 μg of mRNA-1273 on day 1 (prime dose) and again on day 22 (booster dose). Mice were administered 0.1 μg of mRNA-1273.351, encoding a Spike protein with the mutations associated with the B.1.351 SARS-CoV-2 variant, on day 213 (3rd dose), and day 234 (4th dose). Samples were taken at day 212 (before administration of the 3rd dose), day 233 (before administration of the 4th dose), and day 248 (14 days after administration of the 4th dose).
Figure 18B:
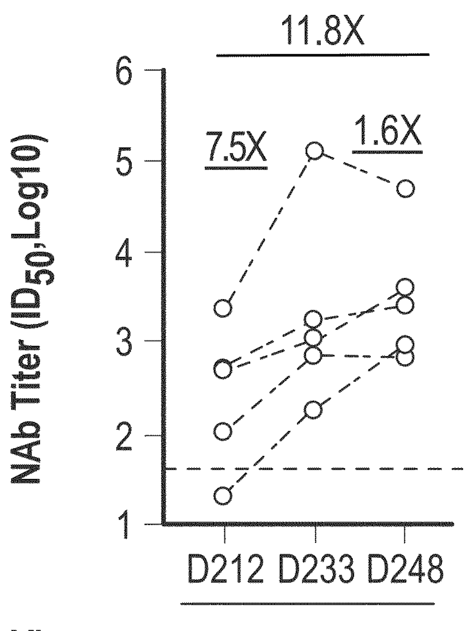
Figure 18B:
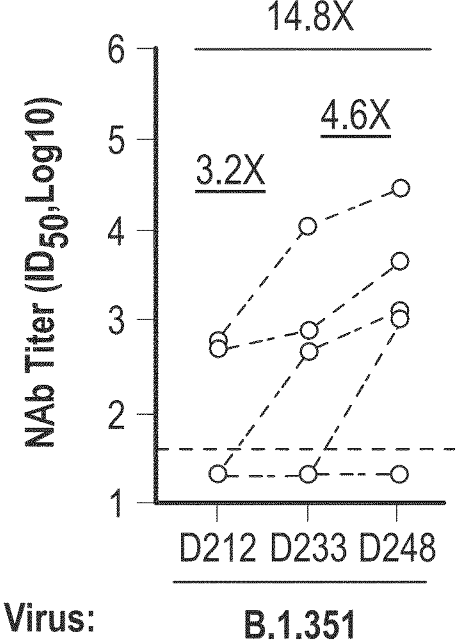
Figure 18C:
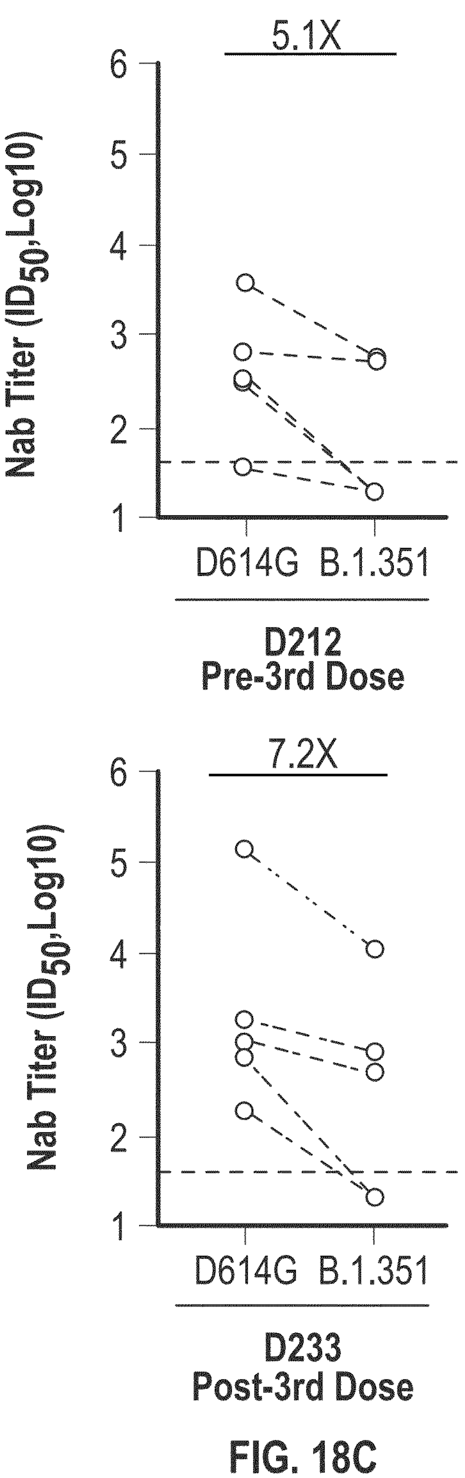
Figure 18C:
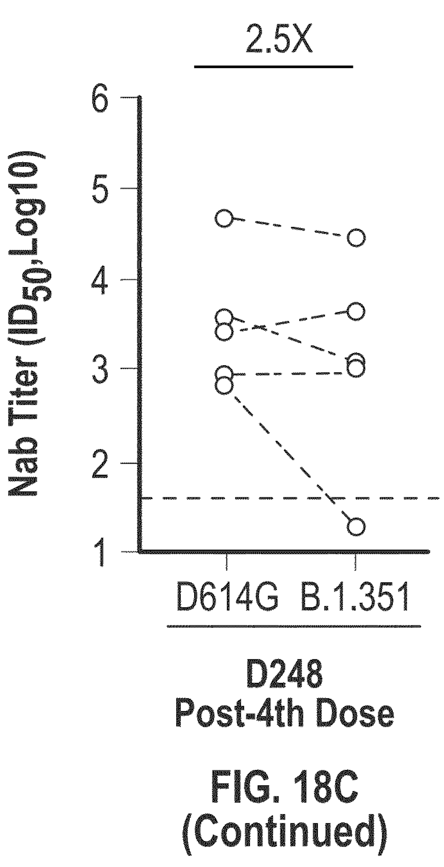
Figure 18D:
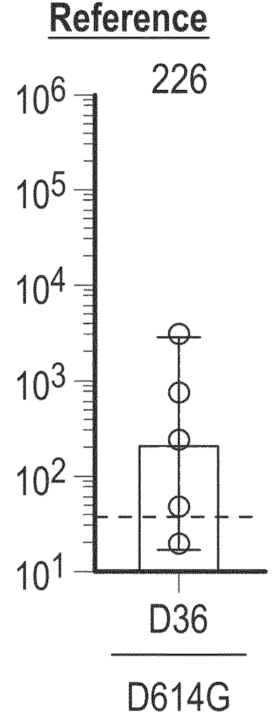

For mice administered 0.1 μg doses of mRNA in each vaccine, the results of these neutralization assays are shown in FIGS. 18A-18D. Each of the 3rd and 4th doses increased mean neutralization titers of sera against the D614G and B.1.351 Spike proteins (FIG. 18A). Neutralization titers towards each Spike protein increased over time, with this increase being more pronounced in neutralization titers towards the B.1.351 Spike protein (FIG. 18B). Prior to the 3rd dose, sera were approximately 5.1 times as effective at neutralizing the D614G Spike protein than the B.1.351 Spike protein (FIG. 18C). However, after the 4th dose, this reduction was less pronounced, with sera neutralizing the D614G Spike-protein only 2.5 times as well as the B.1.351 Spike protein (FIG. 18C). Additionally, neutralization titers towards either Spike protein after the 4th dose were over 5-fold greater than reference neutralization titers towards the D614G Spike protein at day 36, 14 days after the 2nd dose (FIGS. 18A, 18D). These results indicate that the administration of mRNAs encoding variant Spike proteins effectively elicited neutralizing antibodies towards the variant Spike protein, and boost the antibody response to Spike proteins encoded by previously administered mRNAs.

Example 16: Immunization with $3^{rd}$ and $4^{th}$ Booster Doses of mRNAs Encoding Variant Spike Proteins at 2 Months BALB/c mice, 6-8 weeks of age, were administered either 1 μg (FIGS. 19A-19C) or 0.1 μg (FIGS. 20A-20C) of mRNA-1273, or PBS (as a control) intramuscularly in one hind leg (formulated as a 50 μL dose) on day 1 (1st dose, prime) and day 22 (2nd dose, booster). At days 58 (3rd dose) and 78 (4th-dose), mice were administered either 1 μg (FIGS. 19A-19D) or 0.1 μg (FIGS. 20A-20D) 1 μg of mRNA-1273.351, which contained the mutations associated with the B.1.351 variant. In each vaccine, the mRNA was formulated in lipid nanoparticles (LNPs) including 0.5-15% PEG-modified lipid, 5-25% non-cationic lipid, 25-55% sterol, and 20-60% ionizable amino lipid. The PEG-modified lipid was 1,2 dimyristoyl-sn-glycerol, methoxypolyethyleneglycol (PEG2000 DMG), was non-cationic lipid is 1,2 distearoyl-sn-glycero-3-phosphocholine (DSPC); the sterol was cholesterol, and the ionizable amino lipid had the structure of Compound 1, for example. Sera were collected from mice on days 57 (prior to 3rd dose), 77 (19 days after 3rd dose, prior to 4th dose), and 92 (14 days after 4th dose), and analyzed for neutralization titers against VSV-based pseudoviruses expressing a SARS-CoV-2 Spike protein comprising either 1) a D614G mutation relative to the sequence of the WH2020 full-length Spike protein, or 2) mutations associated with the B.1.351 variant.

Figure 19A:
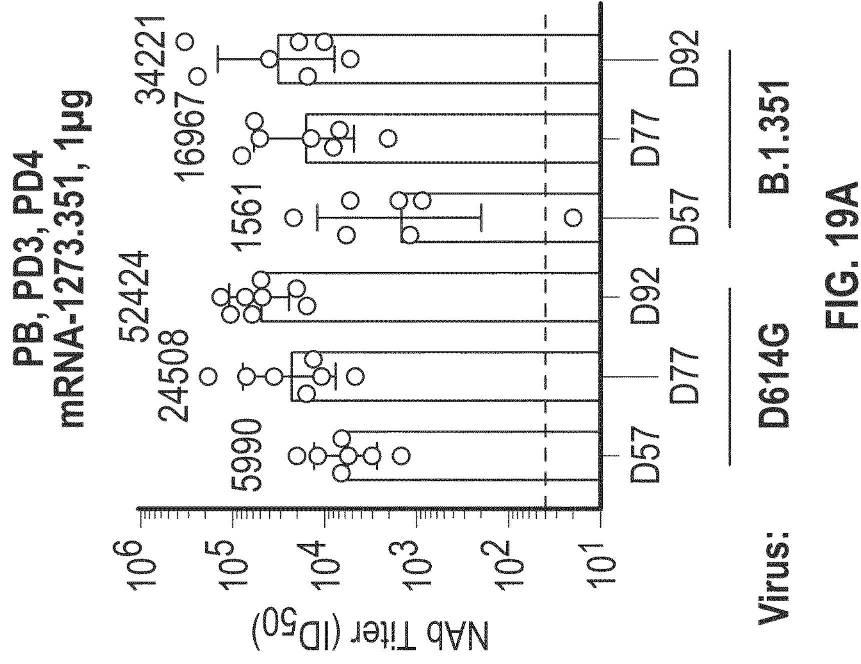
FIGS. 19A-19C show neutralization titers of murine serum samples. Sera was obtained from mice that were administered 1 μg of mRNA-1273 on day 1 (prime dose) and again on day 22 (booster dose). Mice were administered 1 μg of mRNA-1273.351, encoding a Spike protein with the mutations associated with the B.1.351 SARS-CoV-2 variant, on day 58 (3rd dose), and day 78 (4th dose). Samples were taken at day 57 (before administration of the 3rd dose), day 77 (before administration of the 4th dose), and day 92 (14 days after administration of the 4th dose).
Figure 19B:
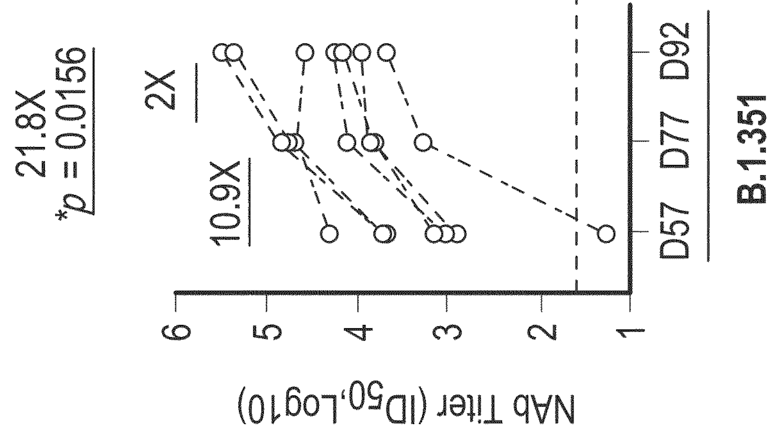
Figure 19B:
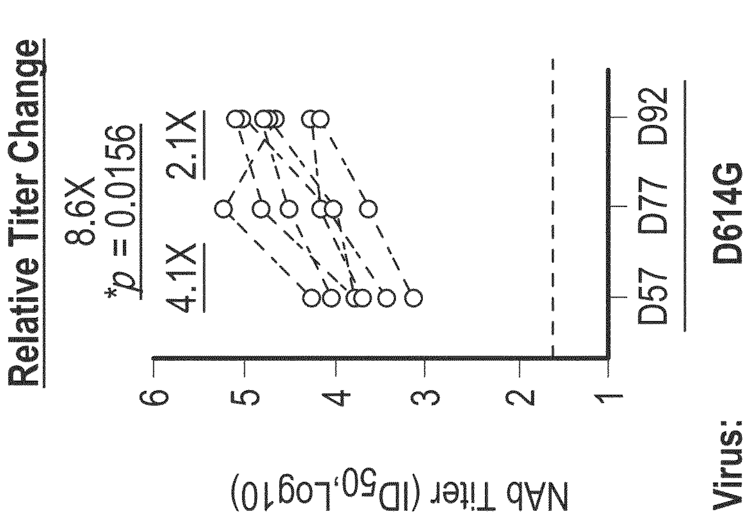
Figure 19C:
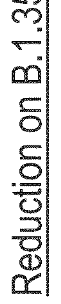
Figure 19C:
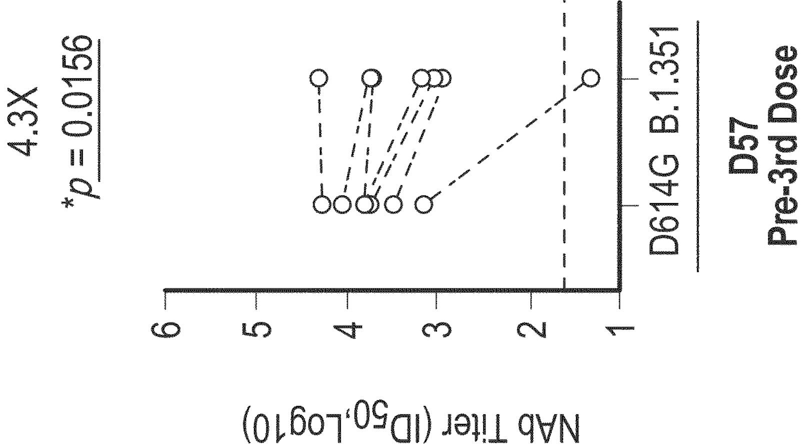
Figure 19C:
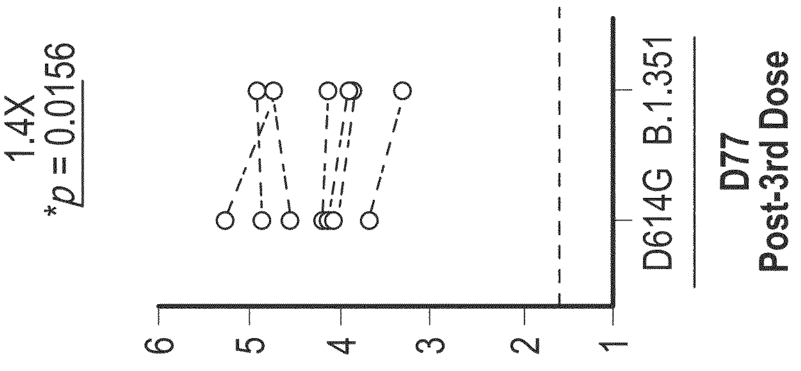
Figure 19C:
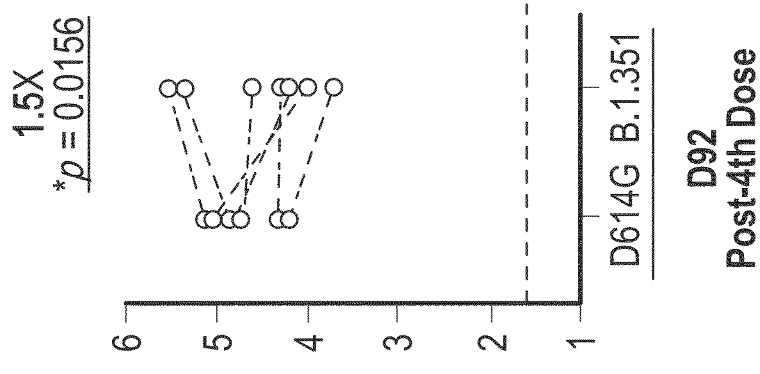

For mice administered 1 μg doses of mRNA in each vaccine, the results of these neutralization assays are shown in FIGS. 19A-19C. Each of the 3rd and 4th doses increased mean neutralization titers of sera against the D614G and B.1.351 Spike proteins (FIG. 19A). Neutralization titers towards each Spike protein increased over time, with this increase being more pronounced in neutralization titers towards the B.1.351 Spike protein (FIG. 19B). Prior to the 3rd dose, sera were approximately 4.3 times as effective at neutralizing the D614G Spike protein than the B.1.351 Spike protein (FIG. 19C). However, after each of the 3rd and 4th doses, the reduction was less pronounced, with sera neutralizing the D614G Spike protein only 1.4 times as well as the B.1.351 Spike protein after the $3^{rd}$ dose, and 1.5 times as well after the $4^{th}$ dose (FIG. 19C). These results indicate that the administration of mRNAs encoding variant Spike proteins effectively elicit neutralizing antibodies towards the variant Spike protein, and boost the antibody response to Spike proteins encoded by previously administered mRNAs.

Figures 20A, 20B:
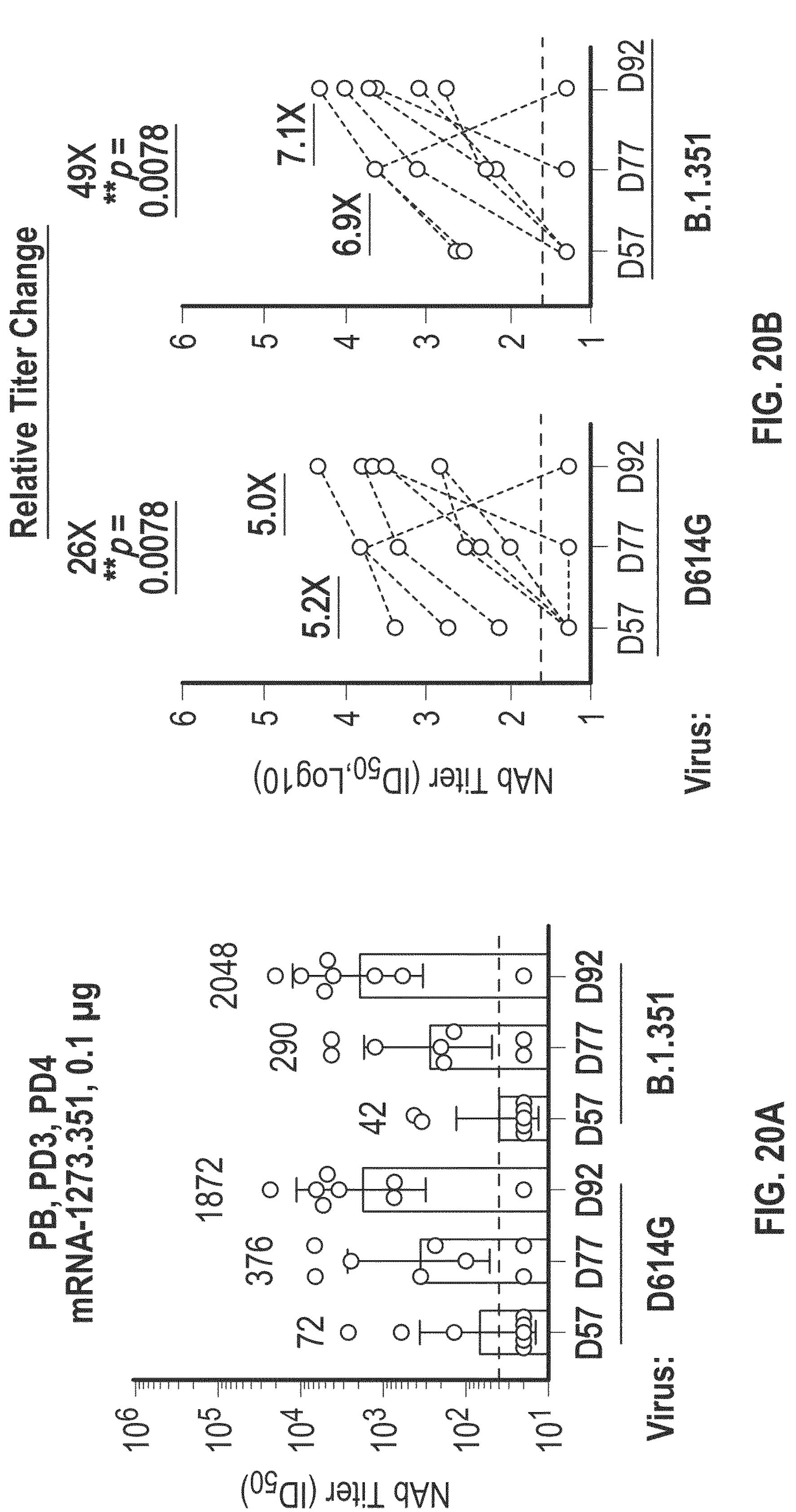

For mice administered 0.1 μg doses of mRNA in each vaccine, the results of these neutralization assays are shown in FIGS. 20A-20C. Each of the 3rd and 4th doses increased mean neutralization titers of sera against the D614G and B.1.351 Spike proteins (FIG. 20A). Neutralization titers towards each Spike protein increased over time, with this increase being more pronounced in neutralization titers towards the B.1.351 Spike protein (FIG. 20B). Prior to the 3rd dose, sera were approximately 3 times as effective at neutralizing the D614G Spike protein than the B.1.351 Spike protein (FIG. 20C). However, after each of the $3^{rd}$ and 4th doses, this reduction was less pronounced, with sera neutralizing the D614G Spike protein only 1.3 times as well as the B.1.351 Spike protein after the third dose, and neutralization titers towards both Spike proteins were approximately equivalent after the $4^{th}$ dose (FIG. 20C). These results indicate that the administration of mRNAs encoding variant Spike proteins effectively elicit neutralizing antibodies towards the variant Spike protein, and boost the antibody response to Spike proteins encoded by previously administered mRNAs.

Figure 21A:
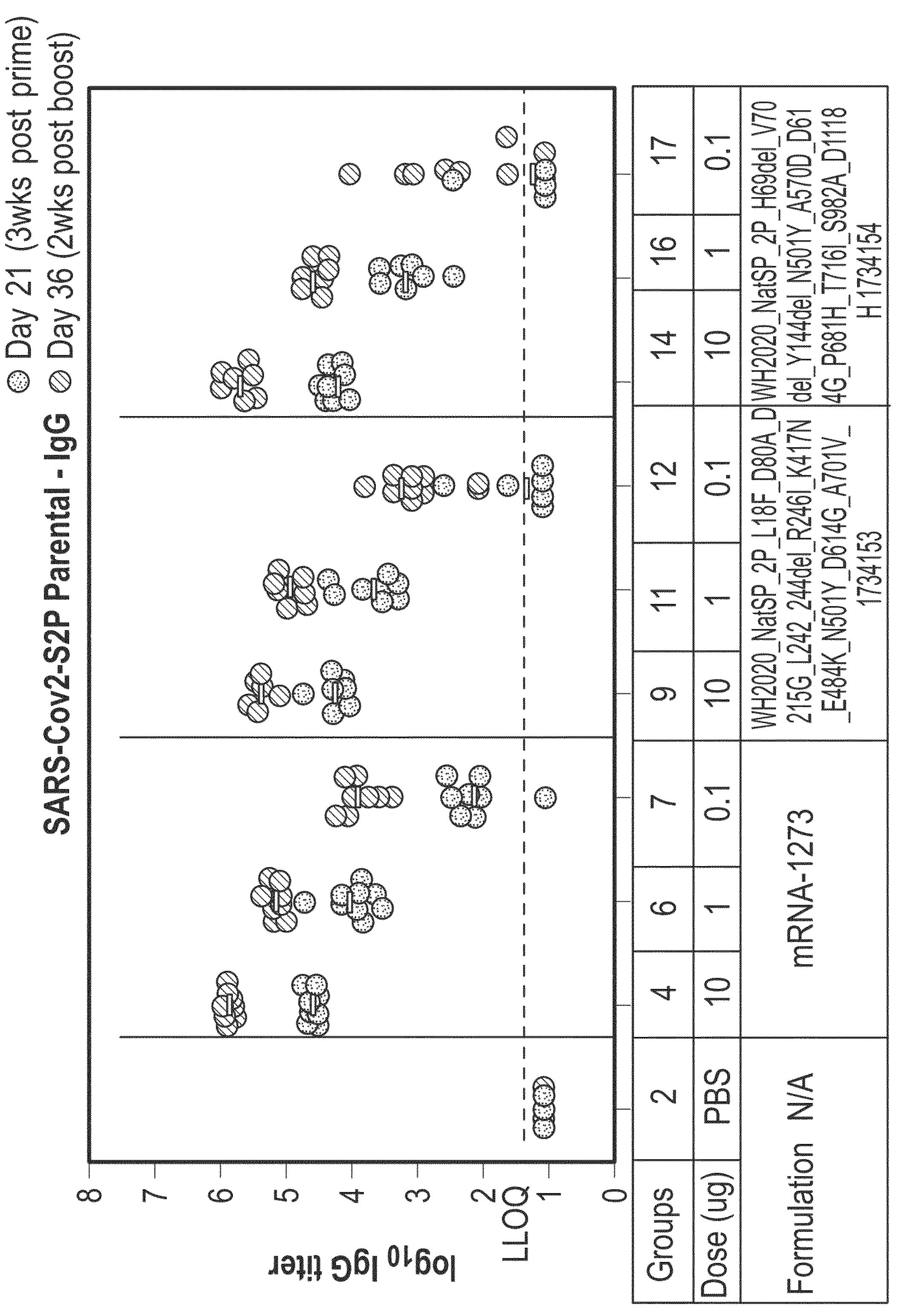
FIGS. 21A-21H show Spike protein-specific IgG and neutralization titers of murine serum samples. Sera were collected from mice administered 10, 1, or 0.1 μg mRNA encoding a 2P-stabilized from of the wild-type Spike protein (mRNA-1273), B.1.351 Spike protein (mRNA-1273.351), or B.1.1.7 Spike protein (mRNA-1273.117) on day 1 (prime dose), and again on day 22 (2nd dose). Sera were collected at day 36 (14 days after 2nd dose).

Example 17: Immunization with Two Doses of mRNAs Encoding Variant Spike Proteins to Generate Neutralizing Antibodies to Variant Spike Proteins in Mice BALB/c mice, 6-8 weeks of age, were administered 0.1 μg, 1 μg, or 10 μg of mRNA encoding a SARS-CoV-2 antigen, specifically mRNA-1273, mRNA-1273.351, or mRNA-1273.117, encoding the Spike protein of the B.1.1.7 variant, or PBS (as a control) intramuscularly in one hind leg (formulated as a 50 μL dose) on day 1 ($1^{st}$ dose, prime) and day 22 ($2^{nd}$ dose, booster). Sera were collected from mice at days 21 (3 weeks after $1^{st}$ dose, before $2^{nd}$ dose), and 36 (2 weeks after $2^{nd}$ dose), and tested by ELISA to quantify total IgG specific to a parental SARS-CoV-2 Spike protein with the USA-WA1/2020 isolate amino acid sequence. Each $1^{st}$ dose of mRNA encoding a Spike protein antigen elicited a robust SARS-CoV-2 Spike protein-specific antibody response, with the $2^{nd}$ dose boosting IgG titers by 10- to 100-fold in each dose group (FIG. 21A).

Figures 21B, 21C:
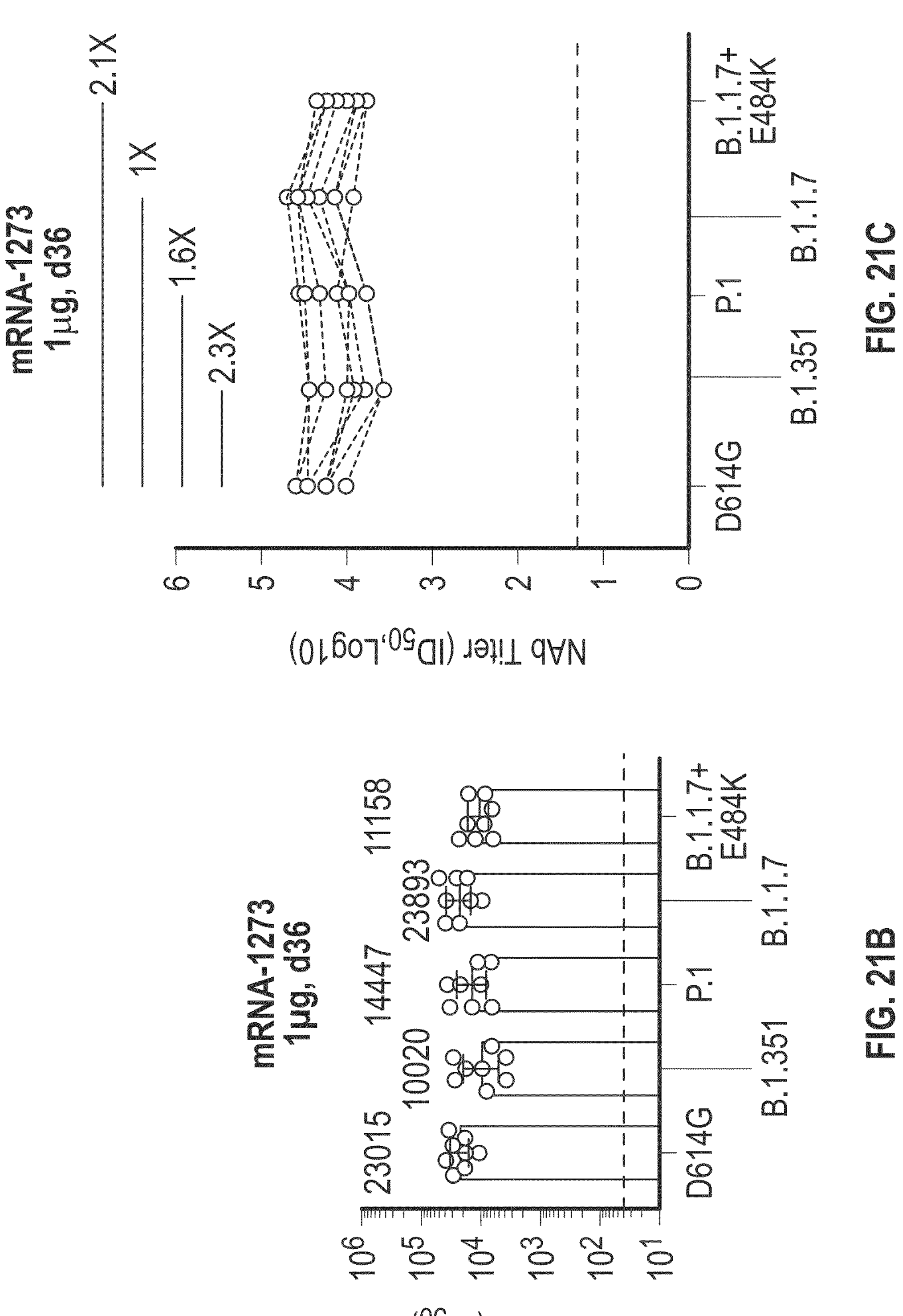
Figure 21E:
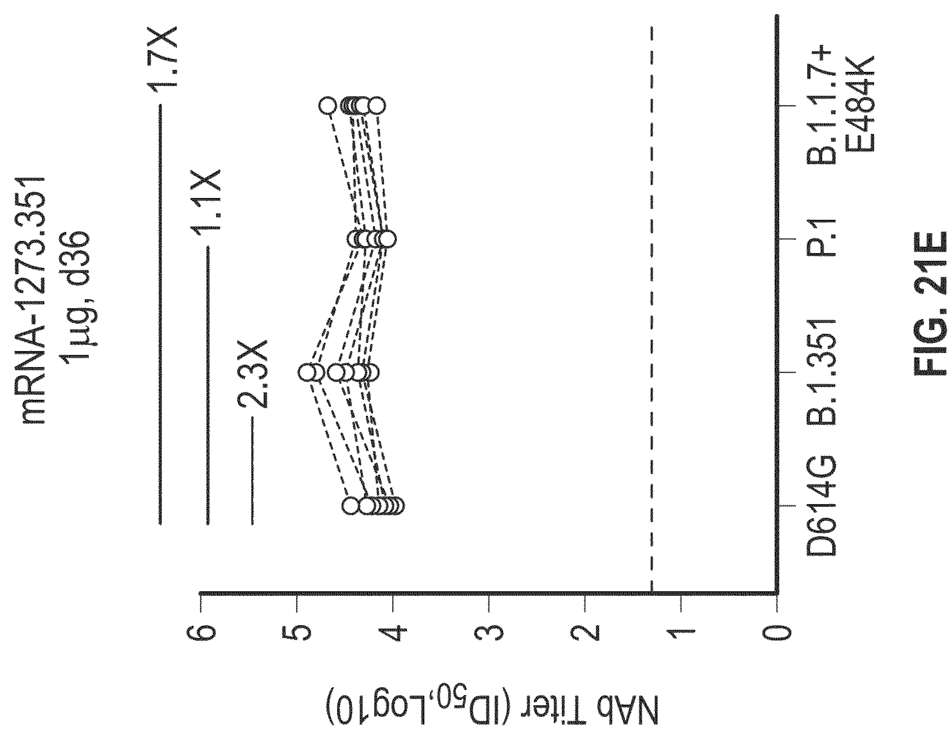
Figure 21D:
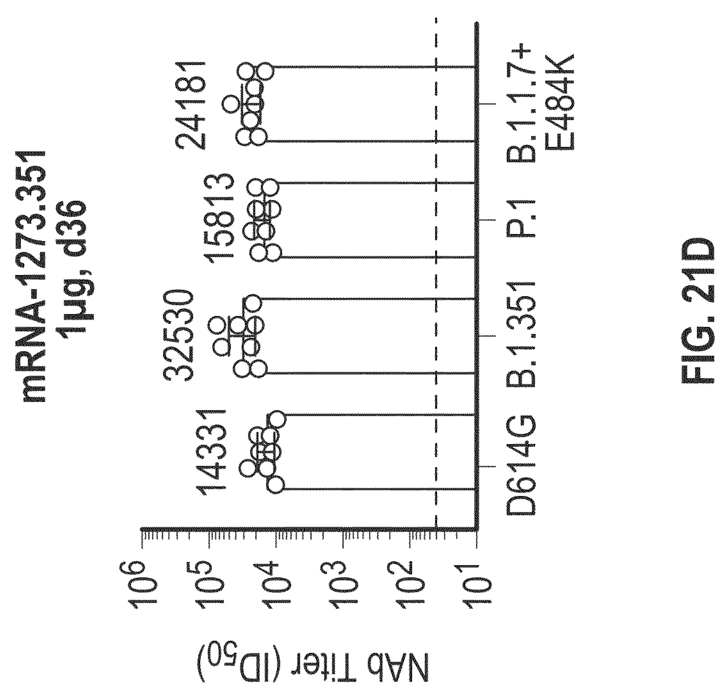
Figure 21G:
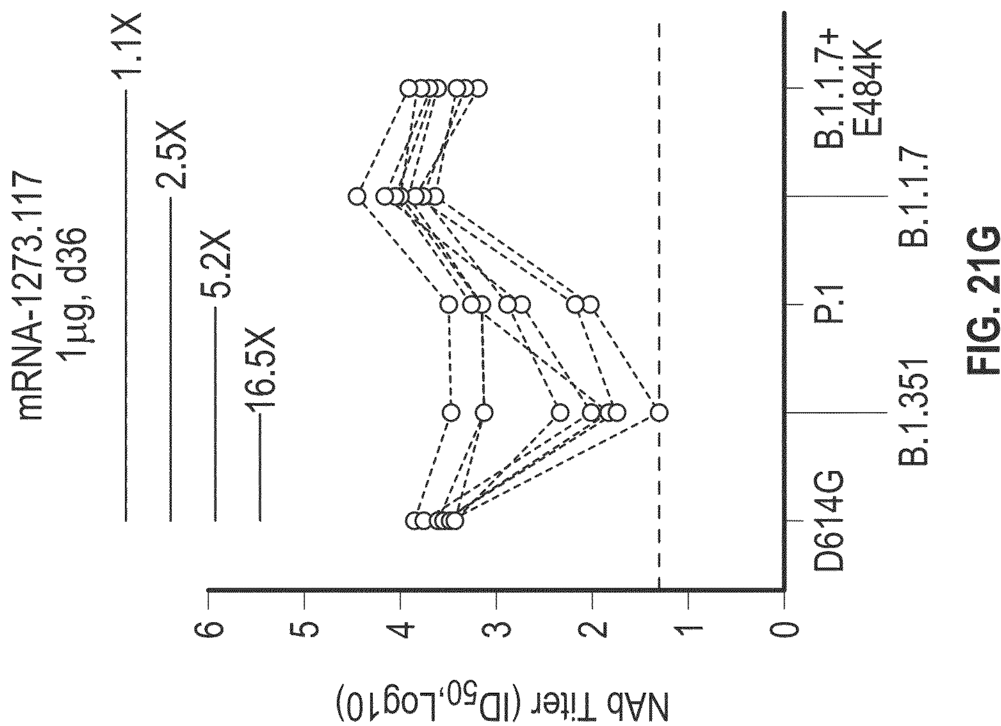
Figure 21F:
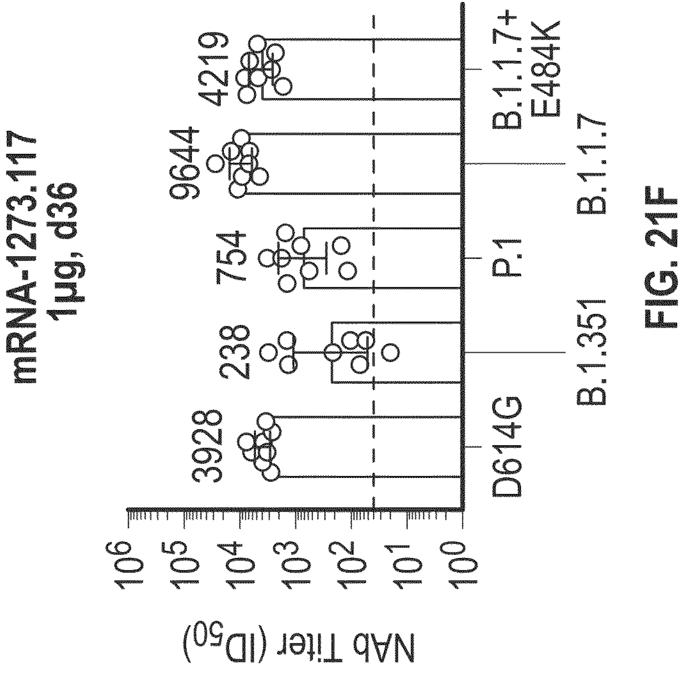

Sera obtained at day 36 from mice vaccinated with two 1 μg doses of mRNA-1273, mRNA-1273.351, or mRNA-1273.117 were also evaluated for neutralization activity against a panel of VSV-based pseudoviruses, each expressing a different SARS-CoV-2 Spike protein. The panel of Spike proteins tested is shown in Table 15, and included a D614G Spike protein, a B.1.351 Spike protein, a P.1 Spike protein, a B.1.1.7 Spike protein, and a B.1.1.7 Spike protein comprising an E484K mutation. The results of these neutralization assays are shown in FIGS. 21B-21D. Two 1 μg doses of mRNA-1273 elicited robust neutralizing antibody responses towards each of the Spike proteins tested (FIG. 21B). Neutralization titers towards each of the variant Spike proteins, B.1.351, P.1, and B.1.1.7 with E484K mutation, were about 2-fold lower than neutralization titers towards the D614G reference Spike protein (FIGS. 21B-21C). However, mRNA-1273 elicited roughly equivalent neutralization titers towards both D614G and B.1.1.7 Spike proteins that did not contain an E484K mutation (FIGS. 21B-21C). Two 1 μg doses of mRNA-1273.351 elicited robust neutralizing antibody responses towards all Spike proteins tested, with neutralizing antibody titers towards variant Spike proteins that were at least equivalent to, or up to 2.3 times greater than, titers towards the reference D614G Spike protein (FIGS. 21D-21E). Two 1 μg doses of mRNA-1273.351 elicited robust neutralizing antibody responses towards all Spike proteins tested (FIG. 21F). While neutralizing antibody titers towards B.1.351 Spike protein were 16.5-fold lower than titers against D614G Spike protein, sera were 2.5 times more effective at neutralizing B.1.1.7 Spike protein-containing pseudoviruses than those containing the D614G Spike protein. The E484K mutation partially abrogated this increase, but titers against the B.1.1.7+E8484K Spike protein were roughly equivalent to, not markedly lower than, titers against the D614G Spike protein (FIG. 21G).

TABLE 15

Geometric mean neutralizing antibody titers towards variant Spike proteins elicited by two doses of mRNA-1273, mRNA-1273.351, or mRNA-1273.117

| Spike protein | NAb titer ($ID_{50}$) after two 1 μg doses mRNA- 1273 | NAb titer ($ID_{50}$) after two 1 μg doses mRNA- 1273.351 | NAb titer ($ID_{50}$) after two 1 μg doses mRNA- 1273.117 | Neutralization titer elicited by PBS ($ID_{50}$) |
|---|---|---|---|---|
| D614G | 23015 | 14331 | 3928 | 20 (below L.O.D.) |
| B.1.351 | 10020 | 32530 | 238 | 20 (below L.O.D.) |
| P.1 | 14447 | 15813 | 754 | 20 (below L.O.D.) |
| B.1.1.7 | 23893 | (not tested) | 9644 | (not tested) |
| B.1.1.7 + E484K | 11158 | 24181 | 4219 | (not tested) |

Figure 21H:
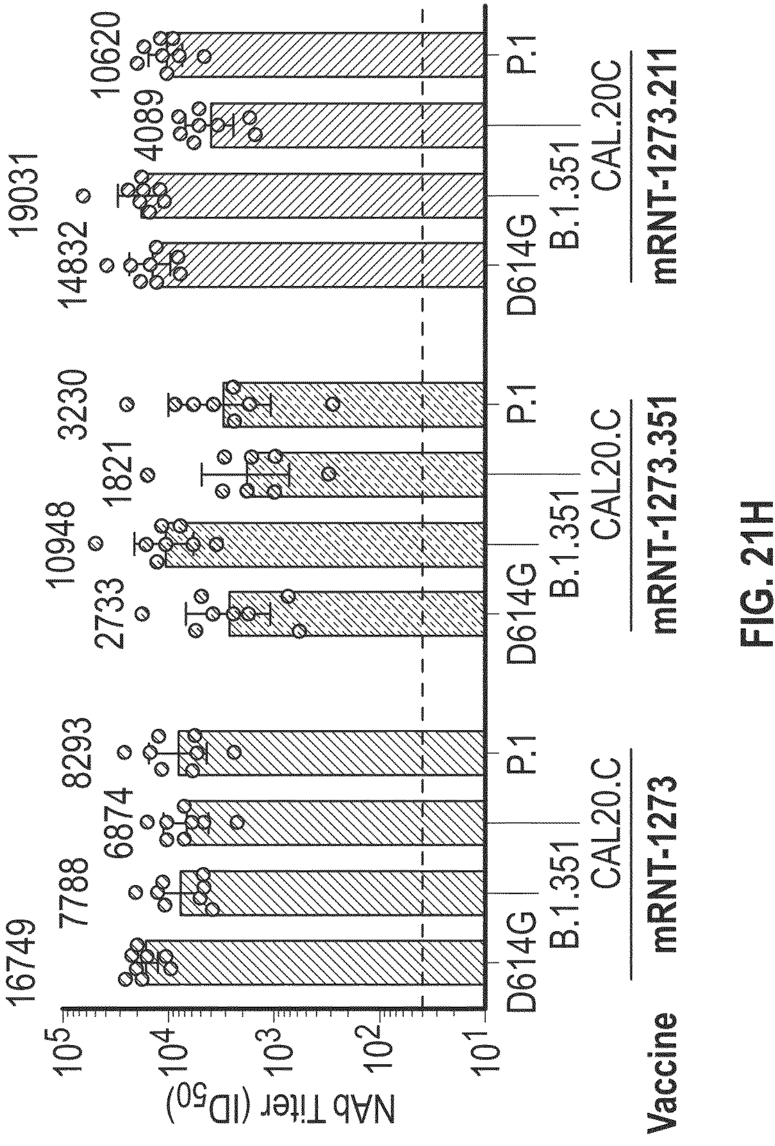

In a separate experiment, BALB/c mice, 6-8 weeks of age, were administered 1 μg of mRNA encoding a SARS-CoV-2 antigen, specifically mRNA-1273, mRNA-1273.351, or mRNA-1273.211 (1:1 mixture of mRNA-1273 and mRNA-1273.351, 0.5 μg each), intramuscularly in one hind leg (formulated as a 50 μL dose) on day 1 ($1^{st}$ dose, prime) and day 22 ($2^{nd}$ dose, booster). Sera obtained at day 36 (14 days post-$2^{nd}$ dose) and evaluated for neutralization activity against a panel of VSV-based pseudoviruses, each expressing a different SARS-CoV-2 Spike protein. The Spike proteins tested included 1) D614G Spike protein, 2) B.1.3.51 Spike protein, 3) CAL20.C Spike protein, and 4) P.1 Spike protein. The results of these neutralization assays are shown in FIG. 21H.

Each mRNA composition elicited robust neutralizing antibody responses towards each of the Spike proteins tested. Antibodies elicited by two doses of mRNA-1273 had the greatest neutralizing effect towards the reference D614G Spike protein, but neutralization titers towards variant (B.1.351, CAL20.C, and P.1) Spike proteins were only about 2-fold lower, and not severely reduced. mRNA-1273.351 elicited the most focused response towards the B.1.351 Spike protein, with neutralization titers towards other (D614G, CAL20.C, and P.1) Spike proteins being 3- to 5-fold lower. However, mRNA-1273.211, a 1:1 mixture of both mRNA-1273 and mRNA-1273.351, elicited robust neutralizing antibody responses to both D614G and B.1.351 Spike proteins encoded by the mRNAs, as well as to the other Spike proteins tested. These results indicate that administration of mRNAs elicited robust neutralizing antibody response to encoded SARS-CoV-2 Spike proteins, and that multivalent mRNA compositions containing multiple mRNAs are useful for elicited broad responses to a diverse group of viral antigens.

Example 18: Immunization with Two Doses of mRNAs Encoding Variant Spike Proteins to Generate Neutralizing Antibodies to Variant Spike Proteins in Mice BALB/c mice, 6-8 weeks of age, were administered 1 μg of mRNA encoding a SARS-CoV-2 antigen, specifically mRNA-1273 or mRNA-1273.351, or PBS (as a control) intramuscularly in one hind leg (formulated as a 50 μL dose) on day 1 ($1^{st}$ dose, prime) and day 22 ($2^{nd}$ dose, booster).

Figure 22:
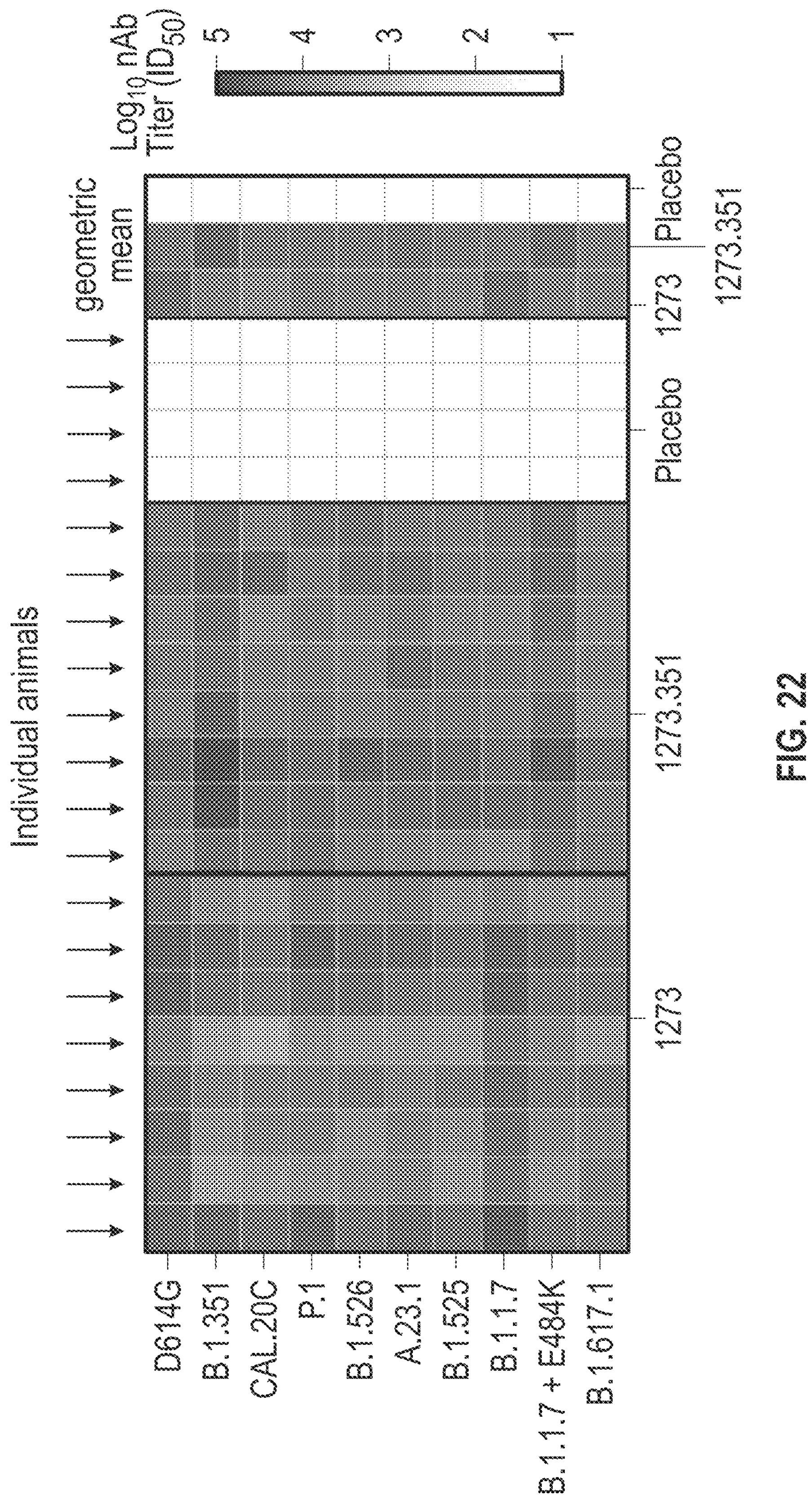
FIG. 22 is a graph depicting the neutralizing antibody titers ($\log_{10}$) elicited against a panel of SARS-CoV-2 variants.

Sera obtained at day 36 from mice vaccinated with two 1 μg doses of mRNA-1273, mRNA-1273.351 were evaluated for neutralization activity against a panel of VSV-based pseudoviruses, each expressing a different SARS-CoV-2 Spike protein. The panel of Spike proteins tested included a D614G Spike protein, a B.1.351 Spike protein, a CAL.20C Spike protein, a P.1 Spike protein, a B.1.526 Spike protein, a A.23.1 Spike protein, a B.1.525 Spike protein, a B.1.1.7 Spike protein, a B.1.1.7 Spike protein comprising an E484K mutation, and a B.1.617.1 Spike protein. The results of these neutralization assays are shown in FIG. 22. Two 1 μg doses of mRNA-1273 or mRNA-1273.351 elicited robust neutralizing antibody responses towards each of the Spike proteins tested.

Example 19—Immunogenicity of SARS-CoV-2 mRNA Variants ($3^{rd}$ Doses)

BALB/c mice were immunized at days 1 and 22 with 1 μg of SEQ ID NO: 18 (WH2020_NatSP_2P) (n=8/group). The mice were subsequently administered a booster dose (dose 3; 1 μg) on day 57. The booster dose comprised mRNA-1273 (SEQ ID NO: 18), mRNA-1273.351 (SEQ ID NO: 9), or mRNA-1273.617.2 (SEQ ID NO: 28) (monovalent vaccines); or mRNA-1273+mRNA-1273.617.2, mRNA-1273+mRNA-1273.351, mRNA-1273+mRNA-1273.617.1, mRNA-1273+mRNA-1273.Angola, mRNA-1273.351+mRNA-1273.617.2, mRNA-1273.351+mRNA-1273.Angola, mRNA-1273+mRNA-1273.351+mRNA-1273.617.2, mRNA-1273+mRNA-1273.351+mRNA-1273.Angola, mRNA-1273+mRNA-1273.617.2+mRNA-1273.Angola, or mRNA-1273+mRNA-1273.351+mRNA-1273.617.2+mRNA-1273.Angola (multivalent vaccines at a 1:1 or 1:1:1 or 1:1:1:1 ratio). In each vaccine, the mRNA was formulated in lipid nanoparticles (LNPs) including 0.5-15% PEG-modified lipid, 5-25% non-cationic lipid, 25-55% sterol, and 20-60% ionizable amino lipid. The PEG-modified lipid was 1,2 dimyristoyl-sn-glycerol, methoxypolyethyleneglycol (PEG2000 DMG), the non-cationic lipid was 1,2 distearoyl-sn-glycero-3-phosphocholine (DSPC), the sterol was cholesterol, and the ionizable amino lipid had the structure of Compound 1, for example.

Blood was collected on days 36, 56, and 77 and analyzed by ELISA and neutralization assays as described herein. The results for days 36 (after the second dose) and 77 (after the booster dose) are shown in Table 16 below and demonstrate dramatically increased titers three weeks after administration of the booster dose compared to two weeks after the second dose of the vaccine (mRNA-1273) among the monovalent vaccines.

TABLE 16

| Geometric Mean Titers (GMT) (1 μg Dose) - Monovalent Vaccines | | | |
|---|---|---|---|
| Formulation | Dose (ug) | Day 36 - GMT | Day 77 - GMT |
| PBS | 0 | 13 | 13 |
| mRNA-1273 | 1.0 | 79719 | 265697 |
| mRNA-1273.351 | 1.0 | 91875 | 317243 |
| mRNA-1273.617.2 | 1.0 | 71716 | 330799 |

Similar trends were seen with respect to the multivalent vaccines over the timepoints analyzed (Table 17).

TABLE 17

| Geometric Mean Titers (GMT) (1 μg Dose) | | | | |
|---|---|---|---|---|
| Formulation | Dose (ug) | Day 21 - GMT | Day 36 - GMT | Day 77 - GMT |
| PBS | 0 | 13 | 13 | 13 |
| | 0 | 13 | 13 | 13 |
| | 0 | 13 | 13 | 13 |
| mRNA-1273 | 1 | 11569 | 79719 | 265697 |
| mRNA-1273.351 | | 12107 | 91875 | 317243 |
| mRNA-1273.617.2 | | 6216 | 71716 | 330799 |
| mRNA-1273 + mRNA-1273.617.2 | | 8111 | 64622 | 289459 |
| mRNA-1273 + mRNA-1273.351 | | 10242 | 82166 | 282784 |
| mRNA-1273 + mRNA-1273.617.1 | | 12984 | 137997 | 359572 |
| mRNA-1273 + mRNA-1273.Angola | | 6698 | 81956 | 327273 |
| mRNA-1273.351 + mRNA-1273.617.2 | | 7907 | 88324 | 341445 |
| mRNA-1273.351 + mRNA-1273.Angola | | 11733 | 100648 | 425029 |
| mRNA-1273 + mRNA-1273.351 + mRNA-1273.617.2 | | 8548 | 88211 | 373908 |
| mRNA-1273 + mRNA-1273.351 + mRNA-1273.Angola | | 7871 | 97012 | 328856 |
| mRNA-1273 + mRNA-1273.617.2 + mRNA-1273.Angola | | 5469 | 88499 | 346611 |
| mRNA-1273 + mRNA-1273.351 + mRNA-1273.617.2 + mRNA-1273.Angola | | 5295 | 77195 | 346006 |

Neutralizing antibody titers against the D614G variant, the B.1.351 (beta) variant (L18F-D80A-D215G-ΔLAL242-244-R246I-K417N-E484K-N501Y-D614G-A701V), the P.1 (gamma) variant (L18F-T20N-P26S-D138Y-R190S-K417T-E484K-N501Y-D614G-H655Y-T1027I-V1176F), and the B.1.617.2 (delta) variant (T19R-G142D-E156G-F157del-R158del-L452R-T478K-D614G-P681R-D950N) were measured on day 56 (before the third dose) and day 77 using methods described above. The data for day 56 is shown in Table 18 below.

TABLE 18

| Neutralization Titers (1 μg Dose) - Day 56 (all groups combined) | | | |
|---|---|---|---|
| Virus | Day | NAb Titer ($ID_{50}$) | Fold Change on D614G |
| D614G | 56 | 7104 | N/A |
| B.1.351 | 56 | 2625 | 2.7 |
| P.1 | 56 | 3128 | 2.3 |
| B.1.617.2 | 56 | 1821 | 3.9 |
| A.VOI.V2 | 56 | 567 | 12.5 |
| B.1.621 | 56 | 2286 | 3.1 |

Compared to what has been observed at two weeks post-vaccination, titers against D614G (WT) virus decreased one month after the mRNA-1273 primary series (at day 36, the D614G GMT was approximately 15,000). The highest reduction (12.5-fold) in neutralizing titers were observed for A.VOI.V2 when compared to D614G (WT).

Booster vaccination was observed to increase neutralizing titers, as shown in Tables 19-25 below.

TABLE 20

| Neutralization Titers (1 μg Dose) - Day 56 vs. Day 77 (B.1.351 GMT) | | | |
|---|---|---|---|
| | B.1.351 GMT | | Fold increase |
| 3rd dose (Day 57) | D 56 | D 77 | on D 77 |
| mRNA-1273 | 1793 | 7192 | 4.0 |
| mRNA-1273.351 | 3665 | 29008 | 7.9 |
| mRNA-1273.617.2 | 2217 | 22180 | 10.0 |
| mRNA-1273.Angola | 2850 | 9257 | 3.2 |
| mRNA-1273 + mRNA-1273.351 (mRNA-1273.211) | 2929 | 26766 | 9.1 |
| mRNA-1273 + mRNA-1273.617.2 | 3074 | 27674 | 9.0 |
| mRNA-1273 + mRNA-1273.Angola | 2702 | 16729 | 6.2 |
| mRNA-1273.351 + mRNA-1273.617.2 | 3076 | 49894 | 16.2 |
| mRNA-1273.351 + mRNA-1273.Angola | 2084 | 22926 | 11.0 |
| mRNA-1273 + mRNA-1273.351 + mRNA-1273.617.2 | 2363 | 18562 | 7.9 |
| mRNA-1273 + mRNA-1273.351 + mRNA-1273.Angola | 3534 | 22109 | 6.3 |
| mRNA-1273 + mRNA-1273.617.2 + mRNA-1273.Angola | 1961 | 10116 | 5.2 |
| mRNA-1273 + mRNA-1273.351 + mRNA-1273.617.2 + mRNA-1273.Angola | 2653 | 23235 | 8.8 |

TABLE 21

| Neutralization Titers (1 μg Dose) - Day 56 vs. Day 77 (B.1.617.2 (delta) GMT) | | | |
|---|---|---|---|
| | B.1.617.2 GMT | | Fold increase |
| 3rd dose (Day 57) | D 56 | D 77 | on D 77 |
| mRNA-1273 | 879 | 4611 | 5.2 |
| mRNA-1273.351 | 3634 | 17822 | 4.9 |
| mRNA-1273.617.2 | 2423 | 21713 | 9.0 |
| mRNA-1273.Angola | 1380 | 9216 | 6.7 |
| mRNA-1273 + mRNA-1273.351 (mRNA-1273.211) | 1750 | 12064 | 6.9 |
| mRNA-1273 + mRNA-1273.617.2 | 3187 | 25999 | 8.2 |
| mRNA-1273 + mRNA-1273.Angola | 1336 | 13911 | 10.4 |
| mRNA-1273.351 + mRNA-1273.617.2 | 1807 | 22294 | 12.3 |
| mRNA-1273.351 + mRNA-1273.Angola | 1938 | 10752 | 5.5 |
| mRNA-1273 + mRNA-1273.351 + mRNA-1273.617.2 | 1217 | 10099 | 8.3 |
| mRNA-1273 + mRNA-1273.351 + mRNA-1273.Angola | 1880 | 8037 | 4.3 |
| mRNA-1273 + mRNA-1273.617.2 + mRNA-1273.Angola | 1886 | 9939 | 5.3 |
| mRNA-1273 + mRNA-1273.351 + mRNA-1273.617.2 + mRNA-1273.Angola | 2018 | 14229 | 7.1 |

TABLE 22

| Neutralization Titers (1 μg Dose) - Day 56 vs. Day 77 (B.1.621 (mu) GMT) | | | |
|---|---|---|---|
| | B.1.621 GMT | | Fold increase |
| 3rd dose (Day 57) | D 56 | D 77 | on D 77 |
| mRNA-1273 | | | — |
| mRNA-1273.351 | | | — |
| mRNA-1273.617.2 | 1626 | 15183 | 9.3 |
| mRNA-1273.Angola | | | — |
| mRNA-1273 + mRNA-1273.351 (mRNA-1273.211) | 3149 | 19405 | 6.2 |
| mRNA-1273 + mRNA-1273.617.2 | 2400 | 13340 | 5.6 |
| mRNA-1273 + mRNA-1273.Angola | | | — |

TABLE 22-continued

| Neutralization Titers (1 μg Dose) - Day 56 vs. Day 77 (B.1.621 (mu) GMT) | | | |
|---|---|---|---|
| | B.1.621 GMT | | Fold increase |
| 3rd dose (Day 57) | D 56 | D 77 | on D 77 |
| mRNA-1273.351 + mRNA-1273.617.2 | 2223 | 33417 | 15.0 |
| mRNA-1273.351 + mRNA-1273.Angola | | | — |
| mRNA-1273 + mRNA-1273.351 + mRNA-1273.617.2 | | | — |
| mRNA-1273 + mRNA-1273.351 + mRNA-1273.Angola | | | — |
| mRNA-1273 + mRNA-1273.617.2 + mRNA-1273.Angola | | | — |
| mRNA-1273 + mRNA-1273.351 + mRNA-1273.617.2 + mRNA-1273.Angola | | | — |

TABLE 23

| Neutralization Titers (1 μg Dose) - Day 56 vs. Day 77 (P.1 (gamma) GMT) | | | |
|---|---|---|---|
| | P.1 GMT | | Fold increase |
| 3rd dose (Day 57) | D 56 | D 77 | on D 77 |
| mRNA-1273 | 2289 | 7340 | 3.2 |
| mRNA-1273.351 | 3221 | 28300 | 8.8 |
| mRNA-1273.617.2 | 2680 | 22183 | 8.3 |
| mRNA-1273.Angola | | | — |
| mRNA-1273 + mRNA-1273.351 (mRNA-1273.211) | 3474 | 29127 | 8.4 |
| mRNA-1273 + mRNA-1273.617.2 | 3481 | 26000 | 7.5 |
| mRNA-1273 + mRNA-1273.Angola | | | — |
| mRNA-1273.351 + mRNA-1273.617.2 | 4330 | 43279 | 10.0 |
| mRNA-1273.351 + mRNA-1273.Angola | | | |
| mRNA-1273 + mRNA-1273.351 + mRNA-1273.617.2 | 2831 | 23265 | 8.2 |
| mRNA-1273 + mRNA-1273.351 + mRNA-1273.Angola | | | — |
| mRNA-1273 + mRNA-1273.617.2 + mRNA-1273.Angola | | | — |
| mRNA-1273 + mRNA-1273.351 + mRNA-1273.617.2 + mRNA-1273.Angola | | | — |

TABLE 24

| Neutralization Titers (1 μg Dose) - Day 56 vs. Day 77 (A.VOI.V2 GMT) | | | |
|---|---|---|---|
| | A.VOL.V2 GMT | | Fold increase |
| 3rd dose (Day 57) | D 56 | D 77 | on D 77 |
| mRNA-1273 | | | — |
| mRNA-1273.351 | | | — |
| mRNA-1273.617.2 | | | — |
| mRNA-1273.Angola | 536 | 4337 | 8.1 |
| mRNA-1273 + mRNA-1273.351 (mRNA-1273.211) | | | — |
| mRNA-1273 + mRNA-1273.617.2 | | | — |
| mRNA-1273 + mRNA-1273.Angola | 407 | 5569 | 13.7 |
| mRNA-1273.351 + mRNA-1273.617.2 | | | — |
| mRNA-1273.351 + mRNA-1273.Angola | 498 | 4296 | 8.6 |
| mRNA-1273 + mRNA-1273.351 + mRNA-1273.617.2 | | | — |
| mRNA-1273 + mRNA-1273.351 + mRNA-1273.Angola | 796 | 4201 | 5.3 |
| mRNA-1273 + mRNA-1273.617.2 + mRNA-1273.Angola | 736 | 2649 | 3.6 |
| mRNA-1273 + mRNA-1273.351 + mRNA-1273.617.2 + mRNA-1273.Angola | 521 | 5669 | 10.9 |

TABLE 25

| Fold-Decrease on D614G | | | | | | | | | | |
|---|---|---|---|---|---|---|---|---|---|---|
| | B.1.351 Fold decrease on D614G | | B.1.617.2 Fold decrease on D614G | | P.1 Fold decrease on D614G | | A.VOI.V2 Fold decrease on D614G | | B.1.621 Fold decrease on D614G | |
| 3rd dose (Day 77) | D56 | D77 | D56 | D77 | D56 | D77 | D56 | D77 | D56 | D77 |
| mRNA-1273 | 2.9 | 2.4 | 5.9 | 3.8 | 2.3 | 2.4 | | | | |
| mRNA-1273.351 | 2.3 | 1.2 | 2.4 | 1.9 | 2.7 | 1.2 | | | | |
| mRNA-1273.617.2 | 2.8 | 1.8 | 2.6 | 1.9 | 2.3 | 1.8 | | | 3.8 | 2.7 |

TABLE 25-continued

| Fold-Decrease on D614G | | | | | | | | | | |
|---|---|---|---|---|---|---|---|---|---|---|
| | B.1.351 Fold decrease on D614G | | B.1.617.2 Fold decrease on D614G | | P.1 Fold decrease on D614G | | A.VOI.V2 Fold decrease on D614G | | B.1.621 Fold decrease on D614G | |
| 3rd dose (Day 77) | D56 | D77 | D56 | D77 | D56 | D77 | D56 | D77 | D56 | D77 |
| mRNA-1273.Angola | 2.2 | 2.4 | 4.5 | 2.4 | | | 11.5 | 5.1 | | |
| mRNA-1273 + mRNA-1273.351 (mRNA-1273.211) | 1.8 | 1.8 | 3.1 | 4.1 | 1.6 | 1.7 | | | 1.7 | 2.5 |
| mRNA-1273 + mRNA-1273.617.2 | 3.3 | 2.2 | 3.1 | 2.3 | 2.9 | 2.3 | | | 4.2 | 4.6 |
| mRNA-1273 + mRNA-1273.Angola | 1.7 | 2.3 | 3.4 | 2.7 | | | 11.0 | 6.8 | | |
| mRNA-1273.351 + mRNA-1273.617.2 | 3.1 | 1.6 | 5.2 | 3.5 | 2.2 | 1.8 | | | 4.2 | 2.3 |
| mRNA-1273.351 + mRNA-1273.Angola | 3.6 | 1.6 | 3.9 | 3.3 | | | 15.1 | 8.3 | | |
| mRNA-1273 + mRNA-1273.351 + mRNA-1273.617.2 | 3.0 | 1.6 | 5.9 | 2.9 | 2.5 | 1.2 | | | | |
| mRNA-1273 + mRNA-1273.351 + mRNA-1273.Angola | 2.8 | 2.1 | 5.3 | 5.7 | | | 12.6 | 11.0 | | |
| mRNA-1273 + mRNA-1273.617.2 + mRNA-1273.Angola | 3.7 | 2.3 | 3.8 | 2.3 | | | 9.8 | 8.8 | | |
| mRNA-1273 + mRNA-1273.351 + mRNA-1273.617.2 + mRNA-1273.Angola | 2.9 | 2.2 | 3.9 | 3.6 | | | 15.0 | 8.9 | | |

| Formulation/Material | Dose(ug) | Day 21 - GMT | Day 36 - GMT | Day 78 - GMT |
|---|---|---|---|---|
| PBS | | 13 | 13 | 13 |
| PBS | | 13 | 13 | 13 |
| PBS | | 13 | 13 | 13 |
| mRNA-1273 | 1 | 4831 | 164775 | 370729 |
| mRNA 1273.351 | 1 | 4296 | 126671 | 254320 |
| mRNA-1273.617.2-v2 | 1 | 3518 | 133100 | 332117 |
| mRNA-1273 + .1273.351 | 1 | 4892 | 113168 | 275097 |
| mRNA-1273 + .1273.617.2-v2 | 1 | 5886 | 185834 | 375110 |
| mRNA-1273 + 1273.351 + 1273.617.2-v2 | 1 | 6358 | 178206 | 371299 |
| mRNA1273.351 + 1273.617.2-v2 | 1 | 4705 | 118779 | 293289 |
| mRNA-1283 | 1 | 6179 | 135176 | 424079 |
| mRNA-1283.351 | 1 | 11888 | 100389 | 451348 |
| mRNA-1283.617.2 | 1 | 5287 | 130957 | 504622 |
| mRNA-1283 + 1283.351 | 1 | 5055 | 141217 | 429434 |
| mRNA-1283 + 1283.617.2 | 1 | 4763 | 115615 | 593690 |
| mRNA-1283 + 1283.351 + 1283.617.2 | 1 | 5398 | 98220 | 516556 |

As demonstrated above, neutralizing titers were lower one month post-primary series in mice than what is normally observed 2 weeks post vaccination (D36; D614G: ~15000 GMT), and the highest fold-reduction was seen against the A.VOI.V2 variant after the primary series. About a 2.7-, 2.3-, and 3.9-fold reduction were observed on the beta (B.1.351), gamma (P.1), and delta (B.1.617.2) variants, respectively, when compared to D614G (WT). Against mu (B.1.621), about a 3.1-fold reduction was seen when compared to D614G.

After the third booster dose, all vaccine constructs produced an increase in neutralizing titers against all variants compared to what was observed on day 56. Variant vaccine constructs resulted in higher titers than the mRNA-1273 vaccine booster. Overall, the highest increase in titers against the variants were observed with the bivalent mRNA-1273.351+mRNA-1273.617 combination vaccine. Vaccination formulations that included mRNA-1273.617.2 gave high neutralizing titers against the matched B.1.617.2 pseudovirus in mice. Interference from combining different vaccine constructs was not observed in the neutralization titers when mice were administered the bi-, tri-, and quadrivalent vaccines.

In addition, the fold-decrease on D614G (WT) that was observed against variants after the primary series was less after the third booster dose. For example, the mRNA-1273+mRNA-1273.617.2 and mRNA-1273.351+mRNA-1273.617.2 formulations showed higher fold-reduction than other formulations; however, these two groups also produced the highest titer against each variant tested. Almost all booster vaccines were able to minimize the gap between the titers observed against the variant of interest or variant of concern and D614G (WT) pseudovirus. While some booster vaccinations resulted in higher fold-reduction than the results after one month after the primary series, the GMT after the booster dose were found to be still higher. Overall, administration of the mRNA-1273.351+mRNA-1273.617.2 vaccine in mice was found to decrease the fold-drop against the beta, delta, and mu variants.

The experiment was repeated with selected vaccine formulations and similar results were obtained. The results are shown below:

TABLE 26

Demographics and Characteristics of Subjects

| Characteristic n (%) | mRNA-1273 (50 μg) N = 20 | mRNA-1273.351 (20 μg) N = 20 | mRNA-1273.351 (50 μg) N = 20 | mRNA-1273.211 (50 μg) N = 20 |
|---|---|---|---|---|
| Age (years) | | | | |
| Mean (range) yr. | 63.8 (38-76) | 47.5 (26-67) | 53.9 (27-70) | 55.6 (28-79) |
| Gender | | | | |
| Male | 8 (40) | 5 (25) | 11 (55) | 12 (60) |
| Female | 12 (60) | 15 (75) | 9 (45) | 8 (40) |
| Race | | | | |
| White | 20 (100) | 20 (100) | 19 (95) | 19 (95) |
| Black or African-American | 0 | 0 | 0 | 0 |
| Asian | 0 | 0 | 1 (5) | 0 |
| American Indian or Alaska Native | 0 | 0 | 0 | 1 (5) |
| Native Hawaiian or other Pacific Islander, Multiracial, Other, Not reported, Unknown | 0 | 0 | 0 | 0 |
| Ethnicity | | | | |
| Hispanic or Latino | 0 | 1 (5) | 0 | 1 (5) |
| Not Hispanic or Latino | 20 (100) | 19 (95) | 20 (100) | 19 (95) |
| Not reported or Unknown | 0 | 0 | 0 | 0 |
| Time interval between second dose of mRNA-1273 during the primary series and the booster dose | | | | |
| Mean (SD) (months†) | 6.7 (0.5) | 6.2 (0.3) | 6.2 (0.3) | 6.2 (0.4) |
| Range (months) | 5.9-7.5 | 5.5-6.6 | 5.6-6.6 | 5.4-6.8 |
| Body Mass Index ($kg/m^2$) | | | | |
| Mean (SD) | 26.2 (2.1) | 33.3 (6.6) | 30.3 (6.5)* | 33.0 (7.5) |

Legend:
SD = standard deviation.
*Missing data for 1 participant.
†Calculated with 30 days/month.

Example 20: Neutralizing Activity Against Variants (Two Doses of mRNA-1273)

Figure 23A:
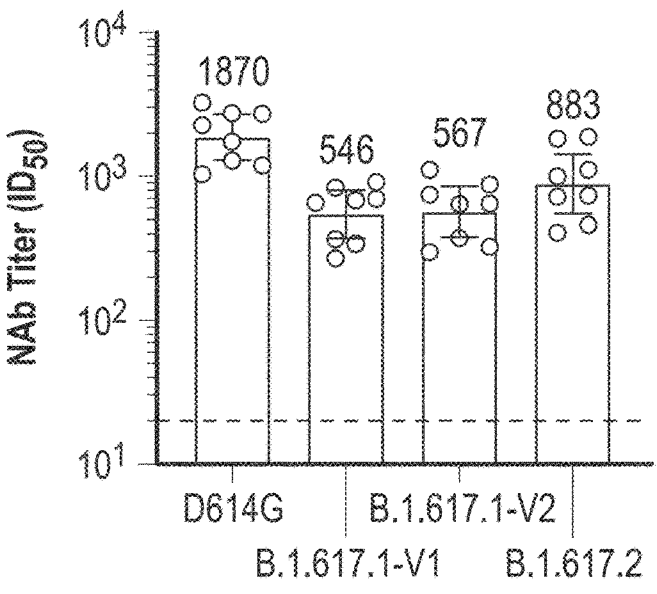
FIGS. 23A-23B show neutralization titers of serum samples taken from human Phase 1 participants.
Figure 23B:
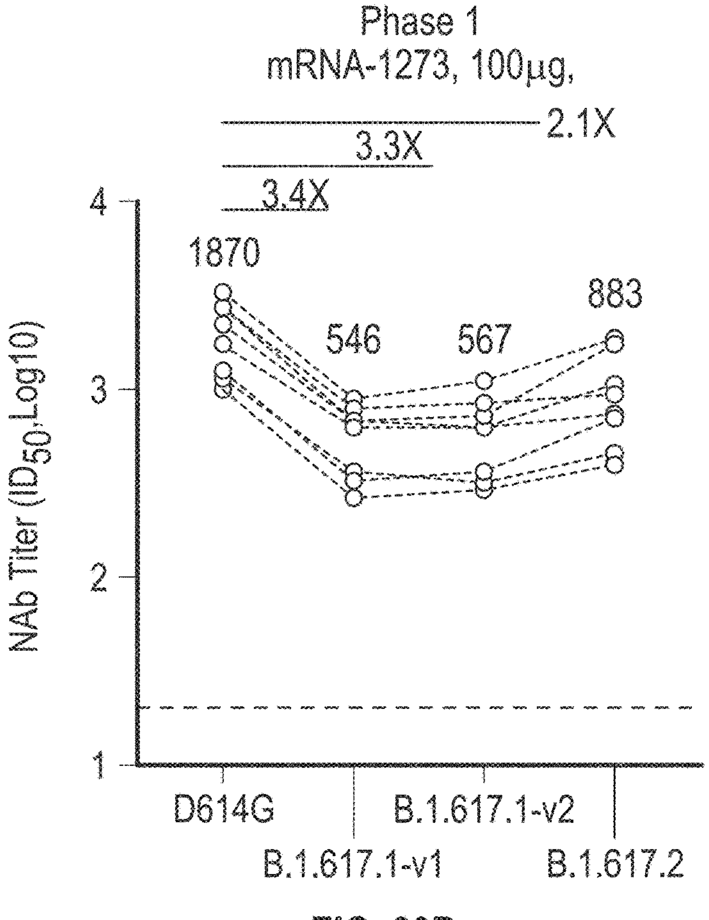
Figure 31A:
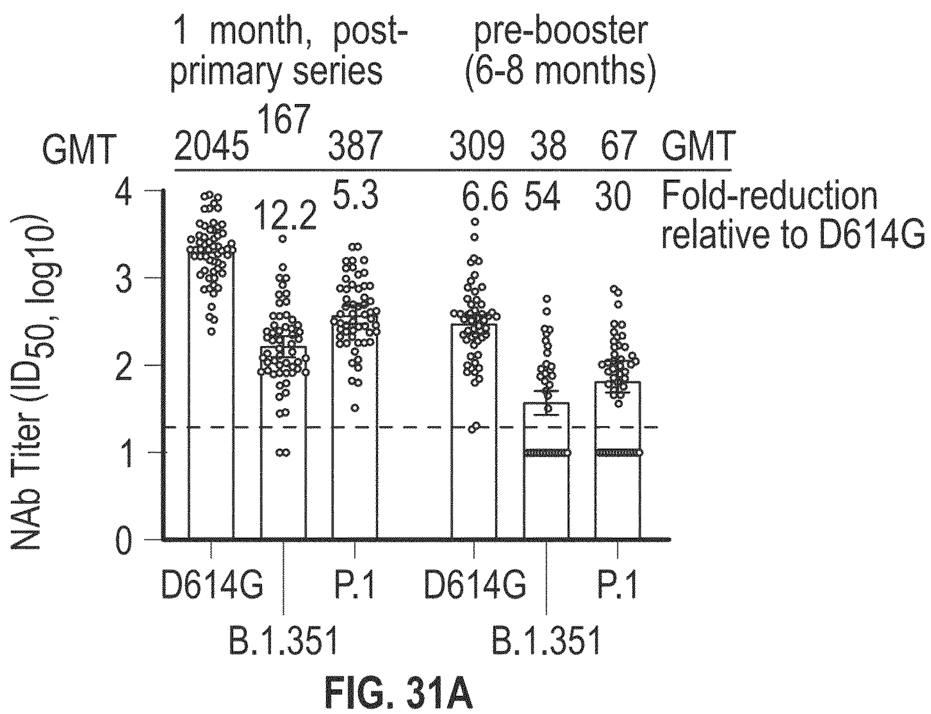
FIGS. 31A-31B show the neutralization of recombinant SARS-CoV-2 VSV-based pseudoviruses (D614G, B.1.351 and P.1) by serum from participants 1 month after the primary series (two doses of mRNA-1273) and 6-8 months later. The geometric mean neutralizing antibody titer is denoted by the top of the box, and 95% confidence intervals are shown by the brackets. The titers for individual participants are shown by the circles. The horizontal dotted lines indicate the lower limit of quantification (LLOQ).
Figure 31B:
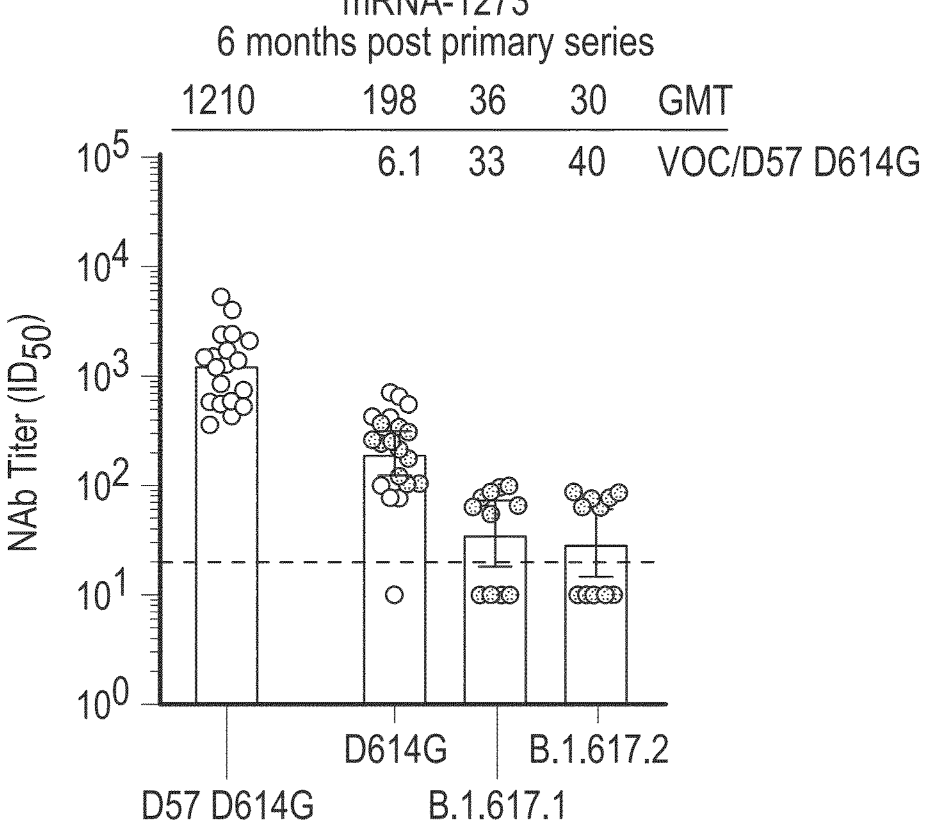

Human subjects were immunized with two doses of 100 μg mRNA-1273, as described in Example 13. FIG. 23A shows the neutralizing antibody titer of sera taken from participants against D614G, B.1.617.1-v1, B.1.617.1-v2, and B.1.617.2. FIG. 23B shows the relative decrease in neutralizing antibody titer compared to D614G. One month and 6-8 months after administration of the second dose, neutralizing antibodies against D614, B.1.351, P.1, and B.1.617 were measured. As can be seen in FIG. 31A, titers against the prototype strain were high after one month, with a significant reduction seen against both the B.1.351 variant (12.2 fold) and the P.1 variant (5.3 fold). Six to eight months after the primary series, neutralizing antibodies wane—they were 6.6 fold lower against the original D614G virus, and titers against B.1.351 and P.1 were 30-54-fold reduced versus peak titers measured after the primary series against the prototype strain virus (D614G) (FIG. 31B).

In a further study, neutralization activity of sera was measured against the following virus strains: D614G pseudovirus (predominant strain in 2020), B.1.1.7, B.1.1.7+E484K, B.1.427/B.1.429, P.1, B.1.351-v1, B.1.351-v2, B.1.351-v3, B.1.526, B.1.617.1-v1, B.1.617.1-v2, B.1.617.2, A.23.1-v1, A.23.1-v2, B.1.525, and A.VOI.V2. Sera from the phase 1 mRNA-1273 clinical trial (8 participants, 1 week following Dose 2) were evaluated against each variant. Results showed minimal effects on neutralization titers against B.1.1.7 and A.23.1-v1 compared to D614G (data not shown). In contrast, all other variants examined showed decreased neutralization titers compared with D614G, although all remained completely susceptible to mRNA-1273-elicited serum neutralization, but with reduced titers. Reductions in neutralization titers for these variants ranged from a factor of 2.1 to 8.4 compared with D614G, with the greatest effect on neutralization observed for A.VOI.V2 and B.1.351-v3 (8.0-fold and 8.4-fold reductions compared with D614G, respectively).

Example 21. Neutralization Against Variants Post Third Dose (Booster)

Figure 32:
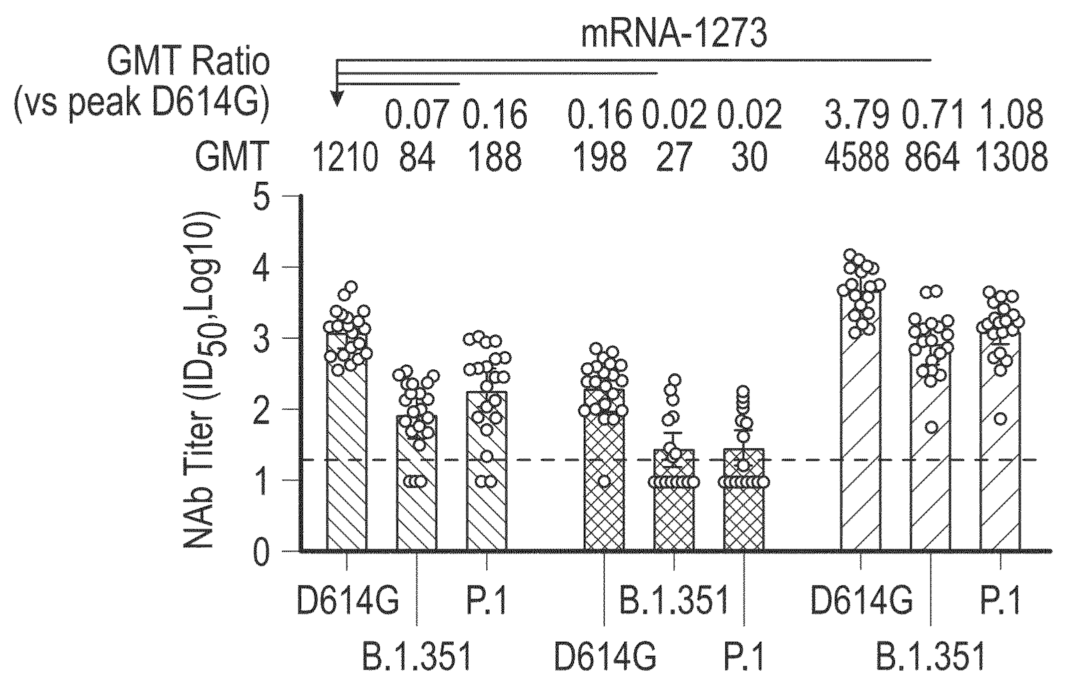
FIG. 32 includes three graphs showing that administration of a booster shot increases neutralizing antibody titers against wild-type (D614) and variants of concern (B.1.351 and P.1). Three boosting strategies were tested: mRNA-1273, mRNA-1273.351, and mRNA-1273.211.
Figure 32:
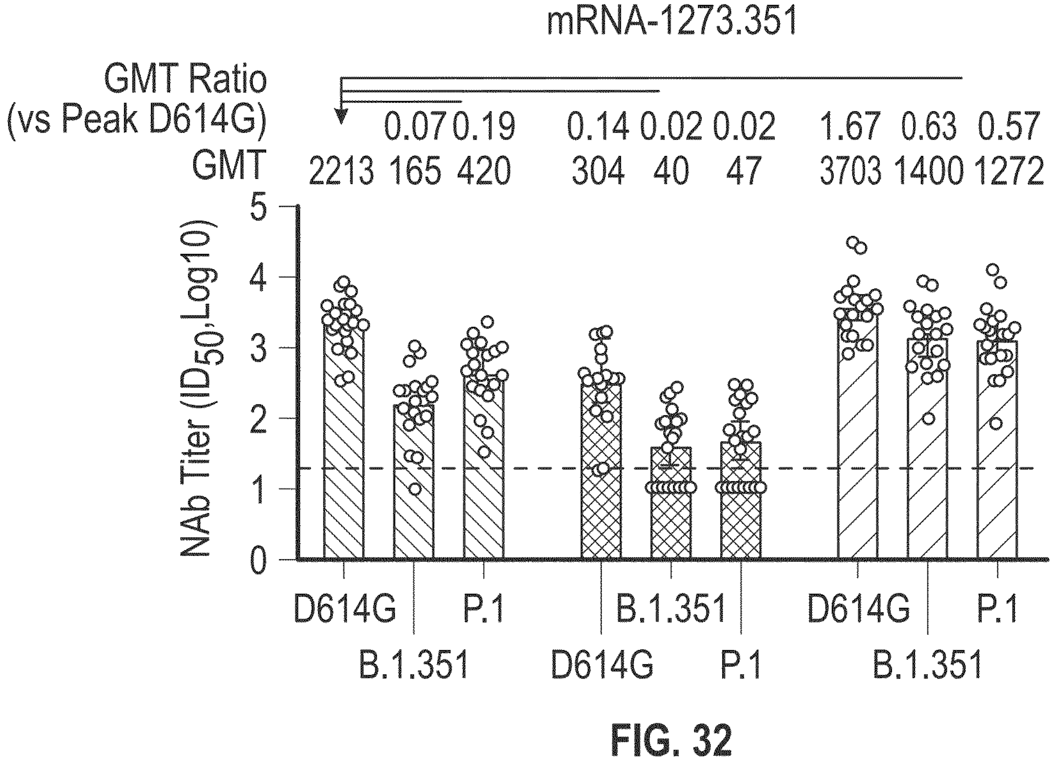
Figure 32:
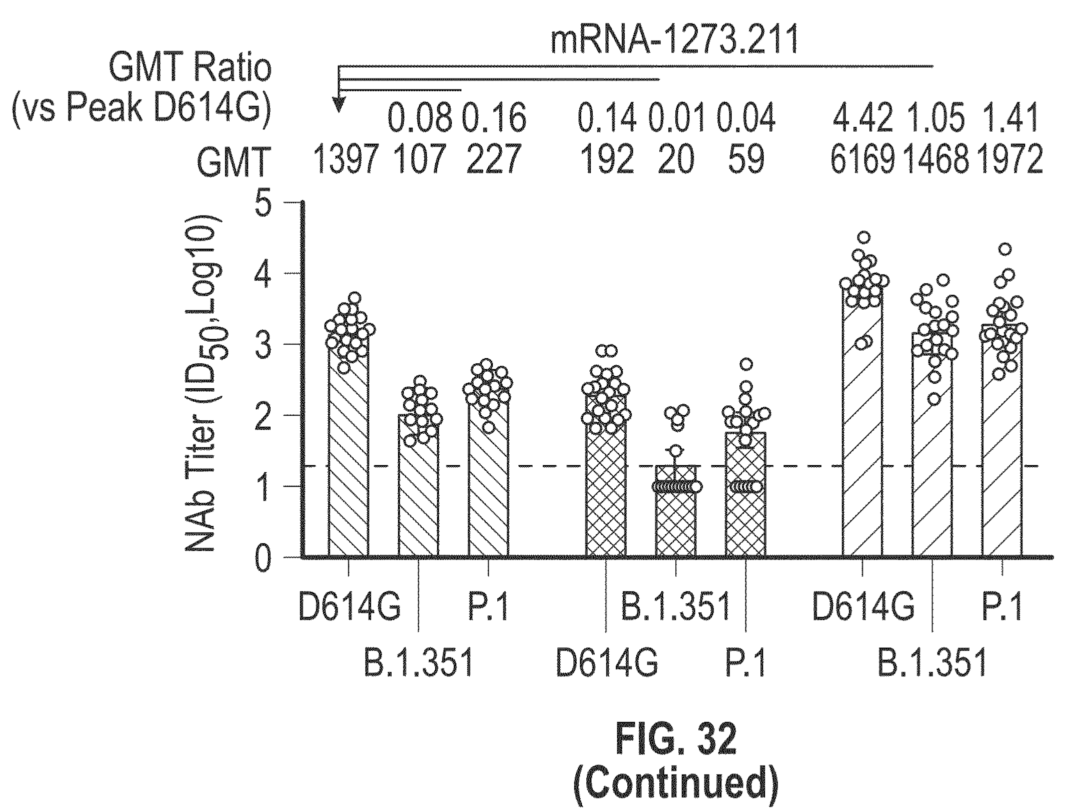

Human subjects were immunized with two doses of 100 μg mRNA-1273, as described in Example 13. A third dose was administered 6-8 months after the primary vaccination was complete. Neutralizing titers against B.1.351 and P.1 were measured over time. The results are shown in FIG. 32. The booster dose (mRNA-1273, mRNA-1273.351, or mRNA-1273.211) was found to increase neutralizing antibody in a surprising manner against both the wild type (D614G) and two variants tested (B.1.351 and P.1).

Figure 33B:
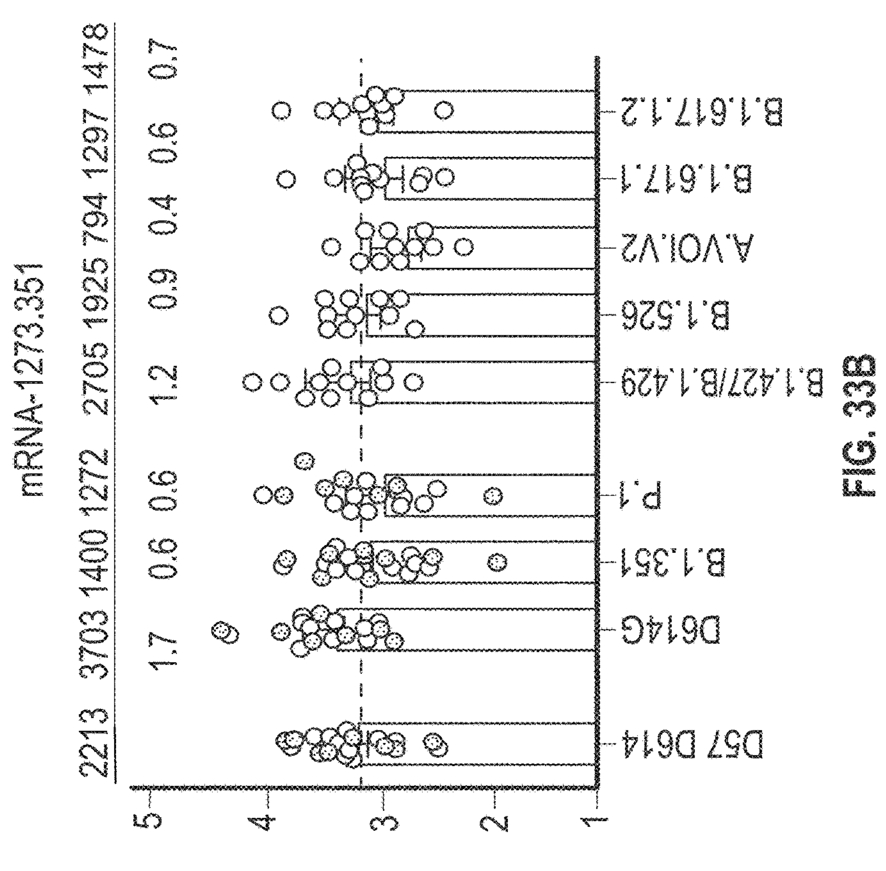
FIGS. 33A-33C show neutralization titers after administration of a booster shot. Three different boosting strategies were tested: mRNA-1273 (FIG. 33A), mRNA-1273.351 (FIG. 33B), and mRNA-1273.211 (FIG. 33C). The variants of concern/interest surveyed were: B.1.351, P.1, B.1.427/B.1.429, B.1.526, A.VOI.V2, B.1.617.1, and B.1.617.2.
Figure 33A:
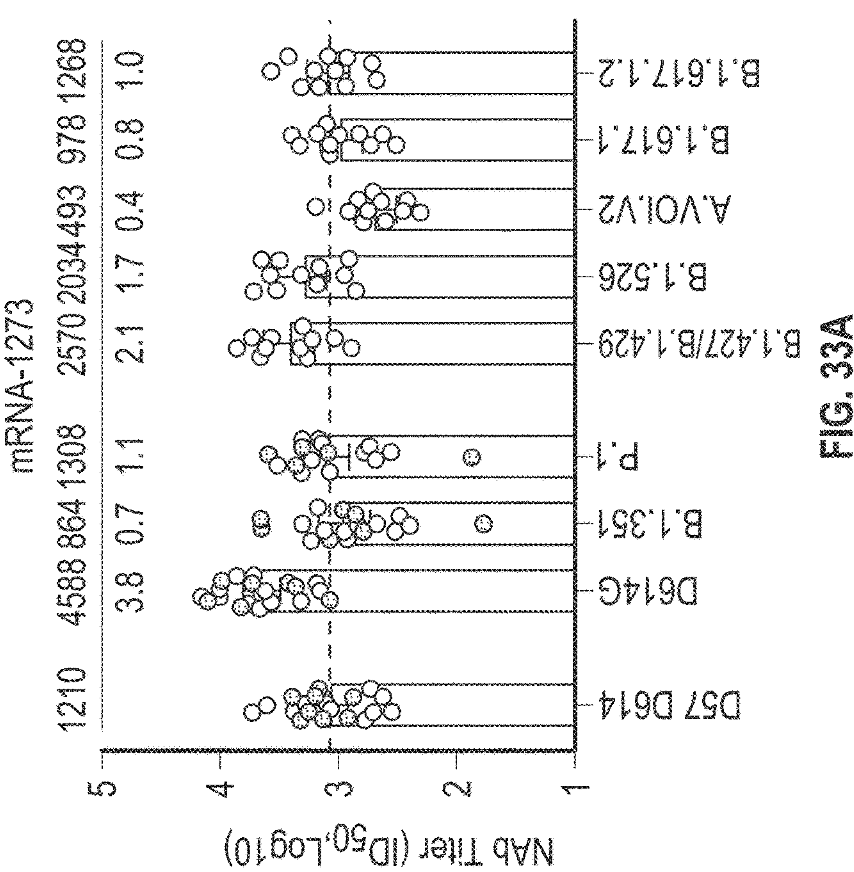
Figure 33C:
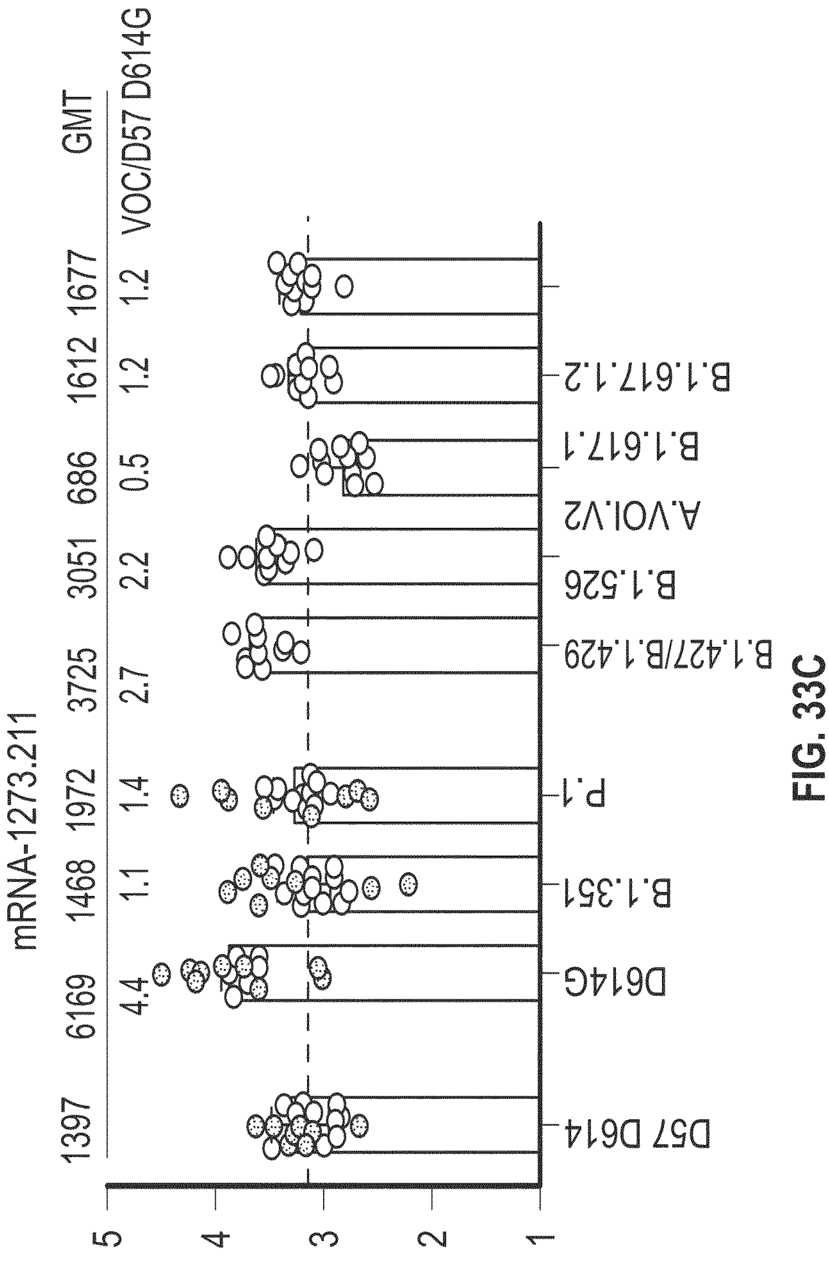
Figure 34:
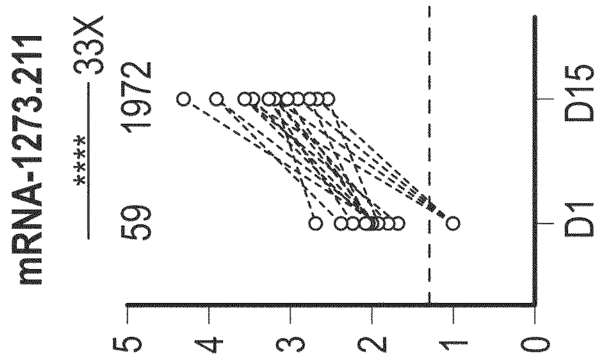
FIG. 34 is a cohort comparison between different boosting strategies with respect to two variants of concern: B.1.351 and P.1. D614G is shown as a comparator.
Figure 34:
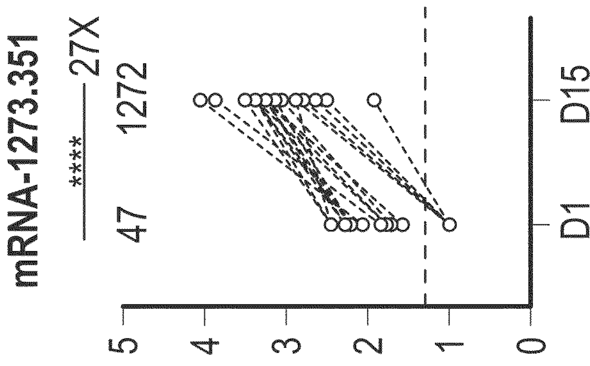
Figure 34:
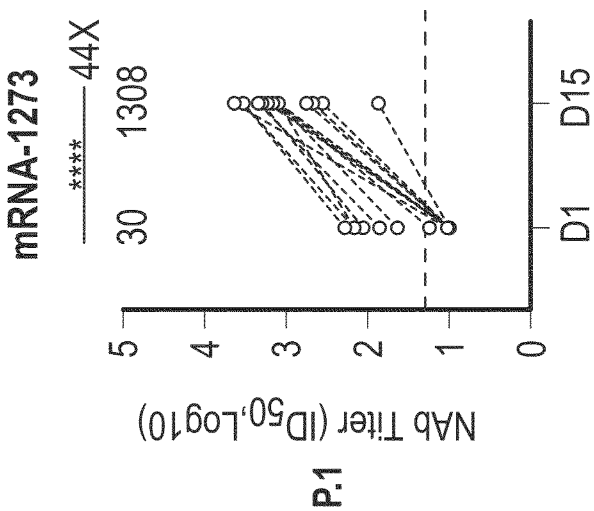

Further variants of concern and variants of interest were screened. As can be seen in FIGS. 33A-33C, the booster shots were found to neutralize each variant as well. A comparison of the neutralizing titers resulting from administration of one of the three booster shots is shown in FIG. 34. mRNA-1273.211 was found to outperform the two other booster shot strategies against all variants tested.

Example 22. Safety and Immunogenicity of SARS-CoV-2 Variant mRNA Booster in Adults mRNA-1273, a lipid nanoparticle-encapsulated messenger RNA vaccine encoding a prefusion stabilized S protein of the WA1/2020 isolate, demonstrated anti-SARS-CoV-2 immune responses in phase 1 (NCT04283461) and phase 2 (NCT04405076) trials in adults, an acceptable safety profile, and 94% efficacy against symptomatic Covid-19 disease in the phase 3 Coronavirus Efficacy (COVE) (NCT04470427) trial in over 30,000 participants. The vaccine received authorization from several global regulatory bodies including the U.S. Food and Drug Administration. Although the vaccine is highly effective in reducing the symptoms and severe complications of Covid-19, several viral variants with changes in the S protein have arisen, some of which have been identified as variants of concern (VOCs): Alpha [B.1.1.7], Beta [B.1.351], Gamma [P.1], and Delta [B.1.617.2]. Reduction in efficacy has been reported against some Covid-19 vaccines versus B.1.351 and more recently B.1.617.2.

Described herein are the preliminary safety and immunogenicity of single booster doses of mRNA-1273 (50 μg), modified mRNA-1273.351 (20 or 50 μg) encoding the spike protein of B.1.351 (beta variant), and multivalent mRNA-1273.211 (a 1:1 mix of mRNA-1273 [25 μg] and mRNA-1273.351 [25 μg]) in a Phase 2 trial.

Results

Trial Population

The Phase 2 trial consisted of a total of 660 participants. Upon study unblinding and implementation of Part B, 20 of the 186 participants who had originally received 2 priming doses of 100 μg mRNA-1273 were randomly selected based on visit assessments completed and sample availability to receive a single booster dose of 50 μg mRNA-1273. Sixty of the 14,711 participants, 12 who received two priming doses of 100 μg mRNA-1273, were selected to receive single booster doses of 50 μg of mRNA-1273.351 (Part C, cohort 1) or mRNA-1273.211 (Part C, cohort 2) or 20 μg of mRNA-1273.351 (Part C, cohort 3).

The baseline demographic characteristics of the 4 groups of participants who received booster doses of the prototype or the modified mRNA-1273 vaccines were generally similar (Table 26). Most of the participants were White and not Hispanic or Latino. The mean age of the participants who received boosters of mRNA-1273 (50 μg), mRNA-1273.351 (20 μg), mRNA-1273.351 (50 μg) or mRNA-1273.211 was 63.8, 47.5, 53.9 and 55.6 years, respectively. The duration (mean [SD]) between the second dose of mRNA-1273 in the primary series and the booster for mRNA-1273 (50 μg), mRNA-1273.351 (20 μg), mRNA-1273.351 (50 μg) or mRNA-1273.211 (50 μg) was 6.7 [0.5], 6.2 [0.3], 6.2 [0.3] and 6.2 [0.4] months, respectively.

TABLE 27

Immune response after Booster Dose (50 μg) vs. Two Doses of 100 μg mRNA-1273

| | Pseudovirus Neutralizing Antibody ID50 All ages | | Pseudovirus Neutralizing Antibody ID50 Ages 18-<65 | | Pseudovirus Neutralizing Antibody ID50 Ages 65+ | |
|---|---|---|---|---|---|---|
| | P201 Part B | P301 | P201 Part B | P301 | P201 Part B | P301 |
| Baseline GMT | 125.7 | 9.6 | 145.6 | 9.8 | 82.5 | 9.4 |
| GMT (observed) | 1892.7 | 1081.1 | 1940.4 | 1206.6 | 1761.8 | 871.2 |
| Ratio of GMT (P201 Part B vs. P301) | 1.75 | | 1.61 | | 2.02 | |
| Seroresponse Rate (95% CI) | 90.1 (86.1, 93.3) | 98.4 (97.4, 99.1) | 89.0 (84.1, 92.8) | 98.4 (97.2, 99.2) | 93.4 (85.3, 97.8) | 98.3 (96.3, 99.4) |
| Difference in SSR (95% CI) | −8.2 (−12.2, −5.2) | | −9.4 | | −4.9 | |

Figure 35A:
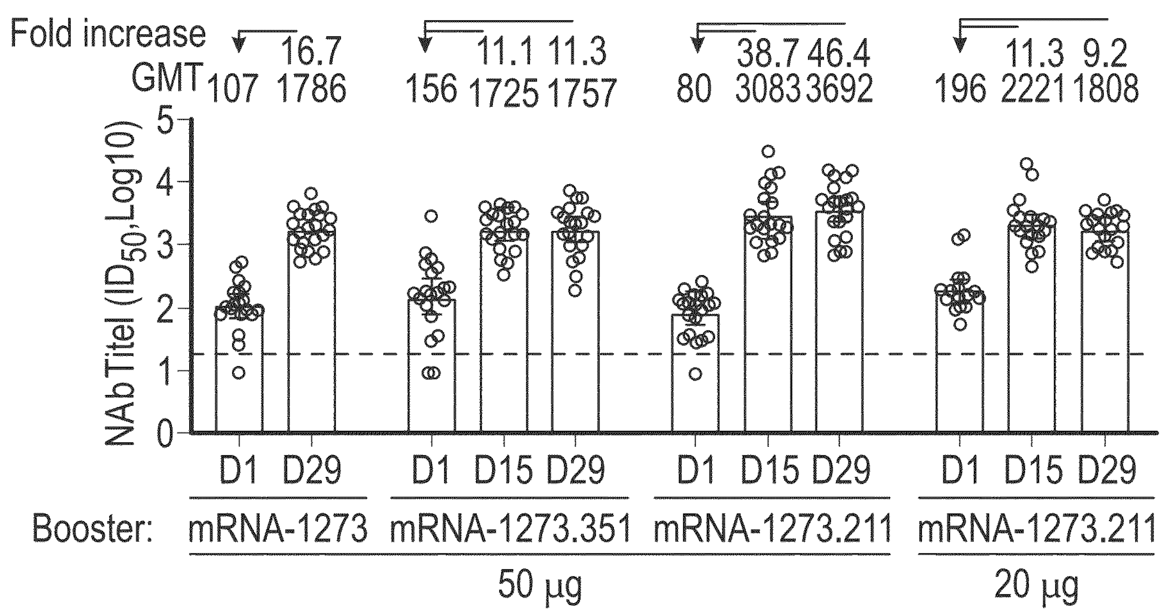
FIGS. 35A-35B show the neutralization of wild-type (FIG. 35A) and B.1.351 (FIG. 35B) lentivirus-based pseudoviruses by participant serum immediately before and after boosters using a clinically validated recombinant lentivirus-based SARS-CoV-2 pseudovirus assay (D614G and B.1.351). Sera was collected immediately prior to receiving a booster (D1) and on day 15 (D15) and 29 (D29) after the booster dose of 50 μg of mRNA-1273, 50 or 20 μg of mRNA-1273.351, or 50 μg mRNA-1273.211. The geometric mean neutralizing antibody titers with 95% confidence intervals are denoted. The titers for individual participants are shown by the circles. The fold increase versus titers measured versus samples collected prior to the boost are shown. The horizontal dotted lines indicate the lower limit of quantification (LLOQ). N=20 participants per booster cohort.
Figure 35B:
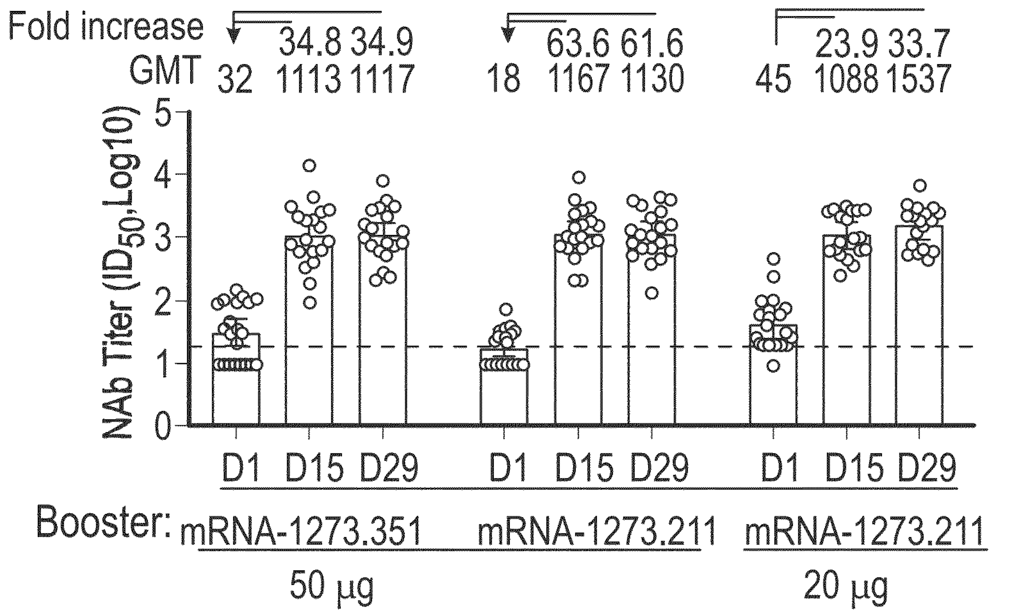

Neutralizing Responses to Wild-Type D614G and B.1.351 Immediately Prior to and after the Booster Dose Wild-type D614G and B.1.351 neutralization was measured in samples collected ~6 months after the primary series of mRNA-1273, but immediately before the booster dose (D1), and in samples collected on day 15 (D15) or 29 (D29) after the booster dose in a clinically validated Lentivirus PsVN assay. The wild-type D614G virus was neutralized by samples collected prior to the booster from participants in Part B and Part C cohorts 1, 2, and 3 (FIG. 35A), while neutralization of B.1.351 was low or nondetectable prior to the boost from participants in Part C cohorts 1, 2, and 3 (FIG. 35B).

After the booster dose, participant sera were collected on day 29 from Part B participants (mRNA-1273 booster) or on day 15 and 29 from Part C cohorts 1, 2, and 3 (50 μg mRNA-1273.351, 50 μg mRNA-1273.211, and 20 μg mRNA-1273.351 boosters, respectively). Neutralization of the wild-type D614G and B.1.351 viruses significantly increased after each booster dose. Against the wild-type D614G virus, 16.7, 11.3, 46.4, and 9.2-fold higher GMTs were measured in the mRNA-1273 (50 μg), mRNA-1273.351 (50 μg), mRNA-1273.211 (50 μg), and mRNA-1273.351 (20 μg) cohorts, respectively, on D29. Against the B.1.351 variant, 34.9, 61.6, and 33.7-fold higher GMTs were measured in the mRNA-1273.351 (50 μg), mRNA-1273.211 (50 μg), and mRNA-1273.351 (20 μg) cohorts, respectively, on D29. In addition, participants who did not have measurable titers against the wild-type D614G or B.1.351 virus ~6 months after the primary series, prior to the boost, all had regained significant titers after the boost.

Figure 36A:
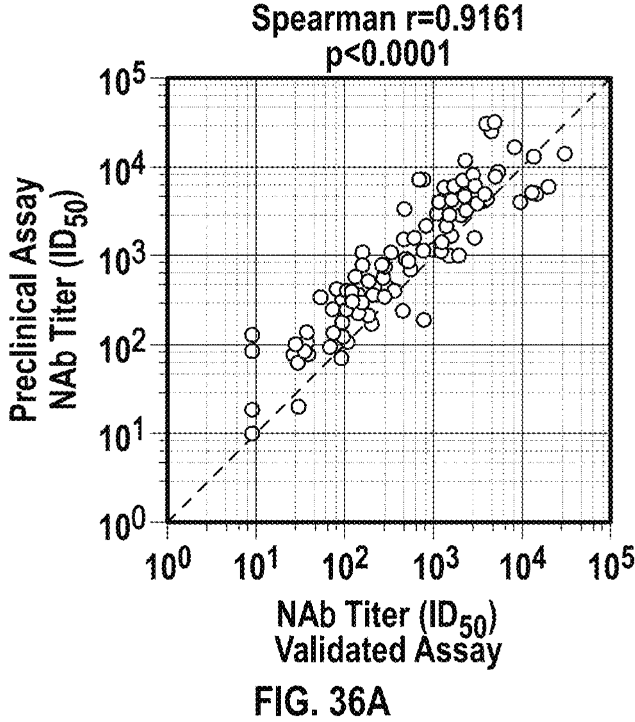
FIGS. 36A-36B show correlation of results from clinically validated pseudovirus assay and VSV-based pseudovirus assay used for exploratory analysis of SARS-CoV-2 variants. Neutralizing Ab titers from participant sera in the clinically validated recombinant lentivirus-based SARS-CoV-2 pseudovirus assay was correlated to a VSV-based SARS-CoV-2 pseudoviruses assay used for exploratory analysis of SARS-CoV-2 variants (D614G (FIG. 36A) and B.1.351 (FIG. 36B)). Sera was collected immediately prior to receiving a booster (D1) and 2 weeks after (D15) the booster dose of 50 μg of mRNA-1273, mRNA-1273.351, or mRNA-1273.211. The titers for individual participants are shown by the circles. For wild-type assay, the available Part B (D1) and Part C (D1 and D15) data points were used for correlation analysis. For B.1.351 assay, the available Part C (D1 and D15) data points were used. Spearman nonparametric analysis was performed for correlation analysis of both assays.
Figure 36B:
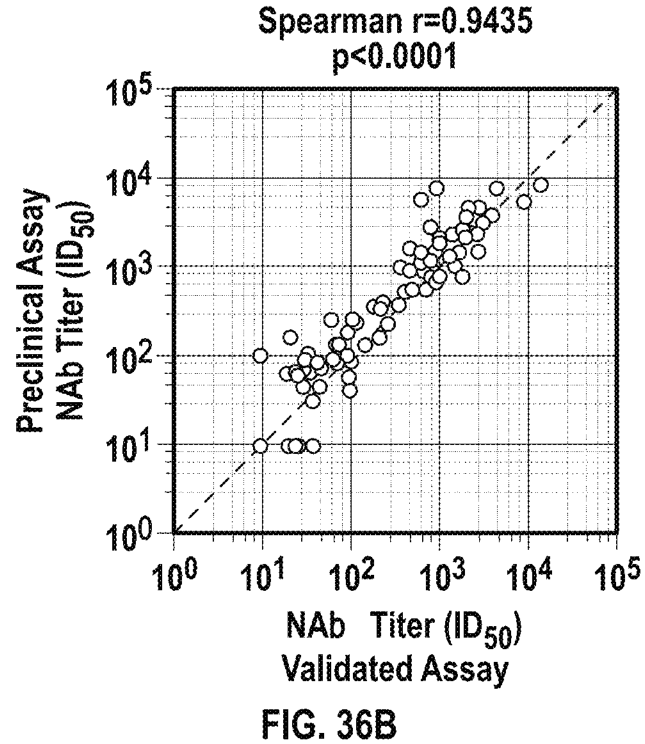

Correlation of the Clinically Validated Lentivirus PsVN Assay with a Research-Grade VSV-Based PsVN Assay In order to support exploratory analysis of the Part B and Part C Cohort 1 and 2 clinical samples against SARS-CoV-2 variants, participant samples were analyzed in a research-grade VSV-based PsVN assay that has previously been used to evaluate the impact of SARS-CoV-2 variants on mRNA-1273 neutralization. Analysis of the results from the clinically validated and research-grade wild-type D614G and B.1.351 PsVN assays demonstrates significant correlation, with r=0.9160 against wild-type D614G and 0.9411 against B.1.351 in an analysis of results from D1 and D15 samples (FIGS. 36A-36B).

Exploratory Analysis of the Kinetics of Neutralizing Responses to Wild-Type D614G and VOCs Post-Primary Series Vaccination Exploratory analysis of samples collected after the primary mRNA-1273 vaccination series was performed using the VSV-based PsVN assay. Twenty-eight days after the primary 2-dose series, wild-type D614G neutralizing antibody GMTs were 1210 in the mRNA-1273, 2213 in the mRNA-1273.351 and 1397 in the mRNA-1273.211 Cohorts (FIGS. 37A-37D), with significant reductions seen against both B.1.351 (13-17-fold) and P.1 variants (5-7-fold). Approximately 6 months after the second dose of mRNA-1273, neutralizing antibody GMTs further decreased in comparison to peak titers measured against the D614G virus 1 month after the primary series. Titers against the wild-type D614G were 6 to 7-fold lower, while titers against the B.1.351 and P.1 variants were 24 to 69-fold lower. Approximately 44% and 30% of combined samples from Part B and C cohorts 1 and 2 were below the assay LLOQ against B.1.351 and P.1 viral variants.

Figure 38A:
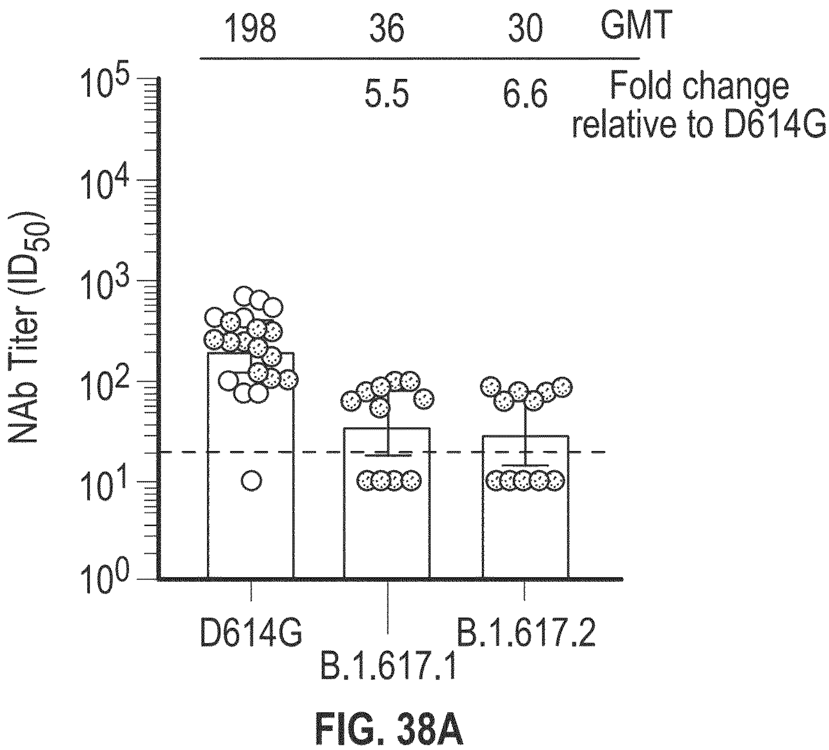
FIGS. 38A-38D show the effect of B.1.617 on neutralization and wild-type D614G and VOCs neutralization post-boost versus peak D614G titers after the primary series. Sera was collected from trial participants 1 month after the primary series vaccination with 100 μg mRNA-1273, immediately prior to the booster dose, and two weeks after the 50 μg boosters.

Similar to B.1.351 and P.1, neutralization of the B.1.617.2 variant, was considerably reduced 6 months after completion of the primary series. Sera from a random subset of the Part B cohort collected prior to the booster dose of mRNA-1273 showed a 5-6-fold reduction against B.1.617.1 and B.1.617.2 versus the wild-type D614G neutralizing titers measured at the same timepoint, with neutralization in 5 of 11 samples falling below the assay LLOQ against B.1.617.2 (FIG. 38A).

Exploratory Analysis of Neutralizing Responses Against Wild-Type D614G Virus and VOCs from Boosters Wild-type D614G virus neutralizing titers were measured with the VSV-based PsVN assay in order to compare titers from samples collected 15 days after the booster dose versus peak titers measured from samples collected 28 days after the second dose of the mRNA-1273 primary series. After the boost, wild-type virus neutralization GMTs were 3.8, 1.7, and 4.4-fold higher from the mRNA-1273, mRNA-1273.351, and mRNA-1273.211 boosters, respectively, relative to the peak titers 28 days after the primary series vaccination (FIGS. 37A-37D). Against VOCs or VOIs, each of the booster strategies significantly increased variant-specific neutralization titers relative to those measured after the primary series. mRNA-1273.211 increased both B.1.351 and P.1 neutralization titers above the GMT level against the D614G strain measured after the primary series, with GMT titers increasing to 1468 against B.1.351 and 1973 against P.1 in the Part C cohort 2 participants 2-weeks after the booster dose.

Exploratory Analysis of Booster Response to VOC Compared to a Primary Series GMT Benchmark The VSV PsVN assay was used to assess COVE study samples collected 28 days after the primary series to establish a GMT benchmark. This benchmark was used to determine whether the boosters reached the same neutralization level shown in the pivotal study where efficacy was demonstrated, i.e., to levels seen in the D614G assay where 94% efficacy was measured, indicated by a GMT ratio (GMTr) ≥1.12 In the Part C, day 57 primary series participant samples (n=59) from the COVE study, a GMT of 2045 was established as the D614G neutralization benchmark, with GMTs per cohort that ranged from 1397-2758 (FIGS. 37A-37D).

Figure 24A:
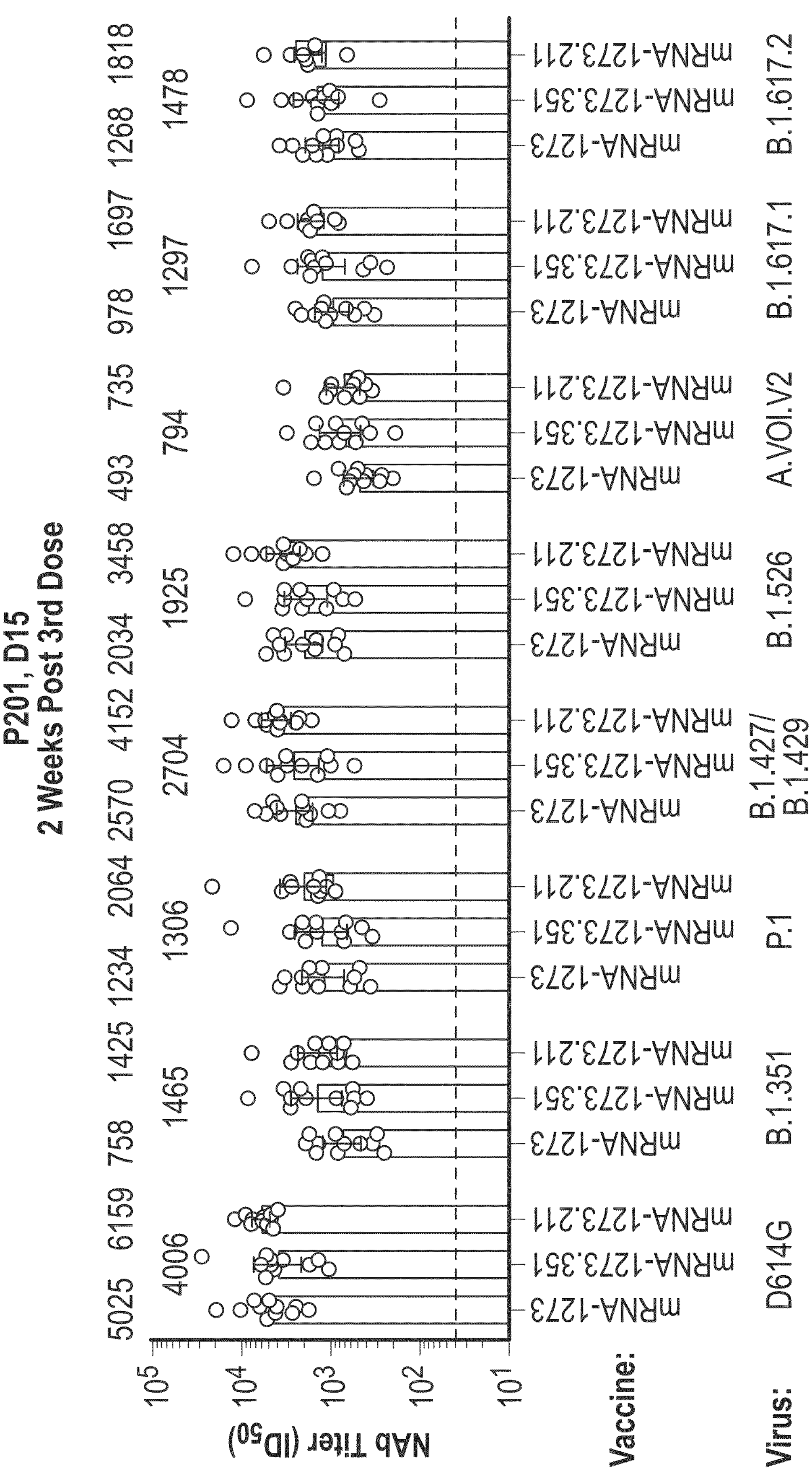
FIGS. 24A-24B show neutralization titers of serum samples taken two weeks after a third dose (booster) of vaccine comprising mRNA-1273, mRNA-1273.351, or mRNA-1273.211. The serum samples were tested against D614G and variants B.1.351, P.1, B.1.427/1.429, B.1.526, A.VOI.V2, B.1.617.1, and B.1.617.2. Neutralization titers are shown in FIG. 24A
Figure 24B:
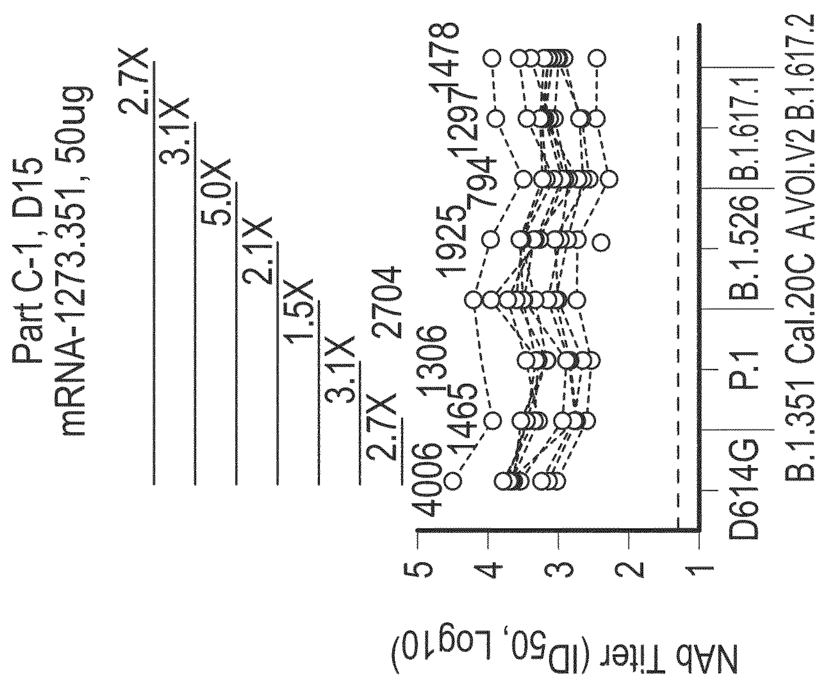
Figure 24B:
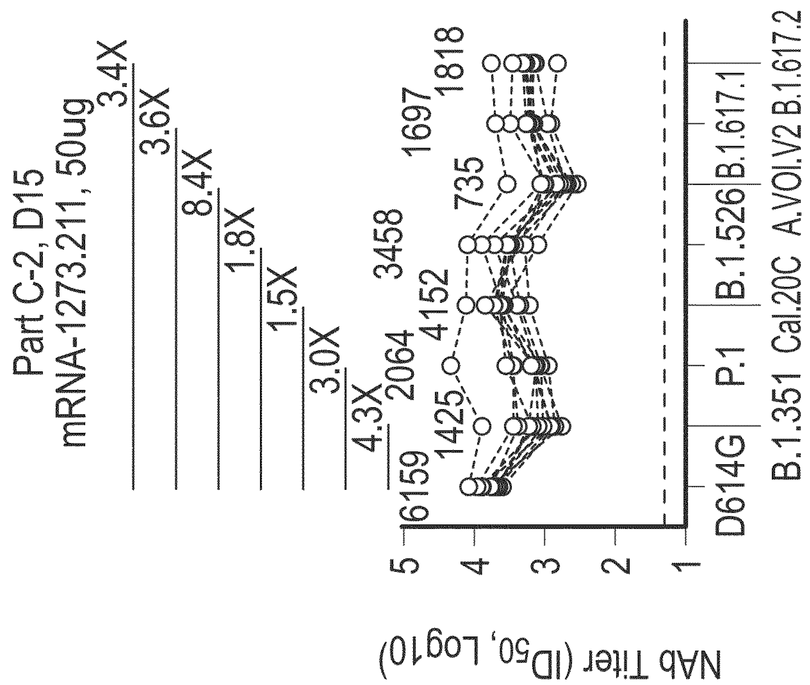

When samples collected 2-weeks after the respective booster dose were assessed against a panel of variants (FIGS. 24A-24B; 38B-38D), each mRNA booster significantly increased neutralization against all variants assessed, including B.1.617.2 and P.1, with neutralization against some of the variants approaching or exceeding the COVE study wild-type D614G GMT benchmarks. Of the three booster vaccines assessed, the multivalent mRNA-1273.211 booster showed the greatest increase in GMTs against the majority of VOCs (FIGS. 24A-24B; 38A-38D).

Figure 38B:
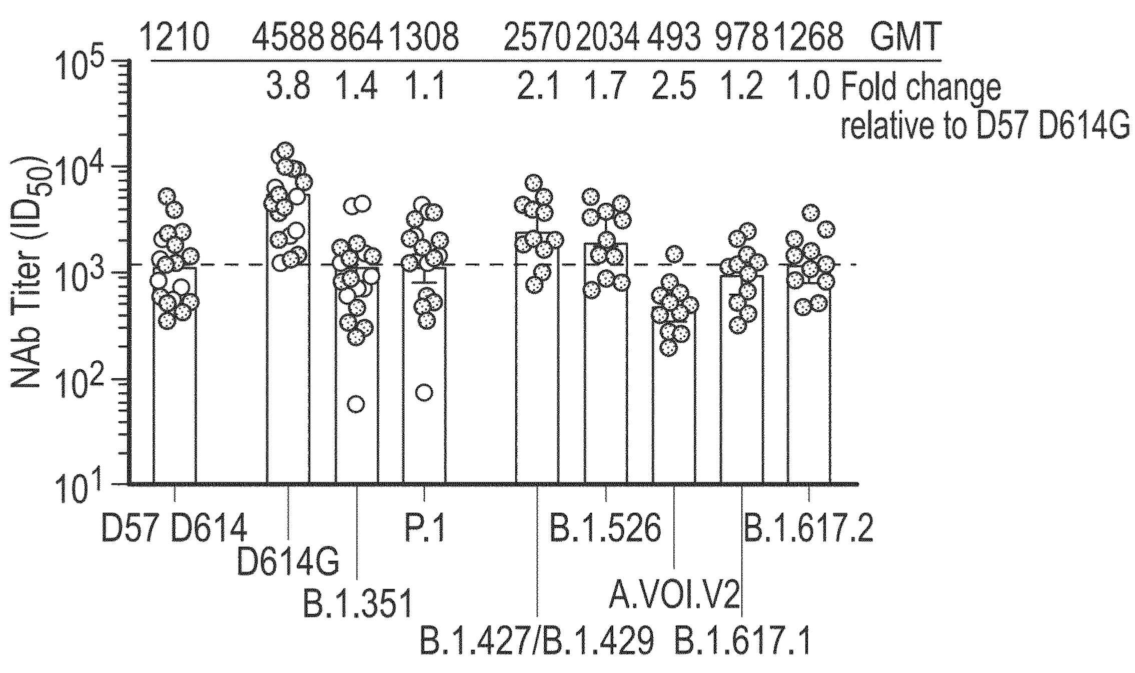
Figure 38C:
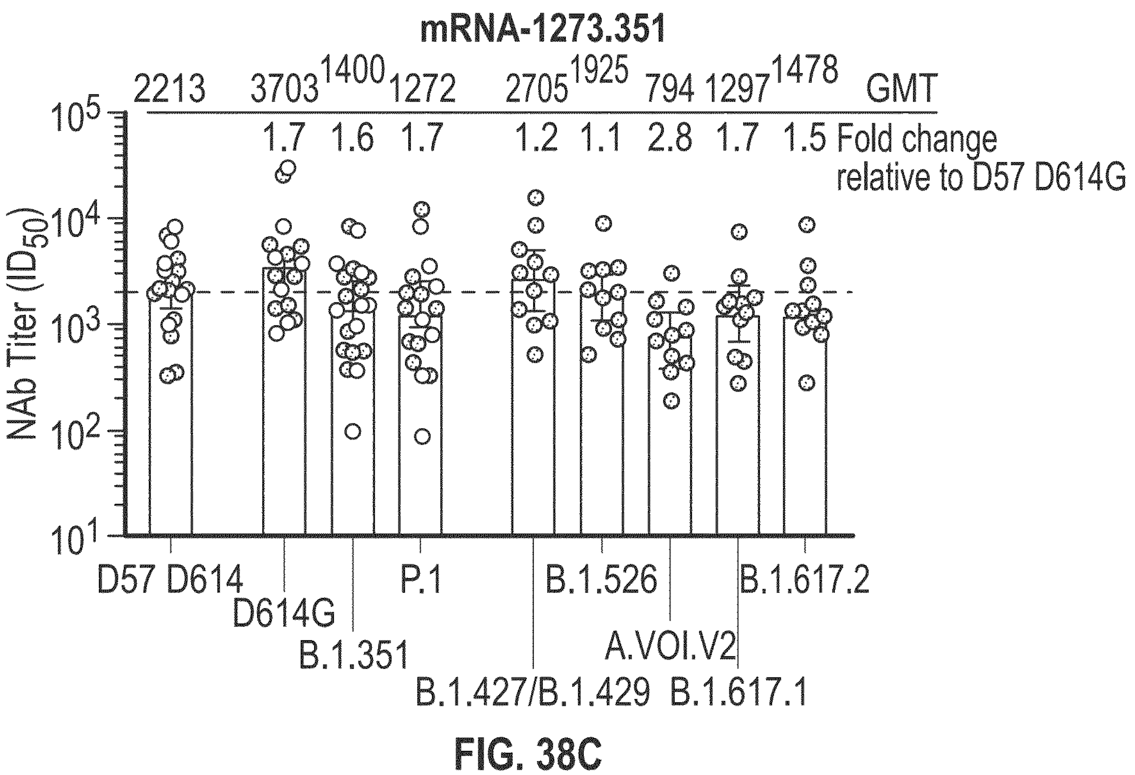
Figure 38D:
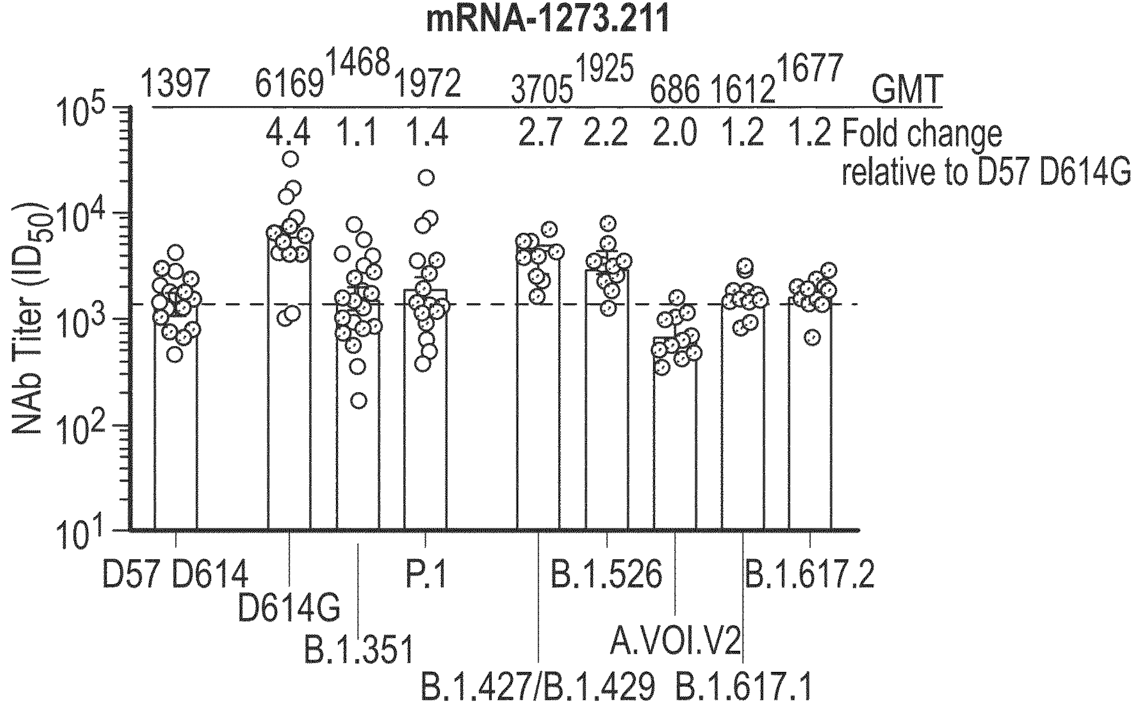
Figures 39A, 39B:
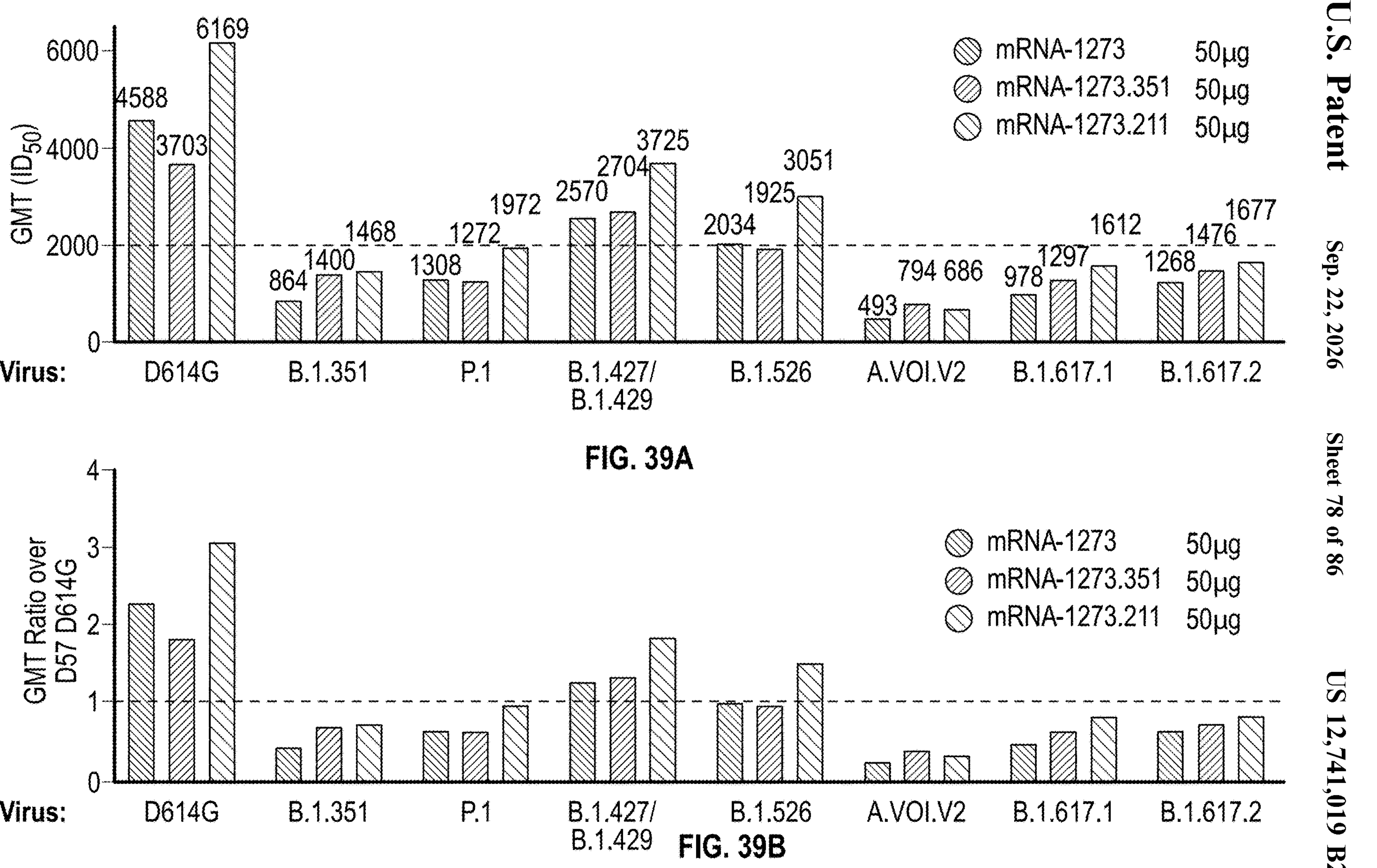
FIGS. 39A-39B show wild-type D614G and VOCs GMT neutralization after boosting versus COVE study GMT benchmark. Sera from trial participants two weeks after the 50 μg boost with mRNA-1273, mRNA-1273.351, or mRNA-1273.211 were analyzed for neutralizing antibody using the recombinant VSV-based SARS-CoV-2 pseudovirus assay.

Compared to the COVE study D614G benchmark, the booster vaccines yielded higher GMTs against the wild-type D614G virus and several VOCs or VOIs, including B.1.617.2, based on a GMTr rise≥1 (FIGS. 38B-38D). However, only the multivalent variant vaccine mRNA-1273.211 achieved a GMTr rise of >1 against all VOCs assessed. Of the three boosters, the multivalent mRNA-1273.211 50 μg booster also yielded higher variant GMTs versus the D57 D614G benchmark and against the largest number of variants including B.1.351, P.1, B.1.427/B.1.429; B.1.526, B.1.617.1, and B.1.617.2. A comparison of the GMT versus the overall COVE GMT D614G benchmark is shown in FIGS. 39A-39B.

Discussion

This preliminary evaluation describes the antibody persistence of mRNA-1273 and administration of booster doses of mRNA-1273, mRNA-1273.351 and mRNA-1273.211 in a subset of 80 participants who had been vaccinated ~6 months previously with the authorized dose and schedule of mRNA-1273. Antibody titers against the wild-type D614G peaked one month after the second dose of the primary series, and subsequently declined over the next 5 months prior to the delivery of the booster dose. These results are consistent with those reported in a lentiviral PsVN assay, where monitoring of neutralizing antibody levels was performed up to 6 months after the second dose of mRNA-12731. Reduction of neutralizing antibody was evident 28 days after the primary series vaccination against B.1.351 and P.1 to greater levels than measured against samples collected 7 days after the primary series, likely due to further affinity maturation of B-cells and alteration of the available antibody repertoire. Additional reduction or complete loss of detectible levels of neutralizing antibody ~6 months after the primary vaccination was evident against B.1.351, P.1, and B.1.617.2.

The safety profiles following single injections of 50 μg mRNA-1273, 20 or 50 μg mRNA-1273.351, and 50 μg mRNA-1273.211 boosters were generally similar to those observed after a second dose of mRNA-1273 in the previously reported phase 2 and 3 studies.

Figure 37A:
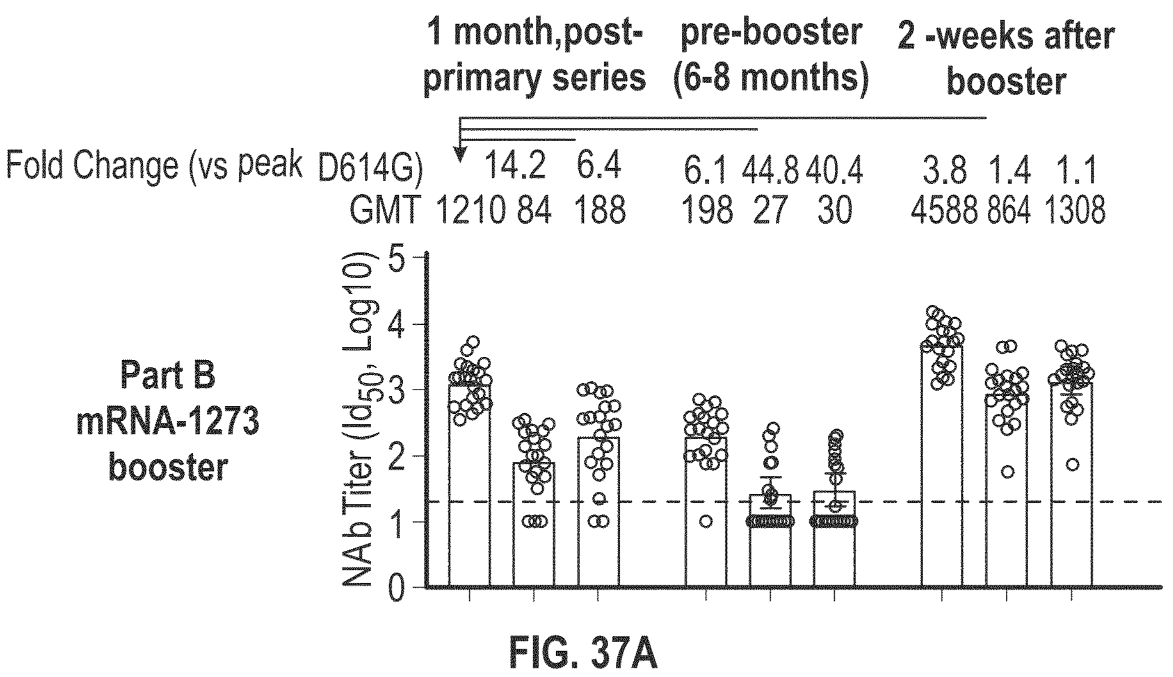
FIGS. 37A-37D show an exploratory analysis of neutralization of wild-type and variants VSV-based pseudoviruses by participant serum. Neutralization of recombinant VSV-based SARS-CoV-2 pseudoviruses (D614G, B.1.351 and P.1) by serum from participants 1 month after the primary series vaccination with 100 μg mRNA-1273, immediately prior to receiving a booster, and 2 weeks after the booster dose of 50 μg of mRNA-1273 (FIG. 37A), 50 μg of mRNA-1273.351 (FIG. 37B), 50 μg of mRNA-1273.211 (FIG. 37C), or 20 μg of mRNA-1273.351 (FIG. 37D). The groups, from left to right, in each group are D614G, B.1.351, and P.1 (as shown in FIG. 37C). The geometric mean neutralizing antibody titers with 95% confidence intervals are denoted. The titers for individual participants are shown by the circles. The GMT fold change versus the peak titers against the wild-type D614G virus after the primary vaccination series are shown. The horizontal dotted lines indicate the lower limit of quantification (LLOQ). N=20 participants per booster cohort.
Figure 37B:
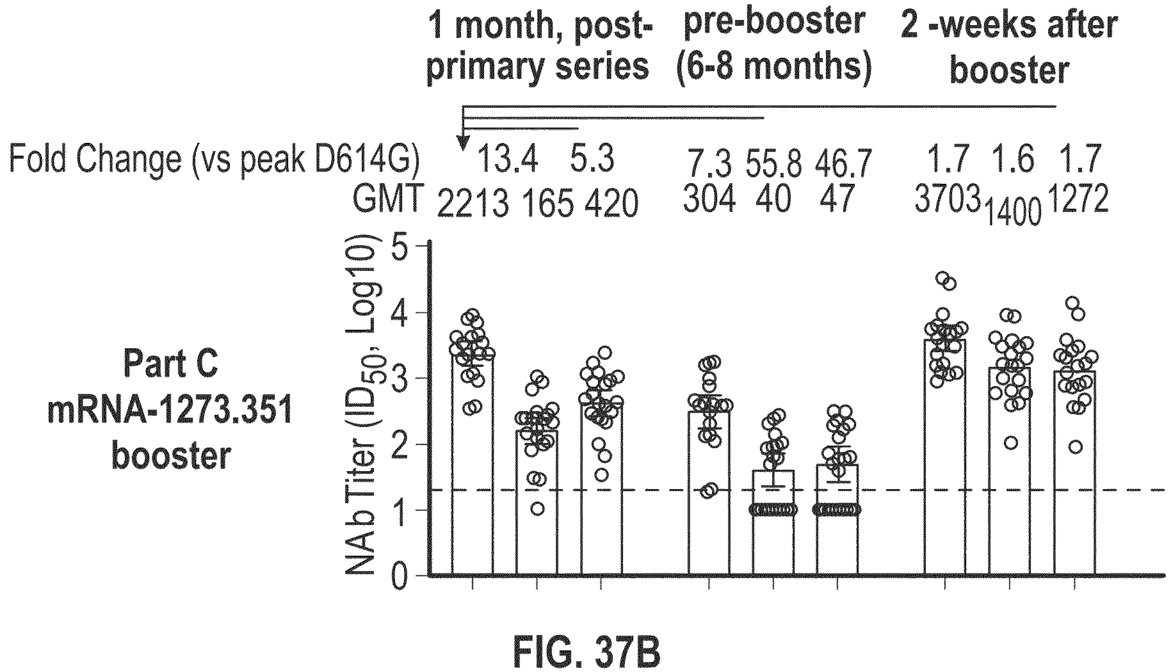
Figure 37C:
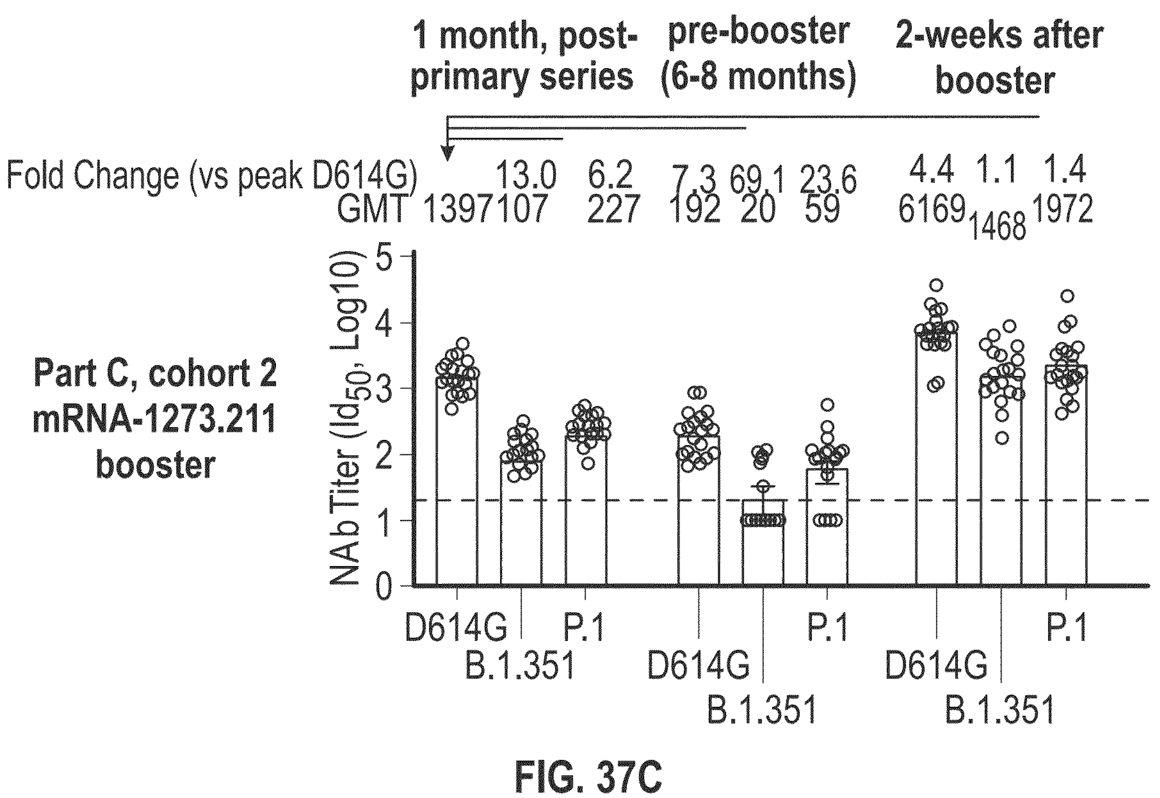
Figure 37D:
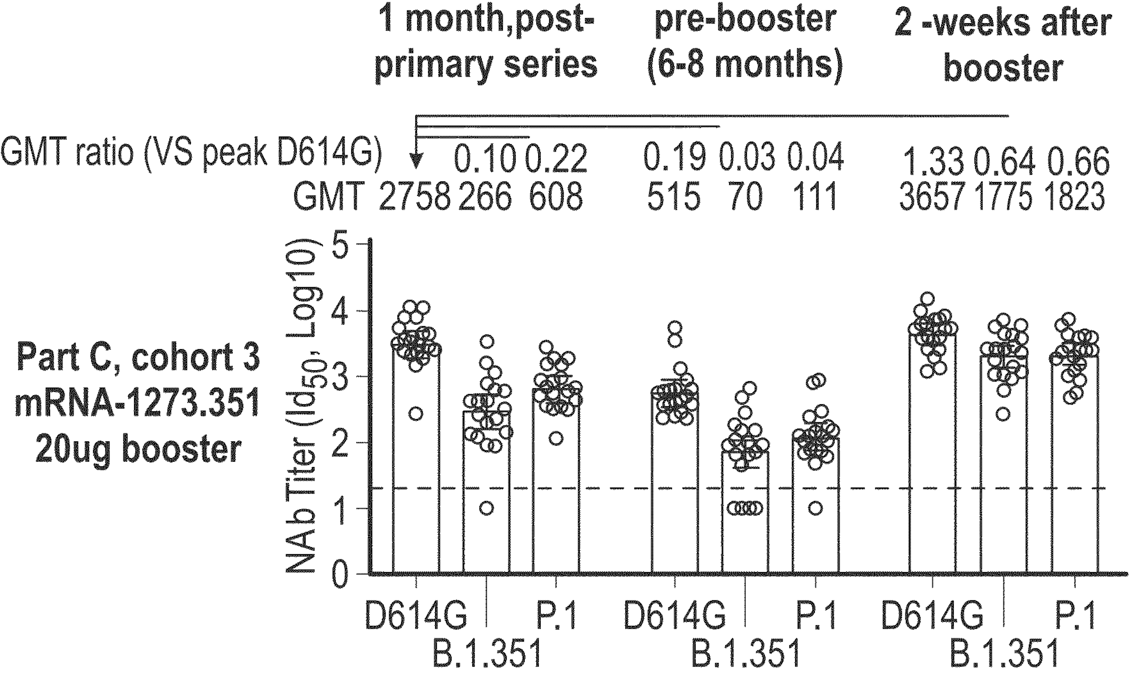

Booster vaccination with mRNA-1273, mRNA-1273.351, and mRNA-1273.211 induced robust anamnestic responses, confirming that the robust B-cell memory generated by mRNA vaccines can be quickly and potently boosted. High neutralizing titers were measured against the wild-type D614G strain after a booster dose which were up to 4.4-fold higher than peak titers after the primary series. Increased VSV PsVN titers were measured against variant viruses including the key VOCs, B.1.351, P.1, and B.1.617.2, with titers against several variants approaching or exceeding those measured after the primary series against the wild-type D614G virus, particularly after boosting with mRNA-1273.211 (FIG. 37C). Increased titers against the VOCs suggest that further maturation of antibodies is feasible after a two-dose primary series of mRNA-1273, regardless of the composition of the booster dose. Additionally, boosting with mRNA-1273.351 and mRNA-1273.211 appeared to be more effective at increasing neutralization against the B.1.351 variant than with mRNA-1273.

For comparison to GMT titers measured in the Phase 3 COVE study where efficacy was established, 59 COVE participant samples were evaluated in the VSV PsVN assay with the wild-type D614G assay titers used to support additional analyses. The mRNA boosters each significantly increased-neutralization against all variants assessed, including B.1.617.2 and P.1, with neutralization against some of the variants approaching or exceeding the COVE study benchmark. The multivalent mRNA-1273.211 50 μg booster yielded a GMTr rise 1 against all VOCs (FIG. 38D), indicating that variant neutralization GMTs after the booster exceeded peak wild-type virus GMTs after the primary series, potentially increasing breadth of coverage against VOCs or VOIs.

Methods

Study Design

The phase 2 mRNA-1273 P201 study (NCT04405076) enrolled adults at 8 sites in the U.S. Preliminary safety and immunogenicity results following two doses of 50 or 100 μg of mRNA-1273 have been previously reported. Once the primary efficacy endpoint for mRNA-1273 against Covid-19 was met in the phase 3 COVE trial and EUA was granted, both the phase 2 and 3 trial protocols were amended to transition the studies to open-label phases. The phase 2 study offered participants previously primed with two doses (50 or 100 μg) of mRNA-1273 in Part A an option to receive a single booster of 50 μg mRNA-1273 in Part B, however only 20 individuals primed with two doses of 100 μg of mRNA-1273 were included in this analysis. Part C was added to the phase 2 study, and participants at a single site from the phase 3 COVE trial who completed a two-dose series of 100 μg of mRNA-1273 were enrolled to receive a single booster of either 20 or 50 μg doses of mRNA-1273.351 or 50 μg of the multivalent mRNA-1273.211.

Trial Participants

Eligible participants were adults, ≥18 years of age, considered by the investigator to be healthy at screening and were enrolled at one of the 8 participating study sites. Twenty Part B participants who received a single booster dose of mRNA-1273 50 μg in Part B were randomly selected for this sub-study analysis. For Part C, participants must have been previously enrolled in the mRNA-1273 phase 3 COVE study and received two doses of mRNA-1273 in Part A of that study, with a second dose at least 6 months prior to enrollment in Part C of the P201 study. Sixty participants were sequentially enrolled to receive mRNA-1273.351 50 μg, mRNA-1273-211 50 μg, or mRNA-1273.351 20 μg (20/group).

Trial Vaccines

The mRNA-1273.351 vaccine, like mRNA-1273, encodes the S protein of SARS-CoV-2 B.1.351 variant. mRNA-1273.211 was a 1:1 mix of 25 μg of mRNA-1273 and 25 μg of mRNA-1273.351, for a total dose of 50 μg of mRNA. All vaccines were formulated in lipid nanoparticles as previously described.

Safety Assessment

Participants completed an electronic diary for 7 days post-booster to record solicited systemic and local adverse reactions, daily oral body temperatures, injection site erythema and swelling/induration. Trained site personnel called participants to assess safety every 4 weeks.

Immunogenicity Assessments

For this sub-study analysis of 80 participants, samples were collected 28 days post-primary vaccination series, immediately prior to the booster vaccination (Day 1), and at days 8, 15, 29, 57, and 181 post-booster vaccination. In this preliminary analysis, neutralization results of sera collected 28 days after the primary series, immediately prior to the booster dose, and 15 and 29 days after the booster are provided. A clinically validated lentivirus PsVN assay, used to test the samples from phase 2 and 3 (COVE) trials, was used to analyze samples collected immediately prior to the booster (D1) and at D15 and D29 respectively. To enable exploratory analysis across a panel of SARS-CoV-2 variants, sera were analyzed for neutralizing antibody titers using a research-grade recombinant vesicular stomatitis virus (VSV)-based pseudovirus assay previously used to assess the impact of neutralization from variants against sera collected 7 days after the second dose of mRNA-1273. In this assay, the S protein of the prototype WA1/2020 isolate with the D614G mutation (wild-type D614G) or the S proteins from variants are encoded. The VSV PsVN neutralization assay demonstrates strong correlation and concordance with the clinically validated Lentivirus PsVN assay (FIGS. 36A-36B).

Statistical Analysis

Geometric mean titer (GMT) and geometric mean fold rise (GMFR) were calculated based on log-transformed titers, and 95% confidence intervals (CI) based on the t-distribution of the log-transformed titers or the difference in the log-transformed titers for GMT and GMFR, respectively, then back transformed to the original scale. Analysis of the COVE study participant sera collected 28 days after the primary series was used to establish a GMT benchmark further used to derive GMT ratios after boosting. Wilcoxon matched-pairs signed rank test was used to compare results. Spearman nonparametric correlation was used for assay correlation.

Example 23—Variant Booster Study

Subjects were administered two doses of mRNA-1273 as described in Example 13 (either two doses of 50 μg or two doses of 100 μg each). Booster doses were administered at least 6 months later. The booster doses tested include: mRNA-1273.211 (50 μg), mRNA-1273.211 (100 μg), mRNA-1273 (100 μg), mRNA-1273.617, and mRNA-1273.213 (100 μg dose: 50 μg mRNA-1273 and 50 μg 1273.617; SEQ ID NO: 28). The safety and immunogenicity of the booster dose were examined. —In particular, the results from day 29 (after the booster dose) were compared to the results described in Example 22. The results relative to subjects who only received two 100 μg doses of mRNA-1273 (P301) are shown in Table 27 below and demonstrate that the booster dose increased geometric mean titer (GMT) levels relative to the subjects who only received two 100 μg doses of mRNA-1273 (P301). The booster dose also induced neutralizing antibodies that are significantly higher than at day 29 after dose 2 (e.g., the booster resulted in a 17-fold increase over pre-booster titers). The booster titers were comparable between the younger and older adult cohorts.

TABLE 28

| Log10 SP2/SP2.529-specific IgG Titer (Day 21) | | | |
|---|---|---|---|
| Virus | Vaccine | Dose | IgG Titer |
| SP2 | mRNA-1273 | 1 μg | 818 |
| B.1.1.529 | mRNA-1273 | 1 μg | 75 |
| SP2 | mRNA-1273.529 (m-mu) | 1 μg | 260 |
| B.1.1.529 | mRNA-1273.529 (m-mu) | 1 μg | 406 |
| SP2 | mRNA-1273.529 (PBSko_match) | 1 μg | 309 |
| B.1.1.529 | mRNA-1273.529 (PBSko_match) | 1 μg | 228 |
| SP2 | mRNA-1273.529.IDR14A | 1 μg | 104 |
| B.1.1.529 | mRNA-1273.529.IDR14A | 1 μg | 212 |
| SP2 | mRNA-1273.529.IDR14B | 1 μg | 1082 |
| B.1.1.529 | mRNA-1273.529.IDR14B | 1 μg | 1292 |
| SP2 | mRNA-1273 | 0.1 μg | 14 |
| B.1.1.529 | mRNA-1273 | 0.1 μg | 7 |
| SP2 | mRNA-1273.529 (m-mu) | 0.1 μg | 8 |
| B.1.1.529 | mRNA-1273.529 (m-mu) | 0.1 μg | 11 |
| SP2 | mRNA-1273.529 (PBSko_match) | 0.1 μg | 28 |
| B.1.1.529 | mRNA-1273.529 (PBSko_match) | 0.1 μg | 15 |
| SP2 | mRNA-1273.529.IDR14A | 0.1 μg | 7 |
| B.1.1.529 | mRNA-1273.529.IDR14A | 0.1 μg | 10 |
| SP2 | mRNA-1273.529.IDR14B | 0.1 μg | 145 |
| B.1.1.529 | mRNA-1273.529.IDR14B | 0.1 μg | 80 |

Figure 40:
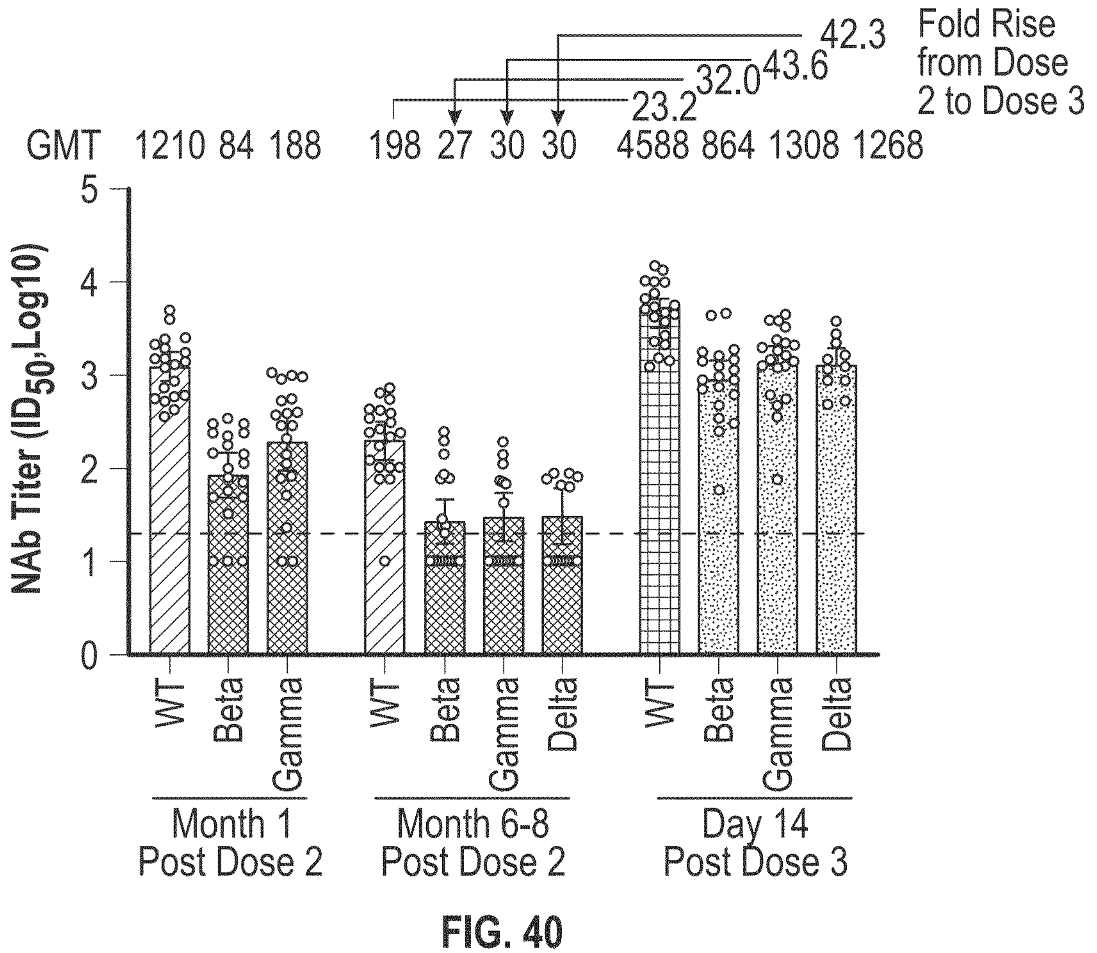
FIG. 40 is a graph showing that administration of a booster shot (mRNA-1273, 50 μg) increases neutralizing antibody titers against wild-type (D614) and variants of concern (B.1.351 (beta), P.1 (gamma), and B.1.617.2 (delta)) relative to two time points after the second administration of the vaccine.

The samples were further analyzed by examining neutralizing titers against broader variants of concern over time using a VSV assay, as described above. The results are shown in FIG. 40. The booster dose (mRNA-1273, 50 μg) was found to increase neutralizing antibody against the wild type (D614G) and three variants tested (B.1.351 (beta), P.1 (gamma), and B.1.617.2 (delta)). While neutralizing titers against the ancestral strain ("WT" in FIG. 40) remained above the GMT, the GMTs waned substantially by 6 months post-dose 2 against the variants of concern. The booster increased the GMTs for all viruses tested, and the fold-rise from dose 2 to the booster dose (dose 3) ranged from 23.2-fold against the D614G (wild-type) virus to 43.6-fold against the gamma variant (FIG. 40).

Example 24—Phase 2/3 Variant Booster Study

Subjects are administered two doses of mRNA-1273 as described in Example 13. Booster doses are administered 6-8 months later. The booster doses tested include: mRNA-1273.211 (50 μg), mRNA-1273.211 (100 μg), mRNA-1273 (100 μg), mRNA-1273.617, and mRNA-1273.213 (100 μg dose: 50 μg mRNA-1273 and 50 μg 1273.617; SEQ ID NO: 28). In some studies, three different-doses of mRNA-1273.213 are tested: 25 μg (12.5 μg mRNA-1273+12.5 μg 1273.617), 50 μg (25 μg mRNA-1273+25 μg 1273.617) and 100 μg (50 μg mRNA-1273+50 μg 1273.617). The endpoints are immunogenicity and safety of the dosages.

Example 25—Immunogenicity of Omicron-Related Vaccines

BALB/c mice were immunized at days 1 and 22 with 1 μg or 0.1 μg of mRNA-1273 (SEQ ID NO: 18), mRNA-1273.529 (m-mu) (SEQ ID NO: 40), mRNA-1273.529 (PBSko_match) (SEQ ID NO: 37), mRNA-1273.529.IDR14A (SEQ ID NO: 43), or mRNA.529.IDR14B (SEQ ID NO: 45) (n=8/group). In each vaccine, the mRNA was formulated in lipid nanoparticles (LNPs) including 0.5-15% PEG-modified lipid, 5-25% non-cationic lipid, 25-55% sterol, and 20-60% ionizable amino lipid. The PEG-modified lipid was 1,2 dimyristoyl-sn-glycerol, methoxypolyethyleneglycol (PEG2000 DMG), the non-cationic lipid was 1,2 distearoyl-sn-glycero-3-phosphocholine (DSPC), the sterol was cholesterol, and the ionizable amino lipid had the structure of Compound 1, for example.

Blood was collected one day before the second dose (day 21), and serum and spleen samples will be taken on day 36 and analyzed by ELISA and neutralization assays as described herein. ELISAs were performed to quantify total IgG specific to a parental SARS-CoV-2 Spike protein with the USA-WA1/2020 isolate amino acid sequence and IgG specific to B.1.1.529 (the omicron variant) from the samples collected on day 21.

The antibody titers with respect to the parental SARS-CoV-2 spike protein and B.1.529 are shown in Table 28 below.

```
5' UTR:
                                        (SEQ ID NO: 50)
GGGAAAUAAGAGAGAAAAGAAGAGUAAGAAGAAAUAUAAGAGCCACC

5' UTR:
                                        (SEQ ID NO: 2)
GGGAAAUAAGAGAGAAAAGAAGAGUAAGAAGAAAUAUAAGACCCCGGCG

CCGCCACC

3' UTR:
                                        (SEQ ID NO: 51)
UGAUAAUAGGCUGGAGCCUCGGUGGCCAUGCUUCUUGCCCCUUGGGCCU

CCCCCCAGCCCCUCCUCCCCUUCCUGCACCCGUACCCCCGUGGUCUUUG

AAUAAAGUCUGAGUGGGCGGC

3' UTR:
                                        (SEQ ID NO: 4)
UGAUAAUAGGCUGGAGCCUCGGUGGCCUAGCUUCUUGCCCCUUGGGCCU

CCCCCCAGCCCCUCCUCCCCUUCCUGCACCCGUACCCCCGUGGUCUUUG

AAUAAAGUCUGAGUGGGCGGC
```

As shown in Table 28, the B.1.529 IgG antibody titer was increased in the groups administered the B.1.529-specific vaccines compared to the mRNA-1273 group at both dosage levels.

REFERENCES

1 Zhou, P. et al. A pneumonia outbreak associated with a new coronavirus of probable bat origin. Nature 579, 270-273, doi:10.1038/s41586-020-2012-7 (2020).

2 Coronaviridae Study Group of the International Committee on Taxonomy of, V. The species Severe acute respiratory syndrome-related coronavirus: classifying 2019-nCoV and naming it SARS-CoV-2. Nat Microbiol 5, 536-544, doi:10.1038/s41564-020-0695-z (2020).

3 Wrapp, D. et al. Cryo-EM structure of the 2019-nCoV spike in the prefusion conformation. Science 367, 1260-1263, doi:10.1126/science.abb2507 (2020).

4 Jackson, L. A. et al. An mRNA Vaccine against SARS-CoV-2—Preliminary Report. N Engl J Med 383, 1920-1931, doi:10.1056/NEJMoa2022483 (2020).

5 Baden, L. R. et al. Safety and immunogenicity of two heterologous HIV vaccine regimens in healthy, HIV-uninfected adults (TRAVERSE): a randomised, parallel-group, placebo-controlled, double-blind, phase 1/2a study. Lancet HIV 7, e688-e698, doi:10.1016/S2352-3018(20)30229-0 (2020).

6 FDA (2021) COVID-19 Vaccines. https://www.fda.gov/emergency-preparedness-and-response/coronavirus-disease-2019-covid-19/covid-19-vaccines.

7 Korber, B. et al. Tracking Changes in SARS-CoV-2 Spike: Evidence that D614G Increases Infectivity of the COVID-19 Virus. Cell 182, 812-827 e819, doi:10.1016/j.cell.2020.06.043 (2020).

8 Plante, J. A. et al. Spike mutation D614G alters SARS-CoV-2 fitness. Nature 592, 116-121, doi:10.1038/s41586-020-2895-3 (2021).

9 Volz, E. et al. Evaluating the Effects of SARS-CoV-2 Spike Mutation D614G on Transmissibility and Pathogenicity. Cell 184, 64-75 e11, doi:10.1016/j.cell.2020.11.020 (2021).

10 Yurkovetskiy, L. et al. Structural and Functional Analysis of the D614G SARS-CoV-2 Spike Protein Variant. Cell 183, 739-751 e738, doi:10.1016/j.cell.2020.09.032 (2020).

11 Walls; A: C et al. Structure; Function, and Antigenicity of the SARS-CoV-2 Spike Glycoprotein. Cell 181, 281-292 e286, doi:10.1016/j.cell.2020.02.058 (2020).

12 Letko, M., Marzi, A. & Munster, V. Functional assessment of cell entry and receptor usage for SARS-CoV-2 and other lineage B betacoronaviruses. Nat Microbiol 5, 562-569, doi:10.1038/s41564-020-0688-y (2020).

13 Wang, Q. et al. Structural and Functional Basis of SARS-CoV-2 Entry by Using Human ACE2. Cell 181, 894-904 e899, doi:10.1016/j.cell.2020.03.045 (2020).

14 Shang, J. et al. Cell entry mechanisms of SARS-CoV-2. Proc Natl Acad Sci USA 117, 11727-11734, doi:10.1073/pnas.2003138117 (2020).

15 Keech, C. et al. Phase 1-2 Trial of a SARS-CoV-2 Recombinant Spike Protein Nanoparticle Vaccine. N Engl-J Med 383, 2320-2332, doi:10.1056/NEJMoa2026920_(2020).

16 Walsh, E. E. et al. Safety and Immunogenicity of Two RNA-Based Covid-19 Vaccine Candidates. N Engl J Med 383, 2439-2450, doi:10.1056/NEJMoa2027906 (2020).

17 Anderson, E. J. et al. Safety and Immunogenicity of SARS-CoV-2 mRNA-1273 Vaccine in Older Adults. N Engl J Med 383, 2427-2438, doi:10.1056/NEJMoa2028436 (2020).

18 McCallum, M. et al. N-terminal domain antigenic mapping reveals a site of vulnerability for SARS-CoV-2. Cell, doi:10.1016/j.cell.2021.03.028 (2021).

19 Li, Q. et al. The Impact of Mutations in SARS-CoV-2 Spike on Viral Infectivity and Antigenicity. Cell 182, 1284-1294 e1289, doi:10.1016/j.cell.2020.07.012 (2020).

20 Tegally, H. et al. Detection of a SARS-CoV-2 variant of concern in South Africa. Nature, doi:10.1038/s41586-021-03402-9 (2021).

21 Shen, X. et al. SARS-CoV-2 variant B.1.1.7 is susceptible to neutralizing antibodies elicited by ancestral spike vaccines. Cell Host Microbe, doi:10.1016/j.chom.2021.03.002 (2021).

22 Wibmer, C. K. et al. SARS-CoV-2 501Y.V2 escapes neutralization by South African COVID-19 donor plasma. Nat Med, doi:10.1038/s41591-021-01285-x (2021).

23 Voysey, M. et al. Safety and efficacy of the ChAdOx1 nCoV-19 vaccine (AZD1222) against SARS-CoV-2: an interim analysis of four randomised controlled trials in Brazil, South Africa, and the UK. Lancet 397, 99-111, doi:10.1016/S0140-6736(20)32661-1 (2021).

24 Voysey, M. et al. Single-dose administration and the influence of the timing of the booster dose on immunogenicity and efficacy of ChAdOx1 nCoV-19 (AZD1222) vaccine: a pooled analysis of four randomised trials. Lancet 397, 881-891, doi:10.1016/S0140-6736(21)00432-3 (2021).

25 Andreano, E. et al. SARS-CoV-2 escape in vitro from a highly neutralizing COVID-19 convalescent plasma. bioRxiv, doi:10.1101/2020.12.28.424451 (2020).

26 Hoffmann, M. et al. SARS-CoV-2 variants B.1.351 and P.1 escape from neutralizing antibodies. Cell, doi:10.1016/j.cell.2021.03.036 (2021).

27 Garcia-Beltran, W. F. et al. Multiple SARS-CoV-2 variants escape neutralization by vaccine-induced humoral immunity. Cell, doi:10.1016/j.cell.2021.03.013 (2021).

28 Starr, T. N. et al. Deep Mutational Scanning of SARS-CoV-2 Receptor Binding Domain Reveals Constraints on Folding and ACE2 Binding. Cell 182, 1295-1310 e1220, doi:10.1016/j.cell.2020.08.012 (2020).

29 Starr, T. N. et al. Deep mutational scanning of SARS-CoV-2 receptor binding domain reveals constraints on folding and ACE2 binding. bioRxiv, doi:10.1101/2020.06.17.157982 (2020).

30 Tada, T. et al. Decreased neutralization of SARS-CoV-2 global variants by therapeutic anti-spike protein monoclonal antibodies. bioRxiv, doi:10.1101/2021.02.18.431897 (2021).

31 Tada, T. et al. Neutralization of viruses with European, South African, and United States SARS-CoV-2 variant spike proteins by convalescent sera and BNT162b2 mRNA vaccine-elicited antibodies. bioRxiv, doi:10.1101/2021.02.05.430003 (2021).

32 Deng, X. et al. Transmission, infectivity, and antibody neutralization of an emerging SARS-CoV-2 variant in California carrying a L452R spike protein mutation. medRxiv, doi:10.1101/2021.03.07.21252647 (2021).

33 Greaney, A. J. et al. Comprehensive mapping of mutations in the SARS-CoV-2 receptor-binding domain that affect recognition by polyclonal human plasma antibodies. Cell Host Microbe 29, 463-476 e466, doi:10.1016/j.chom.2021.02.003 (2021).

34 Wang, P. et al. Antibody resistance of SARS-CoV-2 variants B.1.351 and B.1.1.7. Nature, doi:10.1038/s41586-021-03398-2 (2021).

35 Zhou, H. et al. B.1.526 SARS-CoV-2 variants identified in New York City are neutralized by vaccine-elicited and therapeutic monoclonal antibodies. bioRxiv, doi:10.1101/2021.03.24.436620 (2021).

36 Wu, K. et al. Serum Neutralizing Activity Elicited by mRNA-1273 Vaccine. N Engl J Med, doi:10.1056/NEJMc2102179 (2021).

37 Novavax (2021). Novavax COVID-19 Vaccine Demonstrates 89.3% Efficacy in UK Phase 3 Trial. Press Release Jan. 28, 2021: https://ir.novavax.com/node/15506/pdf 38 K, E. et al. Efficacy of ChAdOx1 nCoV-19 (AZD1222) vaccine against SARS-CoV-2 variant of concern 202012/01(B.1.1.7): an exploratory analysis of a randomised controlled trial. Lancet, doi:10.1016/S0140-6736(21)00628-0 (2021).

39 Pfizer (2021) Pfizer and BioNTech confirm high efficacy and no serious safety concerns through up to six months following second dose in updated topline analysis of landmark COVID-19 vaccine study. Press Release Apr. 1, 2021: https://www.pfizer.com/news/press-release/press-release-detail/pfizer-and-biontech-confirm-high-efficacy-and-no-serious.

40 Corbett, K. S. et al. SARS-CoV-2 mRNA vaccine design enabled by prototype pathogen preparedness. Nature 586, 567-571, doi:10.1038/s41586-020-2622-0 (2020).

41 Ho, D. et al. Increased Resistance of SARS-CoV-2 Variants B.1.351 and B.1.1.7 to Antibody Neutralization. Res Sq, doi:10.21203/rs.3.rs-155394/v1 (2021).

42 Wrobel, A. G. et al. SARS-CoV-2 and bat RaTG13 spike glycoprotein structures inform on virus evolution and furin-cleavage effects. Nat Struct Mol Biol 27, 763-767, doi:10.1038/s41594-020-0468-7 (2020).

43 Lan, J. et al. Structure of the SARS-CoV-2 spike receptor-binding domain bound to the ACE2 receptor. Nature 581, 215-220, doi:10.1038/s41586-020-2180-5 (2020).

44 Nelson, J. et al. Impact of mRNA chemistry and manufacturing process on innate immune activation. Sci Adv 6, eaaz6893, doi:10.1126/sciadv.aaz6893 (2020).

45 Hassett, K. J. et al. Optimization of Lipid Nanoparticles for Intramuscular Administration of mRNA Vaccines. Mol Ther Nucleic Acids 15, 1-11, doi:10.1016/j.omtn.2019.01.013 (2019).

46 John, S. et al. Multi-antigenic human cytomegalovirus mRNA vaccines that elicit potent humoral and cell-mediated immunity. Vaccine 36, 1689-1699, doi:10.1016/j.vaccine.2018.01.029 (2018).

47 Bahl, K. et al. Preclinical and Clinical Demonstration of Immunogenicity by mRNA Vaccines against H10N8 and H7N9 Influenza Viruses. Mol Ther 25, 1316-1327, doi:10.1016/j.ymthe.2017.03.035 (2017).

48 Vogel, A. B. et al. Self-Amplifying RNA Vaccines Give Equivalent Protection against Influenza to mRNA Vaccines but at Much Lower Doses. Mol Ther 26, 446-455, doi:10.1016/j.ymthe.2017.11.017 (2018).

49 Whitt, M. A. Generation of VSV pseudotypes using recombinant DeltaG-VSV for studies on virus entry, identification of entry inhibitors, and immune responses to vaccines. J Virol Methods 169, 365-374, doi:10.1016/j.jviromet.2010.08.006 (2010).

Additional Sequences

It should be understood that any of the mRNA sequences described herein may include a 5' UTR and/or a 3' UTR. The UTR sequences may be selected from the following sequences, or other known UTR sequences may be used. It should also be understood that any of the mRNA constructs described herein may further comprise a poly(A) tail and/or cap (e.g., 7mG(5')ppp(5')N7mpNp). Further, while many of the mRNAs and encoded antigen sequences described herein include a signal peptide and/or a peptide tag (e.g., C-terminal His tag), it should be understood that the indicated signal peptide and/or peptide tag may be substituted for a different signal peptide and/or peptide tag, or the signal peptide and/or peptide tag may be omitted.

5' UTR: GGGAAAUAAGAGAGAAAAGAAGAGUAAGAAGAAAUAUAAGAGCCACC (SEQ ID NO: 50)

5'UTR: GGGAAAUAAGAGAGAAAAGAAGAGUAAGAAGAAAUAUAAGACCCCGGCGCCGCCACC (SEQ ID NO: 2)

3' UTR: UGAUAAUAGGCUGGAGCCUCGGUGGC-CAUGCUUCUUGCCCCUUGGC-CUCCCCCCAGCCCCUCCUCCCCUUCCUCA CCCGUACCCCCGUGGUCUUUGAAUAAGU-CUGACUGGGCGGCG (SEQ ID NO: 51)

3' UTR: UcAUAAUAGGCUGGAGCCUCGGUGGCC-UAGCUUCUUGCCCCUUGGGC-CUCCCCCCAGCCCCUCCUCCCCUUCCUGCA CCCGUACCCCCGUGGUCUUUGAAUAAAGU-CUGAGUGGGCGGCA (SEQ ID NO: 4)

TABLE 1

| Sequence Listing | | |
|---|---|---|
| WH2020_NatSP_2P_E484K_D614G | | |
| SEQ ID NO: 1 consists of from 5' end to 3' end: 5' UTR SEQ ID NO: 2, mRNA ORF SEQ ID NO: 3, and 3' UTR SEQ ID NO: 4. | | 1 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUA<br>AGACCCCGGCGCCGCCACC | 2 |
| ORF of mRNA Construct (excluding the stop codon) | AUGUUCGUGUUCCUGGUGCUGCUGCCCCUGGUGAGCAGC<br>CAGUGCGUGAACCUGACCACCCGGACCCAGCUGCCACCAG<br>CCUACACCAACAGCUUCACCCGGGGCGUCUACUACCCCGA<br>CAAGGUGUUCCGGAGCAGCGUCCUGCACAGCACCCAGGA<br>CCUGUUCCUGCCCUUCUUCAGCAACGUGACCUGGUUCCAC<br>GCCAUCCACGUGAGCGGCACCAACGGCACCAAGCGGUUCG<br>ACAACCCCGUGCUGCCCUUCAACGACGGCGUGUACUUCGC<br>CAGCACCGAGAAGAGCAACAUCAUCCGGGGCUGGAUCUU<br>CGGCACCACCCUGGACAGCAAGACCCAGAGCCUGCUGAUC<br>GUGAAUAACGCCACCAACGUGGUGAUCAAGGUGUGCGAG<br>UUCCAGUUCUGCAACGACCCCUUCCUGGGCGUGUACUACC<br>ACAAGAACAACAAGAGCUGGAUGGAGAGCGAGUUCCGGG<br>UGUACAGCAGCGCCAACAACUGCACCUUCGAGUACGUGA<br>GCCAGCCCUUCCUGAUGGACCUGGAGGGCAAGCAGGGCA<br>ACUUCAAGAACCUGCGGGAGUUCGUGUUCAAGAACAUCG<br>ACGGCUACUUCAAGAUCUACAGCAAGCACACCCCAAUCA<br>ACCUGGUGCGGGAUCUGCCCCAGGGCUUCUCAGCCCUGG<br>AGCCCCUGGUGGACCUGCCCAUCGGCAUCAACAUCACCCG<br>GUUCCAGACCCUGCUGGCCCUGCACCGGAGCUACCUGACC<br>CCAGGCGACAGCAGCAGCGGGUGGACAGCAGGCGCGGCU<br>GCUUACUACGUGGGCUACCUGCAGCCCCGGACCUUCCUGC<br>UGAAGUACAACGAGAACGGCACCAUCACCGACGCCGUGG<br>ACUGCGCCCUGGACCCUCUGAGCGAGACCAAGUGCACCCU<br>GAAGAGCUUCACCGUGGAGAAGGGCAUCUACCAGACCAG<br>CAACUUCCGGGUGCAGCCCACCGAGAGCAUCGUGCGGUU<br>CCCCAACAUCACCAACCUGUGCCCCUUCGGCGAGGUGUUC<br>AACGCCACCCGGUUCGCCAGCGUGUACGCCUGGAACCGGA<br>AGCGGAUCAGCAACUGCGUGGCCGACUACAGCGUGCUGU<br>ACAACAGCGCCAGCUUCAGCACCUUCAAGUGCUACGGCG | 3 |

TABLE 1-continued

| Sequence Listing | | |
|---|---|---|
| | UGAGCCCCACCAAGCUGAACGACCUGUGCUUCACCAACGU<br>GUACGCCGACAGCUUCGUGAUCCGUGGCGACGAGGUGCG<br>GCAGAUCGCACCCGGCCAGACAGGCAAGAUCGCCGACUAC<br>AACUACAAGCUGCCCGACGACUUCACCGGCUGCGUGAUC<br>GCCUGGAACAGCAACAACCUCGACAGCAAGGUGGGCGGC<br>AACUACAACUACCUGUACCGGCUGUUCCGGAAGAGCAAC<br>CUGAAGCCCUUCGAGCGGGACAUCAGCACCGAGAUCUAC<br>CAAGCCGGCUCCACCCCUUGCAACGGCGUGAAGGGCUUCA<br>ACUGCUACUUCCCUCUGCAGAGCUACGGCUUCCAGCCCAC<br>CAACGGCGUGGGCUACCAGCCCUACCGGGUGGUGGUGCU<br>GAGCUUCGAGCUGCUGCACGCCCCAGCCACCGUGUGUGGC<br>CCCAAGAAGAGCACCAACCUGGUGAAGAACAAGUGCGUG<br>AACUUCAACUUCAACGGCCUUACCGGCACCGGCGUGCUG<br>ACCGAGAGCAACAAGAAAUUCCUGCCCUUUCAGCAGUUC<br>GGCCGGGACAUCGCCGACACCACCGACGCUGUGCGGGAUC<br>CCCAGACCCUGGAGAUCCUGGACAUCACCCCUUGCAGCUU<br>CGGCGGCGUGAGCGUGAUCACCCCAGGCACCAACACCAGC<br>AACCAGGUGGCCGUGCUGUACCAGGGCGUGAACUGCACC<br>GAGGUGCCCGUGGCCAUCCACGCCGACCAGCUGACACCCA<br>CCUGGCGGGUCUACAGCACCGGCAGCAACGUGUUCCAGA<br>CCCGGGCCGGUUGCCUGAUCGGCGCCGAGCACGUGAACA<br>ACAGCUACGAGUGCGACAUCCCCAUCGGCGCCGGCAUCUG<br>UGCCAGCUACCAGACCCAGACCAAUUCACCCCGGAGGGCA<br>AGGAGCGUGGCCAGCCAGAGCAUCAUCGCCUACACCAUG<br>AGCCUGGGCGCCGAGAACAGCGUGGCCUACAGCAACAAC<br>AGCAUCGCCAUCCCCACCAACUUCACCAUCAGCGUGACCA<br>CCGAGAUUCUGCCCGUGAGCAUGACCAAGACCAGCGUGG<br>ACUGCACCAUGUACAUCUGCGGCGACAGCACCGAGUGCA<br>GCAACCUGCUGCUGCAGUACGGCAGCUUCUGCACCCAGCU<br>GAACCGGGCCCUGACCGGCAUCGCCGUGGAGCAGGACAA<br>GAACACCCAGGAGGUGUUCGCCCAGGUGAAGCAGAUCUA<br>CAAGACCCCUCCCAUCAAGGACUUCGGCGGCUUCAACUUC<br>AGCCAGAUCCUGCCCGACCCCAGCAAGCCCAGCAAGCGGA<br>GCUUCAUCGAGGACCUGCUGUUCAACAAGGUGACCCUAG<br>CCGACGCCGGCUUCAUCAAGCAGUACGGCGACUGCCUCGG<br>CGACAUAGCCGCCCGGGACCUGAUCUGCGCCCAGAAGUUC<br>AACGGCCUGACCGUGCUGCCUCCCCUGCUGACCGACGAGA<br>UGAUCGCCCAGUACACCAGCGCCCUGUUAGCCGGAACCAU<br>CACCAGCGGCUGGACUUUCGGCGCUGGAGCCGCUCUGCA<br>GAUCCCCUUCGCCAUGCAGAUGGCCUACCGGUUCAACGGC<br>AUCGGCGUGACCCAGAACGUGCUGUACGAGAACCAGAAG<br>CUGAUCGCCAACCAGUUCAACAGCGCCAUCGGCAAGAUCC<br>AGGACAGCCUGAGCAGCACCGCUAGCGCCCUGGGCAAGC<br>UGCAGGACGUGGUGAACCAGAACGCCCAGGCCCUGAACA<br>CCCUGGUGAAGCAGCUGAGCAGCAACUUCGGCGCCAUCA<br>GCAGCGUGCUGAACGACAUCCUGAGCCGGCUGGACCCUCC<br>CGAGGCCGAGGUGCAGAUCGACCGGCUGAUCACUGGCCG<br>GCUGCAGAGCCUGCAGACCUACGUGACCCAGCAGCUGAU<br>CCGGGCCGCCGAGAUUCGGGCCAGCGCCAACCUGGCCGCC<br>ACCAAGAUGAGCGAGUGCGUGCUGGGCCAGAGCAAGCGG<br>GUGGACUUCUGCGGCAAGGGCUACCACCUGAUGAGCUUU<br>CCCCAGAGCGCACCCCACGGAGUGGUGUUCCUGCACGUGA<br>CCUACGUGCCCGCCCAGGAGAAGAACUUCACCACCGCCCC<br>AGCCAUCUGCCACGACGGCAAGGCCCACUUUCCCCGGGAG<br>GGCGUGUUCGUGAGCAACGGCACCCACUGGUUCGUGACC<br>CAGCGGAACUUCUACGAGCCCCAGAUCAUCACCACCGACA<br>ACACCUUCGUGAGCGGCAACUGCGACGUGGUGAUCGGCA<br>UCGUGAACAACACCGUGUACGAUCCCCUGCAGCCCGAGCU<br>GGACAGCUUCAAGGAGGAGCUGGACAAGUACUUCAAGAA<br>UCACACCAGCCCCGACGUGGACCUGGGCGACAUCAGCGGC<br>AUCAACGCCAGCGUGGUGAACAUCCAGAAGGAGAUCGAU<br>CGGCUGAACGAGGUGGCCAAGAACCUGAACGAGAGCCUG<br>AUCGACCUGCAGGAGCUGGGCAAGUACGAGCAGUACAUC<br>AAGUGGCCCUGGUACAUCUGGCUGGGCUUCAUCGCCGGC<br>CUGAUCGCCAUCGUGAUGGUGACCAUCAUGCUGUGCUGC<br>AUGACCAGCUGCUGCAGCUGCCUGAAGGGCUGUUGCAGC<br>UGCGGCAGCUGCUGCAAGUUCGACGAGGACGACAGCGAG<br>CCCGUGCUGAAGGGCGUGAAGCUGCACUACACC | |
| 3' UTR | UGAUAAUAGGCUGGAGCCUCGGUGGCCUAGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 4 |
| Corresponding amino acid sequence | MFVFLVLLPLVSSQCVNLTTRTQLPPAYTNSFTRGVYYPDKVF<br>RSSVLHSTQDLFLPFFSNVTWFHAIHVSGTNGTKRFDNPVLPF<br>NDGVYFASTEKSNIIRGWIFGTTLDSKTQSLLIVNNATNVVIKV<br>CEFQFCNDPFLGVYYHKNNKSWMESEFRVYSSANNCTFEYVS<br>QPFLMDLEGKQGNFKNLREFVFKNIDGYFKIYSKHTPINLVRD<br>LPQGFSALEPLVDLPIGINITRFQTLLALHRSYLTPGDSSSGWT | 5 |

TABLE 1-continued

| Sequence Listing | | |
|---|---|---|
| | AGAAAYYVGYLQPRTFLLKYNENGTITDAVDCALDPLSETKC<br>TLKSFTVEKGIYQTSNFRVQPTESIVRFPNITNLCPFGEVENATR<br>FASVYAWNRKRISNCVADYSVLYNSASFSTFKCYGVSPTKLN<br>DLCFTNVYADSFVIRGDEVRQIAPGQTGKIADYNYKLPDDFTG<br>CVIAWNSNNLDSKVGGNYNYLYRLFRKSNLKPFERDISTEIYQ<br>AGSTPCNGVKGFNCYFPLQSYGFQPTNGVGYQPYRVVVLSFE<br>LLHAPATVCGPKKSTNLVKNKCVNFNFNGLTGTGVLTESNKK<br>FLPFQQFGRDIADTTDAVRDPQTLEILDITPCSFGGVSVITPGTN<br>TSNQVAVLYQGVNCTEVPVAIHADQLTPTWRVYSTGSNVFQT<br>RAGCLIGAEHVNNSYECDIPIGAGICASYQTQTNSPRRARSVA<br>SQSIIAYTMSLGAENSVAYSNNSIAIPTNFTISVTTEILPVSMTK<br>TSVDCTMYICGDSTECSNLLLQYGSFCTQLNRALTGIAVEQDK<br>NTQEVFAQVKQIYKTPPIKDFGGFNFSQILPDPSKPSKRSFIEDL<br>LFNKVTLADAGFIKQYGDCLGDIAARDLICAQKFNGLTVLPPL<br>LTDEMIAQYTSALLAGTITSGWTFGAGAALQIPFAMQMAYRF<br>NGIGVTQNVLYENQKLIANQFNSAIGKIQDSLSSTASALGKLQ<br>DVVNQNAQALNTLVKQLSSNFGAISSVLNDILSRLDPPEAEVQ<br>IDRLITGRLQSLQTYVTQQLIRAAEIRASANLAATKMSECVLG<br>QSKRVDFCGKGYHLMSFPQSAPHGVVFLHVTYVPAQEKNFTT<br>APAICHDGKAHFPREGVFVSNGTHWFVTQRNFYEPQIITTDNT<br>FVSGNCDVVIGIVNNTVYDPLQPELDSFKEELDKYFKNHTSPD<br>VDLGDISGINASVVNIQKEIDRLNEVAKNLNESLIDLQELGKYE<br>QYIKWPWYIWLGFIAGLIAIVMVTIMLCCMTSCCSCLKGCCSC<br>GSCCKFDEDDSEPVLKGVKLHYT | |
| PolyA tail | 100 nt | |
| | WH2020_NatSP_2P_K417N_E484K_N501Y_D614G | |
| SEQ ID NO: 6 consists of from 5' end to 3' end: 5' UTR SEQ ID NO: 2, mRNA ORF SEQ ID NO: 7, and 3' UTR SEQ ID NO: 4. | | 6 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA<br>AGACCCCGGCGCCGCCACC | 2 |
| ORF of mRNA Construct (excluding the stop codon) | AUGUUCGUGUUCCUGGUGCUGCUGCCCCUGGUGAGCAGC<br>CAGUGCGUGAACCUGACCACCCGGACCCAGCUGCCACCAG<br>CCUACACCAACAGCUUCACCCGGGGCGUCUACUACCCCGA<br>CAAGGUGUUCCGGAGCAGCGUCCUGCACAGCACCCAGGA<br>CCUGUUCCUGCCCUUCUUCAGCAACGUGACCUGGUUCCAC<br>GCCAUCCACGUGAGCGGCACCAACGGCACCAAGCGGUUCG<br>ACAACCCCGUGCUGCCCUUCAACGACGGCGUGUACUUCGC<br>CAGCACCGAGAAGAGCAACAUCAUCCGGGGCUGGAUCUU<br>CGGCACCACCCUGGACAGCAAGACCCAGAGCCUGCUGAUC<br>GUGAAUAACGCCACCAACGUGGUGAUCAAGGUGUGCGAG<br>UUCCAGUUCUGCAACGACCCCUUCCUGGGCGUGUACUACC<br>ACAAGAACAACAAGAGCUGGAUGGAGAGCGAGUUCCGGG<br>UGUACAGCAGCGCCAACAACUGCACCUUCGAGUACGUGA<br>GCCAGCCCUUCCUGAUGGACCUGGAGGGCAAGCAGGGCA<br>ACUUCAAGAACCUGCGGGAGUUCGUGUUCAAGAACAUCG<br>ACGGCUACUUCAAGAUCUACAGCAAGCACACCCCAAUCA<br>ACCUGGUGCGGGAUCUGCCCCAGGGCUUCUCAGCCCUGG<br>AGCCCCUGGUGGACCUGCCCAUCGGCAUCAACAUCACCCG<br>GUUCCAGACCCUGCUGGCCCUGCACCGGAGCUACCUGACC<br>CCAGGCGACAGCAGCAGCGGGUGGACAGCAGGCGCGGCU<br>GCUUACUACGUGGGCUACCUGCAGCCCCGGACCUUCCUGC<br>UGAAGUACAACGAGAACGGCACCAUCACCGACGCCGUGG<br>ACUGCGCCCUGGACCCUCUGAGCGAGACCAAGUGCACCCU<br>GAAGAGCUUCACCGUGGAGAAGGGCAUCUACCAGACCAG<br>CAACUUCCGGGUGCAGCCCACCGAGAGCAUCGUGCGGUU<br>CCCCAACAUCACCAACCUGUGCCCCUUCGGCGAGGUGUUC<br>AACGCCACCCGGUUCGCCAGCGUGUACGCCUGGAACCGGA<br>AGCGGAUCAGCAACUGCGUGGCCGACUACAGCGUGCUGU<br>ACAACAGCGCCAGCUUCAGCACCUUCAAGUGCUACGGCG<br>UGAGCCCCACCAAGCUGAACGACCUGUGCUUCACCAACGU<br>GUACGCCGACAGCUUCGUGAUCCGUGGCGACGAGGUGCG<br>GCAGAUCGCACCCGGCCAGACAGGCAACAUCGCCGACUAC<br>AACUACAAGCUGCCCGACGACUUCACCGGCUGCGUGAUC<br>GCCUGGAACAGCAACAACCUCGACAGCAAGGUGGGCGGC<br>AACUACAACUACCUGUACCGGCUGUUCCGGAAGAGCAAC<br>CUGAAGCCCUUCGAGCGGGACAUCAGCACCGAGAUCUAC<br>CAAGCCGGCUCCACCCCUUGCAACGGCGUGAAGGGCUUCA<br>ACUGCUACUUCCCUCUGCAGAGCUACGGCUUCCAGCCCAC<br>CUACGGCGUGGGCUACCAGCCCUACCGGGUGGUGGUGCU<br>GAGCUUCGAGCUGCUGCACGCCCCAGCCACCGUGUGUGGC<br>CCCAAGAAGAGCACCAACCUGGUGAAGAACAAGUGCGUG<br>AACUUCAACUUCAACGGCCUUACCGGCACCGGCGUGCUG<br>ACCGAGAGCAACAAGAAAUUCCUGCCCUUUCAGCAGUUC<br>GGCCGGGACAUCGCCGACACCACCGACGCUGUGCGGGAUC | 7 |

TABLE 1-continued

| | Sequence Listing | |
|---|---|---|
| | CCCAGACCCUGGAGAUCCUGGACAUCACCCCUUGCAGCUU<br>CGGCGGCGUGAGCGUGAUCACCCCAGGCACCAACACCAGC<br>AACCAGGUGGCCGUGCUGUACCAGGGCGUGAACUGCACC<br>GAGGUGCCCGUGGCCAUCCACGCCGACCAGCUGACACCCA<br>CCUGGCGGGUCUACAGCACCGGCAGCAACGUGUUCCAGA<br>CCCGGGCCGGUUGCCUGAUCGGCGCCGAGCACGUGAACA<br>ACAGCUACGAGUGCGACAUCCCCAUCGGCGCCGGCAUCUG<br>UGCCAGCUACCAGACCCAGACCAAUUCACCCCGGAGGGCA<br>AGGAGCGUGGCCAGCCAGAGCAUCAUCGCCUACACCAUG<br>AGCCUGGGCGCCGAGAACAGCGUGGCCUACAGCAACAAC<br>AGCAUCGCCAUCCCCACCAACUUCACCAUCAGCGUGACCA<br>CCGAGAUUCUGCCCGUGAGCAUGACCAAGACCAGCGUGG<br>ACUGCACCAUGUACAUCUGCGGCGACAGCACCGAGUGCA<br>GCAACCUGCUGCUGCAGUACGGCAGCUUCUGCACCCAGCU<br>GAACCGGGCCCUGACCGGCAUCGCCGUGGAGCAGGACAA<br>GAACACCCAGGAGGUGUUCGCCCAGGUGAAGCAGAUCUA<br>CAAGACCCCUCCCAUCAAGGACUUCGGCGGCUUCAACUUC<br>AGCCAGAUCCUGCCCGACCCCAGCAAGCCCAGCAAGCGGA<br>GCUUCAUCGAGGACCUGCUGUUCAACAAGGUGACCCUAG<br>CCGACGCCGGCUUCAUCAAGCAGUACGGCGACUGCCUCGG<br>CGACAUAGCCGCCCGGGACCUGAUCUGCGCCCAGAAGUUC<br>AACGGCCUGACCGUGCUGCCUCCCCUGCUGACCGACGAGA<br>UGAUCGCCCAGUACACCAGCGCCCUGUUAGCCGGAACCAU<br>CACCAGCGGCUGGACUUUCGGCGCUGGAGCCGCUCUGCA<br>GAUCCCCUUCGCCAUGCAGAUGGCCUACCGGUUCAACGGC<br>AUCGGCGUGACCCAGAACGUGCUGUACGAGAACCAGAAG<br>CUGAUCGCCAACCAGUUCAACAGCGCCAUCGGCAAGAUCC<br>AGGACAGCCUGAGCAGCACCGCUAGCGCCCUGGGCAAGC<br>UGCAGGACGUGGUGAACCAGAACGCCCAGGCCCUGAACA<br>CCCUGGUGAAGCAGCUGAGCAGCAACUUCGGCGCCAUCA<br>GCAGCGUGCUGAACGACAUCCUGAGCCGGCUGGACCCUCC<br>CGAGGCCGAGGUGCAGAUCGACCGGCUGAUCACUGGCCG<br>GCUGCAGAGCCUGCAGACCUACGUGACCCAGCAGCUGAU<br>CCGGGCCGCCGAGAUUCGGGCCAGCGCCAACCUGGCCGCC<br>ACCAAGAUGAGCGAGUGCGUGCUGGGCCAGAGCAAGCGG<br>GUGGACUUCUGCGGCAAGGGCUACCACCUGAUGAGCUUU<br>CCCCAGAGCGCACCCCACGGAGUGGUGUUCCUGCACGUGA<br>CCUACGUGCCCGCCCAGGAGAAGAACUUCACCACCGCCCC<br>AGCCAUCUGCCACGACGGCAAGGCCCACUUUCCCCGGGAG<br>GGCGUGUUCGUGAGCAACGGCACCCACUGGUUCGUGACC<br>CAGCGGAACUUCUACGAGCCCCAGAUCAUCACCACCGACA<br>ACACCUUCGUGAGCGGCAACUGCGACGUGGUGAUCGGCA<br>UCGUGAACAACACCGUGUACGAUCCCCUGCAGCCCGAGCU<br>GGACAGCUUCAAGGAGGAGCUGGACAAGUACUUCAAGAA<br>UCACACCAGCCCCGACGUGGACCUGGGCGACAUCAGCGGC<br>AUCAACGCCAGCGUGGUGAACAUCCAGAAGGAGAUCGAU<br>CGGCUGAACGAGGUGGCCAAGAACCUGAACGAGAGCCUG<br>AUCGACCUGCAGGAGCUGGGCAAGUACGAGCAGUACAUC<br>AAGUGGCCCUGGUACAUCUGGCUGGGCUUCAUCGCCGGC<br>CUGAUCGCCAUCGUGAUGGUGACCAUCAUGCUGUGCUGC<br>AUGACCAGCUGCUGCAGCUGCCUGAAGGGCUGUUGCAGC<br>UGCGGCAGCUGCUGCAAGUUCGACGAGGACGACAGCGAG<br>CCCGUGCUGAAGGGCGUGAAGCUGCACUACACC | |
| 3' UTR | UGAUAAUAGGCUGGAGCCUCGGUGGCCUAGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 4 |
| Corresponding amino acid sequence | MFVFLVLLPLVSSQCVNLTTRTQLPPAYTNSFTRGVYYPDKVF<br>RSSVLHSTQDLFLPFFSNVTWFHAIHVSGTNGTKRFDNPVLPF<br>NDGVYFASTEKSNIIRGWIFGTTLDSKTQSLLIVNNATNVVIKV<br>CEFQFCNDPFLGVYYHKNNKSWMESEFRVYSSANNCTFEYVS<br>QPFLMDLEGKQGNFKNLREFVFKNIDGYFKIYSKHTPINLVRD<br>LPQGFSALEPLVDLPIGINITRFQTLLALHRSYLTPGDSSSGWT<br>AGAAAYYVGYLQPRTFLLKYNENGTITDAVDCALDPLSETKC<br>TLKSFTVEKGIYQTSNFRVQPTESIVRFPNITNLCPFGEVENATR<br>FASVYAWNRKRISNCVADYSVLYNSASFSTFKCYGVSPTKLN<br>DLCFTNVYADSFVIRGDEVRQIAPGQTGNIADYNYKLPDDFTG<br>CVIAWNSNNLDSKVGGNYNYLYRLFRKSNLKPFERDISTEIYQ<br>AGSTPCNGVKGFNCYFPLQSYGFQPTYGVGYQPYRVVVLSFE<br>LLHAPATVCGPKKSTNLVKNKCVNFNFNGLTGTGVLTESNKK<br>FLPFQQFGRDIADTTDAVRDPQTLEILDITPCSFGGVSVITPGTN<br>TSNQVAVLYQGVNCTEVPVAIHADQLTPTWRVYSTGSNVFQT<br>RAGCLIGAEHVNNSYECDIPIGAGICASYQTQTNSPRRARSVA<br>SQSIIAYTMSLGAENSVAYSNNSIAIPTNFTISVTTEILPVSMTK<br>TSVDCTMYICGDSTECSNLLLQYGSFCTQLNRALTGIAVEQDK<br>NTQEVFAQVKQIYKTPPIKDFGGFNFSQILPDPSKPSKRSFIEDL<br>LFNKVTLADAGFIKQYGDCLGDIAARDLICAQKFNGLTVLPPL<br>LTDEMIAQYTSALLAGTITSGWTFGAGAALQIPFAMQMAYRF | 8 |

TABLE 1-continued

| Sequence Listing | | |
|---|---|---|
| | NGIGVTQNVLYENQKLIANQFNSAIGKIQDSLSSTASALGKLQ<br>DVVNQNAQALNTLVKQLSSNFGAISSVLNDILSRLDPPEAEVQ<br>IDRLITGRLQSLQTYVTQQLIRAAEIRASANLAATKMSECVLG<br>QSKRVDFCGKGYHLMSFPQSAPHGVVFLHVTYVPAQEKNFTT<br>APAICHDGKAHFPREGVFVSNGTHWFVTQRNFYEPQIITTDNT<br>FVSGNCDVVIGIVNNTVYDPLQPELDSFKEELDKYFKNHTSPD<br>VDLGDISGINASVVNIQKEIDRLNEVAKNLNESLIDLQELGKYE<br>QYIKWPWYIWLGFIAGLIAIVMVTIMLCCMTSCCSCLKGCCSC<br>GSCCKFDEDDSEPVLKGVKLHYT | |
| PolyA tail | 100 nt | |
| WH2020_NatSP_2P_L18F_D80A_D215G_L242_244del_R246I_K417N_E484K_N501Y_D614G_A701V | | |
| SEQ ID NO: 9 consists of from 5' end to 3' end: 5' UTR SEQ ID NO: 2, mRNA ORF SEQ ID NO: 10, and 3' UTR SEQ ID NO: 4. | | 9 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUA<br>AGACCCCGGCGCCGCCACC | 2 |
| ORF of mRNA Construct (excluding the stop codon) | AUGUUCGUGUUCCUGGUGCUGCUGCCCCUGGUGAGCAGC<br>CAGUGCGUGAACUUUACCACCCGGACCCAGCUGCCACCAG<br>CCUACACCAACAGCUUCACCCGGGGCGUCUACUACCCCGA<br>CAAGGUGUUCCGGAGCAGCGUCCUGCACAGCACCCAGGA<br>CCUGUUCCUGCCCUUCUUCAGCAACGUGACCUGGUUCCAC<br>GCCAUCCACGUGAGCGGCACCAACGGCACCAAGCGGUUCG<br>CCAACCCCGUGCUGCCCUUCAACGACGGCGUGUACUUCGC<br>CAGCACCGAGAAGAGCAACAUCAUCCGGGGCUGGAUCUU<br>CGGCACCACCCUGGACAGCAAGACCCAGAGCCUGCUGAUC<br>GUGAAUAACGCCACCAACGUGGUGAUCAAGGUGUGCGAG<br>UUCCAGUUCUGCAACGACCCCUUCCUGGGCGUGUACUACC<br>ACAAGAACAACAAGAGCUGGAUGGAGAGCGAGUUCCGGG<br>UGUACAGCAGCGCCAACAACUGCACCUUCGAGUACGUGA<br>GCCAGCCCUUCCUGAUGGACCUGGAGGGCAAGCAGGGCA<br>ACUUCAAGAACCUGCGGGAGUUCGUGUUCAAGAACAUCG<br>ACGGCUACUUCAAGAUCUACAGCAAGCACACCCCAAUCA<br>ACCUGGUGCGGGGCCUGCCCCAGGGCUUCUCAGCCCUGGA<br>GCCCCUGGUGGACCUGCCCAUCGGCAUCAACAUCACCCGG<br>UUCCAGACCCUGCACAUCAGCUACCUGACCCCAGGCGACA<br>GCAGCAGCGGGUGGACAGCAGGCGCGGCUGCUUACUACG<br>UGGGCUACCUGCAGCCCCGGACCUUCCUGCUGAAGUACA<br>ACGAGAACGGCACCAUCACCGACGCCGUGGACUGCGCCCU<br>GGACCCUCUGAGCGAGACCAAGUGCACCCUGAAGAGCUU<br>CACCGUGGAGAAGGGCAUCUACCAGACCAGCAACUUCCG<br>GGUGCAGCCCACCGAGAGCAUCGUGCGGUUCCCCAACAUC<br>ACCAACCUGUGCCCCUUCGGCGAGGUGUUCAACGCCACCC<br>GGUUCGCCAGCGUGUACGCCUGGAACCGGAAGCGGAUCA<br>GCAACUGCGUGGCCGACUACAGCGUGCUGUACAACAGCG<br>CCAGCUUCAGCACCUUCAAGUGCUACGGCGUGAGCCCCAC<br>CAAGCUGAACGACCUGUGCUUCACCAACGUGUACGCCGA<br>CAGCUUCGUGAUCCGUGGCGACGAGGUGCGGCAGAUCGC<br>ACCCGGCCAGACAGGCAACAUCGCCGACUACAACUACAAG<br>CUGCCCGACGACUUCACCGGCUGCGUGAUCGCCUGGAACA<br>GCAACAACCUCGACAGCAAGGUGGGCGGCAACUACAACU<br>ACCUGUACCGGCUGUUCCGGAAGAGCAACCUGAAGCCCU<br>UCGAGCGGGACAUCAGCACCGAGAUCUACCAAGCCGGCU<br>CCACCCCUUGCAACGGCGUGAAGGGCUUCAACUGCUACU<br>UCCCUCUGCAGAGCUACGGCUUCCAGCCCACCUACGGCGU<br>GGGCUACCAGCCCUACCGGGUGGUGGUGCUGAGCUUCGA<br>GCUGCUGCACGCCCCAGCCACCGUGUGUGGCCCCAAGAAG<br>AGCACCAACCUGGUGAAGAACAAGUGCGUGAACUUCAAC<br>UUCAACGGCCUUACCGGCACCGGCGUGCUGACCGAGAGC<br>AACAAGAAAUUCCUGCCCUUUCAGCAGUUCGGCCGGGAC<br>AUCGCCGACACCACCGACGCUGUGCGGGAUCCCCAGACCC<br>UGGAGAUCCUGGACAUCACCCCUUGCAGCUUCGGCGGCG<br>UGAGCGUGAUCACCCCAGGCACCAACACCAGCAACCAGGU<br>GGCCGUGCUGUACCAGGGCGUGAACUGCACCGAGGUGCC<br>CGUGGCCAUCCACGCCGACCAGCUGACACCCACCUGGCGG<br>GUCUACAGCACCGGCAGCAACGUGUUCCAGACCCGGGCCG<br>GUUGCCUGAUCGGCGCCGAGCACGUGAACAACAGCUACG<br>AGUGCGACAUCCCCAUCGGCGCCGGCAUCUGUGCCAGCUA<br>CCAGACCCAGACCAAUUCACCCCGGAGGGCAAGGAGCGU<br>GGCCAGCCAGAGCAUCAUCGCCUACACCAUGAGCCUGGGC<br>GUGGAGAACAGCGUGGCCUACAGCAACAACAGCAUCGCC<br>AUCCCCACCAACUUCACCAUCAGCGUGACCACCGAGAUUC<br>UGCCCGUGAGCAUGACCAAGACCAGCGUGGACUGCACCA<br>UGUACAUCUGCGGCGACAGCACCGAGUGCAGCAACCUGC<br>UGCUGCAGUACGGCAGCUUCUGCACCCAGCUGAACCGGG<br>CCCUGACCGGCAUCGCCGUGGAGCAGGACAAGAACACCCA | 10 |

TABLE 1-continued

| Sequence Listing | | |
|---|---|---|
| | GGAGGUGUUCGCCCAGGUGAAGCAGAUCUACAAGACCCC<br>UCCCAUCAAGGACUUCGGCGGCUUCAACUUCAGCCAGAU<br>CCUGCCCGACCCCAGCAAGCCCAGCAAGCGGAGCUUCAUC<br>GAGGACCUGCUGUUCAACAAGGUGACCCUAGCCGACGCC<br>GGCUUCAUCAAGCAGUACGGCGACUGCCUCGGCGACAUA<br>GCCGCCCGGGACCUGAUCUGCGCCCAGAAGUUCAACGGCC<br>UGACCGUGCUGCCUCCCCUGCUGACCGACGAGAUGAUCGC<br>CCAGUACACCAGCGCCCUGUUAGCCGGAACCAUCACCAGC<br>GGCUGGACUUUCGGCGCUGGAGCCGCUCUGCAGAUCCCC<br>UUCGCCAUGCAGAUGGCCUACCGGUUCAACGGCAUCGGC<br>GUGACCCAGAACGUGCUGUACGAGAACCAGAAGCUGAUC<br>GCCAACCAGUUCAACAGCGCCAUCGGCAAGAUCCAGGAC<br>AGCCUGAGCAGCACCGCUAGCGCCCUGGGCAAGCUGCAG<br>GACGUGGUGAACCAGAACGCCCAGGCCCUGAACACCCUG<br>GUGAAGCAGCUGAGCAGCAACUUCGGCGCCAUCAGCAGC<br>GUGCUGAACGACAUCCUGAGCCGGCUGGACCCUCCCGAG<br>GCCGAGGUGCAGAUCGACCGGCUGAUCACUGGCCGGCUG<br>CAGAGCCUGCAGACCUACGUGACCCAGCAGCUGAUCCGG<br>GCCGCCGAGAUUCGGGCCAGCGCCAACCUGGCCGCCACCA<br>AGAUGAGCGAGUGCGUGCUGGGCCAGAGCAAGCGGGUGG<br>ACUUCUGCGGCAAGGGCUACCACCUGAUGAGCUUUCCCC<br>AGAGCGCACCCCACGGAGUGGUGUUCCUGCACGUGACCU<br>ACGUGCCCGCCCAGGAGAAGAACUUCACCACCGCCCCAGC<br>CAUCUGCCACGACGGCAAGGCCCACUUUCCCCGGGAGGGC<br>GUGUUCGUGAGCAACGGCACCCACUGGUUCGUGACCCAG<br>CGGAACUUCUACGAGCCCCAGAUCAUCACCACCGACAACA<br>CCUUCGUGAGCGGCAACUGCGACGUGGUGAUCGGCAUCG<br>UGAACAACACCGUGUACGAUCCCCUGCAGCCCGAGCUGG<br>ACAGCUUCAAGGAGGAGCUGGACAAGUACUUCAAGAAUC<br>ACACCAGCCCCGACGUGGACCUGGGCGACAUCAGCGGCAU<br>CAACGCCAGCGUGGUGAACAUCCAGAAGGAGAUCGAUCG<br>GCUGAACGAGGUGGCCAAGAACCUGAACGAGAGCCUGAU<br>CGACCUGCAGGAGCUGGGCAAGUACGAGCAGUACAUCAA<br>GUGGCCCUGGUACAUCUGGCUGGGCUUCAUCGCCGGCCU<br>GAUCGCCAUCGUGAUGGUGACCAUCAUGCUGUGCUGCAU<br>GACCAGCUGCUGCAGCUGCCUGAAGGGCUGUUGCAGCUG<br>CGGCAGCUGCUGCAAGUUCGACGAGGACGACAGCGAGCC<br>CGUGCUGAAGGGCGUGAAGCUGCACUACACC | |
| 3' UTR | UGAUAAUAGGCUGGAGCCUCGGUGGCCUAGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 4 |
| Corresponding amino acid sequence | MFVFLVLLPLVSSQCVNFTTRTQLPPAYTNSFTRGVYYPDKVF<br>RSSVLHSTQDLFLPFFSNVTWFHAIHVSGTNGTKRFANPVLPF<br>NDGVYFASTEKSNIIRGWIFGTTLDSKTQSLLIVNNATNVVIKV<br>CEFQFCNDPFLGVYYHKNNKSWMESEFRVYSSANNCTFEYVS<br>QPFLMDLEGKQGNFKNLREFVFKNIDGYFKIYSKHTPINLVRG<br>LPQGFSALEPLVDLPIGINITRFQTLHISYLTPGDSSSGWTAGAA<br>AYYVGYLQPRTFLLKYNENGTITDAVDCALDPLSETKCTLKSF<br>TVEKGIYQTSNFRVQPTESIVRFPNITNLCPFGEVENATRFASV<br>YAWNRKRISNCVADYSVLYNSASFSTFKCYGVSPTKLNDLCF<br>TNVYADSFVIRGDEVRQIAPGQTGNIADYNYKLPDDFTGCVIA<br>WNSNNLDSKVGGNYNYLYRLFRKSNLKPFERDISTEIYQAGS<br>TPCNGVKGFNCYFPLQSYGFQPTYGVGYQPYRVVVLSFELLH<br>APATVCGPKKSTNLVKNKCVNFNFNGLTGTGVLTESNKKFLP<br>FQQFGRDIADTTDAVRDPQTLEILDITPCSFGGVSVITPGTNTS<br>NQVAVLYQGVNCTEVPVAIHADQLTPTWRVYSTGSNVFQTR<br>AGCLIGAEHVNNSYECDIPIGAGICASYQTQTNSPRRARSVAS<br>QSIIAYTMSLGVENSVAYSNNSIAIPTNFTISVTTEILPVSMTKT<br>SVDCTMYICGDSTECSNLLLQYGSFCTQLNRALTGIAVEQDK<br>NTQEVFAQVKQIYKTPPIKDFGGFNFSQILPDPSKPSKRSFIEDL<br>LFNKVTLADAGFIKQYGDCLGDIAARDLICAQKFNGLTVLPPL<br>LTDEMIAQYTSALLAGTITSGWTFGAGAALQIPFAMQMAYRF<br>NGIGVTQNVLYENQKLIANQFNSAIGKIQDSLSSTASALGKLQ<br>DVVNQNAQALNTLVKQLSSNFGAISSVLNDILSRLDPPEAEVQ<br>IDRLITGRLQSLQTYVTQQLIRAAEIRASANLAATKMSECVLG<br>QSKRVDFCGKGYHLMSFPQSAPHGVVFLHVTYVPAQEKNFTT<br>APAICHDGKAHFPREGVFVSNGTHWFVTQRNFYEPQIITTDNT<br>FVSGNCDVVIGIVNNTVYDPLQPELDSFKEELDKYFKNHTSPD<br>VDLGDISGINASVVNIQKEIDRLNEVAKNLNESLIDLQELGKYE<br>QYIKWPWYIWLGFIAGLIAIVMVTIMLCCMTSCCSCLKGCCSC<br>GSCCKFDEDDSEPVLKGVKLHYT | 11 |
| PolyA tail | 100 nt | |

WH2020_NatSP_2P_H69del_V70del_Y144del_N501Y_A570D_D614G_P681H_T716I_S982A_D1118H SEQ ID NO: 12 consists of from 5' end to 3' end: 5' UTR SEQ ID NO: 2, mRNA ORF SEQ ID NO: 13, and 3' UTR SEQ ID NO: 4. 12

TABLE 1-continued

| Sequence Listing | | |
|---|---|---|
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUA<br>AGACCCCGGCGCCGCCACC | 2 |
| ORF of mRNA Construct (excluding the stop codon) | AUGUUCGUGUUCCUGGUGCUGCUGCCCCUGGUGAGCAGC<br>CAGUGCGUGAACCUGACCACCCGGACCCAGCUGCCACCAG<br>CCUACACCAACAGCUUCACCCGGGGCGUCUACUACCCCGA<br>CAAGGUGUUCCGGAGCAGCGUCCUGCACAGCACCCAGGA<br>CCUGUUCCUGCCCUUCUUCAGCAACGUGACCUGGUUCCAC<br>GCCAUCAGCGGCACCAACGGCACCAAGCGGUUCGACAACC<br>CCGUGCUGCCCUUCAACGACGGCGUGUACUUCGCCAGCAC<br>CGAGAAGAGCAACAUCAUCCGGGGCUGGAUCUUCGGCAC<br>CACCCUGGACAGCAAGACCCAGAGCCUGCUGAUCGUGAA<br>UAACGCCACCAACGUGGUGAUCAAGGUGUGCGAGUUCCA<br>GUUCUGCAACGACCCCUUCCUGGGCGUGUACCACAAGAA<br>CAACAAGAGCUGGAUGGAGAGCGAGUUCCGGGUGUACAG<br>CAGCGCCAACAACUGCACCUUCGAGUACGUGAGCCAGCCC<br>UUCCUGAUGGACCUGGAGGGCAAGCAGGGCAACUUCAAG<br>AACCUGCGGGAGUUCGUGUUCAAGAACAUCGACGGCUAC<br>UUCAAGAUCUACAGCAAGCACACCCCAAUCAACCUGGUG<br>CGGGAUCUGCCCCAGGGCUUCUCAGCCCUGGAGCCCCUGG<br>UGGACCUGCCCAUCGGCAUCAACAUCACCCGGUUCCAGAC<br>CCUGCUGGCCCUGCACCGGAGCUACCUGACCCCAGGCGAC<br>AGCAGCAGCGGGUGGACAGCAGGCGCGGCUGCUUACUAC<br>GUGGGCUACCUGCAGCCCCGGACCUUCCUGCUGAAGUAC<br>AACGAGAACGGCACCAUCACCGACGCCGUGGACUGCGCCC<br>UGGACCCUCUGAGCGAGACCAAGUGCACCCUGAAGAGCU<br>UCACCGUGGAGAAGGGCAUCUACCAGACCAGCAACUUCC<br>GGGUGCAGCCCACCGAGAGCAUCGUGCGGUUCCCCAACA<br>UCACCAACCUGUGCCCCUUCGGCGAGGUGUUCAACGCCAC<br>CCGGUUCGCCAGCGUGUACGCCUGGAACCGGAAGCGGAU<br>CAGCAACUGCGUGGCCGACUACAGCGUGCUGUACAACAG<br>CGCCAGCUUCAGCACCUUCAAGUGCUACGGCGUGAGCCCC<br>ACCAAGCUGAACGACCUGUGCUUCACCAACGUGUACGCC<br>GACAGCUUCGUGAUCCGUGGCGACGAGGUGCGGCAGAUC<br>GCACCCGGCCAGACAGGCAAGAUCGCCGACUACAACUACA<br>AGCUGCCCGACGACUUCACCGGCUGCGUGAUCGCCUGGA<br>ACAGCAACAACCUCGACAGCAAGGUGGGCGGCAACUACA<br>ACUACCUGUACCGGCUGUUCCGGAAGAGCAACCUGAAGC<br>CCUUCGAGCGGGACAUCAGCACCGAGAUCUACCAAGCCG<br>GCUCCACCCCUUGCAACGGCGUGGAGGGCUUCAACUGCU<br>ACUUCCCUCUGCAGAGCUACGGCUUCCAGCCCACCUACGG<br>CGUGGGCUACCAGCCCUACCGGGUGGUGGUGCUGAGCUU<br>CGAGCUGCUGCACGCCCCAGCCACCGUGUGUGGCCCCAAG<br>AAGAGCACCAACCUGGUGAAGAACAAGUGCGUGAACUUC<br>AACUUCAACGGCCUUACCGGCACCGGCGUGCUGACCGAG<br>AGCAACAAGAAAUUCCUGCCCUUUCAGCAGUUCGGCCGG<br>GACAUCGACGACACCACCGACGCUGUGCGGGAUCCCCAGA<br>CCCUGGAGAUCCUGGACAUCACCCCUUGCAGCUUCGGCGG<br>CGUGAGCGUGAUCACCCCAGGCACCAACACCAGCAACCAG<br>GUGGCCGUGCUGUACCAGGGCGUGAACUGCACCGAGGUG<br>CCCGUGGCCAUCCACGCCGACCAGCUGACACCCACCUGGC<br>GGGUCUACAGCACCGGCAGCAACGUGUUCCAGACCCGGG<br>CCGGUUGCCUGAUCGGCGCCGAGCACGUGAACAACAGCU<br>ACGAGUGCGACAUCCCCAUCGGCGCCGGCAUCUGUGCCAG<br>CUACCAGACCCAGACCAAUUCACACCGGAGGGCAAGGAG<br>CGUGGCCAGCCAGAGCAUCAUCGCCUACACCAUGAGCCUG<br>GGCGCCGAGAACAGCGUGGCCUACAGCAACAACAGCAUC<br>GCCAUCCCCAUCAACUUCACCAUCAGCGUGACCACCGAGA<br>UUCUGCCCGUGAGCAUGACCAAGACCAGCGUGGACUGCA<br>CCAUGUACAUCUGCGGCGACAGCACCGAGUGCAGCAACC<br>UGCUGCUGCAGUACGGCAGCUUCUGCACCCAGCUGAACC<br>GGGCCCUGACCGGCAUCGCCGUGGAGCAGGACAAGAACA<br>CCCAGGAGGUGUUCGCCCAGGUGAAGCAGAUCUACAAGA<br>CCCCUCCCAUCAAGGACUUCGGCGGCUUCAACUUCAGCCA<br>GAUCCUGCCCGACCCCAGCAAGCCCAGCAAGCGGAGCUUC<br>AUCGAGGACCUGCUGUUCAACAAGGUGACCCUAGCCGAC<br>GCCGGCUUCAUCAAGCAGUACGGCGACUGCCUCGGCGAC<br>AUAGCCGCCCGGGACCUGAUCUGCGCCCAGAAGUUCAAC<br>GGCCUGACCGUGCUGCCUCCCCUGCUGACCGACGAGAUGA<br>UCGCCCAGUACACCAGCGCCCUGUUAGCCGGAACCAUCAC<br>CAGCGGCUGGACUUUCGGCGCUGGAGCCGCUCUGCAGAU<br>CCCCUUCGCCAUGCAGAUGGCCUACCGGUUCAACGGCAUC<br>GGCGUGACCCAGAACGUGCUGUACGAGAACCAGAAGCUG<br>AUCGCCAACCAGUUCAACAGCGCCAUCGGCAAGAUCCAG<br>GACAGCCUGAGCAGCACCGCUAGCGCCCUGGGCAAGCUGC<br>AGGACGUGGUGAACCAGAACGCCCAGGCCCUGAACACCC<br>UGGUGAAGCAGCUGAGCAGCAACUUCGGCGCCAUCAGCA | 13 |

TABLE 1-continued

| Sequence Listing | | |
|---|---|---|
| | GCGUGCUGAACGACAUCCUGGCCCGGCUGGACCCUCCCGA GGCCGAGGUGCAGAUCGACCGGCUGAUCACUGGCCGGCU GCAGAGCCUGCAGACCUACGUGACCCAGCAGCUGAUCCG GGCCGCCGAGAUUCGGGCCAGCGCCAACCUGGCCGCCACC AAGAUGAGCGAGUGCGUGCUGGGCCAGAGCAAGCGGGUG GACUUCUGCGGCAAGGGCUACCACCUGAUGAGCUUUCCC CAGAGCGCACCCCACGGAGUGGUGUUCCUGCACGUGACC UACGUGCCCGCCCAGGAGAAGAACUUCACCACCGCCCCAG CCAUCUGCCACGACGGCAAGGCCCACUUUCCCCGGGAGGG CGUGUUCGUGAGCAACGGCACCCACUGGUUCGUGACCCA GCGGAACUUCUACGAGCCCCAGAUCAUCACCACCCACAAC ACCUUCGUGAGCGGCAACUGCGACGUGGUGAUCGGCAUC GUGAACAACACCGUGUACGAUCCCCUGCAGCCCGAGCUG GACAGCUUCAAGGAGGAGCUGGACAAGUACUUCAAGAAU CACACCAGCCCCGACGUGGACCUGGGCGACAUCAGCGGCA UCAACGCCAGCGUGGUGAACAUCCAGAAGGAGAUCGAUC GGCUGAACGAGGUGGCCAAGAACCUGAACGAGAGCCUGA UCGACCUGCAGGAGCUGGGCAAGUACGAGCAGUACAUCA AGUGGCCCUGGUACAUCUGGCUGGGCUUCAUCGCCGGCC UGAUCGCCAUCGUGAUGGUGACCAUCAUGCUGUGCUGCA UGACCAGCUGCUGCAGCUGCCUGAAGGGCUGUUGCAGCU GCGGCAGCUGCUGCAAGUUCGACGAGGACGACAGCGAGC CCGUGCUGAAGGGCGUGAAGCUGCACUACACC | |
| 3' UTR | UGAUAAUAGGCUGGAGCCUCGGUGGCCUAGCUUCUUGCC CCUUGGGCCUCCCCCCAGCCCCUCCUCCCCUUCCUGCACC CGUACCCCCGUGGUCUUUGAAUAAAGUCUGAGUGGGCGG C | 4 |
| Corresponding amino acid sequence | MFVFLVLLPLVSSQCVNLTTRTQLPPAYTNSFTRGVYYPDKVF RSSVLHSTQDLFLPFFSNVTWFHAISGTNGTKRFDNPVLPEND GVYFASTEKSNIIRGWIFGTTLDSKTQSLLIVNNATNVVIKVCE FQFCNDPFLGVYHKNNKSWMESEFRVYSSANNCTFEYVSQPF LMDLEGKQGNFKNLREFVFKNIDGYFKIYSKHTPINLVRDLPQ GFSALEPLVDLPIGINITRFQTLLALHRSYLTPGDSSSGWTAGA AAYYVGYLQPRTFLLKYNENGTITDAVDCALDPLSETKCTLK SFTVEKGIYQTSNFRVQPTESIVRFPNITNLCPFGEVFNATRFAS VYAWNRKRISNCVADYSVLYNSASFSTFKCYGVSPTKLNDLC FTNVYADSFVIRGDEVRQIAPGQTGKIADYNYKLPDDFTGCVI AWNSNNLDSKVGGNYNYLYRLFRKSNLKPFERDISTEIYQAG STPCNGVEGFNCYFPLQSYGFQPTYGVGYQPYRVVVLSFELL HAPATVCGPKKSTNLVKNKCVNFNFNGLTGTGVLTESNKKFL PFQQFGRDIDDTTDAVRDPQTLEILDITPCSFGGVSVITPGTNTS NQVAVLYQGVNCTEVPVAIHADQLTPTWRVYSTGSNVFQTR AGCLIGAEHVNNSYECDIPIGAGICASYQTQTNSHRRARSVAS QSIIAYTMSLGAENSVAYSNNSIAIPINFTISVTTEILPVSMTKTS VDCTMYICGDSTECSNLLLQYGSFCTQLNRALTGIAVEQDKN TQEVFAQVKQIYKTPPIKDFGGFNFSQILPDPSKPSKRSFIEDLL FNKVTLADAGFIKQYGDCLGDIAARDLICAQKFNGLTVLPPLL TDEMIAQYTSALLAGTITSGWTFGAGAALQIPFAMQMAYRFN GIGVTQNVLYENQKLIANQFNSAIGKIQDSLSSTASALGKLQD VVNQNAQALNTLVKQLSSNFGAISSVLNDILARLDPPEAEVQI DRLITGRLQSLQTYVTQQLIRAAEIRASANLAATKMSECVLGQ SKRVDFCGKGYHLMSFPQSAPHGVVFLHVTYVPAQEKNFTTA PAICHDGKAHFPREGVFVSNGTHWFVTQRNFYEPQIITTHNTF VSGNCDVVIGIVNNTVYDPLQPELDSFKEELDKYFKNHTSPDV DLGDISGINASVVNIQKEIDRLNEVAKNLNESLIDLQELGKYEQ YIKWPWYIWLGFIAGLIAIVMVTIMLCCMTSCCSCLKGCCSCG SCCKFDEDDSEPVLKGVKLHYT | 14 |
| PolyA tail | 100 nt | |

WH2020_NatSP_2P_L18F_H69del_V70del_D80A_Y144del_D215G_L242_244del_R246I_K417N_E484K_N501Y_A570D_D614G_P681H_A701V_T716I_S982A_D1118H

| | | |
|---|---|---|
| SEQ ID NO: 15 consists of from 5' end to 3' end: 5' UTR SEQ ID NO: 2, mRNA ORF SEQ ID NO: 16, and 3' UTR SEQ ID NO: 4. | | 15 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUA AGACCCCGGCGCCGCCACC | 2 |
| ORF of mRNA Construct (excluding the stop codon) | AUGUUCGUGUUCCUGGUGCUGCUGCCCCUGGUGAGCAGC CAGUGCGUGAACUUUACCACCCGGACCCAGCUGCCACCAG CCUACACCAACAGCUUCACCCGGGGCGUCUACUACCCCGA CAAGGUGUUCCGGAGCAGCGUCCUGCACAGCACCCAGGA CCUGUUCCUGCCCUUCUUCAGCAACGUGACCUGGUUCCAC GCCAUCAGCGGCACCAACGGCACCAAGCGGUUCGCCAACC CCGUGCUGCCCUUCAACGACGGCGUGUACUUCGCCAGCAC CGAGAAGAGCAACAUCAUCCGGGGCUGGAUCUUCGGCAC CACCCUGGACAGCAAGACCCAGAGCCUGCUGAUCGUGAA UAACGCCACCAACGUGGUGAUCAAGGUGUGCGAGUUCCA | 16 |

TABLE 1-continued

| Sequence Listing |
| --- |
| GUUCUGCAACGACCCCUUCCUGGGCGUGUACCACAAGAA<br>CAACAAGAGCUGGAUGGAGAGCGAGUUCCGGGUGUACAG<br>CAGCGCCAACAACUGCACCUUCGAGUACGUGAGCCAGCCC<br>UUCCUGAUGGACCUGGAGGGCAAGCAGGGCAACUUCAAG<br>AACCUGCGGGAGUUCGUGUUCAAGAACAUCGACGGCUAC<br>UUCAAGAUCUACAGCAAGCACACCCCAAUCAACCUGGUG<br>CGGGGCCUGCCCCAGGGCUUCUCAGCCCUGGAGCCCCUGG<br>UGGACCUGCCCAUCGGCAUCAACAUCACCCGGUUCCAGAC<br>CCUGCACAUCAGCUACCUGACCCCAGGCGACAGCAGCAGC<br>GGGUGGACAGCAGGCGCGGCUGCUUACUACGUGGGCUAC<br>CUGCAGCCCCGGACCUUCCUGCUGAAGUACAACGAGAAC<br>GGCACCAUCACCGACGCCGUGGACUGCGCCCUGGACCCUC<br>UGAGCGAGACCAAGUGCACCCUGAAGAGCUUCACCGUGG<br>AGAAGGGCAUCUACCAGACCAGCAACUUCCGGGUGCAGC<br>CCACCGAGAGCAUCGUGCGGUUCCCCAACAUCACCAACCU<br>GUGCCCCUUCGGCGAGGUGUUCAACGCCACCCGGUUCGCC<br>AGCGUGUACGCCUGGAACCGGAAGCGGAUCAGCAACUGC<br>GUGGCCGACUACAGCGUGCUGUACAACAGCGCCAGCUUC<br>AGCACCUUCAAGUGCUACGGCGUGAGCCCCACCAAGCUG<br>AACGACCUGUGCUUCACCAACGUGUACGCCGACAGCUUC<br>GUGAUCCGUGGCGACGAGGUGCGGCAGAUCGCACCCGGC<br>CAGACAGGCAACAUCGCCGACUACAACUACAAGCUGCCCG<br>ACGACUUCACCGGCUGCGUGAUCGCCUGGAACAGCAACA<br>ACCUCGACAGCAAGGUGGGCGGCAACUACAACUACCUGU<br>ACCGGCUGUUCCGGAAGAGCAACCUGAAGCCCUUCGAGC<br>GGGACAUCAGCACCGAGAUCUACCAAGCCGGCUCCACCCC<br>UUGCAACGGCGUGAAGGGCUUCAACUGCUACUUCCCUCU<br>GCAGAGCUACGGCUUCCAGCCCACCUACGGCGUGGGCUAC<br>CAGCCCUACCGGGUGGUGGUGCUGAGCUUCGAGCUGCUG<br>CACGCCCCAGCCACCGUGUGUGGCCCCAAGAAGAGCACCA<br>ACCUGGUGAAGAACAAGUGCGUGAACUUCAACUUCAACG<br>GCCUUACCGGCACCGGCGUGCUGACCGAGAGCAACAAGA<br>AAUUCCUGCCCUUUCAGCAGUUCGGCCGGGACAUCGACG<br>ACACCACCGACGCUGUGCGGGAUCCCCAGACCCUGGAGAU<br>CCUGGACAUCACCCCUUGCAGCUUCGGCGGCGUGAGCGU<br>GAUCACCCCAGGCACCAACACCAGCAACCAGGUGGCCGUG<br>CUGUACCAGGGCGUGAACUGCACCGAGGUGCCCGUGGCC<br>AUCCACGCCGACCAGCUGACACCCACCUGGCGGGUCUACA<br>GCACCGGCAGCAACGUGUUCCAGACCCGGGCCGGUUGCCU<br>GAUCGGCGCCGAGCACGUGAACAACAGCUACGAGUGCGA<br>CAUCCCCAUCGGCGCCGGCAUCUGUGCCAGCUACCAGACC<br>CAGACCAAUUCACACCGGAGGGCAAGGAGCGUGGCCAGC<br>CAGAGCAUCAUCGCCUACACCAUGAGCCUGGGCGUGGAG<br>AACAGCGUGGCCUACAGCAACAACAGCAUCGCCAUCCCCA<br>UCAACUUCACCAUCAGCGUGACCACCGAGAUUCUGCCCGU<br>GAGCAUGACCAAGACCAGCGUGGACUGCACCAUGUACAU<br>CUGCGGCGACAGCACCGAGUGCAGCAACCUGCUGCUGCA<br>GUACGGCAGCUUCUGCACCCAGCUGAACCGGGCCCUGACC<br>GGCAUCGCCGUGGAGCAGGACAAGAACACCCAGGAGGUG<br>UUCGCCCAGGUGAAGCAGAUCUACAAGACCCCUCCCAUCA<br>AGGACUUCGGCGGCUUCAACUUCAGCCAGAUCCUGCCCG<br>ACCCCAGCAAGCCCAGCAAGCGGAGCUUCAUCGAGGACCU<br>GCUGUUCAACAAGGUGACCCUAGCCGACGCCGGCUUCAU<br>CAAGCAGUACGGCGACUGCCUCGGCGACAUAGCCGCCCGG<br>GACCUGAUCUGCGCCCAGAAGUUCAACGGCCUGACCGUG<br>CUGCCUCCCCUGCUGACCGACGAGAUGAUCGCCCAGUACA<br>CCAGCGCCCUGUUAGCCGGAACCAUCACCAGCGGCUGGAC<br>UUUCGGCGCUGGAGCCGCUCUGCAGAUCCCCUUCGCCAUG<br>CAGAUGGCCUACCGGUUCAACGGCAUCGGCGUGACCCAG<br>AACGUGCUGUACGAGAACCAGAAGCUGAUCGCCAACCAG<br>UUCAACAGCGCCAUCGGCAAGAUCCAGGACAGCCUGAGC<br>AGCACCGCUAGCGCCCUGGGCAAGCUGCAGGACGUGGUG<br>AACCAGAACGCCCAGGCCCUGAACACCCUGGUGAAGCAGC<br>UGAGCAGCAACUUCGGCGCCAUCAGCAGCGUGCUGAACG<br>ACAUCCUGGCCCGGCUGGACCCUCCCGAGGCCGAGGUGCA<br>GAUCGACCGGCUGAUCACUGGCCGGCUGCAGAGCCUGCA<br>GACCUACGUGACCCAGCAGCUGAUCCGGGCCGCCGAGAU<br>UCGGGCCAGCGCCAACCUGGCCGCCACCAAGAUGAGCGAG<br>UGCGUGCUGGGCCAGAGCAAGCGGGUGGACUUCUGCGGC<br>AAGGGCUACCACCUGAUGAGCUUUCCCCAGAGCGCACCCC<br>ACGGAGUGGUGUUCCUGCACGUGACCUACGUGCCCGCCC<br>AGGAGAAGAACUUCACCACCGCCCCAGCCAUCUGCCACGA<br>CGGCAAGGCCCACUUUCCCCGGGAGGGCGUGUUCGUGAG<br>CAACGGCACCCACUGGUUCGUGACCCAGCGGAACUUCUAC<br>GAGCCCCAGAUCAUCACCACCCACAACACCUUCGUGAGCG<br>GCAACUGCGACGUGGUGAUCGGCAUCGUGAACAACACCG<br>UGUACGAUCCCCUGCAGCCCGAGCUGGACAGCUUCAAGG<br>AGGAGCUGGACAAGUACUUCAAGAAUCACACCAGCCCCG |

TABLE 1-continued

| Sequence Listing | | |
|---|---|---|
| | ACGUGGACCUGGGCGACAUCAGCGGCAUCAACGCCAGCG<br>UGGUGAACAUCCAGAAGGAGAUCGAUCGGCUGAACGAGG<br>UGGCCAAGAACCUGAACGAGAGCCUGAUCGACCUGCAGG<br>AGCUGGGCAAGUACGAGCAGUACAUCAAGUGGCCCUGGU<br>ACAUCUGGCUGGGCUUCAUCGCCGGCCUGAUCGCCAUCG<br>UGAUGGUGACCAUCAUGCUGUGCUGCAUGACCAGCUGCU<br>GCAGCUGCCUGAAGGGCUGUUGCAGCUGCGGCAGCUGCU<br>GCAAGUUCGACGAGGACGACAGCGAGCCCGUGCUGAAGG<br>GCGUGAAGCUGCACUACACC | |
| 3' UTR | UGAUAAUAGGCUGGAGCCUCGGUGGCCUAGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 4 |
| Corresponding amino acid sequence | MFVFLVLLPLVSSQCVNFTTRTQLPPAYTNSFTRGVYYPDKVF<br>RSSVLHSTQDLFLPFFSNVTWFHAISGTNGTKRFANPVLPFND<br>GVYFASTEKSNIIRGWIFGTTLDSKTQSLLIVNNATNVVIKVCE<br>FQFCNDPFLGVYHKNNKSWMESEFRVYSSANNCTFEYVSQPF<br>LMDLEGKQGNFKNLREFVFKNIDGYFKIYSKHTPINLVRGLPQ<br>GFSALEPLVDLPIGINITRFQTLHISYLTPGDSSSGWTAGAAAY<br>YVGYLQPRTFLLKYNENGTITDAVDCALDPLSETKCTLKSFTV<br>EKGIYQTSNFRVQPTESIVRFPNITNLCPFGEVENATRFASVYA<br>WNRKRISNCVADYSVLYNSASFSTFKCYGVSPTKLNDLCFTN<br>VYADSFVIRGDEVRQIAPGQTGNIADYNYKLPDDFTGCVIAW<br>NSNNLDSKVGGNYNYLYRLFRKSNLKPFERDISTEIYQAGSTP<br>CNGVKGFNCYFPLQSYGFQPTYGVGYQPYRVVVLSFELLHAP<br>ATVCGPKKSTNLVKNKCVNFNFNGLTGTGVLTESNKKFLPFQ<br>QFGRDIDDTTDAVRDPQTLEILDITPCSFGGVSVITPGTNTSNQ<br>VAVLYQGVNCTEVPVAIHADQLTPTWRVYSTGSNVFQTRAG<br>CLIGAEHVNNSYECDIPIGAGICASYQTQTNSHRRARSVASQSI<br>IAYTMSLGVENSVAYSNNSIAIPINFTISVTTEILPVSMTKTSVD<br>CTMYICGDSTECSNLLLQYGSFCTQLNRALTGIAVEQDKNTQE<br>VFAQVKQIYKTPPIKDFGGFNFSQILPDPSKPSKRSFIEDLLENK<br>VTLADAGFIKQYGDCLGDIAARDLICAQKFNGLTVLPPLLTDE<br>MIAQYTSALLAGTITSGWTFGAGAALQIPFAMQMAYRENGIG<br>VTQNVLYENQKLIANQFNSAIGKIQDSLSSTASALGKLQDVVN<br>QNAQALNTLVKQLSSNFGAISSVLNDILARLDPPEAEVQIDRLI<br>TGRLQSLQTYVTQQLIRAAEIRASANLAATKMSECVLGQSKR<br>VDFCGKGYHLMSFPQSAPHGVVFLHVTYVPAQEKNFTTAPAI<br>CHDGKAHFPREGVFVSNGTHWFVTQRNFYEPQIITTHNTFVSG<br>NCDVVIGIVNNTVYDPLQPELDSFKEELDKYFKNHTSPDVDLG<br>DISGINASVVNIQKEIDRLNEVAKNLNESLIDLQELGKYEQYIK<br>WPWYIWLGFIAGLIAIVMVTIMLCCMTSCCSCLKGCCSCGSCC<br>KFDEDDSEPVLKGVKLHYT | 17 |
| PolyA tail | 100 nt | |

| WH2020_NatSP_2P | | |
|---|---|---|
| SEQ ID NO: 18 consists of from 5' end to 3' end: 5' UTR SEQ ID NO: 2, mRNA ORF SEQ ID NO: 19, and 3' UTR SEQ ID NO: 4. | | 18 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA<br>AGACCCCGGCGCCGCCACC | 2 |
| ORF of mRNA Construct (excluding the stop codon) | AUGUUCGUGUUCCUGGUGCUGCUGCCCCUGGUGAGCAGC<br>CAGUGCGUGAACCUGACCACCCGGACCCAGCUGCCACCAG<br>CCUACACCAACAGCUUCACCCGGGGCGUCUACUACCCCGA<br>CAAGGUGUUCCGGAGCAGCGUCCUGCACAGCACCCAGGA<br>CCUGUUCCUGCCCUUCUUCAGCAACGUGACCUGGUUCCAC<br>GCCAUCCACGUGAGCGGCACCAACGGCACCAAGCGGUUCG<br>ACAACCCCGUGCUGCCCUUCAACGACGGCGUGUACUUCGC<br>CAGCACCGAGAAGAGCAACAUCAUCCGGGGCUGGAUCUU<br>CGGCACCACCCUGGACAGCAAGACCCAGAGCCUGCUGAUC<br>GUGAAUAACGCCACCAACGUGGUGAUCAAGGUGUGCGAG<br>UUCCAGUUCUGCAACGACCCCUUCCUGGGCGUGUACUACC<br>ACAAGAACAACAAGAGCUGGAUGGAGAGCGAGUUCCGGG<br>UGUACAGCAGCGCCAACAACUGCACCUUCGAGUACGUGA<br>GCCAGCCCUUCCUGAUGGACCUGGAGGGCAAGCAGGGCA<br>ACUUCAAGAACCUGCGGGAGUUCGUGUUCAAGAACAUCG<br>ACGGCUACUUCAAGAUCUACAGCAAGCACACCCCAAUCA<br>ACCUGGUGCGGGAUCUGCCCCAGGGCUUCUCAGCCCUGG<br>AGCCCCUGGUGGACCUGCCCAUCGGCAUCAACAUCACCCG<br>GUUCCAGACCCUGCUGGCCCUGCACCGGAGCUACCUGACC<br>CCAGGCGACAGCAGCAGCGGGUGGACAGCAGGCGCGGCU<br>GCUUACUACGUGGGCUACCUGCAGCCCCGGACCUUCCUGC<br>UGAAGUACAACGAGAACGGCACCAUCACCGACGCCGUGG<br>ACUGCGCCCUGGACCCUCUGAGCGAGACCAAGUGCACCCU<br>GAAGAGCUUCACCGUGGAGAAGGGCAUCUACCAGACCAG<br>CAACUUCCGGGUGCAGCCCACCGAGAGCAUCGUGCGGUU | 19 |

TABLE 1-continued

| Sequence Listing | | |
|---|---|---|
| | CCCCAACAUCACCAACCUGUGCCCCUUCGGCGAGGUGUUC | |
| | AACGCCACCCGGUUCGCCAGCGUGUACGCCUGGAACCGGA | |
| | AGCGGAUCAGCAACUGCGUGGCCGACUACAGCGUGCUGU | |
| | ACAACAGCGCCAGCUUCAGCACCUUCAAGUGCUACGGCG | |
| | UGAGCCCCACCAAGCUGAACGACCUGUGCUUCACCAACGU | |
| | GUACGCCGACAGCUUCGUGAUCCGUGGCGACGAGGUGCG | |
| | GCAGAUCGCACCCGGCCAGACAGGCAAGAUCGCCGACUAC | |
| | AACUACAAGCUGCCCGACGACUUCACCGGCUGCGUGAUC | |
| | GCCUGGAACAGCAACAACCUCGACAGCAAGGUGGGCGGC | |
| | AACUACAACUACCUGUACCGGCUGUUCCGGAAGAGCAAC | |
| | CUGAAGCCCUUCGAGCGGGACAUCAGCACCGAGAUCUAC | |
| | CAAGCCGGCUCCACCCCUUGCAACGGCGUGGAGGGCUUCA | |
| | ACUGCUACUUCCCUCUGCAGAGCUACGGCUUCCAGCCCAC | |
| | CAACGGCGUGGGCUACCAGCCCUACCGGGUGGUGGUGCU | |
| | GAGCUUCGAGCUGCUGCACGCCCCAGCCACCGUGUGUGGC | |
| | CCCAAGAAGAGCACCAACCUGGUGAAGAACAAGUGCGUG | |
| | AACUUCAACUUCAACGGCCUUACCGGCACCGGCGUGCUG | |
| | ACCGAGAGCAACAAGAAAUUCCUGCCCUUUCAGCAGUUC | |
| | GGCCGGGACAUCGCCGACACCACCGACGCUGUGCGGGAUC | |
| | CCCAGACCCUGGAGAUCCUGGACAUCACCCCUUGCAGCUU | |
| | CGGCGGCGUGAGCGUGAUCACCCCAGGCACCAACACCAGC | |
| | AACCAGGUGGCCGUGCUGUACCAGGACGUGAACUGCACC | |
| | GAGGUGCCCGUGGCCAUCCACGCCGACCAGCUGACACCCA | |
| | CCUGGCGGGUCUACAGCACCGGCAGCAACGUGUUCCAGA | |
| | CCCGGGCCGGUUGCCUGAUCGGCGCCGAGCACGUGAACA | |
| | ACAGCUACGAGUGCGACAUCCCCAUCGGCGCCGGCAUCUG | |
| | UGCCAGCUACCAGACCCAGACCAAUUCACCCCGGAGGGCA | |
| | AGGAGCGUGGCCAGCCAGAGCAUCAUCGCCUACACCAUG | |
| | AGCCUGGGCGCCGAGAACAGCGUGGCCUACAGCAACAAC | |
| | AGCAUCGCCAUCCCCACCAACUUCACCAUCAGCGUGACCA | |
| | CCGAGAUUCUGCCCGUGAGCAUGACCAAGACCAGCGUGG | |
| | ACUGCACCAUGUACAUCUGCGGCGACAGCACCGAGUGCA | |
| | GCAACCUGCUGCUGCAGUACGGCAGCUUCUGCACCCAGCU | |
| | GAACCGGGCCCUGACCGGCAUCGCCGUGGAGCAGGACAA | |
| | GAACACCCAGGAGGUGUUCGCCCAGGUGAAGCAGAUCUA | |
| | CAAGACCCCUCCCAUCAAGGACUUCGGCGGCUUCAACUUC | |
| | AGCCAGAUCCUGCCCGACCCCAGCAAGCCCAGCAAGCGGA | |
| | GCUUCAUCGAGGACCUGCUGUUCAACAAGGUGACCCUAG | |
| | CCGACGCCGGCUUCAUCAAGCAGUACGGCGACUGCCUCGG | |
| | CGACAUAGCCGCCCGGGACCUGAUCUGCGCCCAGAAGUUC | |
| | AACGGCCUGACCGUGCUGCCUCCCCUGCUGACCGACGAGA | |
| | UGAUCGCCCAGUACACCAGCGCCCUGUUAGCCGGAACCAU | |
| | CACCAGCGGCUGGACUUUCGGCGCUGGAGCCGCUCUGCA | |
| | GAUCCCCUUCGCCAUGCAGAUGGCCUACCGGUUCAACGGC | |
| | AUCGGCGUGACCCAGAACGUGCUGUACGAGAACCAGAAG | |
| | CUGAUCGCCAACCAGUUCAACAGCGCCAUCGGCAAGAUCC | |
| | AGGACAGCCUGAGCAGCACCGCUAGCGCCCUGGGCAAGC | |
| | UGCAGGACGUGGUGAACCAGAACGCCCAGGCCCUGAACA | |
| | CCCUGGUGAAGCAGCUGAGCAGCAACUUCGGCGCCAUCA | |
| | GCAGCGUGCUGAACGACAUCCUGAGCCGGCUGGACCCUCC | |
| | CGAGGCCGAGGUGCAGAUCGACCGGCUGAUCACUGGCCG | |
| | GCUGCAGAGCCUGCAGACCUACGUGACCCAGCAGCUGAU | |
| | CCGGGCCGCCGAGAUUCGGGCCAGCGCCAACCUGGCCGCC | |
| | ACCAAGAUGAGCGAGUGCGUGCUGGGCCAGAGCAAGCGG | |
| | GUGGACUUCUGCGGCAAGGGCUACCACCUGAUGAGCUUU | |
| | CCCCAGAGCGCACCCCACGGAGUGGUGUUCCUGCACGUGA | |
| | CCUACGUGCCCGCCCAGGAGAAGAACUUCACCACCGCCCC | |
| | AGCCAUCUGCCACGACGGCAAGGCCCACUUUCCCCGGGAG | |
| | GGCGUGUUCGUGAGCAACGGCACCCACUGGUUCGUGACC | |
| | CAGCGGAACUUCUACGAGCCCCAGAUCAUCACCACCGACA | |
| | ACACCUUCGUGAGCGGCAACUGCGACGUGGUGAUCGGCA | |
| | UCGUGAACAACACCGUGUACGAUCCCCUGCAGCCCGAGCU | |
| | GGACAGCUUCAAGGAGGAGCUGGACAAGUACUUCAAGAA | |
| | UCACACCAGCCCCGACGUGGACCUGGGCGACAUCAGCGGC | |
| | AUCAACGCCAGCGUGGUGAACAUCCAGAAGGAGAUCGAU | |
| | CGGCUGAACGAGGUGGCCAAGAACCUGAACGAGAGCCUG | |
| | AUCGACCUGCAGGAGCUGGGCAAGUACGAGCAGUACAUC | |
| | AAGUGGCCCUGGUACAUCUGGCUGGGCUUCAUCGCCGGC | |
| | CUGAUCGCCAUCGUGAUGGUGACCAUCAUGCUGUGCUGC | |
| | AUGACCAGCUGCUGCAGCUGCCUGAAGGGCUGUUGCAGC | |
| | UGCGGCAGCUGCUGCAAGUUCGACGAGGACGACAGCGAG | |
| | CCCGUGCUGAAGGGCGUGAAGCUGCACUACACC | |
| 3' UTR | UGAUAAUAGGCUGGAGCCUCGGUGGCCUAGCUUCUUGCC | 4 |
| | CCUUGGGCCUCCCCCCAGCCCCUCCUCCCCUUCCUGCACC | |
| | CGUACCCCCGUGGUCUUUGAAUAAAGUCUGAGUGGGCGG | |
| | C | |
| Corresponding amino | MFVFLVLLPLVSSQCVNLTTRTQLPPAYTNSFTRGVYYPDKVF | 20 |
| acid sequence | RSSVLHSTQDLFLPFFSNVTWFHAIHVSGTNGTKRFDNPVLPF | |

TABLE 1-continued

| Sequence Listing | | |
|---|---|---|
| | NDGVYFASTEKSNIIRGWIFGTTLDSKTQSLLIVNNATNVVIKV<br>CEFQFCNDPFLGVYYHKNNKSWMESEFRVYSSANNCTFEYVS<br>QPFLMDLEGKQGNFKNLREFVFKNIDGYFKIYSKHTPINLVRD<br>LPQGFSALEPLVDLPIGINITRFQTLLALHRSYLTPGDSSSGWT<br>AGAAAYYVGYLQPRTFLLKYNENGTITDAVDCALDPLSETKC<br>TLKSFTVEKGIYQTSNFRVQPTESIVRFPNITNLCPFGEVFNATR<br>FASVYAWNRKRISNCVADYSVLYNSASFSTFKCYGVSPTKLN<br>DLCFTNVYADSFVIRGDEVRQIAPGQTGKIADYNYKLPDDFTG<br>CVIAWNSNNLDSKVGGNYNYLYRLFRKSNLKPFERDISTEIYQ<br>AGSTPCNGVEGENCYFPLQSYGFQPTNGVGYQPYRVVVLSFE<br>LLHAPATVCGPKKSTNLVKNKCVNFNFNGLTGTGVLTESNKK<br>FLPFQQFGRDIADTTDAVRDPQTLEILDITPCSFGGVSVITPGTN<br>TSNQVAVLYQDVNCTEVPVAIHADQLTPTWRVYSTGSNVFQT<br>RAGCLIGAEHVNNSYECDIPIGAGICASYQTQTNSPRRARSVA<br>SQSIIAYTMSLGAENSVAYSNNSIAIPTNFTISVTTEILPVSMTK<br>TSVDCTMYICGDSTECSNLLLQYGSFCTQLNRALTGIAVEQDK<br>NTQEVFAQVKQIYKTPPIKDFGGFNFSQILPDPSKPSKRSFIEDL<br>LFNKVTLADAGFIKQYGDCLGDIAARDLICAQKFNGLTVLPPL<br>LTDEMIAQYTSALLAGTITSGWTFGAGAALQIPFAMQMAYRF<br>NGIGVTQNVLYENQKLIANQFNSAIGKIQDSLSSTASALGKLQ<br>DVVNQNAQALNTLVKQLSSNFGAISSVLNDILSRLDPPEAEVQ<br>IDRLITGRLQSLQTYVTQQLIRAAEIRASANLAATKMSECVLG<br>QSKRVDFCGKGYHLMSFPQSAPHGVVFLHVTYVPAQEKNFTT<br>APAICHDGKAHFPREGVFVSNGTHWFVTQRNFYEPQIITTDNT<br>FVSGNCDVVIGIVNNTVYDPLQPELDSFKEELDKYFKNHTSPD<br>VDLGDISGINASVVNIQKEIDRLNEVAKNLNESLIDLQELGKYE<br>QYIKWPWYIWLGFIAGLIAIVMVTIMLCCMTSCCSCLKGCCSC<br>GSCCKFDEDDSEPVLKGVKLHYT | |
| PolyA tail | 100 nt | |
| **S2P_IN_[T95I, G142D, E154K, L452R, E484Q, D614G, P681R, Q1071H]** | | |
| SEQ ID NO: 21 consists of from 5' end to 3' end: 5' UTR SEQ ID NO: 2, mRNA ORF SEQ ID NO: 22, and 3' UTR SEQ ID NO: 4. | | 21 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUA<br>AGACCCCGGCGCCGCCACC | 2 |
| ORF of mRNA Construct (excluding the stop codon) | AUGUUCGUGUUCCUGGUGCUGCUGCCCCUGGUGAGCAGC<br>CAGUGCGUGAACCUGACCACCCGGACCCAGCUGCCACCAG<br>CCUACACCAACAGCUUCACCCGGGGCGUCUACUACCCCGA<br>CAAGGUGUUCCGGAGCAGCGUCCUGCACAGCACCCAGGA<br>CCUGUUCCUGCCCUUCUUCAGCAACGUGACCUGGUUCCAC<br>GCCAUCCACGUGAGCGGCACCAACGGCACCAAGCGGUUCG<br>ACAACCCCGUGCUGCCCUUCAACGACGGCGUGUACUUCGC<br>CAGCAUCGAGAAGAGCAACAUCAUCCGGGGCUGGAUCUU<br>CGGCACCACCCUGGACAGCAAGACCCAGAGCCUGCUGAUC<br>GUGAAUAACGCCACCAACGUGGUGAUCAAGGUGUGCGAG<br>UUCCAGUUCUGCAACGACCCCUUCCUGGACGUGUACUACC<br>ACAAGAACAACAAGAGCUGGAUGAAGAGCGAGUUCCGGG<br>UGUACAGCAGCGCCAACAACUGCACCUUCGAGUACGUGA<br>GCCAGCCCUUCCUGAUGGACCUGGAGGGCAAGCAGGGCA<br>ACUUCAAGAACCUGCGGGAGUUCGUGUUCAAGAACAUCG<br>ACGGCUACUUCAAGAUCUACAGCAAGCACACCCCAAUCA<br>ACCUGGUGCGGGAUCUGCCCCAGGGCUUCUCAGCCCUGG<br>AGCCCCUGGUGGACCUGCCCAUCGGCAUCAACAUCACCCG<br>GUUCCAGACCCUGCUGGCCCUGCACCGGAGCUACCUGACC<br>CCAGGCGACAGCAGCAGCGGGUGGACAGCAGGCGCGGCU<br>GCUUACUACGUGGGCUACCUGCAGCCCCGGACCUUCCUGC<br>UGAAGUACAACGAGAACGGCACCAUCACCGACGCCGUGG<br>ACUGCGCCCUGGACCCUCUGAGCGAGACCAAGUGCACCCU<br>GAAGAGCUUCACCGUGGAGAAGGGCAUCUACCAGACCAG<br>CAACUUCCGGGUGCAGCCCACCGAGAGCAUCGUGCGGUU<br>CCCCAACAUCACCAACCUGUGCCCCUUCGGCGAGGUGUUC<br>AACGCCACCCGGUUCGCCAGCGUGUACGCCUGGAACCGGA<br>AGCGGAUCAGCAACUGCGUGGCCGACUACAGCGUGCUGU<br>ACAACAGCGCCAGCUUCAGCACCUUCAAGUGCUACGGCG<br>UGAGCCCCACCAAGCUGAACGACCUGUGCUUCACCAACGU<br>GUACGCCGACAGCUUCGUGAUCCGUGGCGACGAGGUGCG<br>GCAGAUCGCACCCGGCCAGACAGGCAAGAUCGCCGACUAC<br>AACUACAAGCUGCCCGACGACUUCACCGGCUGCGUGAUC<br>GCCUGGAACAGCAACAACCUCGACAGCAAGGUGGGCGGC<br>AACUACAACUACAGAUACCGGCUGUUCCGGAAGAGCAAC<br>CUGAAGCCCUUCGAGCGGGACAUCAGCACCGAGAUCUAC<br>CAAGCCGGCUCCACCCCUUGCAACGGCGUGCAGGGCUUCA<br>ACUGCUACUUCCCUCUGCAGAGCUACGGCUUCCAGCCCAC<br>CAACGGCGUGGGCUACCAGCCCUACCGGGUGGUGGUGCU<br>GAGCUUCGAGCUGCUGCACGCCCCAGCCACCGUGUGUGGC | 22 |

TABLE 1-continued

| | Sequence Listing | |
|---|---|---|
| | CCCAAGAAGAGCACCAACCUGGUGAAGAACAAGUGCGUG<br>AACUUCAACUUCAACGGCCUUACCGGCACCGGCGUGCUG<br>ACCGAGAGCAACAAGAAAUUCCUGCCCUUUCAGCAGUUC<br>GGCCGGGACAUCGCCGACACCACCGACGCUGUGCGGGAUC<br>CCCAGACCCUGGAGAUCCUGGACAUCACCCCUUGCAGCUU<br>CGGCGGCGUGAGCGUGAUCACCCCAGGCACCAACACCAGC<br>AACCAGGUGGCCGUGCUGUACCAGGGCGUGAACUGCACC<br>GAGGUGCCCGUGGCCAUCCACGCCGACCAGCUGACACCCA<br>CCUGGCGGGUCUACAGCACCGGCAGCAACGUGUUCCAGA<br>CCCGGGCCGGUUGCCUGAUCGGCGCCGAGCACGUGAACA<br>ACAGCUACGAGUGCGACAUCCCCAUCGGCGCCGGCAUCUG<br>UGCCAGCUACCAGACCCAGACCAAUUCAAGACGGAGGGC<br>AAGGAGCGUGGCCAGCCAGAGCAUCAUCGCCUACACCAU<br>GAGCCUGGGCGCCGAGAACAGCGUGGCCUACAGCAACAA<br>CAGCAUCGCCAUCCCCACCAACUUCACCAUCAGCGUGACC<br>ACCGAGAUUCUGCCCGUGAGCAUGACCAAGACCAGCGUG<br>GACUGCACCAUGUACAUCUGCGGCGACAGCACCGAGUGC<br>AGCAACCUGCUGCUGCAGUACGGCAGCUUCUGCACCCAGC<br>UGAACCGGGCCCUGACCGGCAUCGCCGUGGAGCAGGACA<br>AGAACACCCAGGAGGUGUUCGCCCAGGUGAAGCAGAUCU<br>ACAAGACCCCUCCCAUCAAGGACUUCGGCGGCUUCAACUU<br>CAGCCAGAUCCUGCCCGACCCCAGCAAGCCCAGCAAGCGG<br>AGCUUCAUCGAGGACCUGCUGUUCAACAAGGUGACCCUA<br>GCCGACGCCGGCUUCAUCAAGCAGUACGGCGACUGCCUCG<br>GCGACAUAGCCGCCCGGGACCUGAUCUGCGCCCAGAAGU<br>UCAACGGCCUGACCGUGCUGCCUCCCCUGCUGACCGACGA<br>GAUGAUCGCCCAGUACACCAGCGCCCUGUUAGCCGGAACC<br>AUCACCAGCGGCUGGACUUUCGGCGCUGGAGCCGCUCUG<br>CAGAUCCCCUUCGCCAUGCAGAUGGCCUACCGGUUCAACG<br>GCAUCGGCGUGACCCAGAACGUGCUGUACGAGAACCAGA<br>AGCUGAUCGCCAACCAGUUCAACAGCGCCAUCGGCAAGA<br>UCCAGGACAGCCUGAGCAGCACCGCUAGCGCCCUGGGCAA<br>GCUGCAGGACGUGGUGAACCAGAACGCCCAGGCCCUGAA<br>CACCCUGGUGAAGCAGCUGAGCAGCAACUUCGGCGCCAU<br>CAGCAGCGUGCUGAACGACAUCCUGAGCCGGCUGGACCC<br>UCCCGAGGCCGAGGUGCAGAUCGACCGGCUGAUCACUGG<br>CCGGCUGCAGAGCCUGCAGACCUACGUGACCCAGCAGCUG<br>AUCCGGGCCGCCGAGAUUCGGGCCAGCGCCAACCUGGCCG<br>CCACCAAGAUGAGCGAGUGCGUGCUGGGCCAGAGCAAGC<br>GGGUGGACUUCUGCGGCAAGGGCUACCACCUGAUGAGCU<br>UUCCCCAGAGCGCACCCCACGGAGUGGUGUUCCUGCACGU<br>GACCUACGUGCCCGCCCACGAGAAGAACUUCACCACCGCC<br>CCAGCCAUCUGCCACGACGGCAAGGCCCACUUUCCCCGGG<br>AGGGCGUGUUCGUGAGCAACGGCACCCACUGGUUCGUGA<br>CCCAGCGGAACUUCUACGAGCCCCAGAUCAUCACCACCGA<br>CAACACCUUCGUGAGCGGCAACUGCGACGUGGUGAUCGG<br>CAUCGUGAACAACACCGUGUACGAUCCCCUGCAGCCCGAG<br>CUGGACAGCUUCAAGGAGGAGCUGGACAAGUACUUCAAG<br>AAUCACACCAGCCCCGACGUGGACCUGGGCGACAUCAGCG<br>GCAUCAACGCCAGCGUGGUGAACAUCCAGAAGGAGAUCG<br>AUCGGCUGAACGAGGUGGCCAAGAACCUGAACGAGAGCC<br>UGAUCGACCUGCAGGAGCUGGGCAAGUACGAGCAGUACA<br>UCAAGUGGCCCUGGUACAUCUGGCUGGGCUUCAUCGCCG<br>GCCUGAUCGCCAUCGUGAUGGUGACCAUCAUGCUGUGCU<br>GCAUGACCAGCUGCUGCAGCUGCCUGAAGGGCUGUUGCA<br>GCUGCGGCAGCUGCUGCAAGUUCGACGAGGACGACAGCG<br>AGCCCGUGCUGAAGGGCGUGAAGCUGCACUACACC | |
| 3' UTR | UGAUAAUAGGCUGGAGCCUCGGUGGCCUAGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 4 |
| Corresponding amino acid sequence | MFVFLVLLPLVSSQCVNLTTRTQLPPAYTNSFTRGVYYPDKVF<br>RSSVLHSTQDLFLPFFSNVTWFHAIHVSGTNGTKRFDNPVLPF<br>NDGVYFASIEKSNIIRGWIFGTTLDSKTQSLLIVNNATNVVIKV<br>CEFQFCNDPFLDVYYHKNNKSWMKSEFRVYSSANNCTFEYV<br>SQPFLMDLEGKQGNFKNLREFVFKNIDGYFKIYSKHTPINLVR<br>DLPQGFSALEPLVDLPIGINITRFQTLLALHRSYLTPGDSSSGW<br>TAGAAAYYVGYLQPRTFLLKYNENGTITDAVDCALDPLSETK<br>CTLKSFTVEKGIYQTSNFRVQPTESIVRFPNITNLCPFGEVENAT<br>RFASVYAWNRKRISNCVADYSVLYNSASFSTFKCYGVSPTKL<br>NDLCFTNVYADSFVIRGDEVRQIAPGQTGKIADYNYKLPDDFT<br>GCVIAWNSNNLDSKVGGNYNYRYRLFRKSNLKPFERDISTEIY<br>QAGSTPCNGVQGFNCYFPLQSYGFQPTNGVGYQPYRVVVLSF<br>ELLHAPATVCGPKKSTNLVKNKCVNFNFNGLTGTGVLTESNK<br>KFLPFQQFGRDIADTTDAVRDPQTLEILDITPCSFGGVSVITPGT<br>NTSNQVAVLYQGVNCTEVPVAIHADQLTPTWRVYSTGSNVF<br>QTRAGCLIGAEHVNNSYECDIPIGAGICASYQTQTNSRRRARS<br>VASQSIIAYTMSLGAENSVAYSNNSIAIPTNFTISVTTEILPVSM | 23 |

TABLE 1-continued

| Sequence Listing | | |
|---|---|---|
| | TKTSVDCTMYICGDSTECSNLLLQYGSFCTQLNRALTGIAVEQ<br>DKNTQEVFAQVKQIYKTPPIKDFGGFNFSQILPDPSKPSKRSFIE<br>DLLFNKVTLADAGFIKQYGDCLGDIAARDLICAQKFNGLTVLP<br>PLLTDEMIAQYTSALLAGTITSGWTFGAGAALQIPFAMQMAY<br>RFNGIGVTQNVLYENQKLIANQFNSAIGKIQDSLSSTASALGK<br>LQDVVNQNAQALNTLVKQLSSNFGAISSVLNDILSRLDPPEAE<br>VQIDRLITGRLQSLQTYVTQQLIRAAEIRASANLAATKMSECV<br>LGQSKRVDFCGKGYHLMSFPQSAPHGVVFLHVTYVPAHEKN<br>FTTAPAICHDGKAHFPREGVFVSNGTHWFVTQRNFYEPQIITT<br>DNTFVSGNCDVVIGIVNNTVYDPLQPELDSFKEELDKYFKNHT<br>SPDVDLGDISGINASVVNIQKEIDRLNEVAKNLNESLIDLQELG<br>KYEQYIKWPWYIWLGFIAGLIAIVMVTIMLCCMTSCCSCLKG<br>CCSCGSCCKFDEDDSEPVLKGVKLHYT | |
| PolyA tail | 100 nt | |

S2P_IN_B.1.617.2_[T19R, G142D, E156G, F157-, R158-, L452R, T478K, D614G, P681R, D950N

| | | |
|---|---|---|
| SEQ ID NO: 24 consists of from 5' end to 3' end: 5' UTR SEQ ID NO: 2, mRNA ORF SEQ ID NO: 25, and 3' UTR SEQ ID NO: 4. | | 24 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUA<br>AGACCCCGGCGCCGCCACC | 2 |
| ORF of mRNA Construct (excluding the stop codon) | AUGUUCGUGUUCCUGGUGCUGCUGCCCCUGGUGAGCAGC<br>CAGUGCGUGAACCUGAGAACCCGGACCCAGCUGCCACCAG<br>CCUACACCAACAGCUUCACCCGGGGCGUCUACUACCCCGA<br>CAAGGUGUUCCGGAGCAGCGUCCUGCACAGCACCCAGGA<br>CCUGUUCCUGCCCUUCUUCAGCAACGUGACCUGGUUCCAC<br>GCCAUCCACGUGAGCGGCACCAACGGCACCAAGCGGUUCG<br>ACAACCCCGUGCUGCCCUUCAACGACGGCGUGUACUUCGC<br>CAGCACCGAGAAGAGCAACAUCAUCCGGGGCUGGAUCUU<br>CGGCACCACCCUGGACAGCAAGACCCAGAGCCUGCUGAUC<br>GUGAAUAACGCCACCAACGUGGUGAUCAAGGUGUGCGAG<br>UUCCAGUUCUGCAACGACCCCUUCCUGGACGUGUACUACC<br>ACAAGAACAACAAGAGCUGGAUGGAGAGCGGCGUGUACA<br>GCAGCGCCAACAACUGCACCUUCGAGUACGUGAGCCAGCC<br>CUUCCUGAUGGACCUGGAGGGCAAGCAGGGCAACUUCAA<br>GAACCUGCGGGAGUUCGUGUUCAAGAACAUCGACGGCUA<br>CUUCAAGAUCUACAGCAAGCACACCCCAAUCAACCUGGU<br>GCGGGAUCUGCCCCAGGGCUUCUCAGCCCUGGAGCCCCUG<br>GUGGACCUGCCCAUCGGCAUCAACAUCACCCGGUUCCAGA<br>CCCUGCUGGCCCUGCACCGGAGCUACCUGACCCCAGGCGA<br>CAGCAGCAGCGGGUGGACAGCAGGCGCGGCUGCUUACUA<br>CGUGGGCUACCUGCAGCCCCGGACCUUCCUGCUGAAGUAC<br>AACGAGAACGGCACCAUCACCGACGCCGUGGACUGCGCCC<br>UGGACCCUCUGAGCGAGACCAAGUGCACCCUGAAGAGCU<br>UCACCGUGGAGAAGGGCAUCUACCAGACCAGCAACUUCC<br>GGGUGCAGCCCACCGAGAGCAUCGUGCGGUUCCCCAACA<br>UCACCAACCUGUGCCCCUUCGGCGAGGUGUUCAACGCCAC<br>CCGGUUCGCCAGCGUGUACGCCUGGAACCGGAAGCGGAU<br>CAGCAACUGCGUGGCCGACUACAGCGUGCUGUACAACAG<br>CGCCAGCUUCAGCACCUUCAAGUGCUACGGCGUGAGCCCC<br>ACCAAGCUGAACGACCUGUGCUUCACCAACGUGUACGCC<br>GACAGCUUCGUGAUCCGUGGCGACGAGGUGCGGCAGAUC<br>GCACCCGGCCAGACAGGCAAGAUCGCCGACUACAACUACA<br>AGCUGCCCGACGACUUCACCGGCUGCGUGAUCGCCUGGA<br>ACAGCAACAACCUCGACAGCAAGGUGGGCGGCAACUACA<br>ACUACAGAUACCGGCUGUUCCGGAAGAGCAACCUGAAGC<br>CCUUCGAGCGGGACAUCAGCACCGAGAUCUACCAAGCCG<br>GCUCCAAGCCUUGCAACGGCGUGGAGGGCUUCAACUGCU<br>ACUUCCCUCUGCAGAGCUACGGCUUCCAGCCCACCAACGG<br>CGUGGGCUACCAGCCCUACCGGGUGGUGGUGCUGAGCUU<br>CGAGCUGCUGCACGCCCCAGCCACCGUGUGUGGCCCCAAG<br>AAGAGCACCAACCUGGUGAAGAACAAGUGCGUGAACUUC<br>AACUUCAACGGCCUUACCGGCACCGGCGUGCUGACCGAG<br>AGCAACAAGAAAUUCCUGCCCUUUCAGCAGUUCGGCCGG<br>GACAUCGCCGACACCACCGACGCUGUGCGGGAUCCCCAGA<br>CCCUGGAGAUCCUGGACAUCACCCCUUGCAGCUUCGGCGG<br>CGUGAGCGUGAUCACCCCAGGCACCAACACCAGCAACCAG<br>GUGGCCGUGCUGUACCAGGGCGUGAACUGCACCGAGGUG<br>CCCGUGGCCAUCCACGCCGACCAGCUGACACCCACCUGGC<br>GGGUCUACAGCACCGGCAGCAACGUGUUCCAGACCCGGG<br>CCGGUUGCCUGAUCGGCGCCGAGCACGUGAACAACAGCU<br>ACGAGUGCGACAUCCCCAUCGGCGCCGGCAUCUGUGCCAG<br>CUACCAGACCCAGACCAAUUCAAGACGGAGGGCAAGGAG<br>CGUGGCCAGCCAGAGCAUCAUCGCCUACACCAUGAGCCUG<br>GGCGCCGAGAACAGCGUGGCCUACAGCAACAACAGCAUC | 25 |

TABLE 1-continued

| Sequence Listing | | |
|---|---|---|
| | GCCAUCCCCACCAACUUCACCAUCAGCGUGACCACCGAGA<br>UUCUGCCCGUGAGCAUGACCAAGACCAGCGUGGACUGCA<br>CCAUGUACAUCUGCGGCGACAGCACCGAGUGCAGCAACC<br>UGCUGCUGCAGUACGGCAGCUUCUGCACCCAGCUGAACC<br>GGGCCCUGACCGGCAUCGCCGUGGAGCAGGACAAGAACA<br>CCCAGGAGGUGUUCGCCCAGGUGAAGCAGAUCUACAAGA<br>CCCCUCCCAUCAAGGACUUCGGCGGCUUCAACUUCAGCCA<br>GAUCCUGCCCGACCCCAGCAAGCCCAGCAAGCGGAGCUUC<br>AUCGAGGACCUGCUGUUCAACAAGGUGACCCUAGCCGAC<br>GCCGGCUUCAUCAAGCAGUACGGCGACUGCCUCGGCGAC<br>AUAGCCGCCCGGGACCUGAUCUGCGCCCAGAAGUUCAAC<br>GGCCUGACCGUGCUGCCUCCCCUGCUGACCGACGAGAUGA<br>UCGCCCAGUACACCAGCGCCCUGUUAGCCGGAACCAUCAC<br>CAGCGGCUGGACUUUCGGCGCUGGAGCCGCUCUGCAGAU<br>CCCCUUCGCCAUGCAGAUGGCCUACCGGUUCAACGGCAUC<br>GGCGUGACCCAGAACGUGCUGUACGAGAACCAGAAGCUG<br>AUCGCCAACCAGUUCAACAGCGCCAUCGGCAAGAUCCAG<br>GACAGCCUGAGCAGCACCGCUAGCGCCCUGGGCAAGCUGC<br>AGAACGUGGUGAACCAGAACGCCCAGGCCCUGAACACCC<br>UGGUGAAGCAGCUGAGCAGCAACUUCGGCGCCAUCAGCA<br>GCGUGCUGAACGACAUCCUGAGCCGGCUGGACCCUCCCGA<br>GGCCGAGGUGCAGAUCGACCGGCUGAUCACUGGCCGGCU<br>GCAGAGCCUGCAGACCUACGUGACCCAGCAGCUGAUCCG<br>GGCCGCCGAGAUUCGGGCCAGCGCCAACCUGGCCGCCACC<br>AAGAUGAGCGAGUGCGUGCUGGGCCAGAGCAAGCGGGUG<br>GACUUCUGCGGCAAGGGCUACCACCUGAUGAGCUUUCCC<br>CAGAGCGCACCCCACGGAGUGGUGUUCCUGCACGUGACC<br>UACGUGCCCGCCCAGGAGAAGAACUUCACCACCGCCCCAG<br>CCAUCUGCCACGACGGCAAGGCCCACUUUCCCCGGGAGGG<br>CGUGUUCGUGAGCAACGGCACCCACUGGUUCGUGACCCA<br>GCGGAACUUCUACGAGCCCCAGAUCAUCACCACCGACAAC<br>ACCUUCGUGAGCGGCAACUGCGACGUGGUGAUCGGCAUC<br>GUGAACAACACCGUGUACGAUCCCCUGCAGCCCGAGCUG<br>GACAGCUUCAAGGAGGAGCUGGACAAGUACUUCAAGAAU<br>CACACCAGCCCCGACGUGGACCUGGGCGACAUCAGCGGCA<br>UCAACGCCAGCGUGGUGAACAUCCAGAAGGAGAUCGAUC<br>GGCUGAACGAGGUGGCCAAGAACCUGAACGAGAGCCUGA<br>UCGACCUGCAGGAGCUGGGCAAGUACGAGCAGUACAUCA<br>AGUGGCCCUGGUACAUCUGGCUGGGCUUCAUCGCCGGCC<br>UGAUCGCCAUCGUGAUGGUGACCAUCAUGCUGUGCUGCA<br>UGACCAGCUGCUGCAGCUGCCUGAAGGGCUGUUGCAGCU<br>GCGGCAGCUGCUGCAAGUUCGACGAGGACGACAGCGAGC<br>CCGUGCUGAAGGGCGUGAAGCUGCACUACACC | |
| 3' UTR | UGAUAAUAGGCUGGAGCCUCGGUGGCCUAGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 4 |
| Corresponding amino acid sequence | MFVFLVLLPLVSSQCVNLRTRTQLPPAYTNSFTRGVYYPDKVF<br>RSSVLHSTQDLFLPFFSNVTWFHAIHVSGTNGTKRFDNPVLPF<br>NDGVYFASTEKSNIIRGWIFGTTLDSKTQSLLIVNNATNVVIKV<br>CEFQFCNDPFLDVYYHKNNKSWMESGVYSSANNCTFEYVSQ<br>PFLMDLEGKQGNFKNLREFVFKNIDGYFKIYSKHTPINLVRDL<br>PQGFSALEPLVDLPIGINITRFQTLLALHRSYLTPGDSSSGWTA<br>GAAAYYVGYLQPRTFLLKYNENGTITDAVDCALDPLSETKCT<br>LKSFTVEKGIYQTSNFRVQPTESIVRFPNITNLCPFGEVFNATRF<br>ASVYAWNRKRISNCVADYSVLYNSASFSTFKCYGVSPTKLND<br>LCFTNVYADSFVIRGDEVRQIAPGQTGKIADYNYKLPDDFTGC<br>VIAWNSNNLDSKVGGNYNYRYRLFRKSNLKPFERDISTEIYQA<br>GSKPCNGVEGFNCYFPLQSYGFQPTNGVGYQPYRVVVLSFEL<br>LHAPATVCGPKKSTNLVKNKCVNFNFNGLTGTGVLTESNKKF<br>LPFQQFGRDIADTTDAVRDPQTLEILDITPCSFGGVSVITPGTNT<br>SNQVAVLYQGVNCTEVPVAIHADQLTPTWRVYSTGSNVFQT<br>RAGCLIGAEHVNNSYECDIPIGAGICASYQTQTNSRRRARSVA<br>SQSIIAYTMSLGAENSVAYSNNSIAIPTNFTISVTTEILPVSMTK<br>TSVDCTMYICGDSTECSNLLLQYGSFCTQLNRALTGIAVEQDK<br>NTQEVFAQVKQIYKTPPIKDFGGFNFSQILPDPSKPSKRSFIEDL<br>LFNKVTLADAGFIKQYGDCLGDIAARDLICAQKFNGLTVLPPL<br>LTDEMIAQYTSALLAGTITSGWTFGAGAALQIPFAMQMAYRF<br>NGIGVTQNVLYENQKLIANQFNSAIGKIQDSLSSTASALGKLQ<br>NVVNQNAQALNTLVKQLSSNFGAISSVLNDILSRLDPPEAEVQ<br>IDRLITGRLQSLQTYVTQQLIRAAEIRASANLAATKMSECVLG<br>QSKRVDFCGKGYHLMSFPQSAPHGVVFLHVTYVPAQEKNFTT<br>APAICHDGKAHFPREGVFVSNGTHWFVTQRNFYEPQIITTDNT<br>FVSGNCDVVIGIVNNTVYDPLQPELDSFKEELDKYFKNHTSPD<br>VDLGDISGINASVVNIQKEIDRLNEVAKNLNESLIDLQELGKYE<br>QYIKWPWYIWLGFIAGLIAIVMVTIMLCCMTSCCSCLKGCCSC<br>GSCCKFDEDDSEPVLKGVKLHYT | 26 |

TABLE 1-continued

| Sequence Listing | | |
|---|---|---|
| PolyA tail | 100 nt | |
| WH2020_NatSP | MFVFLVLLPLVSSQCVNLTTRTQLPPAYTNSFTRGVYYPDKVF<br>RSSVLHSTQDLFLPFFSNVTWFHAIHVSGTNGTKRFDNPVLPF<br>NDGVYFASTEKSNIIRGWIFGTTLDSKTQSLLIVNNATNVVIKV<br>CEFQFCNDPFLGVYYHKNNKSWMESEFRVYSSANNCTFEYVS<br>QPFLMDLEGKQGNFKNLREFVFKNIDGYFKIYSKHTPINLVRD<br>LPQGFSALEPLVDLPIGINITRFQTLLALHRSYLTPGDSSSGWT<br>AGAAAYYVGYLQPRTFLLKYNENGTITDAVDCALDPLSETKC<br>TLKSFTVEKGIYQTSNFRVQPTESIVRFPNITNLCPFGEVENATR<br>FASVYAWNRKRISNCVADYSVLYNSASFSTFKCYGVSPTKLN<br>DLCFTNVYADSFVIRGDEVRQIAPGQTGKIADYNYKLPDDFTG<br>CVIAWNSNNLDSKVGGNYNYLYRLFRKSNLKPFERDISTEIYQ<br>AGSTPCNGVEGENCYFPLQSYGFQPTNGVGYQPYRVVVLSFE<br>LLHAPATVCGPKKSTNLVKNKCVNFNFNGLTGTGVLTESNKK<br>FLPFQQFGRDIADTTDAVRDPQTLEILDITPCSFGGVSVITPGTN<br>TSNQVAVLYQDVNCTEVPVAIHADQLTPTWRVYSTGSNVFQT<br>RAGCLIGAEHVNNSYECDIPIGAGICASYQTQTNSPRRARSVA<br>SQSIIAYTMSLGAENSVAYSNNSIAIPTNFTISVTTEILPVSMTK<br>TSVDCTMYICGDSTECSNLLLQYGSFCTQLNRALTGIAVEQDK<br>NTQEVFAQVKQIYKTPPIKDFGGFNFSQILPDPSKPSKRSFIEDL<br>LFNKVTLADAGFIKQYGDCLGDIAARDLICAQKFNGLTVLPPL<br>LTDEMIAQYTSALLAGTITSGWTFGAGAALQIPFAMQMAYRF<br>NGIGVTQNVLYENQKLIANQFNSAIGKIQDSLSSTASALGKLQ<br>DVVNQNAQALNTLVKQLSSNFGAISSVLNDILSRLDKVEAEV<br>QIDRLITGRLQSLQTYVTQQLIRAAEIRASANLAATKMSECVL<br>GQSKRVDFCGKGYHLMSFPQSAPHGVVFLHVTYVPAQEKNF<br>TTAPAICHDGKAHFPREGVFVSNGTHWFVTQRNFYEPQIITTD<br>NTFVSGNCDVVIGIVNNTVYDPLQPELDSFKEELDKYFKNHTS<br>PDVDLGDISGINASVVNIQKEIDRLNEVAKNLNESLIDLQELGK<br>YEQYIKWPWYIWLGFIAGLIAIVMVTIMLCCMTSCCSCLKGCC<br>SCGSCCKFDEDDSEPVLKGVKLHYT | 27 |
| S2P_IN_B.1.617.2_[T19R, T95I, G142D, E156G, F157-, R158-, L452R, T478K, D614G, P681R, D950N] | | |
| SEQ ID NO: 28 consists of from 5' end to 3' end: 5' UTR SEQ ID NO: 2, mRNA ORF SEQ ID NO: 29, and 3' UTR SEQ ID NO: 4. | | 28 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUAA<br>GACCCCGGCGCCGCCACC | 2 |
| ORF of mRNA Construct (excluding the stop codon) | AUGUUCGUGUUCCUGGUGCUGCUGCCCCUGGUGAGCAGC<br>CAGUGCGUGAACCUGAGAACCCGGACCCAGCUGCCACCAG<br>CCUACACCAACAGCUUCACCCGGGGCGUCUACUACCCCGA<br>CAAGGUGUUCCGGAGCAGCGUCCUGCACAGCACCCAGGAC<br>CUGUUCCUGCCCUUCUUCAGCAACGUGACCUGGUUCCACG<br>CCAUCCACGUGAGCGGCACCAACGGCACCAAGCGGUUCGA<br>CAACCCCGUGCUGCCCUUCAACGACGGCGUGUACUUCGCC<br>AGCAUCGAGAAGAGCAACAUCAUCCGGGGCUGGAUCUUC<br>GGCACCACCCUGGACAGCAAGACCCAGAGCCUGCUGAUCG<br>UGAAUAACGCCACCAACGUGGUGAUCAAGGUGUGCGAGU<br>UCCAGUUCUGCAACGACCCCUUCCUGGACGUGUACUACCA<br>CAAGAACAACAAGAGCUGGAUGGAGAGCGGCGUGUACAG<br>CAGCGCCAACAACUGCACCUUCGAGUACGUGAGCCAGCCC<br>UUCCUGAUGGACCUGGAGGGCAAGCAGGGCAACUUCAAG<br>AACCUGCGGGAGUUCGUGUUCAAGAACAUCGACGGCUAC<br>UUCAAGAUCUACAGCAAGCACACCCCAAUCAACCUGGUGC<br>GGGAUCUGCCCCAGGGCUUCUCAGCCCUGGAGCCCCUGGU<br>GGACCUGCCCAUCGGCAUCAACAUCACCCGGUUCCAGACC<br>CUGCUGGCCCUGCACCGGAGCUACCUGACCCCAGGCGACA<br>GCAGCAGCGGGUGGACAGCAGGCGCGGCUGCUUACUACG<br>UGGGCUACCUGCAGCCCCGGACCUUCCUGCUGAAGUACAA<br>CGAGAACGGCACCAUCACCGACGCCGUGGACUGCGCCCUG<br>GACCCUCUGAGCGAGACCAAGUGCACCCUGAAGAGCUUCA<br>CCGUGGAGAAGGGCAUCUACCAGACCAGCAACUUCCGGG<br>UGCAGCCCACCGAGAGCAUCGUGCGGUUCCCCAACAUCAC<br>CAACCUGUGCCCCUUCGGCGAGGUGUUCAACGCCACCCGG<br>UUCGCCAGCGUGUACGCCUGGAACCGGAAGCGGAUCAGC<br>AACUGCGUGGCCGACUACAGCGUGCUGUACAACAGCGCCA<br>GCUUCAGCACCUUCAAGUGCUACGGCGUGAGCCCCACCAA<br>GCUGAACGACCUGUGCUUCACCAACGUGUACGCCGACAGC<br>UUCGUGAUCCGUGGCGACGAGGUGCGGCAGAUCGCACCC<br>GGCCAGACAGGCAAGAUCGCCGACUACAACUACAAGCUGC<br>CCGACGACUUCACCGGCUGCGUGAUCGCCUGGAACAGCAA<br>CAACCUCGACAGCAAGGUGGGGGCAACUACAACUACAG<br>AUACCGGCUGUUCCGGAAGAGCAACCUGAAGCCCUUCGA<br>GCGGGACAUCAGCACCGAGAUCUACCAAGCCGGCUCCAAG<br>CCUUGCAACGGCGUGGAGGGCUUCAACUGCUACUUCCCUC | 29 |

TABLE 1-continued

| Sequence Listing | | |
|---|---|---|
| | UGCAGAGCUACGGCUUCCAGCCCACCAACGGCGUGGGCUA<br>CCAGCCCUACCGGGUGGUGGUGCUGAGCUUCGAGCUGCU<br>GCACGCCCCAGCCACCGUGUGUGGCCCCAAGAAGAGCACC<br>AACCUGGUGAAGAACAAGUGCGUGAACUUCAACUUCAAC<br>GGCCUUACCGGCACCGGCGUGCUGACCGAGAGCAACAAGA<br>AAUUCCUGCCCUUUCAGCAGUUCGGCCGGGACAUCGCCGA<br>CACCACCGACGCUGUGCGGGAUCCCCAGACCCUGGAGAUC<br>CUGGACAUCACCCCUUGCAGCUUCGGCGGCGUGAGCGUGA<br>UCACCCCAGGCACCAACACCAGCAACCAGGUGGCCGUGCU<br>GUACCAGGGCGUGAACUGCACCGAGGUGCCCGUGGCCAUC<br>CACGCCGACCAGCUGACACCCACCUGGCGGGUCUACAGCA<br>CCGGCAGCAACGUGUUCCAGACCCGGGCCGGUUGCCUGAU<br>CGGCGCCGAGCACGUGAACAACAGCUACGAGUGCGACAUC<br>CCCAUCGGCGCCGGCAUCUGUGCCAGCUACCAGACCCAGA<br>CCAAUUCAAGACGGAGGGCAAGGAGCGUGGCCAGCCAGA<br>GCAUCAUCGCCUACACCAUGAGCCUGGGCGCCGAGAACAG<br>CGUGGCCUACAGCAACAACAGCAUCGCCAUCCCCACCAAC<br>UUCACCAUCAGCGUGACCACCGAGAUUCUGCCCGUGAGCA<br>UGACCAAGACCAGCGUGGACUGCACCAUGUACAUCUGCG<br>GCGACAGCACCGAGUGCAGCAACCUGCUGCUGCAGUACGG<br>CAGCUUCUGCACCCAGCUGAACCGGGCCCUGACCGGCAUC<br>GCCGUGGAGCAGGACAAGAACACCCAGGAGGUGUUCGCC<br>CAGGUGAAGCAGAUCUACAAGACCCCUCCCAUCAAGGACU<br>UCGGCGGCUUCAACUUCAGCCAGAUCCUGCCCGACCCCAG<br>CAAGCCCAGCAAGCGGAGCUUCAUCGAGGACCUGCUGUUC<br>AACAAGGUGACCCUAGCCGACGCCGGCUUCAUCAAGCAGU<br>ACGGCGACUGCCUCGGCGACAUAGCCGCCCGGGACCUGAU<br>CUGCGCCCAGAAGUUCAACGGCCUGACCGUGCUGCCUCCC<br>CUGCUGACCGACGAGAUGAUCGCCCAGUACACCAGCGCCC<br>UGUUAGCCGGAACCAUCACCAGCGGCUGGACUUUCGGCGC<br>UGGAGCCGCUCUGCAGAUCCCCUUCGCCAUGCAGAUGGCC<br>UACCGGUUCAACGGCAUCGGCGUGACCCAGAACGUGCUG<br>UACGAGAACCAGAAGCUGAUCGCCAACCAGUUCAACAGC<br>GCCAUCGGCAAGAUCCAGGACAGCCUGAGCAGCACCGCUA<br>GCGCCCUGGGCAAGCUGCAGAACGUGGUGAACCAGAACG<br>CCCAGGCCCUGAACACCCUGGUGAAGCAGCUGAGCAGCAA<br>CUUCGGCGCCAUCAGCAGCGUGCUGAACGACAUCCUGAGC<br>CGGCUGGACCCUCCCGAGGCCGAGGUGCAGAUCGACCGGC<br>UGAUCACUGGCCGGCUGCAGAGCCUGCAGACCUACGUGAC<br>CCAGCAGCUGAUCCGGGCCGCCGAGAUUCGGGCCAGCGCC<br>AACCUGGCCGCCACCAAGAUGAGCGAGUGCGUGCUGGGCC<br>AGAGCAAGCGGGUGGACUUCUGCGGCAAGGGCUACCACC<br>UGAUGAGCUUUCCCCAGAGCGCACCCCACGGAGUGGUGU<br>UCCUGCACGUGACCUACGUGCCCGCCCAGGAGAAGAACUU<br>CACCACCGCCCCAGCCAUCUGCCACGACGGCAAGGCCCAC<br>UUUCCCCGGGAGGGCGUGUUCGUGAGCAACGGCACCCACU<br>GGUUCGUGACCCAGCGGAACUUCUACGAGCCCCAGAUCAU<br>CACCACCGACAACACCUUCGUGAGCGGCAACUGCGACGUG<br>GUGAUCGGCAUCGUGAACAACACCGUGUACGAUCCCCUGC<br>AGCCCGAGCUGGACAGCUUCAAGGAGGAGCUGGACAAGU<br>ACUUCAAGAAUCACACCAGCCCCGACGUGGACCUGGGCGA<br>CAUCAGCGGCAUCAACGCCAGCGUGGUGAACAUCCAGAA<br>GGAGAUCGAUCGGCUGAACGAGGUGGCCAAGAACCUGAA<br>CGAGAGCCUGAUCGACCUGCAGGAGCUGGGCAAGUACGA<br>GCAGUACAUCAAGUGGCCCUGGUACAUCUGGCUGGGCUU<br>CAUCGCCGGCCUGAUCGCCAUCGUGAUGGUGACCAUCAUG<br>CUGUGCUGCAUGACCAGCUGCUGCAGCUGCCUGAAGGGC<br>UGUUGCAGCUGCGGCAGCUGCUGCAAGUUCGACGAGGAC<br>GACAGCGAGCCCGUGCUGAAGGGCGUGAAGCUGCACUAC<br>ACC | |
| 3' UTR | UGAUAAUAGGCUGGAGCCUCGGUGGCCUAGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 4 |
| Corresponding amino acid sequence | MFVFLVLLPLVSSQCVNLRTRTQLPPAYTNSFTRGVYYPDKVF<br>RSSVLHSTQDLFLPFFSNVTWFHAIHVSGTNGTKRFDNPVLPF<br>NDGVYFASIEKSNIIRGWIFGTTLDSKTQSLLIVNNATNVVIKV<br>CEFQFCNDPFLDVYYHKNNKSWMESGVYSSANNCTFEYVSQ<br>PFLMDLEGKQGNFKNLREFVFKNIDGYFKIYSKHTPINLVRDL<br>PQGFSALEPLVDLPIGINITRFQTLLALHRSYLTPGDSSSGWTA<br>GAAAYYVGYLQPRTFLLKYNENGTITDAVDCALDPLSETKCT<br>LKSFTVEKGIYQTSNFRVQPTESIVRFPNITNLCPFGEVENATRF<br>ASVYAWNRKRISNCVADYSVLYNSASFSTFKCYGVSPTKLND<br>LCFTNVYADSFVIRGDEVRQIAPGQTGKIADYNYKLPDDFTGC<br>VIAWNSNNLDSKVGGNYNYRYRLFRKSNLKPFERDISTEIYQA<br>GSKPCNGVEGENCYFPLQSYGFQPTNGVGYQPYRVVVLSFEL<br>LHAPATVCGPKKSTNLVKNKCVNFNFNGLTGTGVLTESNKKF<br>LPFQQFGRDIADTTDAVRDPQTLEILDITPCSFGGVSVITPGTNT | 30 |

TABLE 1-continued

| Sequence Listing | | |
|---|---|---|
| | SNQVAVLYQGVNCTEVPVAIHADQLTPTWRVYSTGSNVFQTR<br>AGCLIGAEHVNNSYECDIPIGAGICASYQTQTNSRRRARSVAS<br>QSIIAYTMSLGAENSVAYSNNSIAIPTNFTISVTTEILPVSMTKTS<br>VDCTMYICGDSTECSNLLLQYGSFCTQLNRALTGIAVEQDKNT<br>QEVFAQVKQIYKTPPIKDFGGFNFSQILPDPSKPSKRSFIEDLLF<br>NKVTLADAGFIKQYGDCLGDIAARDLICAQKFNGLTVLPPLLT<br>DEMIAQYTSALLAGTITSGWTFGAGAALQIPFAMQMAYRENG<br>IGVTQNVLYENQKLIANQFNSAIGKIQDSLSSTASALGKLQNV<br>VNQNAQALNTLVKQLSSNFGAISSVLNDILSRLDPPEAEVQIDR<br>LITGRLQSLQTYVTQQLIRAAEIRASANLAATKMSECVLGQSK<br>RVDFCGKGYHLMSFPQSAPHGVVFLHVTYVPAQEKNFTTAPA<br>ICHDGKAHFPREGVFVSNGTHWFVTQRNFYEPQIITTDNTFVS<br>GNCDVVIGIVNNTVYDPLQPELDSFKEELDKYFKNHTSPDVDL<br>GDISGINASVVNIQKEIDRLNEVAKNLNESLIDLQELGKYEQYI<br>KWPWYIWLGFIAGLIAIVMVTIMLCCMTSCCSCLKGCCSCGSC<br>CKFDEDDSEPVLKGVKLHYT | |
| PolyA tail | 100 nt | |
| | Botswana-variant-1273 | |
| SEQ ID NO: 31 consists of from 5' end to 3' end: 5' UTR SEQ ID NO: 2, mRNA ORF SEQ ID NO: 32, and 3' UTR SEQ ID NO: 4. | | 31 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAA<br>GACCCCGGCGCCGCCACC | 2 |
| ORF of mRNA Construct (excluding the stop codon) | AUGUUCGUGUUCCUGGUGCUGCUGCCCCUGGUGAGCAGC<br>CAGUGCGUGAACCUGACCACCCGGACCCAGCUGCCACCAG<br>CCUACACCAACAGCUUCACCCGGGGCGUCUACUACCCCGA<br>CAAGGUGUUCCGGAGCAGCGUCCUGCACAGCACCCAGGAC<br>CUGUUCCUGCCCUUCUUCAGCAACGUGACCUGGUUCCACG<br>UGAUCAGCGGCACCAACGGCACCAAGCGGUUCGACAACCC<br>CGUGCUGCCCUUCAACGACGGCGUGUACUUCGCCAGCAUC<br>GAGAAGAGCAACAUCAUCCGGGGCUGGAUCUUCGGCACC<br>ACCCUGGACAGCAAGACCCAGAGCCUGCUGAUCGUGAAU<br>AACGCCACCAACGUGGUGAUCAAGGUGUGCGAGUUCCAG<br>UUCUGCAACGACCCCUUCCUGGACCACAAGAACAACAAGA<br>GCUGGAUGGAGAGCGAGUUCCGGGUGUACAGCAGCGCCA<br>ACAACUGCACCUUCGAGUACGUGAGCCAGCCCUUCCUGAU<br>GGACCUGGAGGGCAAGCAGGGCAACUUCAAGAACCUGCG<br>GGAGUUCGUGUUCAAGAACAUCGACGGCUACUUCAAGAU<br>CUACAGCAAGCACACCCCAAUCAUCGUGCGGGAGCCCGAG<br>GAUCUGCCCCAGGGCUUCUCAGCCCUGGAGCCCCUGGUGG<br>ACCUGCCCAUCGGCAUCAACAUCACCCGGUUCCAGACCCU<br>GCUGGCCCUGCACCGGAGCUACCUGACCCCAGGCGACAGC<br>AGCAGCGGGUGGACAGCAGGCGCGGCUGCUUACUACGUG<br>GGCUACCUGCAGCCCCGGACCUUCCUGCUGAAGUACAACG<br>AGAACGGCACCAUCACCGACGCCGUGGACUGCGCCCUGGA<br>CCCUCUGAGCGAGACCAAGUGCACCCUGAAGAGCUUCACC<br>GUGGAGAAGGGCAUCUACCAGACCAGCAACUUCCGGGUG<br>CAGCCCACCGAGAGCAUCGUGCGGUUCCCCAACAUCACCA<br>ACCUGUGCCCCUUCGACGAGGUGUUCAACGCCACCCGGUU<br>CGCCAGCGUGUACGCCUGGAACCGGAAGCGGAUCAGCAAC<br>UGCGUGGCCGACUACAGCGUGCUGUACAACCUGGCCCCCU<br>UCUUCACCUUCAAGUGCUACGGCGUGAGCCCCACCAAGCU<br>GAACGACCUGUGCUUCACCAACGUGUACGCCGACAGCUUC<br>GUGAUCCGUGGCGACGAGGUGCGGCAGAUCGCACCCGGCC<br>AGACAGGCAACAUCGCCGACUACAACUACAAGCUGCCCGA<br>CGACUUCACCGGCUGCGUGAUCGCCUGGAACAGCAACAAG<br>CUCGACAGCAAGGUGAGCGGCAACUACAACUACCUGUACC<br>GGCUGUUCCGGAAGAGCAACCUGAAGCCCUUCGAGCGGG<br>ACAUCAGCACCGAGAUCUACCAAGCCGGCAACAAGCCUUG<br>CAACGGCGUGGCCGGCUUCAACUGCUACUUCCCUCUGCGG<br>AGCUACAGCUUCCGGCCCACCUACGGCGUGGGCCACCAGC<br>CCUACCGGGUGGUGGUGCUGAGCUUCGAGCUGCUGCACG<br>CCCCAGCCACCGUGUGUGGCCCCAAGAAGAGCACCAACCU<br>GGUGAAGAACAAGUGCGUGAACUUCAACUUCAACGGCCU<br>UAAGGGCACCGGCGUGCUGACCGAGAGCAACAAGAAAUU<br>CCUGCCCUUUCAGCAGUUCGGCCGGGACAUCGCCGACACC<br>ACCGACGCUGUGCGGGAUCCCCAGACCCUGGAGAUCCUGG<br>ACAUCACCCCUUGCAGCUUCGGCGGCGUGAGCGUGAUCAC<br>CCCAGGCACCAACACCAGCAACCAGGUGGCCGUGCUGUAC<br>CAGGGCGUGAACUGCACCGAGGUGCCCGUGGCCAUCCACG<br>CCGACCAGCUGACACCCACCUGGCGGGUCUACAGCACCGG<br>CAGCAACGUGUUCCAGACCCGGGCCGGUUGCCUGAUCGGC<br>GCCGAGUACGUGAACAACAGCUACGAGUGCGACAUCCCCA<br>UCGGCGCCGGCAUCUGUGCCAGCUACCAGACCCAGACCAA<br>GUCACACCGGAGGGCAAGGAGCGUGGCCAGCCAGAGCAU | 32 |

TABLE 1-continued

| Sequence Listing | | |
|---|---|---|
| | CAUCGCCUACACCAUGAGCCUGGGCGCCGAGAACAGCGUG<br>GCCUACAGCAACAACAGCAUCGCCAUCCCCACCAACUUCA<br>CCAUCAGCGUGACCACCGAGAUUCUGCCCGUGAGCAUGAC<br>CAAGACCAGCGUGGACUGCACCAUGUACAUCUGCGGCGAC<br>AGCACCGAGUGCAGCAACCUGCUGCUGCAGUACGGCAGCU<br>UCUGCACCCAGCUGAAGCGGGCCCUGACCGGCAUCGCCGU<br>GGAGCAGGACAAGAACACCCAGGAGGUGUUCGCCCAGGU<br>GAAGCAGAUCUACAAGACCCCUCCCAUCAAGUACUUCGGC<br>GGCUUCAACUUCAGCCAGAUCCUGCCCGACCCCAGCAAGC<br>CCAGCAAGCGGAGCUUCAUCGAGGACCUGCUGUUCAACA<br>AGGUGACCCUAGCCGACGCCGGCUUCAUCAAGCAGUACGG<br>CGACUGCCUCGGCGACAUAGCCGCCCGGGACCUGAUCUGC<br>GCCCAGAAGUUCAAGGGCCUGACCGUGCUGCCUCCCCUGC<br>UGACCGACGAGAUGAUCGCCCAGUACACCAGCGCCCUGUU<br>AGCCGGAACCAUCACCAGCGGCUGGACUUUCGGCGCUGGA<br>GCCGCUCUGCAGAUCCCCUUCGCCAUGCAGAUGGCCUACC<br>GGUUCAACGGCAUCGGCGUGACCCAGAACGUGCUGUACG<br>AGAACCAGAAGCUGAUCGCCAACCAGUUCAACAGCGCCAU<br>CGGCAAGAUCCAGGACAGCCUGAGCAGCACCGCUAGCGCC<br>CUGGGCAAGCUGCAGGACGUGGUGAACCACAACGCCCAG<br>GCCCUGAACACCCUGGUGAAGCAGCUGAGCAGCAAGUUC<br>GGCGCCAUCAGCAGCGUGCUGAACGACAUCUUCAGCCGGC<br>UGGACCCUCCCGAGGCCGAGGUGCAGAUCGACCGGCUGAU<br>CACUGGCCGGCUGCAGAGCCUGCAGACCUACGUGACCCAG<br>CAGCUGAUCCGGGCCGCCGAGAUUCGGGCCAGCGCCAACC<br>UGGCCGCCACCAAGAUGAGCGAGUGCGUGCUGGGCCAGA<br>GCAAGCGGGUGGACUUCUGCGGCAAGGGCUACCACCUGA<br>UGAGCUUUCCCCAGAGCGCACCCCACGGAGUGGUGUUCCU<br>GCACGUGACCUACGUGCCCGCCCAGGAGAAGAACUUCACC<br>ACCGCCCCAGCCAUCUGCCACGACGGCAAGGCCCACUUUC<br>CCCGGGAGGGCGUGUUCGUGAGCAACGGCACCCACUGGU<br>UCGUGACCCAGCGGAACUUCUACGAGCCCCAGAUCAUCAC<br>CACCGACAACACCUUCGUGAGCGGCAACUGCGACGUGGUG<br>AUCGGCAUCGUGAACAACACCGUGUACGAUCCCCUGCAGC<br>CCGAGCUGGACAGCUUCAAGGAGGAGCUGGACAAGUACU<br>UCAAGAAUCACACCAGCCCCGACGUGGACCUGGGCGACAU<br>CAGCGGCAUCAACGCCAGCGUGGUGAACAUCCAGAAGGA<br>GAUCGAUCGGCUGAACGAGGUGGCCAAGAACCUGAACGA<br>GAGCCUGAUCGACCUGCAGGAGCUGGGCAAGUACGAGCA<br>GUACAUCAAGUGGCCCUGGUACAUCUGGCUGGGCUUCAU<br>CGCCGGCCUGAUCGCCAUCGUGAUGGUGACCAUCAUGCUG<br>UGCUGCAUGACCAGCUGCUGCAGCUGCCUGAAGGGCUGU<br>UGCAGCUGCGGCAGCUGCUGCAAGUUCGACGAGGACGAC<br>AGCGAGCCCGUGCUGAAGGGCGUGAAGCUGCACUACACC | |
| 3' UTR | UGAUAAUAGGCUGGAGCCUCGGUGGCCUAGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 4 |
| Corresponding amino acid sequence | MFVFLVLLPLVSSQCVNLTTRTQLPPAYTNSFTRGVYYPDKVF<br>RSSVLHSTQDLFLPFFSNVTWFHVISGTNGTKRFDNPVLPEND<br>GVYFASIEKSNIIRGWIFGTTLDSKTQSLLIVNNATNVVIKVCEF<br>QFCNDPFLDHKNNKSWMESEFRVYSSANNCTFEYVSQPFLMD<br>LEGKQGNFKNLREFVFKNIDGYFKIYSKHTPIIVREPEDLPQGF<br>SALEPLVDLPIGINITRFQTLLALHRSYLTPGDSSSGWTAGAAA<br>YYVGYLQPRTFLLKYNENGTITDAVDCALDPLSETKCTLKSFT<br>VEKGIYQTSNFRVQPTESIVRFPNITNLCPFDEVFNATRFASVY<br>AWNRKRISNCVADYSVLYNLAPFFTFKCYGVSPTKLNDLCFT<br>NVYADSFVIRGDEVRQIAPGQTGNIADYNYKLPDDFTGCVIA<br>WNSNKLDSKVSGNYNYLYRLFRKSNLKPFERDISTEIYQAGN<br>KPCNGVAGENCYFPLRSYSFRPTYGVGHQPYRVVVLSFELLH<br>APATVCGPKKSTNLVKNKCVNFNFNGLKGTGVLTESNKKFLP<br>FQQFGRDIADTTDAVRDPQTLEILDITPCSFGGVSVITPGTNTSN<br>QVAVLYQGVNCTEVPVAIHADQLTPTWRVYSTGSNVFQTRA<br>GCLIGAEYVNNSYECDIPIGAGICASYQTQTKSHRRARSVASQS<br>IIAYTMSLGAENSVAYSNNSIAIPTNFTISVTTEILPVSMTKTSV<br>DCTMYICGDSTECSNLLLQYGSFCTQLKRALTGIAVEQDKNTQ<br>EVFAQVKQIYKTPPIKYFGGFNFSQILPDPSKPSKRSFIEDLLEN<br>KVTLADAGFIKQYGDCLGDIAARDLICAQKFKGLTVLPPLLTD<br>EMIAQYTSALLAGTITSGWTFGAGAALQIPFAMQMAYRENGI<br>GVTQNVLYENQKLIANQFNSAIGKIQDSLSSTASALGKLQDVV<br>NHNAQALNTLVKQLSSKFGAISSVLNDIFSRLDPPEAEVQIDRL<br>ITGRLQSLQTYVTQQLIRAAEIRASANLAATKMSECVLGQSKR<br>VDFCGKGYHLMSFPQSAPHGVVFLHVTYVPAQEKNFTTAPAI<br>CHDGKAHFPREGVFVSNGTHWFVTQRNFYEPQIITTDNTFVSG<br>NCDVVIGIVNNTVYDPLQPELDSFKEELDKYFKNHTSPDVDLG<br>DISGINASVVNIQKEIDRLNEVAKNLNESLIDLQELGKYEQYIK | 33 |

TABLE 1-continued

| Sequence Listing | | |
|---|---|---|
| | WPWYIWLGFIAGLIAIVMVTIMLCCMTSCCSCLKGCCSCGSCC KFDEDDSEPVLKGVKLHYT | |
| PolyA tail | 100 nt | |
| | mRNA-1273.B.1.1.529_PBSko | |
| SEQ ID NO: 34 consists of from 5' end to 3' end: 5' UTR SEQ ID NO: 2, mRNA ORF SEQ ID NO: 35, and 3' UTR SEQ ID NO: 4. | | 34 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUAA GACCCCGGCGCCGCCACC | 2 |
| ORF of mRNA Construct (excluding the stop codon) | AUGUUCGUGUUCCUGGUGCUGCUGCCCCUGGUGAGCAGC CAGUGCGUGAACCUGACCACCCGGACCCAGCUGCCACCAG CCUACACCAACAGCUUCACCCGGGGCGUCUACUACCCCGA CAAGGUGUUCCGGAGCAGCGUCCUGCACAGCACCCAGGAC CUGUUCCUGCCCUUCUUCAGCAACGUGACCUGGUUCCACG UGAUCAGCGGCACCAACGGCACCAAGCGGUUCGACAACCC CGUGCUGCCCUUCAACGACGGCGUGUACUUCGCCAGCAUC GAGAAGAGCAACAUCAUCCGGGGCUGGAUCUUCGGCACC ACCCUGGACAGCAAGACCCAGAGCCUGCUGAUCGUGAAU AACGCCACCAACGUGGUGAUCAAGGUGUGCGAGUUCCAG UUCUGCAACGACCCCUUCCUGGACCACAAGAACAACAAGA GCUGGAUGGAGAGCGAGUUCCGGGUGUACAGCAGCGCCA ACAACUGCACCUUCGAGUACGUGAGCCAGCCCUUCCUGAU GGACCUGGAGGGCAAGCAGGGCAACUUCAAGAACCUGCG GGAGUUCGUGUUCAAGAACAUCGACGGCUACUUCAAGAU CUACAGCAAGCACACCCCAAUCAUCGUGCGGGAGCCCGAG GAUCUGCCCCAGGGCUUCUCAGCCCUGGAGCCCCUGGUGG ACCUGCCCAUCGGCAUCAACAUCACCCGGUUCCAGACCCU GCUGGCCCUGCACCGGAGCUACCUGACCCCAGGCGACAGC AGCAGCGGGUGGACAGCAGGCGCGGCUGCUUACUACGUG GGCUACCUGCAGCCCCGGACCUUCCUGCUGAAGUACAACG AGAACGGCACCAUCACCGACGCCGUGGACUGCGCCCUGGA CCCUCUGAGCGAGACCAAGUGCACCCUGAAGAGCUUCACC GUGGAGAAGGGCAUCUACCAGACCAGCAACUUCCGGGUG CAGCCCACCGAGAGCAUCGUGCGGUUCCCCAACAUCACCA ACCUGUGCCCCUUCGACGAGGUGUUCAACGCCACCCGGUU CGCCAGCGUGUACGCCUGGAACCGGAAGCGGAUCAGCAAC UGCGUGGCCGACUACAGCGUGCUGUACAACCUGGCCCCCU UCUUCACCUUCAAGUGCUACGGCGUGAGCCCCACCAAGCU GAACGACCUGUGCUUCACCAACGUGUACGCCGACAGCUUC GUGAUCCGUGGCGACGAGGUGCGGCAGAUCGCACCCGGCC AGACAGGCAACAUCGCCGACUACAACUACAAGCUGCCCGA CGACUUCACCGGCUGCGUGAUCGCCUGGAACAGCAACAAG CUCGACAGCAAGGUGAGCGGCAACUACAACUACCUGUACC GGCUGUUCCGGAAGAGCAACCUGAAGCCCUUCGAGCGGG ACAUCAGCACCGAGAUCUACCAAGCCGGCAACAAGCCUUG CAACGGCGUGGCCGGCUUCAACUGCUACUUCCCUCUGCGG AGCUACAGCUUCCGGCCCACCUACGGCGUGGGCCACCAGC CCUACCGGGUGGUGGUGCUGAGCUUCGAGCUGCUGCACG CCCCAGCCACCGUGUGUGGCCCCAAGAAGAGCACCAACCU GGUGAAGAACAAGUGCGUGAACUUCAACUUCAACGGCCU UAAGGGCACCGGCGUGCUGACCGAGAGCAACAAGAAAUU CCUGCCCUUUCAGCAGUUCGGCCGGGACAUCGCCGACACC ACCGACGCUGUGCGGGAUCCCCAGACCCUGGAGAUCCUGG ACAUCACCCCUUGCAGCUUCGGCGGCGUGAGCGUGAUCAC CCCAGGCACCAACACCAGCAACCAGGUGGCCGUGCUGUAC CAGGGCGUGAACUGCACCGAGGUGCCCGUGGCCAUCCACG CCGACCAGCUGACACCCACCUGGCGGGUCUACAGCACCGG CAGCAACGUGUUCCAGACCCGGGCCGGUUGCCUGAUCGGC GCCGAGUACGUGAACAACAGCUACGAGUGCGACAUCCCCA UCGGCGCCGGCAUCUGUGCCAGCUACCAGACCCAGACCAA UUCACCCGGCGGCGCAGGCAGCGUGGCCAGCCAGAGCAUC AUCGCCUACACCAUGAGCCUGGGCGCCGAGAACAGCGUGG CCUACAGCAACAACAGCAUCGCCAUCCCCACCAACUUCAC CAUCAGCGUGACCACCGAGAUUCUGCCCGUGAGCAUGACC AAGACCAGCGUGGACUGCACCAUGUACAUCUGCGGCGAC AGCACCGAGUGCAGCAACCUGCUGCUGCAGUACGGCAGCU UCUGCACCCAGCUGAAGCGGGCCCUGACCGGCAUCGCCGU GGAGCAGGACAAGAACACCCAGGAGGUGUUCGCCCAGGU GAAGCAGAUCUACAAGACCCCUCCCAUCAAGUACUUCGGC GGCUUCAACUUCAGCCAGAUCCUGCCCGACCCCAGCAAGC CCAGCAAGCGGAGCUUCAUCGAGGACCUGCUGUUCAACA AGGUGACCCUAGCCGACGCCGGCUUCAUCAAGCAGUACGG CGACUGCCUCGGCGACAUAGCCGCCCGGGACCUGAUCUGC GCCCAGAAGUUCAAGGGCCUGACCGUGCUGCCUCCCCUGC UGACCGACGAGAUGAUCGCCCAGUACACCAGCGCCCUGUU | 35 |

TABLE 1-continued

| Sequence Listing | | |
|---|---|---|
| | AGCCGGAACCAUCACCAGCGGCUGGACUUUCGGCGCUGGA<br>GCCGCUCUGCAGAUCCCCUUCGCCAUGCAGAUGGCCUACC<br>GGUUCAACGGCAUCGGCGUGACCCAGAACGUGCUGUACG<br>AGAACCAGAAGCUGAUCGCCAACCAGUUCAACAGCGCCAU<br>CGGCAAGAUCCAGGACAGCCUGAGCAGCACCGCUAGCGCC<br>CUGGGCAAGCUGCAGGACGUGGUGAACCACAACGCCCAG<br>GCCCUGAACACCCUGGUGAAGCAGCUGAGCAGCAAGUUC<br>GGCGCCAUCAGCAGCGUGCUGAACGACAUCUUCAGCCGGC<br>UGGACCCUCCCGAGGCCGAGGUGCAGAUCGACCGGCUGAU<br>CACUGGCCGGCUGCAGAGCCUGCAGACCUACGUGACCCAG<br>CAGCUGAUCCGGGCCGCCGAGAUUCGGGCCAGCGCCAACC<br>UGGCCGCCACCAAGAUGAGCGAGUGCGUGCUGGGCCAGA<br>GCAAGCGGGUGGACUUCUGCGGCAAGGGCUACCACCUGA<br>UGAGCUUUCCCCAGAGCGCACCCCACGGAGUGGUGUUCCU<br>GCACGUGACCUACGUGCCCGCCCAGGAGAAGAACUUCACC<br>ACCGCCCCAGCCAUCUGCCACGACGGCAAGGCCCACUUUC<br>CCCGGGAGGGCGUGUUCGUGAGCAACGGCACCCACUGGU<br>UCGUGACCCAGCGGAACUUCUACGAGCCCCAGAUCAUCAC<br>CACCGACAACACCUUCGUGAGCGGCAACUGCGACGUGGUG<br>AUCGGCAUCGUGAACAACACCGUGUACGAUCCCCUGCAGC<br>CCGAGCUGGACAGCUUCAAGGAGGAGCUGGACAAGUACU<br>UCAAGAAUCACACCAGCCCCGACGUGGACCUGGGCGACAU<br>CAGCGGCAUCAACGCCAGCGUGGUGAACAUCCAGAAGGA<br>GAUCGAUCGGCUGAACGAGGUGGCCAAGAACCUGAACGA<br>GAGCCUGAUCGACCUGCAGGAGCUGGGCAAGUACGAGCA<br>GUACAUCAAGUGGCCCUGGUACAUCUGGCUGGGCUUCAU<br>CGCCGGCCUGAUCGCCAUCGUGAUGGUGACCAUCAUGCUG<br>UGCUGCAUGACCAGCUGCUGCAGCUGCCUGAAGGGCUGU<br>UGCAGCUGCGGCAGCUGCUGCAAGUUCGACGAGGACGAC<br>AGCGAGCCCGUGCUGAAGGGCGUGAAGCUGCACUACACC | |
| 3' UTR | UGAUAAUAGGCUGGAGCCUCGGUGGCCUAGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 4 |
| Corresponding amino acid sequence | MFVFLVLLPLVSSQCVNLTTRTQLPPAYTNSFTRGVYYPDKVF<br>RSSVLHSTQDLFLPFFSNVTWFHVISGTNGTKRFDNPVLPFND<br>GVYFASIEKSNIIRGWIFGTTLDSKTQSLLIVNNATNVVIKVCEF<br>QFCNDPFLDHKNNKSWMESEFRVYSSANNCTFEYVSQPFLMD<br>LEGKQGNFKNLREFVFKNIDGYFKIYSKHTPIIVREPEDLPQGF<br>SALEPLVDLPIGINITRFQTLLALHRSYLTPGDSSSGWTAGAAA<br>YYVGYLQPRTFLLKYNENGTITDAVDCALDPLSETKCTLKSFT<br>VEKGIYQTSNFRVQPTESIVRFPNITNLCPFDEVENATRFASVY<br>AWNRKRISNCVADYSVLYNLAPFFTFKCYGVSPTKLNDLCFT<br>NVYADSFVIRGDEVRQIAPGQTGNIADYNYKLPDDFTGCVIA<br>WNSNKLDSKVSGNYNYLYRLFRKSNLKPFERDISTEIYQAGN<br>KPCNGVAGFNCYFPLRSYSFRPTYGVGHQPYRVVVLSFELLH<br>APATVCGPKKSTNLVKNKCVNFNFNGLKGTGVLTESNKKFLP<br>FQQFGRDIADTTDAVRDPQTLEILDITPCSFGGVSVITPGTNTSN<br>QVAVLYQGVNCTEVPVAIHADQLTPTWRVYSTGSNVFQTRA<br>GCLIGAEYVNNSYECDIPIGAGICASYQTQTNSPGGAGSVASQS<br>IIAYTMSLGAENSVAYSNNSIAIPTNFTISVTTEILPVSMTKTSV<br>DCTMYICGDSTECSNLLLQYGSFCTQLKRALTGIAVEQDKNTQ<br>EVFAQVKQIYKTPPIKYFGGFNFSQILPDPSKPSKRSFIEDLLEN<br>KVTLADAGFIKQYGDCLGDIAARDLICAQKFKGLTVLPPLLTD<br>EMIAQYTSALLAGTITSGWTFGAGAALQIPFAMQMAYRENGI<br>GVTQNVLYENQKLIANQFNSAIGKIQDSLSSTASALGKLQDVV<br>NHNAQALNTLVKQLSSKFGAISSVLNDIFSRLDPPEAEVQIDRL<br>ITGRLQSLQTYVTQQLIRAAEIRASANLAATKMSECVLGQSKR<br>VDFCGKGYHLMSFPQSAPHGVVFLHVTYVPAQEKNFTTAPAI<br>CHDGKAHFPREGVFVSNGTHWFVTQRNFYEPQIITTDNTFVSG<br>NCDVVIGIVNNTVYDPLQPELDSFKEELDKYFKNHTSPDVDLG<br>DISGINASVVNIQKEIDRLNEVAKNLNESLIDLQELGKYEQYIK<br>WPWYIWLGFIAGLIAIVMVTIMLCCMTSCCSCLKGCCSCGSCC<br>KFDEDDSEPVLKGVKLHYT | 36 |
| PolyA tail | 100 nt | |

| mRNA-1273.B.1.1.529_PBSko_match | | |
|---|---|---|
| SEQ ID NO: 37 consists of from 5' end to 3' end: 5' UTR SEQ ID NO: 2, mRNA ORF SEQ ID NO: 38, and 3' UTR SEQ ID NO: 4. | | 37 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAA<br>GACCCCGGCGCCGCCACC | 2 |
| ORF of mRNA Construct (excluding the stop codon) | AUGUUCGUGUUCCUGGUGCUGCUGCCCCUGGUGAGCAGC<br>CAGUGCGUGAACCUGACCACCCGGACCCAGCUGCCACCAG<br>CCUACACCAACAGCUUCACCCGGGGCGUGUACUACCCCGA<br>CAAGGUGUUCCGGAGCAGCGUGCUGCACAGCACCCAGGAC | 38 |

TABLE 1-continued

| Sequence Listing |
| --- |
| CUGUUCCUGCCCUUCUUCAGCAACGUGACCUGGUUCCACG<br>UGAUCAGCGGCACCAACGGCACCAAGCGGUUCGACAACCC<br>CGUGCUGCCCUUCAACGACGGCGUGUACUUCGCCAGCAUC<br>GAGAAGAGCAACAUCAUCCGGGGCUGGAUCUUCGGCACC<br>ACCCUGGACAGCAAGACCCAGAGCCUGCUGAUCGUGAACA<br>ACGCCACCAACGUGGUGAUCAAGGUGUGCGAGUUCCAGU<br>UCUGCAACGACCCCUUCCUGGACCACAAGAACAACAAGAG<br>CUGGAUGGAGAGCGAGUUCCGGGUGUACAGCAGCGCCAA<br>CAACUGCACCUUCGAGUACGUGAGCCAGCCCUUCCUGAUG<br>GACCUGGAGGGCAAGCAGGGCAACUUCAAGAACCUGCGG<br>GAGUUCGUGUUCAAGAACAUCGACGGCUACUUCAAGAUC<br>UACAGCAAGCACACCCCAAUCAUCGUGCGGGAGCCCGAGG<br>ACCUGCCCCAGGGCUUCAGCGCCCUGGAGCCCCUGGUGGA<br>CCUGCCCAUCGGCAUCAACAUCACCCGGUUCCAGACCCUG<br>CUGGCCCUGCACCGGAGCUACCUGACCCCAGGCGACAGCA<br>GCAGCGGCUGGACCGCCGGCGCCGCCGCCUACUACGUGGG<br>CUACCUGCAGCCCCGGACCUUCCUGCUGAAGUACAACGAG<br>AACGGCACCAUCACCGACGCCGUGGACUGCGCCCUGGACC<br>CUCUGAGCGAGACCAAGUGCACCCUGAAGAGCUUCACCGU<br>GGAGAAGGGCAUCUACCAGACCAGCAACUUCCGGGUGCA<br>GCCCACCGAGAGCAUCGUGCGGUUCCCCAACAUCACCAAC<br>CUGUGCCCCUUCGACGAGGUGUUCAACGCCACCCGGUUCG<br>CCAGCGUGUACGCCUGGAACCGGAAGCGGAUCAGCAACU<br>GCGUGGCCGACUACAGCGUGCUGUACAACCUGGCCCCUUU<br>CUUCACCUUCAAGUGCUACGGCGUGAGCCCCACCAAGCUG<br>AACGACCUGUGCUUCACCAACGUGUACGCCGACAGCUUCG<br>UGAUCCGGGGCGACGAGGUGCGGCAGAUCGCCCCAGGCCA<br>GACCGGCAACAUCGCCGACUACAACUACAAGCUGCCCGAC<br>GACUUCACCGGCUGCGUGAUCGCCUGGAACAGCAACAAGC<br>UGGACAGCAAGGUGAGCGGCAACUACAACUACCUGUACC<br>GGCUGUUCCGGAAGAGCAACCUGAAGCCCUUCGAGCGGG<br>ACAUCAGCACCGAGAUCUACCAGGCCGGCAACAAGCCCUG<br>CAACGGCGUGGCCGGCUUCAACUGCUACUUCCCUCUGCGG<br>AGCUACAGCUUCCGGCCCACCUACGGCGUGGGCCACCAGC<br>CCUACCGGGUGGUGGUGCUGAGCUUCGAGCUGCUGCACG<br>CCCCAGCCACCGUGUGCGGCCCCAAGAAGAGCACCAACCU<br>GGUGAAGAACAAGUGCGUGAACUUCAACUUCAACGGCCU<br>GAAGGGCACCGGCGUGCUGACCGAGAGCAACAAGAAGUU<br>CCUGCCCUUCCAGCAGUUCGGCCGGGACAUCGCCGACACC<br>ACCGACGCCGUGCGGGAUCCCCAGACCCUGGAGAUCCUGG<br>ACAUCACCCCUUGCAGCUUCGGCGGCGUGAGCGUGAUCAC<br>CCCAGGCACCAACACCAGCAACCAGGUGGCCGUGCUGUAC<br>CAGGGCGUGAACUGCACCGAGGUGCCCGUGGCCAUCCACG<br>CCGACCAGCUGACCCCAACCUGGCGGGUGUACAGCACCGG<br>CAGCAACGUGUUCCAGACCCGGGCCGGCUGCCUGAUCGGC<br>GCCGAGUACGUGAACAACAGCUACGAGUGCGACAUCCCCA<br>UCGGCGCCGGCAUCUGCGCCAGCUACCAGACCCAGACCAA<br>CAGCCCCGGCGGCGCCGGCAGCGUGGCCAGCCAGAGCAUC<br>AUCGCCUACACCAUGAGCCUGGGCGCCGAGAACAGCGUGG<br>CCUACAGCAACAACAGCAUCGCCAUCCCCACCAACUUCAC<br>CAUCAGCGUGACCACCGAGAUCCUGCCCGUGAGCAUGACC<br>AAGACCAGCGUGGACUGCACCAUGUACAUCUGCGGCGAC<br>AGCACCGAGUGCAGCAACCUGCUGCUGCAGUACGGCAGCU<br>UCUGCACCCAGCUGAAGCGGGCCCUGACCGGCAUCGCCGU<br>GGAGCAGGACAAGAACACCCAGGAGGUGUUCGCCCAGGU<br>GAAGCAGAUCUACAAGACCCCUCCCAUCAAGUACUUCGGC<br>GGCUUCAACUUCAGCCAGAUCCUGCCCGACCCCAGCAAGC<br>CCAGCAAGCGGAGCUUCAUCGAGGACCUGCUGUUCAACA<br>AGGUGACCCUGGCCGACGCCGGCUUCAUCAAGCAGUACGG<br>CGACUGCCUGGGCGACAUCGCCGCCCGGGACCUGAUCUGC<br>GCCCAGAAGUUCAAGGGCCUGACCGUGCUGCCUCCUCUGC<br>UGACCGACGAGAUGAUCGCCCAGUACACCAGCGCCCUGCU<br>GGCCGGCACCAUCACCAGCGGCUGGACCUUCGGCGCCGGC<br>GCCGCCCUGCAGAUCCCCUUCGCCAUGCAGAUGGCCUACC<br>GGUUCAACGGCAUCGGCGUGACCCAGAACGUGCUGUACG<br>AGAACCAGAAGCUGAUCGCCAACCAGUUCAACAGCGCCAU<br>CGGCAAGAUCCAGGACAGCCUGAGCAGCACCGCCAGCGCC<br>CUGGGCAAGCUGCAGGACGUGGUGAACCACAACGCCCAG<br>GCCCUGAACACCCUGGUGAAGCAGCUGAGCAGCAAGUUC<br>GGCGCCAUCAGCAGCGUGCUGAACGACAUCUUCAGCCGGC<br>UGGACCCUCCCGAGGCCGAGGUGCAGAUCGACCGGCUGAU<br>CACCGGCCGGCUGCAGAGCCUGCAGACCUACGUGACCCAG<br>CAGCUGAUCCGGGCCGCCGAGAUCCGGGCCAGCGCCAACC<br>UGGCCGCCACCAAGAUGAGCGAGUGCGUGCUGGGCCAGA<br>GCAAGCGGGUGGACUUCUGCGGCAAGGGCUACCACCUGA<br>UGAGCUUUCCCCAGAGCGCACCCCACGGCGUGGUGUUCCU<br>GCACGUGACCUACGUGCCCGCCCAGGAGAAGAACUUCACC<br>ACCGCCCCAGCCAUCUGCCACGACGGCAAGGCCCACUUUC |

TABLE 1-continued

| Sequence Listing | | |
|---|---|---|
| | CCCGGGAGGGCGUGUUCGUGAGCAACGGCACCCACUGGU<br>UCGUGACCCAGCGGAACUUCUACGAGCCCCAGAUCAUCAC<br>CACCGACAACACCUUCGUGAGCGGCAACUGCGACGUGGUG<br>AUCGGCAUCGUGAACAACACCGUGUACGAUCCCCUGCAGC<br>CCGAGCUGGACAGCUUCAAGGAGGAGCUGGACAAGUACU<br>UCAAGAACCACACCAGCCCCGACGUGGACCUGGGCGACAU<br>CAGCGGCAUCAACGCCAGCGUGGUGAACAUCCAGAAGGA<br>GAUCGACAGACUGAACGAGGUGGCCAAGAACCUGAACGA<br>GAGCCUGAUCGACCUGCAGGAGCUGGGCAAGUACGAGCA<br>GUACAUCAAGUGGCCCUGGUACAUCUGGCUGGGCUUCAU<br>CGCCGGCCUGAUCGCCAUCGUGAUGGUGACCAUCAUGCUG<br>UGCUGCAUGACCAGCUGCUGCAGCUGCCUGAAGGGCUGC<br>UGCAGCUGCGGCAGCUGCUGCAAGUUCGACGAGGACGAC<br>AGCGAGCCCGUGCUGAAGGGCGUGAAGCUGCACUACACC | |
| 3' UTR | UGAUAAUAGGCUGGAGCCUCGGUGGCCUAGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 4 |
| Corresponding amino acid sequence | MFVFLVLLPLVSSQCVNLTTRTQLPPAYTNSFTRGVYYPDKVF<br>RSSVLHSTQDLFLPFFSNVTWFHVISGTNGTKRFDNPVLPEND<br>GVYFASIEKSNIIRGWIFGTTLDSKTQSLLIVNNATNVVIKVCEF<br>QFCNDPFLDHKNNKSWMESEFRVYSSANNCTFEYVSQPFLMD<br>LEGKQGNFKNLREFVFKNIDGYFKIYSKHTPIIVREPEDLPQGF<br>SALEPLVDLPIGINITRFQTLLALHRSYLTPGDSSSGWTAGAAA<br>YYVGYLQPRTFLLKYNENGTITDAVDCALDPLSETKCTLKSFT<br>VEKGIYQTSNFRVQPTESIVRFPNITNLCPFDEVFNATRFASVY<br>AWNRKRISNCVADYSVLYNLAPFFTFKCYGVSPTKLNDLCFT<br>NVYADSFVIRGDEVRQIAPGQTGNIADYNYKLPDDFTGCVIA<br>WNSNKLDSKVSGNYNYLYRLFRKSNLKPFERDISTEIYQAGN<br>KPCNGVAGENCYFPLRSYSFRPTYGVGHQPYRVVVLSFELLH<br>APATVCGPKKSTNLVKNKCVNFNFNGLKGTGVLTESNKKFLP<br>FQQFGRDIADTTDAVRDPQTLEILDITPCSFGGVSVITPGTNTSN<br>QVAVLYQGVNCTEVPVAIHADQLTPTWRVYSTGSNVFQTRA<br>GCLIGAEYVNNSYECDIPIGAGICASYQTQTNSPGGAGSVASQS<br>IIAYTMSLGAENSVAYSNNSIAIPTNFTISVTTEILPVSMTKTSV<br>DCTMYICGDSTECSNLLLQYGSFCTQLKRALTGIAVEQDKNTQ<br>EVFAQVKQIYKTPPIKYFGGFNFSQILPDPSKPSKRSFIEDLLEN<br>KVTLADAGFIKQYGDCLGDIAARDLICAQKFKGLTVLPPLLTD<br>EMIAQYTSALLAGTITSGWTFGAGAALQIPFAMQMAYRENGI<br>GVTQNVLYENQKLIANQFNSAIGKIQDSLSSTASALGKLQDVV<br>NHNAQALNTLVKQLSSKFGAISSVLNDIFSRLDPPEAEVQIDRL<br>ITGRLQSLQTYVTQQLIRAAEIRASANLAATKMSECVLGQSKR<br>VDFCGKGYHLMSFPQSAPHGVVFLHVTYVPAQEKNFTTAPAI<br>CHDGKAHFPREGVFVSNGTHWFVTQRNFYEPQIITTDNTFVSG<br>NCDVVIGIVNNTVYDPLQPELDSFKEELDKYFKNHTSPDVDLG<br>DISGINASVVNIQKEIDRLNEVAKNLNESLIDLQELGKYEQYIK<br>WPWYIWLGFIAGLIAIVMVTIMLCCMTSCCSCLKGCCSCGSCC<br>KFDEDDSEPVLKGVKLHYT | 39 |
| PolyA tail | 100 nt | |

| B.1.1.529-1273_m_mu | | |
|---|---|---|
| SEQ ID NO: 40 consists of from 5' end to 3' end: 5' UTR SEQ ID NO: 2, mRNA ORF SEQ ID NO: 41, and 3' UTR SEQ ID NO: 4. | | 40 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUAA<br>GACCCCGGCGCCGCCACC | 2 |
| ORF of mRNA Construct (excluding the stop codon) | AUGUUCGUGUUCCUGGUGCUGCUGCCCCUGGUGAGCAGC<br>CAGUGCGUGAACCUGACCACCCGGACCCAGCUGCCACCAG<br>CCUACACCAACAGCUUCACCCGGGGCGUGUACUACCCCGA<br>CAAGGUGUUCCGGAGCAGCGUGCUGCACAGCACCCAGGAC<br>CUGUUCCUGCCCUUCUUCAGCAACGUGACCUGGUUCCACG<br>UGAUCAGCGGCACCAACGGCACCAAGCGGUUCGACAACCC<br>CGUGCUGCCCUUCAACGACGGCGUGUACUUCGCCAGCAUC<br>GAGAAGAGCAACAUCAUCCGGGGCUGGAUCUUCGGCACC<br>ACCCUGGACAGCAAGACCCAGAGCCUGCUGAUCGUGAACA<br>ACGCCACCAACGUGGUGAUCAAGGUGUGCGAGUUCCAGU<br>UCUGCAACGACCCCUUCCUGGACCACAAGAACAACAAGAG<br>CUGGAUGGAGAGCGAGUUCCGGGUGUACAGCAGCGCCAA<br>CAACUGCACCUUCGAGUACGUGAGCCAGCCCUUCCUGAUG<br>GACCUGGAGGGCAAGCAGGGCAACUUCAAGAACCUGCGG<br>GAGUUCGUGUUCAAGAACAUCGACGGCUACUUCAAGAUC<br>UACAGCAAGCACACCCCAAUCAUCGUGCGGGAGCCCGAGG<br>ACCUGCCCCAGGGCUUCAGCGCCCUGGAGCCCCUGGUGGA<br>CCUGCCCAUCGGCAUCAACAUCACCCGGUUCCAGACCCUG<br>CUGGCCCUGCACCGGAGCUACCUGACCCCAGGCGACAGCA<br>GCAGCGGCUGGACCGCCGGCGCCGCCGCCUACUACGUGGG | 41 |

TABLE 1-continued

| Sequence Listing | | |
|---|---|---|
| | CUACCUGCAGCCCCGGACCUUCCUGCUGAAGUACAACGAG | |
| | AACGGCACCAUCACCGACGCCGUGGACUGCGCCCUGGACC | |
| | CUCUGAGCGAGACCAAGUGCACCCUGAAGAGCUUCACCGU | |
| | GGAGAAGGGCAUCUACCAGACCAGCAACUUCCGGGUGCA | |
| | GCCCACCGAGAGCAUCGUGCGGUUCCCCAACAUCACCAAC | |
| | CUGUGCCCCUUCGACGAGGUGUUCAACGCCACCCGGUUCG | |
| | CCAGCGUGUACGCCUGGAACCGGAAGCGGAUCAGCAACU | |
| | GCGUGGCCGACUACAGCGUGCUGUACAACCUGGCCCCUUU | |
| | CUUCACCUUCAAGUGCUACGGCGUGAGCCCCACCAAGCUG | |
| | AACGACCUGUGCUUCACCAACGUGUACGCCGACAGCUUCG | |
| | UGAUCCGGGGCGACGAGGUGCGGCAGAUCGCCCCAGGCCA | |
| | GACCGGCAACAUCGCCGACUACAACUACAAGCUGCCCGAC | |
| | GACUUCACCGGCUGCGUGAUCGCCUGGAACAGCAACAAGC | |
| | UGGACAGCAAGGUGAGCGGCAACUACAACUACCUGUACC | |
| | GGCUGUUCCGGAAGAGCAACCUGAAGCCCUUCGAGCGGG | |
| | ACAUCAGCACCGAGAUCUACCAGGCCGGCAACAAGCCCUG | |
| | CAACGGCGUGGCCGGCUUCAACUGCUACUUCCCUCUGCGG | |
| | AGCUACAGCUUCCGGCCCACCUACGGCGUGGGCCACCAGC | |
| | CCUACCGGGUGGUGGUGCUGAGCUUCGAGCUGCUGCACG | |
| | CCCCAGCCACCGUGUGCGGCCCCAAGAAGAGCACCAACCU | |
| | GGUGAAGAACAAGUGCGUGAACUUCAACUUCAACGGCCU | |
| | GAAGGGCACCGGCGUGCUGACCGAGAGCAACAAGAAGUU | |
| | CCUGCCCUUCCAGCAGUUCGGCCGGGACAUCGCCGACACC | |
| | ACCGACGCCGUGCGGGAUCCCCAGACCCUGGAGAUCCUGG | |
| | ACAUCACCCCUUGCAGCUUCGGCGGCGUGAGCGUGAUCAC | |
| | CCCAGGCACCAACACCAGCAACCAGGUGGCCGUGCUGUAC | |
| | CAGGGCGUGAACUGCACCGAGGUGCCCGUGGCCAUCCACG | |
| | CCGACCAGCUGACCCCAACCUGGCGGGUGUACAGCACCGG | |
| | CAGCAACGUGUUCCAGACCCGGGCCGGCUGCCUGAUCGGC | |
| | GCCGAGUACGUGAACAACAGCUACGAGUGCGACAUCCCCA | |
| | UCGGCGCCGGCAUCUGCGCCAGCUACCAGACCCAGACCAA | |
| | GAGCCACCGGCGGGCCCGGAGCGUGGCCAGCCAGAGCAUC | |
| | AUCGCCUACACCAUGAGCCUGGGCGCCGAGAACAGCGUGG | |
| | CCUACAGCAACAACAGCAUCGCCAUCCCCACCAACUUCAC | |
| | CAUCAGCGUGACCACCGAGAUCCUGCCCGUGAGCAUGACC | |
| | AAGACCAGCGUGGACUGCACCAUGUACAUCUGCGGCGAC | |
| | AGCACCGAGUGCAGCAACCUGCUGCUGCAGUACGGCAGCU | |
| | UCUGCACCCAGCUGAAGCGGGCCCUGACCGGCAUCGCCGU | |
| | GGAGCAGGACAAGAACACCCAGGAGGUGUUCGCCCAGGU | |
| | GAAGCAGAUCUACAAGACCCCUCCCAUCAAGUACUUCGGC | |
| | GGCUUCAACUUCAGCCAGAUCCUGCCCGACCCCAGCAAGC | |
| | CCAGCAAGCGGAGCUUCAUCGAGGACCUGCUGUUCAACA | |
| | AGGUGACCCUGGCCGACGCCGGCUUCAUCAAGCAGUACGG | |
| | CGACUGCCUGGGCGACAUCGCCGCCCGGGACCUGAUCUGC | |
| | GCCCAGAAGUUCAAGGGCCUGACCGUGCUGCCUCCUCUGC | |
| | UGACCGACGAGAUGAUCGCCCAGUACACCAGCGCCCUGCU | |
| | GGCCGGCACCAUCACCAGCGGCUGGACCUUCGGCGCCGGC | |
| | GCCGCCCUGCAGAUCCCCUUCGCCAUGCAGAUGGCCUACC | |
| | GGUUCAACGGCAUCGGCGUGACCCAGAACGUGCUGUACG | |
| | AGAACCAGAAGCUGAUCGCCAACCAGUUCAACAGCGCCAU | |
| | CGGCAAGAUCCAGGACAGCCUGAGCAGCACCGCCAGCGCC | |
| | CUGGGCAAGCUGCAGGACGUGGUGAACCACAACGCCCAG | |
| | GCCCUGAACACCCUGGUGAAGCAGCUGAGCAGCAAGUUC | |
| | GGCGCCAUCAGCAGCGUGCUGAACGACAUCUUCAGCCGGC | |
| | UGGACCCUCCCGAGGCCGAGGUGCAGAUCGACCGGCUGAU | |
| | CACCGGCCGGCUGCAGAGCCUGCAGACCUACGUGACCCAG | |
| | CAGCUGAUCCGGGCCGCCGAGAUCCGGGCCAGCGCCAACC | |
| | UGGCCGCCACCAAGAUGAGCGAGUGCGUGCUGGGCCAGA | |
| | GCAAGCGGGUGGACUUCUGCGGCAAGGGCUACCACCUGA | |
| | UGAGCUUUCCCCAGAGCGCACCCCACGGCGUGGUGUUCCU | |
| | GCACGUGACCUACGUGCCCGCCCAGGAGAAGAACUUCACC | |
| | ACCGCCCCAGCCAUCUGCCACGACGGCAAGGCCCACUUUC | |
| | CCCGGGAGGGCGUGUUCGUGAGCAACGGCACCCACUGGU | |
| | UCGUGACCCAGCGGAACUUCUACGAGCCCCAGAUCAUCAC | |
| | CACCGACAACACCUUCGUGAGCGGCAACUGCGACGUGGUG | |
| | AUCGGCAUCGUGAACAACACCGUGUACGAUCCCCUGCAGC | |
| | CCGAGCUGGACAGCUUCAAGGAGGAGCUGGACAAGUACU | |
| | UCAAGAACCACACCAGCCCCGACGUGGACCUGGGCGACAU | |
| | CAGCGGCAUCAACGCCAGCGUGGUGAACAUCCAGAAGGA | |
| | GAUCGACAGACUGAACGAGGUGGCCAAGAACCUGAACGA | |
| | GAGCCUGAUCGACCUGCAGGAGCUGGGCAAGUACGAGCA | |
| | GUACAUCAAGUGGCCCUGGUACAUCUGGCUGGGCUUCAU | |
| | CGCCGGCCUGAUCGCCAUCGUGAUGGUGACCAUCAUGCUG | |
| | UGCUGCAUGACCAGCUGCUGCAGCUGCCUGAAGGGCUGC | |
| | UGCAGCUGCGGCAGCUGCUGCAAGUUCGACGAGGACGAC | |
| | AGCGAGCCCGUGCUGAAGGGCGUGAAGCUGCACUACACC | |
| 3' UTR | UGAUAAUAGGCUGGAGCCUCGGUGGCCUAGCUUCUUGCC | 4 |
| | CCUUGGGCCUCCCCCCAGCCCCUCCUCCCCUUCCUGCACC | |

TABLE 1-continued

| | Sequence Listing | |
|---|---|---|
| | CGUACCCCCGUGGUCUUUGAAUAAAGUCUGAGUGGGCGG<br>C | |
| Corresponding amino acid sequence | MFVFLVLLPLVSSQCVNLTTRTQLPPAYTNSFTRGVYYPDKVF<br>RSSVLHSTQDLFLPFFSNVTWFHVISGTNGTKRFDNPVLPEND<br>GVYFASIEKSNIIRGWIFGTTLDSKTQSLLIVNNATNVVIKVCEF<br>QFCNDPFLDHKNNKSWMESEFRVYSSANNCTFEYVSQPFLMD<br>LEGKQGNFKNLREFVFKNIDGYFKIYSKHTPIIVREPEDLPQGF<br>SALEPLVDLPIGINITRFQTLLALHRSYLTPGDSSSGWTAGAAA<br>YYVGYLQPRTFLLKYNENGTITDAVDCALDPLSETKCTLKSFT<br>VEKGIYQTSNFRVQPTESIVRFPNITNLCPFDEVFNATRFASVY<br>AWNRKRISNCVADYSVLYNLAPFFTFKCYGVSPTKLNDLCFT<br>NVYADSFVIRGDEVRQIAPGQTGNIADYNYKLPDDFTGCVIA<br>WNSNKLDSKVSGNYNYLYRLFRKSNLKPFERDISTEIYQAGN<br>KPCNGVAGFNCYFPLRSYSFRPTYGVGHQPYRVVVLSFELLH<br>APATVCGPKKSTNLVKNKCVNFNFNGLKGTGVLTESNKKFLP<br>FQQFGRDIADTTDAVRDPQTLEILDITPCSFGGVSVITPGTNTSN<br>QVAVLYQGVNCTEVPVAIHADQLTPTWRVYSTGSNVFQTRA<br>GCLIGAEYVNNSYECDIPIGAGICASYQTQTKSHRRARSVASQS<br>IIAYTMSLGAENSVAYSNNSIAIPTNFTISVTTEILPVSMTKTSV<br>DCTMYICGDSTECSNLLLQYGSFCTQLKRALTGIAVEQDKNTQ<br>EVFAQVKQIYKTPPIKYFGGFNFSQILPDPSKPSKRSFIEDLLEN<br>KVTLADAGFIKQYGDCLGDIAARDLICAQKFKGLTVLPPLLTD<br>EMIAQYTSALLAGTITSGWTFGAGAALQIPFAMQMAYRENGI<br>GVTQNVLYENQKLIANQFNSAIGKIQDSLSSTASALGKLQDVV<br>NHNAQALNTLVKQLSSKFGAISSVLNDIFSRLDPPEAEVQIDRL<br>ITGRLQSLQTYVTQQLIRAAEIRASANLAATKMSECVLGQSKR<br>VDFCGKGYHLMSFPQSAPHGVVFLHVTYVPAQEKNFTTAPAI<br>CHDGKAHFPREGVFVSNGTHWFVTQRNFYEPQIITTDNTFVSG<br>NCDVVIGIVNNTVYDPLQPELDSFKEELDKYFKNHTSPDVDLG<br>DISGINASVVNIQKEIDRLNEVAKNLNESLIDLQELGKYEQYIK<br>WPWYIWLGFIAGLIAIVMVTIMLCCMTSCCSCLKGCCSCGSCC<br>KFDEDDSEPVLKGVKLHYT | 42 |
| PolyA tail | 100 nt | |
| | 1273.529.IDR14A | |
| SEQ ID NO: 43 consists of from 5' end to 3' end: 5' UTR SEQ ID NO: 2, mRNA ORF SEQ ID NO: 41, and 3' UTR SEQ ID NO: 44. | | 43 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAA<br>GACCCCGGCGCCGCCACC | 2 |
| ORF of mRNA Construct (excluding the stop codon) | AUGUUCGUGUUCCUGGUGCUGCUGCCCCUGGUGAGCAGC<br>CAGUGCGUGAACCUGACCACCCGGACCCAGCUGCCACCAG<br>CCUACACCAACAGCUUCACCCGGGGCGUGUACUACCCCGA<br>CAAGGUGUUCCGGAGCAGCGUGCUGCACAGCACCCAGGAC<br>CUGUUCCUGCCCUUCUUCAGCAACGUGACCUGGUUCCACG<br>UGAUCAGCGGCACCAACGGCACCAAGCGGUUCGACAACCC<br>CGUGCUGCCCUUCAACGACGGCGUGUACUUCGCCAGCAUC<br>GAGAAGAGCAACAUCAUCCGGGGCUGGAUCUUCGGCACC<br>ACCCUGGACAGCAAGACCCAGAGCCUGCUGAUCGUGAACA<br>ACGCCACCAACGUGGUGAUCAAGGUGUGCGAGUUCCAGU<br>UCUGCAACGACCCCUUCCUGGACCACAAGAACAACAAGAG<br>CUGGAUGGAGAGCGAGUUCCGGGUGUACAGCAGCGCCAA<br>CAACUGCACCUUCGAGUACGUGAGCCAGCCCUUCCUGAUG<br>GACCUGGAGGGCAAGCAGGGCAACUUCAAGAACCUGCGG<br>GAGUUCGUGUUCAAGAACAUCGACGGCUACUUCAAGAUC<br>UACAGCAAGCACACCCCAAUCAUCGUGCGGGAGCCCGAGG<br>ACCUGCCCCAGGGCUUCAGCGCCCUGGAGCCCCUGGUGGA<br>CCUGCCCAUCGGCAUCAACAUCACCCGGUUCCAGACCCUG<br>CUGGCCCUGCACCGGAGCUACCUGACCCCAGGCGACAGCA<br>GCAGCGGCUGGACCGCCGGCGCCGCCGCCUACUACGUGGG<br>CUACCUGCAGCCCCGGACCUUCCUGCUGAAGUACAACGAG<br>AACGGCACCAUCACCGACGCCGUGGACUGCGCCCUGGACC<br>CUCUGAGCGAGACCAAGUGCACCCUGAAGAGCUUCACCGU<br>GGAGAAGGGCAUCUACCAGACCAGCAACUUCCGGGUGCA<br>GCCCACCGAGAGCAUCGUGCGGUUCCCCAACAUCACCAAC<br>CUGUGCCCCUUCGACGAGGUGUUCAACGCCACCCGGUUCG<br>CCAGCGUGUACGCCUGGAACCGGAAGCGGAUCAGCAACU<br>GCGUGGCCGACUACAGCGUGCUGUACAACCUGGCCCCUUU<br>CUUCACCUUCAAGUGCUACGGCGUGAGCCCCACCAAGCUG<br>AACGACCUGUGCUUCACCAACGUGUACGCCGACAGCUUCG<br>UGAUCCGGGGCGACGAGGUGCGGCAGAUCGCCCCAGGCCA<br>GACCGGCAACAUCGCCGACUACAACUACAAGCUGCCCGAC<br>GACUUCACCGGCUGCGUGAUCGCCUGGAACAGCAACAAGC<br>UGGACAGCAAGGUGAGCGGCAACUACAACUACCUGUACC<br>GGCUGUUCCGGAAGAGCAACCUGAAGCCCUUCGAGCGGG<br>ACAUCAGCACCGAGAUCUACCAGGCCGGCAACAAGCCCUG | 41 |

TABLE 1-continued

| Sequence Listing | | |
|---|---|---|
| | CAACGGCGUGGCCGGCUUCAACUGCUACUUCCCUCUGCGG<br>AGCUACAGCUUCCGGCCCACCUACGGCGUGGGCCACCAGC<br>CCUACCGGGUGGUGGUGCUGAGCUUCGAGCUGCUGCACG<br>CCCCAGCCACCGUGUGCGGCCCCAAGAAGAGCACCAACCU<br>GGUGAAGAACAAGUGCGUGAACUUCAACUUCAACGGCCU<br>GAAGGGCACCGGCGUGCUGACCGAGAGCAACAAGAAGUU<br>CCUGCCCUUCCAGCAGUUCGGCCGGGACAUCGCCGACACC<br>ACCGACGCCGUGCGGGAUCCCCAGACCCUGGAGAUCCUGG<br>ACAUCACCCCUUGCAGCUUCGGCGGCGUGAGCGUGAUCAC<br>CCCAGGCACCAACACCAGCAACCAGGUGGCCGUGCUGUAC<br>CAGGGCGUGAACUGCACCGAGGUGCCCGUGGCCAUCCACG<br>CCGACCAGCUGACCCCAACCUGGCGGGUGUACAGCACCGG<br>CAGCAACGUGUUCCAGACCCGGGCCGGCUGCCUGAUCGGC<br>GCCGAGUACGUGAACAACAGCUACGAGUGCGACAUCCCCA<br>UCGGCGCCGGCAUCUGCGCCAGCUACCAGACCCAGACCAA<br>GAGCCACCGGCGGGCCCGGAGCGUGGCCAGCCAGAGCAUC<br>AUCGCCUACACCAUGAGCCUGGGCGCCGAGAACAGCGUGG<br>CCUACAGCAACAACAGCAUCGCCAUCCCCACCAACUUCAC<br>CAUCAGCGUGACCACCGAGAUCCUGCCCGUGAGCAUGACC<br>AAGACCAGCGUGGACUGCACCAUGUACAUCUGCGGCGAC<br>AGCACCGAGUGCAGCAACCUGCUGCUGCAGUACGGCAGCU<br>UCUGCACCCAGCUGAAGCGGGCCCUGACCGGCAUCGCCGU<br>GGAGCAGGACAAGAACACCCAGGAGGUGUUCGCCCAGGU<br>GAAGCAGAUCUACAAGACCCCUCCCAUCAAGUACUUCGGC<br>GGCUUCAACUUCAGCCAGAUCCUGCCCGACCCCAGCAAGC<br>CCAGCAAGCGGAGCUUCAUCGAGGACCUGCUGUUCAACA<br>AGGUGACCCUGGCCGACGCCGGCUUCAUCAAGCAGUACGG<br>CGACUGCCUGGGCGACAUCGCCGCCCGGGACCUGAUCUGC<br>GCCCAGAAGUUCAAGGGCCUGACCGUGCUGCCUCCUCUGC<br>UGACCGACGAGAUGAUCGCCCAGUACACCAGCGCCCUGCU<br>GGCCGGCACCAUCACCAGCGGCUGGACCUUCGGCGCCGGC<br>GCCGCCCUGCAGAUCCCCUUCGCCAUGCAGAUGGCCUACC<br>GGUUCAACGGCAUCGGCGUGACCCAGAACGUGCUGUACG<br>AGAACCAGAAGCUGAUCGCCAACCAGUUCAACAGCGCCAU<br>CGGCAAGAUCCAGGACAGCCUGAGCAGCACCGCCAGCGCC<br>CUGGGCAAGCUGCAGGACGUGGUGAACCACAACGCCCAG<br>GCCCUGAACACCCUGGUGAAGCAGCUGAGCAGCAAGUUC<br>GGCGCCAUCAGCAGCGUGCUGAACGACAUCUUCAGCCGGC<br>UGGACCCUCCCGAGGCCGAGGUGCAGAUCGACCGGCUGAU<br>CACCGGCCGGCUGCAGAGCCUGCAGACCUACGUGACCCAG<br>CAGCUGAUCCGGGCCGCCGAGAUCCGGGCCAGCGCCAACC<br>UGGCCGCCACCAAGAUGAGCGAGUGCGUGCUGGGCCAGA<br>GCAAGCGGGUGGACUUCUGCGGCAAGGGCUACCACCUGA<br>UGAGCUUUCCCCAGAGCGCACCCCACGGCGUGGUGUUCCU<br>GCACGUGACCUACGUGCCCGCCCAGGAGAAGAACUUCACC<br>ACCGCCCCAGCCAUCUGCCACGACGGCAAGGCCCACUUUC<br>CCCGGGAGGGCGUGUUCGUGAGCAACGGCACCCACUGGU<br>UCGUGACCCAGCGGAACUUCUACGAGCCCCAGAUCAUCAC<br>CACCGACAACACCUUCGUGAGCGGCAACUGCGACGUGGUG<br>AUCGGCAUCGUGAACAACACCGUGUACGAUCCCCUGCAGC<br>CCGAGCUGGACAGCUUCAAGGAGGAGCUGGACAAGUACU<br>UCAAGAACCACACCAGCCCCGACGUGGACCUGGGCGACAU<br>CAGCGGCAUCAACGCCAGCGUGGUGAACAUCCAGAAGGA<br>GAUCGACAGACUGAACGAGGUGGCCAAGAACCUGAACGA<br>GAGCCUGAUCGACCUGCAGGAGCUGGGCAAGUACGAGCA<br>GUACAUCAAGUGGCCCUGGUACAUCUGGCUGGGCUUCAU<br>CGCCGGCCUGAUCGCCAUCGUGAUGGUGACCAUCAUGCUG<br>UGCUGCAUGACCAGCUGCUGCAGCUGCCUGAAGGGCUGC<br>UGCAGCUGCGGCAGCUGCUGCAAGUUCGACGAGGACGAC<br>AGCGAGCCCGUGCUGAAGGGCGUGAAGCUGCACUACACC | |
| 3' UTR | UGAUAAUAGGCUGGAGCCUCGGUGGCCUAGCUUCUUGCC<br>CCUUGGGCCUCCCCCCAGCCCCUCCUCCCCUUCCUGCAGG<br>AUAGAUAGCGAAGUGGUCUUUGAAUAAAGUCUGAGUGGG<br>CGGC | 44 |
| Corresponding amino acid sequence | MFVFLVLLPLVSSQCVNLTTRTQLPPAYTNSFTRGVYYPDKVF<br>RSSVLHSTQDLFLPFFSNVTWFHVISGTNGTKRFDNPVLPEND<br>GVYFASIEKSNIIRGWIFGTTLDSKTQSLLIVNNATNVVIKVCEF<br>QFCNDPFLDHKNNKSWMESEFRVYSSANNCTFEYVSQPFLMD<br>LEGKQGNFKNLREFVFKNIDGYFKIYSKHTPIIVREPEDLPQGF<br>SALEPLVDLPIGINITRFQTLLALHRSYLTPGDSSSGWTAGAAA<br>YYVGYLQPRTFLLKYNENGTITDAVDCALDPLSETKCTLKSFT<br>VEKGIYQTSNFRVQPTESIVRFPNITNLCPFDEVFNATRFASVY<br>AWNRKRISNCVADYSVLYNLAPFFTFKCYGVSPTKLNDLCFT<br>NVYADSFVIRGDEVRQIAPGQTGNIADYNYKLPDDFTGCVIA<br>WNSNKLDSKVSGNYNYLYRLFRKSNLKPFERDISTEIYQAGN<br>KPCNGVAGENCYFPLRSYSFRPTYGVGHQPYRVVVLSFELLH<br>APATVCGPKKSTNLVKNKCVNFNFNGLKGTGVLTESNKKFLP<br>FQQFGRDIADTTDAVRDPQTLEILDITPCSFGGVSVITPGTNTSN | 42 |

TABLE 1-continued

| Sequence Listing | | |
|---|---|---|
| | QVAVLYQGVNCTEVPVAIHADQLTPTWRVYSTGSNVFQTRA<br>GCLIGAEYVNNSYECDIPIGAGICASYQTQTKSHRRARSVASQS<br>IIAYTMSLGAENSVAYSNNSIAIPTNFTISVTTEILPVSMTKTSV<br>DCTMYICGDSTECSNLLLQYGSFCTQLKRALTGIAVEQDKNTQ<br>EVFAQVKQIYKTPPIKYFGGFNFSQILPDPSKPSKRSFIEDLLEN<br>KVTLADAGFIKQYGDCLGDIAARDLICAQKFKGLTVLPPLLTD<br>EMIAQYTSALLAGTITSGWTFGAGAALQIPFAMQMAYRENGI<br>GVTQNVLYENQKLIANQFNSAIGKIQDSLSSTASALGKLQDVV<br>NHNAQALNTLVKQLSSKFGAISSVLNDIFSRLDPPEAEVQIDRL<br>ITGRLQSLQTYVTQQLIRAAEIRASANLAATKMSECVLGQSKR<br>VDFCGKGYHLMSFPQSAPHGVVFLHVTYVPAQEKNFTTAPAI<br>CHDGKAHFPREGVFVSNGTHWFVTQRNFYEPQIITTDNTFVSG<br>NCDVVIGIVNNTVYDPLQPELDSFKEELDKYFKNHTSPDVDLG<br>DISGINASVVNIQKEIDRLNEVAKNLNESLIDLQELGKYEQYIK<br>WPWYIWLGFIAGLIAIVMVTIMLCCMTSCCSCLKGCCSCGSCC<br>KFDEDDSEPVLKGVKLHYT | |
| PolyA tail | 100 nt | |
| 1273.529.IDR14B | | |
| SEQ ID NO: 45 consists of from 5' end to 3' end: 5' UTR SEQ ID NO: 2, mRNA ORF SEQ ID NO: 41, and 3' UTR SEQ ID NO: 46. | | 45 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAA<br>GACCCCGGCGCCGCCACC | 2 |
| ORF of mRNA Construct (excluding the stop codon) | AUGUUCGUGUUCCUGGUGCUGCUGCCCCUGGUGAGCAGC<br>CAGUGCGUGAACCUGACCACCCGGACCCAGCUGCCACCAG<br>CCUACACCAACAGCUUCACCCGGGGCGUGUACUACCCCGA<br>CAAGGUGUUCCGGAGCAGCGUGCUGCACAGCACCCAGGAC<br>CUGUUCCUGCCCUUCUUCAGCAACGUGACCUGGUUCCACG<br>UGAUCAGCGGCACCAACGGCACCAAGCGGUUCGACAACCC<br>CGUGCUGCCCUUCAACGACGGCGUGUACUUCGCCAGCAUC<br>GAGAAGAGCAACAUCAUCCGGGGCUGGAUCUUCGGCACC<br>ACCCUGGACAGCAAGACCCAGAGCCUGCUGAUCGUGAACA<br>ACGCCACCAACGUGGUGAUCAAGGUGUGCGAGUUCCAGU<br>UCUGCAACGACCCCUUCCUGGACCACAAGAACAACAAGAG<br>CUGGAUGGAGAGCGAGUUCCGGGUGUACAGCAGCGCCAA<br>CAACUGCACCUUCGAGUACGUGAGCCAGCCCUUCCUGAUG<br>GACCUGGAGGGCAAGCAGGGCAACUUCAAGAACCUGCGG<br>GAGUUCGUGUUCAAGAACAUCGACGGCUACUUCAAGAUC<br>UACAGCAAGCACACCCCAAUCAUCGUGCGGGAGCCCGAGG<br>ACCUGCCCCAGGGCUUCAGCGCCCUGGAGCCCCUGGUGGA<br>CCUGCCCAUCGGCAUCAACAUCACCCGGUUCCAGACCCUG<br>CUGGCCCUGCACCGGAGCUACCUGACCCCAGGCGACAGCA<br>GCAGCGGCUGGACCGCCGGCGCCGCCGCCUACUACGUGGG<br>CUACCUGCAGCCCCGGACCUUCCUGCUGAAGUACAACGAG<br>AACGGCACCAUCACCGACGCCGUGGACUGCGCCCUGGACC<br>CUCUGAGCGAGACCAAGUGCACCCUGAAGAGCUUCACCGU<br>GGAGAAGGGCAUCUACCAGACCAGCAACUUCCGGGUGCA<br>GCCCACCGAGAGCAUCGUGCGGUUCCCCAACAUCACCAAC<br>CUGUGCCCCUUCGACGAGGUGUUCAACGCCACCCGGUUCG<br>CCAGCGUGUACGCCUGGAACCGGAAGCGGAUCAGCAACU<br>GCGUGGCCGACUACAGCGUGCUGUACAACCUGGCCCCUUU<br>CUUCACCUUCAAGUGCUACGGCGUGAGCCCCACCAAGCUG<br>AACGACCUGUGCUUCACCAACGUGUACGCCGACAGCUUCG<br>UGAUCCGGGGCGACGAGGUGCGGCAGAUCGCCCCAGGCCA<br>GACCGGCAACAUCGCCGACUACAACUACAAGCUGCCCGAC<br>GACUUCACCGGCUGCGUGAUCGCCUGGAACAGCAACAAGC<br>UGGACAGCAAGGUGAGCGGCAACUACAACUACCUGUACC<br>GGCUGUUCCGGAAGAGCAACCUGAAGCCCUUCGAGCGGG<br>ACAUCAGCACCGAGAUCUACCAGGCCGGCAACAAGCCCUG<br>CAACGGCGUGGCCGGCUUCAACUGCUACUUCCCUCUGCGG<br>AGCUACAGCUUCCGGCCCACCUACGGCGUGGGCCACCAGC<br>CCUACCGGGUGGUGGUGCUGAGCUUCGAGCUGCUGCACG<br>CCCCAGCCACCGUGUGCGGCCCCAAGAAGAGCACCAACCU<br>GGUGAAGAACAAGUGCGUGAACUUCAACUUCAACGGCCU<br>GAAGGGCACCGGCGUGCUGACCGAGAGCAACAAGAAGUU<br>CCUGCCCUUCCAGCAGUUCGGCCGGGACAUCGCCGACACC<br>ACCGACGCCGUGCGGGAUCCCCAGACCCUGGAGAUCCUGG<br>ACAUCACCCCUUGCAGCUUCGGCGGCGUGAGCGUGAUCAC<br>CCCAGGCACCAACACCAGCAACCAGGUGGCCGUGCUGUAC<br>CAGGGCGUGAACUGCACCGAGGUGCCCGUGGCCAUCCACG<br>CCGACCAGCUGACCCCAACCUGGCGGGUGUACAGCACCGG<br>CAGCAACGUGUUCCAGACCCGGGCCGGCUGCCUGAUCGGC<br>GCCGAGUACGUGAACAACAGCUACGAGUGCGACAUCCCCA<br>UCGGCGCCGGCAUCUGCGCCAGCUACCAGACCCAGACCAA<br>GAGCCACCGGCGGGCCCGGAGCGUGGCCAGCCAGAGCAUC | 41 |

TABLE 1-continued

| Sequence Listing | | |
|---|---|---|
| | AUCGCCUACACCAUGAGCCUGGGCGCCGAGAACAGCGUGG<br>CCUACAGCAACAACAGCAUCGCCAUCCCCACCAACUUCAC<br>CAUCAGCGUGACCACCGAGAUCCUGCCCGUGAGCAUGACC<br>AAGACCAGCGUGGACUGCACCAUGUACAUCUGCGGCGAC<br>AGCACCGAGUGCAGCAACCUGCUGCUGCAGUACGGCAGCU<br>UCUGCACCCAGCUGAAGCGGGCCCUGACCGGCAUCGCCGU<br>GGAGCAGGACAAGAACACCCAGGAGGUGUUCGCCCAGGU<br>GAAGCAGAUCUACAAGACCCCUCCCAUCAAGUACUUCGGC<br>GGCUUCAACUUCAGCCAGAUCCUGCCCGACCCCAGCAAGC<br>CCAGCAAGCGGAGCUUCAUCGAGGACCUGCUGUUCAACA<br>AGGUGACCCUGGCCGACGCCGGCUUCAUCAAGCAGUACGG<br>CGACUGCCUGGGCGACAUCGCCGCCCGGGACCUGAUCUGC<br>GCCCAGAAGUUCAAGGGCCUGACCGUGCUGCCUCCUCUGC<br>UGACCGACGAGAUGAUCGCCCAGUACACCAGCGCCCUGCU<br>GGCCGGCACCAUCACCAGCGGCUGGACCUUCGGCGCCGGC<br>GCCGCCCUGCAGAUCCCCUUCGCCAUGCAGAUGGCCUACC<br>GGUUCAACGGCAUCGGCGUGACCCAGAACGUGCUGUACG<br>AGAACCAGAAGCUGAUCGCCAACCAGUUCAACAGCGCCAU<br>CGGCAAGAUCCAGGACAGCCUGAGCAGCACCGCCAGCGCC<br>CUGGGCAAGCUGCAGGACGUGGUGAACCACAACGCCCAG<br>GCCCUGAACACCCUGGUGAAGCAGCUGAGCAGCAAGUUC<br>GGCGCCAUCAGCAGCGUGCUGAACGACAUCUUCAGCCGGC<br>UGGACCCUCCCGAGGCCGAGGUGCAGAUCGACCGGCUGAU<br>CACCGGCCGGCUGCAGAGCCUGCAGACCUACGUGACCCAG<br>CAGCUGAUCCGGGCCGCCGAGAUCCGGGCCAGCGCCAACC<br>UGGCCGCCACCAAGAUGAGCGAGUGCGUGCUGGGCCAGA<br>GCAAGCGGGUGGACUUCUGCGGCAAGGGCUACCACCUGA<br>UGAGCUUUCCCCAGAGCGCACCCCACGGCGUGGUGUUCCU<br>GCACGUGACCUACGUGCCCGCCCAGGAGAAGAACUUCACC<br>ACCGCCCCAGCCAUCUGCCACGACGGCAAGGCCCACUUUC<br>CCCGGGAGGGCGUGUUCGUGAGCAACGGCACCCACUGGU<br>UCGUGACCCAGCGGAACUUCUACGAGCCCCAGAUCAUCAC<br>CACCGACAACACCUUCGUGAGCGGCAACUGCGACGUGGUG<br>AUCGGCAUCGUGAACAACACCGUGUACGAUCCCCUGCAGC<br>CCGAGCUGGACAGCUUCAAGGAGGAGCUGGACAAGUACU<br>UCAAGAACCACACCAGCCCCGACGUGGACCUGGGCGACAU<br>CAGCGGCAUCAACGCCAGCGUGGUGAACAUCCAGAAGGA<br>GAUCGACAGACUGAACGAGGUGGCCAAGAACCUGAACGA<br>GAGCCUGAUCGACCUGCAGGAGCUGGGCAAGUACGAGCA<br>GUACAUCAAGUGGCCCUGGUACAUCUGGCUGGGCUUCAU<br>CGCCGGCCUGAUCGCCAUCGUGAUGGUGACCAUCAUGCUG<br>UGCUGCAUGACCAGCUGCUGCAGCUGCCUGAAGGGCUGC<br>UGCAGCUGCGGCAGCUGCUGCAAGUUCGACGAGGACGAC<br>AGCGAGCCCGUGCUGAAGGGCGUGAAGCUGCACUACACC | |
| 3' UTR | UGAUAAUAGGCUGGAGCCUCGGUGGCCUAGCUUCUUGCC<br>CCUUGGGCCUCCCCCCAGCCCCUCCUCCCCUUCCUGCAGG<br>CCACAUAGCGAAGUGGUCUUUGAAUAAAGUCUGAGUGGG<br>CGGC | 46 |
| Corresponding amino acid sequence | MFVFLVLLPLVSSQCVNLTTRTQLPPAYTNSFTRGVYYPDKVF<br>RSSVLHSTQDLFLPFFSNVTWFHVISGTNGTKRFDNPVLPEND<br>GVYFASIEKSNIIRGWIFGTTLDSKTQSLLIVNNATNVVIKVCEF<br>QFCNDPFLDHKNNKSWMESEFRVYSSANNCTFEYVSQPFLMD<br>LEGKQGNFKNLREFVFKNIDGYFKIYSKHTPIIVREPEDLPQGF<br>SALEPLVDLPIGINITRFQTLLALHRSYLTPGDSSSGWTAGAAA<br>YYVGYLQPRTFLLKYNENGTITDAVDCALDPLSETKCTLKSFT<br>VEKGIYQTSNFRVQPTESIVRFPNITNLCPFDEVFNATRFASVY<br>AWNRKRISNCVADYSVLYNLAPFFTFKCYGVSPTKLNDLCFT<br>NVYADSFVIRGDEVRQIAPGQTGNIADYNYKLPDDFTGCVIA<br>WNSNKLDSKVSGNYNYLYRLFRKSNLKPFERDISTEIYQAGN<br>KPCNGVAGENCYFPLRSYSFRPTYGVGHQPYRVVVLSFELLH<br>APATVCGPKKSTNLVKNKCVNFNFNGLKGTGVLTESNKKFLP<br>FQQFGRDIADTTDAVRDPQTLEILDITPCSFGGVSVITPGTNTSN<br>QVAVLYQGVNCTEVPVAIHADQLTPTWRVYSTGSNVFQTRA<br>GCLIGAEYVNNSYECDIPIGAGICASYQTQTKSHRRARSVASQS<br>IIAYTMSLGAENSVAYSNNSIAIPTNFTISVTTEILPVSMTKTSV<br>DCTMYICGDSTECSNLLLQYGSFCTQLKRALTGIAVEQDKNTQ<br>EVFAQVKQIYKTPPIKYFGGFNFSQILPDPSKPSKRSFIEDLLEN<br>KVTLADAGFIKQYGDCLGDIAARDLICAQKFKGLTVLPPLLTD<br>EMIAQYTSALLAGTITSGWTFGAGAALQIPFAMQMAYRENGI<br>GVTQNVLYENQKLIANQFNSAIGKIQDSLSSTASALGKLQDVV<br>NHNAQALNTLVKQLSSKFGAISSVLNDIFSRLDPPEAEVQIDRL<br>ITGRLQSLQTYVTQQLIRAAEIRASANLAATKMSECVLGQSKR<br>VDFCGKGYHLMSFPQSAPHGVVFLHVTYVPAQEKNFTTAPAI<br>CHDGKAHFPREGVFVSNGTHWFVTQRNFYEPQIITTDNTFVSG<br>NCDVVIGIVNNTVYDPLQPELDSFKEELDKYFKNHTSPDVDLG<br>DISGINASVVNIQKEIDRLNEVAKNLNESLIDLQELGKYEQYIK<br>WPWYIWLGFIAGLIAIVMVTIMLCCMTSCCSCLKGCCSCGSCC | 42 |

TABLE 1-continued

| Sequence Listing | |
|---|---|
| | KFDEDDSEPVLKGVKLHYT |
| PolyA tail | 100 nt |

EQUIVALENTS

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one." It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean 10% of the recited numerical value.

Where a range of values is provided, each value between and including the upper and lower ends of the range are specifically contemplated and described herein.

What is claimed is:

1. A pharmaceutical composition comprising a messenger RNA (mRNA) comprising a nucleotide sequence encoding an immunogenic SARS-COV-2 Spike(S) protein, wherein the SARS-COV-2 S protein comprises: (a) at least 10 of the following mutations: A69-70, T951, G142D, ΔY144, R190S, K417N, N439K, E484K, S477N, T478K, N501Y, D614G, H655Y, and P681H, wherein said numbering is based upon the SARS-CoV-2 S protein set forth in SEQ ID NO:20; and (b) an amino acid sequence that is at least 97% identical to SEQ ID NO:14, or to an immunogenic fragment thereof; wherein the mRNA is formulated in lipid nanoparticles, and wherein the mRNA comprises a 5'-cap, a 5'-UTR, a 3'-UTR, a poly(A) sequence, and 1-methyl-pseudouridine substitutions at one or more uridine positions of the mRNA.

2. The pharmaceutical composition of claim 1, wherein the nucleotide sequence is at least 90% identical to SEQ ID NO:13.

3. The pharmaceutical composition of claim 1, wherein the nucleotide sequence is at least about 90% identical to SEQ ID NO:13.

4. The pharmaceutical composition of claim 1, wherein the mRNA comprises 1-methyl-pseudouridine substitutions at all uridine positions of the nucleotide sequence.

5. The pharmaceutical composition of claim 1, wherein the mRNA is present in an amount within a range of about 25 μg to about 100 μg.

6. The pharmaceutical composition of claim 1, wherein the mRNA is present in an amount of about 10 μg.

7. The pharmaceutical composition of claim 1, wherein the mRNA is present in an amount of about 30 μg.

8. A method of eliciting an immune response against SARS-COV-2 in a human subject, comprising administering to the human subject the pharmaceutical composition of claim 1 in an effective amount to induce the immune response.

9. A method of eliciting an immune response against SARS-COV-2 in a human subject, comprising administering to the human subject the pharmaceutical composition of claim 2 in an effective amount to induce the immune response.

10. A method of eliciting an immune response against SARS-COV-2 in a human subject, comprising administering to the human subject the pharmaceutical composition of claim 3 in an effective amount to induce the immune response.

11. A method of eliciting an immune response against SARS-COV-2 in a human subject, comprising administering to the human subject the pharmaceutical composition of claim 4 in an effective amount to induce the immune response.

12. A method of eliciting an immune response against SARS-COV-2 in a human subject, comprising administering to the human subject the pharmaceutical composition of claim 5 in an effective amount to induce the immune response.

13. A method of eliciting an immune response against SARS-COV-2 in a human subject, comprising administering to the human subject the pharmaceutical composition of claim 6 in an effective amount to induce the immune response.

14. A method of eliciting an immune response against SARS-COV-2 in a human subject, comprising administering to the human subject the pharmaceutical composition of claim 7 in an effective amount to induce the immune response.

* * * * *

SEQUENCE LISTING

```
Sequence total quantity: 53
SEQ ID NO: 1            moltype = RNA  length = 3995
FEATURE                 Location/Qualifiers
source                  1..3995
                        mol_type = other RNA
                        organism = synthetic construct
SEQUENCE: 1
gggaaataag agagaaaaga agagtaagaa gaaatataag accccggcgc cgccaccatg  60
ttcgtgttcc tggtgctgct gcccctggtg agcagccagt gcgtgaacct gaccacccgg  120
acccagctgc caccagccta caccaacagc ttcacccggg gcgtctacta ccccgacaag  180
gtgttccgga gcagcgtcct gcacagcacc caggacctgt tcctgccctt cttcagcaac  240
gtgacctggt tccacgccat ccacgtgagc ggcaccaacg gcaccaagcg gttcgacaac  300
cccgtgctgc ccttcaacga cggcgtgtac ttcgccagca ccgagaagag caacatcatc  360
cggggctgga tcttcggcac caccctggac agcaagaccc agagcctgct gatcgtgaat  420
aacgccacca acgtggtgat caaggtgtgc gagttccagt tctgcaacga ccccttcctg  480
ggcgtgtact accacaagaa caacaagagc tggatggaga gcgagttccg ggtgtacagc  540
agcgccaaca actgcacctt cgagtacgtg agccagccct tcctgatgga cctggagggc  600
aagcagggca acttcaagaa cctgcgggag ttcgtgttca agaacatcga cggctacttc  660
aagatctaca gcaagcacac ccccaatcaac ctggtgcggg atctgcccca gggcttctca  720
gccctggagc ccctggtgga cctgcccatc ggcatcaaca tcacccggtt ccagaccctg  780
ctggccctgc accggagcta cctgacccca ggcgacagca gcagcgggtg gacagcaggc  840
gcggctgctt actacgtggg ctacctgcag ccccggacct tcctgctgaa gtacaacgag  900
aacggcacca tcaccgacgc cgtggactgc gccctggacc ctctgagcga gaccaagtgc  960
accctgaaga gcttcaccgt ggagaagggc atctaccaga ccagcaactt ccgggtgcag  1020
cccaccgaga gcatcgtgcg gttccccaac atcaccaacc tgtgcccctt cggcgaggtg  1080
ttcaacgcca cccggttcgc cagcgtgtac gcctggaacc ggaagcggat cagcaactgc  1140
gtggccgact acagcgtgct gtacaacagc gccagcttca gcaccttcaa gtgctacggc  1200
gtgagcccca ccaagctgaa cgacctgtgc ttcaccaacg tgtacgccga cagcttcgtg  1260
atccgtggcg acgaggtgcg gcagatcgca cccggccaga caggcaagat cgccgactac  1320
aactacaagc tgcccgacga cttcaccggc tgcgtgatcg cctggaacag caacaacctc  1380
gacagcaagg tgggcggcaa ctacaactac ctgtaccggc tgttccggaa gagcaacctg  1440
aagcccttcg agcgggacat cagcaccgag atctaccaag ccggctccac cccttgcaac  1500
ggcgtgaagg gcttcaactg ctacttccct ctgcagagct acggcttcca gcccaccaac  1560
ggcgtgggct accagcccta ccgggtggtg gtgctgagct tcgagctgct gcacgcccca  1620
gccaccgtgt gtggccccaa gaagagcacc aacctggtga agaacaagtg cgtgaacttc  1680
aacttcaacg gccttaccgg caccggcgtg ctgaccgaga gcaacaagaa attcctgccc  1740
tttcagcagt tcggccggga catcgccgac accaccgacg ctgtgcggga tccccagacc  1800
ctggagatcc tggacatcac cccttgcagc ttcggcggcg tgagcgtgat caccccaggc  1860
accaacacca gcaaccaggt ggccgtgctg taccagggcg tgaactgcac cgaggtgccc  1920
gtggccatcc acgccgacca gctgacaccc acctggcggg tctacagcac cggcagcaac  1980
gtgttccaga cccgggccgg ttgcctgatc ggcgccgagc acgtgaacaa cagctacgag  2040
tgcgacatcc ccatcggcgc cggcatctgt gccagctacc agacccagac caattcaccc  2100
cggagggcaa ggagcgtggc cagccagagc atcatcgcct acaccatgag cctgggcgcc  2160
gagaacagcg tggcctacag caacaacagc atcgccatcc ccaccaactt caccatcagc  2220
gtgaccaccg agattctgcc cgtgagcatg accaagacca gcgtggactg caccatgtac  2280
atctgcggcg acagcaccga gtgcagcaac ctgctgctgc agtacggcag cttctgcacc  2340
cagctgaacc gggccctgac cggcatcgcc gtggagcagg acaagaacac ccaggaggtg  2400
ttcgcccagg tgaagcagat ctacaagacc cctcccatca aggacttcgg cggcttcaac  2460
ttcagccaga tcctgcccga ccccagcaag cccagcaagc ggagcttcat cgaggacctg  2520
```

```
ctgttcaaca aggtgaccct agccgacgcc ggcttcatca agcagtacgg cgactgcctc  2580
ggcgacatag ccgcccggga cctgatctgc gcccagaagt tcaacggcct gaccgtgctg  2640
cctcccctgc tgaccgacga gatgatcgcc cagtacacca gcgccctgtt agccggaacc  2700
atcaccagcg gctggacttt cggcgctgga gccgctctgc agatcccctt cgccatgcag  2760
atggcctacc ggttcaacgg catcggcgtg acccagaacg tgctgtacga gaaccagaag  2820
ctgatcgcca accagttcaa cagcgccatc ggcaagatcc aggacagcct gagcagcacc  2880
gctagcgccc tgggcaagct gcaggacgtg gtgaaccaga acgcccaggc cctgaacacc  2940
ctggtgaagc agctgagcag caacttcggc gccatcagca gcgtgctgaa cgacatcctg  3000
agccggctgg accctcccga ggccgaggtg cagatcgacc ggctgatcac tggccggctg  3060
cagagcctgc agacctacgt gacccagcag ctgatccggg ccgccgagat tcgggccagc  3120
gccaacctgg ccgccaccaa gatgagcgag tgcgtgctgg gccagagcaa gcgggtggac  3180
ttctgcggca agggctacca cctgatgagc tttccccaga gcgcacccca cggagtggtg  3240
ttcctgcacg tgacctacgt gcccgcccag gagaagaact tcaccaccgc cccagccatc  3300
tgccacgacg gcaaggccca ctttccccgg gagggcgtgt tcgtgagcaa cggcacccac  3360
tggttcgtga cccagcggaa cttctacgag ccccagatca tcaccaccga caacaccttc  3420
gtgagcggca actgcgacgt ggtgatcggc atcgtgaaca acaccgtgta cgatcccctg  3480
cagcccgagc tggacagctt caaggaggag ctggacaagt acttcaagaa tcacaccagc  3540
cccgacgtgg acctgggcga catcagcggc atcaacgcca gcgtggtgaa catccagaag  3600
gagatcgatc ggctgaacga ggtggccaag aacctgaacg agagcctgat cgacctgcag  3660
gagctgggca agtacgagca gtacatcaag tggccctggt acatctggct gggcttcatc  3720
gccggcctga tcgccatcgt gatggtgacc atcatgctgt gctgcatgac cagctgctgc  3780
agctgcctga agggctgttg cagctgcggc agctgctgca agttcgacga ggacgacagc  3840
gagcccgtgc tgaagggcgt gaagctgcac tacacctgat aataggctgg agcctcggtg  3900
gcctagcttc ttgccccttg ggcctccccc cagcccctcc tccccttcct gcacccgtac  3960
ccccgtggtc tttgaataaa gtctgagtgg gcggc                             3995

SEQ ID NO: 2            moltype = RNA  length = 57
FEATURE                 Location/Qualifiers
source                  1..57
                        mol_type = other RNA
                        organism = synthetic construct
SEQUENCE: 2
gggaaataag agagaaaaga agagtaagaa gaaatataag accccggcgc cgccacc     57

SEQ ID NO: 3            moltype = RNA  length = 3819
FEATURE                 Location/Qualifiers
source                  1..3819
                        mol_type = other RNA
                        organism = synthetic construct
SEQUENCE: 3
atgttcgtgt tcctggtgct gctgcccctg gtgagcagcc agtgcgtgaa cctgaccacc  60
cggacccagc tgccaccagc ctacaccaac agcttcaccc ggggcgtcta ctaccccgac  120
aaggtgttcc ggagcagcgt cctgcacagc acccaggacc tgttcctgcc cttcttcagc  180
aacgtgacct ggttccacgc catccacgtg agcggcacca acggcaccaa gcggttcgac  240
aaccccgtgc tgcccttcaa cgacggcgtg tacttcgcca gcaccgagaa gagcaacatc  300
atccggggct ggatcttcgg caccaccctg gacagcaaga cccagagcct gctgatcgtg  360
aataacgcca ccaacgtggt gatcaaggtg tgcgagttcc agttctgcaa cgaccccttc  420
ctgggcgtgt actaccacaa gaacaacaag agctggatgg agagcgagtt ccgggtgtac  480
agcagcgcca acaactgcac cttcgagtac gtgagccagc ccttcctgat ggacctggag  540
ggcaagcagg gcaacttcaa gaacctgcgg gagttcgtgt tcaagaacat cgacggctac  600
ttcaagatct acagcaagca caccccaatc aacctggtgc gggatctgcc ccagggcttc  660
tcagccctgg agcccctggt ggacctgccc atcggcatca acatcacccg gttccagacc  720
ctgctggccc tgcaccggag ctacctgacc ccaggcgaca gcagcagcgg gtggacagca  780
ggcgcggctg cttactacgt gggctacctg cagccccgga ccttcctgct gaagtacaac  840
gagaacggca ccatcaccga cgccgtggac tgcgccctgg accctctgag cgagaccaag  900
tgcaccctga agagcttcac cgtggagaag ggcatctacc agaccagcaa cttccgggtg  960
cagcccaccg agagcatcgt gcggttcccc aacatcacca acctgtgccc cttcggcgag  1020
gtgttcaacg ccacccggtt cgccagcgtg tacgcctgga accggaagcg gatcagcaac  1080
tgcgtggccg actacagcgt gctgtacaac agcgccagct tcagcacctt caagtgctac  1140
ggcgtgagcc ccaccaagct gaacgacctg tgcttcacca acgtgtacgc cgacagcttc  1200
gtgatccgtg gcgacgaggt gcggcagatc gcacccggcc agacaggcaa gatcgccgac  1260
tacaactaca agctgcccga cgacttcacc ggctgcgtga tcgcctggaa cagcaacaac  1320
ctcgacagca aggtgggcgg caactacaac tacctgtacc ggctgttccg gaagagcaac  1380
ctgaagccct tcgagcggga catcagcacc gagatctacc aagccggctc caccccttgc  1440
aacggcgtga agggcttcaa ctgctacttc cctctgcaga gctacggctt ccagcccacc  1500
aacggcgtgg gctaccagcc ctaccgggtg gtggtgctga gcttcgagct gctgcacgcc  1560
ccagccaccg tgtgtggccc caagaagagc accaacctgg tgaagaacaa gtgcgtgaac  1620
ttcaacttca acggccttac cggcaccggc gtgctgaccg agagcaacaa gaaattcctg  1680
ccctttcagc agttcggccg ggacatcgcc gacaccaccg acgctgtgcg ggatccccag  1740
accctggaga tcctggacat caccccttgc agcttcggcg gcgtgagcgt gatcacccca  1800
ggcaccaaca ccagcaacca ggtggccgtg ctgtaccagg gcgtgaactg caccgaggtg  1860
cccgtggcca tccacgccga ccagctgaca cccacctggc gggtctacag caccggcagc  1920
aacgtgttcc agacccgggc cggttgcctg atcggcgccg agcacgtgaa caacagctac  1980
gagtgcgaca tccccatcgg cgccggcatc tgtgccagct accagaccca gaccaattca  2040
ccccggaggg caaggagcgt ggccagccag agcatcatcg cctacaccat gagcctgggc  2100
gccgagaaca gcgtggccta cagcaacaac agcatcgcca tccccaccaa cttcaccatc  2160
agcgtgacca ccgagattct gcccgtgagc atgaccaaga ccagcgtgga ctgcaccatg  2220
tacatctgcg gcgacagcac cgagtgcagc aacctgctgc tgcagtacgg cagcttctgc  2280
acccagctga accgggccct gaccggcatc gccgtggagc aggacaagaa cacccaggag  2340
```

```
gtgttcgccc aggtgaagca gatctacaag accccctccca tcaaggactt cggcggcttc  2400
aacttcagcc agatcctgcc cgaccccagc aagcccagca agcggagctt catcgaggac  2460
ctgctgttca acaaggtgac cctagccgac gccggcttca tcaagcagta cggcgactgc  2520
ctcggcgaca tagccgcccg ggacctgatc tgcgcccaga agttcaacgg cctgaccgtg  2580
ctgcctcccc tgctgaccga cgagatgatc gcccagtaca ccagcgccct gttagccgga  2640
accatcacca gcggctggac tttcggcgct ggagccgctc tgcagatccc cttcgccatg  2700
cagatggcct accggttcaa cggcatcggc gtgacccaga acgtgctgta cgagaaccag  2760
aagctgatcg ccaaccagtt caacagcgcc atcggcaaga tccaggacag cctgagcagc  2820
accgctagcg ccctgggcaa gctgcaggac gtggtgaacc agaacgccca ggccctgaac  2880
accctggtga agcagctgag cagcaacttc ggcgccatca gcagcgtgct gaacgacatc  2940
ctgagccggc tggaccctcc cgaggccgag gtgcagatcg accggctgat cactggccgg  3000
ctgcagagcc tgcagaccta cgtgacccag cagctgatcc gggccgccga gattcgggcc  3060
agcgccaacc tggccgccac caagatgagc gagtgcgtgc tgggccagag caagcgggtg  3120
gacttctgcg gcaagggcta ccacctgatg agctttcccc agagcgcacc ccacggagtg  3180
gtgttcctgc acgtgaccta cgtgcccgcc caggagaaga acttcaccac cgccccagcc  3240
atctgccacg acggcaaggc ccactttccc cgggagggcg tgttcgtgag caacggcacc  3300
cactggttcg tgacccagcg gaacttctac gagccccaga tcatcaccac cgacaacacc  3360
ttcgtgagcg gcaactgcga cgtggtgatc ggcatcgtga acaacaccgt gtacgatccc  3420
ctgcagcccg agctggacag cttcaaggag gagctggaca agtacttcaa gaatcacacc  3480
agccccgacg tggacctggg cgacatcagc ggcatcaacg ccagcgtggt gaacatccag  3540
aaggagatcg atcggctgaa cgaggtggcc aagaacctga acgagagcct gatcgacctg  3600
caggagctgg gcaagtacga gcagtacatc aagtggccct ggtacatctg gctgggcttc  3660
atcgccggcc tgatcgccat cgtgatggtg accatcatgc tgtgctgcat gaccagctgc  3720
tgcagctgcc tgaagggctg ttgcagctgc ggcagctgct gcaagttcga cgaggacgac  3780
agcgagcccg tgctgaaggg cgtgaagctg cactacacc                          3819

SEQ ID NO: 4            moltype = RNA  length = 119
FEATURE                 Location/Qualifiers
source                  1..119
                        mol_type = other RNA
                        organism = synthetic construct
SEQUENCE: 4
tgataatagg ctggagcctc ggtggcctag cttcttgccc cttgggcctc cccccagccc  60
ctcctcccct tcctgcaccc gtacccccgt ggtctttgaa taaagtctga gtgggcggc   119

SEQ ID NO: 5            moltype = AA  length = 1273
FEATURE                 Location/Qualifiers
source                  1..1273
                        mol_type = protein
                        organism = synthetic construct
SEQUENCE: 5
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVKGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQGVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDPPEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                      1273

SEQ ID NO: 6            moltype = RNA  length = 3995
FEATURE                 Location/Qualifiers
source                  1..3995
                        mol_type = other RNA
                        organism = synthetic construct
SEQUENCE: 6
gggaaataag agagaaaaga agagtaagaa gaaatataag accccggcgc cgccaccatg  60
ttcgtgttcc tggtgctgct gcccctggtg agcagccagt gcgtgaacct gaccacccgg  120
acccagctgc caccagccta caccaacagc ttcacccggg gcgtctacta ccccgacaag  180
gtgttccgga gcagcgtcct gcacagcacc caggacctgt tcctgccctt cttcagcaac  240
gtgacctggt tccacgccat ccacgtgagc ggcaccaacg gcaccaagcg gttcgacaac  300
cccgtgctgc ccttcaacga cggcgtgtac ttcgccagca ccgagaagag caacatcatc  360
cggggctgga tcttcggcac caccctggac agcaagaccc agagcctgct gatcgtgaat  420
aacgccacca acgtggtgat caaggtgtgc gagttccagt tctgcaacga ccccttcctg  480
ggcgtgtact accacaagaa caacaagagc tggatggaga gcgagttccg ggtgtacagc  540
```

-continued

```
agcgccaaca actgcacctt cgagtacgtg agccagccct tcctgatgga cctggagggc  600
aagcagggca acttcaagaa cctgcgggag ttcgtgttca agaacatcga cggctacttc  660
aagatctaca gcaagcacac cccaatcaac ctggtgcggg atctgcccca gggcttctca  720
gccctggagc ccctggtgga cctgcccatc ggcatcaaca tcacccggtt ccagaccctg  780
ctggccctgc accggagcta cctgacccca ggcgacagca gcagcgggtg gacagcaggc  840
gcggctgctt actacgtggg ctacctgcag ccccggacct tcctgctgaa gtacaacgag  900
aacggcacca tcaccgacgc cgtggactgc gccctggacc ctctgagcga gaccaagtgc  960
accctgaaga gcttcaccgt ggagaagggc atctaccaga ccagcaactt ccgggtgcag  1020
cccaccgaga gcatcgtgcg gttccccaac atcaccaacc tgtgcccctt cggcgaggtg  1080
ttcaacgcca cccggttcgc cagcgtgtac gcctggaacc ggaagcggat cagcaactgc  1140
gtggccgact acagcgtgct gtacaacagc gccagcttca gcaccttcaa gtgctacggc  1200
gtgagcccca ccaagctgaa cgacctgtgc ttcaccaacg tgtacgccga cagcttcgtg  1260
atccgtggcg acgaggtgcg gcagatcgca cccggccaga caggcaacat cgccgactac  1320
aactacaagc tgcccgacga cttcaccggc tgcgtgatcg cctggaacag caacaacctc  1380
gacagcaagg tgggcggcaa ctacaactac ctgtaccggc tgttccggaa gagcaacctg  1440
aagcccttcg agcgggacat cagcaccgag atctaccaag ccggctccac cccttgcaac  1500
ggcgtgaagg gcttcaactg ctacttccct ctgcagagct acggcttcca gcccacctac  1560
ggcgtgggct accagcccta ccgggtggtg gtgctgagct tcgagctgct gcacgcccca  1620
gccaccgtgt gtggccccaa gaagagcacc aacctggtga agaacaagtg cgtgaacttc  1680
aacttcaacg gccttaccgg caccggcgtg ctgaccgaga gcaacaagaa attcctgccc  1740
tttcagcagt tcggccggga catcgccgac accaccgacg ctgtgcggga tccccagacc  1800
ctggagatcc tggacatcac cccttgcagc ttcggcggcg tgagcgtgat caccccaggc  1860
accaacacca gcaaccaggt ggccgtgctg taccagggcg tgaactgcac cgaggtgccc  1920
gtggccatcc acgccgacca gctgacaccc acctggcggg tctacagcac cggcagcaac  1980
gtgttccaga cccgggccgg ttgcctgatc ggcgccgagc acgtgaacaa cagctacgag  2040
tgcgacatcc ccatcggcgc cggcatctgt gccagctacc agacccagac caattcaccc  2100
cggagggcaa ggagcgtggc cagccagagc atcatcgcct acaccatgag cctgggcgcc  2160
gagaacagcg tggcctacag caacaacagc atcgccatcc ccaccaactt caccatcagc  2220
gtgaccaccg agattctgcc cgtgagcatg accaagacca gcgtggactg caccatgtac  2280
atctgcggcg acagcaccga gtgcagcaac ctgctgctgc agtacggcag cttctgcacc  2340
cagctgaacc gggccctgac cggcatcgcc gtggagcagg acaagaacac ccaggaggtg  2400
ttcgcccagg tgaagcagat ctacaagacc cctcccatca aggacttcgg cggcttcaac  2460
ttcagccaga tcctgcccga ccccagcaag cccagcaagc ggagcttcat cgaggacctg  2520
ctgttcaaca aggtgaccct agccgacgcc ggcttcatca agcagtacgg cgactgcctc  2580
ggcgacatag ccgcccggga cctgatctgc gcccagaagt tcaacggcct gaccgtgctg  2640
cctcccctgc tgaccgacga gatgatcgcc cagtacacca gcgccctgtt agccggaacc  2700
atcaccagcg gctggacttt cggcgctgga gccgctctgc agatcccctt cgccatgcag  2760
atggcctacc ggttcaacgg catcggcgtg acccagaacg tgctgtacga gaaccagaag  2820
ctgatcgcca accagttcaa cagcgccatc ggcaagatcc aggacagcct gagcagcacc  2880
gctagcgccc tgggcaagct gcaggacgtg gtgaaccaga acgcccaggc cctgaacacc  2940
ctggtgaagc agctgagcag caacttcggc gccatcagca gcgtgctgaa cgacatcctg  3000
agccggctgg accctcccga ggccgaggtg cagatcgacc ggctgatcac tggccggctg  3060
cagagcctgc agacctacgt gacccagcag ctgatccggg ccgccgagat tcgggccagc  3120
gccaacctgg ccgccaccaa gatgagcgag tgcgtgctgg gccagagcaa gcgggtggac  3180
ttctgcggca agggctacca cctgatgagc tttccccaga gcgcacccca cggagtggtg  3240
ttcctgcacg tgacctacgt gcccgcccag gagaagaact tcaccaccgc cccagccatc  3300
tgccacgacg gcaaggccca ctttccccgg gagggcgtgt tcgtgagcaa cggcacccac  3360
tggttcgtga cccagcggaa cttctacgag ccccagatca tcaccaccga caacaccttc  3420
gtgagcggca actgcgacgt ggtgatcggc atcgtgaaca acaccgtgta cgatcccctg  3480
cagcccgagc tggacagctt caaggaggag ctggacaagt acttcaagaa tcacaccagc  3540
cccgacgtgg acctgggcga catcagcggc atcaacgcca gcgtggtgaa catccagaag  3600
gagatcgatc ggctgaacga ggtggccaag aacctgaacg agagcctgat cgacctgcag  3660
gagctgggca agtacgagca gtacatcaag tggccctggt acatctggct gggcttcatc  3720
gccggcctga tcgccatcgt gatggtgacc atcatgctgt gctgcatgac cagctgctgc  3780
agctgcctga agggctgttg cagctgcggc agctgctgca agttcgacga ggacgacagc  3840
gagcccgtgc tgaagggcgt gaagctgcac tacacctgat aataggctgg agcctcggtg  3900
gcctagcttc ttgccccttg ggcctccccc cagcccctcc tccccttcct gcacccgtac  3960
cccgtggtc tttgaataaa gtctgagtgg gcggc                              3995
```

```
SEQ ID NO: 7           moltype = RNA  length = 3819
FEATURE                Location/Qualifiers
source                 1..3819
                       mol_type = other RNA
                       organism = synthetic construct
SEQUENCE: 7
atgttcgtgt tcctggtgct gctgcccctg gtgagcagcc agtgcgtgaa cctgaccacc  60
cggacccagc tgccaccagc ctacaccaac agcttcaccc ggggcgtcta ctaccccgac  120
aaggtgttcc ggagcagcgt cctgcacagc acccaggacc tgttcctgcc cttcttcagc  180
aacgtgacct ggttccacgc catccacgtg agcggcacca acggcaccaa gcggttcgac  240
aaccccgtgc tgcccttcaa cgacggcgtg tacttcgcca gcaccgagaa gagcaacatc  300
atccggggct ggatcttcgg caccaccctg gacagcaaga cccagagcct gctgatcgtg  360
aataacgcca ccaacgtggt gatcaaggtg tgcgagttcc agttctgcaa cgaccccttc  420
ctgggcgtgt actaccacaa gaacaacaag agctggatgg agagcgagtt ccgggtgtac  480
agcagcgcca acaactgcac cttcgagtac gtgagccagc ccttcctgat ggacctggag  540
ggcaagcagg gcaacttcaa gaacctgcgg gagttcgtgt tcaagaacat cgacggctac  600
ttcaagatct acagcaagca caccccaatc aacctggtgc gggatctgcc ccagggcttc  660
tcagccctgg agcccctggt ggacctgccc atcggcatca acatcacccg gttccagacc  720
ctgctggccc tgcaccggag ctacctgacc ccaggcgaca gcagcagcgg gtggacagca  780
ggcgcggctg cttactacgt gggctacctg cagccccgga ccttcctgct gaagtacaac  840
```

-continued

```
gagaacggca ccatcaccga cgccgtggac tgcgccctgg accctctgag cgagaccaag  900
tgcaccctga agagcttcac cgtggagaag ggcatctacc agaccagcaa cttccgggtg  960
cagcccaccg agagcatcgt gcggttcccc aacatcacca acctgtgccc cttcggcgag  1020
gtgttcaacg ccacccggtt cgccagcgtg tacgcctgga accggaagcg gatcagcaac  1080
tgcgtggccg actacagcgt gctgtacaac agcgccagct tcagcacctt caagtgctac  1140
ggcgtgagcc ccaccaagct gaacgacctg tgcttcacca acgtgtacgc cgacagcttc  1200
gtgatccgtg gcgacgaggt gcggcagatc gcacccggcc agacaggcaa catcgccgac  1260
tacaactaca agctgcccga cgacttcacc ggctgcgtga tcgcctggaa cagcaacaac  1320
ctcgacagca aggtgggcgg caactacaac tacctgtacc ggctgttccg gaagagcaac  1380
ctgaagccct tcgagcggga catcagcacc gagatctacc aagccggctc caccccttgc  1440
aacggcgtga agggcttcaa ctgctacttc cctctgcaga gctacggctt ccagcccacc  1500
tacggcgtgg gctaccagcc ctaccgggtg gtggtgctga gcttcgagct gctgcacgcc  1560
ccagccaccg tgtgtggccc caagaagagc accaacctgg tgaagaacaa gtgcgtgaac  1620
ttcaacttca acggccttac cggcaccggc gtgctgaccg agagcaacaa gaaattcctg  1680
ccctttcagc agttcggccg ggacatcgcc gacaccaccg acgctgtgcg ggatccccag  1740
accctggaga tcctggacat caccccttgc agcttcggcg gcgtgagcgt gatcacccca  1800
ggcaccaaca ccagcaacca ggtggccgtg ctgtaccagg gcgtgaactg caccgaggtg  1860
cccgtggcca tccacgccga ccagctgaca cccacctggc gggtctacag caccggcagc  1920
aacgtgttcc agacccgggc cggttgcctg atcggcgccg agcacgtgaa caacagctac  1980
gagtgcgaca tccccatcgg cgccggcatc tgtgccagct accagaccca gaccaattca  2040
ccccggaggg caaggagcgt ggccagccag agcatcatcg cctacaccat gagcctgggc  2100
gccgagaaca gcgtggccta cagcaacaac agcatcgcca tccccaccaa cttcaccatc  2160
agcgtgacca ccgagattct gcccgtgagc atgaccaaga ccagcgtgga ctgcaccatg  2220
tacatctgcg gcgacagcac cgagtgcagc aacctgctgc tgcagtacgg cagcttctgc  2280
acccagctga accgggccct gaccggcatc gccgtggagc aggacaagaa cacccaggag  2340
gtgttcgccc aggtgaagca gatctacaag acccctccca tcaaggactt cggcggcttc  2400
aacttcagcc agatcctgcc cgaccccagc aagcccagca agcggagctt catcgaggac  2460
ctgctgttca acaaggtgac cctagccgac gccggcttca tcaagcagta cggcgactgc  2520
ctcggcgaca tagccgcccg ggacctgatc tgcgcccaga agttcaacgg cctgaccgtg  2580
ctgcctcccc tgctgaccga cgagatgatc gcccagtaca ccagcgccct gttagccgga  2640
accatcacca gcggctggac tttcggcgct ggagccgctc tgcagatccc cttcgccatg  2700
cagatggcct accggttcaa cggcatcggc gtgacccaga acgtgctgta cgagaaccag  2760
aagctgatcg ccaaccagtt caacagcgcc atcggcaaga tccaggacag cctgagcagc  2820
accgctagcg ccctgggcaa gctgcaggac gtggtgaacc agaacgccca ggccctgaac  2880
accctggtga agcagctgag cagcaacttc ggcgccatca gcagcgtgct gaacgacatc  2940
ctgagccggc tggaccctcc cgaggccgag gtgcagatcg accggctgat cactggccgg  3000
ctgcagagcc tgcagaccta cgtgacccag cagctgatcc gggccgccga gattcgggcc  3060
agcgccaacc tggccgccac caagatgagc gagtgcgtgc tgggccagag caagcgggtg  3120
gacttctgcg gcaagggcta ccacctgatg agctttcccc agagcgcacc ccacggagtg  3180
gtgttcctgc acgtgaccta cgtgcccgcc caggagaaga acttcaccac cgccccagcc  3240
atctgccacg acggcaaggc ccactttccc cgggagggcg tgttcgtgag caacggcacc  3300
cactggttcg tgacccagcg gaacttctac gagccccaga tcatcaccac cgacaacacc  3360
ttcgtgagcg gcaactgcga cgtggtgatc ggcatcgtga acaacaccgt gtacgatccc  3420
ctgcagcccg agctggacag cttcaaggag gagctggaca agtacttcaa gaatcacacc  3480
agccccgacg tggacctggg cgacatcagc ggcatcaacg ccagcgtggt gaacatccag  3540
aaggagatcg atcggctgaa cgaggtggcc aagaacctga acgagagcct gatcgacctg  3600
caggagctgg gcaagtacga gcagtacatc aagtggccct ggtacatctg gctgggcttc  3660
atcgccggcc tgatcgccat cgtgatggtg accatcatgc tgtgctgcat gaccagctgc  3720
tgcagctgcc tgaagggctg ttgcagctgc ggcagctgct gcaagttcga cgaggacgac  3780
agcgagcccg tgctgaaggg cgtgaagctg cactacacc                        3819

SEQ ID NO: 8            moltype = AA  length = 1273
FEATURE                 Location/Qualifiers
source                  1..1273
                        mol_type = protein
                        organism = synthetic construct
SEQUENCE: 8
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGNIAD  420
YNYKLPDDFT GCVIAWNSNN LDSKVGGNYN YLYRLFRKSN LKPFERDIST EIYQAGSTPC  480
NGVKGFNCYF PLQSYGFQPT YGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQGVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDPPEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                    1273
```

```
SEQ ID NO: 9            moltype = RNA  length = 3986
FEATURE                 Location/Qualifiers
source                  1..3986
                        mol_type = other RNA
                        organism = synthetic construct
SEQUENCE: 9
gggaaataag agagaaaaga agagtaagaa gaaatataag accccggcgc cgccaccatg  60
ttcgtgttcc tggtgctgct gcccctggtg agcagccagt gcgtgaactt taccacccgg  120
acccagctgc caccagccta caccaacagc ttcacccggg gcgtctacta ccccgacaag  180
gtgttccgga gcagcgtcct gcacagcacc caggacctgt tcctgccctt cttcagcaac  240
gtgacctggt tccacgccat ccacgtgagc ggcaccaacg gcaccaagcg gttcgccaac  300
cccgtgctgc ccttcaacga cggcgtgtac ttcgccagca ccgagaagag caacatcatc  360
cggggctgga tcttcggcac caccctggac agcaagaccc agagcctgct gatcgtgaat  420
aacgccacca acgtggtgat caaggtgtgc gagttccagt tctgcaacga ccccttcctg  480
ggcgtgtact accacaagaa caacaagagc tggatggaga gcgagttccg ggtgtacagc  540
agcgccaaca actgcacctt cgagtacgtg agccagccct tcctgatgga cctggagggc  600
aagcagggca acttcaagaa cctgcgggag ttcgtgttca agaacatcga cggctacttc  660
aagatctaca gcaagcacac ccccaatcaac ctggtgcggg gcctgcccca gggcttctca  720
gccctggagc ccctggtgga cctgcccatc ggcatcaaca tcacccggtt ccagaccctg  780
cacatcagct acctgacccc aggcgacagc agcagcgggt ggacagcagg cgcggctgct  840
tactacgtgg gctacctgca gccccggacc ttcctgctga agtacaacga gaacggcacc  900
atcaccgacg ccgtggactg cgccctggac cctctgagcg agaccaagtg caccctgaag  960
agcttcaccg tggagaaggg catctaccag accagcaact tccgggtgca gcccaccgag  1020
agcatcgtgc ggttccccaa catcaccaac ctgtgcccct tcggcgaggt gttcaacgcc  1080
acccggttcg ccagcgtgta cgcctggaac cggaagcgga tcagcaactg cgtggccgac  1140
tacagcgtgc tgtacaacag cgccagcttc agcaccttca agtgctacgg cgtgagcccc  1200
accaagctga acgacctgtg cttcaccaac gtgtacgccg acagcttcgt gatccgtggc  1260
gacgaggtgc ggcagatcgc acccggccag acaggcaaca tcgccgacta caactacaag  1320
ctgcccgacg acttcaccgg ctgcgtgatc gcctggaaca gcaacaacct cgacagcaag  1380
gtgggcggca actacaacta cctgtaccgg ctgttccgga agagcaacct gaagcccttc  1440
gagcgggaca tcagcaccga gatctaccaa gccggctcca ccccttgcaa cggcgtgaag  1500
ggcttcaact gctacttccc tctgcagagc tacggcttcc agcccaccta cggcgtgggc  1560
taccagccct accgggtggt ggtgctgagc ttcgagctgc tgcacgcccc agccaccgtg  1620
tgtggcccca agaagagcac caacctggtg aagaacaagt gcgtgaactt caacttcaac  1680
ggccttaccg gcaccggcgt gctgaccgag agcaacaaga aattcctgcc ctttcagcag  1740
ttcggccggg acatcgccga caccaccgac gctgtgcggg atccccagac cctggagatc  1800
ctggacatca ccccttgcag cttcggcggc gtgagcgtga tcaccccagg caccaacacc  1860
agcaaccagg tggccgtgct gtaccagggc gtgaactgca ccgaggtgcc cgtggccatc  1920
cacgccgacc agctgacacc cacctggcgg gtctacagca ccggcagcaa cgtgttccag  1980
acccgggccg gttgcctgat cggcgccgag cacgtgaaca acagctacga gtgcgacatc  2040
cccatcggcg ccggcatctg tgccagctac cagacccaga ccaattcacc ccggagggca  2100
aggagcgtgg ccagccagag catcatcgcc tacaccatga gcctgggcgt ggagaacagc  2160
gtggcctaca gcaacaacag catcgccatc cccaccaact tcaccatcag cgtgaccacc  2220
gagattctgc ccgtgagcat gaccaagacc agcgtggact gcaccatgta catctgcggc  2280
gacagcaccg agtgcagcaa cctgctgctg cagtacggca gcttctgcac ccagctgaac  2340
cgggccctga ccggcatcgc cgtggagcag gacaagaaca cccaggaggt gttcgcccag  2400
gtgaagcaga tctacaagac ccctcccatc aaggacttcg gcggcttcaa cttcagccag  2460
atcctgcccg accccagcaa gcccagcaag cggagcttca tcgaggacct gctgttcaac  2520
aaggtgaccc tagccgacgc cggcttcatc aagcagtacg gcgactgcct cggcgacata  2580
gccgcccggg acctgatctg cgcccagaag ttcaacggcc tgaccgtgct gcctcccctg  2640
ctgaccgacg agatgatcgc ccagtacacc agcgccctgt tagccggaac catcaccagc  2700
ggctggactt tcggcgctgg agccgctctg cagatcccct tcgccatgca gatggcctac  2760
cggttcaacg gcatcggcgt gacccagaac gtgctgtacg agaaccagaa gctgatcgcc  2820
aaccagttca acagcgccat cggcaagatc caggacagcc tgagcagcac cgctagcgcc  2880
ctgggcaagc tgcaggacgt ggtgaaccag aacgcccagg ccctgaacac cctggtgaag  2940
cagctgagca gcaacttcgg cgccatcagc agcgtgctga acgacatcct gagccggctg  3000
gaccctcccg aggccgaggt gcagatcgac cggctgatca ctggccggct gcagagcctg  3060
cagacctacg tgacccagca gctgatccgg gccgccgaga ttcgggccag cgccaacctg  3120
gccgccacca agatgagcga gtgcgtgctg ggccagagca agcgggtgga cttctgcggc  3180
aagggctacc acctgatgag ctttccccag agcgcacccc acggagtggt gttcctgcac  3240
gtgacctacg tgcccgccca ggagaagaac ttcaccaccg ccccagccat ctgccacgac  3300
ggcaaggccc actttccccg ggagggcgtg ttcgtgagca acggcaccca ctggttcgtg  3360
acccagcgga acttctacga gccccagatc atcaccaccg acaacacctt cgtgagcggc  3420
aactgcgacg tggtgatcgg catcgtgaac aacaccgtgt acgatcccct gcagcccgag  3480
ctggacagct tcaaggagga gctggacaag tacttcaaga atcacaccag ccccgacgtg  3540
gacctgggcg acatcagcgg catcaacgcc agcgtggtga acatccagaa ggagatcgat  3600
cggctgaacg aggtggccaa gaacctgaac gagagcctga tcgacctgca ggagctgggc  3660
aagtacgagc agtacatcaa gtggccctgg tacatctggc tgggcttcat cgccggcctg  3720
atcgccatcg tgatggtgac catcatgctg tgctgcatga ccagctgctg cagctgcctg  3780
aagggctgtt gcagctgcgg cagctgctgc aagttcgacg aggacgacag cgagcccgtg  3840
ctgaagggcg tgaagctgca ctacacctga taataggctg gagcctcggt ggcctagctt  3900
cttgcccctt gggcctcccc ccagcccctc ctccccttcc tgcacccgta cccccgtggt  3960
ctttgaataa agtctgagtg ggcggc                                    3986

SEQ ID NO: 10           moltype = RNA  length = 3810
FEATURE                 Location/Qualifiers
source                  1..3810
                        mol_type = other RNA
```

```
                         organism = synthetic construct
SEQUENCE: 10
atgttcgtgt tcctggtgct gctgcccctg gtgagcagcc agtgcgtgaa ctttaccacc  60
cggacccagc tgccaccagc ctacaccaac agcttcaccc ggggcgtcta ctaccccgac  120
aaggtgttcc ggagcagcgt cctgcacagc acccaggacc tgttcctgcc cttcttcagc  180
aacgtgacct ggttccacgc catccacgtg agcggcacca acggcaccaa gcggttcgcc  240
aaccccgtgc tgcccttcaa cgacggcgtg tacttcgcca gcaccgagaa gagcaacatc  300
atccggggct ggatcttcgg caccaccctg gacagcaaga cccagagcct gctgatcgtg  360
aataacgcca ccaacgtggt gatcaaggtg tgcgagttcc agttctgcaa cgaccccttc  420
ctgggcgtgt actaccacaa gaacaacaag agctggatgg agagcgagtt ccgggtgtac  480
agcagcgcca acaactgcac cttcgagtac gtgagccagc ccttcctgat ggacctggag  540
ggcaagcagg gcaacttcaa gaacctgcgg gagttcgtgt tcaagaacat cgacggctac  600
ttcaagatct acagcaagca caccccaatc aacctggtgc ggggcctgcc ccagggcttc  660
tcagccctgg agcccctggt ggacctgccc atcggcatca acatcacccg gttccagacc  720
ctgcacatca gctacctgac ccccggcgac agcagcagcg ggtggacagc aggcgcggct  780
gcttactacg tgggctacct gcagccccgg accttcctgc tgaagtacaa cgagaacggc  840
accatcaccg acgccgtgga ctgcgccctg gaccctctga gcgagaccaa gtgcaccctg  900
aagagcttca ccgtggagaa gggcatctac cagaccagca acttccgggt gcagcccacc  960
gagagcatcg tgcggttccc caacatcacc aacctgtgcc ccttcggcga ggtgttcaac  1020
gccacccggt tcgccagcgt gtacgcctgg aaccggaagc ggatcagcaa ctgcgtggcc  1080
gactacagcg tgctgtacaa cagcgccagc ttcagcacct tcaagtgcta cggcgtgagc  1140
cccaccaagc tgaacgacct gtgcttcacc aacgtgtacg ccgacagctt cgtgatccgt  1200
ggcgacgagg tgcggcagat cgcacccggc cagacaggca acatcgccga ctacaactac  1260
aagctgcccg acgacttcac cggctgcgtg atcgcctgga acagcaacaa cctcgacagc  1320
aaggtgggcg gcaactacaa ctacctgtac cggctgttcc ggaagagcaa cctgaagccc  1380
ttcgagcggg acatcagcac cgagatctac caagccggct ccaccccttg caacggcgtg  1440
aagggcttca actgctactt ccctctgcag agctacggct tccagcccac ctacggcgtg  1500
ggctaccagc cctaccgggt ggtggtgctg agcttcgagc tgctgcacgc cccagccacc  1560
gtgtgtggcc ccaagaagag caccaacctg gtgaagaaca agtgcgtgaa cttcaacttc  1620
aacggcctta ccggcaccgg cgtgctgacc gagagcaaca agaaattcct gccctttcag  1680
cagttcggcc gggacatcgc cgacaccacc gacgctgtgc gggatcccca gaccctggag  1740
atcctggaca tcacccctt g cagcttcggc ggcgtgagcg tgatcacccc aggcaccaac  1800
accagcaacc aggtggccgt gctgtaccag ggcgtgaact gcaccgaggt gcccgtggcc  1860
atccacgccg accagctgac acccacctgg cgggtctaca gcaccggcag caacgtgttc  1920
cagacccggg ccggttgcct gatcggcgcc gagcacgtga acaacagcta cgagtgcgac  1980
atccccatcg gcgccggcat ctgtgccagc taccagaccc agaccaattc accccggagg  2040
gcaaggagcg tggccagcca gagcatcatc gcctacacca tgagcctggg cgtggagaac  2100
agcgtggcct acagcaacaa cagcatcgcc atccccacca acttcaccat cagcgtgacc  2160
accgagattc tgcccgtgag catgaccaag accagcgtgg actgcaccat gtacatctgc  2220
ggcgacagca ccgagtgcag caacctgctg ctgcagtacg gcagcttctg cacccagctg  2280
aaccgggccc tgaccggcat cgccgtggag caggacaaga acacccagga ggtgttcgcc  2340
caggtgaagc agatctacaa gacccctccc atcaaggact tcggcggctt caacttcagc  2400
cagatcctgc ccgaccccag caagcccagc aagcggagct tcatcgagga cctgctgttc  2460
aacaaggtga ccctagccga cgccggcttc atcaagcagt acggcgactg cctcggcgac  2520
atagccgccc gggacctgat ctgcgcccag aagttcaacg gcctgaccgt gctgcctccc  2580
ctgctgaccg acgagatgat cgcccagtac accagcgccc tgttagccgg aaccatcacc  2640
agcggctgga ctttcggcgc tggagccgct ctgcagatcc ccttcgccat gcagatggcc  2700
taccggttca acggcatcgg cgtgacccag aacgtgctgt acgagaacca gaagctgatc  2760
gccaaccagt tcaacagcgc catcggcaag atccaggaca gcctgagcag caccgctagc  2820
gccctgggca agctgcagga cgtggtgaac cagaacgccc aggccctgaa caccctggtg  2880
aagcagctga gcagcaactt cggcgccatc agcagcgtgc tgaacgacat cctgagccgg  2940
ctggaccctc ccgaggccga ggtgcagatc gaccggctga tcactggccg gctgcagagc  3000
ctgcagacct acgtgaccca gcagctgatc cgggccgccg agattcgggc cagcgccaac  3060
ctggccgcca ccaagatgag cgagtgcgtg ctgggccaga gcaagcgggt ggacttctgc  3120
ggcaagggct accacctgat gagctttccc cagagcgcac cccacggagt ggtgttcctg  3180
cacgtgacct acgtgcccgc ccaggagaag aacttcacca ccgcccccagc catctgccac  3240
gacggcaagg cccactttcc ccgggagggc gtgttcgtga gcaacggcac ccactggttc  3300
gtgacccagc ggaacttcta cgagccccag atcatcacca ccgacaacac cttcgtgagc  3360
ggcaactgcg acgtggtgat cggcatcgtg aacaacaccg tgtacgatcc cctgcagccc  3420
gagctggaca gcttcaagga ggagctggac aagtacttca agaatcacac cagccccgac  3480
gtggacctgg gcgacatcag cggcatcaac gccagcgtgg tgaacatcca gaaggagatc  3540
gatcggctga acgaggtggc caagaacctg aacgagagcc tgatcgacct gcaggagctg  3600
ggcaagtacg agcagtacat caagtggccc tggtacatct ggctgggctt catcgccggc  3660
ctgatcgcca tcgtgatggt gaccatcatg ctgtgctgca tgaccagctg ctgcagctgc  3720
ctgaagggct gttgcagctg cggcagctgc tgcaagttcg acgaggacga cagcgagccc  3780
gtgctgaagg gcgtgaagct gcactacacc                                  3810

SEQ ID NO: 11            moltype = AA  length = 1270
FEATURE                  Location/Qualifiers
source                   1..1270
                         mol_type = protein
                         organism = synthetic construct
SEQUENCE: 11
MFVFLVLLPL VSSQCVNFTT RTQLPPAYTN SFTRGVYYPD KVFRSSVLHS TQDLFLPFFS  60
NVTWFHAIHV SGTNGTKRFA NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRGLPQGF SALEPLVDLP IGINITRFQT  240
LHISYLTPGD SSSGWTAGAA AYYVGYLQPR TFLLKYNENG TITDAVDCAL DPLSETKCTL  300
KSFTVEKGIY QTSNFRVQPT ESIVRFPNIT NLCPFGEVFN ATRFASVYAW NRKRISNCVA  360
```

-continued

```
DYSVLYNSAS FSTFKCYGVS PTKLNDLCFT NVYADSFVIR GDEVRQIAPG QTGNIADYNY  420
KLPDDFTGCV IAWNSNNLDS KVGGNYNYLY RLFRKSNLKP FERDISTEIY QAGSTPCNGV  480
KGFNCYFPLQ SYGFQPTYGV GYQPYRVVVL SFELLHAPAT VCGPKKSTNL VKNKCVNFNF  540
NGLTGTGVLT ESNKKFLPFQ QFGRDIADTT DAVRDPQTLE ILDITPCSFG GVSVITPGTN  600
TSNQVAVLYQ GVNCTEVPVA IHADQLTPTW RVYSTGSNVF QTRAGCLIGA EHVNNSYECD  660
IPIGAGICAS YQTQTNSPRR ARSVASQSII AYTMSLGVEN SVAYSNNSIA IPTNFTISVT  720
TEILPVSMTK TSVDCTMYIC GDSTECSNLL LQYGSFCTQL NRALTGIAVE QDKNTQEVFA  780
QVKQIYKTPP IKDFGGFNFS QILPDPSKPS KRSFIEDLLF NKVTLADAGF IKQYGDCLGD  840
IAARDLICAQ KFNGLTVLPP LLTDEMIAQY TSALLAGTIT SGWTFGAGAA LQIPFAMQMA  900
YRFNGIGVTQ NVLYENQKLI ANQFNSAIGK IQDSLSSTAS ALGKLQDVVN QNAQALNTLV  960
KQLSSNFGAI SSVLNDILSR LDPPEAEVQI DRLITGRLQS LQTYVTQQLI RAAEIRASAN  1020
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTDNTFVS GNCDVVIGIV NNTVYDPLQP  1140
ELDSFKEELD KYFKNHTSPD VDLGDISGIN ASVVNIQKEI DRLNEVAKNL NESLIDLQEL  1200
GKYEQYIKWP WYIWLGFIAG LIAIVMVTIM LCCMTSCCSC LKGCCSCGSC CKFDEDDSEP  1260
VLKGVKLHYT                                                        1270

SEQ ID NO: 12          moltype = RNA  length = 3986
FEATURE                Location/Qualifiers
source                 1..3986
                       mol_type = other RNA
                       organism = synthetic construct
SEQUENCE: 12
gggaaataag agagaaaaga agagtaagaa gaaatataag accccggcgc cgccaccatg  60
ttcgtgttcc tggtgctgct gcccctggtg agcagccagt gcgtgaacct gaccacccgg  120
acccagctgc caccagccta caccaacagc ttcacccggg gcgtctacta ccccgacaag  180
gtgttccgga gcagcgtcct gcacagcacc caggacctgt tcctgccctt cttcagcaac  240
gtgacctggt tccacgccat cagcggcacc aacggcacca agcggttcga caaccccgtg  300
ctgcccttca acgacggcgt gtacttcgcc agcaccgaga agagcaacat catccggggc  360
tggatcttcg gcaccaccct ggacagcaag acccagagcc tgctgatcgt gaataacgcc  420
accaacgtgg tgatcaaggt gtgcgagttc cagttctgca acgacccctt cctgggcgtg  480
taccacaaga acaacaagag ctggatggag agcgagttcc gggtgtacag cagcgccaac  540
aactgcacct tcgagtacgt gagccagccc ttcctgatgg acctggaggg caagcagggc  600
aacttcaaga acctgcggga gttcgtgttc aagaacatcg acggctactt caagatctac  660
agcaagcaca ccccaatcaa cctggtgcgg gatctgcccc agggcttctc agccctggag  720
cccctggtgg acctgcccat cggcatcaac atcacccggt tccagaccct gctggccctg  780
caccggagct acctgacccc aggcgacagc agcagcgggt ggacagcagg cgcggctgct  840
tactacgtgg gctacctgca gccccggacc ttcctgctga agtacaacga gaacggcacc  900
atcaccgacg ccgtggactg cgccctggac cctctgagcg agaccaagtg caccctgaag  960
agcttcaccg tggagaaggg catctaccag accagcaact tccgggtgca gcccaccgag  1020
agcatcgtgc ggttccccaa catcaccaac ctgtgcccct tcggcgaggt gttcaacgcc  1080
acccggttcg ccagcgtgta cgcctggaac cggaagcgga tcagcaactg cgtggccgac  1140
tacagcgtgc tgtacaacag cgccagcttc agcaccttca agtgctacgg cgtgagcccc  1200
accaagctga acgacctgtg cttcaccaac gtgtacgccg acagcttcgt gatccgtggc  1260
gacgaggtgc ggcagatcgc acccggccag acaggcaaga tcgccgacta caactacaag  1320
ctgcccgacg acttcaccgg ctgcgtgatc gcctggaaca gcaacaacct cgacagcaag  1380
gtgggcggca actacaacta cctgtaccgg ctgttccgga agagcaacct gaagcccttc  1440
gagcgggaca tcagcaccga gatctaccaa gccggctcca ccccttgcaa cggcgtggag  1500
ggcttcaact gctacttccc tctgcagagc tacggcttcc agcccaccta cggcgtgggc  1560
taccagccct accgggtggt ggtgctgagc ttcgagctgc tgcacgcccc agccaccgtg  1620
tgtggcccca agaagagcac caacctggtg aagaacaagt gcgtgaactt caacttcaac  1680
ggccttaccg gcaccggcgt gctgaccgag agcaacaaga aattcctgcc ctttcagcag  1740
ttcggccggg acatcgacga caccaccgac gctgtgcggg atccccagac cctggagatc  1800
ctggacatca ccccttgcag cttcggcggc gtgagcgtga tcaccccagg caccaacacc  1860
agcaaccagg tggccgtgct gtaccagggc gtgaactgca ccgaggtgcc cgtggccatc  1920
cacgccgacc agctgacacc cacctggcgg gtctacagca ccggcagcaa cgtgttccag  1980
acccgggccg gttgcctgat cggcgccgag cacgtgaaca acagctacga gtgcgacatc  2040
cccatcggcg ccggcatctg tgccagctac cagacccaga ccaattcaca ccggagggca  2100
aggagcgtgg ccagccagag catcatcgcc tacaccatga gcctgggcgc cgagaacagc  2160
gtggcctaca gcaacaacag catcgccatc cccatcaact tcaccatcag cgtgaccacc  2220
gagattctgc ccgtgagcat gaccaagacc agcgtggact gcaccatgta catctgcggc  2280
gacagcaccg agtgcagcaa cctgctgctg cagtacggca gcttctgcac ccagctgaac  2340
cgggccctga ccggcatcgc cgtggagcag gacaagaaca cccaggaggt gttcgcccag  2400
gtgaagcaga tctacaagac ccctcccatc aaggacttcg gcggcttcaa cttcagccag  2460
atcctgcccg accccagcaa gcccagcaag cggagcttca tcgaggacct gctgttcaac  2520
aaggtgaccc tagccgacgc cggcttcatc aagcagtacg gcgactgcct cggcgacata  2580
gccgcccggg acctgatctg cgcccagaag ttcaacggcc tgaccgtgct gcctcccctg  2640
ctgaccgacg agatgatcgc ccagtacacc agcgccctgt tagccggaac catcaccagc  2700
ggctggactt tcggcgctgg agccgctctg cagatcccct tcgccatgca gatggcctac  2760
cggttcaacg gcatcggcgt gacccagaac gtgctgtacg agaaccagaa gctgatcgcc  2820
aaccagttca acagcgccat cggcaagatc caggacagcc tgagcagcac cgctagcgcc  2880
ctgggcaagc tgcaggacgt ggtgaaccag aacgcccagg ccctgaacac cctggtgaag  2940
cagctgagca gcaacttcgg cgccatcagc agcgtgctga acgacatcct ggcccggctg  3000
gaccctcccg aggccgaggt gcagatcgac cggctgatca ctggccggct gcagagcctg  3060
cagacctacg tgacccagca gctgatccgg gccgccgaga ttcgggccag cgccaacctg  3120
gccgccacca agatgagcga gtgcgtgctg ggccagagca agcgggtgga cttctgcggc  3180
aagggctacc acctgatgag ctttccccag agcgcacccc acggagtggt gttcctgcac  3240
gtgacctacg tgcccgccca ggagaagaac ttcaccaccg ccccagccat ctgccacgac  3300
ggcaaggccc actttccccg ggagggcgtg ttcgtgagca acggcaccca ctggttcgtg  3360
```

```
acccagcgga acttctacga gccccagatc atcaccaccc acaacacctt cgtgagcggc  3420
aactgcgacg tggtgatcgg catcgtgaac aacaccgtgt acgatcccct gcagcccgag  3480
ctggacagct tcaaggagga gctggacaag tacttcaaga atcacaccag ccccgacgtg  3540
gacctgggcg acatcagcgg catcaacgcc agcgtggtga acatccagaa ggagatcgat  3600
cggctgaacg aggtggccaa gaacctgaac gagagcctga tcgacctgca ggagctgggc  3660
aagtacgagc agtacatcaa gtggccctgg tacatctggc tgggcttcat cgccggcctg  3720
atcgccatcg tgatggtgac catcatgctg tgctgcatga ccagctgctg cagctgcctg  3780
aagggctgtt gcagctgcgg cagctgctgc aagttcgacg aggacgacag cgagcccgtg  3840
ctgaagggcg tgaagctgca ctacacctga taataggctg gagcctcggt ggcctagctt  3900
cttgcccctt gggcctcccc ccagcccctc ctccccttcc tgcacccgta cccccgtggt  3960
ctttgaataa agtctgagtg ggcggc                                     3986
```

```
SEQ ID NO: 13          moltype = RNA  length = 3810
FEATURE                Location/Qualifiers
source                 1..3810
                       mol_type = other RNA
                       organism = synthetic construct
SEQUENCE: 13
atgttcgtgt tcctggtgct gctgcccctg gtgagcagcc agtgcgtgaa cctgaccacc  60
cggacccagc tgccaccagc ctacaccaac agcttcaccc ggggcgtcta ctaccccgac  120
aaggtgttcc ggagcagcgt cctgcacagc acccaggacc tgttcctgcc cttcttcagc  180
aacgtgacct ggttccacgc catcagcggc accaacggca ccaagcggtt cgacaacccc  240
gtgctgccct tcaacgacgg cgtgtacttc gccagcaccg agaagagcaa catcatccgg  300
ggctggatct tcggcaccac cctggacagc aagacccaga gcctgctgat cgtgaataac  360
gccaccaacg tggtgatcaa ggtgtgcgag ttccagttct gcaacgaccc cttcctgggc  420
gtgtaccaca agaacaacaa gagctggatg gagagcgagt tccgggtgta cagcagcgcc  480
aacaactgca ccttcgagta cgtgagccag cccttcctga tggacctgga gggcaagcag  540
ggcaacttca agaacctgcg ggagttcgtg ttcaagaaca tcgacggcta cttcaagatc  600
tacagcaagc acaccccaat caacctggtg cgggatctgc cccagggctt ctcagccctg  660
gagcccctgg tggacctgcc catcggcatc aacatcaccc ggttccagac cctgctggcc  720
ctgcaccgga gctacctgac cccaggcgac agcagcagcg ggtggacagc aggcgcggct  780
gcttactacg tgggctacct gcagccccgg accttcctgc tgaagtacaa cgagaacggc  840
accatcaccg acgccgtgga ctgcgccctg gaccctctga gcgagaccaa gtgcaccctg  900
aagagcttca ccgtggagaa gggcatctac cagaccagca acttccgggt gcagcccacc  960
gagagcatcg tgcggttccc caacatcacc aacctgtgcc ccttcggcga ggtgttcaac  1020
gccacccggt tcgccagcgt gtacgcctgg aaccggaagc ggatcagcaa ctgcgtggcc  1080
gactacagcg tgctgtacaa cagcgccagc ttcagcacct tcaagtgcta cggcgtgagc  1140
cccaccaagc tgaacgacct gtgcttcacc aacgtgtacg ccgacagctt cgtgatccgt  1200
ggcgacgagg tgcggcagat cgcacccggc cagacaggca agatcgccga ctacaactac  1260
aagctgcccg acgacttcac cggctgcgtg atcgcctgga acagcaacaa cctcgacagc  1320
aaggtgggcg gcaactacaa ctacctgtac cggctgttcc ggaagagcaa cctgaagccc  1380
ttcgagcggg acatcagcac cgagatctac caagccggct ccacccccttg caacggcgtg  1440
gagggcttca actgctactt ccctctgcag agctacggct tccagcccac ctacggcgtg  1500
ggctaccagc cctaccgggt ggtggtgctg agcttcgagc tgctgcacgc cccagccacc  1560
gtgtgtggcc ccaagaagag caccaacctg gtgaagaaca agtgcgtgaa cttcaacttc  1620
aacggcctta ccggcaccgg cgtgctgacc gagagcaaca agaaattcct gcccttttcag  1680
cagttcggcc gggacatcga cgacaccacc gacgctgtgc gggatcccca gaccctggag  1740
atcctggaca tcaccccttg cagcttcggc ggcgtgagcg tgatcacccc aggcaccaac  1800
accagcaacc aggtggccgt gctgtaccag ggcgtgaact gcaccgaggt gcccgtggcc  1860
atccacgccg accagctgac acccacctgg cgggtctaca gcaccggcag caacgtgttc  1920
cagacccggg ccggttgcct gatcggcgcc gagcacgtga acaacagcta cgagtgcgac  1980
atccccatcg gcgccggcat ctgtgccagc taccagaccc agaccaattc acaccggagg  2040
gcaaggagcg tggccagcca gagcatcatc gcctacacca tgagcctggg cgccgagaac  2100
agcgtggcct acagcaacaa cagcatcgcc atccccatca acttcaccat cagcgtgacc  2160
accgagattc tgcccgtgag catgaccaag accagcgtgg actgcaccat gtacatctgc  2220
ggcgacagca ccgagtgcag caacctgctg ctgcagtacg gcagcttctg cacccagctg  2280
aaccgggccc tgaccggcat cgccgtggag caggacaaga acacccagga ggtgttcgcc  2340
caggtgaagc agatctacaa gacccctccc atcaaggact tcggcggctt caacttcagc  2400
cagatcctgc ccgaccccag caagcccagc aagcggagct tcatcgagga cctgctgttc  2460
aacaaggtga ccctagccga cgccggcttc atcaagcagt acggcgactg cctcggcgac  2520
atagccgccc gggacctgat ctgcgcccag aagttcaacg gcctgaccgt gctgcctccc  2580
ctgctgaccg acgagatgat cgcccagtac accagcgccc tgttagccgg aaccatcacc  2640
agcggctgga ctttcggcgc tggagccgct ctgcagatcc ccttcgccat gcagatggcc  2700
taccggttca acggcatcgg cgtgacccag aacgtgctgt acgagaacca gaagctgatc  2760
gccaaccagt tcaacagcgc catcggcaag atccaggaca gcctgagcag caccgctagc  2820
gccctgggca agctgcagga cgtggtgaac cagaacgccc aggccctgaa caccctggtg  2880
aagcagctga gcagcaactt cggcgccatc agcagcgtgc tgaacgacat cctggcccgg  2940
ctggaccctc ccgaggccga ggtgcagatc gaccggctga tcactggccg gctgcagagc  3000
ctgcagacct acgtgaccca gcagctgatc cgggccgccg agattcgggc cagcgccaac  3060
ctggccgcca ccaagatgag cgagtgcgtg ctgggccaga gcaagcgggt ggacttctgc  3120
ggcaagggct accacctgat gagctttccc cagagcgcac cccacggagt ggtgttcctg  3180
cacgtgacct acgtgcccgc ccaggagaag aacttcacca ccgcccccagc catctgccac  3240
gacggcaagg cccactttcc ccgggagggc gtgttcgtga gcaacggcac ccactggttc  3300
gtgacccagc ggaacttcta cgagccccag atcatcacca cccacaacac cttcgtgagc  3360
ggcaactgcg acgtggtgat cggcatcgtg aacaacaccg tgtacgatcc cctgcagccc  3420
gagctggaca gcttcaagga ggagctggac aagtacttca agaatcacac cagccccgac  3480
gtggacctgg gcgacatcag cggcatcaac gccagcgtgg tgaacatcca gaaggagatc  3540
gatcggctga acgaggtggc caagaacctg aacgagagcc tgatcgacct gcaggagctg  3600
ggcaagtacg agcagtacat caagtggccc tggtacatct ggctgggctt catcgccggc  3660
```

```
ctgatcgcca tcgtgatggt gaccatcatg ctgtgctgca tgaccagctg ctgcagctgc  3720
ctgaagggct gttgcagctg cggcagctgc tgcaagttcg acgaggacga cagcgagccc  3780
gtgctgaagg gcgtgaagct gcactacacc                                    3810

SEQ ID NO: 14          moltype = AA  length = 1270
FEATURE                Location/Qualifiers
source                 1..1270
                       mol_type = protein
                       organism = synthetic construct
SEQUENCE: 14
MFVFLVLLPL VSSQCVNLTT RTQLPPAYTN SFTRGVYYPD KVFRSSVLHS TQDLFLPFFS  60
NVTWFHAISG TNGTKRFDNP VLPFNDGVYF ASTEKSNIIR GWIFGTTLDS KTQSLLIVNN  120
ATNVVIKVCE FQFCNDPFLG VYHKNNKSWM ESEFRVYSSA NNCTFEYVSQ PFLMDLEGKQ  180
GNFKNLREFV FKNIDGYFKI YSKHTPINLV RDLPQGFSAL EPLVDLPIGI NITRFQTLLA  240
LHRSYLTPGD SSSGWTAGAA AYYVGYLQPR TFLLKYNENG TITDAVDCAL DPLSETKCTL  300
KSFTVEKGIY QTSNFRVQPT ESIVRFPNIT NLCPFGEVFN ATRFASVYAW NRKRISNCVA  360
DYSVLYNSAS FSTFKCYGVS PTKLNDLCFT NVYADSFVIR GDEVRQIAPG QTGKIADYNY  420
KLPDDFTGCV IAWNSNNLDS KVGGNYNYLY RLFRKSNLKP FERDISTEIY QAGSTPCNGV  480
EGFNCYFPLQ SYGFQPTYGV GYQPYRVVVL SFELLHAPAT VCGPKKSTNL VKNKCVNFNF  540
NGLTGTGVLT ESNKKFLPFQ QFGRDIDDTT DAVRDPQTLE ILDITPCSFG GVSVITPGTN  600
TSNQVAVLYQ GVNCTEVPVA IHADQLTPTW RVYSTGSNVF QTRAGCLIGA EHVNNSYECD  660
IPIGAGICAS YQTQTNSHRR ARSVASQSII AYTMSLGAEN SVAYSNNSIA IPINFTISVT  720
TEILPVSMTK TSVDCTMYIC GDSTECSNLL LQYGSFCTQL NRALTGIAVE QDKNTQEVFA  780
QVKQIYKTPP IKDFGGFNFS QILPDPSKPS KRSFIEDLLF NKVTLADAGF IKQYGDCLGD  840
IAARDLICAQ KFNGLTVLPP LLTDEMIAQY TSALLAGTIT SGWTFGAGAA LQIPFAMQMA  900
YRFNGIGVTQ NVLYENQKLI ANQFNSAIGK IQDSLSSTAS ALGKLQDVVN QNAQALNTLV  960
KQLSSNFGAI SSVLNDILAR LDPPEAEVQI DRLITGRLQS LQTYVTQQLI RAAEIRASAN  1020
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTHNTFVS GNCDVVIGIV NNTVYDPLQP  1140
ELDSFKEELD KYFKNHTSPD VDLGDISGIN ASVVNIQKEI DRLNEVAKNL NESLIDLQEL  1200
GKYEQYIKWP WYIWLGFIAG LIAIVMVTIM LCCMTSCCSC LKGCCSCGSC CKFDEDDSEP  1260
VLKGVKLHYT                                                          1270

SEQ ID NO: 15          moltype = RNA  length = 3977
FEATURE                Location/Qualifiers
source                 1..3977
                       mol_type = other RNA
                       organism = synthetic construct
SEQUENCE: 15
gggaaataag agagaaaaga agagtaagaa gaaatataag accccggcgc cgccaccatg  60
ttcgtgttcc tggtgctgct gcccctggtg agcagccagt gcgtgaactt taccacccgg  120
acccagctgc caccagccta caccaacagc ttcacccggg gcgtctacta ccccgacaag  180
gtgttccgga gcagcgtcct gcacagcacc caggacctgt tcctgccctt cttcagcaac  240
gtgacctggt tccacgccat cagcggcacc aacggcacca agcggttcgc caaccccgtg  300
ctgcccttca acgacggcgt gtacttcgcc agcaccgaga agagcaacat catccggggc  360
tggatcttcg gcaccaccct ggacagcaag acccagagcc tgctgatcgt gaataacgcc  420
accaacgtgg tgatcaaggt gtgcgagttc cagttctgca acgacccctt cctgggcgtg  480
taccacaaga acaacaagag ctggatggag agcgagttcc gggtgtacag cagcgccaac  540
aactgcacct tcgagtacgt gagccagccc ttcctgatgg acctggaggg caagcagggc  600
aacttcaaga acctgcggga gttcgtgttc aagaacatcg acggctactt caagatctac  660
agcaagcaca ccccaatcaa cctggtgcgg ggcctgcccc agggcttctc agccctggag  720
cccctggtgg acctgcccat cggcatcaac atcacccggt tccagaccct gcacatcagc  780
tacctgaccc caggcgacag cagcagcggg tggacagcag gcgcggctgc ttactacgtg  840
ggctacctgc agccccggac cttcctgctg aagtacaacg agaacggcac catcaccgac  900
gccgtggact gcgccctgga ccctctgagc gagaccaagt gcaccctgaa gagcttcacc  960
gtggagaagg gcatctacca gaccagcaac ttccgggtgc agcccaccga gagcatcgtg  1020
cggttcccca acatcaccaa cctgtgcccc ttcggcgagg tgttcaacgc cacccggttc  1080
gccagcgtgt acgcctggaa ccggaagcgg atcagcaact gcgtggccga ctacagcgtg  1140
ctgtacaaca gcgccagctt cagcaccttc aagtgctacg gcgtgagccc caccaagctg  1200
aacgacctgt gcttcaccaa cgtgtacgcc gacagcttcg tgatccgtgg cgacgaggtg  1260
cggcagatcg cacccggcca gacaggcaac atcgccgact acaactacaa gctgcccgac  1320
gacttcaccg gctgcgtgat cgcctggaac agcaacaacc tcgacagcaa ggtgggcggc  1380
aactacaact acctgtaccg gctgttccgg aagagcaacc tgaagccctt cgagcgggac  1440
atcagcaccg agatctacca agccggctcc accccttgca acggcgtgaa gggcttcaac  1500
tgctacttcc ctctgcagag ctacggcttc cagcccacct acggcgtggg ctaccagccc  1560
taccgggtgg tggtgctgag cttcgagctg ctgcacgccc cagccaccgt gtgtggcccc  1620
aagaagagca ccaacctggt gaagaacaag tgcgtgaact tcaacttcaa cggccttacc  1680
ggcaccggcg tgctgaccga gagcaacaag aaattcctgc cctttcagca gttcggccgg  1740
gacatcgacg acaccaccga cgctgtgcgg gatccccaga ccctggagat cctggacatc  1800
acccccttgca gcttcggcgg cgtgagcgtg atcaccccag gcaccaacac cagcaaccag  1860
gtggccgtgc tgtaccaggg cgtgaactgc accgaggtgc ccgtggccat ccacgccgac  1920
cagctgacac ccacctggcg ggtctacagc accggcagca acgtgttcca gacccgggcc  1980
ggttgcctga tcggcgccga gcacgtgaac aacagctacg agtgcgacat ccccatcggc  2040
gccggcatct gtgccagcta ccagacccag accaattcac accggagggc aaggagcgtg  2100
gccagccaga gcatcatcgc ctacaccatg agcctgggcg tggagaacag cgtggcctac  2160
agcaacaaca gcatcgccat ccccatcaac ttcaccatca gcgtgaccac cgagattctg  2220
cccgtgagca tgaccaagac cagcgtggac tgcaccatgt acatctgcgg cgacagcacc  2280
gagtgcagca acctgctgct gcagtacggc agcttctgca cccagctgaa ccgggccctg  2340
accggcatcg ccgtggagca ggacaagaac acccaggagg tgttcgccca ggtgaagcag  2400
```

-continued

```
atctacaaga cccctcccat caaggacttc ggcggcttca acttcagcca gatcctgccc  2460
gaccccagca agcccagcaa gcggagcttc atcgaggacc tgctgttcaa caaggtgacc  2520
ctagccgacg ccggcttcat caagcagtac ggcgactgcc tcggcgacat agccgcccgg  2580
gacctgatct gcgcccagaa gttcaacggc ctgaccgtgc tgcctcccct gctgaccgac  2640
gagatgatcg cccagtacac cagcgccctg ttagccggaa ccatcaccag cggctggact  2700
ttcggcgctg gagccgctct gcagatcccc ttcgccatgc agatggccta ccggttcaac  2760
ggcatcggcg tgacccagaa cgtgctgtac gagaaccaga agctgatcgc caaccagttc  2820
aacagcgcca tcggcaagat ccaggacagc ctgagcagca ccgctagcgc cctgggcaag  2880
ctgcaggacg tggtgaacca gaacgcccag gccctgaaca ccctggtgaa gcagctgagc  2940
agcaacttcg gcgccatcag cagcgtgctg aacgacatcc tggcccggct ggaccctccc  3000
gaggccgagg tgcagatcga ccggctgatc actggccggc tgcagagcct gcagacctac  3060
gtgacccagc agctgatccg ggccgccgag attcgggcca gcgccaacct ggccgccacc  3120
aagatgagcg agtgcgtgct gggccagagc aagcgggtgg acttctgcgg caagggctac  3180
cacctgatga gctttcccca gagcgcaccc cacggagtgg tgttcctgca cgtgacctac  3240
gtgcccgccc aggagaagaa cttcaccacc gccccagcca tctgccacga cggcaaggcc  3300
cactttcccc gggagggcgt gttcgtgagc aacggcaccc actggttcgt gacccagcgg  3360
aacttctacg agccccagat catcaccacc cacaacacct tcgtgagcgg caactgcgac  3420
gtggtgatcg gcatcgtgaa caacaccgtg tacgatcccc tgcagcccga gctggacagc  3480
ttcaaggagg agctggacaa gtacttcaag aatcacacca gccccgacgt ggacctgggc  3540
gacatcagcg gcatcaacgc cagcgtggtg aacatccaga aggagatcga tcggctgaac  3600
gaggtggcca agaacctgaa cgagagcctg atcgacctgc aggagctggg caagtacgag  3660
cagtacatca agtggccctg gtacatctgg ctgggcttca tcgccggcct gatcgccatc  3720
gtgatggtga ccatcatgct gtgctgcatg accagctgct gcagctgcct gaagggctgt  3780
tgcagctgcg gcagctgctg caagttcgac gaggacgaca gcgagcccgt gctgaagggc  3840
gtgaagctgc actacacctg ataataggct ggagcctcgg tggcctagct tcttgcccct  3900
tgggcctccc cccagcccct cctccccttc ctgcacccgt acccccgtgg tctttgaata  3960
aagtctgagt gggcggc                                                 3977

SEQ ID NO: 16          moltype = RNA  length = 3801
FEATURE                Location/Qualifiers
source                 1..3801
                       mol_type = other RNA
                       organism = synthetic construct
SEQUENCE: 16
atgttcgtgt tcctggtgct gctgcccctg gtgagcagcc agtgcgtgaa ctttaccacc  60
cggacccagc tgccaccagc ctacaccaac agcttcaccc ggggcgtcta ctaccccgac  120
aaggtgttcc ggagcagcgt cctgcacagc acccaggacc tgttcctgcc cttcttcagc  180
aacgtgacct ggttccacgc catcagcggc accaacggca ccaagcggtt cgccaacccc  240
gtgctgccct tcaacgacgg cgtgtacttc gccagcaccg agaagagcaa catcatccgg  300
ggctggatct tcggcaccac cctggacagc aagacccaga gcctgctgat cgtgaataac  360
gccaccaacg tggtgatcaa ggtgtgcgag ttccagttct gcaacgaccc cttcctgggc  420
gtgtaccaca agaacaacaa gagctggatg gagagcgagt tccgggtgta cagcagcgcc  480
aacaactgca ccttcgagta cgtgagccag cccttcctga tggacctgga gggcaagcag  540
ggcaacttca agaacctgcg ggagttcgtg ttcaagaaca tcgacggcta cttcaagatc  600
tacagcaagc acaccccaat caacctggtg cggggcctgc cccagggctt ctcagccctg  660
gagcccctgg tggacctgcc catcggcatc aacatcaccc ggttccagac cctgcacatc  720
agctacctga ccccaggcga cagcagcagc gggtggacag caggcgcggc tgcttactac  780
gtgggctacc tgcagccccg gaccttcctg ctgaagtaca acgagaacgg caccatcacc  840
gacgccgtgg actgcgccct ggaccctctg agcgagacca agtgcaccct gaagagcttc  900
accgtggaga agggcatcta ccagaccagc aacttccggg tgcagcccac cgagagcatc  960
gtgcggttcc ccaacatcac caacctgtgc cccttcggcg aggtgttcaa cgccacccgg  1020
ttcgccagcg tgtacgcctg gaaccggaag cggatcagca actgcgtggc cgactacagc  1080
gtgctgtaca acagcgccag cttcagcacc ttcaagtgct acggcgtgag ccccaccaag  1140
ctgaacgacc tgtgcttcac caacgtgtac gccgacagct tcgtgatccg tggcgacgag  1200
gtgcggcaga tcgcacccgg ccagacaggc aacatcgccg actacaacta caagctgccc  1260
gacgacttca ccggctgcgt gatcgcctgg aacagcaaca acctcgacag caaggtgggc  1320
ggcaactaca actacctgta ccggctgttc cggaagagca acctgaagcc cttcgagcgg  1380
gacatcagca ccgagatcta ccaagccggc tccacccctt gcaacggcgt gaagggcttc  1440
aactgctact tccctctgca gagctacggc ttccagccca cctacggcgt gggctaccag  1500
ccctaccggg tggtggtgct gagcttcgag ctgctgcacg ccccagccac cgtgtgtggc  1560
cccaagaaga gcaccaacct ggtgaagaac aagtgcgtga acttcaactt caacggcctt  1620
accggcaccg gcgtgctgac cgagagcaac aagaaattcc tgccctttca gcagttcggc  1680
cgggacatcg acgacaccac cgacgctgtg cgggatcccc agaccctgga gatcctggac  1740
atcacccctt gcagcttcgg cggcgtgagc gtgatcaccc caggcaccaa caccagcaac  1800
caggtggccg tgctgtacca gggcgtgaac tgcaccgagg tgcccgtggc catccacgcc  1860
gaccagctga cacccacctg gcgggtctac agcaccggca gcaacgtgtt ccagacccgg  1920
gccggttgcc tgatcggcgc cgagcacgtg aacaacagct acgagtgcga catccccatc  1980
ggcgccggca tctgtgccag ctaccagacc cagaccaatt cacaccggag ggcaaggagc  2040
gtggccagcc agagcatcat cgcctacacc atgagcctgg gcgtggagaa cagcgtggcc  2100
tacagcaaca acagcatcgc catccccatc aacttcacca tcagcgtgac caccgagatt  2160
ctgcccgtga gcatgaccaa gaccagcgtg gactgcacca tgtacatctg cggcgacagc  2220
accgagtgca gcaacctgct gctgcagtac ggcagcttct gcacccagct gaaccgggcc  2280
ctgaccggca tcgccgtgga gcaggacaag aacacccagg aggtgttcgc ccaggtgaag  2340
cagatctaca agacccctcc catcaaggac ttcggcggct tcaacttcag ccagatcctg  2400
cccgacccca gcaagcccag caagcggagc ttcatcgagg acctgctgtt caacaaggtg  2460
accctagccg acgccggctt catcaagcag tacggcgact gcctcggcga catagccgcc  2520
cgggacctga tctgcgccca gaagttcaac ggcctgaccg tgctgcctcc cctgctgacc  2580
gacgagatga tcgcccagta caccagcgcc ctgttagccg gaaccatcac cagcggctgg  2640
actttcggcg ctggagccgc tctgcagatc cccttcgcca tgcagatggc ctaccggttc  2700
```

```
aacggcatcg gcgtgaccca gaacgtgctg tacgagaacc agaagctgat cgccaaccag  2760
ttcaacagcg ccatcggcaa gatccaggac agcctgagca gcaccgctag cgccctgggc  2820
aagctgcagg acgtggtgaa ccagaacgcc caggccctga acaccctggt gaagcagctg  2880
agcagcaact tcggcgccat cagcagcgtg ctgaacgaca tcctggcccg gctggaccct  2940
cccgaggccg aggtgcagat cgaccggctg atcactggcc ggctgcagag cctgcagacc  3000
tacgtgaccc agcagctgat ccgggccgcc gagattcggg ccagcgccaa cctggccgcc  3060
accaagatga gcgagtgcgt gctgggccag agcaagcggg tggacttctg cggcaagggc  3120
taccacctga tgagctttcc ccagagcgca ccccacggag tggtgttcct gcacgtgacc  3180
tacgtgcccg cccaggagaa gaacttcacc accgccccag ccatctgcca cgacggcaag  3240
gcccactttc cccgggaggg cgtgttcgtg agcaacggca cccactggtt cgtgacccag  3300
cggaacttct acgagcccca gatcatcacc acccacaaca ccttcgtgag cggcaactgc  3360
gacgtggtga tcggcatcgt gaacaacacc gtgtacgatc ccctgcagcc cgagctggac  3420
agcttcaagg aggagctgga caagtacttc aagaatcaca ccagccccga cgtggacctg  3480
ggcgacatca gcggcatcaa cgccagcgtg gtgaacatcc agaaggagat cgatcggctg  3540
aacgaggtgg ccaagaacct gaacgagagc ctgatcgacc tgcaggagct gggcaagtac  3600
gagcagtaca tcaagtggcc ctggtacatc tggctgggct tcatcgccgg cctgatcgcc  3660
atcgtgatgg tgaccatcat gctgtgctgc atgaccagct gctgcagctg cctgaagggc  3720
tgttgcagct gcggcagctg ctgcaagttc gacgaggacg acagcgagcc cgtgctgaag  3780
ggcgtgaagc tgcactacac c                                              3801

SEQ ID NO: 17          moltype = AA  length = 1267
FEATURE                Location/Qualifiers
source                 1..1267
                       mol_type = protein
                       organism = synthetic construct
SEQUENCE: 17
MFVFLVLLPL VSSQCVNFTT RTQLPPAYTN SFTRGVYYPD KVFRSSVLHS TQDLFLPFFS  60
NVTWFHAISG TNGTKRFANP VLPFNDGVYF ASTEKSNIIR GWIFGTTLDS KTQSLLIVNN  120
ATNVVIKVCE FQFCNDPFLG VYHKNNKSWM ESEFRVYSSA NNCTFEYVSQ PFLMDLEGKQ  180
GNFKNLREFV FKNIDGYFKI YSKHTPINLV RGLPQGFSAL EPLVDLPIGI NITRFQTLHI  240
SYLTPGDSSS GWTAGAAAYY VGYLQPRTFL LKYNENGTIT DAVDCALDPL SETKCTLKSF  300
TVEKGIYQTS NFRVQPTESI VRFPNITNLC PFGEVFNATR FASVYAWNRK RISNCVADYS  360
VLYNSASFST FKCYGVSPTK LNDLCFTNVY ADSFVIRGDE VRQIAPGQTG NIADYNYKLP  420
DDFTGCVIAW NSNNLDSKVG GNYNYLYRLF RKSNLKPFER DISTEIYQAG STPCNGVKGF  480
NCYFPLQSYG FQPTYGVGYQ PYRVVVLSFE LLHAPATVCG PKKSTNLVKN KCVNFNFNGL  540
TGTGVLTESN KKFLPFQQFG RDIDDTTDAV RDPQTLEILD ITPCSFGGVS VITPGTNTSN  600
QVAVLYQGVN CTEVPVAIHA DQLTPTWRVY STGSNVFQTR AGCLIGAEHV NNSYECDIPI  660
GAGICASYQT QTNSHRRARS VASQSIIAYT MSLGVENSVA YSNNSIAIPI NFTISVTTEI  720
LPVSMTKTSV DCTMYICGDS TECSNLLLQY GSFCTQLNRA LTGIAVEQDK NTQEVFAQVK  780
QIYKTPPIKD FGGFNFSQIL PDPSKPSKRS FIEDLLFNKV TLADAGFIKQ YGDCLGDIAA  840
RDLICAQKFN GLTVLPPLLT DEMIAQYTSA LLAGTITSGW TFGAGAALQI PFAMQMAYRF  900
NGIGVTQNVL YENQKLIANQ FNSAIGKIQD SLSSTASALG KLQDVVNQNA QALNTLVKQL  960
SSNFGAISSV LNDILARLDP PEAEVQIDRL ITGRLQSLQT YVTQQLIRAA EIRASANLAA  1020
TKMSECVLGQ SKRVDFCGKG YHLMSFPQSA PHGVVFLHVT YVPAQEKNFT TAPAICHDGK  1080
AHFPREGVFV SNGTHWFVTQ RNFYEPQIIT THNTFVSGNC DVVIGIVNNT VYDPLQPELD  1140
SFKEELDKYF KNHTSPDVDL GDISGINASV VNIQKEIDRL NEVAKNLNES LIDLQELGKY  1200
EQYIKWPWYI WLGFIAGLIA IVMVTIMLCC MTSCCSCLKG CCSCGSCCKF DEDDSEPVLK  1260
GVKLHYT                                                              1267

SEQ ID NO: 18          moltype = RNA  length = 3995
FEATURE                Location/Qualifiers
source                 1..3995
                       mol_type = other RNA
                       organism = synthetic construct
SEQUENCE: 18
gggaaataag agagaaaaga agagtaagaa gaaatataag accccggcgc cgccaccatg  60
ttcgtgttcc tggtgctgct gcccctggtg agcagccagt gcgtgaacct gaccacccgg  120
acccagctgc caccagccta caccaacagc ttcacccggg gcgtctacta ccccgacaag  180
gtgttccgga gcagcgtcct gcacagcacc caggacctgt tcctgccctt cttcagcaac  240
gtgacctggt tccacgccat ccacgtgagc ggcaccaacg gcaccaagcg gttcgacaac  300
cccgtgctgc ccttcaacga cggcgtgtac ttcgccagca ccgagaagag caacatcatc  360
cggggctgga tcttcggcac caccctggac agcaagaccc agagcctgct gatcgtgaat  420
aacgccacca acgtggtgat caaggtgtgc gagttccagt tctgcaacga ccccttcctg  480
ggcgtgtact accacaagaa caacaagagc tggatggaga gcgagttccg ggtgtacagc  540
agcgccaaca actgcacctt cgagtacgtg agccagccct tcctgatgga cctggagggc  600
aagcagggca acttcaagaa cctgcgggag ttcgtgttca agaacatcga cggctacttc  660
aagatctaca gcaagcacac ccccaatcaac ctggtgcggg atctgcccca gggcttctca  720
gccctggagc ccctggtgga cctgcccatc ggcatcaaca tcacccggtt ccagaccctg  780
ctggccctgc accggagcta cctgacccca ggcgacagca gcagcgggtg gacagcaggc  840
gcggctgctt actacgtggg ctacctgcag ccccggacct tcctgctgaa gtacaacgag  900
aacggcacca tcaccgacgc cgtggactgc gccctggacc ctctgagcga gaccaagtgc  960
accctgaaga gcttcaccgt ggagaagggc atctaccaga ccagcaactt ccgggtgcag  1020
cccaccgaga gcatcgtgcg gttccccaac atcaccaacc tgtgcccctt cggcgaggtg  1080
ttcaacgcca cccggttcgc cagcgtgtac gcctggaacc ggaagcggat cagcaactgc  1140
gtggccgact acagcgtgct gtacaacagc gccagcttca gcaccttcaa gtgctacggc  1200
gtgagcccca ccaagctgaa cgacctgtgc ttcaccaacg tgtacgccga cagcttcgtg  1260
atccgtggcg acgaggtgcg gcagatcgca cccggccaga caggcaagat cgccgactac  1320
aactacaagc tgcccgacga cttcaccggc tgcgtgatcg cctggaacag caacaacctc  1380
gacagcaagg tgggcggcaa ctacaactac ctgtaccggc tgttccggaa gagcaacctg  1440
```

-continued

```
aagcccttcg agcgggacat cagcaccgag atctaccaag ccggctccac cccttgcaac  1500
ggcgtggagg gcttcaactg ctacttccct ctgcagagct acggcttcca gcccaccaac  1560
ggcgtgggct accagcccta ccgggtggtg gtgctgagct tcgagctgct gcacgcccca  1620
gccaccgtgt gtggccccaa gaagagcacc aacctggtga agaacaagtg cgtgaacttc  1680
aacttcaacg gccttaccgg caccggcgtg ctgaccgaga gcaacaagaa attcctgccc  1740
tttcagcagt tcggccggga catcgccgac accaccgacg ctgtgcggga tccccagacc  1800
ctggagatcc tggacatcac cccttgcagc ttcggcggcg tgagcgtgat caccccaggc  1860
accaacacca gcaaccaggt ggccgtgctg taccaggacg tgaactgcac cgaggtgccc  1920
gtggccatcc acgccgacca gctgacaccc acctggcggg tctacagcac cggcagcaac  1980
gtgttccaga cccgggccgg ttgcctgatc ggcgccgagc acgtgaacaa cagctacgag  2040
tgcgacatcc ccatcggcgc cggcatctgt gccagctacc agacccagac caattcaccc  2100
cggagggcaa ggagcgtggc cagccagagc atcatcgcct acaccatgag cctgggcgcc  2160
gagaacagcg tggcctacag caacaacagc atcgccatcc ccaccaactt caccatcagc  2220
gtgaccaccg agattctgcc cgtgagcatg accaagacca gcgtggactg caccatgtac  2280
atctgcggcg acagcaccga gtgcagcaac ctgctgctgc agtacggcag cttctgcacc  2340
cagctgaacc gggccctgac cggcatcgcc gtggagcagg acaagaacac ccaggaggtg  2400
ttcgcccagg tgaagcagat ctacaagacc cctcccatca aggacttcgg cggcttcaac  2460
ttcagccaga tcctgcccga ccccagcaag cccagcaagc ggagcttcat cgaggacctg  2520
ctgttcaaca aggtgaccct agccgacgcc ggcttcatca agcagtacgg cgactgcctc  2580
ggcgacatag ccgcccggga cctgatctgc gcccagaagt tcaacggcct gaccgtgctg  2640
cctcccctgc tgaccgacga gatgatcgcc cagtacacca gcgccctgtt agccggaacc  2700
atcaccagcg gctggacttt cggcgctgga gccgctctgc agatcccctt cgccatgcag  2760
atggcctacc ggttcaacgg catcggcgtg acccagaacg tgctgtacga gaaccagaag  2820
ctgatcgcca accagttcaa cagcgccatc ggcaagatcc aggacagcct gagcagcacc  2880
gctagcgccc tgggcaagct gcaggacgtg gtgaaccaga acgcccaggc cctgaacacc  2940
ctggtgaagc agctgagcag caacttcggc gccatcagca gcgtgctgaa cgacatcctg  3000
agccggctgg accctcccga ggccgaggtg cagatcgacc ggctgatcac tggccggctg  3060
cagagcctgc agacctacgt gacccagcag ctgatccggg ccgccgagat tcggccagc   3120
gccaacctgg ccgccaccaa gatgagcgag tgcgtgctgg gccagagcaa gcgggtggac  3180
ttctgcggca agggctacca cctgatgagc tttccccaga gcgcacccca cggagtggtg  3240
ttcctgcacg tgacctacgt gcccgcccag gagaagaact tcaccaccgc cccagccatc  3300
tgccacgacg gcaaggccca ctttccccgg gagggcgtgt tcgtgagcaa cggcacccac  3360
tggttcgtga cccagcggaa cttctacgag ccccagatca tcaccaccga caacaccttc  3420
gtgagcggca actgcgacgt ggtgatcggc atcgtgaaca acaccgtgta cgatcccctg  3480
cagcccgagc tggacagctt caaggaggag ctggacaagt acttcaagaa tcacaccagc  3540
cccgacgtgg acctgggcga catcagcggc atcaacgcca gcgtggtgaa catccagaag  3600
gagatcgatc ggctgaacga ggtggccaag aacctgaacg agagcctgat cgacctgcag  3660
gagctgggca agtacgagca gtacatcaag tggccctggt acatctggct gggcttcatc  3720
gccggcctga tcgccatcgt gatggtgacc atcatgctgt gctgcatgac cagctgctgc  3780
agctgcctga agggctgttg cagctgcggc agctgctgca agttcgacga ggacgacagc  3840
gagcccgtgc tgaagggcgt gaagctgcac tacacctgat aataggctgg agcctcggtg  3900
gcctagcttc ttgccccttg ggcctccccc cagcccctcc tccccttcct gcacccgtac  3960
ccccgtggtc tttgaataaa gtctgagtgg gcggc                             3995

SEQ ID NO: 19          moltype = RNA  length = 3819
FEATURE                Location/Qualifiers
source                 1..3819
                       mol_type = other RNA
                       organism = synthetic construct
SEQUENCE: 19
atgttcgtgt tcctggtgct gctgcccctg gtgagcagcc agtgcgtgaa cctgaccacc  60
cggacccagc tgccaccagc ctacaccaac agcttcaccc ggggcgtcta ctaccccgac  120
aaggtgttcc ggagcagcgt cctgcacagc acccaggacc tgttcctgcc cttcttcagc  180
aacgtgacct ggttccacgc catccacgtg agcggcacca acggcaccaa gcggttcgac  240
aaccccgtgc tgcccttcaa cgacggcgtg tacttcgcca gcaccgagaa gagcaacatc  300
atccggggct ggatcttcgg caccaccctg gacagcaaga cccagagcct gctgatcgtg  360
aataacgcca ccaacgtggt gatcaaggtg tgcgagttcc agttctgcaa cgaccccttc  420
ctgggcgtgt actaccacaa gaacaacaag agctggatgg agagcgagtt ccgggtgtac  480
agcagcgcca acaactgcac cttcgagtac gtgagccagc ccttcctgat ggacctggag  540
ggcaagcagg gcaacttcaa gaacctgcgg gagttcgtgt tcaagaacat cgacggctac  600
ttcaagatct acagcaagca caccccaatc aacctggtgc gggatctgcc ccagggcttc  660
tcagccctgg agcccctggt ggacctgccc atcggcatca acatcacccg gttccagacc  720
ctgctggccc tgcaccggag ctacctgacc ccaggcgaca gcagcagcgg gtggacagca  780
ggcgcggctg cttactacgt gggctacctg cagccccgga ccttcctgct gaagtacaac  840
gagaacggca ccatcaccga cgccgtggac tgcgccctgg accctctgag cgagaccaag  900
tgcaccctga agagcttcac cgtggagaag ggcatctacc agaccagcaa cttccgggtg  960
cagcccaccg agagcatcgt gcggttcccc aacatcacca acctgtgccc cttcggcgag  1020
gtgttcaacg ccacccggtt cgccagcgtg tacgcctgga accggaagcg gatcagcaac  1080
tgcgtggccg actacagcgt gctgtacaac agcgccagct tcagcacctt caagtgctac  1140
ggcgtgagcc ccaccaagct gaacgacctg tgcttcacca acgtgtacgc cgacagcttc  1200
gtgatccgtg gcgacgaggt gcggcagatc gcacccggcc agacaggcaa gatcgccgac  1260
tacaactaca agctgcccga cgacttcacc ggctgcgtga tcgcctggaa cagcaacaac  1320
ctcgacagca aggtgggcgg caactacaac tacctgtacc ggctgttccg gaagagcaac  1380
ctgaagccct tcgagcggga catcagcacc gagatctacc aagccggctc caccccttgc  1440
aacggcgtgg agggcttcaa ctgctacttc cctctgcaga gctacggctt ccagcccacc  1500
aacggcgtgg gctaccagcc ctaccgggtg gtggtgctga gcttcgagct gctgcacgcc  1560
ccagccaccg tgtgtggccc caagaagagc accaacctgg tgaagaacaa gtgcgtgaac  1620
ttcaacttca acggccttac cggcaccggc gtgctgaccg agagcaacaa gaaattcctg  1680
ccctttcagc agttcggccg ggacatcgcc gacaccaccg acgctgtgcg ggatccccag  1740
```

-continued

```
accctggaga tcctggacat caccccttgc agcttcggcg gcgtgagcgt gatcacccca  1800
ggcaccaaca ccagcaacca ggtggccgtg ctgtaccagg acgtgaactg caccgaggtg  1860
cccgtggcca tccacgccga ccagctgaca cccacctggc gggtctacag caccggcagc  1920
aacgtgttcc agacccgggc cggttgcctg atcggcgccg agcacgtgaa caacagctac  1980
gagtgcgaca tccccatcgg cgccggcatc tgtgccagct accagaccca gaccaattca  2040
ccccggaggg caaggagcgt ggccagccag agcatcatcg cctacaccat gagcctgggc  2100
gccgagaaca gcgtggccta cagcaacaac agcatcgcca tccccaccaa cttcaccatc  2160
agcgtgacca ccgagattct gcccgtgagc atgaccaaga ccagcgtgga ctgcaccatg  2220
tacatctgcg gcgacagcac cgagtgcagc aacctgctgc tgcagtacgg cagcttctgc  2280
acccagctga accgggccct gaccggcatc gccgtggagc aggacaagaa cacccaggag  2340
gtgttcgccc aggtgaagca gatctacaag accccctcca tcaaggactt cggcggcttc  2400
aacttcagcc agatcctgcc cgaccccagc aagcccagca agcggagctt catcgaggac  2460
ctgctgttca acaaggtgac cctagccgac gccggcttca tcaagcagta cggcgactgc  2520
ctcggcgaca tagccgcccg ggacctgatc tgcgcccaga agttcaacgg cctgaccgtg  2580
ctgcctcccc tgctgaccga cgagatgatc gcccagtaca ccagcgccct gttagccgga  2640
accatcacca gcggctggac tttcggcgct ggagccgctc tgcagatccc cttcgccatg  2700
cagatggcct accggttcaa cggcatcggc gtgacccaga acgtgctgta cgagaaccag  2760
aagctgatcg ccaaccagtt caacagcgcc atcggcaaga tccaggacag cctgagcagc  2820
accgctagcg ccctgggcaa gctgcaggac gtggtgaacc agaacgccca ggccctgaac  2880
accctggtga agcagctgag cagcaacttc ggcgccatca gcagcgtgct gaacgacatc  2940
ctgagccggc tggaccctcc cgaggccgag gtgcagatcg accggctgat cactggccgg  3000
ctgcagagcc tgcagaccta cgtgacccag cagctgatcc gggccgccga gattcgggcc  3060
agcgccaacc tggccgccac caagatgagc gagtgcgtgc tgggccagag caagcgggtg  3120
gacttctgcg gcaagggcta ccacctgatg agctttcccc agagcgcacc ccacggagtg  3180
gtgttcctgc acgtgaccta cgtgcccgcc caggagaaga acttcaccac cgccccagcc  3240
atctgccacg acggcaaggc ccactttccc cgggagggcg tgttcgtgag caacggcacc  3300
cactggttcg tgacccagcg gaacttctac gagccccaga tcatcaccac cgacaacacc  3360
ttcgtgagcg gcaactgcga cgtggtgatc ggcatcgtga acaacaccgt gtacgatccc  3420
ctgcagcccg agctggacag cttcaaggag gagctggaca agtacttcaa gaatcacacc  3480
agccccgacg tggacctggg cgacatcagc ggcatcaacg ccagcgtggt gaacatccag  3540
aaggagatcg atcggctgaa cgaggtggcc aagaacctga acgagagcct gatcgacctg  3600
caggagctgg gcaagtacga gcagtacatc aagtggccct ggtacatctg gctgggcttc  3660
atcgccggcc tgatcgccat cgtgatggtg accatcatgc tgtgctgcat gaccagctgc  3720
tgcagctgcc tgaagggctg ttgcagctgc ggcagctgct gcaagttcga cgaggacgac  3780
agcgagcccg tgctgaaggg cgtgaagctg cactacacc                         3819

SEQ ID NO: 20           moltype = AA  length = 1273
FEATURE                 Location/Qualifiers
source                  1..1273
                        mol_type = protein
                        organism = synthetic construct
SEQUENCE: 20
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDPPEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                     1273

SEQ ID NO: 21           moltype = RNA  length = 3995
FEATURE                 Location/Qualifiers
source                  1..3995
                        mol_type = other RNA
                        organism = synthetic construct
SEQUENCE: 21
gggaaataag agagaaaaga agagtaagaa gaaatataag accccggcgc cgccaccatg  60
ttcgtgttcc tggtgctgct gcccctggtg agcagccagt gcgtgaacct gaccacccgg  120
acccagctgc caccagccta caccaacagc ttcacccggg gcgtctacta ccccgacaag  180
gtgttccgga gcagcgtcct gcacagcacc caggacctgt tcctgccctt cttcagcaac  240
gtgacctggt tccacgccat ccacgtgagc ggcaccaacg gcaccaagcg gttcgacaac  300
cccgtgctgc ccttcaacga cggcgtgtac ttcgccagca tcgagaagag caacatcatc  360
cggggctgga tcttcggcac caccctggac agcaagaccc agagcctgct gatcgtgaat  420
aacgccacca acgtggtgat caaggtgtgc gagttccagt tctgcaacga ccccttcctg  480
```

-continued

```
gacgtgtact accacaagaa caacaagagc tggatgaaga gcgagttccg ggtgtacagc  540
agcgccaaca actgcacctt cgagtacgtg agccagccct tcctgatgga cctggagggc  600
aagcagggca acttcaagaa cctgcgggag ttcgtgttca agaacatcga cggctacttc  660
aagatctaca gcaagcacac cccaatcaac ctggtgcggg atctgcccca gggcttctca  720
gccctggagc ccctggtgga cctgcccatc ggcatcaaca tcacccggtt ccagaccctg  780
ctggccctgc accggagcta cctgacccca ggcgacagca gcagcgggtg gacagcaggc  840
gcggctgctt actacgtggg ctacctgcag ccccggacct tcctgctgaa gtacaacgag  900
aacggcacca tcaccgacgc cgtggactgc gccctggacc ctctgagcga gaccaagtgc  960
accctgaaga gcttcaccgt ggagaagggc atctaccaga ccagcaactt ccgggtgcag  1020
cccaccgaga gcatcgtgcg gttccccaac atcaccaacc tgtgcccctt cggcgaggtg  1080
ttcaacgcca cccggttcgc cagcgtgtac gcctggaacc ggaagcggat cagcaactgc  1140
gtggccgact acagcgtgct gtacaacagc gccagcttca gcaccttcaa gtgctacggc  1200
gtgagcccca ccaagctgaa cgacctgtgc ttcaccaacg tgtacgccga cagcttcgtg  1260
atccgtggcg acgaggtgcg gcagatcgca cccggccaga caggcaagat cgccgactac  1320
aactacaagc tgcccgacga cttcaccggc tgcgtgatcg cctggaacag caacaacctc  1380
gacagcaagg tgggcggcaa ctacaactac agataccggc tgttccggaa gagcaacctg  1440
aagcccttcg agcgggacat cagcaccgag atctaccaag ccggctccac cccttgcaac  1500
ggcgtgcagg gcttcaactg ctacttccct ctgcagagct acggcttcca gcccaccaac  1560
ggcgtgggct accagcccta ccgggtggtg gtgctgagct tcgagctgct gcacgcccca  1620
gccaccgtgt gtggccccaa gaagagcacc aacctggtga agaacaagtg cgtgaacttc  1680
aacttcaacg gccttaccgg caccggcgtg ctgaccgaga gcaacaagaa attcctgccc  1740
tttcagcagt tcggccggga catcgccgac accaccgacg ctgtgcggga tccccagacc  1800
ctggagatcc tggacatcac cccttgcagc ttcggcggcg tgagcgtgat caccccaggc  1860
accaacacca gcaaccaggt ggccgtgctg taccagggcg tgaactgcac cgaggtgccc  1920
gtggccatcc acgccgacca gctgacaccc acctggcggg tctacagcac cggcagcaac  1980
gtgttccaga cccgggccgg ttgcctgatc ggcgccgagc acgtgaacaa cagctacgag  2040
tgcgacatcc ccatcggcgc cggcatctgt gccagctacc agacccagac caattcaaga  2100
cggagggcaa ggagcgtggc cagccagagc atcatcgcct acaccatgag cctgggcgcc  2160
gagaacagcg tggcctacag caacaacagc atcgccatcc ccaccaactt caccatcagc  2220
gtgaccaccg agattctgcc cgtgagcatg accaagacca gcgtggactg caccatgtac  2280
atctgcggcg acagcaccga gtgcagcaac ctgctgctgc agtacggcag cttctgcacc  2340
cagctgaacc gggccctgac cggcatcgcc gtggagcagg acaagaacac ccaggaggtg  2400
ttcgcccagg tgaagcagat ctacaagacc cctcccatca aggacttcgg cggcttcaac  2460
ttcagccaga tcctgcccga ccccagcaag cccagcaagc ggagcttcat cgaggacctg  2520
ctgttcaaca aggtgaccct agccgacgcc ggcttcatca agcagtacgg cgactgcctc  2580
ggcgacatag ccgcccggga cctgatctgc gcccagaagt tcaacggcct gaccgtgctg  2640
cctcccctgc tgaccgacga gatgatcgcc cagtacacca gcgccctgtt agccggaacc  2700
atcaccagcg gctggacttt cggcgctgga gccgctctgc agatcccctt cgccatgcag  2760
atggcctacc ggttcaacgg catcggcgtg acccagaacg tgctgtacga gaaccagaag  2820
ctgatcgcca accagttcaa cagcgccatc ggcaagatcc aggacagcct gagcagcacc  2880
gctagcgccc tgggcaagct gcaggacgtg gtgaaccaga acgcccaggc cctgaacacc  2940
ctggtgaagc agctgagcag caacttcggc gccatcagca gcgtgctgaa cgacatcctg  3000
agccggctgg accctcccga ggccgaggtg cagatcgacc ggctgatcac tggccggctg  3060
cagagcctgc agacctacgt gacccagcag ctgatccggg ccgccgagat tcgggccagc  3120
gccaacctgg ccgccaccaa gatgagcgag tgcgtgctgg gccagagcaa gcgggtggac  3180
ttctgcggca agggctacca cctgatgagc tttccccaga gcgcacccca cggagtggtg  3240
ttcctgcacg tgacctacgt gcccgcccac gagaagaact tcaccaccgc cccagccatc  3300
tgccacgacg gcaaggccca ctttccccgg gagggcgtgt tcgtgagcaa cggcacccac  3360
tggttcgtga cccagcggaa cttctacgag ccccagatca tcaccaccga caacaccttc  3420
gtgagcggca actgcgacgt ggtgatcggc atcgtgaaca acaccgtgta cgatcccctg  3480
cagcccgagc tggacagctt caaggaggag ctggacaagt acttcaagaa tcacaccagc  3540
cccgacgtgg acctgggcga catcagcggc atcaacgcca gcgtggtgaa catccagaag  3600
gagatcgatc ggctgaacga ggtggccaag aacctgaacg agagcctgat cgacctgcag  3660
gagctgggca agtacgagca gtacatcaag tggccctggt acatctggct gggcttcatc  3720
gccggcctga tcgccatcgt gatggtgacc atcatgctgt gctgcatgac cagctgctgc  3780
agctgcctga agggctgttg cagctgcggc agctgctgca agttcgacga ggacgacagc  3840
gagcccgtgc tgaagggcgt gaagctgcac tacacctgat aataggctgg agcctcggtg  3900
gcctagcttc ttgccccttg ggcctccccc cagcccctcc tccccttcct gcacccgtac  3960
ccccgtggtc tttgaataaa gtctgagtgg gcggc                             3995

SEQ ID NO: 22          moltype = RNA  length = 3819
FEATURE                Location/Qualifiers
source                 1..3819
                       mol_type = other RNA
                       organism = synthetic construct
SEQUENCE: 22
atgttcgtgt tcctggtgct gctgcccctg gtgagcagcc agtgcgtgaa cctgaccacc  60
cggacccagc tgccaccagc ctacaccaac agcttcaccc ggggcgtcta ctaccccgac  120
aaggtgttcc ggagcagcgt cctgcacagc acccaggacc tgttcctgcc cttcttcagc  180
aacgtgacct ggttccacgc catccacgtg agcggcacca acggcaccaa gcggttcgac  240
aaccccgtgc tgcccttcaa cgacggcgtg tacttcgcca gcatcgagaa gagcaacatc  300
atccggggct ggatcttcgg caccaccctg gacagcaaga cccagagcct gctgatcgtg  360
aataacgcca ccaacgtggt gatcaaggtg tgcgagttcc agttctgcaa cgaccccttc  420
ctggacgtgt actaccacaa gaacaacaag agctggatga agagcgagtt ccgggtgtac  480
agcagcgcca acaactgcac cttcgagtac gtgagccagc ccttcctgat ggacctggag  540
ggcaagcagg gcaacttcaa gaacctgcgg gagttcgtgt tcaagaacat cgacggctac  600
ttcaagatct acagcaagca caccccaatc aacctggtgc gggatctgcc ccagggcttc  660
tcagccctgg agcccctggt ggacctgccc atcggcatca acatcacccg gttccagacc  720
ctgctggccc tgcaccggag ctacctgacc ccaggcgaca gcagcagcgg gtggacagca  780
```

```
ggcgcggctg cttactacgt gggctacctg cagccccgga ccttcctgct gaagtacaac  840
gagaacggca ccatcaccga cgccgtggac tgcgccctgg accctctgag cgagaccaag  900
tgcaccctga agagcttcac cgtggagaag ggcatctacc agaccagcaa cttccgggtg  960
cagcccaccg agagcatcgt gcggttcccc aacatcacca acctgtgccc cttcggcgag  1020
gtgttcaacg ccacccggtt cgccagcgtg tacgcctgga accggaagcg gatcagcaac  1080
tgcgtggccg actacagcgt gctgtacaac agcgccagct tcagcacctt caagtgctac  1140
ggcgtgagcc ccaccaagct gaacgacctg tgcttcacca acgtgtacgc cgacagcttc  1200
gtgatccgtg gcgacgaggt gcggcagatc gcacccggcc agacaggcaa gatcgccgac  1260
tacaactaca agctgcccga cgacttcacc ggctgcgtga tcgcctggaa cagcaacaac  1320
ctcgacagca aggtgggcgg caactacaac tacagatacc ggctgttccg gaagagcaac  1380
ctgaagccct tcgagcggga catcagcacc gagatctacc aagccggctc caccccttgc  1440
aacggcgtgc agggcttcaa ctgctacttc cctctgcaga gctacggctt ccagcccacc  1500
aacggcgtgg gctaccagcc ctaccgggtg gtggtgctga gcttcgagct gctgcacgcc  1560
ccagccaccg tgtgtggccc caagaagagc accaacctgg tgaagaacaa gtgcgtgaac  1620
ttcaacttca acggccttac cggcaccggc gtgctgaccg agagcaacaa gaaattcctg  1680
ccctttcagc agttcggccg ggacatcgcc gacaccaccg acgctgtgcg ggatccccag  1740
accctggaga tcctggacat caccccttgc agcttcggcg gcgtgagcgt gatcacccca  1800
ggcaccaaca ccagcaacca ggtggccgtg ctgtaccagg gcgtgaactg caccgaggtg  1860
cccgtggcca tccacgccga ccagctgaca cccacctggc gggtctacag caccggcagc  1920
aacgtgttcc agacccgggc cggttgcctg atcggcgccg agcacgtgaa caacagctac  1980
gagtgcgaca tccccatcgg cgccggcatc tgtgccagct accagaccca gaccaattca  2040
agacggaggg caaggagcgt ggccagccag agcatcatcg cctacaccat gagcctgggc  2100
gccgagaaca gcgtggccta cagcaacaac agcatcgcca tccccaccaa cttcaccatc  2160
agcgtgacca ccgagattct gcccgtgagc atgaccaaga ccagcgtgga ctgcaccatg  2220
tacatctgcg gcgacagcac cgagtgcagc aacctgctgc tgcagtacgg cagcttctgc  2280
acccagctga accgggccct gaccggcatc gccgtggagc aggacaagaa cacccaggag  2340
gtgttcgccc aggtgaagca gatctacaag acccctccca tcaaggactt cggcggcttc  2400
aacttcagcc agatcctgcc cgaccccagc aagcccagca agcggagctt catcgaggac  2460
ctgctgttca acaaggtgac cctagccgac gccggcttca tcaagcagta cggcgactgc  2520
ctcggcgaca tagccgcccg ggacctgatc tgcgcccaga agttcaacgg cctgaccgtg  2580
ctgcctcccc tgctgaccga cgagatgatc gcccagtaca ccagcgccct gttagccgga  2640
accatcacca gcggctggac tttcggcgct ggagccgctc tgcagatccc cttcgccatg  2700
cagatggcct accggttcaa cggcatcggc gtgacccaga acgtgctgta cgagaaccag  2760
aagctgatcg ccaaccagtt caacagcgcc atcggcaaga tccaggacag cctgagcagc  2820
accgctagcg ccctgggcaa gctgcaggac gtggtgaacc agaacgccca ggccctgaac  2880
accctggtga agcagctgag cagcaacttc ggcgccatca gcagcgtgct gaacgacatc  2940
ctgagccggc tggaccctcc cgaggccgag gtgcagatcg accggctgat cactggccgg  3000
ctgcagagcc tgcagaccta cgtgacccag cagctgatcc gggccgccga gattcgggcc  3060
agcgccaacc tggccgccac caagatgagc gagtgcgtgc tgggccagag caagcgggtg  3120
gacttctgcg gcaagggcta ccacctgatg agctttcccc agagcgcacc ccacggagtg  3180
gtgttcctgc acgtgaccta cgtgcccgcc cacgagaaga acttcaccac cgccccagcc  3240
atctgccacg acggcaaggc ccactttccc cgggagggcg tgttcgtgag caacggcacc  3300
cactggttcg tgacccagcg gaacttctac gagccccaga tcatcaccac cgacaacacc  3360
ttcgtgagcg gcaactgcga cgtggtgatc ggcatcgtga acaacaccgt gtacgatccc  3420
ctgcagcccg agctggacag cttcaaggag gagctggaca agtacttcaa gaatcacacc  3480
agccccgacg tggacctggg cgacatcagc ggcatcaacg ccagcgtggt gaacatccag  3540
aaggagatcg atcggctgaa cgaggtggcc aagaacctga acgagagcct gatcgacctg  3600
caggagctgg gcaagtacga gcagtacatc aagtggccct ggtacatctg gctgggcttc  3660
atcgccggcc tgatcgccat cgtgatggtg accatcatgc tgtgctgcat gaccagctgc  3720
tgcagctgcc tgaagggctg ttgcagctgc ggcagctgct gcaagttcga cgaggacgac  3780
agcgagcccg tgctgaaggg cgtgaagctg cactacacc                         3819

SEQ ID NO: 23           moltype = AA  length = 1273
FEATURE                 Location/Qualifiers
source                  1..1273
                        mol_type = protein
                        organism = synthetic construct
SEQUENCE: 23
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASIEKSNI IRGWIFGTTL DSKTQSLLIV  120
NNATNVVIKV CEFQFCNDPF LDVYYHKNNK SWMKSEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YRYRLFRKSN LKPFERDIST EIYQAGSTPC  480
NGVQGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQGVNCTEV PVAIHADQLT PTWRVYSTGS NVFQTRAGCL IGAEHVNNSY  660
ECDIPIGAGI CASYQTQTNS RRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDPPEAE VQIDRLITGR LQSLQTYVTQ QLIRAAEIRA  1020
SANLAATKMS ECVLGQSKRV DFCGKGYHLM SFPQSAPHGV VFLHVTYVPA HEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
```

-continued

```
SEPVLKGVKL HYT                                                   1273

SEQ ID NO: 24           moltype = RNA  length = 3989
FEATURE                 Location/Qualifiers
source                  1..3989
                        mol_type = other RNA
                        organism = synthetic construct
SEQUENCE: 24
gggaaataag agagaaaaga agagtaagaa gaaatataag accccggcgc cgccaccatg  60
ttcgtgttcc tggtgctgct gcccctggtg agcagccagt gcgtgaacct gagaacccgg  120
acccagctgc caccagccta caccaacagc ttcacccggg gcgtctacta ccccgacaag  180
gtgttccgga gcagcgtcct gcacagcacc caggacctgt tcctgccctt cttcagcaac  240
gtgacctggt tccacgccat ccacgtgagc ggcaccaacg gcaccaagcg gttcgacaac  300
cccgtgctgc ccttcaacga cggcgtgtac ttcgccagca ccgagaagag caacatcatc  360
cggggctgga tcttcggcac caccctggac agcaagaccc agagcctgct gatcgtgaat  420
aacgccacca acgtggtgat caaggtgtgc gagttccagt tctgcaacga ccccttcctg  480
gacgtgtact accacaagaa caacaagagc tggatggaga gcggcgtgta cagcagcgcc  540
aacaactgca ccttcgagta cgtgagccag cccttcctga tggacctgga gggcaagcag  600
ggcaacttca agaacctgcg ggagttcgtg ttcaagaaca tcgacggcta cttcaagatc  660
tacagcaagc acaccccaat caacctggtg cgggatctgc cccagggctt ctcagccctg  720
gagcccctgg tggacctgcc catcggcatc aacatcaccc ggttccagac cctgctggcc  780
ctgcaccgga gctacctgac cccaggcgac agcagcagcg ggtggacagc aggcgcggct  840
gcttactacg tgggctacct gcagccccgg accttcctgc tgaagtacaa cgagaacggc  900
accatcaccg acgccgtgga ctgcgccctg gaccctctga gcgagaccaa gtgcaccctg  960
aagagcttca ccgtggagaa gggcatctac cagaccagca acttccgggt gcagcccacc  1020
gagagcatcg tgcggttccc caacatcacc aacctgtgcc ccttcggcga ggtgttcaac  1080
gccacccggt tcgccagcgt gtacgcctgg aaccggaagc ggatcagcaa ctgcgtggcc  1140
gactacagcg tgctgtacaa cagcgccagc ttcagcacct tcaagtgcta cggcgtgagc  1200
cccaccaagc tgaacgacct gtgcttcacc aacgtgtacg ccgacagctt cgtgatccgt  1260
ggcgacgagg tgcggcagat cgcacccggc cagacaggca agatcgccga ctacaactac  1320
aagctgcccg acgacttcac cggctgcgtg atcgcctgga acagcaacaa cctcgacagc  1380
aaggtgggcg gcaactacaa ctacagatac cggctgttcc ggaagagcaa cctgaagccc  1440
ttcgagcggg acatcagcac cgagatctac caagccggct ccaagccttg caacggcgtg  1500
gagggcttca actgctactt ccctctgcag agctacggct tccagcccac caacggcgtg  1560
ggctaccagc cctaccgggt ggtggtgctg agcttcgagc tgctgcacgc cccagccacc  1620
gtgtgtggcc ccaagaagag caccaacctg gtgaagaaca agtgcgtgaa cttcaacttc  1680
aacggcctta ccggcaccgg cgtgctgacc gagagcaaca agaaattcct gccctttcag  1740
cagttcggcc gggacatcgc cgacaccacc gacgctgtgc gggatcccca gaccctggag  1800
atcctggaca tcaccccttg cagcttcggc ggcgtgagcg tgatcacccc aggcaccaac  1860
accagcaacc aggtggccgt gctgtaccag ggcgtgaact gcaccgaggt gcccgtggcc  1920
atccacgccg accagctgac acccacctgg cgggtctaca gcaccggcag caacgtgttc  1980
cagacccggg ccggttgcct gatcggcgcc gagcacgtga acaacagcta cgagtgcgac  2040
atccccatcg gcgccggcat ctgtgccagc taccagaccc agaccaattc aagacggagg  2100
gcaaggagcg tggccagcca gagcatcatc gcctacacca tgagcctggg cgccgagaac  2160
agcgtggcct acagcaacaa cagcatcgcc atccccacca acttcaccat cagcgtgacc  2220
accgagattc tgcccgtgag catgaccaag accagcgtgg actgcaccat gtacatctgc  2280
ggcgacagca ccgagtgcag caacctgctg ctgcagtacg gcagcttctg cacccagctg  2340
aaccgggccc tgaccggcat cgccgtggag caggacaaga acacccagga ggtgttcgcc  2400
caggtgaagc agatctacaa gaccccctcc atcaaggact tcggcggctt caacttcagc  2460
cagatcctgc ccgaccccag caagcccagc aagcggagct tcatcgagga cctgctgttc  2520
aacaaggtga ccctagccga cgccggcttc atcaagcagt acggcgactg cctcggcgac  2580
atagccgccc gggacctgat ctgcgcccag aagttcaacg gcctgaccgt gctgcctccc  2640
ctgctgaccg acgagatgat cgcccagtac accagcgccc tgttagccgg aaccatcacc  2700
agcggctgga ctttcggcgc tggagccgct ctgcagatcc ccttcgccat gcagatggcc  2760
taccggttca acggcatcgg cgtgacccag aacgtgctgt acgagaacca gaagctgatc  2820
gccaaccagt tcaacagcgc catcggcaag atccaggaca gcctgagcag caccgctagc  2880
gccctgggca agctgcagaa cgtggtgaac cagaacgccc aggccctgaa caccctggtg  2940
aagcagctga gcagcaactt cggcgccatc agcagcgtgc tgaacgacat cctgagccgg  3000
ctggaccctc ccgaggccga ggtgcagatc gaccggctga tcactggccg gctgcagagc  3060
ctgcagacct acgtgaccca gcagctgatc cgggccgccg agattcgggc cagcgccaac  3120
ctggccgcca ccaagatgag cgagtgcgtg ctgggccaga gcaagcgggt ggacttctgc  3180
ggcaagggct accacctgat gagctttccc cagagcgcac cccacggagt ggtgttcctg  3240
cacgtgacct acgtgcccgc ccaggagaag aacttcacca ccgcccccagc catctgccac  3300
gacggcaagg cccactttcc ccgggagggc gtgttcgtga gcaacggcac ccactggttc  3360
gtgacccagc ggaacttcta cgagccccag atcatcacca ccgacaacac cttcgtgagc  3420
ggcaactgcg acgtggtgat cggcatcgtg aacaacaccg tgtacgatcc cctgcagccc  3480
gagctggaca gcttcaagga ggagctggac aagtacttca agaatcacac cagccccgac  3540
gtggacctgg gcgacatcag cggcatcaac gccagcgtgg tgaacatcca gaaggagatc  3600
gatcggctga acgaggtggc caagaacctg aacgagagcc tgatcgacct gcaggagctg  3660
ggcaagtacg agcagtacat caagtggccc tggtacatct ggctgggctt catcgccggc  3720
ctgatcgcca tcgtgatggt gaccatcatg ctgtgctgca tgaccagctg ctgcagctgc  3780
ctgaagggct gttgcagctg cggcagctgc tgcaagttcg acgaggacga cagcgagccc  3840
gtgctgaagg gcgtgaagct gcactacacc tgataatagg ctggagcctc ggtggcctag  3900
cttcttgccc cttgggcctc cccccagccc ctcctcccct tcctgcaccc gtacccccgt  3960
ggtctttgaa taaagtctga gtgggcggc                                 3989

SEQ ID NO: 25           moltype = RNA  length = 3813
FEATURE                 Location/Qualifiers
source                  1..3813
```

```
                        mol_type = other RNA
                        organism = synthetic construct
SEQUENCE: 25
atgttcgtgt tcctggtgct gctgcccctg gtgagcagcc agtgcgtgaa cctgagaacc  60
cggacccagc tgccaccagc ctacaccaac agcttcaccc ggggcgtcta ctaccccgac  120
aaggtgttcc ggagcagcgt cctgcacagc acccaggacc tgttcctgcc cttcttcagc  180
aacgtgacct ggttccacgc catccacgtg agcggcacca acggcaccaa gcggttcgac  240
aaccccgtgc tgcccttcaa cgacggcgtg tacttcgcca gcaccgagaa gagcaacatc  300
atccggggct ggatcttcgg caccaccctg gacagcaaga cccagagcct gctgatcgtg  360
aataacgcca ccaacgtggt gatcaaggtg tgcgagttcc agttctgcaa cgaccccttc  420
ctggacgtgt actaccacaa gaacaacaag agctggatgg agagcggcgt gtacagcagc  480
gccaacaact gcaccttcga gtacgtgagc cagcccttcc tgatggacct ggagggcaag  540
cagggcaact tcaagaacct gcgggagttc gtgttcaaga acatcgacgg ctacttcaag  600
atctacagca agcacacccc aatcaacctg gtgcgggatc tgccccaggg cttctcagcc  660
ctggagcccc tggtggacct gcccatcggc atcaacatca cccggttcca gaccctgctg  720
gccctgcacc ggagctacct gaccccaggc gacagcagca gcgggtggac agcaggcgcg  780
gctgcttact acgtgggcta cctgcagccc cggaccttcc tgctgaagta caacgagaac  840
ggcaccatca ccgacgccgt ggactgcgcc ctggaccctc tgagcgagac caagtgcacc  900
ctgaagagct tcaccgtgga gaagggcatc taccagacca gcaacttccg ggtgcagccc  960
accgagagca tcgtgcggtt ccccaacatc accaacctgt gccccttcgg cgaggtgttc  1020
aacgccaccc ggttcgccag cgtgtacgcc tggaaccgga agcggatcag caactgcgtg  1080
gccgactaca gcgtgctgta caacagcgcc agcttcagca ccttcaagtg ctacggcgtg  1140
agccccacca agctgaacga cctgtgcttc accaacgtgt acgccgacag cttcgtgatc  1200
cgtggcgacg aggtgcggca gatcgcaccc ggccagacag gcaagatcgc cgactacaac  1260
tacaagctgc ccgacgactt caccggctgc gtgatcgcct ggaacagcaa caacctcgac  1320
agcaaggtgg gcggcaacta caactacaga taccggctgt tccggaagag caacctgaag  1380
cccttcgagc gggacatcag caccgagatc taccaagccg gctccaagcc ttgcaacggc  1440
gtggagggct tcaactgcta cttccctctg cagagctacg gcttccagcc caccaacggc  1500
gtgggctacc agccctaccg ggtggtggtg ctgagcttcg agctgctgca cgccccagcc  1560
accgtgtgtg gccccaagaa gagcaccaac ctggtgaaga acaagtgcgt gaacttcaac  1620
ttcaacggcc ttaccggcac cggcgtgctg accgagagca acaagaaatt cctgcccttt  1680
cagcagttcg gccgggacat cgccgacacc accgacgctg tgcgggatcc ccagaccctg  1740
gagatcctgg acatcacccc ttgcagcttc ggcggcgtga gcgtgatcac cccaggcacc  1800
aacaccagca accaggtggc cgtgctgtac cagggcgtga actgcaccga ggtgcccgtg  1860
gccatccacg ccgaccagct gacacccacc tggcgggtct acagcaccgg cagcaacgtg  1920
ttccagaccc gggccggttg cctgatcggc gccgagcacg tgaacaacag ctacgagtgc  1980
gacatcccca tcggcgccgg catctgtgcc agctaccaga cccagaccaa ttcaagacgg  2040
agggcaagga gcgtggccag ccagagcatc atcgcctaca ccatgagcct gggcgccgag  2100
aacagcgtgg cctacagcaa caacagcatc gccatcccca ccaacttcac catcagcgtg  2160
accaccgaga ttctgcccgt gagcatgacc aagaccagcg tggactgcac catgtacatc  2220
tgcggcgaca gcaccgagtg cagcaacctg ctgctgcagt acggcagctt ctgcacccag  2280
ctgaaccggg ccctgaccgg catcgccgtg gagcaggaca agaacaccca ggaggtgttc  2340
gcccaggtga agcagatcta caagacccct cccatcaagg acttcggcgg cttcaacttc  2400
agccagatcc tgcccgaccc cagcaagccc agcaagcgga gcttcatcga ggacctgctg  2460
ttcaacaagg tgaccctagc cgacgccggc ttcatcaagc agtacggcga ctgcctcggc  2520
gacatagccg cccgggacct gatctgcgcc cagaagttca acggcctgac cgtgctgcct  2580
cccctgctga ccgacgagat gatcgcccag tacaccagcg ccctgttagc cggaaccatc  2640
accagcggct ggactttcgg cgctggagcc gctctgcaga tccccttcgc catgcagatg  2700
gcctaccggt tcaacggcat cggcgtgacc cagaacgtgc tgtacgagaa ccagaagctg  2760
atcgccaacc agttcaacag cgccatcggc aagatccagg acagcctgag cagcaccgct  2820
agcgccctgg gcaagctgca gaacgtggtg aaccagaacg cccaggccct gaacaccctg  2880
gtgaagcagc tgagcagcaa cttcggcgcc atcagcagcg tgctgaacga catcctgagc  2940
cggctggacc ctcccgaggc cgaggtgcag atcgaccggc tgatcactgg ccggctgcag  3000
agcctgcaga cctacgtgac ccagcagctg atccgggccg ccgagattcg ggccagcgcc  3060
aacctggccg ccaccaagat gagcgagtgc gtgctgggcc agagcaagcg ggtggacttc  3120
tgcggcaagg gctaccacct gatgagcttt ccccagagcg caccccacgg agtggtgttc  3180
ctgcacgtga cctacgtgcc cgcccaggag aagaacttca ccaccgcccc agccatctgc  3240
cacgacggca aggcccactt tccccgggag ggcgtgttcg tgagcaacgg cacccactgg  3300
ttcgtgaccc agcggaactt ctacgagccc cagatcatca ccaccgacaa caccttcgtg  3360
agcggcaact gcgacgtggt gatcggcatc gtgaacaaca ccgtgtacga tcccctgcag  3420
cccgagctgg acagcttcaa ggaggagctg gacaagtact tcaagaatca caccagcccc  3480
gacgtggacc tgggcgacat cagcggcatc aacgccagcg tggtgaacat ccagaaggag  3540
atcgatcggc tgaacgaggt ggccaagaac ctgaacgaga gcctgatcga cctgcaggag  3600
ctgggcaagt acgagcagta catcaagtgg ccctggtaca tctggctggg cttcatcgcc  3660
ggcctgatcg ccatcgtgat ggtgaccatc atgctgtgct gcatgaccag ctgctgcagc  3720
tgcctgaagg gctgttgcag ctgcggcagc tgctgcaagt tcgacgagga cgacagcgag  3780
cccgtgctga agggcgtgaa gctgcactac acc                               3813

SEQ ID NO: 26           moltype = AA  length = 1271
FEATURE                 Location/Qualifiers
source                  1..1271
                        mol_type = protein
                        organism = synthetic construct
SEQUENCE: 26
MFVFLVLLPL VSSQCVNLRT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LDVYYHKNNK SWMESGVYSS ANNCTFEYVS QPFLMDLEGK  180
QGNFKNLREF VFKNIDGYFK IYSKHTPINL VRDLPQGFSA LEPLVDLPIG INITRFQTLL  240
ALHRSYLTPG DSSSGWTAGA AAYYVGYLQP RTFLLKYNEN GTITDAVDCA LDPLSETKCT  300
```

```
LKSFTVEKGI YQTSNFRVQP TESIVRFPNI TNLCPFGEVF NATRFASVYA WNRKRISNCV  360
ADYSVLYNSA SFSTFKCYGV SPTKLNDLCF TNVYADSFVI RGDEVRQIAP GQTGKIADYN  420
YKLPDDFTGC VIAWNSNNLD SKVGGNYNYR YRLFRKSNLK PFERDISTEI YQAGSKPCNG  480
VEGFNCYFPL QSYGFQPTNG VGYQPYRVVV LSFELLHAPA TVCGPKKSTN LVKNKCVNFN  540
FNGLTGTGVL TESNKKFLPF QQFGRDIADT TDAVRDPQTL EILDITPCSF GGVSVITPGT  600
NTSNQVAVLY QGVNCTEVPV AIHADQLTPT WRVYSTGSNV FQTRAGCLIG AEHVNNSYEC  660
DIPIGAGICA SYQTQTNSRR RARSVASQSI IAYTMSLGAE NSVAYSNNSI AIPTNFTISV  720
TTEILPVSMT KTSVDCTMYI CGDSTECSNL LLQYGSFCTQ LNRALTGIAV EQDKNTQEVF  780
AQVKQIYKTP PIKDFGGFNF SQILPDPSKP SKRSFIEDLL FNKVTLADAG FIKQYGDCLG  840
DIAARDLICA QKFNGLTVLP PLLTDEMIAQ YTSALLAGTI TSGWTFGAGA ALQIPFAMQM  900
AYRFNGIGVT QNVLYENQKL IANQFNSAIG KIQDSLSSTA SALGKLQNVV NQNAQALNTL  960
VKQLSSNFGA ISSVLNDILS RLDPPEAEVQ IDRLITGRLQ SLQTYVTQQL IRAAEIRASA  1020
NLAATKMSEC VLGQSKRVDF CGKGYHLMSF PQSAPHGVVF LHVTYVPAQE KNFTTAPAIC  1080
HDGKAHFPRE GVFVSNGTHW FVTQRNFYEP QIITTDNTFV SGNCDVVIGI VNNTVYDPLQ  1140
PELDSFKEEL DKYFKNHTSP DVDLGDISGI NASVVNIQKE IDRLNEVAKN LNESLIDLQE  1200
LGKYEQYIKW PWYIWLGFIA GLIAIVMVTI MLCCMTSCCS CLKGCCSCGS CCKFDEDDSE  1260
PVLKGVKLHY T                                                       1271

SEQ ID NO: 27          moltype = AA  length = 1273
FEATURE                Location/Qualifiers
source                 1..1273
                       mol_type = protein
                       organism = synthetic construct
SEQUENCE: 27
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                     1273

SEQ ID NO: 28          moltype = RNA  length = 3989
FEATURE                Location/Qualifiers
source                 1..3989
                       mol_type = other RNA
                       organism = synthetic construct
SEQUENCE: 28
gggaaataag agagaaaaga agagtaagaa gaaatataag accccggcgc cgccaccatg  60
ttcgtgttcc tggtgctgct gcccctggtg agcagccagt gcgtgaacct gagaacccgg  120
acccagctgc caccagccta caccaacagc ttcacccggg gcgtctacta ccccgacaag  180
gtgttccgga gcagcgtcct gcacagcacc caggacctgt tcctgccctt cttcagcaac  240
gtgacctggt tccacgccat ccacgtgagc ggcaccaacg gcaccaagcg gttcgacaac  300
cccgtgctgc ccttcaacga cggcgtgtac ttcgccagca tcgagaagag caacatcatc  360
cggggctgga tcttcggcac caccctggac agcaagaccc agagcctgct gatcgtgaat  420
aacgccacca acgtggtgat caaggtgtgc gagttccagt tctgcaacga ccccttcctg  480
gacgtgtact accacaagaa caacaagagc tggatggaga gcggcgtgta cagcagcgcc  540
aacaactgca ccttcgagta cgtgagccag cccttcctga tggacctgga gggcaagcag  600
ggcaacttca agaacctgcg ggagttcgtg ttcaagaaca tcgacggcta cttcaagatc  660
tacagcaagc acaccccaat caacctggtg cgggatctgc cccagggctt ctcagccctg  720
gagcccctgg tggacctgcc catcggcatc aacatcaccc ggttccagac cctgctggcc  780
ctgcaccgga gctacctgac ccccggcgac agcagcagcg ggtggacagc aggcgcggct  840
gcttactacg tgggctacct gcagccccgg accttcctgc tgaagtacaa cgagaacggc  900
accatcaccg acgccgtgga ctgcgccctg gaccctctga gcgagaccaa gtgcaccctg  960
aagagcttca ccgtggagaa gggcatctac cagaccagca acttccgggt gcagcccacc  1020
gagagcatcg tgcggttccc caacatcacc aacctgtgcc ccttcggcga ggtgttcaac  1080
gccacccggt tcgccagcgt gtacgcctgg aaccggaagc ggatcagcaa ctgcgtggcc  1140
gactacagcg tgctgtacaa cagcgccagc ttcagcacct tcaagtgcta cggcgtgagc  1200
cccaccaagc tgaacgacct gtgcttcacc aacgtgtacg ccgacagctt cgtgatccgt  1260
ggcgacgagg tgcggcagat cgcacccggc cagacaggca agatcgccga ctacaactac  1320
aagctgcccg acgacttcac cggctgcgtg atcgcctgga acagcaacaa cctcgacagc  1380
aaggtgggcg gcaactacaa ctacagatac cggctgttcc ggaagagcaa cctgaagccc  1440
ttcgagcggg acatcagcac cgagatctac caagccggct ccaagccttg caacggcgtg  1500
gagggcttca actgctactt ccctctgcag agctacggct tccagcccac caacggcgtg  1560
```

```
ggctaccagc cctaccgggt ggtggtgctg agcttcgagc tgctgcacgc cccagccacc  1620
gtgtgtggcc ccaagaagag caccaacctg gtgaagaaca agtgcgtgaa cttcaacttc  1680
aacggcctta ccggcaccgg cgtgctgacc gagagcaaca agaaattcct gccctttcag  1740
cagttcggcc gggacatcgc cgacaccacc gacgctgtgc gggatcccca gaccctggag  1800
atcctggaca tcaccccttg cagcttcggc ggcgtgagcg tgatcacccc aggcaccaac  1860
accagcaacc aggtggccgt gctgtaccag ggcgtgaact gcaccgaggt gcccgtggcc  1920
atccacgccg accagctgac acccacctgg cgggtctaca gcaccggcag caacgtgttc  1980
cagacccggg ccggttgcct gatcggcgcc gagcacgtga acaacagcta cgagtgcgac  2040
atccccatcg gcgccggcat ctgtgccagc taccagaccc agaccaattc aagacggagg  2100
gcaaggagcg tggccagcca gagcatcatc gcctacacca tgagcctggg cgccgagaac  2160
agcgtggcct acagcaacaa cagcatcgcc atccccacca acttcaccat cagcgtgacc  2220
accgagattc tgcccgtgag catgaccaag accagcgtgg actgcaccat gtacatctgc  2280
ggcgacagca ccgagtgcag caacctgctg ctgcagtacg gcagcttctg cacccagctg  2340
aaccgggccc tgaccggcat cgccgtggag caggacaaga acacccagga ggtgttcgcc  2400
caggtgaagc agatctacaa gacccctccc atcaaggact tcggcggctt caacttcagc  2460
cagatcctgc ccgaccccag caagcccagc aagcggagct tcatcgagga cctgctgttc  2520
aacaaggtga ccctagccga cgccggcttc atcaagcagt acggcgactg cctcggcgac  2580
atagccgccc gggacctgat ctgcgcccag aagttcaacg gcctgaccgt gctgcctccc  2640
ctgctgaccg acgagatgat cgcccagtac accagcgccc tgttagccgg aaccatcacc  2700
agcggctgga ctttcggcgc tggagccgct ctgcagatcc ccttcgccat gcagatggcc  2760
taccggttca acggcatcgg cgtgacccag aacgtgctgt acgagaacca gaagctgatc  2820
gccaaccagt tcaacagcgc catcggcaag atccaggaca gcctgagcag caccgctagc  2880
gccctgggca agctgcagaa cgtggtgaac cagaacgccc aggccctgaa caccctggtg  2940
aagcagctga gcagcaactt cggcgccatc agcagcgtgc tgaacgacat cctgagccgg  3000
ctggaccctc ccgaggccga ggtgcagatc gaccggctga tcactggccg gctgcagagc  3060
ctgcagacct acgtgaccca gcagctgatc cgggccgccg agattcgggc cagcgccaac  3120
ctggccgcca ccaagatgag cgagtgcgtg ctgggccaga gcaagcgggt ggacttctgc  3180
ggcaagggct accacctgat gagctttccc cagagcgcac cccacggagt ggtgttcctg  3240
cacgtgacct acgtgcccgc ccaggagaag aacttcacca ccgcccccagc catctgccac  3300
gacggcaagg cccactttcc ccgggagggc gtgttcgtga gcaacggcac ccactggttc  3360
gtgacccagc ggaacttcta cgagccccag atcatcacca ccgacaacac cttcgtgagc  3420
ggcaactgcg acgtggtgat cggcatcgtg aacaacaccg tgtacgatcc cctgcagccc  3480
gagctggaca gcttcaagga ggagctggac aagtacttca agaatcacac cagccccgac  3540
gtggacctgg gcgacatcag cggcatcaac gccagcgtgg tgaacatcca gaaggagatc  3600
gatcggctga acgaggtggc caagaacctg aacgagagcc tgatcgacct gcaggagctg  3660
ggcaagtacg agcagtacat caagtggccc tggtacatct ggctgggctt catcgccggc  3720
ctgatcgcca tcgtgatggt gaccatcatg ctgtgctgca tgaccagctg ctgcagctgc  3780
ctgaagggct gttgcagctg cggcagctgc tgcaagttcg acgaggacga cagcgagccc  3840
gtgctgaagg gcgtgaagct gcactacacc tgataatagg ctggagcctc ggtggcctag  3900
cttcttgccc cttgggcctc cccccagccc ctcctcccct tcctgcaccc gtacccccgt  3960
ggtctttgaa taaagtctga gtgggcggc                                    3989

SEQ ID NO: 29          moltype = RNA  length = 3813
FEATURE                Location/Qualifiers
source                 1..3813
                       mol_type = other RNA
                       organism = synthetic construct
SEQUENCE: 29
atgttcgtgt tcctggtgct gctgcccctg gtgagcagcc agtgcgtgaa cctgagaacc  60
cggacccagc tgccaccagc ctacaccaac agcttcaccc ggggcgtcta ctaccccgac  120
aaggtgttcc ggagcagcgt cctgcacagc acccaggacc tgttcctgcc cttcttcagc  180
aacgtgacct ggttccacgc catccacgtg agcggcacca acggcaccaa gcggttcgac  240
aaccccgtgc tgcccttcaa cgacggcgtg tacttcgcca gcatcgagaa gagcaacatc  300
atccggggct ggatcttcgg caccaccctg gacagcaaga cccagagcct gctgatcgtg  360
aataacgcca ccaacgtggt gatcaaggtg tgcgagttcc agttctgcaa cgaccccttc  420
ctggacgtgt actaccacaa gaacaacaag agctggatgg agagcggcgt gtacagcagc  480
gccaacaact gcaccttcga gtacgtgagc cagcccttcc tgatggacct ggagggcaag  540
cagggcaact tcaagaacct gcgggagttc gtgttcaaga acatcgacgg ctacttcaag  600
atctacagca agcacacccc aatcaacctg gtgcgggatc tgccccaggg cttctcagcc  660
ctggagcccc tggtggacct gcccatcggc atcaacatca cccggttcca gaccctgctg  720
gccctgcacc ggagctacct gaccccaggc gacagcagca gcgggtggac agcaggcgcg  780
gctgcttact acgtgggcta cctgcagccc cggaccttcc tgctgaagta caacgagaac  840
ggcaccatca ccgacgcggt ggactgcgcc ctggaccctc tgagcgagac caagtgcacc  900
ctgaagagct tcaccgtgga gaagggcatc taccagacca gcaacttccg ggtgcagccc  960
accgagagca tcgtgcggtt ccccaacatc accaacctgt gccccttcgg cgaggtgttc  1020
aacgccaccc ggttcgccag cgtgtacgcc tggaaccgga agcggatcag caactgcgtg  1080
gccgactaca gcgtgctgta caacagcgcc agcttcagca ccttcaagtg ctacggcgtg  1140
agccccacca agctgaacga cctgtgcttc accaacgtgt acgccgacag cttcgtgatc  1200
cgtggcgacg aggtgcggca gatcgcaccc ggccagacag gcaagatcgc cgactacaac  1260
tacaagctgc ccgacgactt caccggctgc gtgatcgcct ggaacagcaa caacctcgac  1320
agcaaggtgg gcggcaacta caactacaga taccggctgt tccggaagag caacctgaag  1380
cccttcgagc gggacatcag caccgagatc taccaagccg gctccaagcc ttgcaacggc  1440
gtggagggct tcaactgcta cttccctctg cagagctacg gcttccagcc caccaacggc  1500
gtgggctacc agccctaccg ggtggtggtg ctgagcttcg agctgctgca cgccccagcc  1560
accgtgtgtg gccccaagaa gagcaccaac ctggtgaaga acaagtgcgt gaacttcaac  1620
ttcaacggcc ttaccggcac cggcgtgctg accgagagca acaagaaatt cctgcccttt  1680
cagcagttcg gccgggacat cgccgacacc accgacgctg tgcgggatcc ccagaccctg  1740
gagatcctgg acatcacccc ttgcagcttc ggcggcgtga gcgtgatcac cccaggcacc  1800
aacaccagca accaggtggc cgtgctgtac cagggcgtga actgcaccga ggtgcccgtg  1860
```

```
gccatccacg ccgaccagct gacacccacc tggcgggtct acagcaccgg cagcaacgtg  1920
ttccagaccc gggccggttg cctgatcggc gccgagcacg tgaacaacag ctacgagtgc  1980
gacatcccca tcggcgccgg catctgtgcc agctaccaga cccagaccaa ttcaagacgg  2040
agggcaagga gcgtggccag ccagagcatc atcgcctaca ccatgagcct gggcgccgag  2100
aacagcgtgg cctacagcaa caacagcatc gccatcccca ccaacttcac catcagcgtg  2160
accaccgaga ttctgcccgt gagcatgacc aagaccagcg tggactgcac catgtacatc  2220
tgcggcgaca gcaccgagtg cagcaacctg ctgctgcagt acggcagctt ctgcacccag  2280
ctgaaccggg ccctgaccgg catcgccgtg gagcaggaca agaacaccca ggaggtgttc  2340
gcccaggtga agcagatcta caagacccct cccatcaagg acttcggcgg cttcaacttc  2400
agccagatcc tgcccgaccc cagcaagccc agcaagcgga gcttcatcga ggacctgctg  2460
ttcaacaagg tgaccctagc cgacgccggc ttcatcaagc agtacggcga ctgcctcggc  2520
gacatagccg cccgggacct gatctgcgcc cagaagttca acggcctgac cgtgctgcct  2580
cccctgctga ccgacgagat gatcgcccag tacaccagcg ccctgttagc cggaaccatc  2640
accagcggct ggactttcgg cgctggagcc gctctgcaga tccccttcgc catgcagatg  2700
gcctaccggt tcaacggcat cggcgtgacc cagaacgtgc tgtacgagaa ccagaagctg  2760
atcgccaacc agttcaacag cgccatcggc aagatccagg acagcctgag cagcaccgct  2820
agcgccctgg gcaagctgca gaacgtggtg aaccagaacg cccaggccct gaacaccctg  2880
gtgaagcagc tgagcagcaa cttcggcgcc atcagcagcg tgctgaacga catcctgagc  2940
cggctggacc ctcccgaggc cgaggtgcag atcgaccggc tgatcactgg ccggctgcag  3000
agcctgcaga cctacgtgac ccagcagctg atccgggccg ccgagattcg ggccagcgcc  3060
aacctggccg ccaccaagat gagcgagtgc gtgctgggcc agagcaagcg ggtggacttc  3120
tgcggcaagg gctaccacct gatgagcttt ccccagagcg caccccacgg agtggtgttc  3180
ctgcacgtga cctacgtgcc cgcccaggag aagaacttca ccaccgcccc agccatctgc  3240
cacgacggca aggcccactt tccccgggag ggcgtgttcg tgagcaacgg cacccactgg  3300
ttcgtgaccc agcggaactt ctacgagccc cagatcatca ccaccgacaa caccttcgtg  3360
agcggcaact gcgacgtggt gatcggcatc gtgaacaaca ccgtgtacga tcccctgcag  3420
cccgagctgg acagcttcaa ggaggagctg gacaagtact tcaagaatca caccagcccc  3480
gacgtggacc tgggcgacat cagcggcatc aacgccagcg tggtgaacat ccagaaggag  3540
atcgatcggc tgaacgaggt ggccaagaac ctgaacgaga gcctgatcga cctgcaggag  3600
ctgggcaagt acgagcagta catcaagtgg ccctggtaca tctggctggg cttcatcgcc  3660
ggcctgatcg ccatcgtgat ggtgaccatc atgctgtgct gcatgaccag ctgctgcagc  3720
tgcctgaagg gctgttgcag ctgcggcagc tgctgcaagt tcgacgagga cgacagcgag  3780
cccgtgctga agggcgtgaa gctgcactac acc                                3813
```

```
SEQ ID NO: 30           moltype = AA  length = 1271
FEATURE                 Location/Qualifiers
source                  1..1271
                        mol_type = protein
                        organism = synthetic construct
SEQUENCE: 30
MFVFLVLLPL VSSQCVNLRT RTQLPPAYTN SFTRGVYYPD KVFRSSVLHS TQDLFLPFFS  60
NVTWFHAIHV SGTNGTKRFD NPVLPFNDGV YFASIEKSNI IRGWIFGTTL DSKTQSLLIV  120
NNATNVVIKV CEFQFCNDPF LDVYYHKNNK SWMESGVYSS ANNCTFEYVS QPFLMDLEGK  180
QGNFKNLREF VFKNIDGYFK IYSKHTPINL VRDLPQGFSA LEPLVDLPIG INITRFQTLL  240
ALHRSYLTPG DSSSGWTAGA AAYYVGYLQP RTFLLKYNEN GTITDAVDCA LDPLSETKCT  300
LKSFTVEKGI YQTSNFRVQP TESIVRFPNI TNLCPFGEVF NATRFASVYA WNRKRISNCV  360
ADYSVLYNSA SFSTFKCYGV SPTKLNDLCF TNVYADSFVI RGDEVRQIAP GQTGKIADYN  420
YKLPDDFTGC VIAWNSNNLD SKVGGNYNYR YRLFRKSNLK PFERDISTEI YQAGSKPCNG  480
VEGFNCYFPL QSYGFQPTNG VGYQPYRVVV LSFELLHAPA TVCGPKKSTN LVKNKCVNFN  540
FNGLTGTGVL TESNKKFLPF QQFGRDIADT TDAVRDPQTL EILDITPCSF GGVSVITPGT  600
NTSNQVAVLY QGVNCTEVPV AIHADQLTPT WRVYSTGSNV FQTRAGCLIG AEHVNNSYEC  660
DIPIGAGICA SYQTQTNSRR RARSVASQSI IAYTMSLGAE NSVAYSNNSI AIPTNFTISV  720
TTEILPVSMT KTSVDCTMYI CGDSTECSNL LLQYGSFCTQ LNRALTGIAV EQDKNTQEVF  780
AQVKQIYKTP PIKDFGGFNF SQILPDPSKP SKRSFIEDLL FNKVTLADAG FIKQYGDCLG  840
DIAARDLICA QKFNGLTVLP PLLTDEMIAQ YTSALLAGTI TSGWTFGAGA ALQIPFAMQM  900
AYRFNGIGVT QNVLYENQKL IANQFNSAIG KIQDSLSSTA SALGKLQNVV NQNAQALNTL  960
VKQLSSNFGA ISSVLNDILS RLDPPEAEVQ IDRLITGRLQ SLQTYVTQQL IRAAEIRASA  1020
NLAATKMSEC VLGQSKRVDF CGKGYHLMSF PQSAPHGVVF LHVTYVPAQE KNFTTAPAIC  1080
HDGKAHFPRE GVFVSNGTHW FVTQRNFYEP QIITTDNTFV SGNCDVVIGI VNNTVYDPLQ  1140
PELDSFKEEL DKYFKNHTSP DVDLGDISGI NASVVNIQKE IDRLNEVAKN LNESLIDLQE  1200
LGKYEQYIKW PWYIWLGFIA GLIAIVMVTI MLCCMTSCCS CLKGCCSCGS CCKFDEDDSE  1260
PVLKGVKLHY T                                                        1271
```

```
SEQ ID NO: 31           moltype = RNA  length = 3986
FEATURE                 Location/Qualifiers
source                  1..3986
                        mol_type = other RNA
                        organism = synthetic construct
SEQUENCE: 31
gggaaataag agagaaaaga agagtaagaa gaaatataag accccggcgc cgccaccatg  60
ttcgtgttcc tggtgctgct gcccctggtg agcagccagt gcgtgaacct gaccacccgg  120
acccagctgc caccagccta caccaacagc ttcacccggg gcgtctacta ccccgacaag  180
gtgttccgga gcagcgtcct gcacagcacc caggacctgt tcctgccctt cttcagcaac  240
gtgacctggt tccacgtgat cagcggcacc aacggcacca agcggttcga caaccccgtg  300
ctgcccttca acgacggcgt gtacttcgcc agcatcgaga agagcaacat catccggggc  360
tggatcttcg gcaccaccct ggacagcaag acccagagcc tgctgatcgt gaataacgcc  420
accaacgtgg tgatcaaggt gtgcgagttc cagttctgca acgacccctt cctggaccac  480
aagaacaaca agagctggat ggagagcgag ttccgggtgt acagcagcgc caacaactgc  540
accttcgagt acgtgagcca gcccttcctg atggacctgg agggcaagca gggcaacttc  600
```

```
aagaacctgc gggagttcgt gttcaagaac atcgacggct acttcaagat ctacagcaag  660
cacaccccaa tcatcgtgcg ggagcccgag gatctgcccc agggcttctc agccctggag  720
cccctggtgg acctgcccat cggcatcaac atcacccggt tccagaccct gctggccctg  780
caccggagct acctgacccc aggcgacagc agcagcgggt ggacagcagg cgcggctgct  840
tactacgtgg gctacctgca gccccggacc ttcctgctga agtacaacga gaacggcacc  900
atcaccgacg ccgtggactg cgccctggac cctctgagcg agaccaagtg caccctgaag  960
agcttcaccg tggagaaggg catctaccag accagcaact tccgggtgca gcccaccgag  1020
agcatcgtgc ggttccccaa catcaccaac ctgtgcccct tcgacgaggt gttcaacgcc  1080
acccggttcg ccagcgtgta cgcctggaac cggaagcgga tcagcaactg cgtggccgac  1140
tacagcgtgc tgtacaacct ggccccccttc ttcaccttca agtgctacgg cgtgagcccc  1200
accaagctga acgacctgtg cttcaccaac gtgtacgccg acagcttcgt gatccgtggc  1260
gacgaggtgc ggcagatcgc acccggccag acaggcaaca tcgccgacta caactacaag  1320
ctgcccgacg acttcaccgg ctgcgtgatc gcctggaaca gcaacaagct cgacagcaag  1380
gtgagcggca actacaacta cctgtaccgg ctgttccgga agagcaacct gaagcccttc  1440
gagcgggaca tcagcaccga gatctaccaa gccggcaaca agccttgcaa cggcgtggcc  1500
ggcttcaact gctacttccc tctgcggagc tacagcttcc ggcccaccta cggcgtgggc  1560
caccagccct accgggtggt ggtgctgagc ttcgagctgc tgcacgcccc agccaccgtg  1620
tgtggcccca agaagagcac caacctggtg aagaacaagt gcgtgaactt caacttcaac  1680
ggccttaagg gcaccggcgt gctgaccgag agcaacaaga aattcctgcc ctttcagcag  1740
ttcggccggg acatcgccga caccaccgac gctgtgcggg atccccagac cctggagatc  1800
ctggacatca ccccttgcag cttcggcggc gtgagcgtga tcaccccagg caccaacacc  1860
agcaaccagg tggccgtgct gtaccagggc gtgaactgca ccgaggtgcc cgtggccatc  1920
cacgccgacc agctgacacc cacctggcgg gtctacagca ccggcagcaa cgtgttccag  1980
acccgggccg gttgcctgat cggcgccgag tacgtgaaca acagctacga gtgcgacatc  2040
cccatcggcg ccggcatctg tgccagctac cagacccaga ccaagtcaca ccggagggca  2100
aggagcgtgg ccagccagag catcatcgcc tacaccatga gcctgggcgc cgagaacagc  2160
gtggcctaca gcaacaacag catcgccatc cccaccaact tcaccatcag cgtgaccacc  2220
gagattctgc ccgtgagcat gaccaagacc agcgtggact gcaccatgta catctgcggc  2280
gacagcaccg agtgcagcaa cctgctgctg cagtacggca gcttctgcac ccagctgaag  2340
cgggccctga ccggcatcgc cgtggagcag gacaagaaca cccaggaggt gttcgcccag  2400
gtgaagcaga tctacaagac ccctcccatc aagtacttcg gcggcttcaa cttcagccag  2460
atcctgcccg accccagcaa gcccagcaag cggagcttca tcgaggacct gctgttcaac  2520
aaggtgaccc tagccgacgc cggcttcatc aagcagtacg gcgactgcct cggcgacata  2580
gccgcccggg acctgatctg cgcccagaag ttcaagggcc tgaccgtgct gcctcccctg  2640
ctgaccgacg agatgatcgc ccagtacacc agcgccctgt tagccggaac catcaccagc  2700
ggctggactt tcggcgctgg agccgctctg cagatcccct tcgccatgca gatggcctac  2760
cggttcaacg gcatcggcgt gacccagaac gtgctgtacg agaaccagaa gctgatcgcc  2820
aaccagttca acagcgccat cggcaagatc caggacagcc tgagcagcac cgctagcgcc  2880
ctgggcaagc tgcaggacgt ggtgaaccac aacgcccagg ccctgaacac cctggtgaag  2940
cagctgagca gcaagttcgg cgccatcagc agcgtgctga acgacatctt cagccggctg  3000
gaccctcccg aggccgaggt gcagatcgac cggctgatca ctggccggct gcagagcctg  3060
cagacctacg tgacccagca gctgatccgg gccgccgaga ttcgggccag cgccaacctg  3120
gccgccacca agatgagcga gtgcgtgctg ggccagagca agcgggtgga cttctgcggc  3180
aagggctacc acctgatgag ctttccccag agcgcacccc acggagtggt gttcctgcac  3240
gtgacctacg tgcccgccca ggagaagaac ttcaccaccg ccccagccat ctgccacgac  3300
ggcaaggccc actttccccg ggagggcgtg ttcgtgagca acggcaccca ctggttcgtg  3360
acccagcgga acttctacga gccccagatc atcaccaccg acaacacctt cgtgagcggc  3420
aactgcgacg tggtgatcgg catcgtgaac aacaccgtgt acgatcccct gcagcccgag  3480
ctggacagct tcaaggagga gctggacaag tacttcaaga atcacaccag ccccgacgtg  3540
gacctgggcg acatcagcgg catcaacgcc agcgtggtga acatccagaa ggagatcgat  3600
cggctgaacg aggtggccaa gaacctgaac gagagcctga tcgacctgca ggagctgggc  3660
aagtacgagc agtacatcaa gtggccctgg tacatctggc tgggcttcat cgccggcctg  3720
atcgccatcg tgatggtgac catcatgctg tgctgcatga ccagctgctg cagctgcctg  3780
aagggctgtt gcagctgcgg cagctgctgc aagttcgacg aggacgacag cgagcccgtg  3840
ctgaagggcg tgaagctgca ctacacctga taataggctg gagcctcggt ggcctagctt  3900
cttgcccctt gggcctcccc ccagcccctc ctccccttcc tgcacccgta cccccgtggt  3960
ctttgaataa agtctgagtg ggcggc                                       3986
```

```
SEQ ID NO: 32           moltype = RNA  length = 3810
FEATURE                 Location/Qualifiers
source                  1..3810
                        mol_type = other RNA
                        organism = synthetic construct
SEQUENCE: 32
atgttcgtgt tcctggtgct gctgccccctg gtgagcagcc agtgcgtgaa cctgaccacc  60
cggacccagc tgccaccagc ctacaccaac agcttcaccc ggggcgtcta ctaccccgac  120
aaggtgttcc ggagcagcgt cctgcacagc acccaggacc tgttcctgcc cttcttcagc  180
aacgtgacct ggttccacgt gatcagcggc accaacggca ccaagcggtt cgacaacccc  240
gtgctgccct tcaacgacgg cgtgtacttc gccagcatcg agaagagcaa catcatccgg  300
ggctggatct tcggcaccac cctggacagc aagacccaga gcctgctgat cgtgaataac  360
gccaccaacg tggtgatcaa ggtgtgcgag ttccagttct gcaacgaccc cttcctggac  420
cacaagaaca acaagagctg gatggagagc gagttccggg tgtacagcag cgccaacaac  480
tgcaccttcg agtacgtgag ccagcccttc ctgatggacc tggagggcaa gcagggcaac  540
ttcaagaacc tgcgggagtt cgtgttcaag aacatcgacg gctacttcaa gatctacagc  600
aagcacaccc caatcatcgt gcgggagccc gaggatctgc cccagggctt ctcagccctg  660
gagcccctgg tggacctgcc catcggcatc aacatcaccc ggttccagac cctgctggcc  720
ctgcaccgga gctacctgac ccccaggcgac agcagcagcg ggtggacagc aggcgcggct  780
gcttactacg tgggctacct gcagccccgg accttcctgc tgaagtacaa cgagaacggc  840
accatcaccg acgccgtgga ctgcgccctg gaccctctga gcgagaccaa gtgcaccctg  900
```

```
aagagcttca ccgtggagaa gggcatctac cagaccagca acttccgggt gcagcccacc  960
gagagcatcg tgcggttccc caacatcacc aacctgtgcc ccttcgacga ggtgttcaac  1020
gccacccggt tcgccagcgt gtacgcctgg aaccggaagc ggatcagcaa ctgcgtggcc  1080
gactacagcg tgctgtacaa cctggccccc ttcttcacct tcaagtgcta cggcgtgagc  1140
cccaccaagc tgaacgacct gtgcttcacc aacgtgtacg ccgacagctt cgtgatccgt  1200
ggcgacgagg tgcggcagat cgcacccggc cagacaggca acatcgccga ctacaactac  1260
aagctgcccg acgacttcac cggctgcgtg atcgcctgga acagcaacaa gctcgacagc  1320
aaggtgagcg gcaactacaa ctacctgtac cggctgttcc ggaagagcaa cctgaagccc  1380
ttcgagcggg acatcagcac cgagatctac caagccggca acaagccttg caacggcgtg  1440
gccggcttca actgctactt ccctctgcgg agctacagct tccggcccac ctacggcgtg  1500
ggccaccagc cctaccgggt ggtggtgctg agcttcgagc tgctgcacgc cccagccacc  1560
gtgtgtggcc ccaagaagag caccaacctg gtgaagaaca agtgcgtgaa cttcaacttc  1620
aacggcctta agggcaccgg cgtgctgacc gagagcaaca agaaattcct gccctttcag  1680
cagttcggcc gggacatcgc cgacaccacc gacgctgtgc gggatcccca gaccctggag  1740
atcctggaca tcacccettg cagcttcggc ggcgtgagcg tgatcacccc aggcaccaac  1800
accagcaacc aggtggccgt gctgtaccag ggcgtgaact gcaccgaggt gcccgtggcc  1860
atccacgccg accagctgac acccacctgg cgggtctaca gcaccggcag caacgtgttc  1920
cagacccggg ccggttgcct gatcggcgcc gagtacgtga acaacagcta cgagtgcgac  1980
atccccatcg gcgccggcat ctgtgccagc taccagaccc agaccaagtc acaccggagg  2040
gcaaggagcg tggccagcca gagcatcatc gcctacacca tgagcctggg cgccgagaac  2100
agcgtggcct acagcaacaa cagcatcgcc atccccacca acttcaccat cagcgtgacc  2160
accgagattc tgcccgtgag catgaccaag accagcgtgg actgcaccat gtacatctgc  2220
ggcgacagca ccgagtgcag caacctgctg ctgcagtacg gcagcttctg cacccagctg  2280
aagcgggccc tgaccggcat cgccgtggag caggacaaga acacccagga ggtgttcgcc  2340
caggtgaagc agatctacaa gacccctccc atcaagtact tcggcggctt caacttcagc  2400
cagatcctgc ccgaccccag caagcccagc aagcggagct tcatcgagga cctgctgttc  2460
aacaaggtga ccctagccga cgccggcttc atcaagcagt acggcgactg cctcggcgac  2520
atagccgccc gggacctgat ctgcgcccag aagttcaagg gcctgaccgt gctgcctccc  2580
ctgctgaccg acgagatgat cgcccagtac accagcgccc tgttagccgg aaccatcacc  2640
agcggctgga ctttcggcgc tggagccgct ctgcagatcc ccttcgccat gcagatggcc  2700
taccggttca acggcatcgg cgtgacccag aacgtgctgt acgagaacca gaagctgatc  2760
gccaaccagt tcaacagcgc catcggcaag atccaggaca gcctgagcag caccgctagc  2820
gccctgggca agctgcagga cgtggtgaac cacaacgccc aggccctgaa caccctggtg  2880
aagcagctga gcagcaagtt cggcgccatc agcagcgtgc tgaacgacat cttcagccgg  2940
ctggaccctc ccgaggccga ggtgcagatc gaccggctga tcactggccg gctgcagagc  3000
ctgcagacct acgtgaccca gcagctgatc cgggccgccg agattcgggc cagcgccaac  3060
ctggccgcca ccaagatgag cgagtgcgtg ctgggccaga gcaagcgggt ggacttctgc  3120
ggcaagggct accacctgat gagctttccc cagagcgcac cccacggagt ggtgttcctg  3180
cacgtgacct acgtgcccgc ccaggagaag aacttcacca ccgcccccagc catctgccac  3240
gacggcaagg cccactttcc ccgggagggc gtgttcgtga gcaacggcac ccactggttc  3300
gtgacccagc ggaacttcta cgagccccag atcatcacca ccgacaacac cttcgtgagc  3360
ggcaactgcg acgtggtgat cggcatcgtg aacaacaccg tgtacgatcc cctgcagccc  3420
gagctggaca gcttcaagga ggagctggac aagtacttca agaatcacac cagccccgac  3480
gtggacctgg gcgacatcag cggcatcaac gccagcgtgg tgaacatcca gaaggagatc  3540
gatcggctga acgaggtggc caagaacctg aacgagagcc tgatcgacct gcaggagctg  3600
ggcaagtacg agcagtacat caagtggccc tggtacatct ggctgggctt catcgccggc  3660
ctgatcgcca tcgtgatggt gaccatcatg ctgtgctgca tgaccagctg ctgcagctgc  3720
ctgaagggct gttgcagctg cggcagctgc tgcaagttcg acgaggacga cagcgagccc  3780
gtgctgaagg gcgtgaagct gcactacacc                                   3810

SEQ ID NO: 33          moltype = AA  length = 1270
FEATURE                Location/Qualifiers
source                 1..1270
                       mol_type = protein
                       organism = synthetic construct
SEQUENCE: 33
MFVFLVLLPL VSSQCVNLTT RTQLPPAYTN SFTRGVYYPD KVFRSSVLHS TQDLFLPFFS  60
NVTWFHVISG TNGTKRFDNP VLPFNDGVYF ASIEKSNIIR GWIFGTTLDS KTQSLLIVNN  120
ATNVVIKVCE FQFCNDPFLD HKNNKSWMES EFRVYSSANN CTFEYVSQPF LMDLEGKQGN  180
FKNLREFVFK NIDGYFKIYS KHTPIIVREP EDLPQGFSAL EPLVDLPIGI NITRFQTLLA  240
LHRSYLTPGD SSSGWTAGAA AYYVGYLQPR TFLLKYNENG TITDAVDCAL DPLSETKCTL  300
KSFTVEKGIY QTSNFRVQPT ESIVRFPNIT NLCPFDEVFN ATRFASVYAW NRKRISNCVA  360
DYSVLYNLAP FFTFKCYGVS PTKLNDLCFT NVYADSFVIR GDEVRQIAPG QTGNIADYNY  420
KLPDDFTGCV IAWNSNKLDS KVSGNYNYLY RLFRKSNLKP FERDISTEIY QAGNKPCNGV  480
AGFNCYFPLR SYSFRPTYGV GHQPYRVVVL SFELLHAPAT VCGPKKSTNL VKNKCVNFNF  540
NGLKGTGVLT ESNKKFLPFQ QFGRDIADTT DAVRDPQTLE ILDITPCSFG GVSVITPGTN  600
TSNQVAVLYQ GVNCTEVPVA IHADQLTPTW RVYSTGSNVF QTRAGCLIGA EYVNNSYECD  660
IPIGAGICAS YQTQTKSHRR ARSVASQSII AYTMSLGAEN SVAYSNNSIA IPTNFTISVT  720
TEILPVSMTK TSVDCTMYIC GDSTECSNLL LQYGSFCTQL KRALTGIAVE QDKNTQEVFA  780
QVKQIYKTPP IKYFGGFNFS QILPDPSKPS KRSFIEDLLF NKVTLADAGF IKQYGDCLGD  840
IAARDLICAQ KFKGLTVLPP LLTDEMIAQY TSALLAGTIT SGWTFGAGAA LQIPFAMQMA  900
YRFNGIGVTQ NVLYENQKLI ANQFNSAIGK IQDSLSSTAS ALGKLQDVVN HNAQALNTLV  960
KQLSSKFGAI SSVLNDIFSR LDPPEAEVQI DRLITGRLQS LQTYVTQQLI RAAEIRASAN  1020
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTDNTFVS GNCDVVIGIV NNTVYDPLQP  1140
ELDSFKEELD KYFKNHTSPD VDLGDISGIN ASVVNIQKEI DRLNEVAKNL NESLIDLQEL  1200
GKYEQYIKWP WYIWLGFIAG LIAIVMVTIM LCCMTSCCSC LKGCCSCGSC CKFDEDDSEP  1260
VLKGVKLHYT                                                         1270
```

```
SEQ ID NO: 34           moltype = RNA  length = 3986
FEATURE                 Location/Qualifiers
source                  1..3986
                        mol_type = other RNA
                        organism = synthetic construct
SEQUENCE: 34
gggaaataag agagaaaaga agagtaagaa gaaatataag accccggcgc cgccaccatg  60
ttcgtgttcc tggtgctgct gcccctggtg agcagccagt gcgtgaacct gaccacccgg  120
acccagctgc caccagccta caccaacagc ttcacccggg gcgtctacta ccccgacaag  180
gtgttccgga gcagcgtcct gcacagcacc caggacctgt tcctgccctt cttcagcaac  240
gtgacctggt tccacgtgat cagcggcacc aacggcacca agcggttcga caaccccgtg  300
ctgcccttca acgacggcgt gtacttcgcc agcatcgaga agagcaacat catccggggc  360
tggatcttcg gcaccaccct ggacagcaag acccagagcc tgctgatcgt gaataacgcc  420
accaacgtgg tgatcaaggt gtgcgagttc cagttctgca acgacccctt cctggaccac  480
aagaacaaca agagctggat ggagagcgag ttccgggtgt acagcagcgc caacaactgc  540
accttcgagt acgtgagcca gcccttcctg atggacctgg agggcaagca gggcaacttc  600
aagaacctgc gggagttcgt gttcaagaac atcgacggct acttcaagat ctacagcaag  660
cacaccccaa tcatcgtgcg ggagcccgag gatctgcccc agggcttctc agccctggag  720
cccctggtgg acctgcccat cggcatcaac atcacccggt tccagaccct gctggccctg  780
caccggagct acctgacccc aggcgacagc agcagcgggt ggacagcagg cgcggctgct  840
tactacgtgg gctacctgca gccccggacc ttcctgctga agtacaacga gaacggcacc  900
atcaccgacg ccgtggactg cgccctggac cctctgagcg agaccaagtg caccctgaag  960
agcttcaccg tggagaaggg catctaccag accagcaact tccgggtgca gcccaccgag  1020
agcatcgtgc ggttccccaa catcaccaac ctgtgcccct tcgacgaggt gttcaacgcc  1080
acccggttcg ccagcgtgta cgcctggaac cggaagcgga tcagcaactg cgtggccgac  1140
tacagcgtgc tgtacaacct ggccccctte ttcaccttca agtgctacgg cgtgagcccc  1200
accaagctga acgacctgtg cttcaccaac gtgtacgccg acagcttcgt gatccgtggc  1260
gacgaggtgc ggcagatcgc acccggccag acaggcaaca tcgccgacta caactacaag  1320
ctgcccgacg acttcaccgg ctgcgtgatc gcctggaaca gcaacaagct cgacagcaag  1380
gtgagcggca actacaacta cctgtaccgg ctgttccgga agagcaacct gaagcccttc  1440
gagcgggaca tcagcaccga gatctaccaa gccggcaaca agccttgcaa cggcgtggcc  1500
ggcttcaact gctacttccc tctgcggagc tacagcttcc ggcccaccta cggcgtgggc  1560
caccagccct accgggtggt ggtgctgagc ttcgagctgc tgcacgcccc agccaccgtg  1620
tgtggcccca agaagagcac caacctggtg aagaacaagt gcgtgaactt caacttcaac  1680
ggccttaagg gcaccggcgt gctgaccgag agcaacaaga aattcctgcc ctttcagcag  1740
ttcggccggg acatcgccga caccaccgac gctgtgcggg atccccagac cctggagatc  1800
ctggacatca cccccttgcag cttcggcggc gtgagcgtga tcaccccagg caccaacacc  1860
agcaaccagg tggccgtgct gtaccagggc gtgaactgca ccgaggtgcc cgtggccatc  1920
cacgccgacc agctgacacc cacctggcgg gtctacagca ccggcagcaa cgtgttccag  1980
acccgggccg gttgcctgat cggcgccgag tacgtgaaca acagctacga gtgcgacatc  2040
cccatcggcg ccggcatctg tgccagctac cagacccaga ccaattcacc cggcggcgca  2100
ggcagcgtgg ccagccagag catcatcgcc tacaccatga gcctgggcgc cgagaacagc  2160
gtggcctaca gcaacaacag catcgccatc cccaccaact tcaccatcag cgtgaccacc  2220
gagattctgc ccgtgagcat gaccaagacc agcgtggact gcaccatgta catctgcggc  2280
gacagcaccg agtgcagcaa cctgctgctg cagtacggca gcttctgcac ccagctgaag  2340
cgggccctga ccggcatcgc cgtggagcag gacaagaaca cccaggaggt gttcgcccag  2400
gtgaagcaga tctacaagac ccctcccatc aagtacttcg gcggcttcaa cttcagccag  2460
atcctgcccg accccagcaa gcccagcaag cggagcttca tcgaggacct gctgttcaac  2520
aaggtgaccc tagccgacgc cggcttcatc aagcagtacg gcgactgcct cggcgacata  2580
gccgcccggg acctgatctg cgcccagaag ttcaagggcc tgaccgtgct gcctcccctg  2640
ctgaccgacg agatgatcgc ccagtacacc agcgccctgt tagccggaac catcaccagc  2700
ggctggactt tcggcgctgg agccgctctg cagatcccct tcgccatgca gatggcctac  2760
cggttcaacg gcatcggcgt gacccagaac gtgctgtacg agaaccagaa gctgatcgcc  2820
aaccagttca acagcgccat cggcaagatc caggacagcc tgagcagcac cgctagcgcc  2880
ctgggcaagc tgcaggacgt ggtgaaccac aacgcccagg ccctgaacac cctggtgaag  2940
cagctgagca gcaagttcgg cgccatcagc agcgtgctga acgacatctt cagccggctg  3000
gaccctcccg aggccgaggt gcagatcgac cggctgatca ctggccggct gcagagcctg  3060
cagacctacg tgacccagca gctgatccgg gccgccgaga ttcgggccag cgccaacctg  3120
gccgccacca agatgagcga gtgcgtgctg ggccagagca agcgggtgga cttctgcggc  3180
aagggctacc acctgatgag ctttccccag agcgcacccc acggagtggt gttcctgcac  3240
gtgacctacg tgcccgccca ggagaagaac ttcaccaccg ccccagccat ctgccacgac  3300
ggcaaggccc actttccccg ggagggcgtg ttcgtgagca acggcaccca ctggttcgtg  3360
acccagcgga acttctacga gccccagatc atcaccaccg acaacacctt cgtgagcggc  3420
aactgcgacg tggtgatcgg catcgtgaac aacaccgtgt acgatcccct gcagcccgag  3480
ctggacagct tcaaggagga gctggacaag tacttcaaga atcacaccag ccccgacgtg  3540
gacctgggcg acatcagcgg catcaacgcc agcgtggtga acatccagaa ggagatcgat  3600
cggctgaacg aggtggccaa gaacctgaac gagagcctga tcgacctgca ggagctgggc  3660
aagtacgagc agtacatcaa gtggccctgg tacatctggc tgggcttcat cgccggcctg  3720
atcgccatcg tgatggtgac catcatgctg tgctgcatga ccagctgctg cagctgcctg  3780
aagggctgtt gcagctgcgg cagctgctgc aagttcgacg aggacgacag cgagcccgtg  3840
ctgaagggcg tgaagctgca ctacacctga taataggctg gagcctcggt ggcctagctt  3900
cttgcccctt gggcctcccc ccagcccctc ctccccttcc tgcacccgta cccccgtggt  3960
ctttgaataa agtctgagtg ggcggc                                       3986

SEQ ID NO: 35           moltype = RNA  length = 3810
FEATURE                 Location/Qualifiers
source                  1..3810
                        mol_type = other RNA
                        organism = synthetic construct
```

```
SEQUENCE: 35
atgttcgtgt tcctggtgct gctgcccctg gtgagcagcc agtgcgtgaa cctgaccacc  60
cggacccagc tgccaccagc ctacaccaac agcttcaccc ggggcgtcta ctaccccgac  120
aaggtgttcc ggagcagcgt cctgcacagc acccaggacc tgttcctgcc cttcttcagc  180
aacgtgacct ggttccacgt gatcagcggc accaacggca ccaagcggtt cgacaacccc  240
gtgctgccct tcaacgacgg cgtgtacttc gccagcatcg agaagagcaa catcatccgg  300
ggctggatct tcggcaccac cctggacagc aagacccaga gcctgctgat cgtgaataac  360
gccaccaacg tggtgatcaa ggtgtgcgag ttccagttct gcaacgaccc cttcctggac  420
cacaagaaca acaagagctg gatggagagc gagttccggg tgtacagcag cgccaacaac  480
tgcaccttcg agtacgtgag ccagcccttc ctgatggacc tggagggcaa gcagggcaac  540
ttcaagaacc tgcgggagtt cgtgttcaag aacatcgacg gctacttcaa gatctacagc  600
aagcacaccc caatcatcgt gcgggagccc gaggatctgc cccagggctt ctcagccctg  660
gagcccctgg tggacctgcc catcggcatc aacatcaccc ggttccagac cctgctggcc  720
ctgcaccgga gctacctgac ccaggcgac agcagcagcg ggtggacagc aggcgcggct  780
gcttactacg tgggctacct gcagccccgg accttcctgc tgaagtacaa cgagaacggc  840
accatcaccg acgccgtgga ctgcgccctg gaccctctga gcgagaccaa gtgcaccctg  900
aagagcttca ccgtggagaa gggcatctac cagaccagca acttccgggt gcagcccacc  960
gagagcatcg tgcggttccc caacatcacc aacctgtgcc ccttcgacga ggtgttcaac  1020
gccacccggt tcgccagcgt gtacgcctgg aaccggaagc ggatcagcaa ctgcgtggcc  1080
gactacagcg tgctgtacaa cctggccccc ttcttcacct tcaagtgcta cggcgtgagc  1140
cccaccaagc tgaacgacct gtgcttcacc aacgtgtacg ccgacagctt cgtgatccgt  1200
ggcgacgagg tgcggcagat cgcacccggc cagacaggca acatcgccga ctacaactac  1260
aagctgcccg acgacttcac cggctgcgtg atcgcctgga acagcaacaa gctcgacagc  1320
aaggtgagcg gcaactacaa ctacctgtac cggctgttcc ggaagagcaa cctgaagccc  1380
ttcgagcggg acatcagcac cgagatctac caagccggca acaagccttg caacggcgtg  1440
gccggcttca actgctactt ccctctgcgg agctacagct tccggcccac ctacggcgtg  1500
ggccaccagc cctaccgggt ggtggtgctg agcttcgagc tgctgcacgc cccagccacc  1560
gtgtgtggcc ccaagaagag caccaacctg gtgaagaaca agtgcgtgaa cttcaacttc  1620
aacggcctta agggcaccgg cgtgctgacc gagagcaaca agaaattcct gccctttcag  1680
cagttcggcc gggacatcgc cgacaccacc gacgctgtgc gggatcccca gaccctggag  1740
atcctggaca tcaccccttg cagcttcggc ggcgtgagcg tgatcacccc aggcaccaac  1800
accagcaacc aggtggccgt gctgtaccag ggcgtgaact gcaccgaggt gcccgtggcc  1860
atccacgccg accagctgac acccacctgg cgggtctaca gcaccggcag caacgtgttc  1920
cagacccggg ccggttgcct gatcggcgcc gagtacgtga acaacagcta cgagtgcgac  1980
atccccatcg gcgccggcat ctgtgccagc taccagaccc agaccaattc acccggcggc  2040
gcaggcagcg tggccagcca gagcatcatc gcctacacca tgagcctggg cgccgagaac  2100
agcgtggcct acagcaacaa cagcatcgcc atccccacca acttcaccat cagcgtgacc  2160
accgagattc tgcccgtgag catgaccaag accagcgtgg actgcaccat gtacatctgc  2220
ggcgacagca ccgagtgcag caacctgctg ctgcagtacg gcagcttctg cacccagctg  2280
aagcgggccc tgaccggcat cgccgtggag caggacaaga acacccagga ggtgttcgcc  2340
caggtgaagc agatctacaa gaccccctcc atcaagtact tcggcggctt caacttcagc  2400
cagatcctgc ccgaccccag caagcccagc aagcggagct tcatcgagga cctgctgttc  2460
aacaaggtga ccctagccga cgccggcttc atcaagcagt acggcgactg cctcggcgac  2520
atagccgccc gggacctgat ctgcgcccag aagttcaagg gcctgaccgt gctgcctccc  2580
ctgctgaccg acgagatgat cgcccagtac accagcgccc tgttagccgg aaccatcacc  2640
agcggctgga ctttcggcgc tggagccgct ctgcagatcc ccttcgccat gcagatggcc  2700
taccggttca acggcatcgg cgtgacccag aacgtgctgt acgagaacca gaagctgatc  2760
gccaaccagt tcaacagcgc catcggcaag atccaggaca gcctgagcag caccgctagc  2820
gccctgggca agctgcagga cgtggtgaac cacaacgccc aggccctgaa caccctggtg  2880
aagcagctga gcagcaagtt cggcgccatc agcagcgtgc tgaacgacat cttcagccgg  2940
ctggaccctc ccgaggccga ggtgcagatc gaccggctga tcactggccg gctgcagagc  3000
ctgcagacct acgtgaccca gcagctgatc cgggccgccg agattcgggc cagcgccaac  3060
ctggccgcca ccaagatgag cgagtgcgtg ctgggccaga gcaagcgggt ggacttctgc  3120
ggcaagggct accacctgat gagctttccc cagagcgcac cccacggagt ggtgttcctg  3180
cacgtgacct acgtgcccgc ccaggagaag aacttcacca ccgcccccagc catctgccac  3240
gacggcaagg cccactttcc ccgggagggc gtgttcgtga gcaacggcac ccactggttc  3300
gtgacccagc ggaacttcta cgagccccag atcatcacca ccgacaacac cttcgtgagc  3360
ggcaactgcg acgtggtgat cggcatcgtg aacaacaccg tgtacgatcc cctgcagccc  3420
gagctggaca gcttcaagga ggagctggac aagtacttca agaatcacac cagccccgac  3480
gtggacctgg gcgacatcag cggcatcaac gccagcgtgg tgaacatcca gaaggagatc  3540
gatcggctga acgaggtggc caagaacctg aacgagagcc tgatcgacct gcaggagctg  3600
ggcaagtacg agcagtacat caagtggccc tggtacatct ggctgggctt catcgccggc  3660
ctgatcgcca tcgtgatggt gaccatcatg ctgtgctgca tgaccagctg ctgcagctgc  3720
ctgaagggct gttgcagctg cggcagctgc tgcaagttcg acgaggacga cagcgagccc  3780
gtgctgaagg gcgtgaagct gcactacacc                                   3810

SEQ ID NO: 36          moltype = AA  length = 1270
FEATURE                Location/Qualifiers
source                 1..1270
                       mol_type = protein
                       organism = synthetic construct
SEQUENCE: 36
MFVFLVLLPL VSSQCVNLTT RTQLPPAYTN SFTRGVYYPD KVFRSSVLHS TQDLFLPFFS  60
NVTWFHVISG TNGTKRFDNP VLPFNDGVYF ASIEKSNIIR GWIFGTTLDS KTQSLLIVNN  120
ATNVVIKVCE FQFCNDPFLD HKNNKSWMES EFRVYSSANN CTFEYVSQPF LMDLEGKQGN  180
FKNLREFVFK NIDGYFKIYS KHTPIIVREP EDLPQGFSAL EPLVDLPIGI NITRFQTLLA  240
LHRSYLTPGD SSSGWTAGAA AYYVGYLQPR TFLLKYNENG TITDAVDCAL DPLSETKCTL  300
KSFTVEKGIY QTSNFRVQPT ESIVRFPNIT NLCPFDEVFN ATRFASVYAW NRKRISNCVA  360
DYSVLYNLAP FFTFKCYGVS PTKLNDLCFT NVYADSFVIR GDEVRQIAPG QTGNIADYNY  420
```

-continued

```
KLPDDFTGCV IAWNSNKLDS KVSGNYNYLY RLFRKSNLKP FERDISTEIY QAGNKPCNGV  480
AGFNCYFPLR SYSFRPTYGV GHQPYRVVVL SFELLHAPAT VCGPKKSTNL VKNKCVNFNF  540
NGLKGTGVLT ESNKKFLPFQ QFGRDIADTT DAVRDPQTLE ILDITPCSFG GVSVITPGTN  600
TSNQVAVLYQ GVNCTEVPVA IHADQLTPTW RVYSTGSNVF QTRAGCLIGA EYVNNSYECD  660
IPIGAGICAS YQTQTNSPGG AGSVASQSII AYTMSLGAEN SVAYSNNSIA IPTNFTISVT  720
TEILPVSMTK TSVDCTMYIC GDSTECSNLL LQYGSFCTQL KRALTGIAVE QDKNTQEVFA  780
QVKQIYKTPP IKYFGGFNFS QILPDPSKPS KRSFIEDLLF NKVTLADAGF IKQYGDCLGD  840
IAARDLICAQ KFKGLTVLPP LLTDEMIAQY TSALLAGTIT SGWTFGAGAA LQIPFAMQMA  900
YRFNGIGVTQ NVLYENQKLI ANQFNSAIGK IQDSLSSTAS ALGKLQDVVN HNAQALNTLV  960
KQLSSKFGAI SSVLNDIFSR LDPPEAEVQI DRLITGRLQS LQTYVTQQLI RAAEIRASAN  1020
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTDNTFVS GNCDVVIGIV NNTVYDPLQP  1140
ELDSFKEELD KYFKNHTSPD VDLGDISGIN ASVVNIQKEI DRLNEVAKNL NESLIDLQEL  1200
GKYEQYIKWP WYIWLGFIAG LIAIVMVTIM LCCMTSCCSC LKGCCSCGSC CKFDEDDSEP  1260
VLKGVKLHYT                                                         1270

SEQ ID NO: 37           moltype = RNA  length = 3986
FEATURE                 Location/Qualifiers
source                  1..3986
                        mol_type = other RNA
                        organism = synthetic construct
SEQUENCE: 37
gggaaataag agagaaaaga agagtaagaa gaaatataag accccggcgc cgccaccatg  60
ttcgtgttcc tggtgctgct gcccctggtg agcagccagt gcgtgaacct gaccacccgg  120
acccagctgc caccagccta caccaacagc ttcacccggg gcgtgtacta ccccgacaag  180
gtgttccgga gcagcgtgct gcacagcacc caggacctgt tcctgccctt cttcagcaac  240
gtgacctggt tccacgtgat cagcggcacc aacggcacca agcggttcga caaccccgtg  300
ctgcccttca acgacggcgt gtacttcgcc agcatcgaga agagcaacat catccggggc  360
tggatcttcg gcaccaccct ggacagcaag acccagagcc tgctgatcgt gaacaacgcc  420
accaacgtgg tgatcaaggt gtgcgagttc cagttctgca acgacccctt cctggaccac  480
aagaacaaca agagctggat ggagagcgag ttccgggtgt acagcagcgc caacaactgc  540
accttcgagt acgtgagcca gcccttcctg atggacctgg agggcaagca gggcaacttc  600
aagaacctgc gggagttcgt gttcaagaac atcgacggct acttcaagat ctacagcaag  660
cacaccccaa tcatcgtgcg ggagcccgag gacctgcccc agggcttcag cgccctggag  720
cccctggtgg acctgcccat cggcatcaac atcacccggt tccagaccct gctggccctg  780
caccggagct acctgacccc aggcgacagc agcagcggct ggaccgccgg cgccgccgcc  840
tactacgtgg gctacctgca gccccggacc ttcctgctga agtacaacga gaacggcacc  900
atcaccgacg ccgtggactg cgccctggac cctctgagcg agaccaagtg caccctgaag  960
agcttcaccg tggagaaggg catctaccag accagcaact tccgggtgca gcccaccgag  1020
agcatcgtgc ggttccccaa catcaccaac ctgtgcccct tcgacgaggt gttcaacgcc  1080
acccggttcg ccagcgtgta cgcctggaac cggaagcgga tcagcaactg cgtggccgac  1140
tacagcgtgc tgtacaacct ggcccctttc ttcaccttca agtgctacgg cgtgagcccc  1200
accaagctga acgacctgtg cttcaccaac gtgtacgccg acagcttcgt gatccggggc  1260
gacgaggtgc ggcagatcgc cccaggccag accggcaaca tcgccgacta caactacaag  1320
ctgcccgacg acttcaccgg ctgcgtgatc gcctggaaca gcaacaagct ggacagcaag  1380
gtgagcggca actacaacta cctgtaccgg ctgttccgga agagcaacct gaagcccttc  1440
gagcgggaca tcagcaccga gatctaccag gccggcaaca agccctgcaa cggcgtggcc  1500
ggcttcaact gctacttccc tctgcggagc tacagcttcc ggcccaccta cggcgtgggc  1560
caccagccct accgggtggt ggtgctgagc ttcgagctgc tgcacgcccc agccaccgtg  1620
tgcggcccca agaagagcac caacctggtg aagaacaagt gcgtgaactt caacttcaac  1680
ggcctgaagg gcaccggcgt gctgaccgag agcaacaaga agttcctgcc cttccagcag  1740
ttcggccggg acatcgccga caccaccgac gccgtgcggg atccccagac cctggagatc  1800
ctggacatca ccccttgcag cttcggcggc gtgagcgtga tcaccccagg caccaacacc  1860
agcaaccagg tggccgtgct gtaccagggc gtgaactgca ccgaggtgcc cgtggccatc  1920
cacgccgacc agctgacccc aacctggcgg gtgtacagca ccggcagcaa cgtgttccag  1980
acccgggccg gctgcctgat cggcgccgag tacgtgaaca acagctacga gtgcgacatc  2040
cccatcggcg ccggcatctg cgccagctac cagacccaga ccaacagccc cggcggcgcc  2100
ggcagcgtgg ccagccagag catcatcgcc tacaccatga gcctgggcgc cgagaacagc  2160
gtggcctaca gcaacaacag catcgccatc cccaccaact tcaccatcag cgtgaccacc  2220
gagatcctgc ccgtgagcat gaccaagacc agcgtggact gcaccatgta catctgcggc  2280
gacagcaccg agtgcagcaa cctgctgctg cagtacggca gcttctgcac ccagctgaag  2340
cgggccctga ccggcatcgc cgtggagcag gacaagaaca cccaggaggt gttcgcccag  2400
gtgaagcaga tctacaagac ccctcccatc aagtacttcg gcggcttcaa cttcagccag  2460
atcctgcccg accccagcaa gcccagcaag cggagcttca tcgaggacct gctgttcaac  2520
aaggtgaccc tggccgacgc cggcttcatc aagcagtacg gcgactgcct gggcgacatc  2580
gccgcccggg acctgatctg cgcccagaag ttcaagggcc tgaccgtgct gcctcctctg  2640
ctgaccgacg agatgatcgc ccagtacacc agcgccctgc tggccggcac catcaccagc  2700
ggctggacct tcggcgccgg cgccgccctg cagatcccct tcgccatgca gatggcctac  2760
cggttcaacg gcatcggcgt gacccagaac gtgctgtacg agaaccagaa gctgatcgcc  2820
aaccagttca acagcgccat cggcaagatc caggacagcc tgagcagcac cgccagcgcc  2880
ctgggcaagc tgcaggacgt ggtgaaccac aacgcccagg ccctgaacac cctggtgaag  2940
cagctgagca gcaagttcgg cgccatcagc agcgtgctga acgacatctt cagccggctg  3000
gaccctcccg aggccgaggt gcagatcgac cggctgatca ccggccggct gcagagcctg  3060
cagacctacg tgacccagca gctgatccgg gccgccgaga tccgggccag cgccaacctg  3120
gccgccacca agatgagcga gtgcgtgctg ggccagagca agcgggtgga cttctgcggc  3180
aagggctacc acctgatgag ctttccccag agcgcacccc acggcgtggt gttcctgcac  3240
gtgacctacg tgcccgccca ggagaagaac ttcaccaccg ccccagccat ctgccacgac  3300
ggcaaggccc actttccccg ggagggcgtg ttcgtgagca acggcaccca ctggttcgtg  3360
acccagcgga acttctacga gccccagatc atcaccaccg acaacacctt cgtgagcggc  3420
```

```
aactgcgacg tggtgatcgg catcgtgaac aacaccgtgt acgatcccct gcagcccgag  3480
ctggacagct tcaaggagga gctggacaag tacttcaaga accacaccag ccccgacgtg  3540
gacctgggcg acatcagcgg catcaacgcc agcgtggtga acatccagaa ggagatcgac  3600
agactgaacg aggtggccaa gaacctgaac gagagcctga tcgacctgca ggagctgggc  3660
aagtacgagc agtacatcaa gtggccctgg tacatctggc tgggcttcat cgccggcctg  3720
atcgccatcg tgatggtgac catcatgctg tgctgcatga ccagctgctg cagctgcctg  3780
aagggctgct gcagctgcgg cagctgctgc aagttcgacg aggacgacag cgagcccgtg  3840
ctgaagggcg tgaagctgca ctacacctga taataggctg gagcctcggt ggcctagctt  3900
cttgcccctt gggcctcccc ccagcccctc ctccccttcc tgcacccgta cccccgtggt  3960
ctttgaataa agtctgagtg ggcggc                                     3986
```

```
SEQ ID NO: 38           moltype = RNA  length = 3810
FEATURE                 Location/Qualifiers
source                  1..3810
                        mol_type = other RNA
                        organism = synthetic construct
SEQUENCE: 38
atgttcgtgt tcctggtgct gctgcccctg gtgagcagcc agtgcgtgaa cctgaccacc  60
cggacccagc tgccaccagc ctacaccaac agcttcaccc ggggcgtgta ctaccccgac  120
aaggtgttcc ggagcagcgt gctgcacagc acccaggacc tgttcctgcc cttcttcagc  180
aacgtgacct ggttccacgt gatcagcggc accaacggca ccaagcggtt cgacaacccc  240
gtgctgccct tcaacgacgg cgtgtacttc gccagcatcg agaagagcaa catcatccgg  300
ggctggatct tcggcaccac cctggacagc aagacccaga gcctgctgat cgtgaacaac  360
gccaccaacg tggtgatcaa ggtgtgcgag ttccagttct gcaacgaccc cttcctggac  420
cacaagaaca acaagagctg gatggagagc gagttccggg tgtacagcag cgccaacaac  480
tgcaccttcg agtacgtgag ccagcccttc ctgatggacc tggagggcaa gcagggcaac  540
ttcaagaacc tgcgggagtt cgtgttcaag aacatcgacg gctacttcaa gatctacagc  600
aagcacaccc caatcatcgt gcgggagccc gaggacctgc cccagggctt cagcgccctg  660
gagcccctgg tggacctgcc catcggcatc aacatcaccc ggttccagac cctgctggcc  720
ctgcaccgga gctacctgac ccccggcgac agcagcagcg gctggaccgc cggcgccgcc  780
gcctactacg tgggctacct gcagccccgg accttcctgc tgaagtacaa cgagaacggc  840
accatcaccg acgccgtgga ctgcgccctg gaccctctga gcgagaccaa gtgcaccctg  900
aagagcttca ccgtggagaa gggcatctac cagaccagca acttccgggt gcagcccacc  960
gagagcatcg tgcggttccc caacatcacc aacctgtgcc ccttcgacga ggtgttcaac  1020
gccacccggt tcgccagcgt gtacgcctgg aaccggaagc ggatcagcaa ctgcgtggcc  1080
gactacagcg tgctgtacaa cctggcccct ttcttcacct tcaagtgcta cggcgtgagc  1140
cccaccaagc tgaacgacct gtgcttcacc aacgtgtacg ccgacagctt cgtgatccgg  1200
ggcgacgagg tgcggcagat cgccccaggc cagaccggca acatcgccga ctacaactac  1260
aagctgcccg acgacttcac cggctgcgtg atcgcctgga acagcaacaa gctggacagc  1320
aaggtgagcg gcaactacaa ctacctgtac cggctgttcc ggaagagcaa cctgaagccc  1380
ttcgagcggg acatcagcac cgagatctac caggccggca acaagccctg caacggcgtg  1440
gccggcttca actgctactt ccctctgcgg agctacagct tccggcccac ctacggcgtg  1500
ggccaccagc cctaccgggt ggtggtgctg agcttcgagc tgctgcacgc cccagccacc  1560
gtgtgcggcc ccaagaagag caccaacctg gtgaagaaca agtgcgtgaa cttcaacttc  1620
aacggcctga agggcaccgg cgtgctgacc gagagcaaca agaagttcct gcccttccag  1680
cagttcggcc gggacatcgc cgacaccacc gacgccgtgc gggatcccca gaccctggag  1740
atcctggaca tcaccccttg cagcttcggc ggcgtgagcg tgatcacccc aggcaccaac  1800
accagcaacc aggtggccgt gctgtaccag ggcgtgaact gcaccgaggt gcccgtggcc  1860
atccacgccg accagctgac cccaacctgg cgggtgtaca gcaccggcag caacgtgttc  1920
cagacccggg ccggctgcct gatcggcgcc gagtacgtga acaacagcta cgagtgcgac  1980
atccccatcg gcgccggcat ctgcgccagc taccagaccc agaccaacag ccccggcggc  2040
gccggcagcg tggccagcca gagcatcatc gcctacacca tgagcctggg cgccgagaac  2100
agcgtggcct acagcaacaa cagcatcgcc atccccacca acttcaccat cagcgtgacc  2160
accgagatcc tgcccgtgag catgaccaag accagcgtgg actgcaccat gtacatctgc  2220
ggcgacagca ccgagtgcag caacctgctg ctgcagtacg gcagcttctg cacccagctg  2280
aagcgggccc tgaccggcat cgccgtggag caggacaaga acacccagga ggtgttcgcc  2340
caggtgaagc agatctacaa gacccctccc atcaagtact tcggcggctt caacttcagc  2400
cagatcctgc ccgaccccag caagcccagc aagcggagct tcatcgagga cctgctgttc  2460
aacaaggtga ccctggccga cgccggcttc atcaagcagt acggcgactg cctgggcgac  2520
atcgccgccc gggacctgat ctgcgcccag aagttcaagg gcctgaccgt gctgcctcct  2580
ctgctgaccg acgagatgat cgcccagtac accagcgccc tgctggccgg caccatcacc  2640
agcggctgga ccttcggcgc cggcgccgcc ctgcagatcc ccttcgccat gcagatggcc  2700
taccggttca acggcatcgg cgtgacccag aacgtgctgt acgagaacca gaagctgatc  2760
gccaaccagt tcaacagcgc catcggcaag atccaggaca gcctgagcag caccgccagc  2820
gccctgggca agctgcagga cgtggtgaac cacaacgccc aggccctgaa caccctggtg  2880
aagcagctga gcagcaagtt cggcgccatc agcagcgtgc tgaacgacat cttcagccgg  2940
ctggaccctc ccgaggccga ggtgcagatc gaccggctga tcaccggccg gctgcagagc  3000
ctgcagacct acgtgaccca gcagctgatc cgggccgccg agatccgggc cagcgccaac  3060
ctggccgcca ccaagatgag cgagtgcgtg ctgggccaga gcaagcgggt ggacttctgc  3120
ggcaagggct accacctgat gagctttccc cagagcgcac cccacggcgt ggtgttcctg  3180
cacgtgacct acgtgcccgc ccaggagaag aacttcacca ccgcccccagc catctgccac  3240
gacggcaagg cccactttcc ccgggagggc gtgttcgtga gcaacggcac ccactggttc  3300
gtgacccagc ggaacttcta cgagccccag atcatcacca ccgacaacac cttcgtgagc  3360
ggcaactgcg acgtggtgat cggcatcgtg aacaacaccg tgtacgatcc cctgcagccc  3420
gagctggaca gcttcaagga ggagctggac aagtacttca agaaccacac cagccccgac  3480
gtggacctgg gcgacatcag cggcatcaac gccagcgtgg tgaacatcca gaaggagatc  3540
gacagactga acgaggtggc caagaacctg aacgagagcc tgatcgacct gcaggagctg  3600
ggcaagtacg agcagtacat caagtggccc tggtacatct ggctgggctt catcgccggc  3660
ctgatcgcca tcgtgatggt gaccatcatg ctgtgctgca tgaccagctg ctgcagctgc  3720
```

```
ctgaagggct gctgcagctg cggcagctgc tgcaagttcg acgaggacga cagcgagccc  3780
gtgctgaagg gcgtgaagct gcactacacc                                   3810

SEQ ID NO: 39           moltype = AA  length = 1270
FEATURE                 Location/Qualifiers
source                  1..1270
                        mol_type = protein
                        organism = synthetic construct
SEQUENCE: 39
MFVFLVLLPL VSSQCVNLTT RTQLPPAYTN SFTRGVYYPD KVFRSSVLHS TQDLFLPFFS  60
NVTWFHVISG TNGTKRFDNP VLPFNDGVYF ASIEKSNIIR GWIFGTTLDS KTQSLLIVNN  120
ATNVVIKVCE FQFCNDPFLD HKNNKSWMES EFRVYSSANN CTFEYVSQPF LMDLEGKQGN  180
FKNLREFVFK NIDGYFKIYS KHTPIIVREP EDLPQGFSAL EPLVDLPIGI NITRFQTLLA  240
LHRSYLTPGD SSSGWTAGAA AYYVGYLQPR TFLLKYNENG TITDAVDCAL DPLSETKCTL  300
KSFTVEKGIY QTSNFRVQPT ESIVRFPNIT NLCPFDEVFN ATRFASVYAW NRKRISNCVA  360
DYSVLYNLAP FFTFKCYGVS PTKLNDLCFT NVYADSFVIR GDEVRQIAPG QTGNIADYNY  420
KLPDDFTGCV IAWNSNKLDS KVSGNYNYLY RLFRKSNLKP FERDISTEIY QAGNKPCNGV  480
AGFNCYFPLR SYSFRPTYGV GHQPYRVVVL SFELLHAPAT VCGPKKSTNL VKNKCVNFNF  540
NGLKGTGVLT ESNKKFLPFQ QFGRDIADTT DAVRDPQTLE ILDITPCSFG GVSVITPGTN  600
TSNQVAVLYQ GVNCTEVPVA IHADQLTPTW RVYSTGSNVF QTRAGCLIGA EYVNNSYECD  660
IPIGAGICAS YQTQTNSPGG AGSVASQSII AYTMSLGAEN SVAYSNNSIA IPTNFTISVT  720
TEILPVSMTK TSVDCTMYIC GDSTECSNLL LQYGSFCTQL KRALTGIAVE QDKNTQEVFA  780
QVKQIYKTPP IKYFGGFNFS QILPDPSKPS KRSFIEDLLF NKVTLADAGF IKQYGDCLGD  840
IAARDLICAQ KFKGLTVLPP LLTDEMIAQY TSALLAGTIT SGWTFGAGAA LQIPFAMQMA  900
YRFNGIGVTQ NVLYENQKLI ANQFNSAIGK IQDSLSSTAS ALGKLQDVVN HNAQALNTLV  960
KQLSSKFGAI SSVLNDIFSR LDPPEAEVQI DRLITGRLQS LQTYVTQQLI RAAEIRASAN  1020
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTDNTFVS GNCDVVIGIV NNTVYDPLQP  1140
ELDSFKEELD KYFKNHTSPD VDLGDISGIN ASVVNIQKEI DRLNEVAKNL NESLIDLQEL  1200
GKYEQYIKWP WYIWLGFIAG LIAIVMVTIM LCCMTSCCSC LKGCCSCGSC CKFDEDDSEP  1260
VLKGVKLHYT                                                         1270

SEQ ID NO: 40           moltype = RNA  length = 3986
FEATURE                 Location/Qualifiers
source                  1..3986
                        mol_type = other RNA
                        organism = synthetic construct
SEQUENCE: 40
gggaaataag agagaaaaga agagtaagaa gaaatataag accccggcgc cgccaccatg  60
ttcgtgttcc tggtgctgct gcccctggtg agcagccagt gcgtgaacct gaccacccgg  120
acccagctgc caccagccta caccaacagc ttcacccggg gcgtgtacta ccccgacaag  180
gtgttccgga gcagcgtgct gcacagcacc caggacctgt tcctgccctt cttcagcaac  240
gtgacctggt tccacgtgat cagcggcacc aacggcacca agcggttcga caaccccgtg  300
ctgcccttca acgacggcgt gtacttcgcc agcatcgaga agagcaacat catccggggc  360
tggatcttcg gcaccaccct ggacagcaag acccagagcc tgctgatcgt gaacaacgcc  420
accaacgtgg tgatcaaggt gtgcgagttc cagttctgca acgacccctt cctggaccac  480
aagaacaaca agagctggat ggagagcgag ttccgggtgt acagcagcgc caacaactgc  540
accttcgagt acgtgagcca gcccttcctg atggacctgg agggcaagca gggcaacttc  600
aagaacctgc gggagttcgt gttcaagaac atcgacggct acttcaagat ctacagcaag  660
cacaccccaa tcatcgtgcg ggagcccgag gacctgcccc agggcttcag cgccctggag  720
cccctggtgg acctgcccat cggcatcaac atcacccggt tccagaccct gctggccctg  780
caccggagct acctgacccc aggcgacagc agcagcggct ggaccgccgg cgccgccgcc  840
tactacgtgg gctacctgca gccccggacc ttcctgctga agtacaacga gaacggcacc  900
atcaccgacg ccgtggactg cgccctggac cctctgagcg agaccaagtg caccctgaag  960
agcttcaccg tggagaaggg catctaccag accagcaact tccgggtgca gcccaccgag  1020
agcatcgtgc ggttccccaa catcaccaac ctgtgcccct tcgacgaggt gttcaacgcc  1080
acccggttcg ccagcgtgta cgcctggaac cggaagcgga tcagcaactg cgtggccgac  1140
tacagcgtgc tgtacaacct ggcccctttc ttcaccttca agtgctacgg cgtgagcccc  1200
accaagctga acgacctgtg cttcaccaac gtgtacgccg acagcttcgt gatccggggc  1260
gacgaggtgc ggcagatcgc cccaggccag accggcaaca tcgccgacta caactacaag  1320
ctgcccgacg acttcaccgg ctgcgtgatc gcctggaaca gcaacaagct ggacagcaag  1380
gtgagcggca actacaacta cctgtaccgg ctgttccgga agagcaacct gaagcccttc  1440
gagcgggaca tcagcaccga gatctaccag gccggcaaca agccctgcaa cggcgtggcc  1500
ggcttcaact gctacttccc tctgcggagc tacagcttcc ggcccaccta cggcgtgggc  1560
caccagccct accgggtggt ggtgctgagc ttcgagctgc tgcacgcccc agccaccgtg  1620
tgcggcccca agaagagcac caacctggtg aagaacaagt gcgtgaactt caacttcaac  1680
ggcctgaagg gcaccggcgt gctgaccgag agcaacaaga agttcctgcc cttccagcag  1740
ttcggccggg acatcgccga caccaccgac gccgtgcggg atccccagac cctggagatc  1800
ctggacatca ccccttgcag cttcggcggc gtgagcgtga tcaccccagg caccaacacc  1860
agcaaccagg tggccgtgct gtaccagggc gtgaactgca ccgaggtgcc cgtggccatc  1920
cacgccgacc agctgacccc aacctggcgg gtgtacagca ccggcagcaa cgtgttccag  1980
acccgggccg gctgcctgat cggcgccgag tacgtgaaca acagctacga gtgcgacatc  2040
cccatcggcg ccggcatctg cgccagctac cagacccaga ccaagagcca ccggcgggcc  2100
cggagcgtgg ccagccagag catcatcgcc tacaccatga gcctgggcgc cgagaacagc  2160
gtggcctaca gcaacaacag catcgccatc cccaccaact tcaccatcag cgtgaccacc  2220
gagatcctgc ccgtgagcat gaccaagacc agcgtggact gcaccatgta catctgcggc  2280
gacagcaccg agtgcagcaa cctgctgctg cagtacggca gcttctgcac ccagctgaag  2340
cgggccctga ccggcatcgc cgtggagcag gacaagaaca cccaggaggt gttcgcccag  2400
gtgaagcaga tctacaagac ccctcccatc aagtacttcg gcggcttcaa cttcagccag  2460
```

-continued

```
atcctgcccg accccagcaa gcccagcaag cggagcttca tcgaggacct gctgttcaac  2520
aaggtgaccc tggccgacgc cggcttcatc aagcagtacg gcgactgcct gggcgacatc  2580
gccgcccggg acctgatctg cgcccagaag ttcaagggcc tgaccgtgct gcctcctctg  2640
ctgaccgacg agatgatcgc ccagtacacc agcgccctgc tggccggcac catcaccagc  2700
ggctggacct tcggcgccgg cgccgccctg cagatcccct tcgccatgca gatggcctac  2760
cggttcaacg gcatcggcgt gacccagaac gtgctgtacg agaaccagaa gctgatcgcc  2820
aaccagttca acagcgccat cggcaagatc caggacagcc tgagcagcac cgccagcgcc  2880
ctgggcaagc tgcaggacgt ggtgaaccac aacgcccagg ccctgaacac cctggtgaag  2940
cagctgagca gcaagttcgg cgccatcagc agcgtgctga acgacatctt cagccggctg  3000
gaccctcccg aggccgaggt gcagatcgac cggctgatca ccggccggct gcagagcctg  3060
cagacctacg tgacccagca gctgatccgg gccgccgaga tccgggccag cgccaacctg  3120
gccgccacca agatgagcga gtgcgtgctg ggccagagca agcgggtgga cttctgcggc  3180
aagggctacc acctgatgag ctttccccag agcgcacccc acggcgtggt gttcctgcac  3240
gtgacctacg tgcccgccca ggagaagaac ttcaccaccg ccccagccat ctgccacgac  3300
ggcaaggccc actttccccg ggagggcgtg ttcgtgagca acggcaccca ctggttcgtg  3360
acccagcgga acttctacga gccccagatc atcaccaccg acaacacctt cgtgagcggc  3420
aactgcgacg tggtgatcgg catcgtgaac aacaccgtgt acgatcccct gcagcccgag  3480
ctggacagct tcaaggagga gctggacaag tacttcaaga accacaccag ccccgacgtg  3540
gacctgggcg acatcagcgg catcaacgcc agcgtggtga acatccagaa ggagatcgac  3600
agactgaacg aggtggccaa gaacctgaac gagagcctga tcgacctgca ggagctgggc  3660
aagtacgagc agtacatcaa gtggccctgg tacatctggc tgggcttcat cgccggcctg  3720
atcgccatcg tgatggtgac catcatgctg tgctgcatga ccagctgctg cagctgcctg  3780
aagggctgct gcagctgcgg cagctgctgc aagttcgacg aggacgacag cgagcccgtg  3840
ctgaagggcg tgaagctgca ctacacctga taataggctg gagcctcggt ggcctagctt  3900
cttgcccctt gggcctcccc ccagcccctc ctccccttcc tgcacccgta cccccgtggt  3960
ctttgaataa agtctgagtg ggcggc                                      3986
```

```
SEQ ID NO: 41          moltype = RNA  length = 3810
FEATURE                Location/Qualifiers
source                 1..3810
                       mol_type = other RNA
                       organism = synthetic construct
SEQUENCE: 41
atgttcgtgt tcctggtgct gctgcccctg gtgagcagcc agtgcgtgaa cctgaccacc  60
cggacccagc tgccaccagc ctacaccaac agcttcaccc ggggcgtgta ctaccccgac  120
aaggtgttcc ggagcagcgt gctgcacagc acccaggacc tgttcctgcc cttcttcagc  180
aacgtgacct ggttccacgt gatcagcggc accaacggca ccaagcggtt cgacaacccc  240
gtgctgccct tcaacgacgg cgtgtacttc gccagcatcg agaagagcaa catcatccgg  300
ggctggatct tcggcaccac cctggacagc aagacccaga gcctgctgat cgtgaacaac  360
gccaccaacg tggtgatcaa ggtgtgcgag ttccagttct gcaacgaccc cttcctggac  420
cacaagaaca acaagagctg gatggagagc gagttccggg tgtacagcag cgccaacaac  480
tgcaccttcg agtacgtgag ccagcccttc ctgatggacc tggagggcaa gcagggcaac  540
ttcaagaacc tgcgggagtt cgtgttcaag aacatcgacg gctacttcaa gatctacagc  600
aagcacaccc caatcatcgt gcgggagccc gaggacctgc cccagggctt cagcgccctg  660
gagcccctgg tggacctgcc catcggcatc aacatcaccc ggttccagac cctgctggcc  720
ctgcaccgga gctacctgac cccaggcgac agcagcagcg gctggaccgc cggcgccgcc  780
gcctactacg tgggctacct gcagccccgg accttcctgc tgaagtacaa cgagaacggc  840
accatcaccg acgccgtgga ctgcgccctg gaccctctga gcgagaccaa gtgcaccctg  900
aagagcttca ccgtggagaa gggcatctac cagaccagca acttccgggt gcagcccacc  960
gagagcatcg tgcggttccc caacatcacc aacctgtgcc ccttcgacga ggtgttcaac  1020
gccacccggt tcgccagcgt gtacgcctgg aaccggaagc ggatcagcaa ctgcgtggcc  1080
gactacagcg tgctgtacaa cctggcccct ttcttcacct tcaagtgcta cggcgtgagc  1140
cccaccaagc tgaacgacct gtgcttcacc aacgtgtacg ccgacagctt cgtgatccgg  1200
ggcgacgagg tgcggcagat cgccccaggc cagaccggca acatcgccga ctacaactac  1260
aagctgcccg acgacttcac cggctgcgtg atcgcctgga acagcaacaa gctggacagc  1320
aaggtgagcg gcaactacaa ctacctgtac cggctgttcc ggaagagcaa cctgaagccc  1380
ttcgagcggg acatcagcac cgagatctac caggccggca acaagccctg caacggcgtg  1440
gccggcttca actgctactt ccctctgcgg agctacagct tccggcccac ctacggcgtg  1500
ggccaccagc cctaccgggt ggtggtgctg agcttcgagc tgctgcacgc cccagccacc  1560
gtgtgcggcc ccaagaagag caccaacctg gtgaagaaca agtgcgtgaa cttcaacttc  1620
aacggcctga agggcaccgg cgtgctgacc gagagcaaca agaagttcct gcccttccag  1680
cagttcggcc gggacatcgc cgacaccacc gacgccgtgc gggatcccca gaccctggag  1740
atcctggaca tcaccccttg cagcttcggc ggcgtgagcg tgatcacccc aggcaccaac  1800
accagcaacc aggtggccgt gctgtaccag ggcgtgaact gcaccgaggt gcccgtggcc  1860
atccacgccg accagctgac cccaacctgg cgggtgtaca gcaccggcag caacgtgttc  1920
cagacccggg ccggctgcct gatcggcgcc gagtacgtga acaacagcta cgagtgcgac  1980
atccccatcg gcgccggcat ctgcgccagc taccagaccc agaccaagag ccaccggcgg  2040
gcccggagcg tggccagcca gagcatcatc gcctacacca tgagcctggg cgccgagaac  2100
agcgtggcct acagcaacaa cagcatcgcc atccccacca acttcaccat cagcgtgacc  2160
accgagatcc tgcccgtgag catgaccaag accagcgtgg actgcaccat gtacatctgc  2220
ggcgacagca ccgagtgcag caacctgctg ctgcagtacg gcagcttctg cacccagctg  2280
aagcgggccc tgaccggcat cgccgtggag caggacaaga acacccagga ggtgttcgcc  2340
caggtgaagc agatctacaa gacccctccc atcaagtact tcggcggctt caacttcagc  2400
cagatcctgc ccgaccccag caagcccagc aagcggagct tcatcgagga cctgctgttc  2460
aacaaggtga ccctggccga cgccggcttc atcaagcagt acggcgactg cctgggcgac  2520
atcgccgccc gggacctgat ctgcgcccag aagttcaagg gcctgaccgt gctgcctcct  2580
ctgctgaccg acgagatgat cgcccagtac accagcgccc tgctggccgg caccatcacc  2640
agcggctgga ccttcggcgc cggcgccgcc ctgcagatcc ccttcgccat gcagatggcc  2700
taccggttca acggcatcgg cgtgacccag aacgtgctgt acgagaacca gaagctgatc  2760
```

```
gccaaccagt tcaacagcgc catcggcaag atccaggaca gcctgagcag caccgccagc  2820
gccctgggca agctgcagga cgtggtgaac cacaacgccc aggccctgaa caccctggtg  2880
aagcagctga gcagcaagtt cggcgccatc agcagcgtgc tgaacgacat cttcagccgg  2940
ctggaccctc ccgaggccga ggtgcagatc gaccggctga tcaccggccg gctgcagagc  3000
ctgcagacct acgtgaccca gcagctgatc cgggccgccg agatccgggc cagcgccaac  3060
ctggccgcca ccaagatgag cgagtgcgtg ctgggccaga gcaagcgggt ggacttctgc  3120
ggcaagggct accacctgat gagctttccc cagagcgcac cccacggcgt ggtgttcctg  3180
cacgtgacct acgtgcccgc ccaggagaag aacttcacca ccgcccccagc catctgccac  3240
gacggcaagg cccactttcc ccgggagggc gtgttcgtga gcaacggcac ccactggttc  3300
gtgacccagc ggaacttcta cgagccccag atcatcacca ccgacaacac cttcgtgagc  3360
ggcaactgcg acgtggtgat cggcatcgtg aacaacaccg tgtacgatcc cctgcagccc  3420
gagctggaca gcttcaagga ggagctggac aagtacttca agaaccacac cagccccgac  3480
gtggacctgg gcgacatcag cggcatcaac gccagcgtgg tgaacatcca gaaggagatc  3540
gacagactga acgaggtggc caagaacctg aacgagagcc tgatcgacct gcaggagctg  3600
ggcaagtacg agcagtacat caagtggccc tggtacatct ggctgggctt catcgccggc  3660
ctgatcgcca tcgtgatggt gaccatcatg ctgtgctgca tgaccagctg ctgcagctgc  3720
ctgaagggct gctgcagctg cggcagctgc tgcaagttcg acgaggacga cagcgagccc  3780
gtgctgaagg gcgtgaagct gcactacacc                                  3810

SEQ ID NO: 42           moltype = AA  length = 1270
FEATURE                 Location/Qualifiers
source                  1..1270
                        mol_type = protein
                        organism = synthetic construct
SEQUENCE: 42
MFVFLVLLPL VSSQCVNLTT RTQLPPAYTN SFTRGVYYPD KVFRSSVLHS TQDLFLPFFS  60
NVTWFHVISG TNGTKRFDNP VLPFNDGVYF ASIEKSNIIR GWIFGTTLDS KTQSLLIVNN  120
ATNVVIKVCE FQFCNDPFLD HKNNKSWMES EFRVYSSANN CTFEYVSQPF LMDLEGKQGN  180
FKNLREFVFK NIDGYFKIYS KHTPIIVREP EDLPQGFSAL EPLVDLPIGI NITRFQTLLA  240
LHRSYLTPGD SSSGWTAGAA AYYVGYLQPR TFLLKYNENG TITDAVDCAL DPLSETKCTL  300
KSFTVEKGIY QTSNFRVQPT ESIVRFPNIT NLCPFDEVFN ATRFASVYAW NRKRISNCVA  360
DYSVLYNLAP FFTFKCYGVS PTKLNDLCFT NVYADSFVIR GDEVRQIAPG QTGNIADYNY  420
KLPDDFTGCV IAWNSNKLDS KVSGNYNYLY RLFRKSNLKP FERDISTEIY QAGNKPCNGV  480
AGFNCYFPLR SYSFRPTYGV GHQPYRVVVL SFELLHAPAT VCGPKKSTNL VKNKCVNFNF  540
NGLKGTGVLT ESNKKFLPFQ QFGRDIADTT DAVRDPQTLE ILDITPCSFG GVSVITPGTN  600
TSNQVAVLYQ GVNCTEVPVA IHADQLTPTW RVYSTGSNVF QTRAGCLIGA EYVNNSYECD  660
IPIGAGICAS YQTQTKSHRR ARSVASQSII AYTMSLGAEN SVAYSNNSIA IPTNFTISVT  720
TEILPVSMTK TSVDCTMYIC GDSTECSNLL LQYGSFCTQL KRALTGIAVE QDKNTQEVFA  780
QVKQIYKTPP IKYFGGFNFS QILPDPSKPS KRSFIEDLLF NKVTLADAGF IKQYGDCLGD  840
IAARDLICAQ KFKGLTVLPP LLTDEMIAQY TSALLAGTIT SGWTFGAGAA LQIPFAMQMA  900
YRFNGIGVTQ NVLYENQKLI ANQFNSAIGK IQDSLSSTAS ALGKLQDVVN HNAQALNTLV  960
KQLSSKFGAI SSVLNDIFSR LDPPEAEVQI DRLITGRLQS LQTYVTQQLI RAAEIRASAN  1020
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTDNTFVS GNCDVVIGIV NNTVYDPLQP  1140
ELDSFKEELD KYFKNHTSPD VDLGDISGIN ASVVNIQKEI DRLNEVAKNL NESLIDLQEL  1200
GKYEQYIKWP WYIWLGFIAG LIAIVMVTIM LCCMTSCCSC LKGCCSCGSC CKFDEDDSEP  1260
VLKGVKLHYT                                                        1270

SEQ ID NO: 43           moltype = RNA  length = 3989
FEATURE                 Location/Qualifiers
source                  1..3989
                        mol_type = other RNA
                        organism = synthetic construct
SEQUENCE: 43
gggaaataag agagaaaaga agagtaagaa gaaatataag accccggcgc cgccaccatg  60
ttcgtgttcc tggtgctgct gcccctggtg agcagccagt gcgtgaacct gaccacccgg  120
acccagctgc caccagccta caccaacagc ttcacccggg gcgtgtacta ccccgacaag  180
gtgttccgga gcagcgtgct gcacagcacc caggacctgt tcctgccctt cttcagcaac  240
gtgacctggt tccacgtgat cagcggcacc aacggcacca agcggttcga caaccccgtg  300
ctgcccttca acgacggcgt gtacttcgcc agcatcgaga agagcaacat catccggggc  360
tggatcttcg gcaccaccct ggacagcaag acccagagcc tgctgatcgt gaacaacgcc  420
accaacgtgg tgatcaaggt gtgcgagttc cagttctgca acgacccctt cctggaccac  480
aagaacaaca agagctggat ggagagcgag ttccgggtgt acagcagcgc caacaactgc  540
accttcgagt acgtgagcca gcccttcctg atggacctgg agggcaagca gggcaacttc  600
aagaacctgc gggagttcgt gttcaagaac atcgacggct acttcaagat ctacagcaag  660
cacaccccaa tcatcgtgcg ggagcccgag gacctgcccc agggcttcag cgccctggag  720
cccctggtgg acctgcccat cggcatcaac atcacccggt tccagaccct gctggccctg  780
caccggagct acctgacccc aggcgacagc agcagcggct ggaccgccgg cgccgccgcc  840
tactacgtgg gctacctgca gccccggacc ttcctgctga agtacaacga gaacggcacc  900
atcaccgacg ccgtggactg cgccctggac cctctgagcg agaccaagtg caccctgaag  960
agcttcaccg tggagaaggg catctaccag accagcaact tccgggtgca gcccaccgag  1020
agcatcgtgc ggttccccaa catcaccaac ctgtgcccct tcgacgaggt gttcaacgcc  1080
acccggttcg ccagcgtgta cgcctggaac cggaagcgga tcagcaactg cgtggccgac  1140
tacagcgtgc tgtacaacct ggcccctttc ttcaccttca agtgctacgg cgtgagcccc  1200
accaagctga acgacctgtg cttcaccaac gtgtacgccg acagcttcgt gatccggggc  1260
gacgaggtgc ggcagatcgc cccaggccag accggcaaca tcgccgacta caactacaag  1320
ctgcccgacg acttcaccgg ctgcgtgatc gcctggaaca gcaacaagct ggacagcaag  1380
gtgagcggca actacaacta cctgtaccgg ctgttccgga agagcaacct gaagcccttc  1440
gagcgggaca tcagcaccga gatctaccag gccggcaaca agccctgcaa cggcgtggcc  1500
```

```
ggcttcaact gctacttccc tctgcggagc tacagcttcc ggcccaccta cggcgtgggc  1560
caccagccct accgggtggt ggtgctgagc ttcgagctgc tgcacgcccc agccaccgtg  1620
tgcggcccca agaagagcac caacctggtg aagaacaagt gcgtgaactt caacttcaac  1680
ggcctgaagg gcaccggcgt gctgaccgag agcaacaaga agttcctgcc cttccagcag  1740
ttcggccggg acatcgccga caccaccgac gccgtgcggg atccccagac cctggagatc  1800
ctggacatca ccccttgcag cttcggcggc gtgagcgtga tcaccccagg caccaacacc  1860
agcaaccagg tggccgtgct gtaccagggc gtgaactgca ccgaggtgcc cgtggccatc  1920
cacgccgacc agctgacccc aacctggcgg gtgtacagca ccggcagcaa cgtgttccag  1980
acccgggccg gctgcctgat cggcgccgag tacgtgaaca acagctacga gtgcgacatc  2040
cccatcggcg ccggcatctg cgccagctac cagacccaga ccaagagcca ccggcgggcc  2100
cggagcgtgg ccagccagag catcatcgcc tacaccatga gcctgggcgc cgagaacagc  2160
gtggcctaca gcaacaacag catcgccatc cccaccaact tcaccatcag cgtgaccacc  2220
gagatcctgc ccgtgagcat gaccaagacc agcgtggact gcaccatgta catctgcggc  2280
gacagcaccg agtgcagcaa cctgctgctg cagtacggca gcttctgcac ccagctgaag  2340
cgggccctga ccggcatcgc cgtggagcag gacaagaaca cccaggaggt gttcgcccag  2400
gtgaagcaga tctacaagac ccctcccatc aagtacttcg gcggcttcaa cttcagccag  2460
atcctgcccg accccagcaa gcccagcaag cggagcttca tcgaggacct gctgttcaac  2520
aaggtgaccc tggccgacgc cggcttcatc aagcagtacg gcgactgcct gggcgacatc  2580
gccgcccggg acctgatctg cgcccagaag ttcaagggcc tgaccgtgct gcctcctctg  2640
ctgaccgacg agatgatcgc ccagtacacc agcgccctgc tggccggcac catcaccagc  2700
ggctggacct tcggcgccgg cgccgccctg cagatcccct tcgccatgca gatggcctac  2760
cggttcaacg gcatcggcgt gacccagaac gtgctgtacg agaaccagaa gctgatcgcc  2820
aaccagttca acagcgccat cggcaagatc caggacagcc tgagcagcac cgccagcgcc  2880
ctgggcaagc tgcaggacgt ggtgaaccac aacgcccagg ccctgaacac cctggtgaag  2940
cagctgagca gcaagttcgg cgccatcagc agcgtgctga acgacatctt cagccggctg  3000
gaccctcccg aggccgaggt gcagatcgac cggctgatca ccggccggct gcagagcctg  3060
cagacctacg tgacccagca gctgatccgg gccgccgaga tccgggccag cgccaacctg  3120
gccgccacca agatgagcga gtgcgtgctg ggccagagca agcgggtgga cttctgcggc  3180
aagggctacc acctgatgag ctttccccag agcgcacccc acggcgtggt gttcctgcac  3240
gtgacctacg tgcccgccca ggagaagaac ttcaccaccg ccccagccat ctgccacgac  3300
ggcaaggccc actttccccg ggagggcgtg ttcgtgagca acggcaccca ctggttcgtg  3360
acccagcgga acttctacga gccccagatc atcaccaccg acaacacctt cgtgagcggc  3420
aactgcgacg tggtgatcgg catcgtgaac aacaccgtgt acgatcccct gcagcccgag  3480
ctggacagct tcaaggagga gctggacaag tacttcaaga accacaccag ccccgacgtg  3540
gacctgggcg acatcagcgg catcaacgcc agcgtggtga acatccagaa ggagatcgac  3600
agactgaacg aggtggccaa gaacctgaac gagagcctga tcgacctgca ggagctgggc  3660
aagtacgagc agtacatcaa gtggccctgg tacatctggc tgggcttcat cgccggcctg  3720
atcgccatcg tgatggtgac catcatgctg tgctgcatga ccagctgctg cagctgcctg  3780
aagggctgct gcagctgcgg cagctgctgc aagttcgacg aggacgacag cgagcccgtg  3840
ctgaagggcg tgaagctgca ctacacctga taataggctg gagcctcggt ggcctagctt  3900
cttgcccctt gggcctcccc ccagcccctc ctccccttcc tgcaggatag atagcgaagt  3960
ggtctttgaa taaagtctga gtgggcggc                                    3989
```

```
SEQ ID NO: 44           moltype = RNA  length = 122
FEATURE                 Location/Qualifiers
source                  1..122
                        mol_type = other RNA
                        organism = synthetic construct
SEQUENCE: 44
tgataatagg ctggagcctc ggtggcctag cttcttgccc cttgggcctc cccccagccc  60
ctcctcccct tcctgcagga tagatagcga agtggtcttt gaataaagtc tgagtgggcg  120
gc                                                                 122
```

```
SEQ ID NO: 45           moltype = RNA  length = 3989
FEATURE                 Location/Qualifiers
source                  1..3989
                        mol_type = other RNA
                        organism = synthetic construct
SEQUENCE: 45
gggaaataag agagaaaaga agagtaagaa gaaatataag accccggcgc cgccaccatg  60
ttcgtgttcc tggtgctgct gcccctggtg agcagccagt gcgtgaacct gaccacccgg  120
acccagctgc caccagccta caccaacagc ttcacccggg gcgtgtacta ccccgacaag  180
gtgttccgga gcagcgtgct gcacagcacc caggacctgt tcctgccctt cttcagcaac  240
gtgacctggt tccacgtgat cagcggcacc aacggcacca agcggttcga caaccccgtg  300
ctgcccttca acgacggcgt gtacttcgcc agcatcgaga agagcaacat catccggggc  360
tggatcttcg gcaccaccct ggacagcaag acccagagcc tgctgatcgt gaacaacgcc  420
accaacgtgg tgatcaaggt gtgcgagttc cagttctgca acgacccctt cctggaccac  480
aagaacaaca agagctggat ggagagcgag ttccgggtgt acagcagcgc caacaactgc  540
accttcgagt acgtgagcca gcccttcctg atggacctgg agggcaagca gggcaacttc  600
aagaacctgc gggagttcgt gttcaagaac atcgacggct acttcaagat ctacagcaag  660
cacaccccaa tcatcgtgcg ggagcccgag gacctgcccc agggcttcag cgccctggag  720
cccctggtgg acctgcccat cggcatcaac atcacccggt tccagaccct gctggccctg  780
caccggagct acctgacccc aggcgacagc agcagcggct ggaccgccgg cgccgccgcc  840
tactacgtgg gctacctgca gccccggacc ttcctgctga agtacaacga gaacggcacc  900
atcaccgacg ccgtggactg cgccctggac cctctgagcg agaccaagtg caccctgaag  960
agcttcaccg tggagaaggg catctaccag accagcaact tccgggtgca gcccaccgag  1020
agcatcgtgc ggttccccaa catcaccaac ctgtgcccct tcgacgaggt gttcaacgcc  1080
acccggttcg ccagcgtgta cgcctggaac cggaagcgga tcagcaactg cgtggccgac  1140
tacagcgtgc tgtacaacct ggcccctttc ttcaccttca agtgctacgg cgtgagcccc  1200
```

-continued

```
accaagctga acgacctgtg cttcaccaac gtgtacgccg acagcttcgt gatccggggc  1260
gacgaggtgc ggcagatcgc ccaggccag accggcaaca tcgccgacta caactacaag  1320
ctgcccgacg acttcaccgg ctgcgtgatc gcctggaaca gcaacaagct ggacagcaag  1380
gtgagcggca actacaacta cctgtaccgg ctgttccgga agagcaacct gaagcccttc  1440
gagcgggaca tcagcaccga gatctaccag gccggcaaca agccctgcaa cggcgtggcc  1500
ggcttcaact gctacttccc tctgcggagc tacagcttcc ggcccaccta cggcgtgggc  1560
caccagccct accgggtggt ggtgctgagc ttcgagctgc tgcacgcccc agccaccgtg  1620
tgcggcccca agaagagcac caacctggtg aagaacaagt gcgtgaactt caacttcaac  1680
ggcctgaagg gcaccggcgt gctgaccgag agcaacaaga agttcctgcc cttccagcag  1740
ttcggccggg acatcgccga caccaccgac gccgtgcggg atccccagac cctggagatc  1800
ctggacatca cccttgcag cttcggcggc gtgagcgtga tcaccccagg caccaacacc  1860
agcaaccagg tggccgtgct gtaccagggc gtgaactgca ccgaggtgcc cgtggccatc  1920
cacgccgacc agctgacccc aacctggcgg gtgtacagca ccggcagcaa cgtgttccag  1980
acccgggccg gctgcctgat cggcgccgag tacgtgaaca acagctacga gtgcgacatc  2040
cccatcggcg ccggcatctg cgccagctac cagacccaga ccaagagcca ccggcgggcc  2100
cggagcgtgg ccagccagag catcatcgcc tacaccatga gcctgggcgc cgagaacagc  2160
gtggcctaca gcaacaacag catcgccatc cccaccaact tcaccatcag cgtgaccacc  2220
gagatcctgc ccgtgagcat gaccaagacc agcgtggact gcaccatgta catctgcggc  2280
gacagcaccg agtgcagcaa cctgctgctg cagtacggca gcttctgcac ccagctgaag  2340
cgggccctga ccggcatcgc cgtggagcag gacaagaaca cccaggaggt gttcgcccag  2400
gtgaagcaga tctacaagac ccctcccatc aagtacttcg gcggcttcaa cttcagccag  2460
atcctgcccg accccagcaa gcccagcaag cggagcttca tcgaggacct gctgttcaac  2520
aaggtgaccc tggccgacgc cggcttcatc aagcagtacg gcgactgcct gggcgacatc  2580
gccgcccggg acctgatctg cgcccagaag ttcaagggcc tgaccgtgct gcctcctctg  2640
ctgaccgacg agatgatcgc ccagtacacc agcgccctgc tggccggcac catcaccagc  2700
ggctggacct tcggcgccgg cgccgccctg cagatcccct tcgccatgca gatggcctac  2760
cggttcaacg gcatcggcgt gacccagaac gtgctgtacg agaaccagaa gctgatcgcc  2820
aaccagttca acagcgccat cggcaagatc caggacagcc tgagcagcac cgccagcgcc  2880
ctgggcaagc tgcaggacgt ggtgaaccac aacgcccagg ccctgaacac cctggtgaag  2940
cagctgagca gcaagttcgg cgccatcagc agcgtgctga acgacatctt cagccggctg  3000
gaccctcccg aggccgaggt gcagatcgac cggctgatca ccggccggct gcagagcctg  3060
cagacctacg tgacccagca gctgatccgg gccgccgaga tccgggccag cgccaacctg  3120
gccgccacca agatgagcga gtgcgtgctg ggccagagca agcgggtgga cttctgcggc  3180
aagggctacc acctgatgag ctttccccag agcgcacccc acggcgtggt gttcctgcac  3240
gtgacctacg tgcccgccca ggagaagaac ttcaccaccg ccccagccat ctgccacgac  3300
ggcaaggccc actttccccg ggagggcgtg ttcgtgagca acggcaccca ctggttcgtg  3360
acccagcgga acttctacga gccccagatc atcaccaccg acaacacctt cgtgagcggc  3420
aactgcgacg tggtgatcgg catcgtgaac aacaccgtgt acgatcccct gcagcccgag  3480
ctggacagct tcaaggagga gctggacaag tacttcaaga accacaccag ccccgacgtg  3540
gacctgggcg acatcagcgg catcaacgcc agcgtggtga acatccagaa ggagatcgac  3600
agactgaacg aggtggccaa gaacctgaac gagagcctga tcgacctgca ggagctgggc  3660
aagtacgagc agtacatcaa gtggccctgg tacatctggc tgggcttcat cgccggcctg  3720
atcgccatcg tgatggtgac catcatgctg tgctgcatga ccagctgctg cagctgcctg  3780
aagggctgct gcagctgcgg cagctgctgc aagttcgacg aggacgacag cgagcccgtg  3840
ctgaagggcg tgaagctgca ctacacctga taataggctg gagcctcggt ggcctagctt  3900
cttgcccctt gggcctcccc ccagcccctc ctccccttcc tgcaggccac atagcgaagt  3960
ggtctttgaa taaagtctga gtgggcggc                                 3989
```

```
SEQ ID NO: 46          moltype = RNA  length = 122
FEATURE                Location/Qualifiers
source                 1..122
                       mol_type = other RNA
                       organism = synthetic construct
SEQUENCE: 46
tgataatagg ctggagcctc ggtggcctag cttcttgccc cttgggcctc cccccagccc  60
ctcctcccct tcctgcaggc cacatagcga agtggtcttt gaataaagtc tgagtgggcg  120
gc                                                                 122

SEQ ID NO: 47          moltype = AA  length = 10
FEATURE                Location/Qualifiers
source                 1..10
                       mol_type = protein
                       organism = synthetic construct
SEQUENCE: 47
TQTNSPRRAR                                                         10

SEQ ID NO: 48          moltype = AA  length = 5
FEATURE                Location/Qualifiers
source                 1..5
                       mol_type = protein
                       organism = synthetic construct
SEQUENCE: 48
KPSKR                                                              5

SEQ ID NO: 49          moltype = AA  length = 4
FEATURE                Location/Qualifiers
source                 1..4
                       mol_type = protein
                       organism = synthetic construct
```

-continued

```
SEQUENCE: 49
GGGS                                                            4

SEQ ID NO: 50          moltype = RNA  length = 47
FEATURE                Location/Qualifiers
source                 1..47
                       mol_type = other RNA
                       organism = synthetic construct
SEQUENCE: 50
gggaaataag agagaaaaga agagtaagaa gaaatataag agccacc             47

SEQ ID NO: 51          moltype = RNA  length = 119
FEATURE                Location/Qualifiers
source                 1..119
                       mol_type = other RNA
                       organism = synthetic construct
SEQUENCE: 51
tgataatagg ctggagcctc ggtggccatg cttcttgccc cttgggcctc cccccagccc  60
ctcctcccct tcctgcaccc gtacccccgt ggtctttgaa taaagtctga gtgggcggc   119

SEQ ID NO: 52          moltype =   length =
SEQUENCE: 52
000

SEQ ID NO: 53          moltype = RNA  length = 11
FEATURE                Location/Qualifiers
source                 1..11
                       mol_type = other RNA
                       organism = synthetic construct
SEQUENCE: 53
gggatcctac c                                                    11
```